United States Patent
Kuntz et al.

(10) Patent No.: US 9,637,472 B2
(45) Date of Patent: May 2, 2017

(54) SUBSTITUTED 6,5-FUSED BICYCLIC HETEROARYL COMPOUNDS

(71) Applicant: Epizyme, Inc., Cambridge, MA (US)

(72) Inventors: Kevin Wayne Kuntz, Woburn, MA (US); Edward James Olhava, Newton, MA (US); Richard Chesworth, Concord, MA (US); Kenneth William Duncan, Norwood, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 14/536,162

(22) Filed: Nov. 7, 2014

(65) Prior Publication Data

US 2015/0065483 A1    Mar. 5, 2015

Related U.S. Application Data

(63) Continuation of application No. 14/070,675, filed on Nov. 4, 2013, now Pat. No. 8,962,620, which is a continuation of application No. 13/938,067, filed on Jul. 9, 2013, now Pat. No. 8,598,167, which is a continuation of application No. PCT/US2012/026953, filed on Feb. 28, 2012.

(60) Provisional application No. 61/447,632, filed on Feb. 28, 2011, provisional application No. 61/447,625, filed on Feb. 28, 2011, provisional application No. 61/447,626, filed on Feb. 28, 2011, provisional application No. 61/447,627, filed on Feb. 28, 2011, provisional application No. 61/447,629, filed on Feb. 28, 2011.

(51) Int. Cl.

| | | |
|---|---|---|
| *C07D 401/12* | (2006.01) | |
| *C07D 471/04* | (2006.01) | |
| *C07D 401/04* | (2006.01) | |
| *C07D 401/14* | (2006.01) | |
| *C07D 405/14* | (2006.01) | |
| *C07D 413/14* | (2006.01) | |

(52) U.S. Cl.
CPC ......... *C07D 401/12* (2013.01); *C07D 401/04* (2013.01); *C07D 401/14* (2013.01); *C07D 405/14* (2013.01); *C07D 413/14* (2013.01); *C07D 471/04* (2013.01)

(58) Field of Classification Search
CPC .. C07D 471/04; C07D 401/04; C07D 401/14; C07D 405/14; C07D 413/14
See application file for complete search history.

(56) References Cited

U.S. PATENT DOCUMENTS

| | | |
|---|---|---|
| 5,716,993 A | 2/1998 | Ozaki et al. |
| 5,948,803 A | 9/1999 | Maeda et al. |
| 6,710,058 B2 | 3/2004 | Jacobson et al. |
| 6,951,872 B2 | 10/2005 | Jacobson et al. |
| 7,122,547 B1 | 10/2006 | Huth et al. |
| 8,163,749 B2 | 4/2012 | Corte |
| 8,536,179 B2 | 9/2013 | Miller et al. |
| 8,598,167 B1 | 12/2013 | Kuntz et al. |
| 8,962,620 B2 | 2/2015 | Kuntz et al. |
| 8,975,291 B2 | 3/2015 | Brackley et al. |
| 9,206,157 B2 | 12/2015 | Kuntz et al. |
| 2002/0183324 A1 | 12/2002 | Jacobson et al. |
| 2004/0082619 A1 | 4/2004 | Tada et al. |
| 2004/0147759 A1 | 7/2004 | Hofgen et al. |
| 2008/0103182 A1 | 5/2008 | Ackermann et al. |
| 2008/0182844 A1 | 7/2008 | Bjergarde et al. |
| 2008/0312292 A1 | 12/2008 | Yasui et al. |
| 2010/0113415 A1 | 5/2010 | Rajapakse et al. |
| 2015/0141436 A1 | 5/2015 | Miller et al. |

FOREIGN PATENT DOCUMENTS

| | | |
|---|---|---|
| WO | WO-9809961 A1 | 3/1998 |
| WO | WO-2004014864 A1 | 2/2004 |
| WO | WO-2005014554 A1 | 2/2005 |
| WO | WO-2007070818 A1 | 6/2007 |
| WO | WO-2008005457 A2 | 1/2008 |
| WO | WO-2008103277 A2 | 8/2008 |
| WO | WO-2008104077 A1 | 9/2008 |
| WO | WO-2010036632 A1 | 4/2010 |
| WO | WO-2011140324 A1 | 11/2011 |
| WO | WO-2011140325 A1 | 11/2011 |
| WO | WO-2012005805 A1 | 1/2012 |
| WO | WO-2012075080 A1 | 6/2012 |
| WO | WO-2013024282 A2 | 2/2013 |

OTHER PUBLICATIONS

Nakamura, I. et al. Transition-Metal-Catalyzed Reactions in Heterocyclic Synthesis. Chem. Rev. 2004, vol. 104, p. 2127.*
Anderson (Chem and Biol 10:787-797, 2003.*
Thiel (Nature Biotechnol 2:513-519, 2004.*
Wermuth, CG, "Molecular Variations Based on Isosteric Replacements," Practice of Medicinal Chemistry, Jan. 1996, pp. 203-237.
Anderson, A.C., "The Process of Structure-Based Drug Design," *Chem. Biol.*, 2003, 10(9), 787-797.
Nakamura, I. et al., "Transition-Metal-Catalyzed Reactions in Heterocyclic Synthesis," *Chem. Rev.*, 2004, 104(5), 2127-2198.
Thiel, K. A., "Structure-aided drug design's next generation," *Nat. Biotechnol.*, 2004, 22(5), 513-519.

* cited by examiner

*Primary Examiner* — Savitha Rao
(74) *Attorney, Agent, or Firm* — Cooley LLP; Heidi A. Erlacher; Liam Ouyang

(57) ABSTRACT

The present invention relates to substituted 6,5-fused bicyclic heteroaryl compounds. The present invention also relates to pharmaceutical compositions containing these compounds and methods of treating cancer by administering these compounds and pharmaceutical compositions to subjects in need thereof.

19 Claims, No Drawings

SUBSTITUTED 6,5-FUSED BICYCLIC HETEROARYL COMPOUNDS

RELATED APPLICATIONS

This application is a continuation of U.S. application Ser. No. 14/070,675, filed Nov. 4, 2013 (now allowed), which is a continuation of U.S. application Ser. No. 13/938,067, filed Jul. 9, 2013 (now U.S. Pat. No. 8,598,167), which is a continuation of International Application PCT/US2012/026953, with an international filing date of Feb. 28, 2012, which claims priority to, and the benefit of, U.S. provisional application Nos. 61/447,632, filed Feb. 28, 2011, 61/447,625, filed Feb. 28, 2011, 61/447,626 filed Feb. 28, 2011, 61/447,627 filed Feb. 28, 2011, and 61/447,629 filed Feb. 28, 2011, the entire contents of each of which are incorporated herein by reference in their entireties.

INCORPORATION-BY-REFERENCE OF SEQUENCE LISTING

The contents of the text file named "41478503001WOST25.txt", which was created on Feb. 28, 2012 and is 2 KB in size, are hereby incorporated by reference in their entireties.

BACKGROUND OF THE INVENTION

In eukaryotic cells DNA is packaged with histones to form chromatin. Changes in the ordered structure of chromatin can lead to alterations in transcription of associated genes. Control of changes in chromatin structure (and hence of transcription) is mediated by covalent modifications to histones, most notably of their N-terminal tails. These modifications are often referred to as epigenetic because they can lead to heritable changes in gene expression, but do not affect the sequence of the DNA itself. Covalent modifications (for example, methylation, acetylation, phosphorylation, and ubiquitination) of the side chains of amino acids are enzymatically mediated. The selective addition of methyl groups to specific amino acid sites on histones is controlled by the action of a unique family of enzymes known as histone methyltransferases (HMTs).

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease) and cardiovascular diseases. Therefore, selectively modulating the aberrant action of epigenetic enzymes holds great promise for the treatment of a range of diseases.

Polycomb group (PcG) and trithorax group (trxG) proteins are known to be part of the cellular memory system. See, e.g., Francis et al. (2001) *Nat Rev Mol Cell Biol* 2:409-21 and Simon et al. (2002) *Curr Opin Genet Dev* 12:210-8. In general, PcG proteins are transcriptional repressors that maintain the "off state," and trxG proteins are transcriptional activators that maintain the "on state." Because members of PcG and trxG proteins contain intrinsic histone methyltransferase (HMTase) activity, PcG and trxG proteins may participate in cellular memory through methylation of core histones. See, e.g., Beisel et al. (2002) *Nature* 419:857-62; Cao et al. (2002) *Science* 298:1039-43; Czermin et al. (2002) *Cell* 111:185-96; Kuzmichev et al. (2002) *Genes Dev* 16:2893-905; Milne et al. (2002) *Mol Cell* 10:1107-17; Muller et al. (2002) *Cell* 111:197-208; and Nakamura et al. (2002) *Mol Cell* 10:1119-28.

Biochemical and genetic studies have provided evidence that *Drosophila* PcG proteins function in at least two distinct protein complexes, the Polycomb repressive complex 1 (PRC1) and the ESC-E(Z) complex (also known as Polycomb repressive complex 2 (PRC2)). Otte et al. (2003) *Curr Opin Genet Dev* 13:448-54. Studies in *Drosophila* have demonstrated that the ESC-E(Z)/EED-EZH2 (i.e., PRC2) complexes have intrinsic histone methyltransferase activity. Although the compositions of the complexes isolated by different groups are slightly different, they generally contain EED, EZH2, SUZ12, and RbAp48 or *Drosophila* homologs thereof. However, a reconstituted complex comprising only EED, EZH2, and SUZ12 retains histone methyltransferase activity for lysine 27 of histone H3. U.S. Pat. No. 7,563,589.

Of the various proteins making up PRC2 complexes, EZH2 (Enhancer of Zeste Homolog 2) is the catalytic subunit. The catalytic site of EZH2 in turn is present within a SET domain, a highly conserved sequence motif (named after Su(var)3-9, Enhancer of Zeste, Trithorax) that is found in several chromatin-associated proteins, including members of both the Trithorax group and Polycomb group. SET domain is characteristic of all known histone lysine methyltransferases except the H3-K79 methyltransferase DOT1.

In addition to Hox gene silencing, PRC2-mediated histone H3-K27 methylation has been shown to participate in X-inactivation. Plath et al. (2003) *Science* 300:131-5; Silva et al. (2003) *Dev Cell* 4:481-95. Recruitment of the PRC2 complex to Xi and subsequent trimethylation on histone H3-K27 occurs during the initiation stage of X-inactivation and is dependent on Xist RNA. Furthermore, EZH2 and its associated histone H3-K27 methyltransferase activity were found to mark differentially the pluripotent epiblast cells and the differentiated trophectoderm, and consistent with a role of EZH2 in maintaining the epigenetic modification patterns of pluripotent epiblast cells, Cre-mediated deletion of EZH2 results in loss of histone H3-K27 methylation in the cells. Erhardt et al. (2003) *Development* 130:4235-48). Further, studies in prostate and breast cancer cell lines and tissues have revealed a strong correlation between the levels of EZH2 and SUZ12 and the invasiveness of these cancers, indicating that dysfunction of the PRC2 complex may contribute to cancer. Bracken et al. (2003) *EMBO J* 22:5323-35; Kirmizis et al. (2003) *Mol Cancer Ther* 2:113-21; Kleer et al. (2003) *Proc Natl Acad Sci USA* 100:11606-11; Varambally et al. (2002) *Nature* 419:624-9.

Recently, somatic mutations of tyrosine 641 (Y641C, Y641F, Y641N, Y641S and Y641H; sometimes also referred to as Y646C, Y646F, Y646N, Y646S and Y646H, respectively) of EZH2 were reported to be associated with follicular lymphoma (FL) and the germinal center B cell-like (GCB) subtype of diffuse large B-cell lymphoma (DLBCL). Morin et al. (2010) *Nat Genet.* 42:181-5. In all cases, occurrence of the mutant EZH2 gene was found to be heterozygous, and expression of both wild-type and mutant alleles was detected in the mutant samples profiled by transcriptome sequencing. It was also demonstrated that all of the mutant forms of EZH2 could be incorporated into the multi-protein PRC2 complex, but that the resulting complexes lacked the ability to catalyze methylation of the H3-K27 equivalent residue of a peptidic substrate. Hence, it was concluded that the disease-associated changes at Tyr641 of EZH2 resulted in loss of function with respect to EZH2-catalyzed H3-K27 methylation.

SUMMARY OF THE INVENTION

In one aspect, the present invention features substituted 6,5-fused bicyclic heteroaryl compound of Formula (I) below or a pharmaceutically acceptable salt or ester thereof.

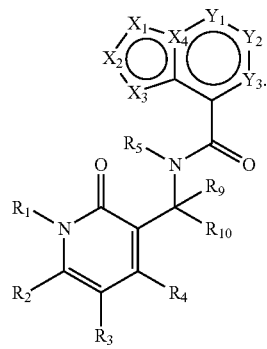

(I)

In this formula:

$X_1$ is $NR_7$ or $CR_7$;

$X_2$ is N, $NR_8$, $CR_8$, O, or S;

$X_3$ is $NR_8$, $CR_8$, O, or S;

$X_4$ is C or N;

$Y_1$ is N or CH;

$Y_2$ is N or $CR_6$;

$Y_3$ is N, or $CR_{11}$, and at least one of $X_1$, $X_2$, $X_3$, $X_4$, $Y_1$, $Y_2$, and $Y_3$ is N or $NR_7$;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, and $C_3$-$C_8$ cycloalkyl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 7-membered heterocycloalkyl, or 5 to 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl;

each $R_6$ independently is H, halo, $OR_a$, —$NR_aR_b$, —C(O)$R_a$, —C(O)O$R_a$, —C(O)N$R_aR_b$, —$NR_bC(O)R_a$, —S(O)$_2R_a$, —S(O)$_2NR_aR_b$, or $R_{S2}$, in which each of $R_a$ and $R_b$, independently is H or $R_{S3}$ and each of $R_{S2}$ and $R_{S3}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl; or $R_a$ and $R_b$, together with the N atom to which they are attached, form a 4 to 7-membered heterocycloalkyl ring having 0 or 1 additional heteroatoms to the N atom; and each of $R_{S2}$, $R_{S3}$, and the 4 to 7-membered heterocycloalkyl ring containing $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —($NR_cR_dR_{d'}$)$^+$$A^-$, —C(O)$R_c$, —C(O)O$R_c$, —C(O)N$R_cR_d$, —$NR_dC(O)R_c$, —$NR_dC(O)OR_c$, —S(O)$_2R_c$, —S(O)$_2NR_cR_d$, or $R_{S4}$, in which each of $R_c$ $R_d$, and $R_{d'}$, independently is H or $R_{S5}$, $A^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —S(O)$_2R_e$, —$NR_eR_f$, and —C(O)N$R_eR_f$, each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H;

each $R_7$ independently is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —C(O)$R_g$, —C(O)O$R_g$, —C(O)N$R_gR_h$, —C(O)N$R_gOR_h$, —$NR_gC(O)R_h$, —S(O)$_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, and each of $R_{S6}$ and $R_{S7}$ is optionally substituted with one or more -$Q_5$-$T_5$, wherein $Q_5$ is a bond, C(O), or $C_1$-$C_3$ alkyl linker, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, or 5 to 6-membered heteroaryl and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl except when $T_5$ is H, halo, hydroxyl, or cyano; or -$Q_5$-$T_5$ is oxo; provided that -$Q_4$-$T_4$ is not H; and each of $R_8$ and $R_{11}$, independently, is H, halo, hydroxyl, COOH, cyano, $R_{S8}$, $OR_{S8}$, or COO$R_{S8}$, in which $R_{S8}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino;

provided that the compound is not
N-((4,6-dimethyl-2-oxo-1,2-dihydropyridin-3-yl)methyl)-6-(2,5-dimethylthiophen-3-yl)-1-isopropyl-1H-pyrazolo[3,4-b]pyridine-4-carboxamide,
6-(2,3-dihydro-1,4-benzodioxin-6-yl)-N-[(1,2-dihydro-4,6-dimethyl-2-oxo-3-pyridinyl)methyl]-1-(1-methylethyl)-1H-pyrazolo[3,4-b]pyridine-4-carboxamide,
6-cyclopropyl-N-((4,6-dimethyl-2-oxo-1,2-dihydropyridin-3-yl)methyl)-1,3-dimethyl-1H-pyrazolo[3,4-b]pyridine-4-carboxamide,
N-[(1,2-dihydro-4,6-dimethyl-2-oxo-3-pyridinyl)methyl]-1,3,6-trimethyl-1H-pyrazolo[3,4-b]pyridine-4-carboxamide,
N-[(1,2-dihydro-4,6-dimethyl-2-oxo-3-pyridinyl)methyl]-6-methyl-1-(1-methylethyl)-1H-pyrazolo[3,4-b]pyridine-4-carboxamide, or
6-cyclopropyl-N-((4,6-dimethyl-2-oxo-1,2-dihydropyridin-3-yl)methyl)-1-isopropyl-1H-pyrazolo[3,4-b]pyridine-4-carboxamide.

In another aspect, the present invention features substituted 6,5-fused bicyclic heteroaryl compound of Formula (I) above or a pharmaceutically acceptable salt or ester thereof, in which $X_1$ is $NR_7$ or $CR_7$;
$X_2$ is N, $NR_8$, $CR_8$, O, or S;
$X_3$ is $NR_8$, $CR_8$, O, or S;
$X_4$ is C or N;
$Y_1$ is N or CH;
$Y_2$ is N or $CR_6$;
$Y_3$ is N, or $CR_{11}$, and at least one of $X_1$, $X_2$, $X_3$, $X_4$, $Y_1$, $Y_2$, and $Y_3$ is N or $NR_7$;
each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, and $C_3$-$C_8$ cycloalkyl;
each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 7-membered heterocycloalkyl, or 5 to 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{11}$, aryl, 4 to 7-membered heterocycloalkyl, and 5 to 6-membered heteroaryl;
each $R_6$ independently is H, halo, $OR_a$, —$NR_aR_b$, —C(O)$R_a$, —C(O)O$R_a$, —C(O)$NR_aR_b$, —$NR_bC(O)R_a$, —S(O)$_2R_a$, —S(O)$_2NR_aR_b$, or $R_{S2}$, in which $R_{S2}$ is $C_2$-$C_6$ alkenyl, $C_2$-$C_6$ alkynyl, $C_3$-$C_8$ cycloalkyl, $C_6$-$C_{11}$, aryl, 4 to 7-membered heterocycloalkyl, or 5 to 6-membered heteroaryl containing at least one N or O atom, each of $R_a$ and $R_b$, independently is H or $R_{S3}$, and $R_{S3}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl; or $R_a$ and $R_b$, together with the N atom to which they are attached, form a 4 to 7-membered heterocycloalkyl ring having 0 or 1 additional heteroatoms to the N atom; and each of $R_{S2}$, $R_{S3}$, and the 4 to 7-membered heterocycloalkyl ring containing $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$NR_cR_d$, —($NR_cR_dR_{d'}$)$^+$$A^-$, —C(O)$R_c$, —C(O)O$R_c$, —C(O)$NR_cR_d$, —$NR_dC(O)R_c$, —$NR_dC(O)OR_c$, —S(O)$_2R_c$, —S(O)$_2NR_cR_d$, or $R_{S4}$, in which each of $R_c$, $R_d$, and $R_{d'}$, independently is H or $R_{S5}$, $A^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —S(O)$_2R_e$, —$NR_eR_f$ and —C(O)$NR_eR_f$, each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H;
each $R_7$ independently is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —C(O)$R_g$, —C(O)O$R_g$, —C(O)$NR_gR_h$, —C(O)$NR_gOR_h$, —$NR_gC(O)R_h$, —S(O)$_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, and each of $R_{S6}$ and $R_{S7}$ is optionally substituted with one or more -$Q_5$-$T_5$, wherein $Q_5$ is a bond, C(O), or $C_1$-$C_3$ alkyl linker, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, or 5 to 6-membered heteroaryl and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl except when $T_5$ is H, halo, hydroxyl, or cyano; or -$Q_5$-$T_5$ is oxo; provided that -$Q_4$-$T_4$ is not H; and each of $R_8$ and $R_{11}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino In one subset of the compounds of Formula (I), at least one of $Y_1$, $Y_3$, and $X_4$ is N and when $X_4$ is C, $Y_1$ is N, $Y_2$ is $CR_6$, and $Y_3$ is $CR_{11}$, then $X_2$ is $CR_8$.

One subset of the compounds of Formula (I) includes those of Formula (Ia):

(Ia)

Another subset of the compounds of Formula (I) includes those of Formula (Ib).

(Ib)

The compounds of Formulae (I), (Ia), and (Ib) can include one or more of the following features:

$X_4$ is C.
$X_2$ is N or CH.
$X_3$ is $CR_8$.
$Y_3$ is $CR_{11}$.
$R_6$ is phenyl substituted with one or more -$Q_2$-$T_2$.
$R_6$ is 5 to 6-membered heteroaryl containing 1-3 additional heteroatoms selected from N, O, and S and optionally substituted with one or more -$Q_2$-$T_2$, provided that the heteroaryl is not thiophenyl.
$R_6$ is pyridinyl, pyrazolyl, pyrimidinyl, or furyl, each of which is optionally substituted with one or more -$Q_2$-$T_2$.
$R_6$ is halo, $C_1$-$C_3$ alkyl substituted with one or more -$Q_2$-$T_2$, $C_2$-$C_6$ alkenyl, $C_4$-$C_6$ cycloalkyl, C(O)H, $OR_a$, or —C(O)$R_a$, in which $R_a$ is $C_1$-$C_6$ alkyl or 4 to 7-membered heterocycloalkyl.
$R_6$ is 4 to 7-membered heterocycloalkyl optionally substituted with one or more -$Q_2$-$T_2$, in which -$Q_2$-$T_2$ is oxo or $Q_2$ is a bond and $T_2$ is —$OR_c$, —C(O)$R_c$, —C(O)$OR_c$, —S(O)$_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

$R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

$Q_3$ is a bond or $C_1$-$C_3$ alkyl linker and $T_3$ is selected from the group consisting of $C_1$-$C_3$ alkyl, halo, $OR_e$, —S(O)$_2R_e$, —$NR_eR_f$, and —C(O)$NR_eR_f$.

$R_7$ is $C_1$-$C_6$ alkyl, $C_2$-$C_4$ alkenyl, $C_4$-$C_6$ cycloalkyl, 4 to 7-membered heterocycloalkyl, or $C_6$-$C_{10}$ aryl, each optionally substituted with one or more -$Q_5$-$T_5$.

$R_7$ is cyclopentyl.
$R_7$ is unsubstituted $C_1$-$C_6$ alkyl.
$R_7$ is isopropyl.
$R_7$ is 5 to 6-membered heterocycloalkyl optionally substituted with one or more -$Q_5$-$T_5$.
$R_7$ is piperidinyl optionally substituted with one -$Q_5$-$T_5$.
$T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.
$Q_5$ is a bond and $T_5$ is $C_1$-$C_6$ alkyl, $C_3$-$C_8$ cycloalkyl, or 4 to 7-membered heterocycloalkyl.
$Q_5$ is CO and $T_5$ is $C_1$-$C_6$ alkyl, $C_1$-$C_6$ alkoxyl, $C_3$-$C_8$ cycloalkyl, or 4 to 7-membered heterocycloalkyl.
$Q_5$ is $C_1$-$C_3$ alkyl linker and $T_5$ is H or $C_6$-$C_{10}$ aryl.
$R_{11}$ is H.
Each of $R_2$ and $R_4$, independently is H or $C_1$-$C_6$ alkyl optionally substituted with amino, mono-$C_1$-$C_6$ alkylamino, di-$C_1$-$C_6$ alkylamino, or $C_6$-$C_{10}$ aryl.
Each of $R_2$ and $R_4$, independently is $C_1$-$C_3$ alkyl optionally substituted with $C_1$-$C_6$ alkoxyl.
Each of $R_2$ and $R_4$ is methyl.
$R_1$ is H.
$R_8$ is H, methyl, or ethyl.
$R_3$ is H.

is selected from the group consisting of indolyl, isoindolyl, indolizinyl, benzofuryl, isobenzofuryl, benzo[b]thienyl, benzoxazolyl, benzthiazolyl, benzimidazolyl, benzotriazolyl, benzoxadiazolyl, benzothiadiazolyl, purinyl, indazolyl, pyrrolopyridinyl, imidazopyridinyl, pyrazolopyridinyl, pyrrolopyrazinyl, imidazopyrazinyl, pyrazolopyrazinyl, pyrrolopyrimidinyl, pyrazolopyrimidinyl, pyrrolopyridazinyl, imidazopyridazinyl, pyrazolopyridazinyl, furopyridinyl, thienopyridinyl, furopyrazinyl, thienopyrazinyl, oxazolopyridinyl, isoxazolopyridinyl, thiazolopyridinyl, isothiazolopyridinyl, oxadiazolopyridinyl, thiadiazolopyridinyl, triazolopyridinyl, oxazolopyrazinyl, isoxazolopyrazinyl, thiazolopyrazinyl, isothiazolopyrazinyl, oxadiazolopyrazinyl, thiadiazolopyrazinyl, triazolopyrazinyl, furopyrimidinyl, thienopyrimidinyl, furopyridazinyl, thienopyridazinyl, oxazopyrimidinyl, isoxazolopyrimidinyl, thiazolopyrimidinyl, isothiazolopyrimidinyl, oxadiazolopyrimidinyl, thiadiazolopyrimidinyl, triazolopyrimidinyl, oxazolopyridazinyl, isoxazolopyridazinyl, thiazolopyridazinyl, isothiazolopyridazinyl, oxadiazolopyridazinyl, thiadiazolopyridazinyl, triazolopyridazinyl, and imidazotriazinyl.

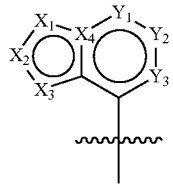

is selected from the group consisting of

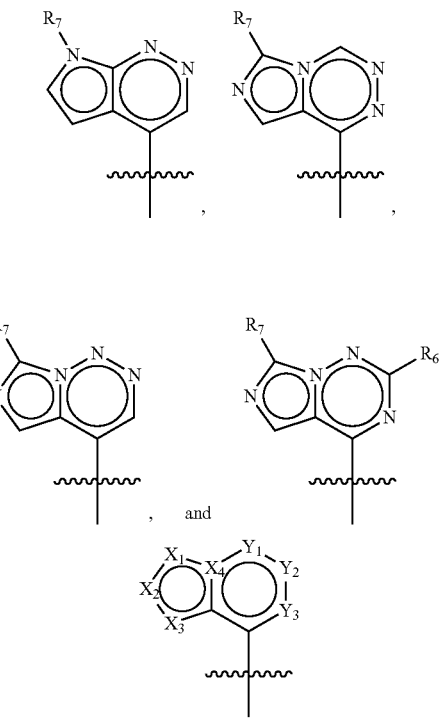

is selected from the group consisting of

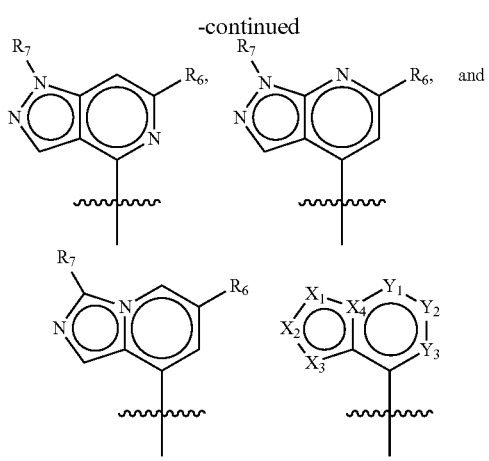

is selected from the group consisting of

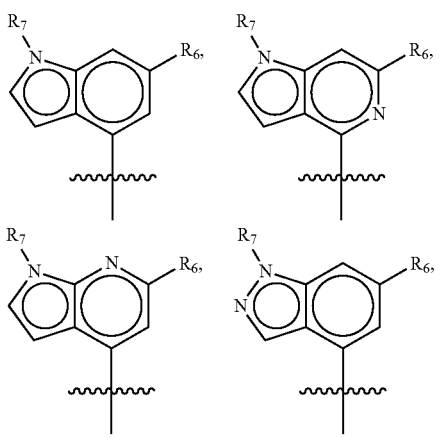

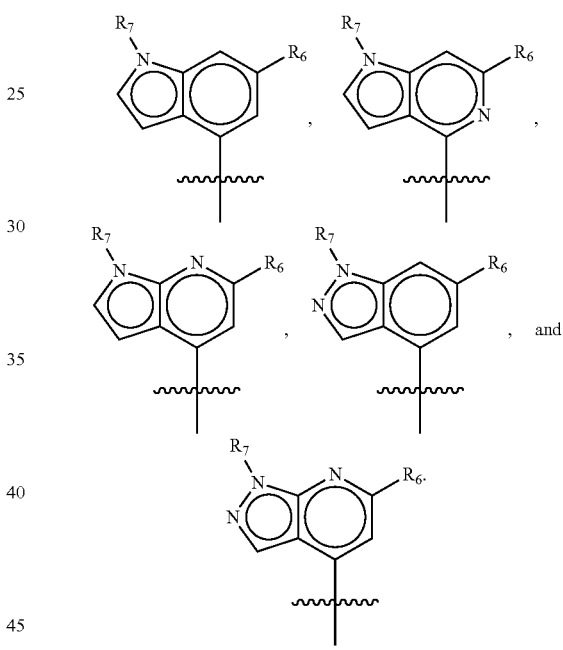

The present invention also provides pharmaceutical compositions comprising one or more pharmaceutically acceptable carriers and one or more compounds selected from those of Formulae (I), (Ia), and (Ib), N-((4,6-dimethyl-2-oxo-1,2-dihydropyridin-3-yl)methyl)-6-(2,5-dimethylthiophen-3-yl)-1-isopropyl-1H-pyrazolo[3,4-b]pyridine-4-carboxamide, 6-(2,3-dihydro-1,4-benzodioxin-6-yl)-N-[(1,2-dihydro-4,6-dimethyl-2-oxo-3-pyridinyl)methyl]-1-(1-methylethyl)-1H-pyrazolo[3,4-b]pyridine-4-carboxamide, 6-cyclopropyl-N-((4,6-dimethyl-2-oxo-1,2-dihydropyridin-3-yl)methyl)-1,3-dimethyl-1H-pyrazolo[3,4-b]pyridine-4-carboxamide, N-[(1,2-dihydro-4,6-dimethyl-2-oxo-3-pyridinyl)methyl]-1,3,6-trimethyl-1H-pyrazolo[3,4-b]pyridine-4-carboxamide, N-[(1,2-dihydro-4,6-dimethyl-2-oxo-3-pyridinyl)methyl]-6-methyl-1-(1-methylethyl)-1H-pyrazolo[3,4-b]pyridine-4-carboxamide, and 6-cyclopropyl-N-((4,6-dimethyl-2-oxo-1,2-dihydropyridin-3-yl)methyl)-1-isopropyl-1H-pyrazolo[3,4-b]pyridine-4-carboxamide.

Another aspect of this invention is a method of treating or preventing cancer. The method includes administering to a subject in need thereof a therapeutically effective amount of one or more compounds selected from those of Formulae (I), (Ia), and (Ib), N-((4,6-dimethyl-2-oxo-1,2-dihydropyridin-3-yl)methyl)-6-(2,5-dimethylthiophen-3-yl)-1-isopropyl-1H-pyrazolo[3,4-b]pyridine-4-carboxamide, 6-(2,3-dihydro-1,4-benzodioxin-6-yl)-N-[(1,2-dihydro-4,6-dimethyl-2-oxo-3-pyridinyl)methyl]-1-(1-methylethyl)-1H-pyrazolo[3,4-b]pyridine-4-carboxamide, 6-cyclopropyl-N-((4,6-dimethyl-2-oxo-1,2-dihydropyridin-3-yl)methyl)-1,3-dimethyl-1H-pyrazolo[3,4-b]pyridine-4-carboxamide, N-[(1,2-dihydro-4,6-dimethyl-2-oxo-3-pyridinyl)methyl]-1,3,6-trimethyl-1H-pyrazolo[3,4-b]pyridine-4-carboxamide, N-[(1,2-dihydro-4,6-dimethyl-2-oxo-3-pyridinyl)methyl]-6-methyl-1-(1-methylethyl)-1H-pyrazolo[3,4-b]pyridine-4-carboxamide, and 6-cyclopropyl-N-((4,6-dimethyl-2-oxo-1,2-dihydropyridin-3-yl)methyl)-1-isopropyl-1H-pyrazolo[3,4-b]pyridine-4-carboxamide.

For example, the method comprises the step of administering to a subject having a cancer with aberrant H3-K27 methylation effective amount of one or more compounds of Formula (I), (Ia), and/or (Ib), wherein the compound(s) inhibits histone methyltransferase activity of EZH2, thereby treating the cancer. Examples of aberrant H3-K27 methylation may include a global increase in and/or altered distribution of H3-K27 di or tri-methylation within the cancer cell chromatin.

For example, the cancer is selected from the group consisting of cancers that overexpress EZH2 or other PRC2 subunits, contain loss-of-function mutations in H3-K27 demethylases such as UTX, or overexpress accessory proteins such as PHF19/PCL3 capable of increasing and or mislocalizing EZH2 activity (see references in Sneeringer et al. *Proc Natl Acad Sci USA* 107(49):20980-5, 2010).

For example, the method comprises the step of administering to a subject having a cancer overexpressing EZH2 a therapeutically effective amount of one or more compounds of Formula (I), (Ia), and/or (Ib), wherein the compound(s) inhibits histone methyltransferase activity of EZH2, thereby treating the cancer.

For example, the method comprises the step of administering to a subject having a cancer with a loss-of-function mutation in the H3-K27 demethylase UTX a therapeutically effective amount of one or more compounds of Formula (I), (Ia), and/or (Ib), wherein the compound(s) inhibits histone methyltransferase activity of EZH2, thereby treating the cancer For example, the method comprises the step of administering to a subject having a cancer overexpressing an accessory component(s) of the PRC2, such as PHF19/PCL3, a therapeutically effective amount of one or more compounds of Formula (I), (Ia), and/or (Ib), wherein the compound(s) inhibits histone methyltransferase activity of EZH2, thereby treating the cancer In still another aspect, this invention relates to a method of modulating the activity of the wild-type EZH2, the catalytic subunit of the PRC2 complex which catalyzes the mono-through tri-methylation of lysine 27 on histone H3 (H3-K27). For example, the present invention relates to a method of inhibiting the activity of EZH2 in a cell.

In yet another aspect, this invention features to a method of inhibiting in a subject conversion of H3-K27 to trimethylated H3-K27. The method comprises administering to a subject a therapeutically effective amount of one or more of the compound of Formula (I), (Ia), or (Ib) to inhibit histone methyltransferase activity of EZH2, thereby inhibiting conversion of H3-K27 to trimethylated H3-K27 in the subject.

For example, the method comprises the step of administering to a subject having a cancer expressing a Y641 mutant of EZH2 a therapeutically effective amount of one or more compounds of Formula (I), (Ia), and/or (Ib), wherein the compound(s) inhibits histone methyltransferase activity of EZH2, thereby treating the cancer.

For example, the cancer is selected from the group consisting of follicular lymphoma and diffuse large B-cell lymphoma (DLBCL) of germinal center B cell-like (GCB) subtype.

For example, the method comprises the step of administering to a subject having a cancer expressing a Y641 mutant of EZH2 a therapeutically effective amount of one or more compounds of Formula (I), (Ia), and/or (Ib), wherein the compound(s) selectively inhibits histone methyltransferase activity of the Y641 mutant of EZH2, thereby treating the cancer.

For example, the method further comprises the steps of performing an assay to detect a Y641 mutant of EZH2 in a sample comprising cancer cells from a subject having a cancer.

In still another aspect, this invention relates to a method of modulating the activity of the wild-type and mutant histone methyltransferase EZH2, the catalytic subunit of the PRC2 complex which catalyzes the mono- through tri-methylation of lysine 27 on histone H3 (H3-K27). For example, the present invention relates to a method of inhibiting the activity of certain mutant forms of EZH2 in a cell. The mutant forms of EZH2 include a substitution of another amino acid residue for tyrosine 641 (Y641, also Tyr641) of wild-type EZH2. The method includes contacting the cell with an effective amount of one or more of the compound of Formula (I), (Ia), or (Ib).

In yet another aspect, this invention features to a method of inhibiting in a subject conversion of H3-K27 to trimethylated H3-K27. The method comprises administering to a subject expressing a Y641 mutant of EZH2 a therapeutically effective amount of one or more of the compound of Formula (I), (Ia), or (Ib) to inhibit histone methyltransferase activity of EZH2, thereby inhibiting conversion of H3-K27 to trimethylated H3-K27 in the subject. For example, the histone methyltransferase activity inhibited is that of the Y641 mutant of EZH2. For example, the compound of this invention selectively inhibits histone methyltransferase activity of the Y641 mutant of EZH2. For example, the Y641 mutant of EZH2 is selected from the group consisting of Y641C, Y641F, Y641H, Y641N, and Y641S.

The method of inhibiting in a subject conversion of H3-K27 to trimethylated H3-K27 may also comprise performing an assay to detect a Y641 mutant of EZH2 in a sample from a subject before administering to the subject expressing a Y641 mutant of EZH2 a therapeutically effective amount of one or more of the compound of Formula (I), (Ia), or (Ib). For example, performing the assay to detect the Y641 mutant of EZH2 includes whole-genome resequencing or target region resequencing that detects a nucleic acid encoding the Y641 mutant of EZH2. For example, performing the assay to detect the Y641 mutant of EZH2 includes contacting the sample with an antibody that binds specifically to a polypeptide or fragment thereof characteristic of the Y641 mutant of EZH2. For example, performing the assay to detect the Y641 mutant of EZH2 includes contacting the sample under highly stringent conditions with a nucleic acid probe that hybridizes to a nucleic acid encoding a polypeptide or fragment thereof characteristic of the Y641 mutant of EZH2.

Further, the invention also relates to a method of identifying an inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 (e.g., formation of trimethylated H3-K27) in the histone substrate, thereby identifying the test compound as an inhibitor of the Y641 mutant of EZH2 when methylation of H3-K27 (e.g., formation of trimethylated H3-K27) in the presence of the test compound is less than methylation of H3-K27 (e.g., formation of trimethylated H3-K27) in the absence of the test compound.

In one embodiment, performing the assay to detect methylation of H3-K27 in the histone substrate comprises measuring incorporation of labeled methyl groups.

In one embodiment, the labeled methyl groups are isotopically labeled methyl groups.

In one embodiment, performing the assay to detect methylation of H3-K27 in the histone substrate comprises contacting the histone substrate with an antibody that binds specifically to trimethylated H3-K27.

Also within the scope of the invention is a method of identifying a selective inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the Y641 mutant of EZH2 and the test compound (M+) to (b) trimethylation with the Y641 mutant of EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the Y641 mutant of EZH2 when the ratio (a)/(b) is less than the ratio (c)/(d).

The present invention further provides a method of identifying a subject as a candidate for treatment with one or more compounds of the invention. The method comprises the steps of performing an assay to detect a Y641 mutant of EZH2 in a sample from a subject; and identifying a subject expressing a Y641 mutant of EZH2 as a candidate for treatment with one or more compounds of the invention, wherein the compound(s) inhibits histone methyltransferase activity of EZH2.

Still another aspect of the invention is a method of inhibiting conversion of H3-K27 to trimethylated H3-K27. The method comprises the step of contacting a Y641 mutant of EZH2 with a histone substrate comprising H3-K27 and an effective amount of a compound of the present invention, wherein the compound inhibits histone methyltransferase activity of EZH2, thereby inhibiting conversion of H3-K27 to trimethylated H3-K27.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

The present invention provides novel substituted 6,5-fused bicyclic heteroaryl compounds, synthetic methods for making the compounds, pharmaceutical compositions containing them and various uses of the compounds.

1. Substituted 6,5-Fused Bicyclic Heteroaryl Compounds

The present invention provides the compounds of Formula (I):

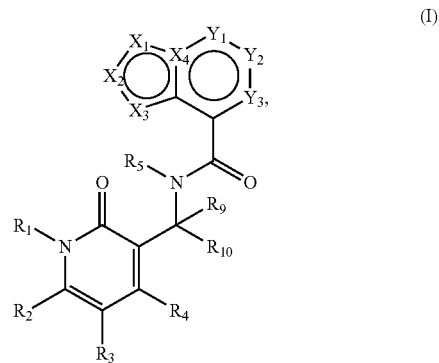

or a pharmaceutically acceptable salt or ester thereof. In this formula:

$X_1$ is $NR_7$ or $CR_7$;
$X_2$ is N, $NR_8$, $CR_8$, O, or S;
$X_3$ is $NR_8$, $CR_8$, O, or S;
$X_4$ is C or N;
$Y_1$ is N or CH;
$Y_2$ is N or $CR_6$;
$Y_3$ is N, or $CR_{11}$, and at least one of $X_1$, $X_2$, $X_3$, $X_4$, $Y_1$, $Y_2$, and $Y_3$ is N or $NR_7$;
each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, and $C_3$-$C_8$ cycloalkyl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 7-membered heterocycloalkyl, or 5 to 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{11}$, aryl, 4 to 7-membered heterocycloalkyl, and 5 to 6-membered heteroaryl;

each $R_6$ independently is H, halo, $OR_a$, —$NR_aR_b$, —C(O)$R_a$, —C(O)O$R_a$, —C(O)N$R_aR_b$, —$NR_bC(O)R_a$, —$S(O)_2R_a$, —$S(O)_2NR_aR_b$, or $R_{S2}$, in which each of $R_a$ and $R_b$, independently is H or $R_{S3}$ and each of $R_{S2}$ and $R_{S3}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl; or $R_a$ and $R_b$, together with the N atom to which they are attached, form a 4 to 7-membered heterocycloalkyl ring having 0 or 1 additional heteroatoms to the N atom; and each of $R_{S2}$, $R_{S3}$, and the 4 to 7-membered heterocycloalkyl ring containing $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —$(NR_cR_dR_{d'})^+A^-$, —C(O)$R_c$, —C(O)O$R_c$, —C(O)N$R_cR_d$, —$NR_dC(O)R_c$, —$NR_dC(O)OR_c$, —$S(O)_2R_c$, —$S(O)_2NR_cR_d$, or $R_{S4}$, in which each of $R_c$, $R_d$, and $R_{d'}$, independently is H or $R_{S5}$, $A^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —$S(O)_2R_e$, —$NR_eR_f$ and —C(O)N$R_eR_f$ each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H;

each $R_7$ independently is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —C(O)$R_g$, —C(O)O$R_g$, —C(O)N$R_gR_h$, —C(O)N$R_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, and each of $R_{S6}$ and $R_{S7}$ is optionally substituted with one or more -$Q_5$-$T_5$, wherein $Q_5$ is a bond, C(O), or $C_1$-$C_3$ alkyl linker, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, or 5 to 6-membered heteroaryl and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl except when $T_5$ is H, halo, hydroxyl, or cyano; or -$Q_5$-$T_5$ is oxo; provided that -$Q_4$-$T_4$ is not H; and each of $R_8$ and $R_{11}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino;

provided that the compound is not

N-((4,6-dimethyl-2-oxo-1,2-dihydropyridin-3-yl)methyl)-6-(2,5-dimethylthiophen-3-yl)-1-isopropyl-1H-pyrazolo[3,4-b]pyridine-4-carboxamide, 6-(2,3-dihydro-1,4-benzodioxin-6-yl)-N-[(1,2-dihydro-4,6-dimethyl-2-oxo-3-pyridinyl)methyl]-1-(1-methylethyl)-1H-pyrazolo[3,4-b]pyridine-4-carboxamide, 6-cyclopropyl-N-((4,6-dimethyl-2-oxo-1,2-dihydropyridin-3-yl)methyl)-1,3-dimethyl-1H-pyrazolo[3,4-b]pyridine-4-carboxamide, N-[(1,2-dihydro-4,6-dimethyl-2-oxo-3-pyridinyl)methyl]-1,3,6-trimethyl-1H-pyrazolo[3,4-b]pyridine-4-carboxamide, N-[(1,2-dihydro-4,6-dimethyl-2-oxo-3-pyridinyl)methyl]-6-methyl-1-(1-methylethyl)-1H-pyrazolo[3,4-b]pyridine-4-carboxamide, or 6-cyclopropyl-N-((4,6-dimethyl-2-oxo-1,2-dihydropyridin-3-yl)methyl)-1-isopropyl-1H-pyrazolo[3,4-b]pyridine-4-carboxamide.

For example, at least one of $Y_1$, $Y_3$, and $X_4$ is N and when $X_4$ is C, $Y_1$ is N, $Y_2$ is $CR_6$, and $Y_3$ is $CR_{11}$ then $X_2$ is $CR_8$.

For example,

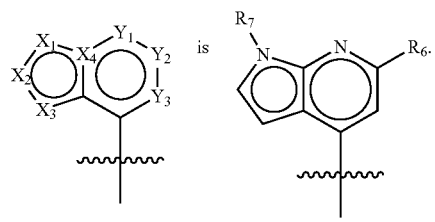

For example, $X_4$ is C.
For example, $X_2$ is N or CH.
For example, $X_3$ is $CR_8$.

For example, $Y_3$ is $CR_{11}$.

For example, $R_6$ is phenyl substituted with one or more -$Q_2$-$T_2$.

For example, $R_6$ is 5 to 6-membered heteroaryl containing 1-3 additional heteroatoms selected from N, O, and S and optionally substituted with one or more -$Q_2$-$T_2$, provided that the heteroaryl is not thiophenyl.

For example, $R_6$ is pyridinyl, pyrazolyl, pyrimidinyl, or furyl, each of which is optionally substituted with one or more -$Q_2$-$T_2$.

For example, $R_6$ is halo (e.g., fluorine, chlorine, bromine, and iodine).

For example, $R_6$ is $C_1$-$C_3$ alkyl substituted with one or more -$Q_2$-$T_2$.

For example, $R_6$ is $C_2$-$C_6$ alkenyl or $C_4$-$C_6$ cycloalkyl each optionally substituted with one or more -$Q_2$-$T_2$.

For example, $R_6$ is C(O)H.

For example, $R_6$ is $OR_a$ or —C(O)$R_a$.

For example, $R_a$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like), which is optionally substituted with one or more -$Q_2$-$T_2$.

For example, $R_6$ is —$NR_aR_b$, —C(O)$R_a$, —C(O)$OR_a$, —C(O)$NR_aR_b$, —$NR_bC(O)R_a$, —S(O)$_2R_a$, or —S(O)$_2NR_aR_b$.

For example, each of $R_a$ and $R_b$, independently is H or $C_1$-$C_6$ alkyl optionally substituted with one or more -$Q_2$-$T_2$ For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, and morpholinyl, and the like) and the ring is optionally substituted with one or more -$Q_2$-$T_2$.

For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_2$-$T_2$.

For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —C(O)$R_c$, —C(O)$OR_c$, —S(O)$_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_2$-$T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_3$-$T_3$.

For example, $T_2$ is —$OR_c$, —$NR_cR_d$, —C(O)$R_c$, —C(O)$OR_c$, or —S(O)$_2R_c$.

For example, $T_2$ is —($NR_cR_dR_{d'}$)$^+A^-$, —C(O)$NR_cR_d$, —$NR_dC(O)R_c$, —$NR_dC(O)OR_c$, or —S(O)$_2NR_cR_d$.

For example, $Q_2$ is a bond or methyl linker and $T_2$ is H, halo, —$OR_c$, —$NR_cR_d$, —($NR_cR_dR_{d'}$)$^+A^-$, or —S(O)$_2NR_cR_d$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like), which is optionally substituted with one or more -$Q_3$-$T_3$.

For example, each of $R_c$ and $R_d$, independently is H or $C_1$-$C_6$ alkyl optionally substituted with one or more -$Q_3$-$T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, and morpholinyl, and the like) and the ring is optionally substituted with one or more -$Q_3$-$T_3$.

For example, $Q_2$ is a bond and $T_2$ is —$OR_c$, —$NR_cR_d$, —C(O)$R_c$, —C(O)$OR_c$, —S(O)$_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $COOR_e$, —S(O)$_2R_e$, —$NR_eR_f$, or —C(O)$NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, —S(O)$_2R_e$, —$NR_eR_f$, and —C(O)$NR_eR_f$.

For example, $R_e$ is H.

For example, $R_f$ is H.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_5$-$T_5$.

For example, $R_7$ is cyclopentyl.

For example, $R_7$ is isopropyl.

For example, $R_7$ is 5 to 6-membered heterocycloalkyl optionally substituted with one or more $-Q_5-T_5$.

For example, $R_7$ is piperidinyl optionally substituted with one $-Q_5-T_5$.

For example, $-Q_5-T_5$ is oxo.

For example, $T_4$ is 4 to 7-membered heterocycloalkyl or $C_3-C_8$ cycloalkyl and one or more $-Q_5-T_5$ are oxo.

For example, $T_5$ is H, halo, $C_1-C_6$ alkyl, $C_1-C_6$ alkoxyl, $C_3-C_8$ cycloalkyl, $C_6-C_{10}$ aryl, or 4 to 7-membered heterocycloalkyl.

For example, $Q_5$ is a bond and $T_5$ is $C_1-C_6$ alkyl, $C_3-C_8$ cycloalkyl, or 4 to 7-membered heterocycloalkyl.

For example, $Q_5$ is CO and $T_5$ is $C_1-C_6$ alkyl, $C_1-C_6$ alkoxyl, $C_3-C_8$ cycloalkyl, or 4 to 7-membered heterocycloalkyl.

For example, $T_5$ is $C_1-C_6$ alkyl optionally substituted with halo, hydroxyl, cyano, $C_1-C_6$ alkoxyl, amino, mono-$C_1-C_6$ alkylamino, di-$C_1-C_6$ alkylamino, or $C_3-C_8$ cycloalkyl.

For example, $Q_5$ is $C_1-C_3$ alkyl linker and $T_5$ is H or $C_6-C_{10}$ aryl.

For example, $R_{11}$ is H.

For example, each of $R_2$ and $R_4$, independently, is H or $C_1-C_6$ alkyl optionally substituted with amino, mono-$C_1-C_6$ alkylamino, di-$C_1-C_6$ alkylamino, or $C_6-C_{10}$ aryl.

For example, each of $R_2$ and $R_4$, independently is $C_1-C_3$ alkyl optionally substituted with $C_1-C_6$ alkoxyl.

For example, each of $R_2$ and $R_4$ is methyl.

For example, $R_1$ is H.

For example, $R_8$ is H, methyl, or ethyl.

For example, $R_3$ is H.

For example, each of $R_5$, $R_9$, and $R_{10}$ is H.

For example, $A^-$ is $Br^-$.

For example,

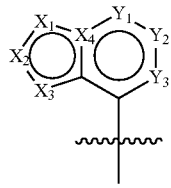

is selected from the group consisting of indolyl, isoindolyl, indolizinyl, benzofuryl, isobenzofuryl, benzo[b]thienyl, benzoxazolyl, benzthiazolyl, benzimidazolyl, benzotriazolyl, benzoxadiazolyl, benzothiadiazolyl, purinyl, indazolyl, pyrrolopyridinyl, imidazopyridinyl, pyrazolopyridinyl, pyrrolopyrazinyl, imidazopyrazinyl, pyrazolopyrazinyl, pyrrolopyrimidinyl, pyrazolopyrimidinyl, pyrrolopyridazinyl, imidazopyridazinyl, pyrazolopyridazinyl, furopyridinyl, thienopyridinyl, furopyrazinyl, thienopyrazinyl, oxazolopyridinyl, isoxazolopyridinyl, thiazolopyridinyl, isothiazolopyridinyl, oxadiazolopyridinyl, thiadiazolopyridinyl, triazolopyridinyl, oxazolopyrazinyl, isoxazolopyrazinyl, thiazolopyrazinyl, isothiazolopyrazinyl, oxadiazolopyrazinyl, thiadiazolopyrazinyl, triazolopyrazinyl, furopyrimidinyl, thienopyrimidinyl, furopyridazinyl, thienopyridazinyl, oxazolopyrimidinyl, isoxazolopyrimidinyl, thiazolopyrimidinyl, isothiazolopyrimidinyl, oxadiazolopyrimidinyl, thiadiazolopyrimidinyl, triazolopyrimidinyl, oxazolopyridazinyl, isoxazolopyridazinyl, thiazolopyridazinyl, isothiazolopyridazinyl, oxadiazolopyridazinyl, thiadiazolopyridazinyl, triazolopyridazinyl, and imidazotriazinyl.

For example,

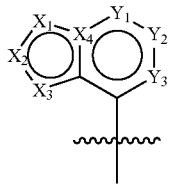

is selected from the group consisting of

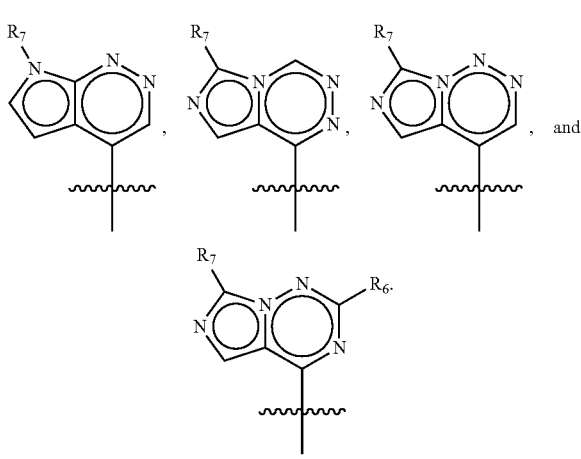

For example,

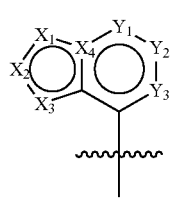

is selected from the group consisting of

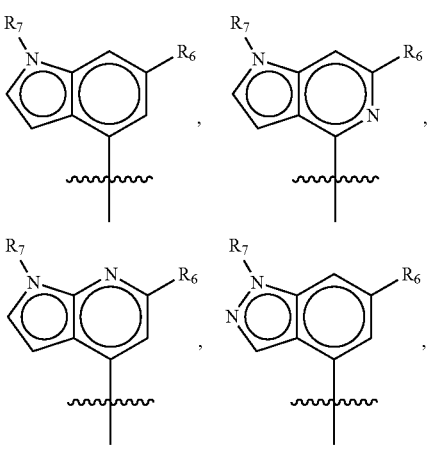

-continued

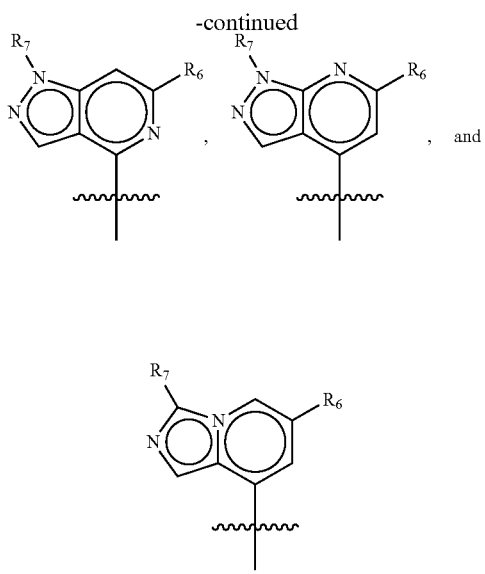

For example,

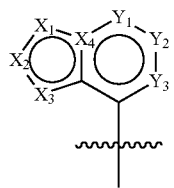

is selected from the group consisting of

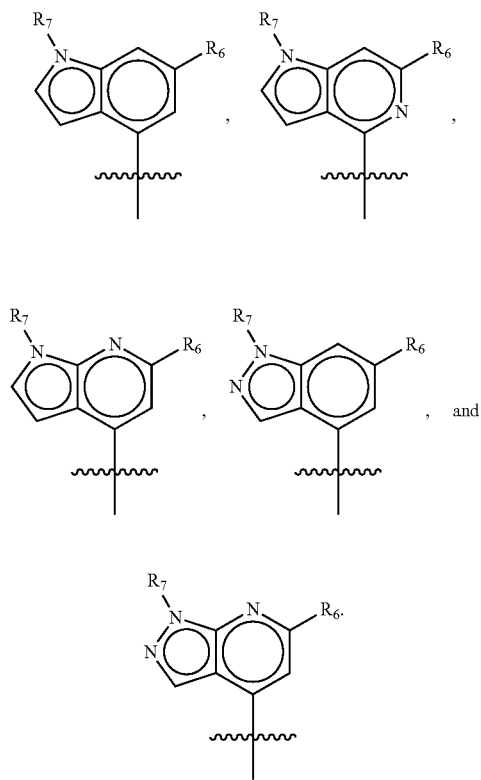

In another aspect, the present invention features substituted 6,5-fused bicyclic heteroaryl compound of Formula (I):

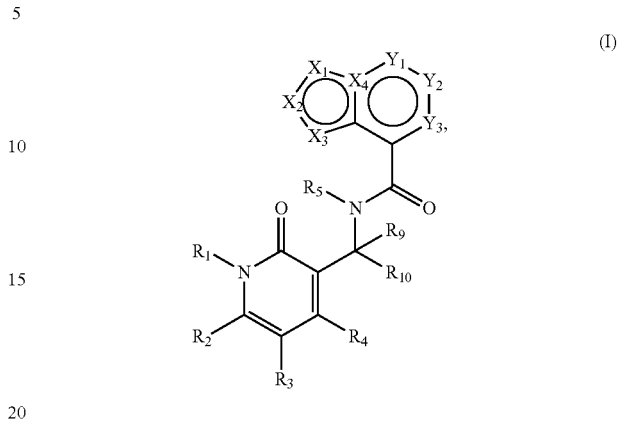

or a pharmaceutically acceptable salt or ester thereof, in which $X_1$ is $NR_7$ or $CR_7$;

$X_2$ is N, $NR_8$, $CR_8$, O, or S;

$X_3$ is $NR_8$, $CR_8$, O, or S;

$X_4$ is C or N;

$Y_1$ is N or CH;

$Y_2$ is N or $CR_6$;

$Y_3$ is N, or $CR_{11}$, and at least one of $X_1$, $X_2$, $X_3$, $X_4$, $Y_1$, $Y_2$, and $Y_3$ is N or $NR_7$;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, and $C_3$-$C_8$ cycloalkyl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 7-membered heterocycloalkyl, or 5 to 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{11}$, aryl, 4 to 7-membered heterocycloalkyl, and 5 to 6-membered heteroaryl;

each $R_6$ independently is H, halo, $OR_a$, —$NR_aR_b$, —C(O)$R_a$, —C(O)$OR_a$, —C(O)$NR_aR_b$, —$NR_bC(O)R_a$, —S(O)$_2R_a$, —S(O)$_2NR_aR_b$, or $R_{S2}$, in which $R_{S2}$ is $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl containing at least one N or O atom, each of $R_a$ and $R_b$, independently is H or $R_{S3}$, and $R_{S3}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl; or $R_a$ and $R_b$, together with the N atom to which they are attached, form a 4 to 7-membered heterocycloalkyl ring having 0 or 1 additional heteroatoms to the N atom; and each of $R_{S2}$, $R_{S3}$, and the 4 to 7-membered heterocycloalkyl ring containing $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$NR_cR_d$, —$(NR_cR_dR_{d'})^+A^-$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S4}$, in which each of $R_c$, $R_d$, and $R_{d'}$, independently is H or $R_{S5}$, $A^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —$S(O)_2R_e$, —$NR_eR_f$, and —$C(O)NR_eR_f$, each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H;

each $R_7$ independently is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —$C(O)R_g$, —$C(O)OR_g$, —$C(O)NR_gR_h$, —$C(O)NR_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, and each of $R_{S6}$ and $R_{S7}$ is optionally substituted with one or more -$Q_5$-$T_5$, wherein $Q_5$ is a bond, C(O), or $C_1$-$C_3$ alkyl linker, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, or 5 to 6-membered heteroaryl and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl except when T5 is H, halo, hydroxyl, or cyano; or -$Q_5$-$T_5$ is oxo; provided that -$Q_4$-$T_4$ is not H; and each of $R_8$ and $R_{11}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

For example, $X_4$ is C.

For example, $X_2$ is N or CH.

For example, $X_3$ is $CR_8$.

For example, $Y_3$ is $CR_{11}$.

For example, $R_6$ is phenyl substituted with one or more -$Q_2$-$T_2$.

For example, $R_6$ is 5 to 6-membered heteroaryl containing at least one N or O atom and is optionally substituted with one or more -$Q_2$-$T_2$.

For example, $R_6$ is pyridinyl, pyrazolyl, pyrimidinyl, or furyl, each of which is optionally substituted with one or more -$Q_2$-$T_2$.

For example, $R_6$ is halo (e.g., fluorine, chlorine, bromine, and iodine).

For example, $R_6$ is $C_2$-$C_6$ alkenyl optionally substituted with one or more -$Q_2$-$T_2$.

For example, $R_6$ is C(O)H.

For example, $R_6$ is $OR_a$ or —$C(O)R_a$.

For example, $R_a$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like), which is optionally substituted with one or more -$Q_2$-$T_2$.

For example, $R_6$ is —$NR_aR_b$, —$C(O)R_a$, —$C(O)OR_a$, —$C(O)NR_aR_b$, —$NR_bC(O)R_a$, —$S(O)_2R_a$, or —$S(O)_2NR_aR_b$.

For example, each of $R_a$ and $R_b$, independently is H or $C_1$-$C_6$ alkyl optionally substituted with one or more -$Q_2$-$T_2$ For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, and morpholinyl, and the like) and the ring is optionally substituted with one or more -$Q_2$-$T_2$ For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_2$-$T_2$.

For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —$C(O)R_c$, —$C(O)OR_c$, —$S(O)_2R_c$ $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_2$-$T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_3$-$T_3$.

For example, $T_2$ is —$OR_c$, —$NR_cR_d$, —$C(O)R_c$, —$C(O)OR_c$, or —$S(O)_2R_c$.

For example, $T_2$ is —$(NR_cR_dR_{d'})^+A^-$, —$C(O)NR_cR_d$, —$NR_dC(O)R_c$, —$NR_dC(O)OR_c$, or —$S(O)_2NR_cR_d$.

For example, $Q_2$ is a bond or methyl linker and $T_2$ is H, halo, —$OR_c$, —$NR_cR_d$, —$(NR_cR_dR_{d'})^+A^-$, or —$S(O)_2NR_cR_d$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like), which is optionally substituted with one or more -$Q_3$-$T_3$.

For example, each of $R_c$ and $R_d$, independently is H or $C_1$-$C_6$ alkyl optionally substituted with one or more -$Q_3$-$T_3$ For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, and morpholinyl, and the like) and the ring is optionally substituted with one or more -$Q_3$-$T_3$.

For example, $Q_2$ is a bond and $T_2$ is —$OR_c$, —$NR_cR_d$, —$C(O)R_c$, —$C(O)OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $COOR_e$, —$S(O)_2R_e$, —$NR_eR_f$, or —$C(O)NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, —$S(O)_2R_e$, —$NR_eR_f$, and —$C(O)NR_eR_f$.

For example, $R_e$ is H.

For example, $R_f$ is H.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_5$-$T_5$.

For example, $R_7$ is cyclopentyl.

For example, $R_7$ is isopropyl.

For example, $R_7$ is 5 to 6-membered heterocycloalkyl optionally substituted with one or more -$Q_5$-$T_5$.

For example, $R_7$ is piperidinyl optionally substituted with one -$Q_5$-$T_5$.

For example, -$Q_5$-$T_5$ is oxo.

For example, $T_4$ is 4 to 7-membered heterocycloalkyl or $C_3$-$C_8$ cycloalkyl and one or more -$Q_5$-$T_5$ are oxo.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond and $T_5$ is $C_1$-$C_6$ alkyl, $C_3$-$C_8$ cycloalkyl, or 4 to 7-membered heterocycloalkyl.

For example, $Q_5$ is CO and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $R_{11}$ is H.

For example, each of $R_2$ and $R_4$, independently, is H or $C_1$-$C_6$ alkyl optionally substituted with amino, mono-$C_1$-$C_6$ alkylamino, di-$C_1$-$C_6$ alkylamino, or $C_6$-$C_{10}$ aryl.

For example, each of $R_2$ and $R_4$, independently is $C_1$-$C_3$ alkyl optionally substituted with $C_1$-$C_6$ alkoxyl.

For example, each of $R_2$ and $R_4$ is methyl.

For example, $R_1$ is H.

For example, $R_8$ is H, methyl, or ethyl.

For example, $R_3$ is H.

For example, each of $R_5$, $R_9$, and $R_{10}$ is H.

For example, $A^-$ is $Br^-$.

For example,

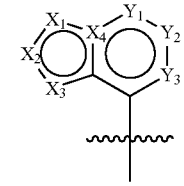

is selected from the group consisting of indolyl, isoindolyl, indolizinyl, benzofuryl, isobenzofuryl, benzo[b]thienyl, benzoxazolyl, benzthiazolyl, benzimidazolyl, benzotriazolyl, benzoxadiazolyl, benzothiadiazolyl, purinyl, indazolyl, pyrrolopyridinyl, imidazopyridinyl, pyrazolopyridinyl, pyrrolopyrazinyl, imidazopyrazinyl, pyrazolopyrazinyl, pyrrolopyrimidinyl, pyrazolopyrimidinyl, pyrrolopyridazinyl, imidazopyridazinyl, pyrazolopyridazinyl, furopyridinyl, thienopyridinyl, furopyrazinyl, thienopyrazinyl, oxazolopyridinyl, isoxazolopyridinyl, thiazolopyridinyl, isothiazolopyridinyl, oxadiazolopyridinyl, thiadiazolopyridinyl, triazolopyridinyl, oxazolopyrazinyl, isoxazolopyrazinyl, thiazolopyrazinyl, isothiazolopyrazinyl, oxadiazolopyrazinyl, thiadiazolopyrazinyl, triazolopyrazinyl, furopyrimidinyl, thienopyrimidinyl, furopyridazinyl, thienopyridazinyl, oxazolopyrimidinyl, isoxazolopyrimidinyl, thiazolopyrimidinyl, isothiazolopyrimidinyl, oxadiazolopyrimidinyl, thiadiazolopyrimidinyl, triazolopyrimidinyl, oxazolopyridazinyl, isoxazolopyridazinyl, thiazolopyridazinyl, isothiazolopyridazinyl, oxadiazolopyridazinyl, thiadiazolopyridazinyl, triazolopyridazinyl, and imidazotriazinyl.
For example,
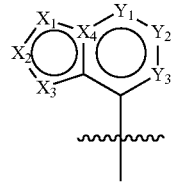
is selected from the group consisting of
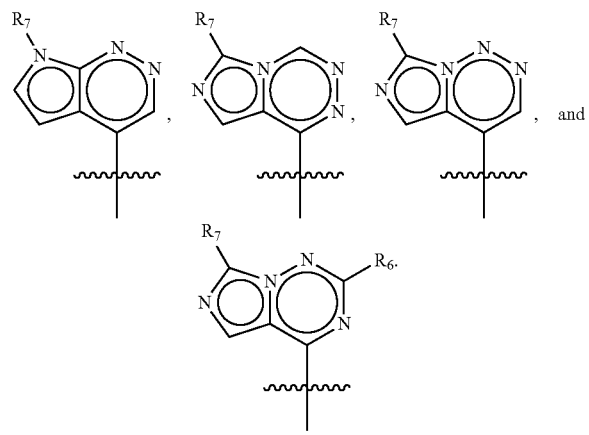
For example,
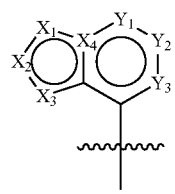
is selected from the group consisting of
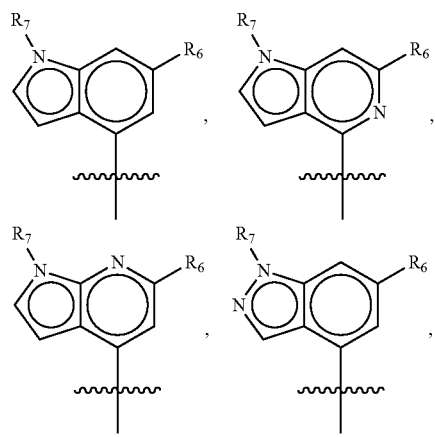
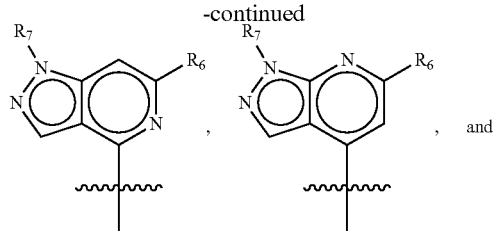
For example,
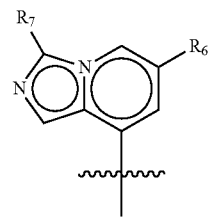
is selected from the group consisting of
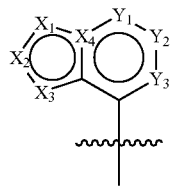
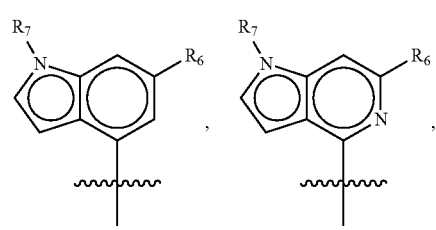
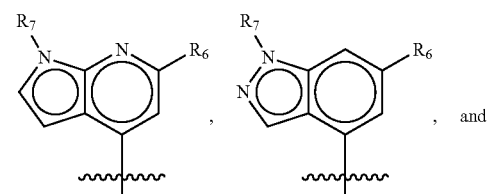
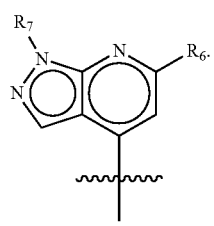

The present invention provides the compounds of Formula (Ia)

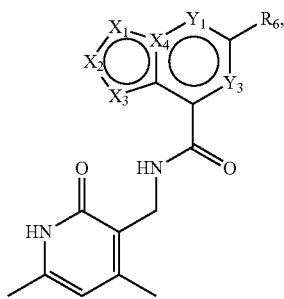

(Ia)

or a pharmaceutically acceptable salt or ester thereof, wherein:

$X_1$ is $NR_7$ or $CR_7$;
$X_2$ is N, $NR_8$, $CR_8$, O, or S;
$X_3$ is $NR_8$, $CR_8$, O, or S;
$X_4$ is C or N;
$Y_1$ is N or CH;
$Y_2$ is N or $CR_6$;
$Y_3$ is N, or $CR_{11}$, and at least one of $X_1$, $X_2$, $X_3$, $X_4$, $Y_1$, $Y_2$, and $Y_3$ is N or $NR_7$;

each $R_6$ independently is H, halo, $OR_a$, —$NR_aR_b$, —C(O)$R_a$, —C(O)$OR_a$, —C(O)$NR_aR_b$, —$NR_bC(O)R_a$, —S(O)$_2R_a$, —S(O)$_2NR_aR_b$, or $R_{S2}$, in which each of $R_a$ and $R_b$, independently is H or $R_{S3}$ and each of $R_{S2}$ and $R_{S3}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl; or $R_a$ and $R_b$, together with the N atom to which they are attached, form a 4 to 7-membered heterocycloalkyl ring having 0 or 1 additional heteroatoms to the N atom; and each of $R_{S2}$, $R_{S3}$, and the 4 to 7-membered heterocycloalkyl ring containing $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —($NR_cR_dR_{d'}$)$^+$A$^-$, —C(O)$R_c$, —C(O)$OR_c$, —C(O)$NR_cR_d$, —$NR_dC(O)R_c$, —$NR_dC(O)OR_c$, —S(O)$_2R_c$, —S(O)$_2NR_cR_d$, or $R_{S4}$, in which each of $R_c$ $R_d$, and $R_{d'}$, independently is H or $R_{S5}$, A$^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —S(O)$_2R_e$, —$NR_eR_f$ and —C(O)$NR_eR_f$ each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H; or each $R_6$ independently is H, halo, $OR_a$, —$NR_aR_b$, —C(O)$R_a$, —C(O)$OR_a$, —C(O)$NR_aR_b$, —$NR_bC(O)R_a$, —S(O)$_2R_a$, —S(O)$_2NR_aR_b$, or $R_{S2}$, in which $R_{S2}$ is $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl containing at least one N or O atom, each of $R_a$ and $R_b$, independently is H or $R_{S3}$, and $R_{S3}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl; or $R_a$ and $R_b$, together with the N atom to which they are attached, form a 4 to 7-membered heterocycloalkyl ring having 0 or 1 additional heteroatoms to the N atom; and each of $R_{S2}$, $R_{S3}$, and the 4 to 7-membered heterocycloalkyl ring containing $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$NR_cR_d$, —($NR_cR_dR_{d'}$)$^+$A$^-$, —C(O)$R_c$, —C(O)$OR_c$, —C(O)$NR_cR_d$, —$NR_dC(O)R_c$, —$NR_dC(O)OR_c$, —S(O)$_2R_c$, —S(O)$_2NR_cR_d$, or $R_{S4}$, in which each of $R_c$ $R_d$, and $R_{d'}$, independently is H or $R_{S5}$, A$^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —S(O)$_2R_e$, —$NR_eR_f$ and —C(O)$NR_eR_f$ each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H;

each $R_7$ independently is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —C(O)$R_g$, —C(O)$OR_g$, —C(O)$NR_gR_h$, —C(O)$NR_gOR_h$, —$NR_gC(O)R_h$, —S(O)$_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, and each of $R_{S6}$ and $R_{S7}$ is optionally substituted with one or more -$Q_5$-$T_5$, wherein $Q_5$ is a bond, C(O), or $C_1$-$C_3$ alkyl linker, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, or 5 to 6-membered heteroaryl and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl except when $T_5$ is H, halo, hydroxyl, or cyano; or -$Q_5$-$T_5$ is oxo; provided that -$Q_4$-$T_4$ is not H; and each of $R_8$ and $R_{11}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino;

provided that the compound is not

N-((4,6-dimethyl-2-oxo-1,2-dihydropyridin-3-yl)methyl)-6-(2,5-dimethylthiophen-3-yl)-1-isopropyl-1H-pyrazolo[3,4-b]pyridine-4-carboxamide, 6-(2,3-dihydro-1,4-benzodioxin-6-yl)-N-[(1,2-dihydro-4,6-dimethyl-2-oxo-3-pyridinyl)methyl]-1-(1-methylethyl)-1H-pyrazolo[3,4-b]pyridine-4-carboxamide, 6-cyclopropyl-N-((4,6-dimethyl-2-oxo-1,2-dihydropyridin-3-yl)methyl)-1,3-dimethyl-1H-pyrazolo[3,4-b]pyridine-4-carboxamide, N-[(1,2-dihydro-4,6-dimethyl-2-oxo-3-pyridinyl)methyl]-1,3,6-trimethyl-1H-pyrazolo[3,4-b]pyridine-4-carboxamide, N-[(1,2-dihydro-4,6-dimethyl-2-oxo-3-pyridinyl)methyl]-6-methyl-1-(1-methylethyl)-1H-pyrazolo[3,4-b]pyridine-4-carboxamide, or 6-cyclopropyl-N-((4,6-dimethyl-2-oxo-1,2-dihydropyridin-3-yl)methyl)-1-isopropyl-1H-pyrazolo[3,4-b]pyridine-4-carboxamide.

For example, $X_4$ is C.

For example, $X_2$ is N or CH.

For example, $X_3$ is $CR_8$.

For example, $Y_3$ is $CR_{11}$.

For example, $R_6$ is phenyl substituted with one or more -$Q_2$-$T_2$.

For example, $R_6$ is 5 to 6-membered heteroaryl containing at least one N or O atom and is optionally substituted with one or more -$Q_2$-$T_2$.

For example, $R_6$ is 5 to 6-membered heteroaryl containing 1-3 additional heteroatoms selected from N, O, and S and optionally substituted with one or more -$Q_2$-$T_2$, provided that the heteroaryl is not thiophenyl.

For example, $R_6$ is pyridinyl, pyrazolyl, pyrimidinyl, or furyl, each of which is optionally substituted with one or more -$Q_2$-$T_2$.

For example, $R_6$ is halo (e.g., fluorine, chlorine, bromine, and iodine).

For example, $R_6$ is $C_1$-$C_3$ alkyl substituted with one or more -$Q_2$-$T_2$.

For example, $R_6$ is $C_4$-$C_6$ cycloalkyl optionally substituted with one or more -$Q_2$-$T_2$.

For example, $R_6$ is $C_2$-$C_6$ alkenyl optionally substituted with one or more -$Q_2$-$T_2$.

For example, $R_6$ is C(O)H.

For example, $R_6$ is $OR_a$ or —C(O)$R_a$.

For example, $R_a$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like), which is optionally substituted with one or more -$Q_2$-$T_2$.

For example, $R_6$ is —$NR_aR_b$, —C(O)$R_a$, —C(O)$OR_a$, —C(O)$NR_aR_b$, —$NR_bC(O)R_a$, —$S(O)_2R_a$, or —$S(O)_2NR_aR_b$.

For example, each of $R_a$ and $R_b$, independently is H or $C_1$-$C_6$ alkyl optionally substituted with one or more -$Q_2$-$T_2$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, and morpholinyl, and the like) and the ring is optionally substituted with one or more -$Q_2$-$T_2$.

For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_2$-$T_2$.

For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —C(O)$R_c$, —C(O)$OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_2$-$T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_3$-$T_3$.

For example, $T_2$ is —$OR_c$, —$NR_cR_d$, —C(O)$R_c$, —C(O)$OR_c$, or —$S(O)_2R_c$.

For example, $T_2$ is —$(NR_cR_dR_{d'})^+A^-$, —C(O)$NR_cR_d$, —$NR_1C(O)R_c$, —$NR_dC(O)OR_c$, or —$S(O)_2NR_cR_d$.

For example, $Q_2$ is a bond or methyl linker and $T_2$ is H, halo, —$OR_c$, —$NR_cR_d$, —$(NR_cR_dR_{d'})^+A^-$, or —$S(O)_2NR_cR_d$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like), which is optionally substituted with one or more -$Q_3$-$T_3$.

For example, each of $R_c$ and $R_d$, independently is H or $C_1$-$C_6$ alkyl optionally substituted with one or more -$Q_3$-$T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, and morpholinyl, and the like) and the ring is optionally substituted with one or more -$Q_3$-$T_3$.

For example, $Q_2$ is a bond and $T_2$ is —$OR_c$, —$NR_cR_d$, —$C(O)R_c$, —$C(O)OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $COOR_e$, —$S(O)_2R_e$, —$NR_eR_f$, or —$C(O)NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, —$S(O)_2R_e$, —$NR_eR_f$, and —$C(O)NR_eR_f$.

For example, $R_e$ is H.

For example, $R_f$ is H.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_5$-$T_5$.

For example, $R_7$ is cyclopentyl.

For example, $R_7$ is isopropyl.

For example, $R_7$ is 5 to 6-membered heterocycloalkyl optionally substituted with one or more -$Q_5$-$T_5$.

For example, $R_7$ is piperidinyl optionally substituted with one -$Q_5$-$T_5$.

For example, -$Q_5$-$T_5$ is oxo.

For example, $T_4$ is 4 to 7-membered heterocycloalkyl or $C_3$-$C_8$ cycloalkyl and one or more -$Q_5$-$T_5$ are oxo.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond and $T_5$ is $C_1$-$C_6$ alkyl, $C_3$-$C_8$ cycloalkyl, or 4 to 7-membered heterocycloalkyl.

For example, $Q_5$ is CO and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $R_{11}$ is H.

For example, $R_8$ is H, methyl, or ethyl.

For example, $A^-$ is $Br^-$.

For example,

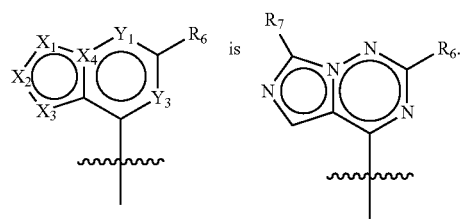

For example,

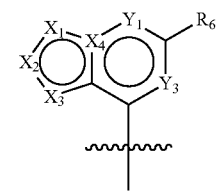

is selected from the group consisting of

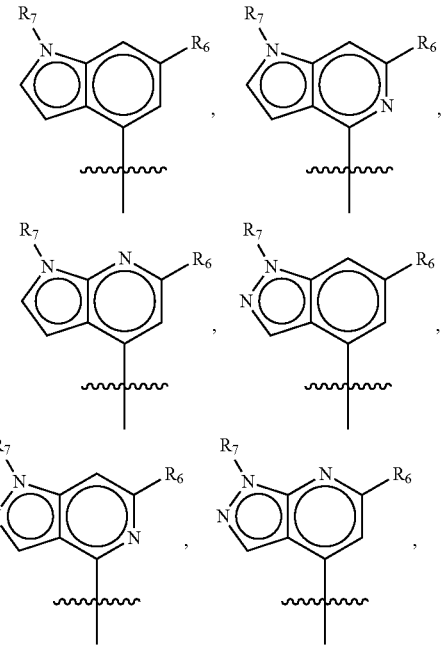

-continued

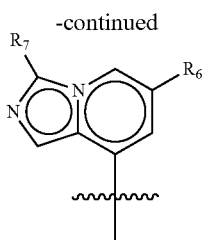

For example,

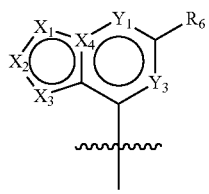

is selected from the group consisting of

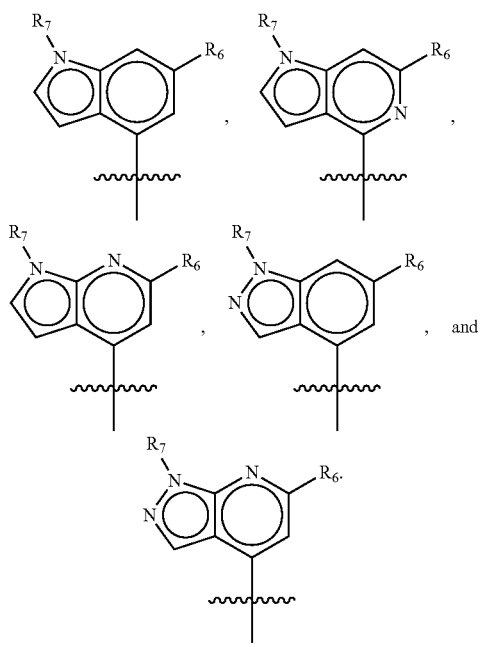

The present invention also provides the compounds of Formula (Ib)

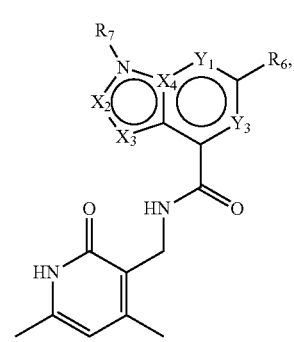

(Ib)

or a pharmaceutically acceptable salt or ester thereof, wherein:

$X_2$ is N, $NR_8$, $CR_8$, O, or S;

$X_3$ is $NR_8$, $CR_8$, O, or S;

$X_4$ is C or N;

$Y_1$ is N or CH;

$Y_2$ is N or $CR_6$;

$Y_3$ is N, or $CR_{11}$, and at least one of $X_1$, $X_2$, $X_3$, $X_4$, $Y_1$, $Y_2$, and $Y_3$ is N or $NR_7$;

each $R_6$ independently is H, halo, $OR_a$, —$NR_aR_b$, —C(O)$R_a$, —C(O)O$R_a$, —C(O)$NR_aR_b$, —$NR_bC(O)R_a$, —S(O)$_2R_a$, —S(O)$_2NR_aR_b$, or $R_{S2}$, in which each of $R_a$ and $R_b$, independently is H or $R_{S3}$ and each of $R_{S2}$ and $R_{S3}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl; or $R_a$ and $R_b$, together with the N atom to which they are attached, form a 4 to 7-membered heterocycloalkyl ring having 0 or 1 additional heteroatoms to the N atom; and each of $R_{S2}$, $R_{S3}$, and the 4 to 7-membered heterocycloalkyl ring containing $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —($NR_cR_dR_{d'}$)$^+$A$^-$, —C(O)$R_c$, —C(O)$OR_c$, —C(O)$NR_cR_d$, —$NR_cC(O)R_c$, —$NR_dC(O)OR_c$, —S(O)$_2R_c$, —S(O)$_2NR_cR_d$, or $R_{S4}$, in which each of $R_c$ $R_d$, and $R_{d'}$, independently is H or $R_{S5}$, A$^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —S(O)$_2R_e$, —$NR_eR_f$, and —C(O)$NR_eR_f$, each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H; or each $R_6$ independently is H, halo, $OR_a$, —$NR_aR_b$, —C(O)$R_a$, —C(O)$OR_a$, —C(O)$NR_aR_b$, —$NR_bC(O)R_a$, —$S(O)_2R_a$, —$S(O)_2NR_aR_b$, or $R_{S2}$, in which $R_{S2}$ is $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl containing at least one N or O atom, each of $R_a$ and $R_b$, independently is H or $R_{S3}$, and $R_{S3}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5 to 6-membered heteroaryl; or $R_a$ and $R_b$, together with the N atom to which they are attached, form a 4 to 7-membered heterocycloalkyl ring having 0 or 1 additional heteroatoms to the N atom; and each of $R_{S2}$, $R_{S3}$, and the 4 to 7-membered heterocycloalkyl ring containing $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$NR_cR_d$, —($NR_cR_dR_{d'}$)$^+$A$^-$, —C(O)$R_c$, —C(O)$OR_c$, —C(O)$NR_cR_d$, —$NR_dC(O)R_c$, —$NR_dC(O)OR_c$, —$S(O)_2R_c$, —$S(O)_2NR_cR_d$, or $R_{S4}$, in which each of $R_c$, $R_d$, and $R_{d'}$, independently is H or $R_{S5}$, A$^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —$S(O)_2R_e$, —$NR_eR_f$, and —C(O)$NR_eR_f$, each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H;

each $R_7$ independently is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —C(O)$R_g$, —C(O)$OR_g$, —C(O)$NR_gR_h$, —C(O)$NR_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, and each of $R_{S6}$ and $R_{S7}$ is optionally substituted with one or more -$Q_5$-$T_5$, wherein $Q_5$ is a bond, C(O), or $C_1$-$C_3$ alkyl linker, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, or 5 to 6-membered heteroaryl and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl except when $T_5$ is H, halo, hydroxyl, or cyano; or -$Q_5$-$T_5$ is oxo; provided that -$Q_4$-$T_4$ is not H; and each of $R_8$ and $R_{11}$, independently, is H, halo, hydroxyl, COOH, cyano, $R_{S8}$, $OR_{S8}$, or COOR$_{S8}$, in which $R_{S8}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino;

provided that the compound is not
N-((4,6-dimethyl-2-oxo-1,2-dihydropyridin-3-yl)methyl)-6-(2,5-dimethylthiophen-3-yl)-1-isopropyl-1H-pyrazolo[3,4-b]pyridine-4-carboxamide, 6-(2,3-dihydro-1,4-benzodioxin-6-yl)-N-[(1,2-dihydro-4,6-dimethyl-2-oxo-3-pyridinyl)methyl]-1-(1-methylethyl)-1H-pyrazolo[3,4-b]pyridine-4-carboxamide, 6-cyclopropyl-N-((4,6-dimethyl-2-oxo-1,2-dihydropyridin-3-yl)methyl)-1,3-dimethyl-1H-pyrazolo[3,4-b]pyridine-4-carboxamide, N-[(1,2-dihydro-4,6-dimethyl-2-oxo-3-pyridinyl)methyl]-1,3,6-trimethyl-1H-pyrazolo[3,4-b]pyridine-4-carboxamide, N-[(1,2-dihydro-4,6-dimethyl-2-oxo-3-pyridinyl)methyl]-6-methyl-1-(1-methylethyl)-1H-pyrazolo[3,4-b]pyridine-4-carboxamide, or 6-cyclopropyl-N-((4,6-dimethyl-2-oxo-1,2-dihydropyridin-3-yl)methyl)-1-isopropyl-1H-pyrazolo[3,4-b]pyridine-4-carboxamide.

For example, $X_4$ is C.
For example, $X_2$ is N or CH.
For example, $X_3$ is $CR_8$.
For example, $Y_3$ is $CR_{11}$.
For example, $R_6$ is phenyl substituted with one or more -$Q_2$-$T_2$.
For example, $R_6$ is 5 to 6-membered heteroaryl containing at least one N or O atom and is optionally substituted with one or more -$Q_2$-$T_2$.
For example, $R_6$ is 5 to 6-membered heteroaryl containing 1-3 additional heteroatoms selected from N, O, and S and optionally substituted with one or more -$Q_2$-$T_2$, provided that the heteroaryl is not thiophenyl.
For example, $R_6$ is pyridinyl, pyrazolyl, pyrimidinyl, or furyl, each of which is optionally substituted with one or more -$Q_2$-$T_2$.
For example, $R_6$ is halo (e.g., fluorine, chlorine, bromine, and iodine).
For example, $R_6$ is $C_1$-$C_3$ alkyl substituted with one or more -$Q_2$-$T_2$.
For example, $R_6$ is $C_4$-$C_6$ cycloalkyl optionally substituted with one or more -$Q_2$-$T_2$.
For example, $R_6$ is $C_2$-$C_6$ alkenyl optionally substituted with one or more -$Q_2$-$T_2$.
For example, $R_6$ is C(O)H.
For example, $R_6$ is $OR_a$ or —C(O)$R_a$.
For example, $R_a$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like), which is optionally substituted with one or more -$Q_2$-$T_2$.

For example, $R_6$ is —$NR_aR_b$, —$C(O)R_a$, —$C(O)OR_a$, —$C(O)NR_aR_b$, —$NR_bC(O)R_a$, —$S(O)_2R_a$, or —$S(O)_2NR_aR_b$.

For example, each of $R_a$ and $R_b$, independently is H or $C_1$-$C_6$ alkyl optionally substituted with one or more -$Q_2$-$T_2$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahydrofuranyl, piperidinyl, 1,2,3,6-tetrahydropyridinyl, piperazinyl, and morpholinyl, and the like) and the ring is optionally substituted with one or more -$Q_2$-$T_2$.

For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_2$-$T_2$.

For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —$C(O)R_c$, —$C(O)OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_2$-$T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyranyl, piperazinyl, tetrahydro-2H-pyranyl, 3,6-dihydro-2H-pyranyl, and morpholinyl, and the like) optionally substituted with one or more -$Q_3$-$T_3$.

For example, $T_2$ is —$OR_c$, —$NR_cR_d$, —$C(O)R_c$, —$C(O)OR_c$, or —$S(O)_2R_c$.

For example, $T_2$ is —$(NR_cR_dR_{d'})^+A^-$, —$C(O)NR_cR_d$, —$NR_dC(O)R_c$, —$NR_dC(O)OR_c$, or —$S(O)_2NR_cR_d$.

For example, $Q_2$ is a bond or methyl linker and $T_2$ is H, halo, —$OR_c$, —$NR_cR_d$, —$(NR_cR_dR_{d'})^+A^-$, or —$S(O)_2NR_cR_d$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like), which is optionally substituted with one or more -$Q_3$-$T_3$.

For example, each of $R_c$ and $R_d$, independently is H or $C_1$-$C_6$ alkyl optionally substituted with one or more -$Q_3$-$T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, and morpholinyl, and the like) and the ring is optionally substituted with one or more -$Q_3$-$T_3$.

For example, $Q_2$ is a bond and $T_2$ is —$OR_c$, —$NR_cR_d$, —$C(O)R_c$, —$C(O)OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $COOR_e$, —$S(O)_2R_e$, —$NR_eR_f$, or —$C(O)NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, —$S(O)_2R_e$, —$NR_eR_f$, and —$C(O)NR_eR_f$.

For example, $R_e$ is H.

For example, $R_f$ is H.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like) optionally substituted with one or more -$Q_5$-$T_5$.

For example, $R_7$ is cyclopentyl.

For example, $R_7$ is isopropyl.

For example, $R_7$ is 5 to 6-membered heterocycloalkyl optionally substituted with one or more -$Q_5$-$T_5$.

For example, $R_7$ is piperidinyl optionally substituted with one -$Q_5$-$T_5$.

For example, -$Q_5$-$T_5$ is oxo.

For example, $T_4$ is 4 to 7-membered heterocycloalkyl or $C_3$-$C_8$ cycloalkyl and one or more -$Q_5$-$T_5$ are oxo.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond and $T_5$ is $C_1$-$C_6$ alkyl, $C_3$-$C_8$ cycloalkyl, or 4 to 7-membered heterocycloalkyl.

For example, $Q_5$ is CO and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $R_{11}$ is H.

For example, $R_8$ is H, methyl, or ethyl.

For example, A⁻ is Br⁻.
For example,
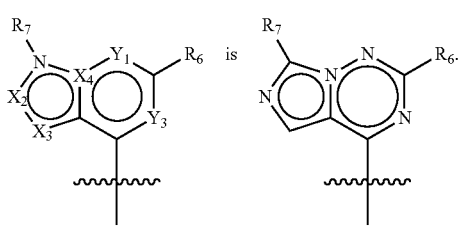 is
For example,
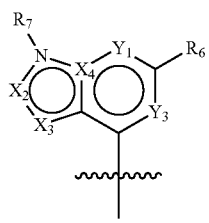
is selected from the group consisting of
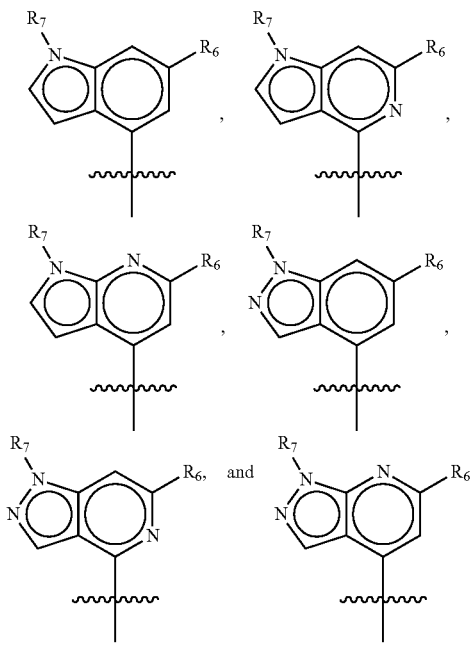
For example,
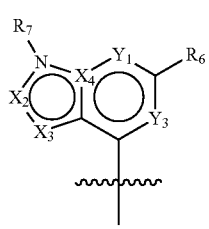
is selected from the group consisting of
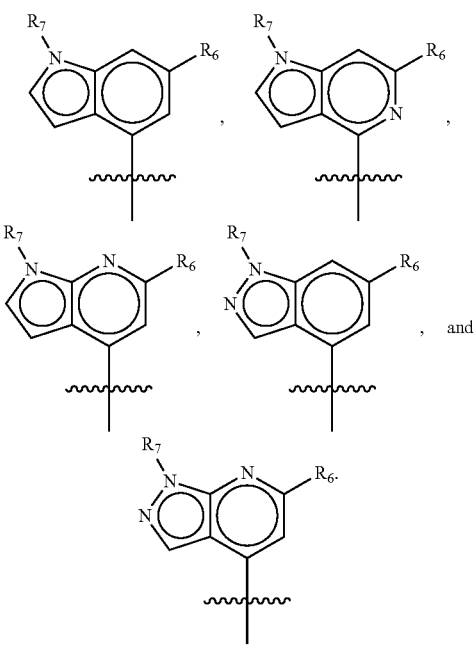
The present invention provides the compounds of Formulae (II) and (III):
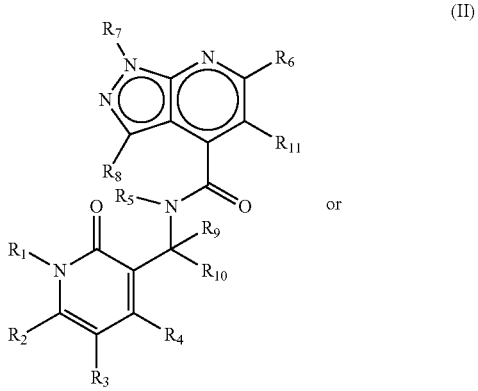
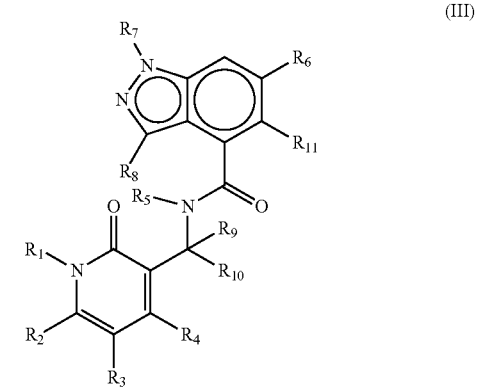
or a pharmaceutically acceptable salt or ester thereof, wherein $R_1$, $R_2$, $R_3$, $R_4$, $R_5$, $R_6$, $R_7$, $R_8$, $R_9$, $R_{10}$, and $R_{11}$ are defined herein.

The present invention provides the compounds of Formulae (IIa)-(IId) and (IIIa)-(IIId):

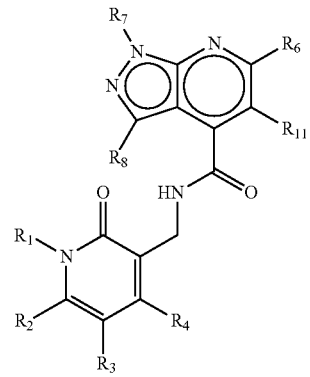
(IIa)

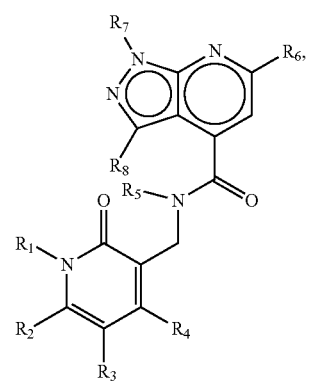
(IIb)

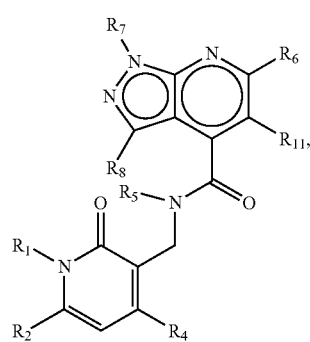
(IIc)

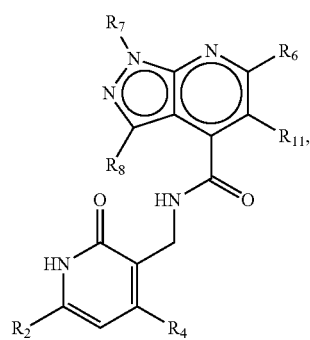
(IId)

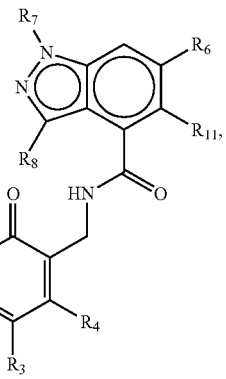
(IIIa)

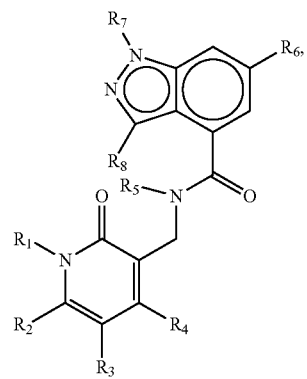
(IIIb)

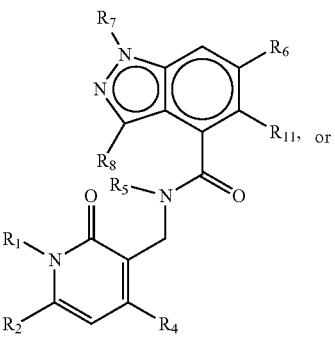
(IIIc)

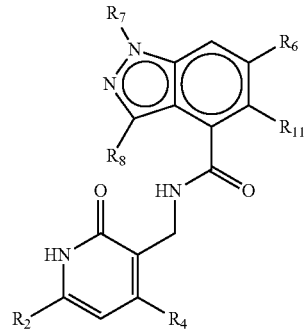
(IIId)

or a pharmaceutically acceptable salt or ester thereof, wherein $R_1$, $R_2$, $R_3$, $R_4$, $R_5$, $R_6$, $R_7$, $R_8$, and $R_{11}$ are defined herein.

Representative compounds of the present invention include compounds listed in Tables 1-6 below. In the tables below, each occurrence of should be construed as
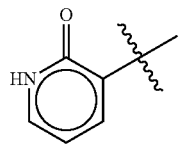 5 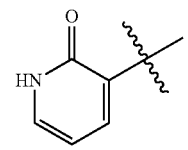
TABLE 1
| Compound Number | Structure |
| --- | --- |
| A-1 | 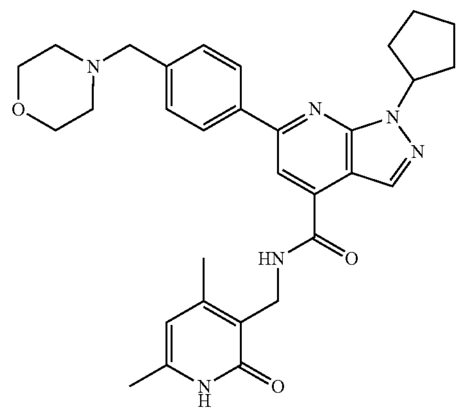 [SMILES: Cc1cc(C)c(CNC(=O)c2cc(-c3ccc(CN4CCOCC4)cc3)nc3c2cnn3C2CCCC2)c(=O)[nH]1] |
| A-2 | 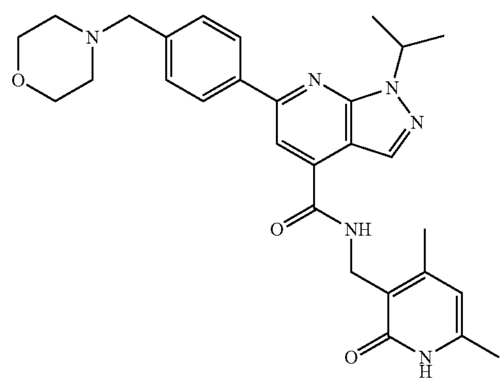 |
| A-3 | 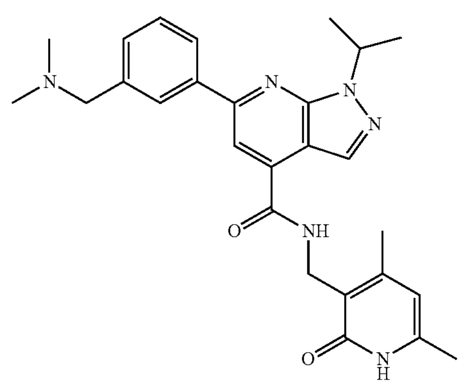 |

TABLE 1-continued

| Compound Number | Structure |
|---|---|
| A-4 | 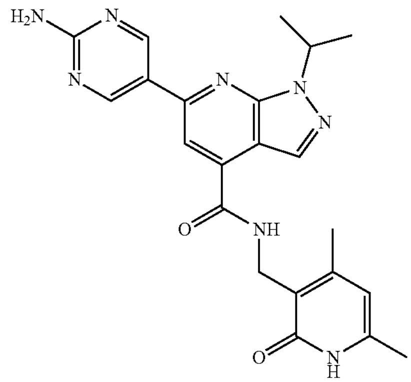 [SMILES: Cc1cc(C)c(CNC(=O)c2cc(-c3cnc(N)nc3)nc3c2cnn3C(C)C)c(=O)[nH]1] |
| A-5 | 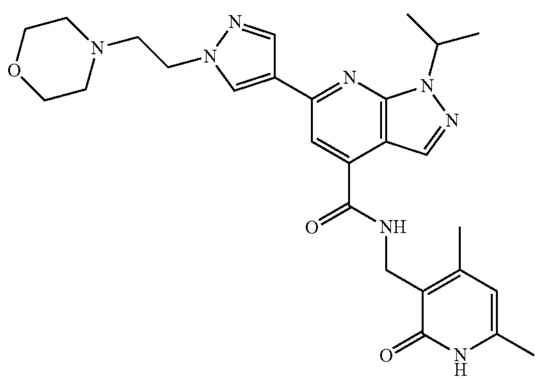 [SMILES: Cc1cc(C)c(CNC(=O)c2cc(-c3cnn(CCN4CCOCC4)c3)nc3c2cnn3C(C)C)c(=O)[nH]1] |
| A-6 | 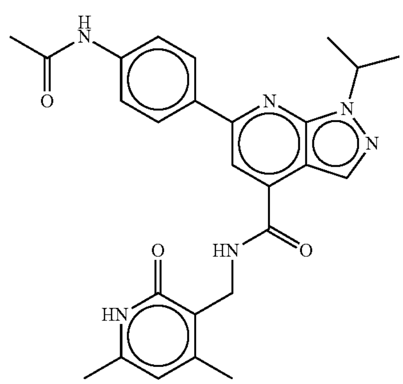 |
| A-7 | 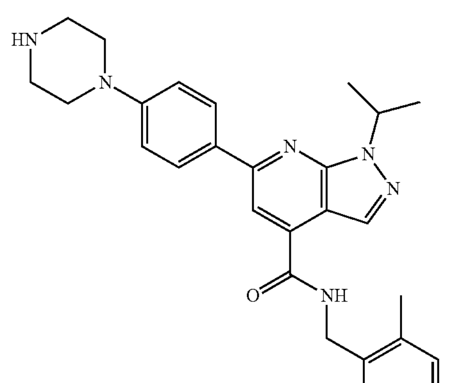 |

TABLE 1-continued

| Compound Number | Structure |
|---|---|
| A-8 | 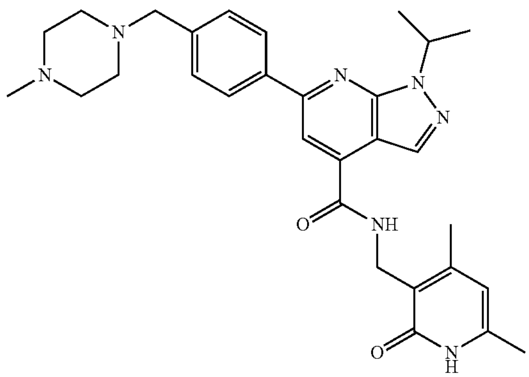 |
| A-9 | 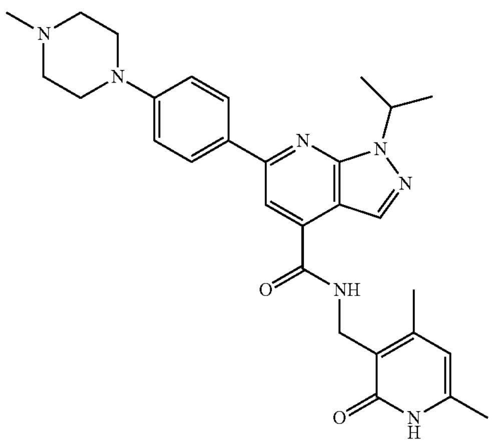 |
| A-10 | 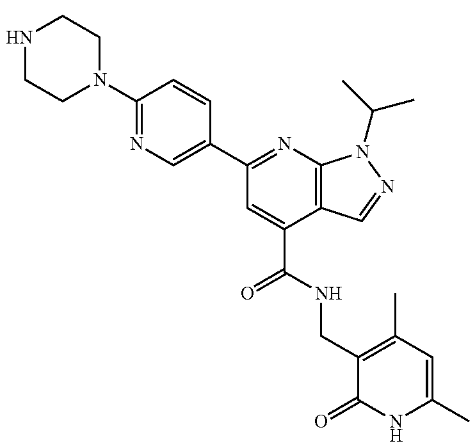 [SMILES: Cc1cc(C)c(CNC(=O)c2cc(-c3ccc(N4CCNCC4)nc3)nc3c2cnn3C(C)C)c(=O)[nH]1] |

TABLE 1-continued

| Compound Number | Structure |
|---|---|
| A-11 | 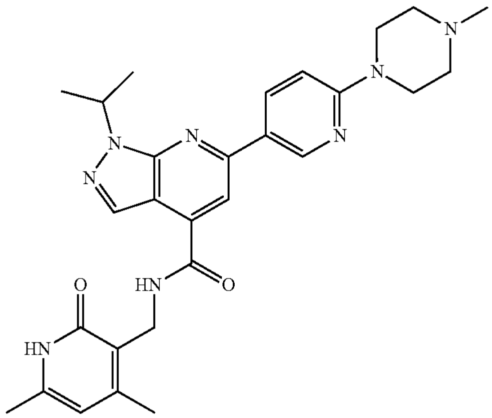 |
| A-12 | 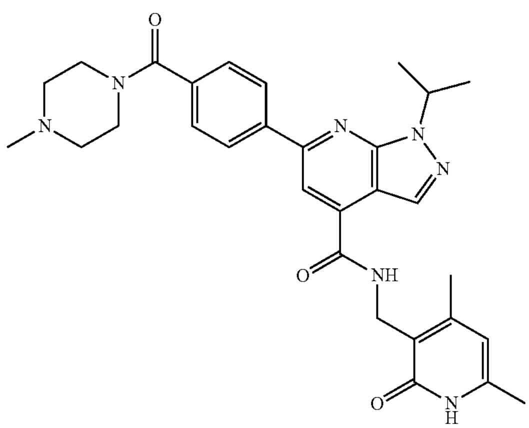 |
| A-13 | 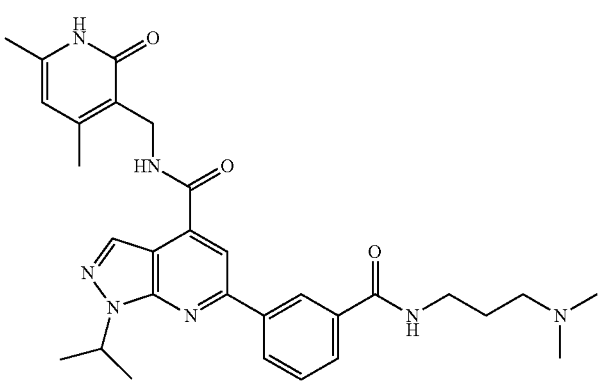 |
| A-14 | 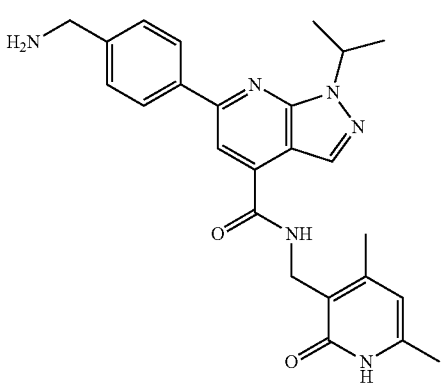 [SMILES: Cc1cc(C)c(CNC(=O)c2cc(-c3ccc(CN)cc3)nc3c2cnn3C(C)C)c(=O)[nH]1] |

TABLE 1-continued

| Compound Number | Structure |
|---|---|
| A-15 | 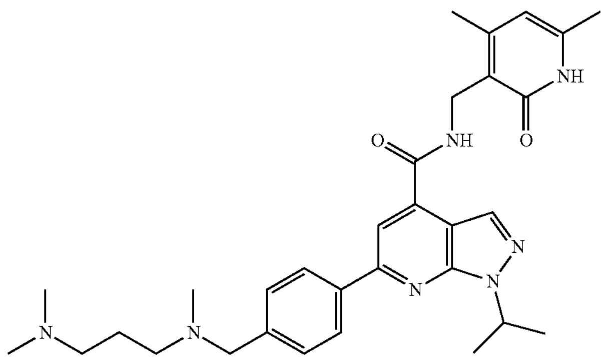 |
| A-16 | 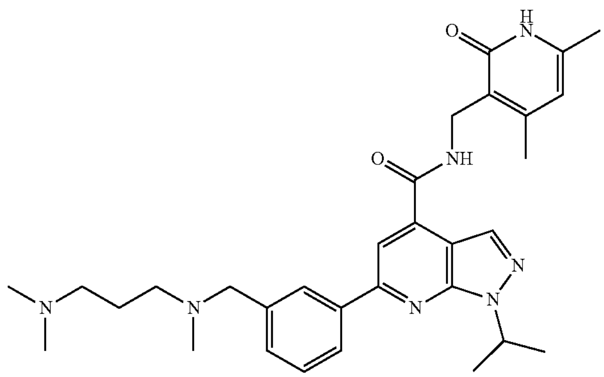 |
| A-17 | 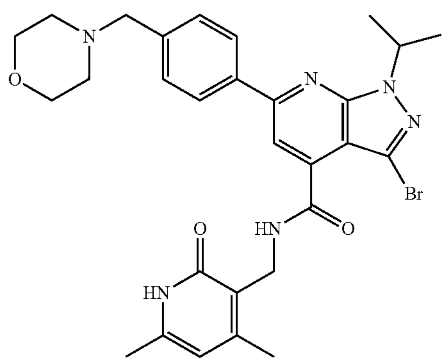 [SMILES: Cc1cc(C)c(CNC(=O)c2cc(-c3ccc(CN4CCOCC4)cc3)nc3c2c(Br)nn3C(C)C)c(=O)[nH]1] |
| A-18 | 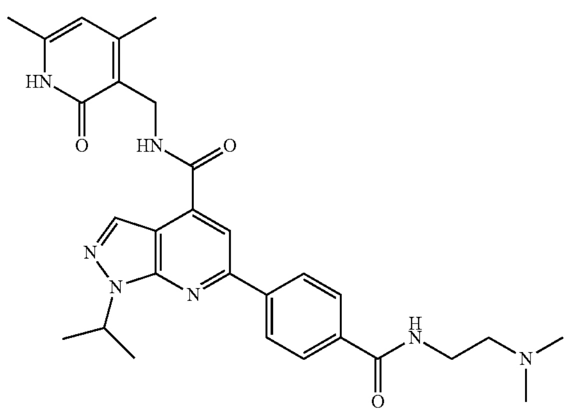 |

TABLE 1-continued

| Compound Number | Structure |
|---|---|
| A-19 | 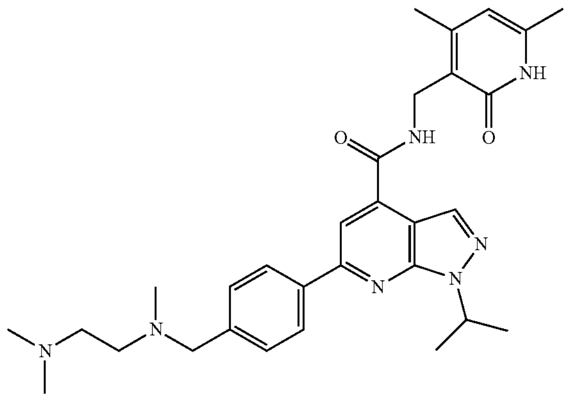 |
| A-20 | 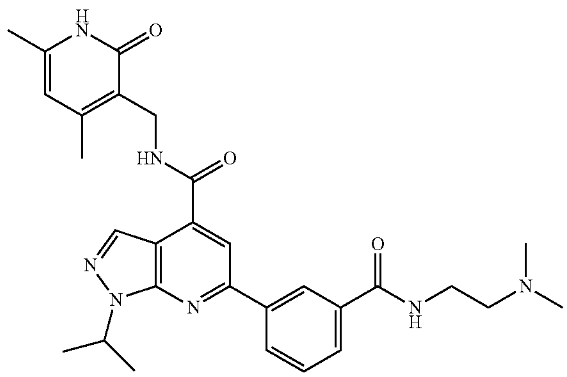 |
| A-21 | 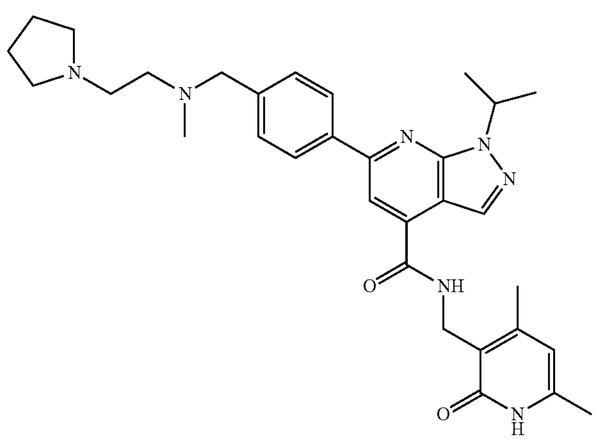 [SMILES: Cc1cc(C)c(CNC(=O)c2cc(-c3ccc(CN(C)CCN4CCCC4)cc3)nc3c2cnn3C(C)C)c(=O)[nH]1] |
| A-22 | 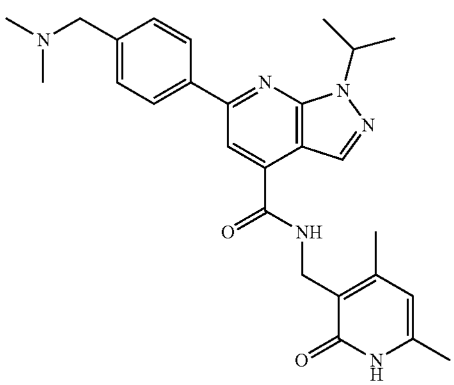 |

TABLE 1-continued

| Compound Number | Structure |
|---|---|
| A-23 | 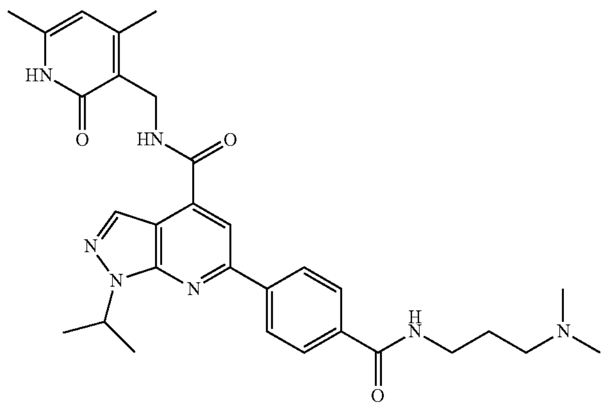 |
| A-24 | 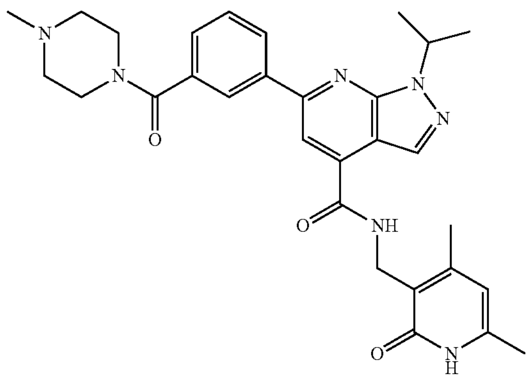 |
| A-25 | 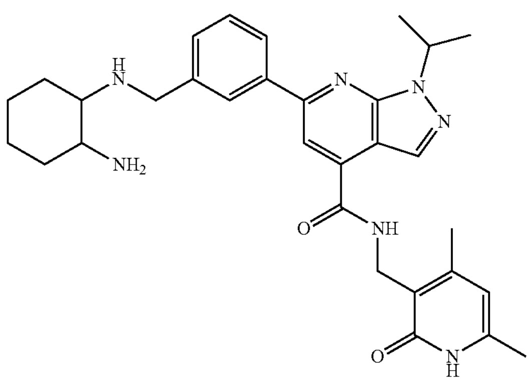 [SMILES: Cc1cc(C)c(CNC(=O)c2cc(-c3cccc(CNC4CCCCC4N)c3)nc3c2cnn3C(C)C)c(=O)[nH]1] |
| A-26 | 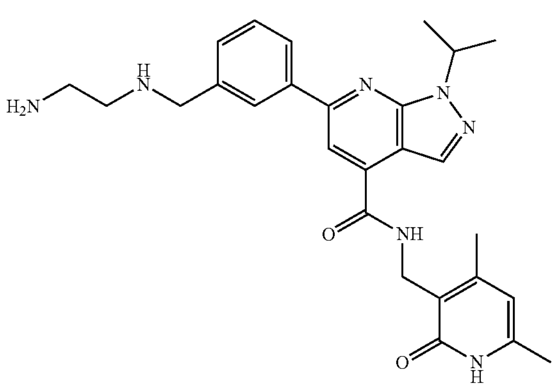 [SMILES: Cc1cc(C)c(CNC(=O)c2cc(-c3cccc(CNCCN)c3)nc3c2cnn3C(C)C)c(=O)[nH]1] |

TABLE 1-continued
| Compound Number | Structure |
|---|---|
| A-27 | 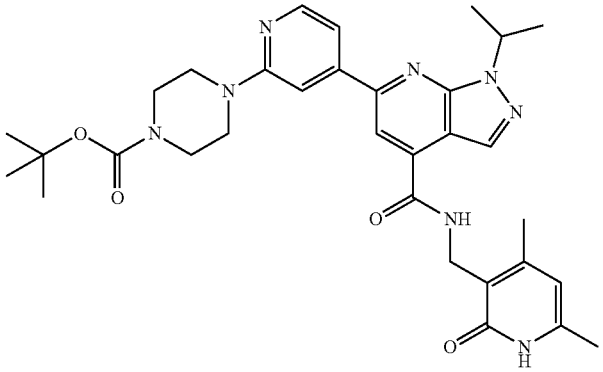 [SMILES: Cc1cc(C)c(CNC(=O)c2cc(-c3ccnc(N4CCN(C(=O)OC(C)(C)C)CC4)c3)nc3c2cnn3C(C)C)c(=O)[nH]1] |
| A-28 | 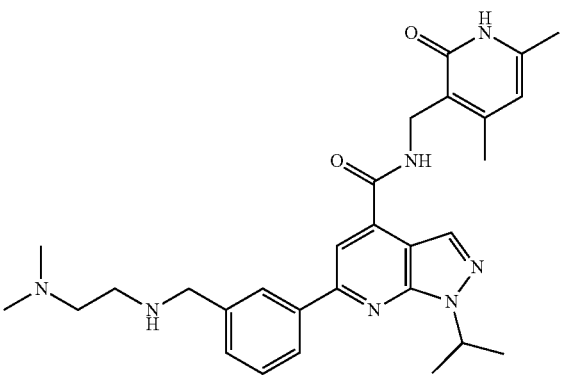 |
| A-29 | 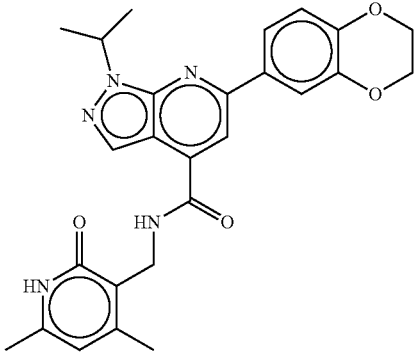 |
| A-30 | 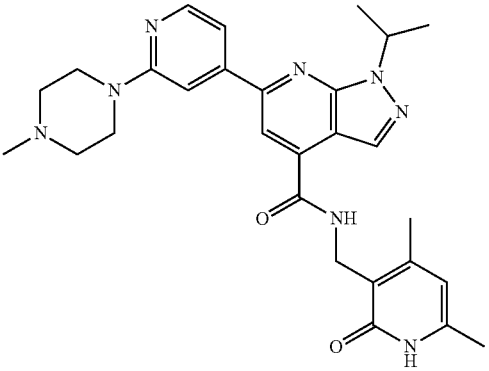 |

TABLE 1-continued

| Compound Number | Structure |
|---|---|
| A-31 | 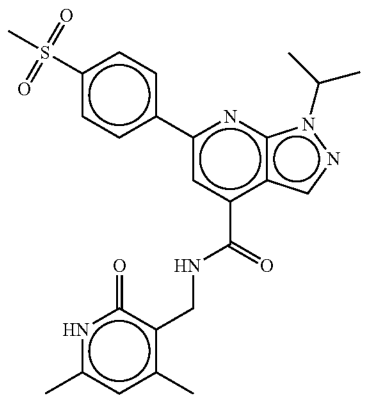 |
| A-32 | 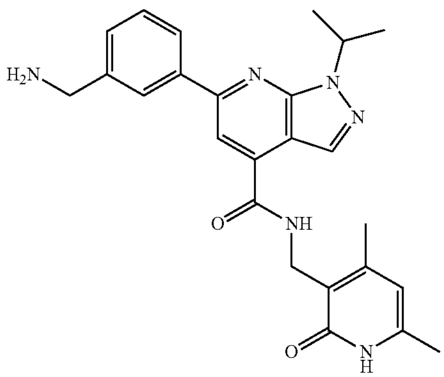 [SMILES: Cc1cc(C)c(CNC(=O)c2cc(-c3cccc(CN)c3)nc3c2cnn3C(C)C)c(=O)[nH]1] |
| A-33 | 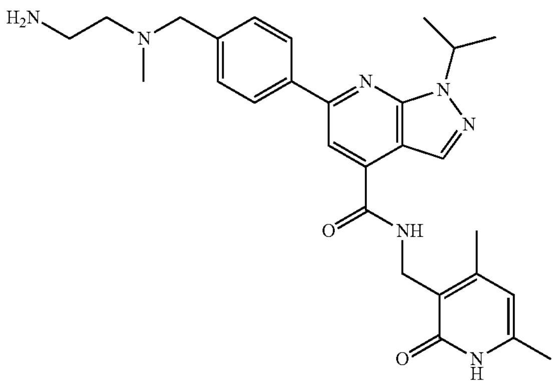 [SMILES: Cc1cc(C)c(CNC(=O)c2cc(-c3ccc(CN(C)CCN)cc3)nc3c2cnn3C(C)C)c(=O)[nH]1] |
| A-34 | 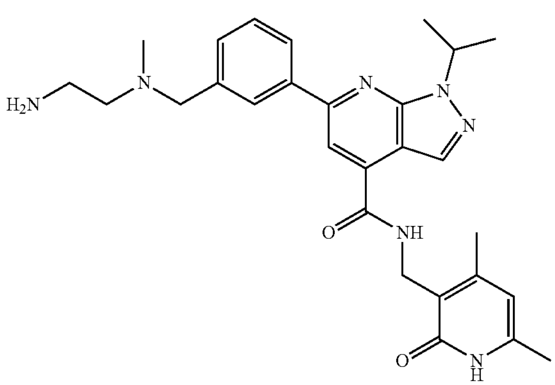 [SMILES: Cc1cc(C)c(CNC(=O)c2cc(-c3cccc(CN(C)CCN)c3)nc3c2cnn3C(C)C)c(=O)[nH]1] |

TABLE 1-continued

| Compound Number | Structure |
|---|---|
| A-35 | 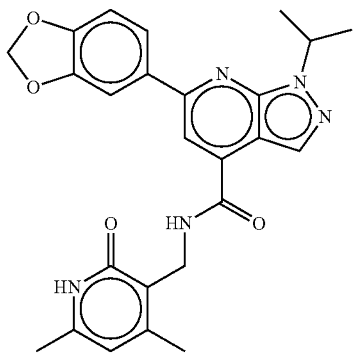 |
| A-36 | 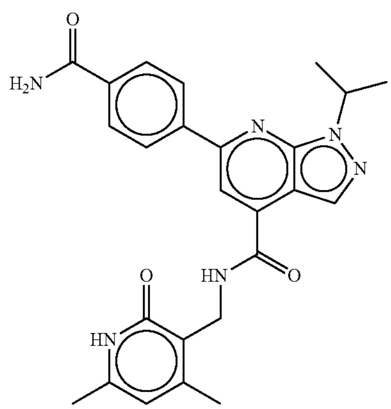 |
| A-37 | 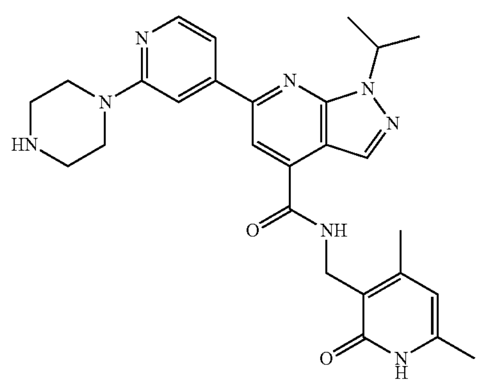 [SMILES: Cc1cc(C)c(CNC(=O)c2cc(-c3ccnc(N4CCNCC4)c3)nc3c2cnn3C(C)C)c(=O)[nH]1] |
| A-38 | 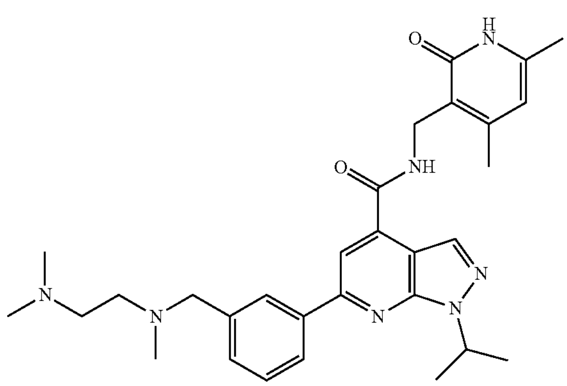 |

TABLE 1-continued

| Compound Number | Structure |
| --- | --- |
| A-39 | 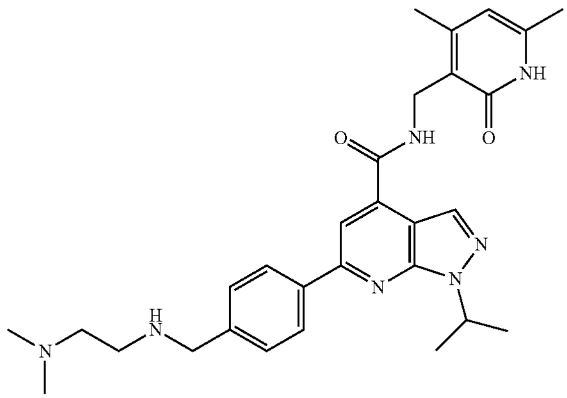 |
| A-40 | 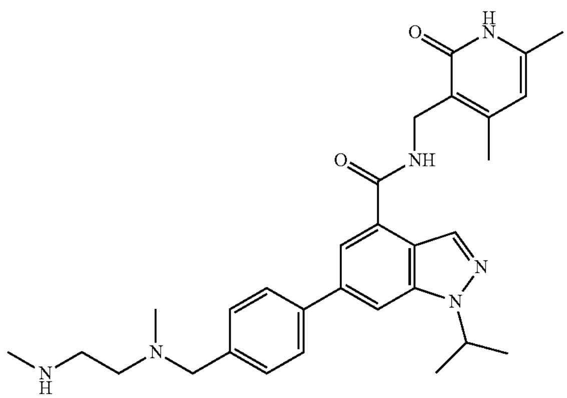 |
| A-41 | 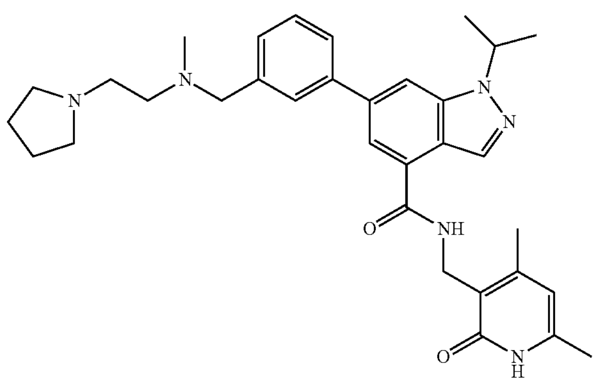 [SMILES: Cc1cc(C)c(CNC(=O)c2cc(-c3cccc(CN(C)CCN4CCCC4)c3)cc3c2cnn3C(C)C)c(=O)[nH]1] |
| A-42 | 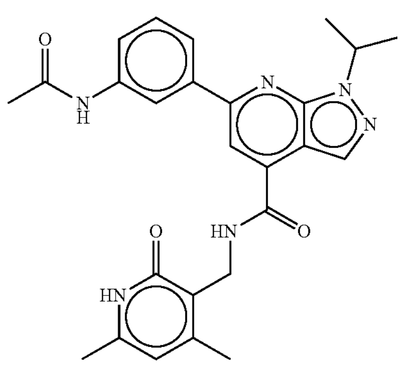 |

TABLE 1-continued
| Compound Number | Structure |
| --- | --- |
| A-43 | 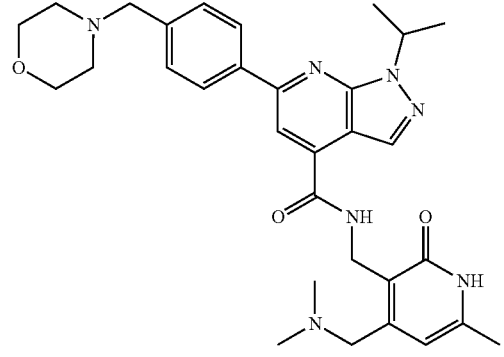 [SMILES: Cc1cc(CN(C)C)c(CNC(=O)c2cc(-c3ccc(CN4CCOCC4)cc3)nc3c2cnn3C(C)C)c(=O)[nH]1] |
| A-44 | 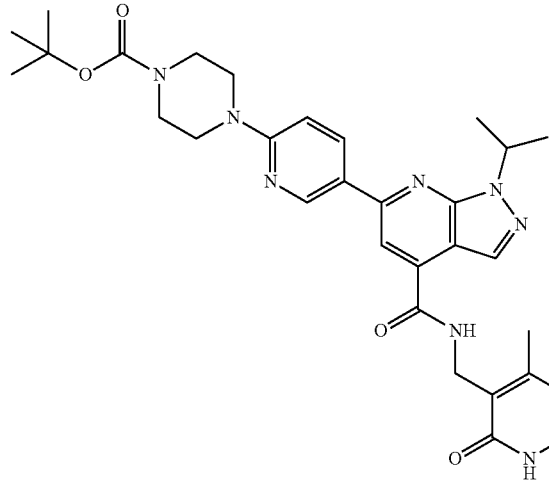 |
| A-45 | 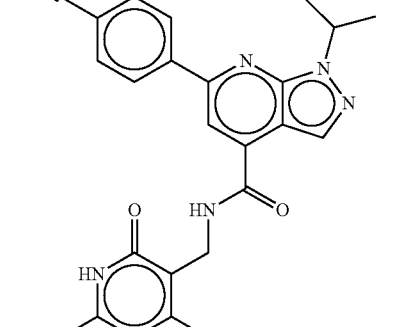 |

TABLE 1-continued

| Compound Number | Structure |
|---|---|
| A-46 | 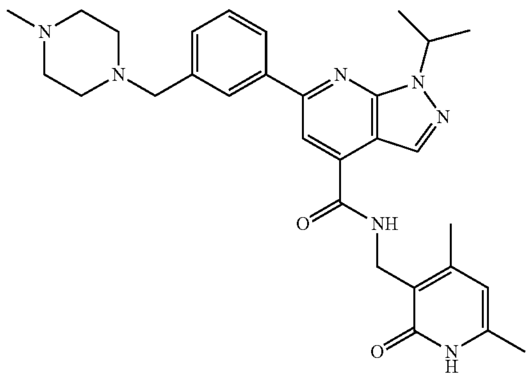 |
| A-47 | 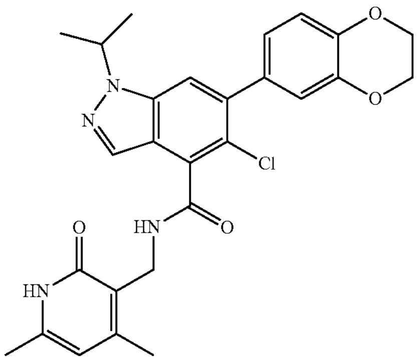 [SMILES: Cc1cc(C)c(CNC(=O)c2c(Cl)c(-c3ccc4c(c3)OCCO4)cc3c2cnn3C(C)C)c(=O)[nH]1] |
| A-48 | 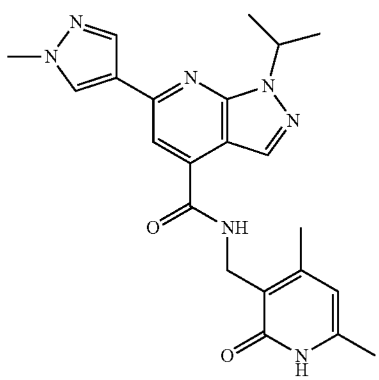 |
| A-49 | 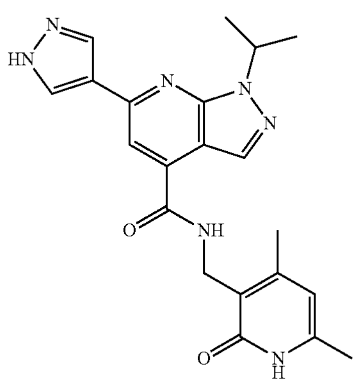 [SMILES: Cc1cc(C)c(CNC(=O)c2cc(-c3cn[nH]c3)nc3c2cnn3C(C)C)c(=O)[nH]1] |

TABLE 1-continued
| Compound Number | Structure |
|---|---|
| A-50 | 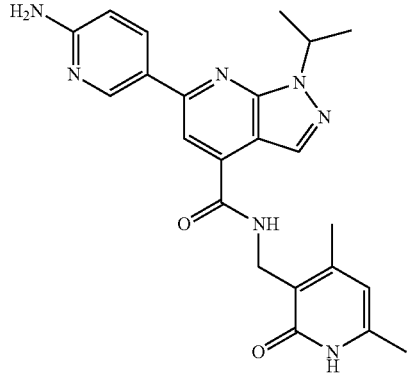 [SMILES: Cc1cc(C)c(CNC(=O)c2cc(-c3ccc(N)nc3)nc3c2cnn3C(C)C)c(=O)[nH]1] |
| A-51 | 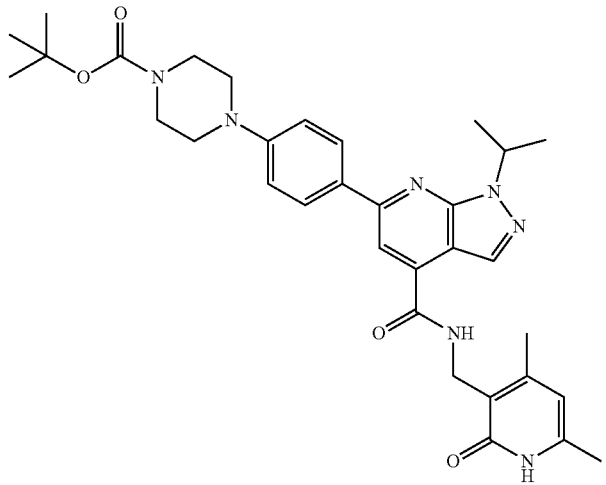 [SMILES: Cc1cc(C)c(CNC(=O)c2cc(-c3ccc(N4CCN(C(=O)OC(C)(C)C)CC4)cc3)nc3c2cnn3C(C)C)c(=O)[nH]1] |
| A-52 | 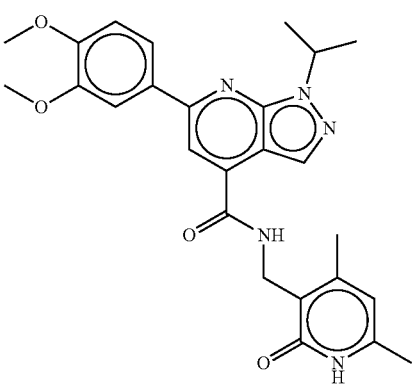 |

TABLE 1-continued

| Compound Number | Structure |
|---|---|
| A-53 | 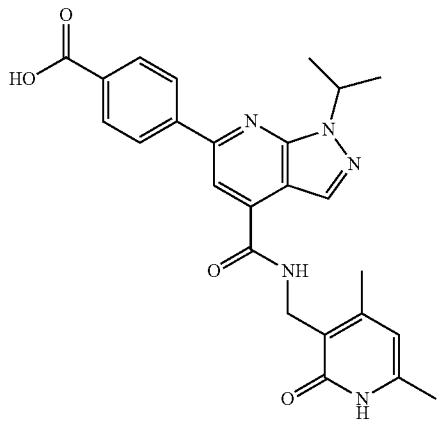 [SMILES: Cc1cc(C)c(CNC(=O)c2cc(-c3ccc(C(=O)O)cc3)nc3c2cnn3C(C)C)c(=O)[nH]1] |
| A-54 | 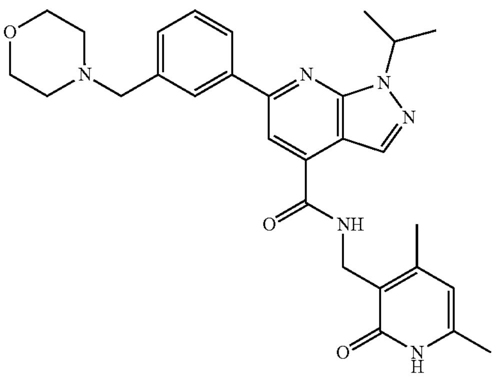 [SMILES: Cc1cc(C)c(CNC(=O)c2cc(-c3cccc(CN4CCOCC4)c3)nc3c2cnn3C(C)C)c(=O)[nH]1] |
| A-55 | 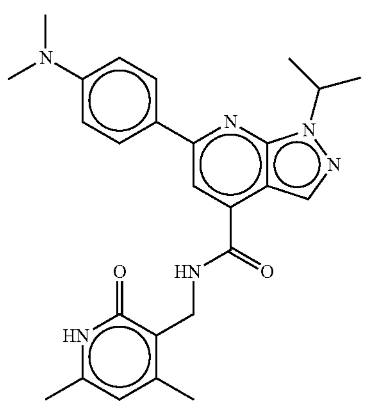 |
| A-56 | 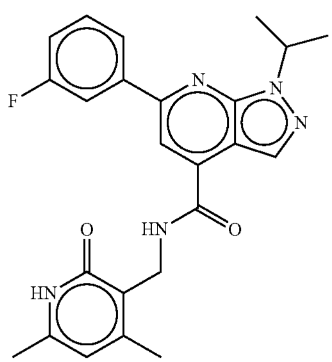 |

TABLE 1-continued

| Compound Number | Structure |
|---|---|
| A-57 | 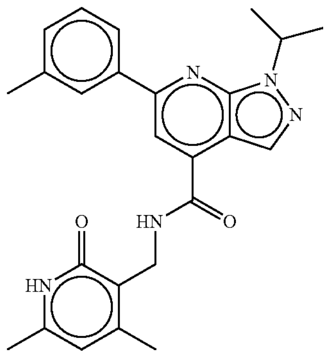 |
| A-58 | 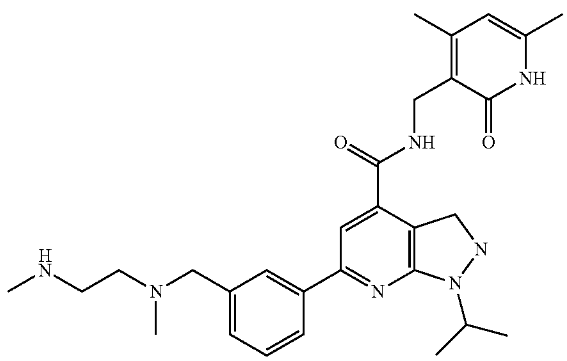 |
| A-59 | 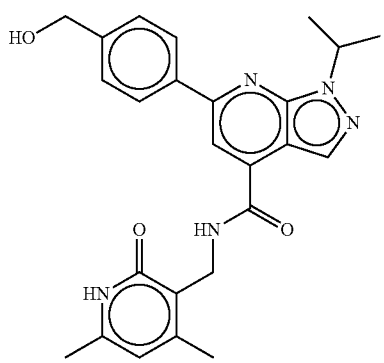 |
| A-60 | 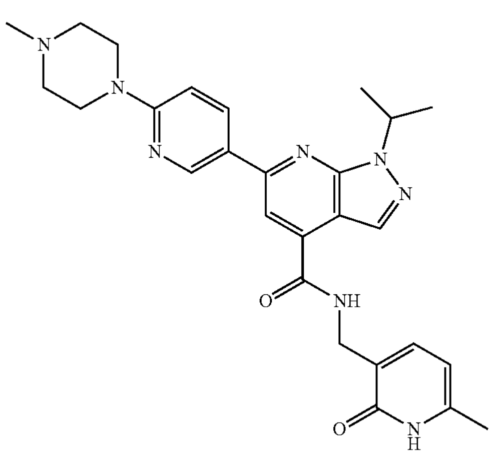 |

TABLE 1-continued

| Compound Number | Structure |
|---|---|
| A-61 | 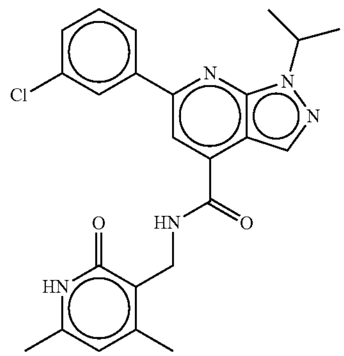 |
| A-62 | 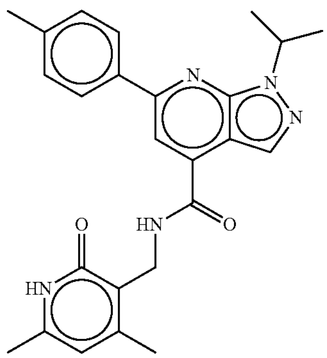 |
| A-63 | 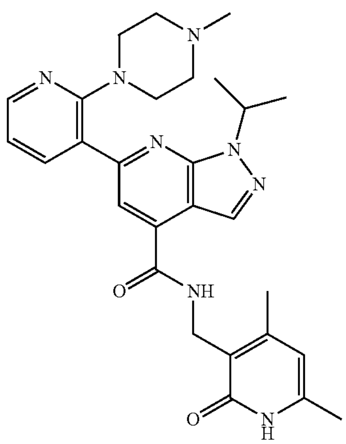 [SMILES: Cc1cc(C)c(CNC(=O)c2cc(-c3cccnc3N3CCN(C)CC3)nc3c2cnn3C(C)C)c(=O)[nH]1] |
| A-64 | 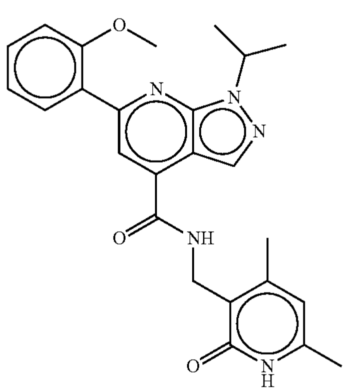 |

TABLE 1-continued
| Compound Number | Structure |
|---|---|
| A-65 | 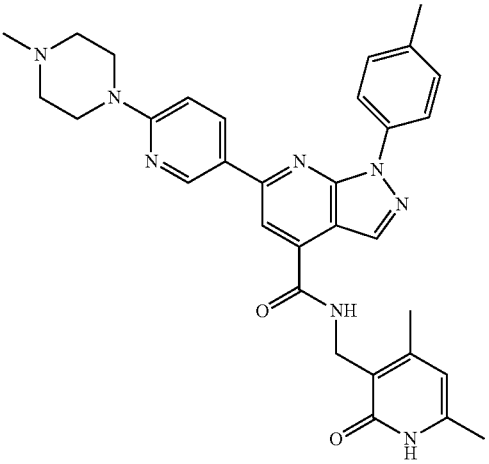 |
| A-66 | 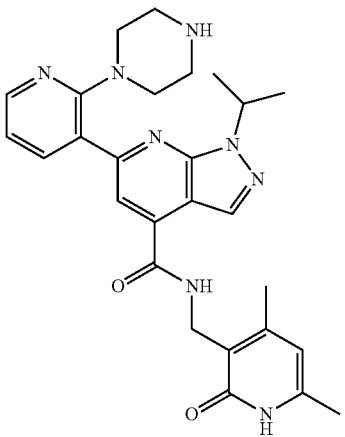 [SMILES: Cc1cc(C)c(CNC(=O)c2cc(-c3cccnc3N3CCNCC3)nc3c2cnn3C(C)C)c(=O)[nH]1] |
| A-67 | 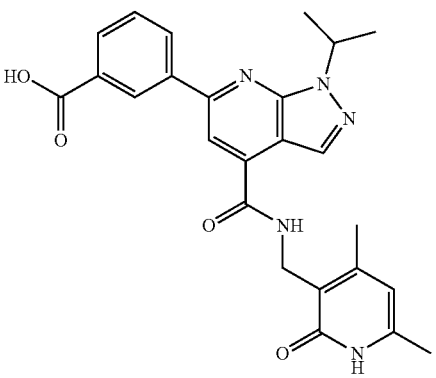 [SMILES: Cc1cc(C)c(CNC(=O)c2cc(-c3cccc(C(=O)O)c3)nc3c2cnn3C(C)C)c(=O)[nH]1] |

TABLE 1-continued

| Compound Number | Structure |
|---|---|
| A-68 | 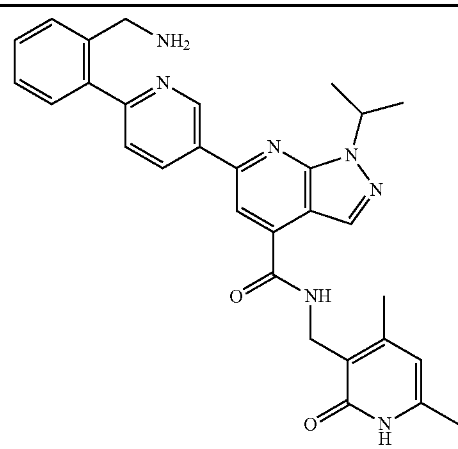 |
| A-69 | 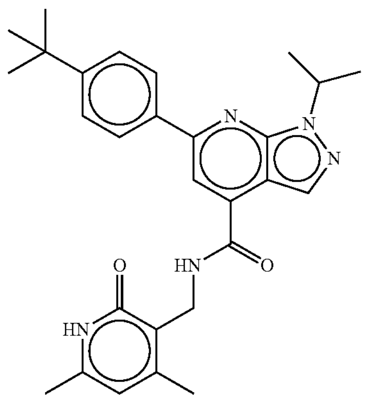 |
| A-70 | 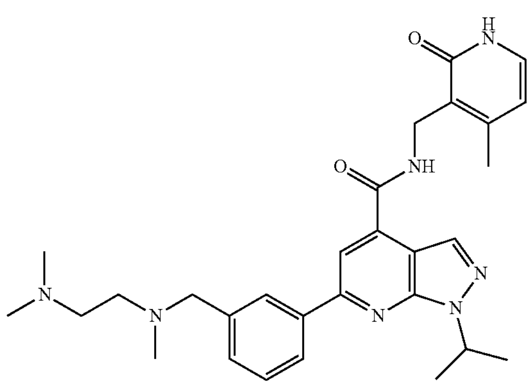 [SMILES: Cc1cc[nH]c(=O)c1CNC(=O)c1cc(-c2cccc(CN(C)CCN(C)C)c2)nc2c1cnn2C(C)C] |
| A-71 | 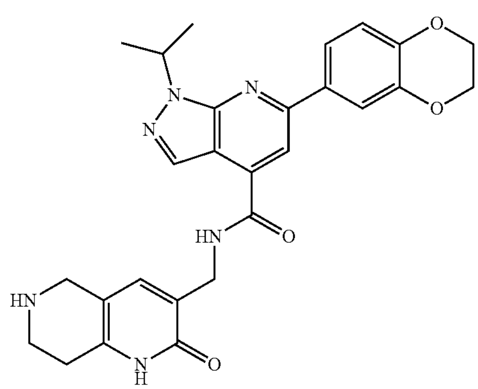 [SMILES: CC(C)n1ncc2c(C(=O)NCc3cc4c([nH]c3=O)CCNC4)cc(-c3ccc4c(c3)OCCO4)nc21] |

TABLE 1-continued

| Compound Number | Structure |
|---|---|
| A-72 | 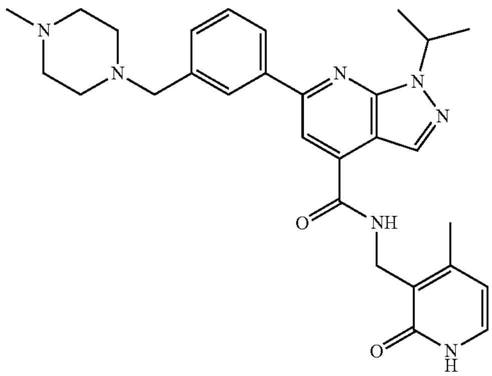 [SMILES: Cc1cc[nH]c(=O)c1CNC(=O)c1cc(-c2cccc(CN3CCN(C)CC3)c2)nc2c1cnn2C(C)C] |
| A-73 | 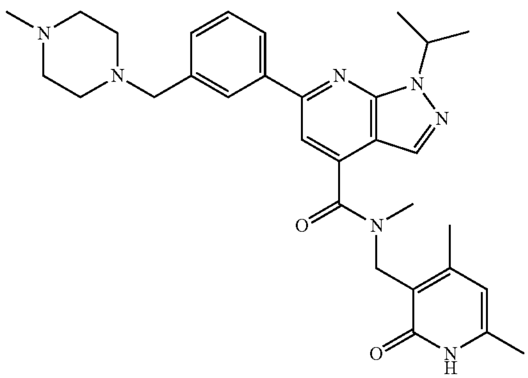 |
| A-74 | 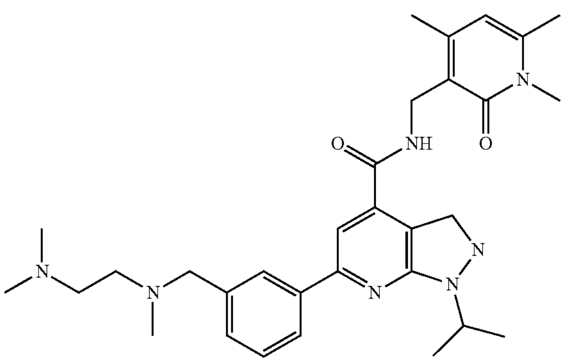 |
| A-75 | 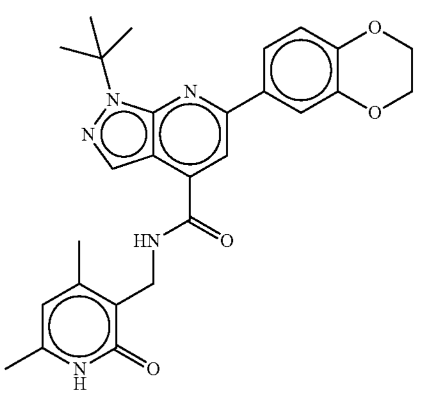 |

TABLE 1-continued

| Compound Number | Structure |
|---|---|
| A-76 | 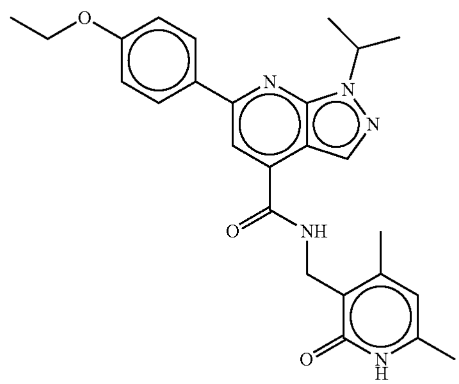 |
| A-77 | 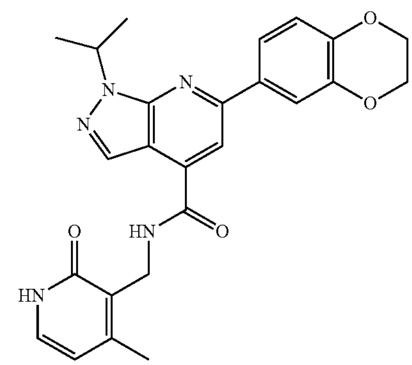 [SMILES: Cc1cc[nH]c(=O)c1CNC(=O)c1cc(-c2ccc3c(c2)OCCO3)nc2c1cnn2C(C)C] |
| A-78 | 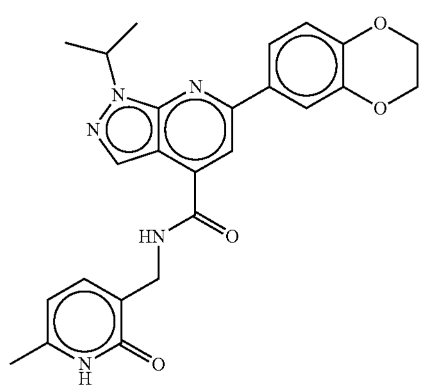 |
| A-91 | 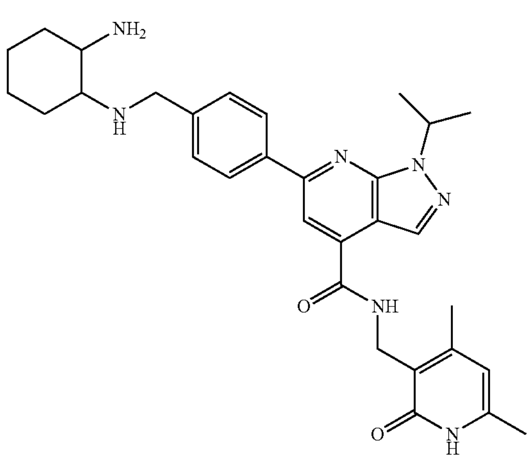 [SMILES: Cc1cc(C)c(CNC(=O)c2cc(-c3ccc(CNC4CCCCC4N)cc3)nc3c2cnn3C(C)C)c(=O)[nH]1] |

TABLE 1-continued

| Compound Number | Structure |
|---|---|
| A-92 | 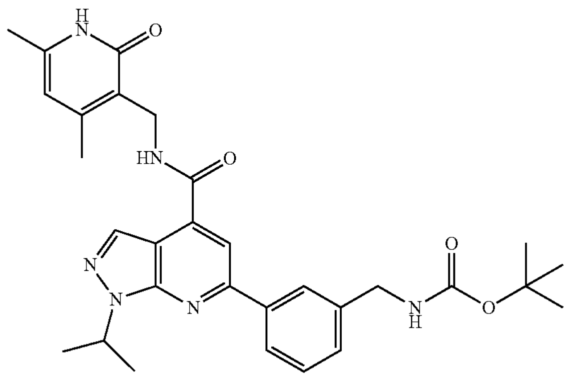 [SMILES: Cc1cc(C)c(CNC(=O)c2cc(-c3cccc(CNC(=O)OC(C)(C)C)c3)nc3c2cnn3C(C)C)c(=O)[nH]1] |
| A-93 | 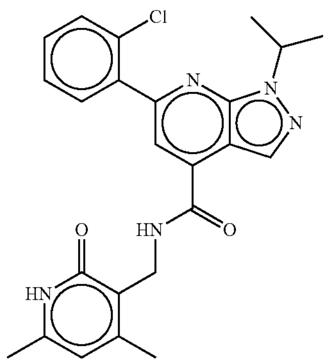 |
| A-94 | 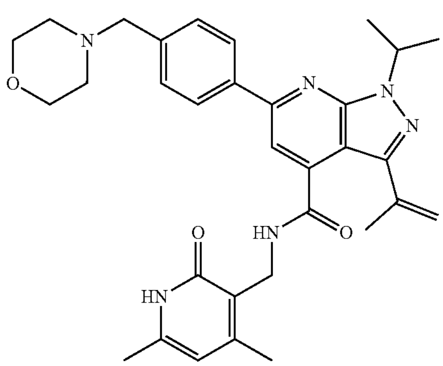 [SMILES: C=C(C)c1nn(C(C)C)c2nc(-c3ccc(CN4CCOCC4)cc3)cc(C(=O)NCc3c(C)cc(C)[nH]c3=O)c12] |
| A-95 | 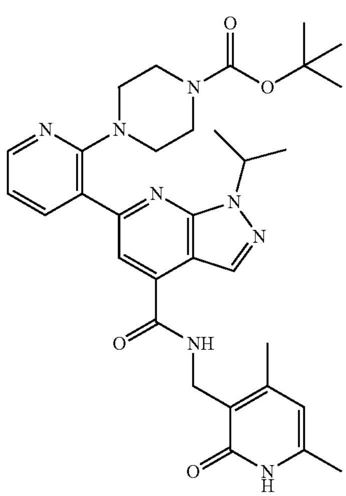 [SMILES: Cc1cc(C)c(CNC(=O)c2cc(-c3cccnc3N3CCN(C(=O)OC(C)(C)C)CC3)nc3c2cnn3C(C)C)c(=O)[nH]1] |

TABLE 1-continued

| Compound Number | Structure |
| --- | --- |
| A-96 | 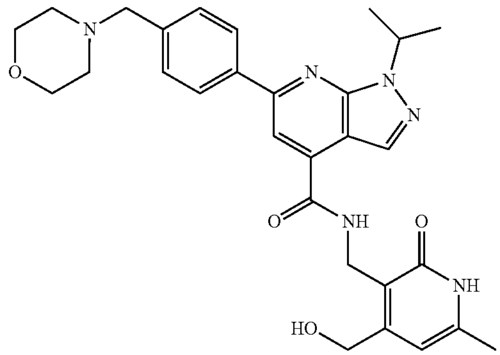 [SMILES: Cc1cc(CO)c(CNC(=O)c2cc(-c3ccc(CN4CCOCC4)cc3)nc3c2cnn3C(C)C)c(=O)[nH]1] |
| A-97 | 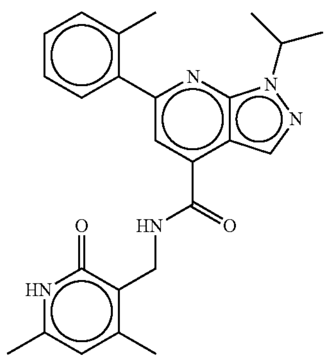 |
| A-98 | 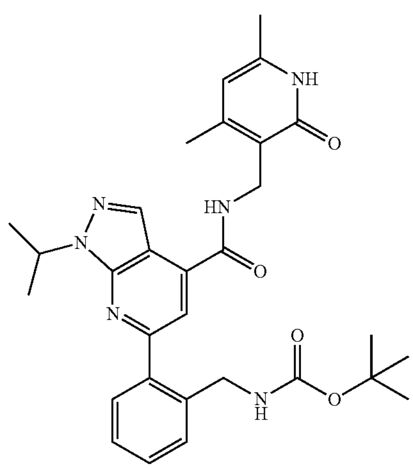 [SMILES: Cc1cc(C)c(CNC(=O)c2cc(-c3ccccc3CNC(=O)OC(C)(C)C)nc3c2cnn3C(C)C)c(=O)[nH]1] |
| A-99 | 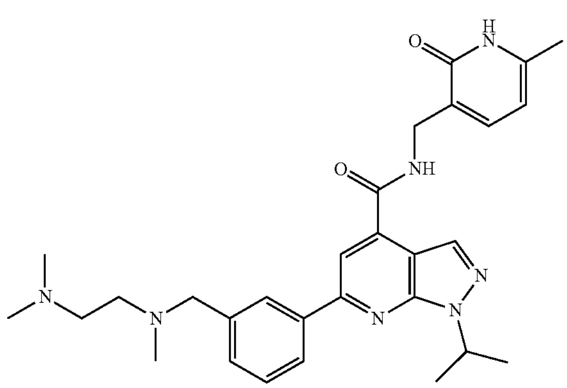 |

TABLE 1-continued
| Compound Number | Structure |
|---|---|
| A-100 | 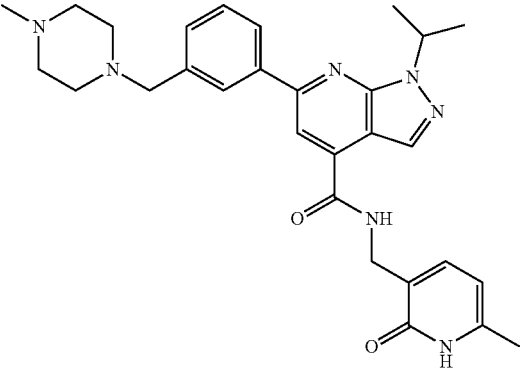 |
| A-101 | 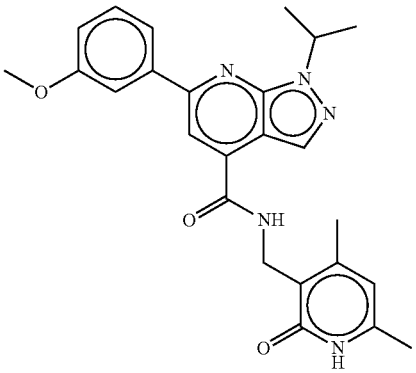 |
| A-102 | 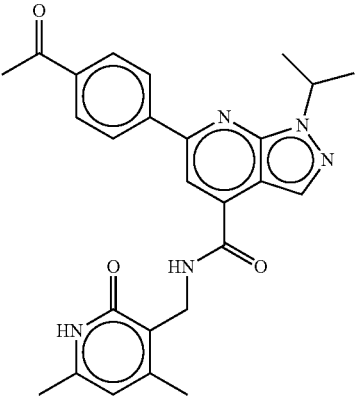 |
| A-103 | 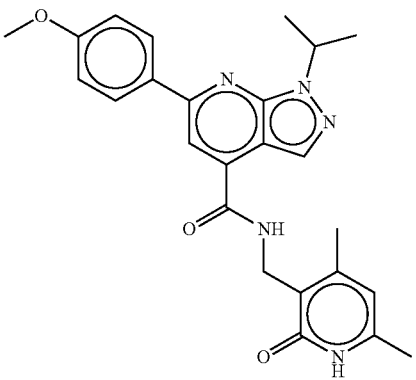 |

TABLE 1-continued

| Compound Number | Structure |
| --- | --- |
| A-104 | 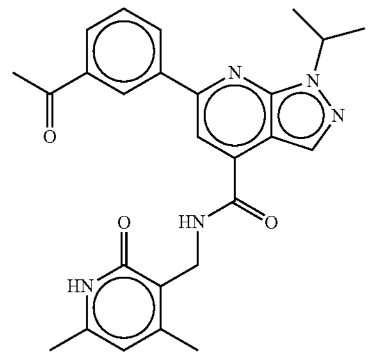 |
| A-105 | 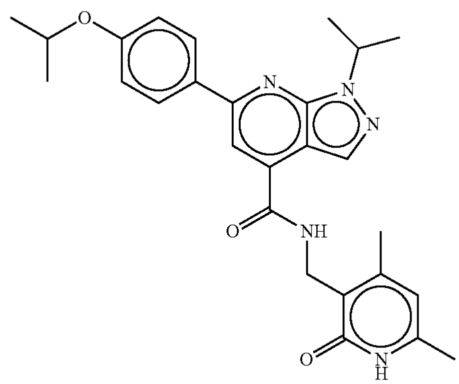 |
| A-106 | 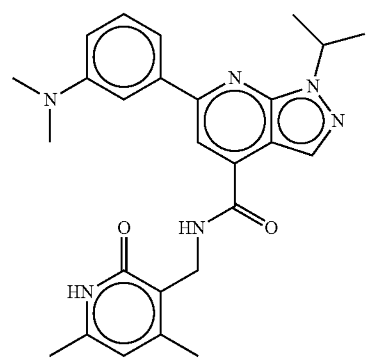 |
| A-107 | 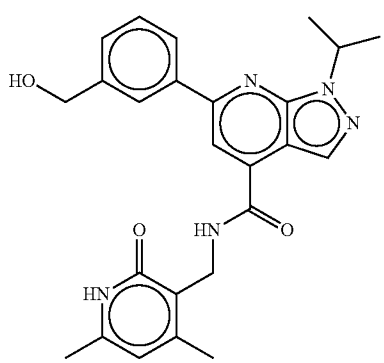 |

TABLE 1-continued

| Compound Number | Structure |
| --- | --- |
| A-108 | 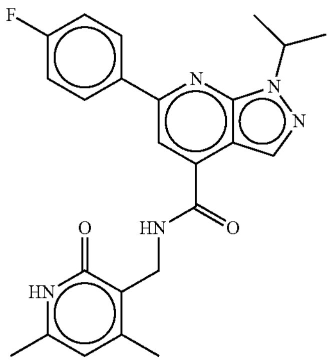 |
| A-109 | 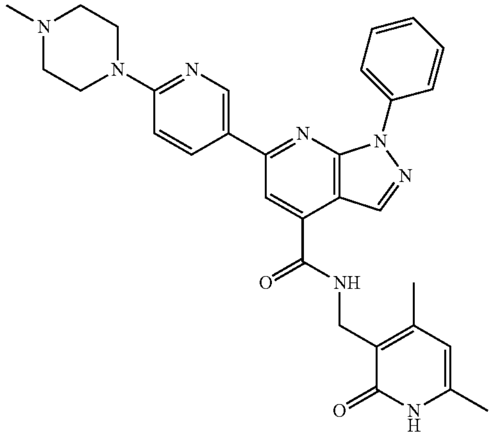 |
| A-110 | 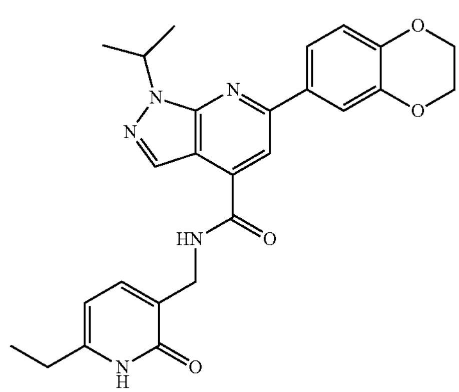 [SMILES: CCc1ccc(CNC(=O)c2cc(-c3ccc4c(c3)OCCO4)nc3c2cnn3C(C)C)c(=O)[nH]1] |
| A-125 | 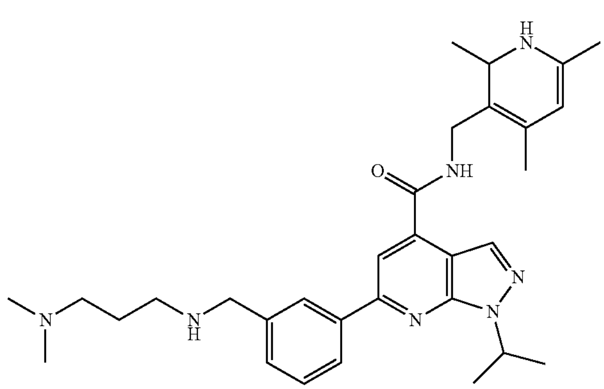 |

TABLE 1-continued
| Compound Number | Structure |
|---|---|
| A-126 | 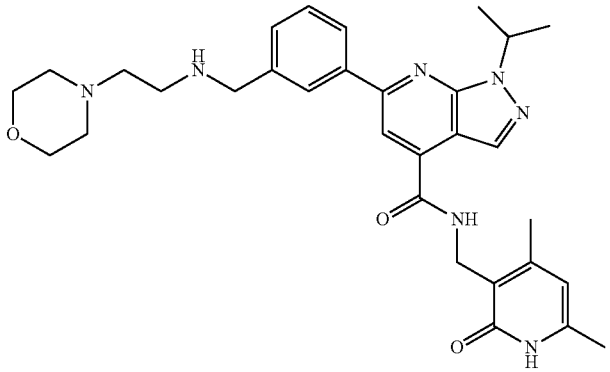 [SMILES: Cc1cc(C)c(CNC(=O)c2cc(-c3cccc(CNCCN4CCOCC4)c3)nc3c2cnn3C(C)C)c(=O)[nH]1] |
TABLE 2
| Compound Number | Structure |
|---|---|
| B-1 | 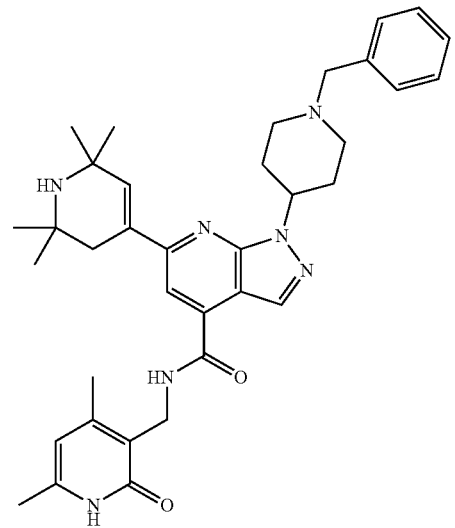 [SMILES: Cc1cc(C)c(CNC(=O)c2cc(C3=CC(C)(C)NC(C)(C)C3)nc3c2cnn3C2CCN(Cc3ccccc3)CC2)c(=O)[nH]1] |
| B-2 | 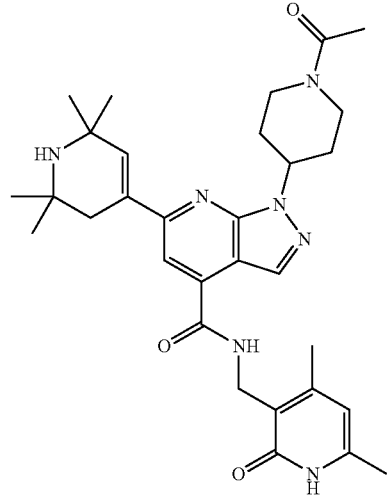 |

TABLE 2-continued
| Compound Number | Structure |
| --- | --- |
| B-3 | 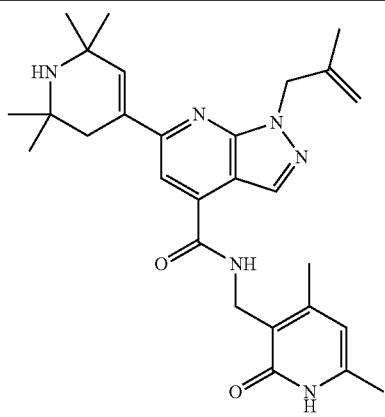 |
| B-4 | 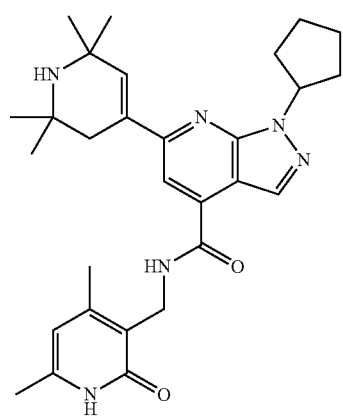 [SMILES: Cc1cc(C)c(CNC(=O)c2cc(C3=CC(C)(C)NC(C)(C)C3)nc3c2cnn3C2CCCC2)c(=O)[nH]1] |
| B-5 | 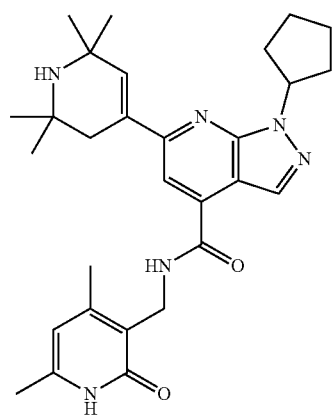 [SMILES: Cc1cc(C)c(CNC(=O)c2cc(C3=CC(C)(C)NC(C)(C)C3)nc3c2cnn3C2CCCC2)c(=O)[nH]1] |
| B-6 | 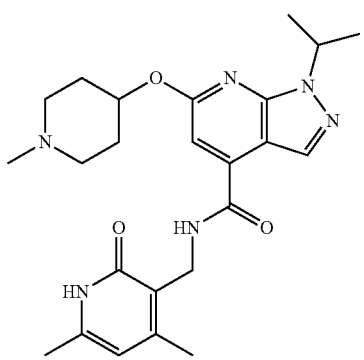 [SMILES: Cc1cc(C)c(CNC(=O)c2cc(OC3CCN(C)CC3)nc3c2cnn3C(C)C)c(=O)[nH]1] |

TABLE 2-continued
| Compound Number | Structure |
|---|---|
| B-7 | 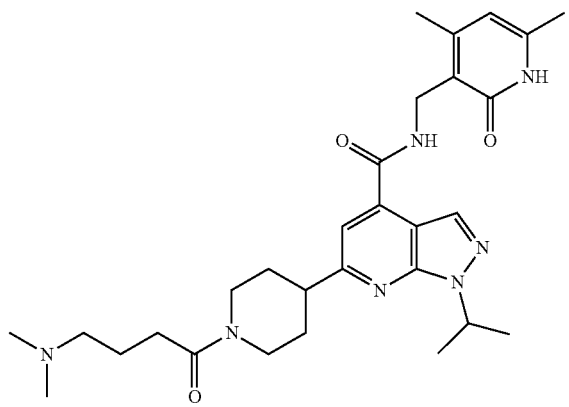 |
| B-8 | 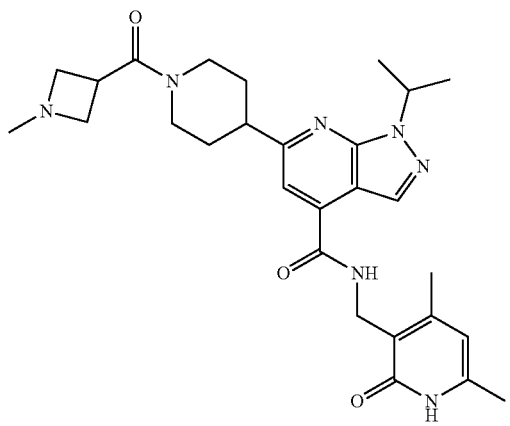 |
| B-9 | 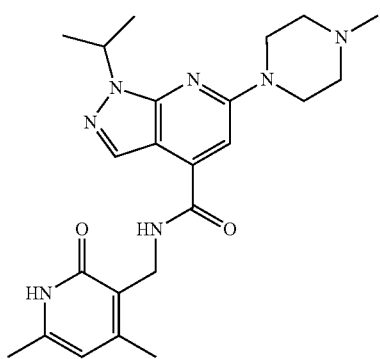 |

TABLE 2-continued
| Compound Number | Structure |
|---|---|
| B-10 | 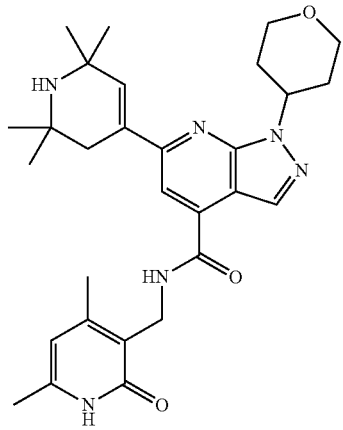 [SMILES: Cc1cc(C)c(CNC(=O)c2cc(C3=CC(C)(C)NC(C)(C)C3)nc3c2cnn3C2CCOCC2)c(=O)[nH]1] |
| B-11 | 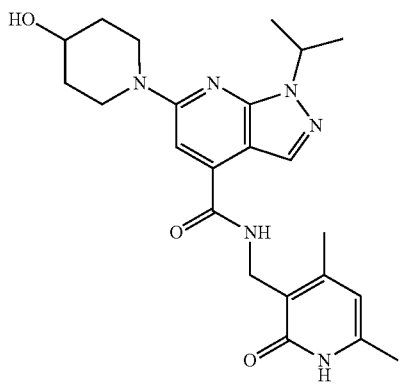 [SMILES: Cc1cc(C)c(CNC(=O)c2cc(N3CCC(O)CC3)nc3c2cnn3C(C)C)c(=O)[nH]1] |
| B-12 | 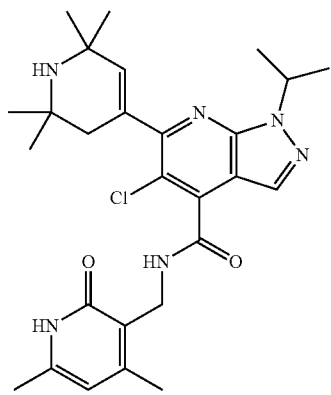 [SMILES: Cc1cc(C)c(CNC(=O)c2c(Cl)c(C3=CC(C)(C)NC(C)(C)C3)nc3c2cnn3C(C)C)c(=O)[nH]1] |
| B-13 | 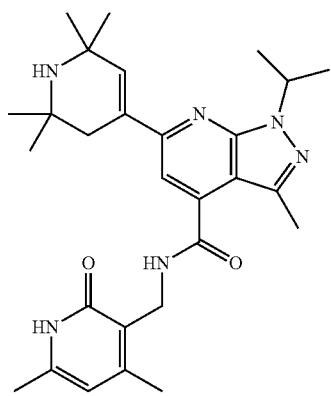 [SMILES: Cc1cc(C)c(CNC(=O)c2cc(C3=CC(C)(C)NC(C)(C)C3)nc3c2c(C)nn3C(C)C)c(=O)[nH]1] |

TABLE 2-continued
| Compound Number | Structure |
|---|---|
| B-14 | 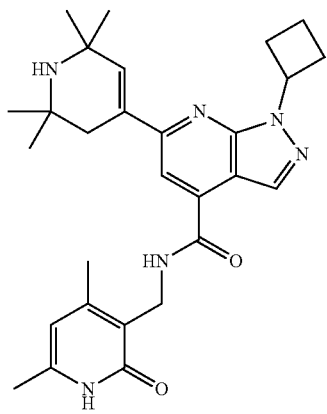 |
| B-15 | 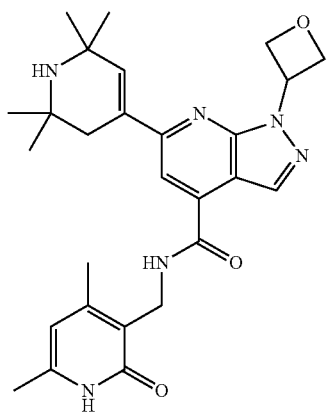 [SMILES: Cc1cc(C)c(CNC(=O)c2cc(C3=CC(C)(C)NC(C)(C)C3)nc3c2cnn3C2CCC2)c(=O)[nH]1] |
| B-16 | 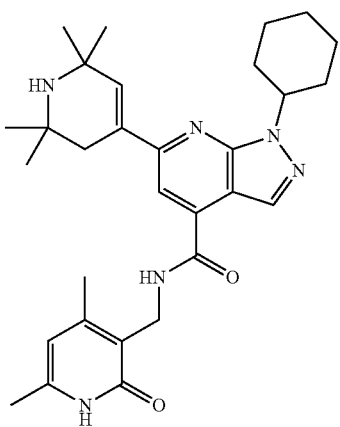 [SMILES: Cc1cc(C)c(CNC(=O)c2cc(C3=CC(C)(C)NC(C)(C)C3)nc3c2cnn3C2CCCCC2)c(=O)[nH]1] |

TABLE 2-continued

| Compound Number | Structure |
|---|---|
| B-17 | 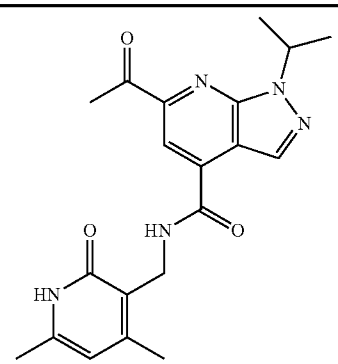 |
| B-18 | 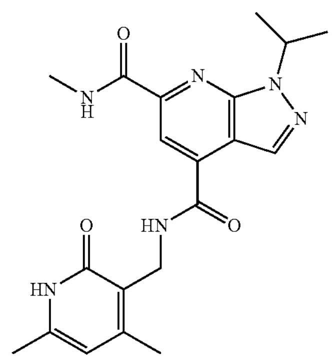 [SMILES: CNC(=O)c1cc(C(=O)NCc2c(C)cc(C)[nH]c2=O)c2cnn(C(C)C)c2n1] |
| B-19 | 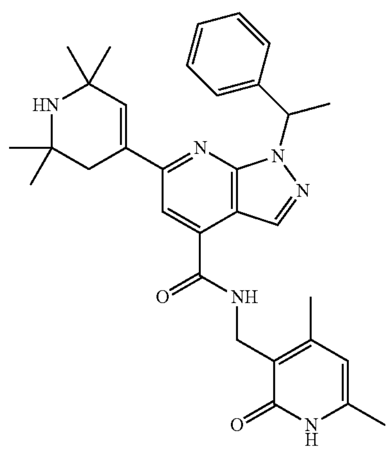 |
| B-20 | 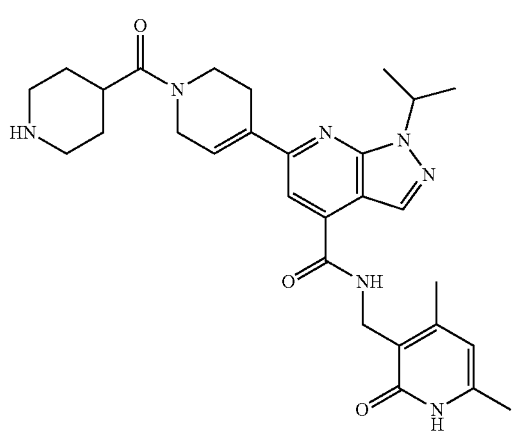 [SMILES: Cc1cc(C)c(CNC(=O)c2cc(C3=CCN(C(=O)C4CCNCC4)CC3)nc3c2cnn3C(C)C)c(=O)[nH]1] |

TABLE 2-continued
| Compound Number | Structure |
|---|---|
| B-21 | 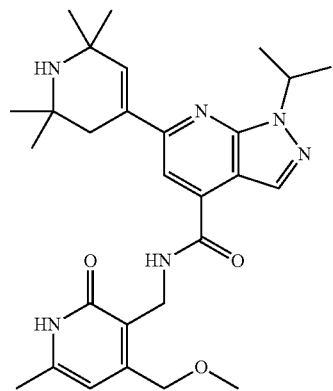 [SMILES: COCc1cc(C)[nH]c(=O)c1CNC(=O)c1cc(C2=CC(C)(C)NC(C)(C)C2)nc2c1cnn2C(C)C] |
| B-22 | 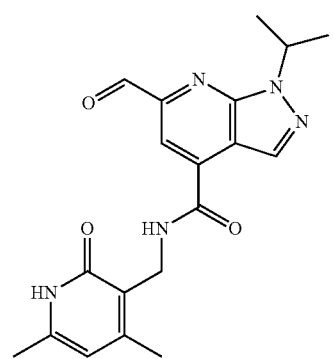 [SMILES: Cc1cc(C)c(CNC(=O)c2cc(C=O)nc3c2cnn3C(C)C)c(=O)[nH]1] |
| B-23 | 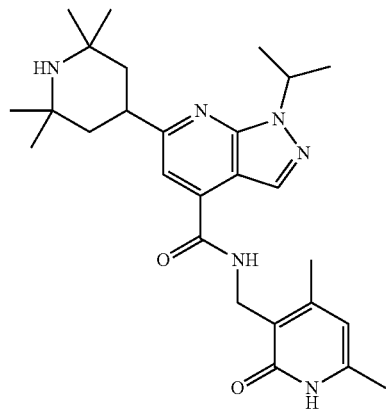 |
| B-24 | 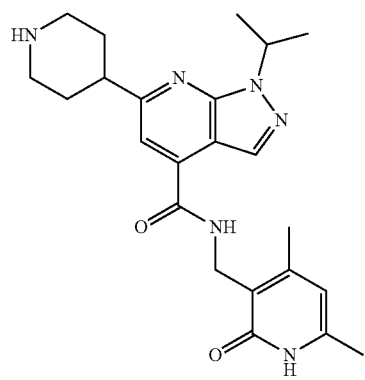 |

TABLE 2-continued
| Compound Number | Structure |
|---|---|
| B-25 | 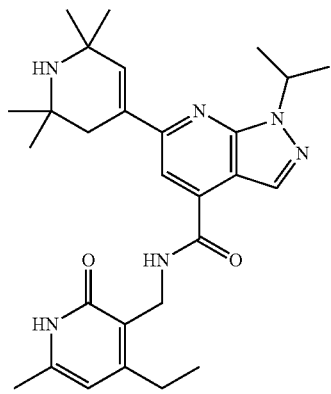 [SMILES: CCc1cc(C)[nH]c(=O)c1CNC(=O)c1cc(C2=CC(C)(C)NC(C)(C)C2)nc2c1cnn2C(C)C] |
| B-26 | 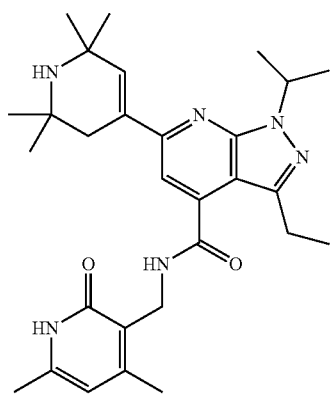 [SMILES: CCc1nn(C(C)C)c2nc(C3=CC(C)(C)NC(C)(C)C3)cc(C(=O)NCc3c(C)cc(C)[nH]c3=O)c12] |
| B-27 | 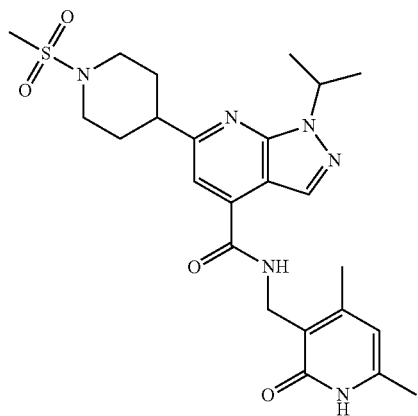 |

TABLE 2-continued
| Compound Number | Structure |
|---|---|
| B-28 | 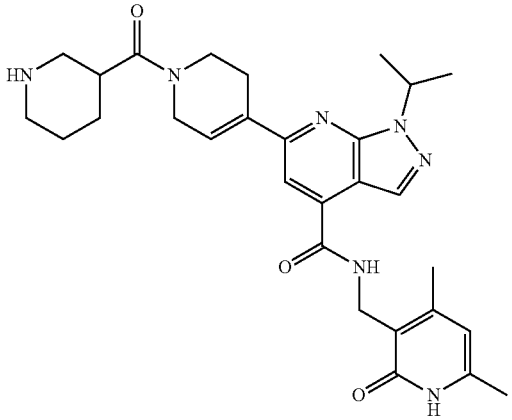 [SMILES: Cc1cc(C)c(CNC(=O)c2cc(C3=CCN(C(=O)C4CCCNC4)CC3)nc3c2cnn3C(C)C)c(=O)[nH]1] |
| B-29 | 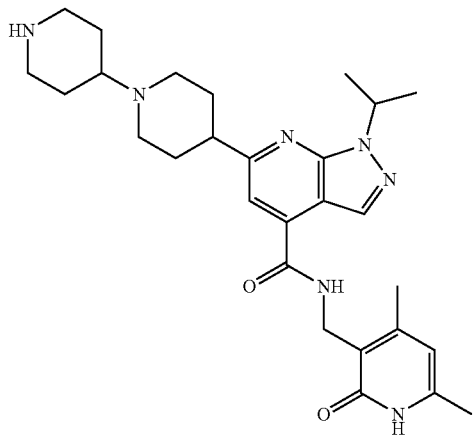 |
| B-30 | 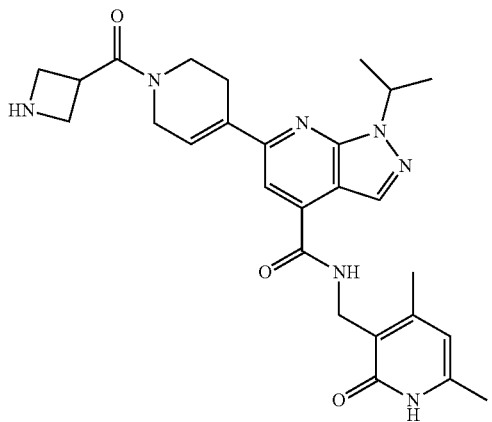 [SMILES: Cc1cc(C)c(CNC(=O)c2cc(C3=CCN(C(=O)C4CNC4)CC3)nc3c2cnn3C(C)C)c(=O)[nH]1] |

115 116
TABLE 2-continued
| Compound Number | Structure |
|---|---|
| B-31 | 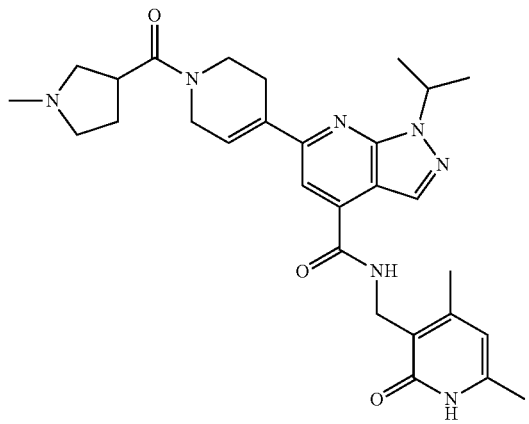 |
| B-32 | 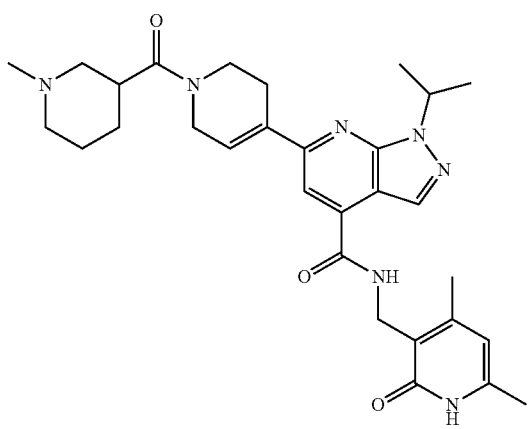 |
| B-33 | 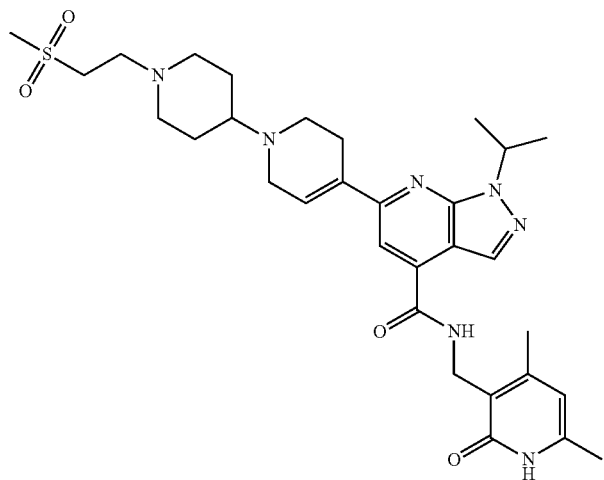 |

TABLE 2-continued

| Compound Number | Structure |
|---|---|
| B-34 | 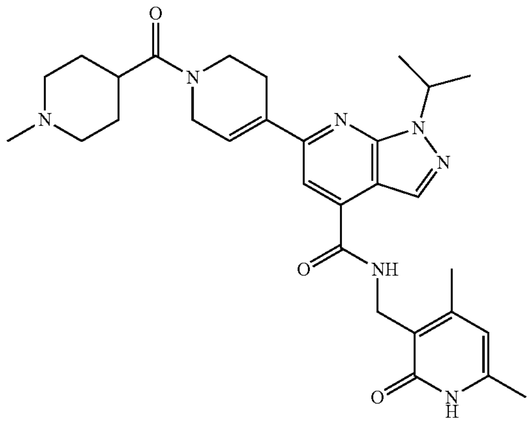 |
| B-35 | 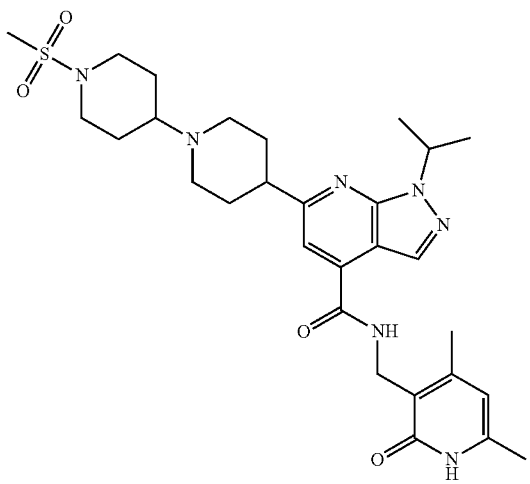 |
| B-36 | 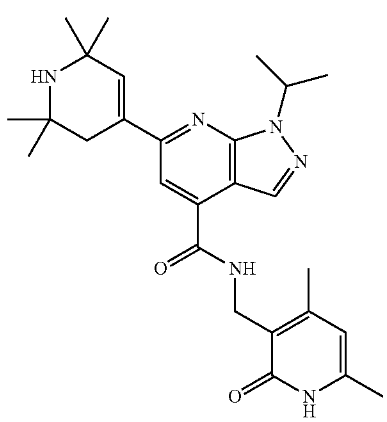 |

TABLE 2-continued
| Compound Number | Structure |
|---|---|
| B-37 | 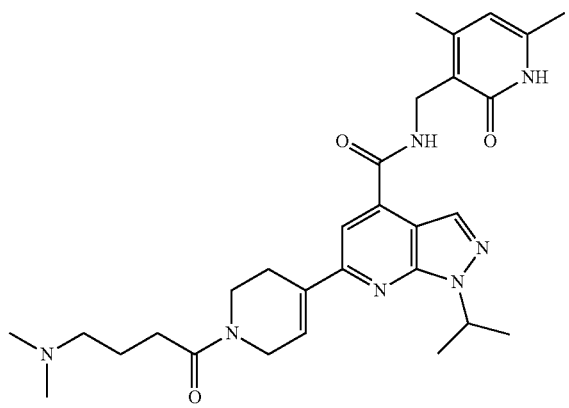 |
| B-38 | 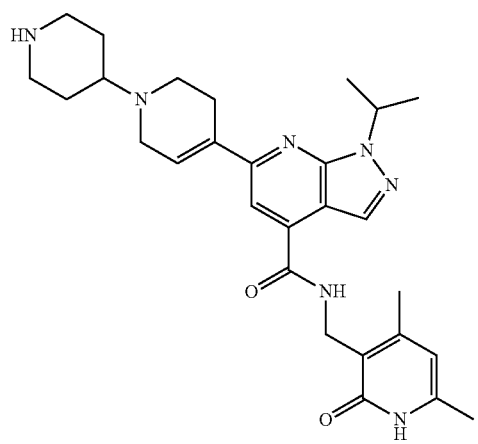 [SMILES: Cc1cc(C)c(CNC(=O)c2cc(C3=CCN(C4CCNCC4)CC3)nc3c2cnn3C(C)C)c(=O)[nH]1] |
| B-39 | 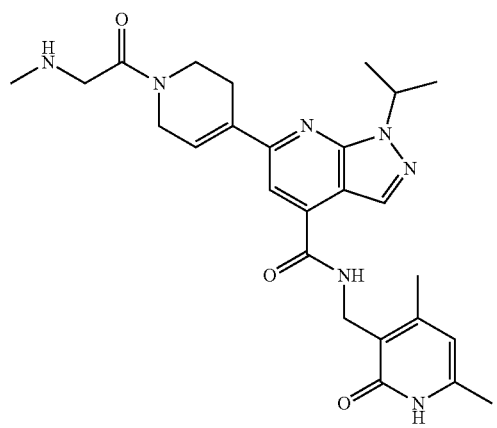 |

TABLE 2-continued
| Compound Number | Structure |
|---|---|
| B-40 | 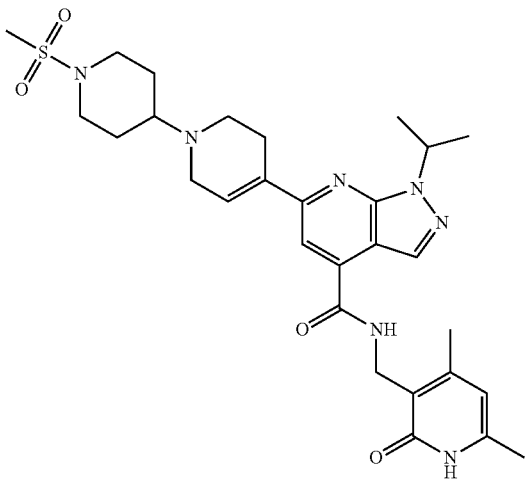 |
| B-41 | 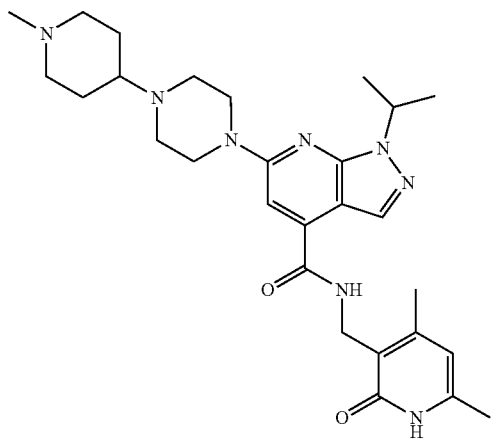 |
| B-42 | 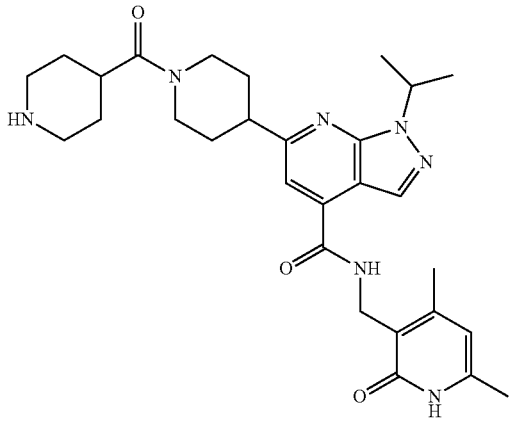 [SMILES: Cc1cc(C)c(CNC(=O)c2cc(C3CCN(C(=O)C4CCNCC4)CC3)nc3c2cnn3C(C)C)c(=O)[nH]1] |

TABLE 2-continued
| Compound Number | Structure |
|---|---|
| B-43 | 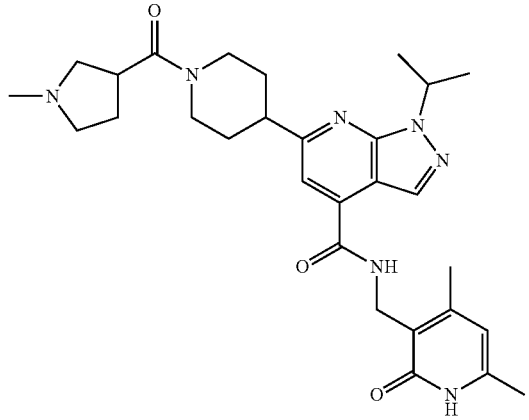 |
| B-44 | 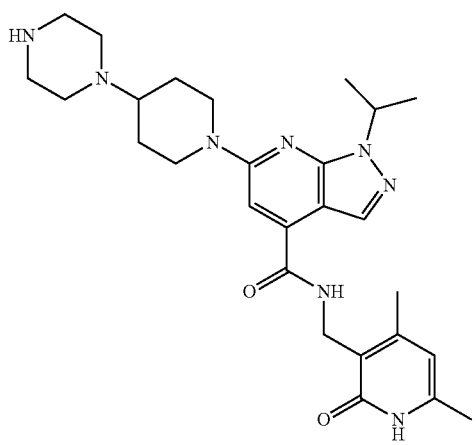 [SMILES: Cc1cc(C)c(CNC(=O)c2cc(N3CCC(N4CCNCC4)CC3)nc3c2cnn3C(C)C)c(=O)[nH]1] |
| B-45 | 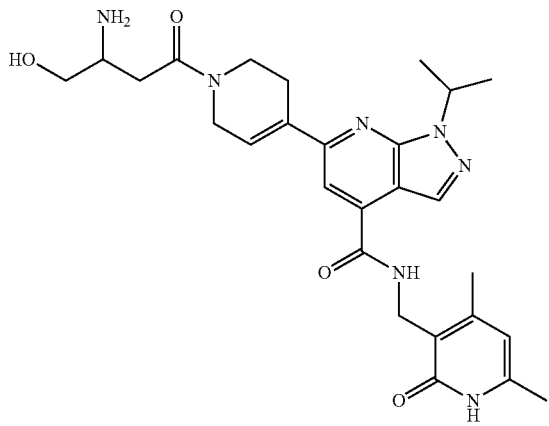 [SMILES: Cc1cc(C)c(CNC(=O)c2cc(C3=CCN(C(=O)CC(N)CO)CC3)nc3c2cnn3C(C)C)c(=O)[nH]1] |

TABLE 2-continued
| Compound Number | Structure |
|---|---|
| B-46 | 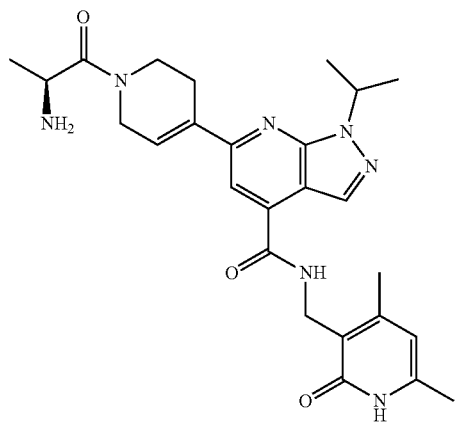 [SMILES: Cc1cc(C)c(CNC(=O)c2cc(C3=CCN(C(=O)[C@H](C)N)CC3)nc3c2cnn3C(C)C)c(=O)[nH]1] |
| B-47 | 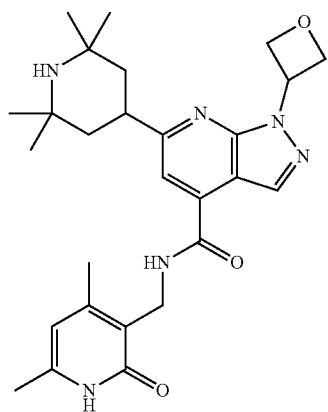 [SMILES: Cc1cc(C)c(CNC(=O)c2cc(C3CC(C)(C)NC(C)(C)C3)nc3c2cnn3C2COC2)c(=O)[nH]1] |
| B-48 | 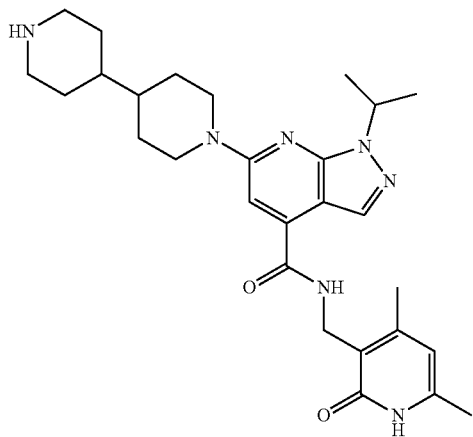 [SMILES: Cc1cc(C)c(CNC(=O)c2cc(N3CCC(C4CCNCC4)CC3)nc3c2cnn3C(C)C)c(=O)[nH]1] |

TABLE 2-continued
| Compound Number | Structure |
|---|---|
| B-49 | 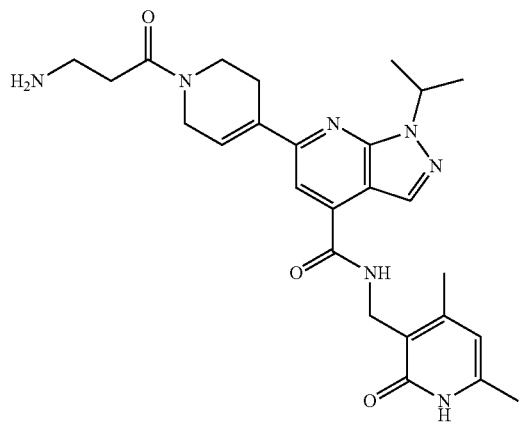 [SMILES: Cc1cc(C)c(CNC(=O)c2cc(C3=CCN(C(=O)CCN)CC3)nc3c2cnn3C(C)C)c(=O)[nH]1] |
| B-50 | 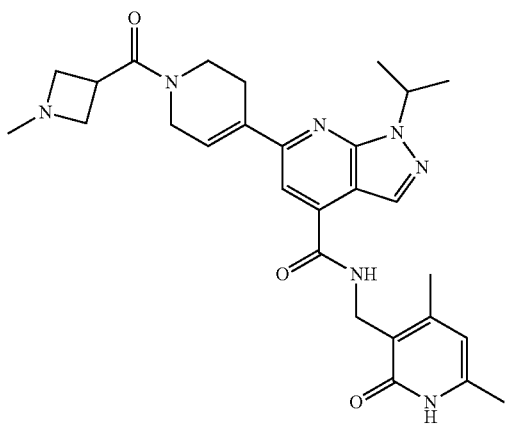 |
| B-51 | 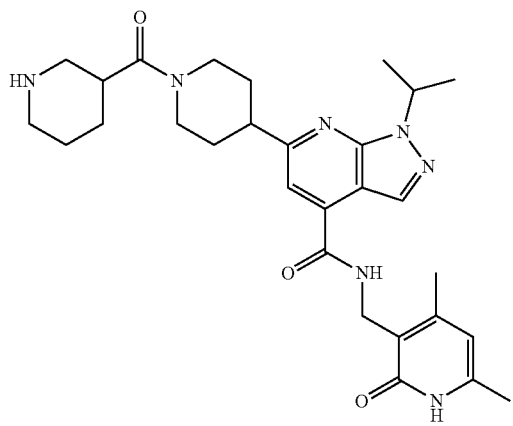 [SMILES: Cc1cc(C)c(CNC(=O)c2cc(C3CCN(C(=O)C4CCCNC4)CC3)nc3c2cnn3C(C)C)c(=O)[nH]1] |

TABLE 2-continued
| Compound Number | Structure |
|---|---|
| B-52 | 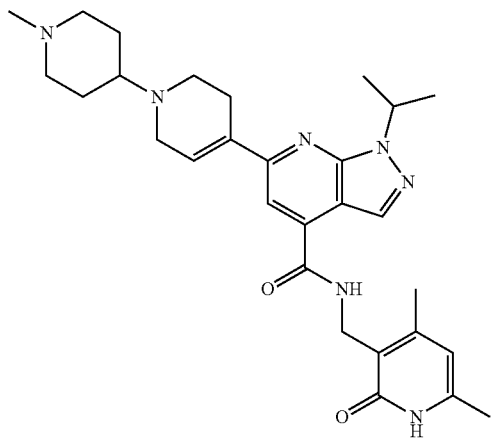 |
| B-53 | 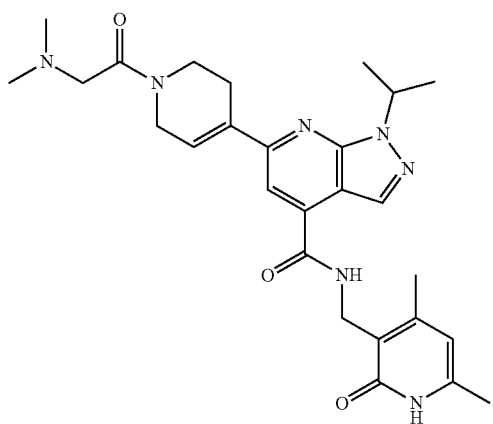 |
| B-54 | 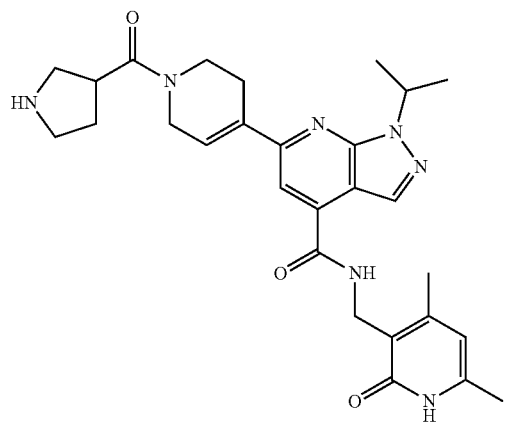 [SMILES: Cc1cc(C)c(CNC(=O)c2cc(C3=CCN(C(=O)C4CCNC4)CC3)nc3c2cnn3C(C)C)c(=O)[nH]1] |

TABLE 2-continued
| Compound Number | Structure |
|---|---|
| B-55 | 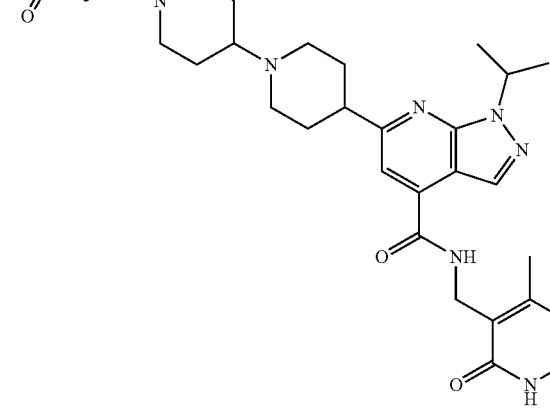 |
| B-56 | 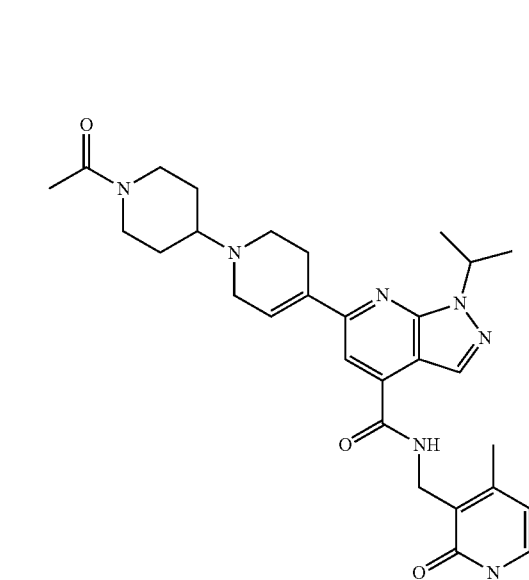 |
| B-57 | 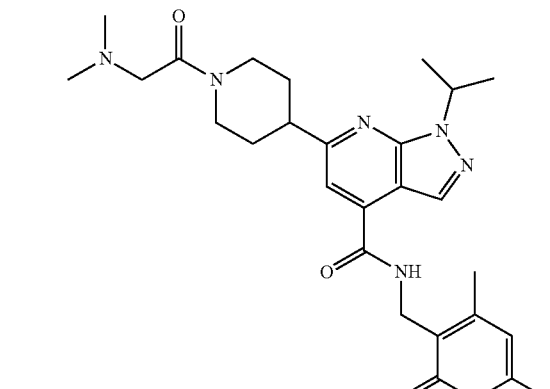 |

TABLE 2-continued
| Compound Number | Structure |
|---|---|
| B-58 | 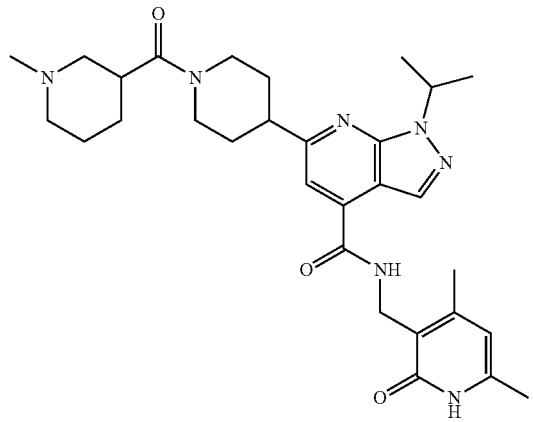 |
| B-59 | 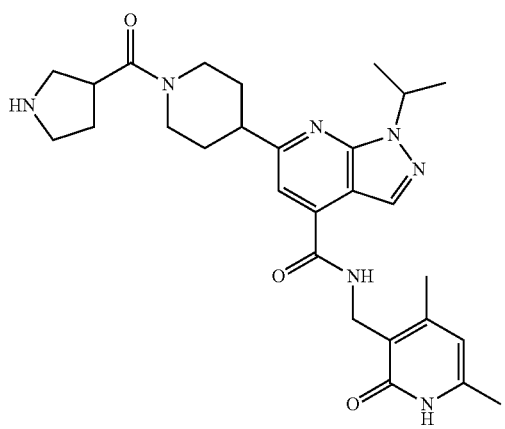 |
| B-60 | 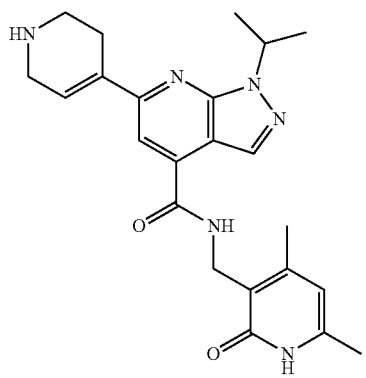 [SMILES: Cc1cc(C)c(CNC(=O)c2cc(C3=CCNCC3)nc3c2cnn3C(C)C)c(=O)[nH]1] |

135
136
TABLE 2-continued
| Compound Number | Structure |
|---|---|
| B-61 | 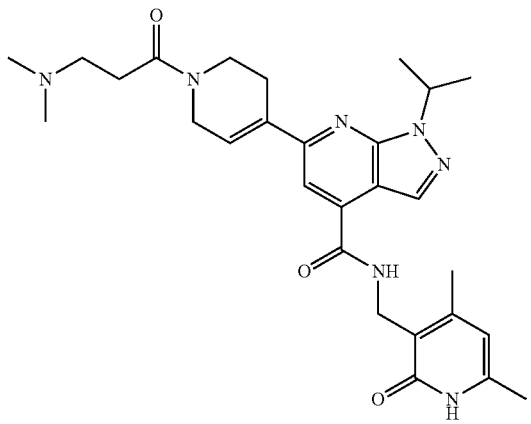 |
| B-62 | 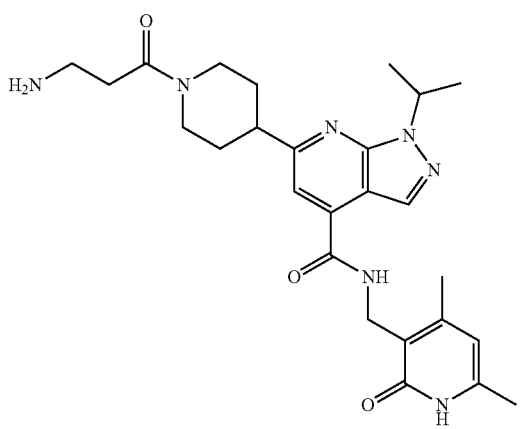 [SMILES: Cc1cc(C)c(CNC(=O)c2cc(C3CCN(C(=O)CCN)CC3)nc3c2cnn3C(C)C)c(=O)[nH]1] |
| B-63 | 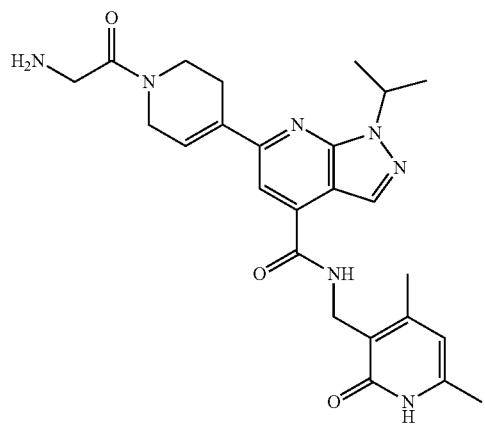 [SMILES: Cc1cc(C)c(CNC(=O)c2cc(C3=CCN(C(=O)CN)CC3)nc3c2cnn3C(C)C)c(=O)[nH]1] |

TABLE 2-continued
| Compound Number | Structure |
|---|---|
| B-64 | 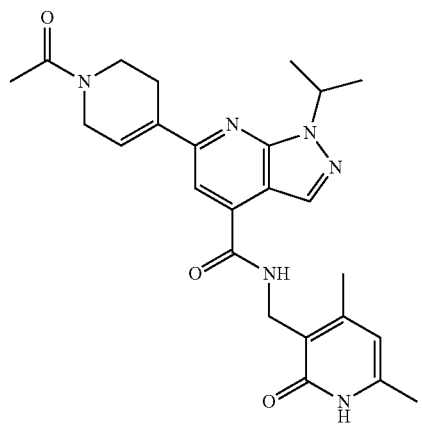 [SMILES: CC(=O)N1CC=C(c2cc(C(=O)NCc3c(C)cc(C)[nH]c3=O)c3cnn(C(C)C)c3n2)CC1] |
| B-65 | 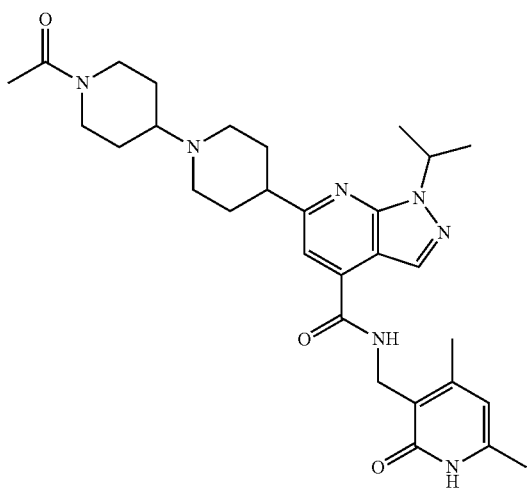 [SMILES: CC(=O)N1CCC(N2CCC(c3cc(C(=O)NCc4c(C)cc(C)[nH]c4=O)c4cnn(C(C)C)c4n3)CC2)CC1] |
| B-66 | 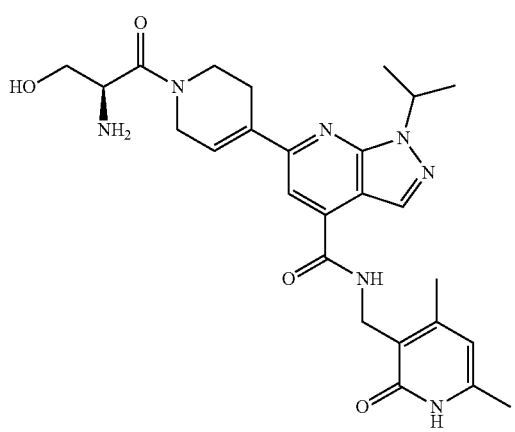 [SMILES: Cc1cc(C)c(CNC(=O)c2cc(C3=CCN(C(=O)[C@@H](N)CO)CC3)nc3c2cnn3C(C)C)c(=O)[nH]1] |

TABLE 2-continued
| Compound Number | Structure |
|---|---|
| B-67 | 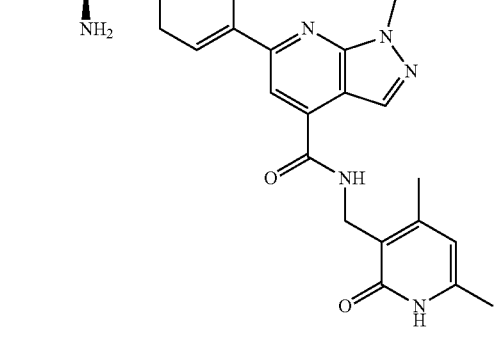 |
| B-68 | 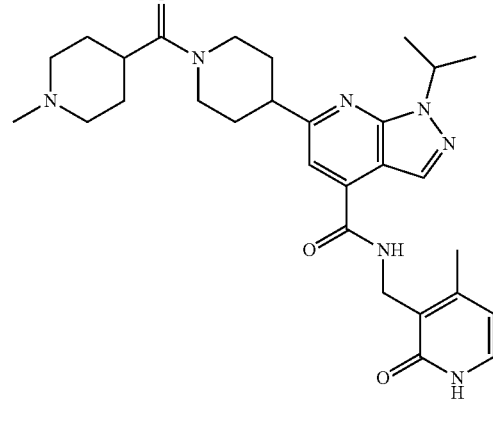 |
| B-69 | 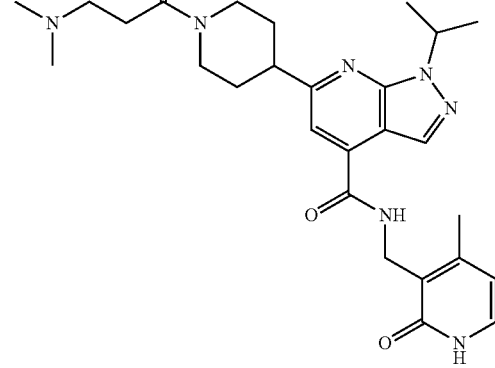 |

141
TABLE 2-continued
| Compound Number | Structure |
| --- | --- |
| B-70 | 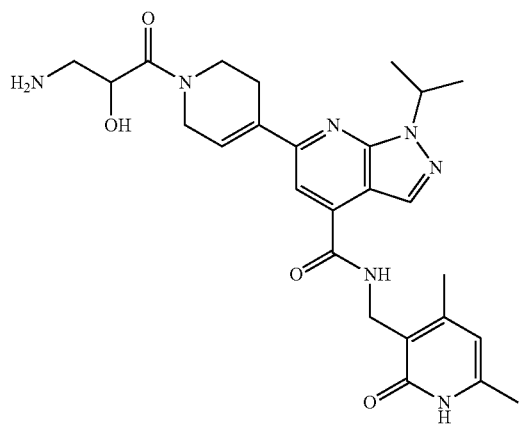 [SMILES: Cc1cc(C)c(CNC(=O)c2cc(C3=CCN(C(=O)C(O)CN)CC3)nc3c2cnn3C(C)C)c(=O)[nH]1] |
| B-71 | 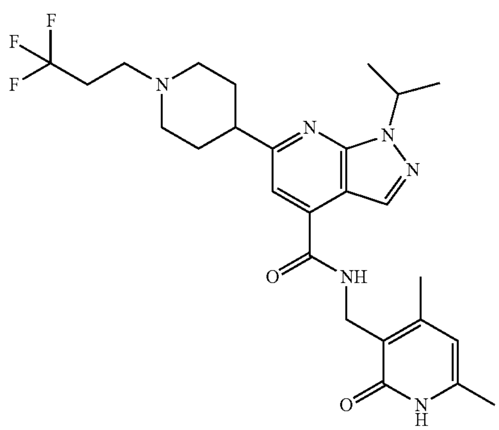 [SMILES: Cc1cc(C)c(CNC(=O)c2cc(C3CCN(CCC(F)(F)F)CC3)nc3c2cnn3C(C)C)c(=O)[nH]1] |
| B-72 | 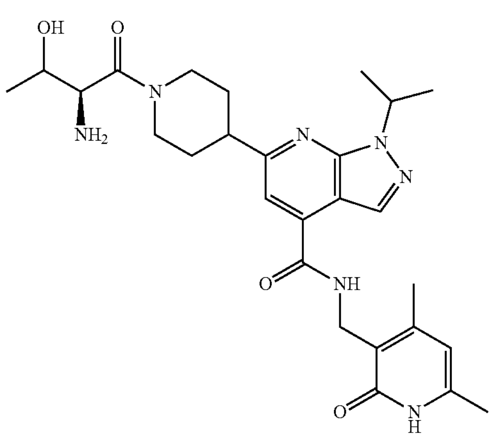 [SMILES: Cc1cc(C)c(CNC(=O)c2cc(C3CCN(C(=O)[C@@H](N)C(C)O)CC3)nc3c2cnn3C(C)C)c(=O)[nH]1] |

TABLE 2-continued
| Compound Number | Structure |
|---|---|
| B-73 | 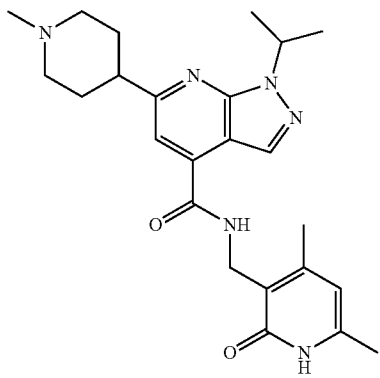 |
| B-74 | 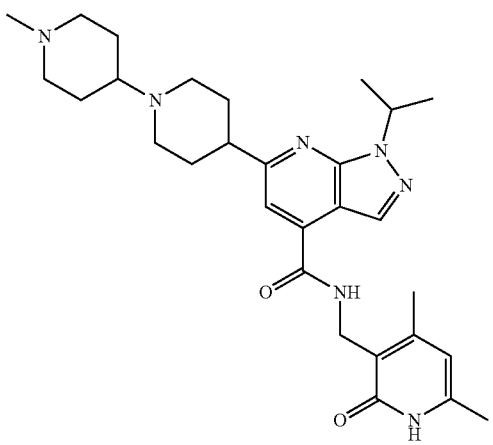 |
| B-75 | 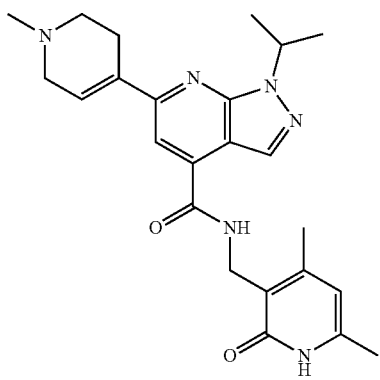 |

TABLE 2-continued
| Compound Number | Structure |
|---|---|
| B-76 | 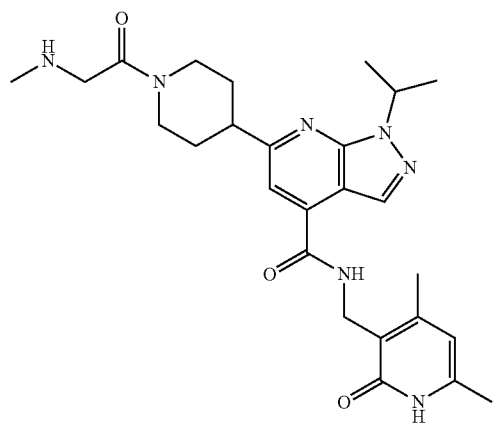 |
| B-77 | 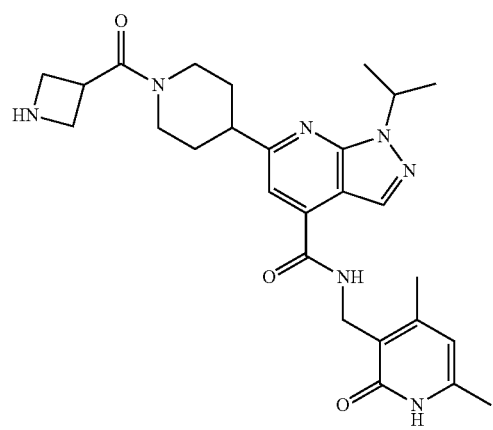 [SMILES: Cc1cc(C)c(CNC(=O)c2cc(C3CCN(C(=O)C4CNC4)CC3)nc3c2cnn3C(C)C)c(=O)[nH]1] |
| B-78 | 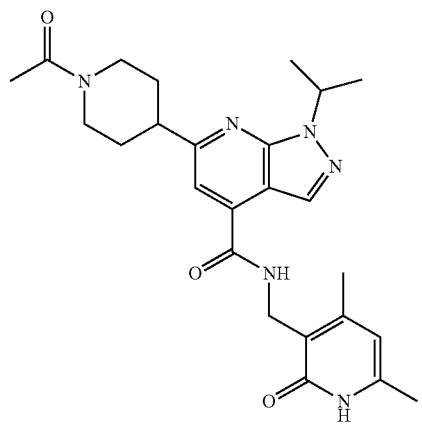 |

TABLE 2-continued

| Compound Number | Structure |
|---|---|
| B-79 | 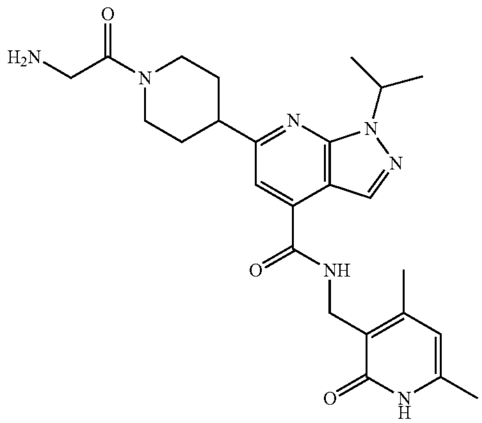 [SMILES: Cc1cc(C)c(CNC(=O)c2cc(C3CCN(C(=O)CN)CC3)nc3c2cnn3C(C)C)c(=O)[nH]1] |
| B-80 | 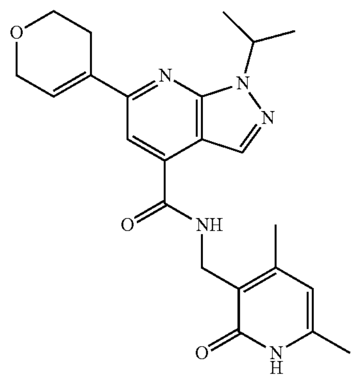 [SMILES: Cc1cc(C)c(CNC(=O)c2cc(C3=CCOCC3)nc3c2cnn3C(C)C)c(=O)[nH]1] |
| B-81 | 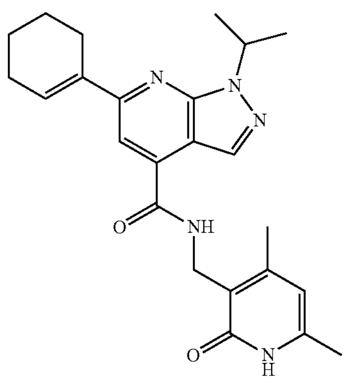 [SMILES: Cc1cc(C)c(CNC(=O)c2cc(C3=CCCCC3)nc3c2cnn3C(C)C)c(=O)[nH]1] |
| B-82 | 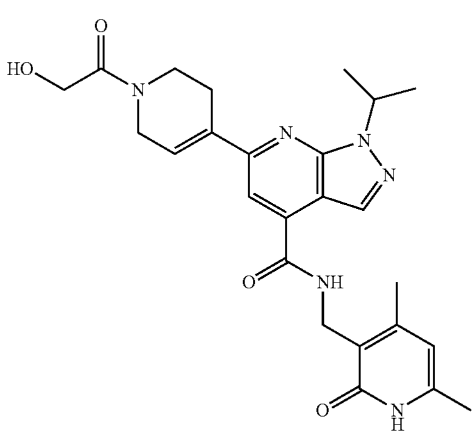 [SMILES: Cc1cc(C)c(CNC(=O)c2cc(C3=CCN(C(=O)CO)CC3)nc3c2cnn3C(C)C)c(=O)[nH]1] |

TABLE 2-continued
| Compound Number | Structure |
|---|---|
| B-83 | 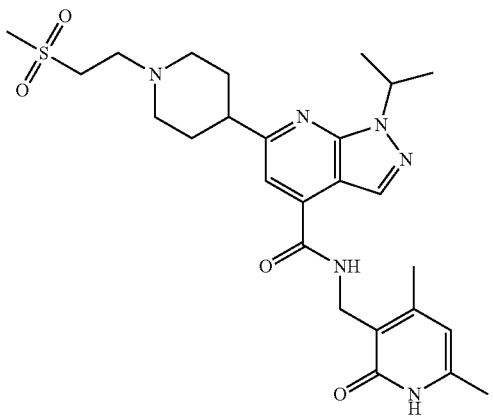 |
| B-84 | 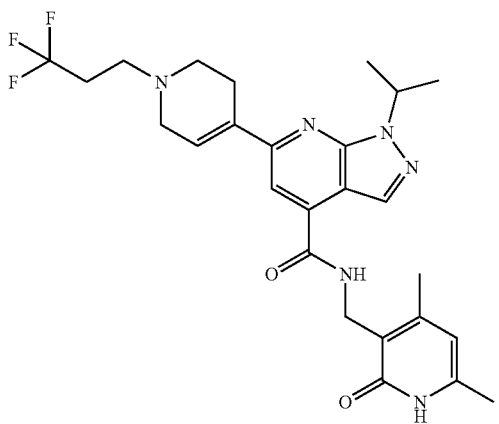 [SMILES: Cc1cc(C)c(CNC(=O)c2cc(C3=CCN(CCC(F)(F)F)CC3)nc3c2cnn3C(C)C)c(=O)[nH]1] |
| B-85 | 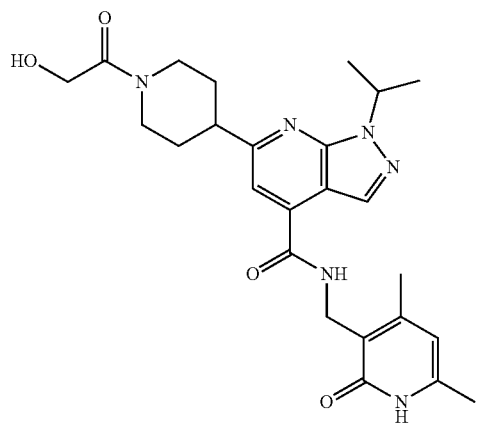 [SMILES: Cc1cc(C)c(CNC(=O)c2cc(C3CCN(C(=O)CO)CC3)nc3c2cnn3C(C)C)c(=O)[nH]1] |

TABLE 2-continued
| Compound Number | Structure |
| --- | --- |
| B-86 | 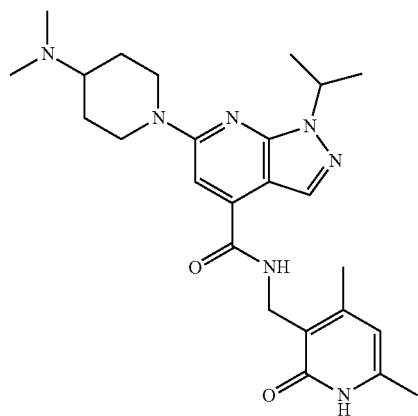 |
| B-87 | 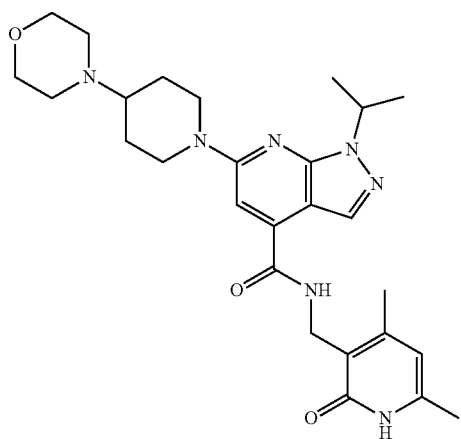 [SMILES: Cc1cc(C)c(CNC(=O)c2cc(N3CCC(N4CCOCC4)CC3)nc3c2cnn3C(C)C)c(=O)[nH]1] |
| B-88 | 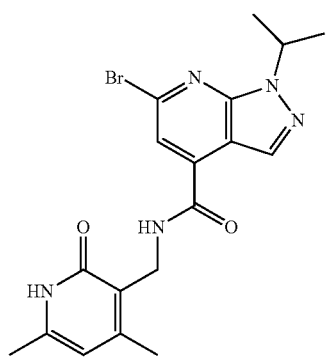 [SMILES: Cc1cc(C)c(CNC(=O)c2cc(Br)nc3c2cnn3C(C)C)c(=O)[nH]1] |

TABLE 2-continued
| Compound Number | Structure |
|---|---|
| B-89 | 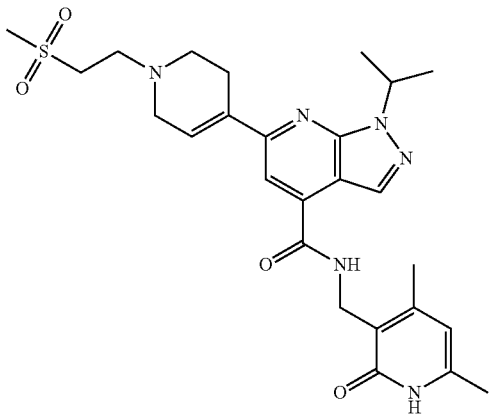 |
| B-90 | 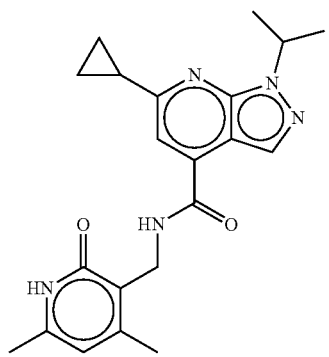 |
| B-91 | 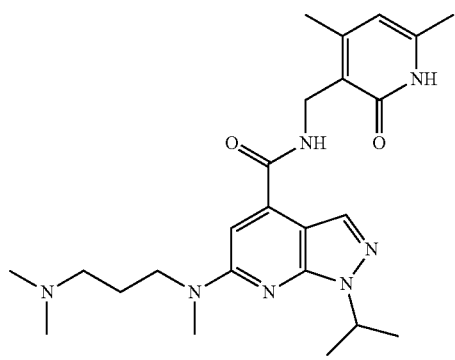 |
| B-92 | 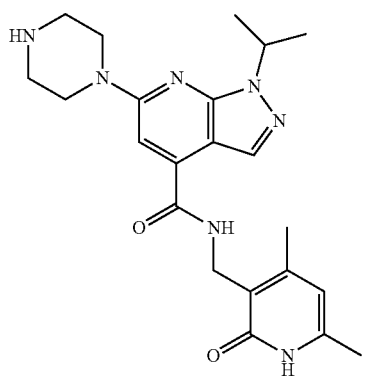 [SMILES: Cc1cc(C)c(CNC(=O)c2cc(N3CCNCC3)nc3c2cnn3C(C)C)c(=O)[nH]1] |

TABLE 2-continued

| Compound Number | Structure |
|---|---|
| B-93 | 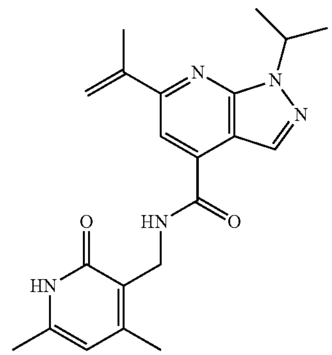 [SMILES: C=C(C)c1cc(C(=O)NCc2c(C)cc(C)[nH]c2=O)c2cnn(C(C)C)c2n1] |
| B-94 | 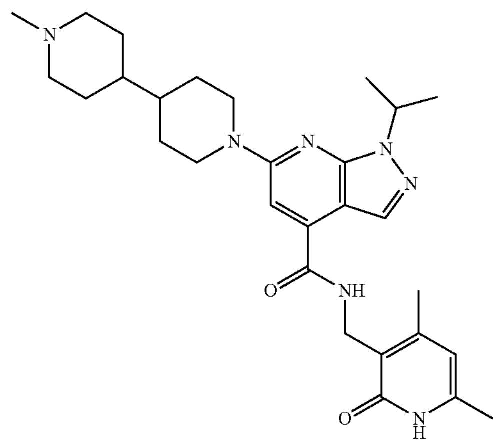 |
| B-95 | 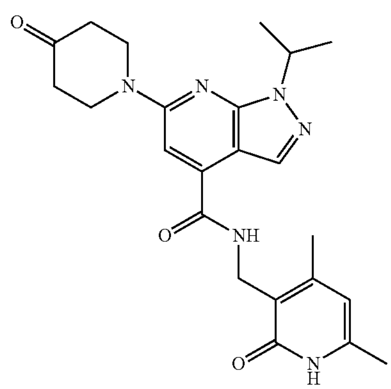 [SMILES: Cc1cc(C)c(CNC(=O)c2cc(N3CCC(=O)CC3)nc3c2cnn3C(C)C)c(=O)[nH]1] |
| B-96 | 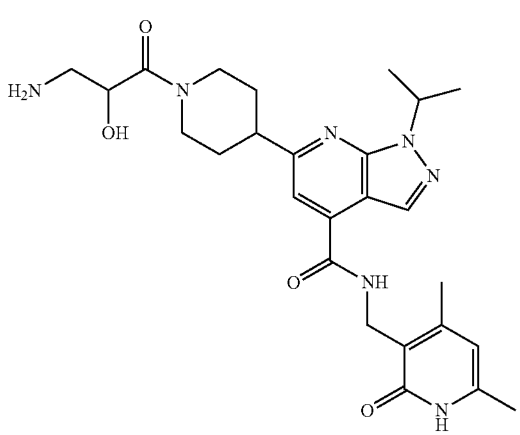 [SMILES: Cc1cc(C)c(CNC(=O)c2cc(C3CCN(C(=O)C(O)CN)CC3)nc3c2cnn3C(C)C)c(=O)[nH]1] |

TABLE 2-continued
| Compound Number | Structure |
|---|---|
| B-97 | 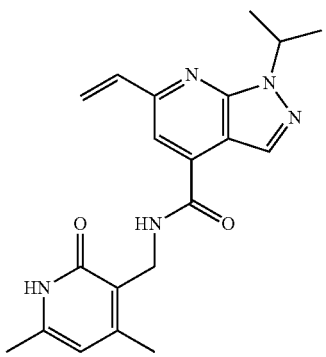 [SMILES: C=Cc1cc(C(=O)NCc2c(C)cc(C)[nH]c2=O)c2cnn(C(C)C)c2n1] |
| B-98 | 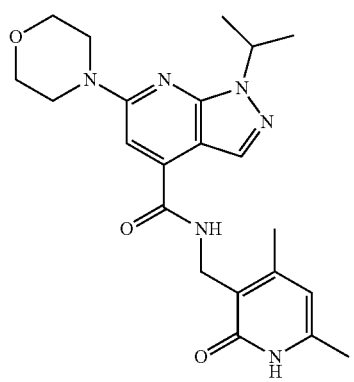 |
| B-99 | 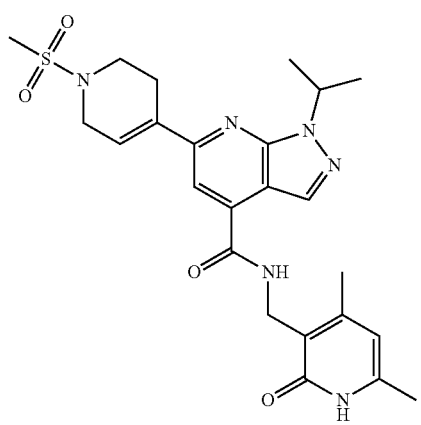 |
| B-100 | 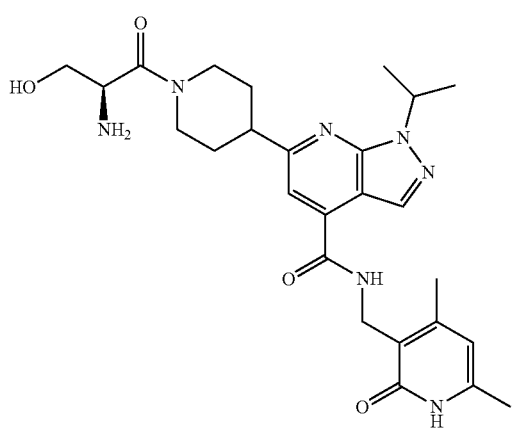 [SMILES: Cc1cc(C)c(CNC(=O)c2cc(C3CCN(C(=O)[C@@H](N)CO)CC3)nc3c2cnn3C(C)C)c(=O)[nH]1] |

TABLE 2-continued
| Compound Number | Structure |
|---|---|
| B-101 | 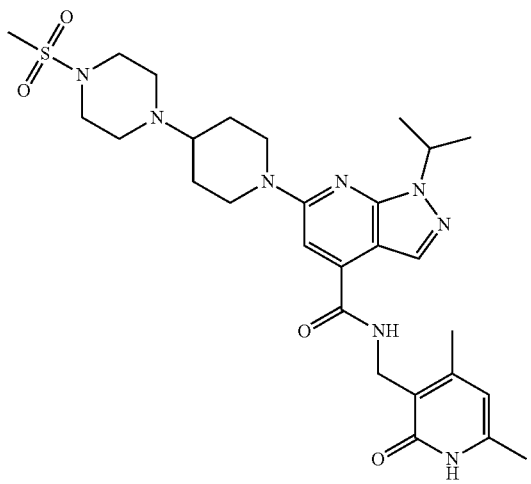 |
| B-102 | 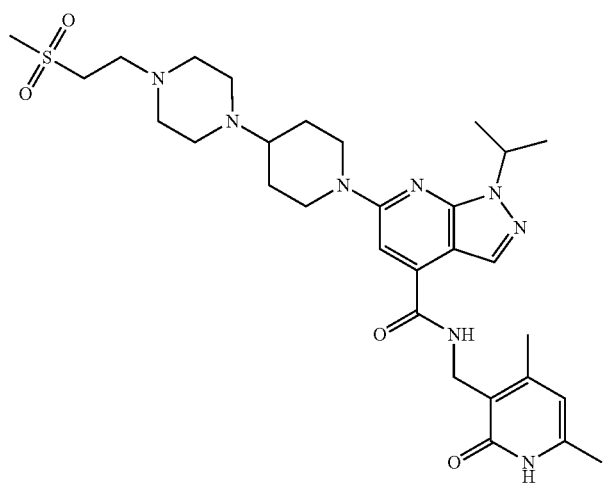 |
| B-103 | 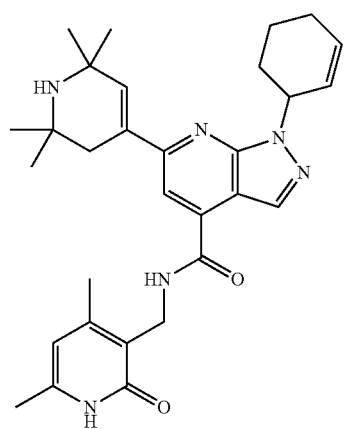 [SMILES: Cc1cc(C)c(CNC(=O)c2cc(C3=CC(C)(C)NC(C)(C)C3)nc3c2cnn3C2C=CCCC2)c(=O)[nH]1] |

TABLE 2-continued
| Compound Number | Structure |
|---|---|
| B-104 | 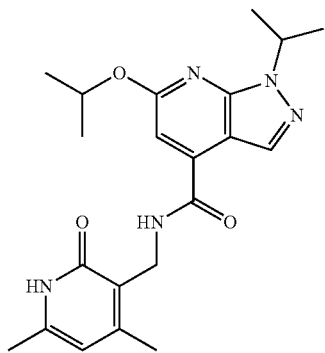 [SMILES: Cc1cc(C)c(CNC(=O)c2cc(OC(C)C)nc3c2cnn3C(C)C)c(=O)[nH]1] |
| B-105 | 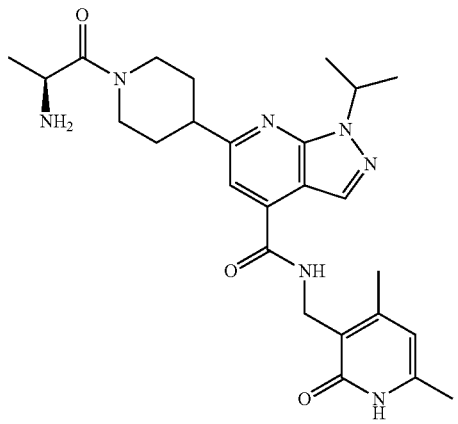 [SMILES: Cc1cc(C)c(CNC(=O)c2cc(C3CCN(C(=O)[C@H](C)N)CC3)nc3c2cnn3C(C)C)c(=O)[nH]1] |
| B-106 | 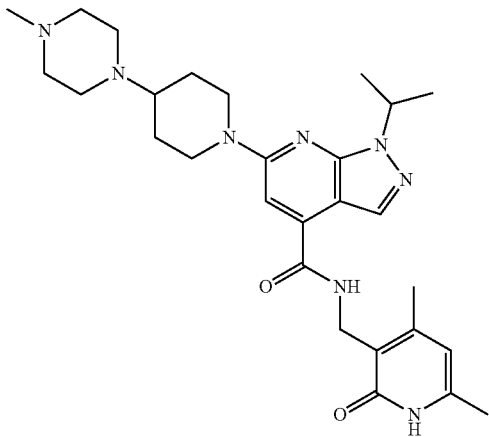 |

TABLE 2-continued
| Compound Number | Structure |
|---|---|
| B-107 | 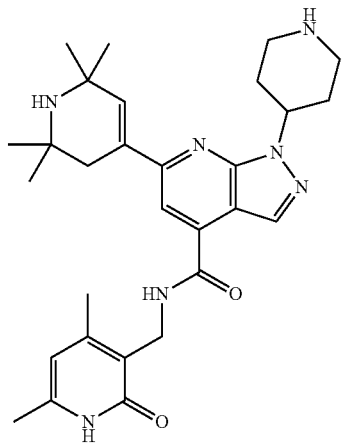 [SMILES: Cc1cc(C)c(CNC(=O)c2cc(C3=CC(C)(C)NC(C)(C)C3)nc3c2cnn3C2CCNCC2)c(=O)[nH]1] |
| B-108 | 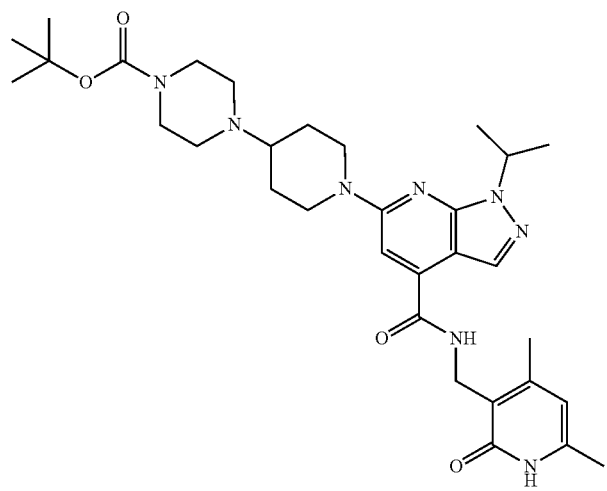 [SMILES: Cc1cc(C)c(CNC(=O)c2cc(N3CCC(N4CCN(C(=O)OC(C)(C)C)CC4)CC3)nc3c2cnn3C(C)C)c(=O)[nH]1] |
| B-109 | 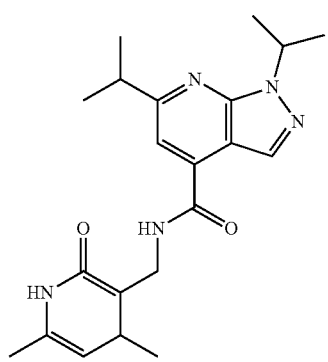 |

TABLE 2-continued
| Compound Number | Structure |
| --- | --- |
| B-110 | 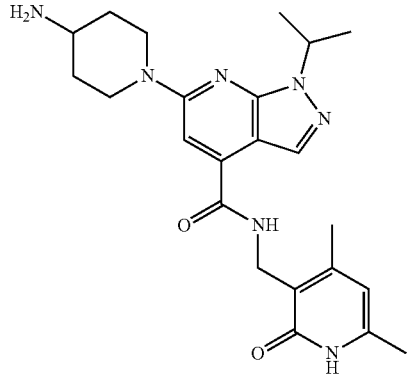 [SMILES: Cc1cc(C)c(CNC(=O)c2cc(N3CCC(N)CC3)nc3c2cnn3C(C)C)c(=O)[nH]1] |
| B-111 | 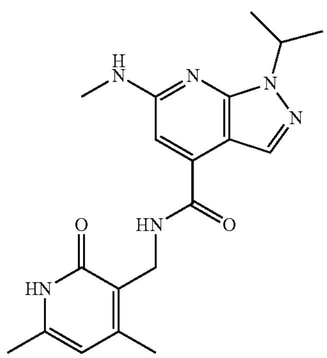 [SMILES: CNc1cc(C(=O)NCc2c(C)cc(C)[nH]c2=O)c2cnn(C(C)C)c2n1] |
| B-112 | 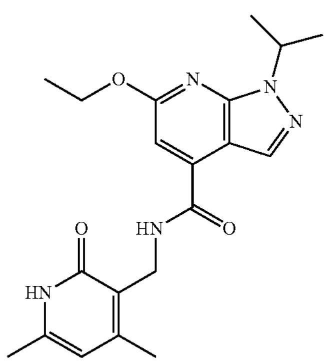 [SMILES: CCOc1cc(C(=O)NCc2c(C)cc(C)[nH]c2=O)c2cnn(C(C)C)c2n1] |
| B-113 | 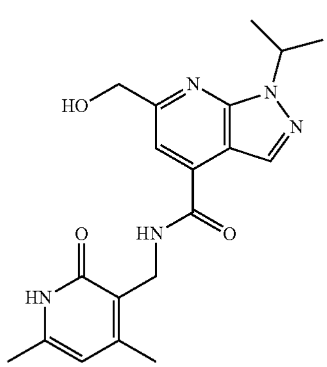 [SMILES: Cc1cc(C)c(CNC(=O)c2cc(CO)nc3c2cnn3C(C)C)c(=O)[nH]1] |

TABLE 2-continued
| Compound Number | Structure |
| --- | --- |
| B-114 | 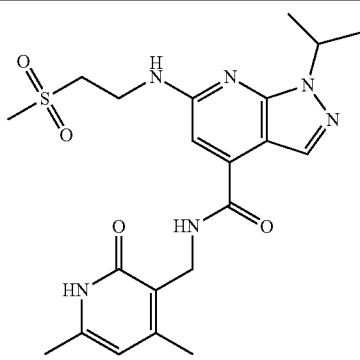 |
| B-115 | 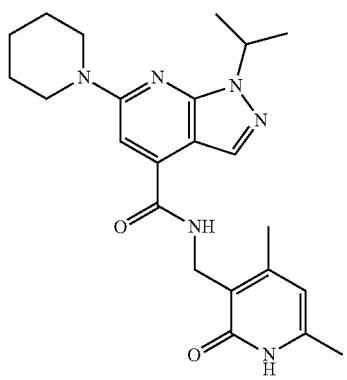 [SMILES: Cc1cc(C)c(CNC(=O)c2cc(N3CCCCC3)nc3c2cnn3C(C)C)c(=O)[nH]1] |
| B-116 | 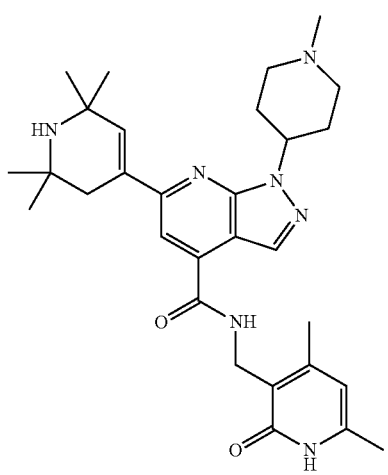 |
| B-117 | 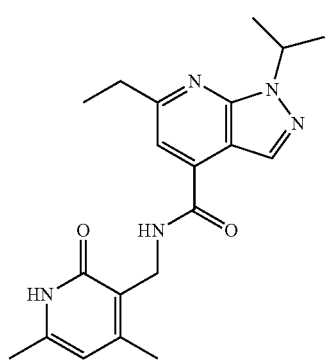 [SMILES: CCc1cc(C(=O)NCc2c(C)cc(C)[nH]c2=O)c2cnn(C(C)C)c2n1] |

TABLE 2-continued
| Compound Number | Structure |
|---|---|
| B-118 | 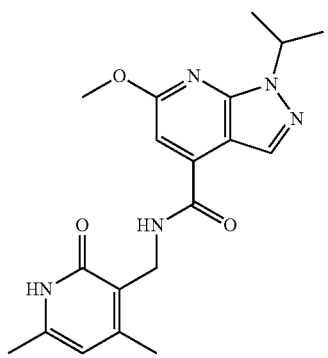 [SMILES: COc1cc(C(=O)NCc2c(C)cc(C)[nH]c2=O)c2cnn(C(C)C)c2n1] |
| B-119 | 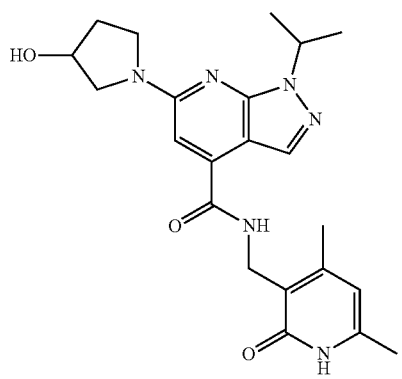 [SMILES: Cc1cc(C)c(CNC(=O)c2cc(N3CCC(O)C3)nc3c2cnn3C(C)C)c(=O)[nH]1] |
| B-120 | 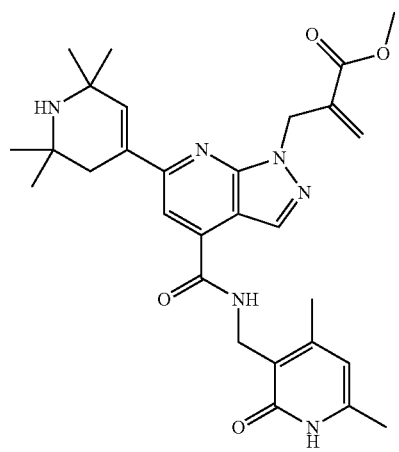 |
| B-121 | 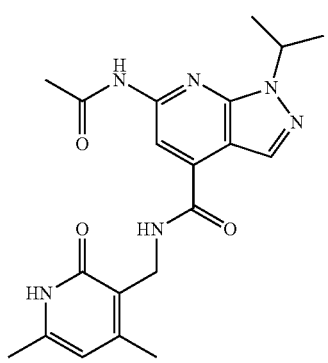 [SMILES: CC(=O)Nc1cc(C(=O)NCc2c(C)cc(C)[nH]c2=O)c2cnn(C(C)C)c2n1] |

TABLE 2-continued

| Compound Number | Structure |
|---|---|
| B-122 | 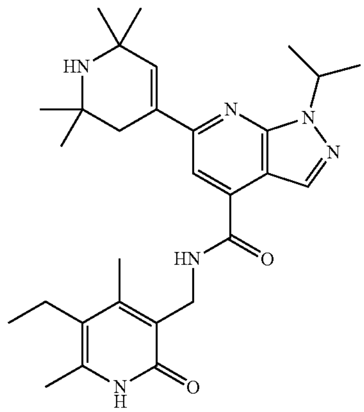 [SMILES: CCc1c(C)[nH]c(=O)c(CNC(=O)c2cc(C3=CC(C)(C)NC(C)(C)C3)nc3c2cnn3C(C)C)c1C] |
| B-123 | 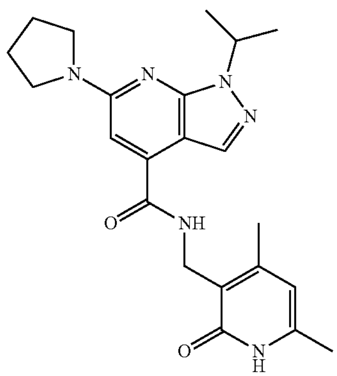 [SMILES: Cc1cc(C)c(CNC(=O)c2cc(N3CCCC3)nc3c2cnn3C(C)C)c(=O)[nH]1] |
| B-124 | 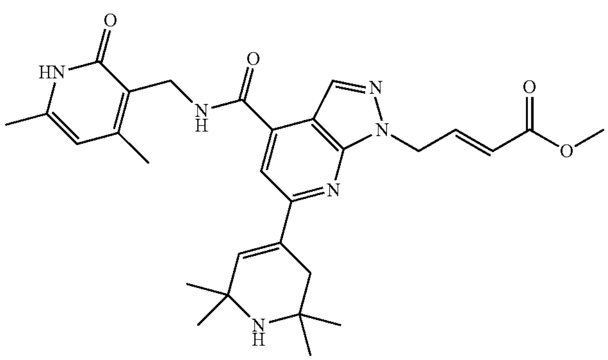 |
| B-125 | 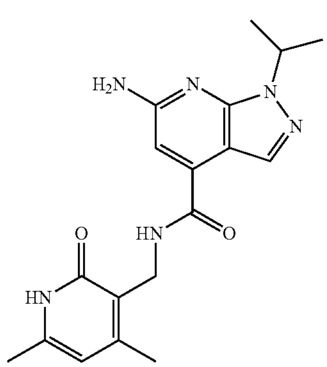 [SMILES: Cc1cc(C)c(CNC(=O)c2cc(N)nc3c2cnn3C(C)C)c(=O)[nH]1] |

TABLE 2-continued

| Compound Number | Structure |
|---|---|
| B-126 | 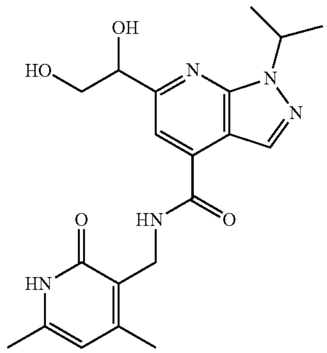 [SMILES: Cc1cc(C)c(CNC(=O)c2cc(C(O)CO)nc3c2cnn3C(C)C)c(=O)[nH]1] |
| B-127 | 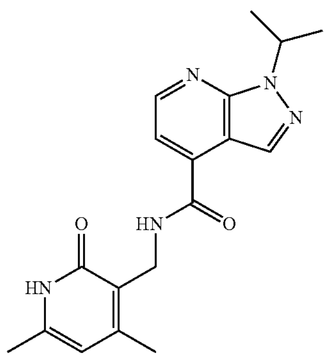 [SMILES: Cc1cc(C)c(CNC(=O)c2ccnc3c2cnn3C(C)C)c(=O)[nH]1] |
| B-128 | 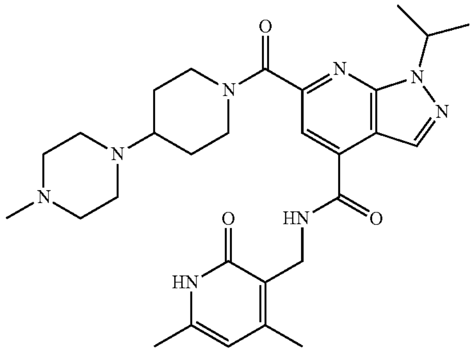 [SMILES: Cc1cc(C)c(CNC(=O)c2cc(C(=O)N3CCC(N4CCN(C)CC4)CC3)nc3c2cnn3C(C)C)c(=O)[nH]1] |
| B-129 | 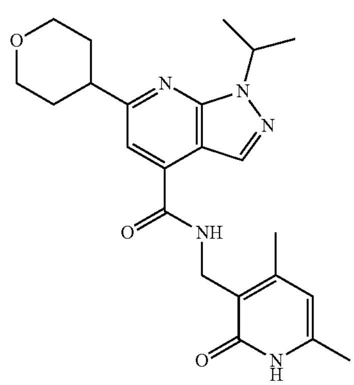 |

TABLE 2-continued
| Compound Number | Structure |
|---|---|
| B-130 | 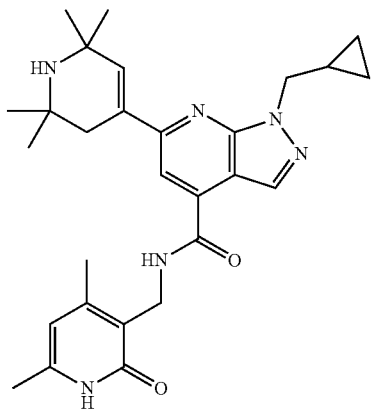 [SMILES: Cc1cc(C)c(CNC(=O)c2cc(C3=CC(C)(C)NC(C)(C)C3)nc3c2cnn3CC2CC2)c(=O)[nH]1] |
| B-131 | 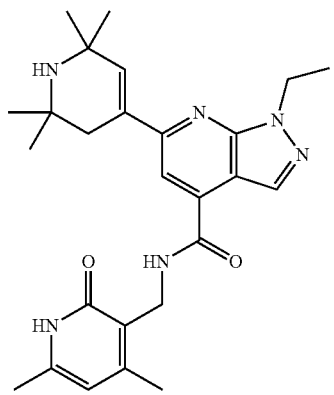 [SMILES: CCn1ncc2c(C(=O)NCc3c(C)cc(C)[nH]c3=O)cc(C3=CC(C)(C)NC(C)(C)C3)nc21] |
| B-132 | 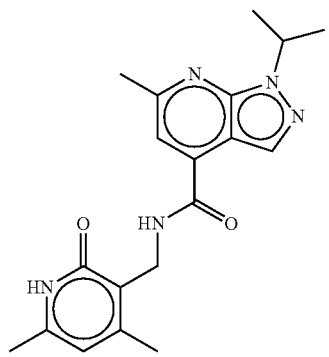 |
| B-133 | 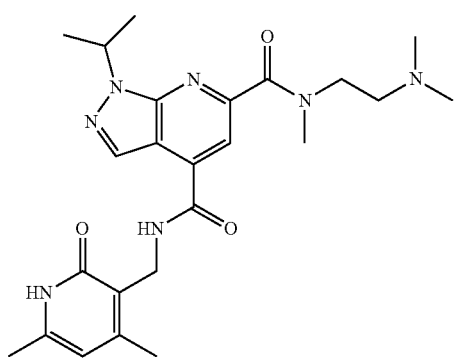 |

TABLE 2-continued

| Compound Number | Structure |
|---|---|
| B-134 | 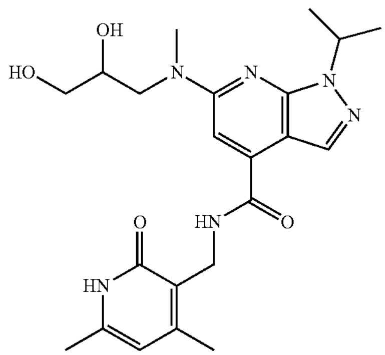 [SMILES: Cc1cc(C)c(CNC(=O)c2cc(N(C)CC(O)CO)nc3c2cnn3C(C)C)c(=O)[nH]1] |
| B-135 | 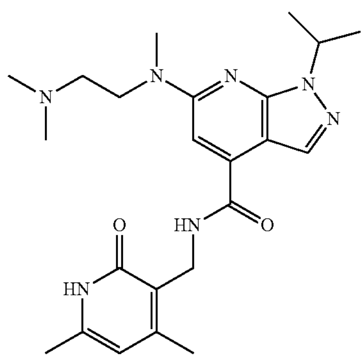 [SMILES: Cc1cc(C)c(CNC(=O)c2cc(N(C)CCN(C)C)nc3c2cnn3C(C)C)c(=O)[nH]1] |
| B-136 | 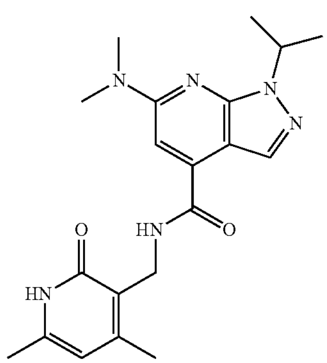 [SMILES: Cc1cc(C)c(CNC(=O)c2cc(N(C)C)nc3c2cnn3C(C)C)c(=O)[nH]1] |
| B-137 | 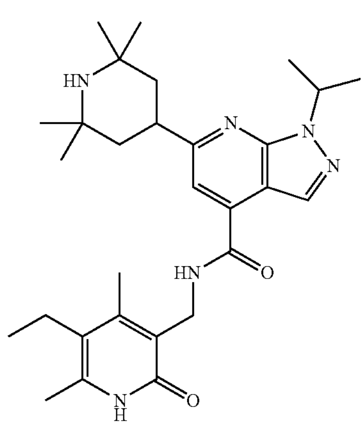 [SMILES: CCc1c(C)[nH]c(=O)c(CNC(=O)c2cc(C3CC(C)(C)NC(C)(C)C3)nc3c2cnn3C(C)C)c1C] |

TABLE 2-continued

| Compound Number | Structure |
|---|---|
| B-138 | 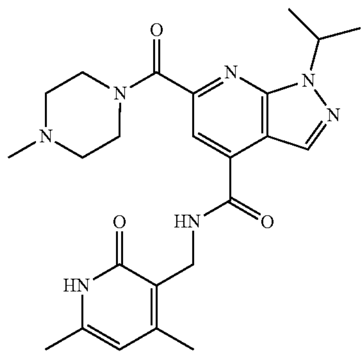 [SMILES: Cc1cc(C)c(CNC(=O)c2cc(C(=O)N3CCN(C)CC3)nc3c2cnn3C(C)C)c(=O)[nH]1] |
| B-139 | 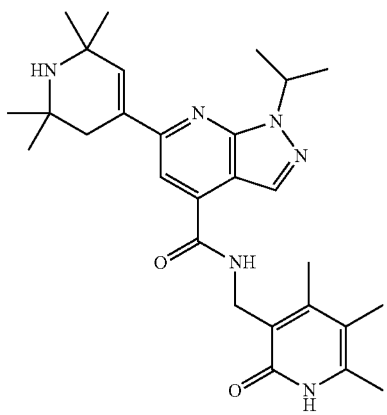 |
| B-140 | 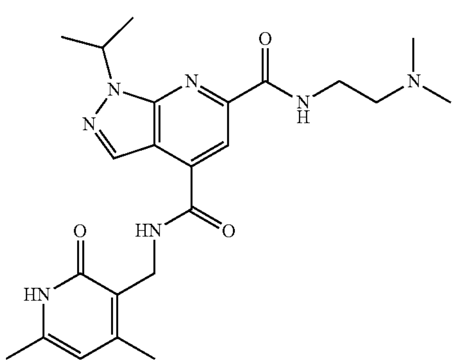 |
| B-141 | 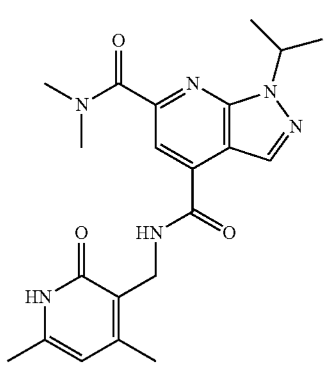 [SMILES: Cc1cc(C)c(CNC(=O)c2cc(C(=O)N(C)C)nc3c2cnn3C(C)C)c(=O)[nH]1] |

TABLE 2-continued
| Compound Number | Structure |
|---|---|
| B-142 | 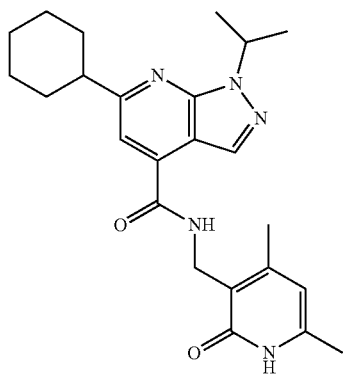 [SMILES: Cc1cc(C)c(CNC(=O)c2cc(C3CCCCC3)nc3c2cnn3C(C)C)c(=O)[nH]1] |
| B-143 | 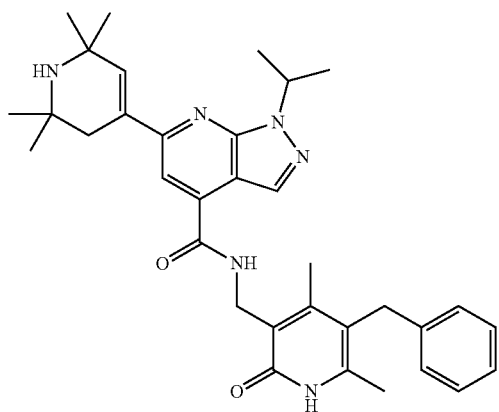 [SMILES: Cc1[nH]c(=O)c(CNC(=O)c2cc(C3=CC(C)(C)NC(C)(C)C3)nc3c2cnn3C(C)C)c(C)c1Cc1ccccc1] |
| B-144 | 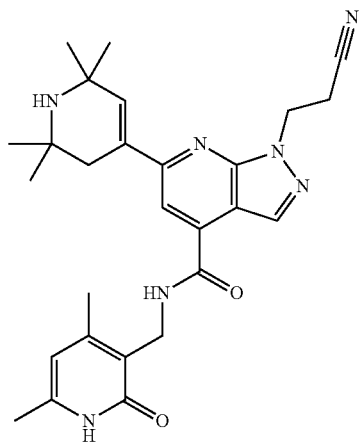 [SMILES: Cc1cc(C)c(CNC(=O)c2cc(C3=CC(C)(C)NC(C)(C)C3)nc3c2cnn3CCC#N)c(=O)[nH]1] |

TABLE 2-continued
| Compound Number | Structure |
|---|---|
| B-145 | 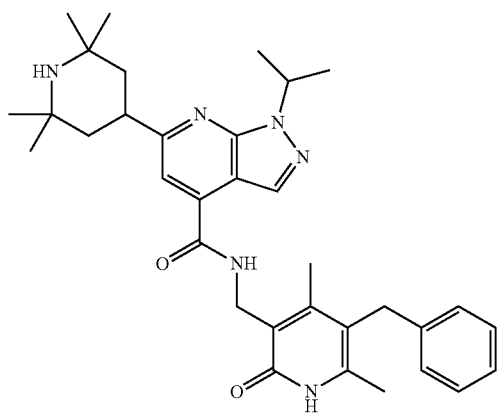 [SMILES: Cc1[nH]c(=O)c(CNC(=O)c2cc(C3CC(C)(C)NC(C)(C)C3)nc3c2cnn3C(C)C)c(C)c1Cc1ccccc1] |
| B-146 | 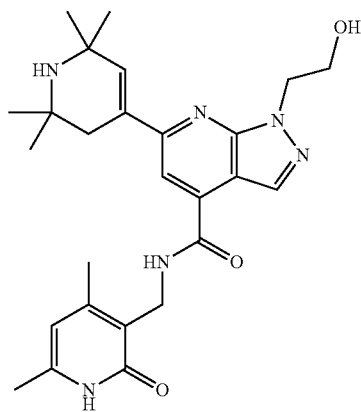 [SMILES: Cc1cc(C)c(CNC(=O)c2cc(C3=CC(C)(C)NC(C)(C)C3)nc3c2cnn3CCO)c(=O)[nH]1] |
| B-147 | 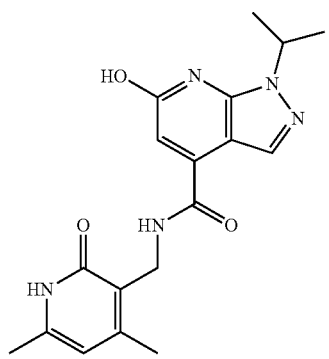 [SMILES: Cc1cc(C)c(CNC(=O)c2cc(O)nc3c2cnn3C(C)C)c(=O)[nH]1] |

TABLE 2-continued
| Compound Number | Structure |
|---|---|
| B-148 | 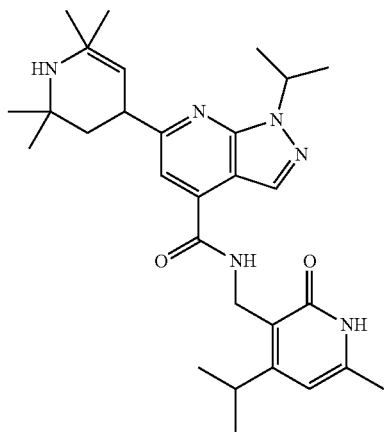 |
| B-151 | 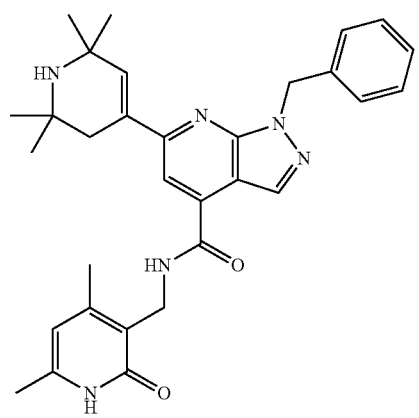 [SMILES: Cc1cc(C)c(CNC(=O)c2cc(C3=CC(C)(C)NC(C)(C)C3)nc3c2cnn3Cc2ccccc2)c(=O)[nH]1] |
| B-152 | 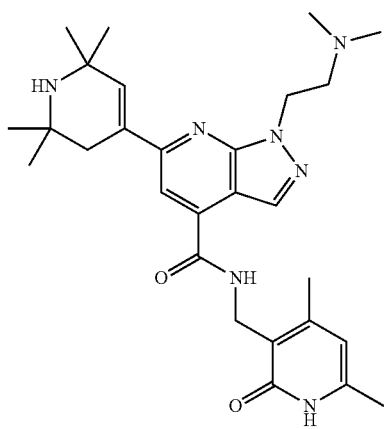 |

TABLE 2-continued
| Compound Number | Structure |
|---|---|
| B-153 | 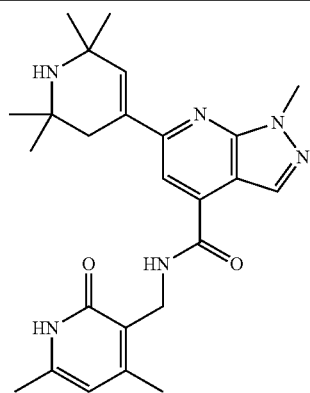 |
| B-154 | 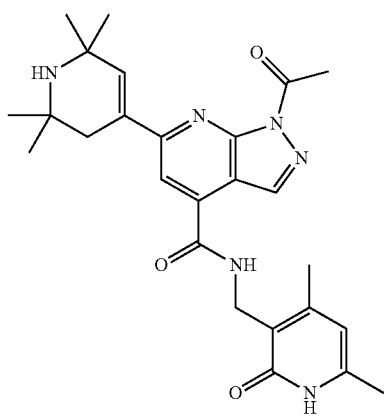 |
| B-155 | 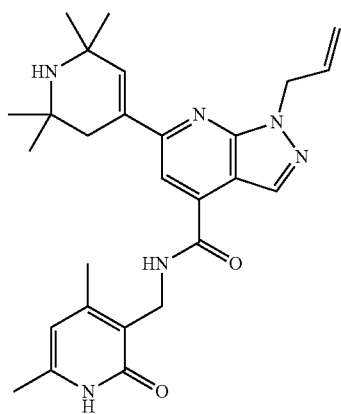 [SMILES: C=CCn1ncc2c(C(=O)NCc3c(C)cc(C)[nH]c3=O)cc(C3=CC(C)(C)NC(C)(C)C3)nc21] |

TABLE 2-continued
| Compound Number | Structure |
|---|---|
| B-156 | 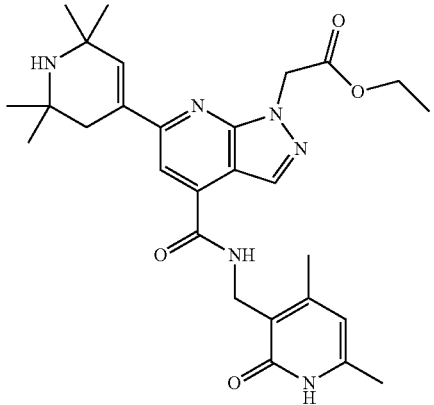 [SMILES: CCOC(=O)Cn1ncc2c(C(=O)NCc3c(C)cc(C)[nH]c3=O)cc(C3=CC(C)(C)NC(C)(C)C3)nc21] |
| B-164 | 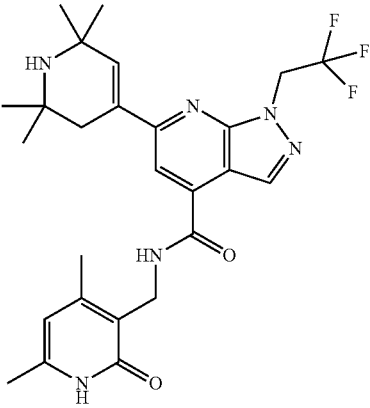 [SMILES: Cc1cc(C)c(CNC(=O)c2cc(C3=CC(C)(C)NC(C)(C)C3)nc3c2cnn3CC(F)(F)F)c(=O)[nH]1] |
TABLE 3
| Compound Number | Structure |
|---|---|
| C-1. | 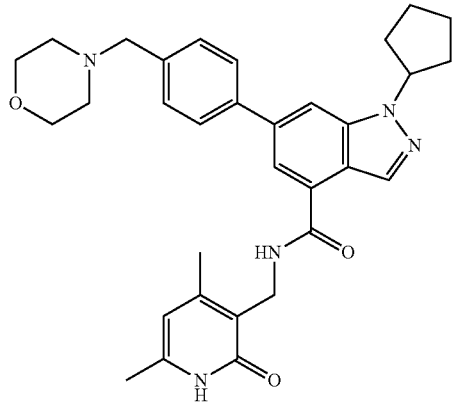 |
TABLE 3-continued
| Compound Number | Structure |
|---|---|
| C-2. | 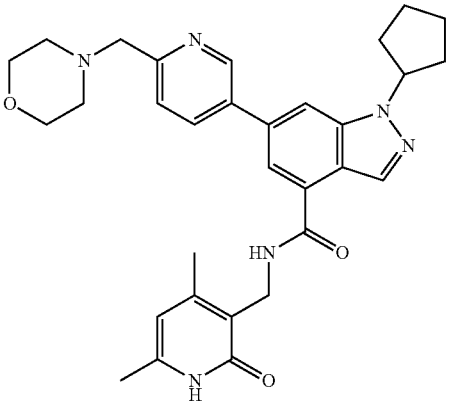 |

TABLE 3-continued

| Compound Number | Structure |
|---|---|
| C-3. | 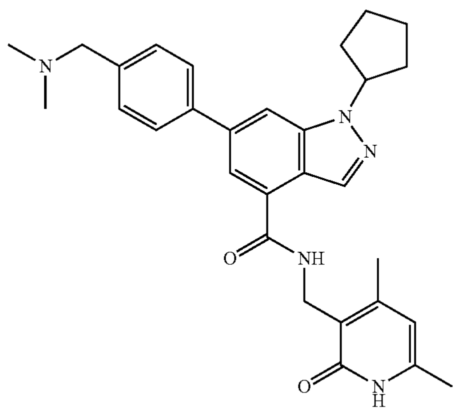 |
| C-4. | 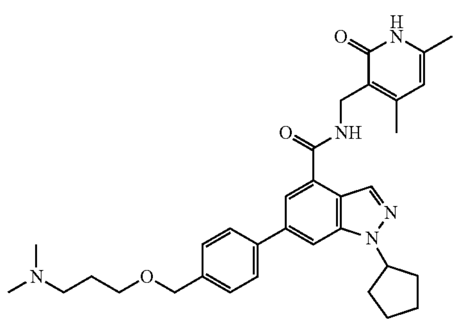 |
| C-5. | 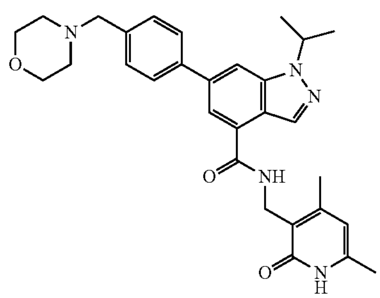 [SMILES: Cc1cc(C)c(CNC(=O)c2cc(-c3ccc(CN4CCOCC4)cc3)cc3c2cnn3C(C)C)c(=O)[nH]1] |
| C-6. | 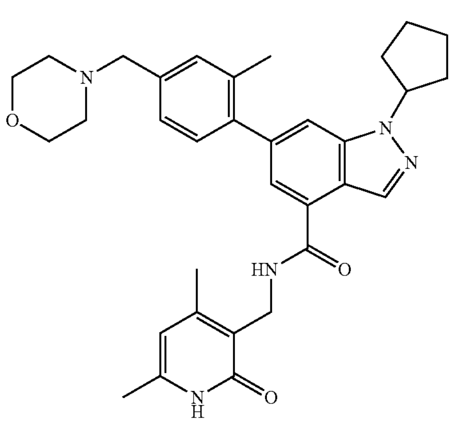 [SMILES: Cc1cc(C)c(CNC(=O)c2cc(-c3ccc(CN4CCOCC4)cc3C)cc3c2cnn3C2CCCC2)c(=O)[nH]1] |
| C-7. | |
| C-8. | |
| C-9. | |
| C-10. | |

TABLE 3-continued
| Compound Number | Structure |
|---|---|
| C-11. | 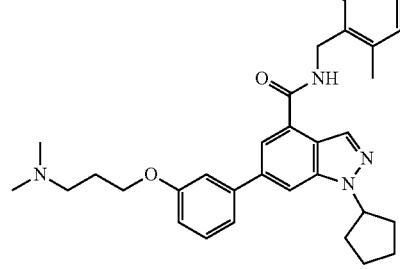 |
| C-12. | 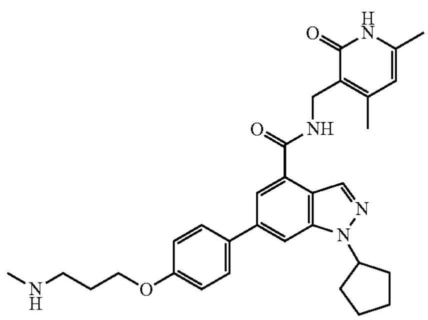 |
| C-13. | 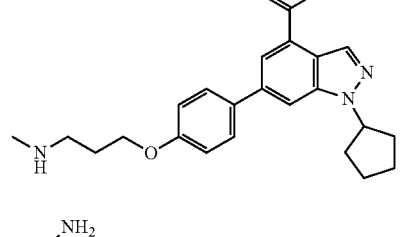 |
| C-14. | 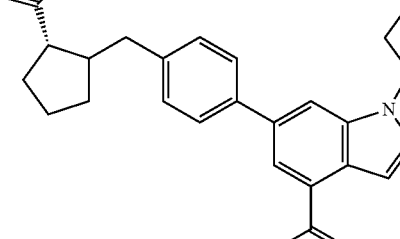 |
| C-15. | 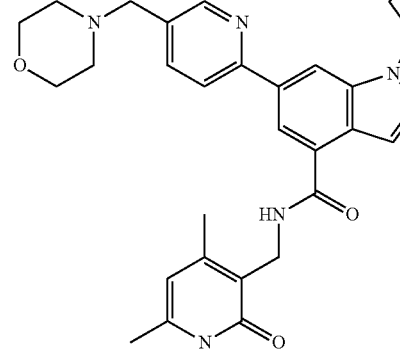 |
| C-16. | 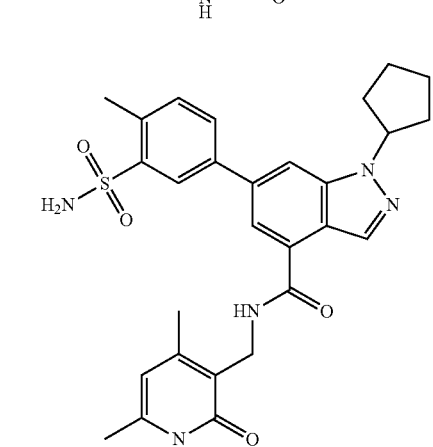 |
| C-17. | 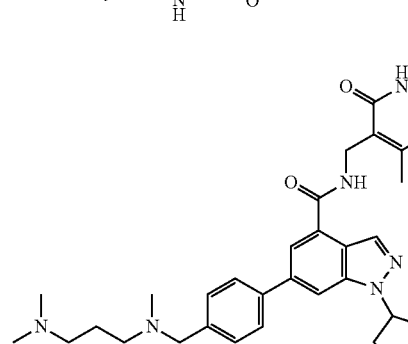 |
| C-18. | 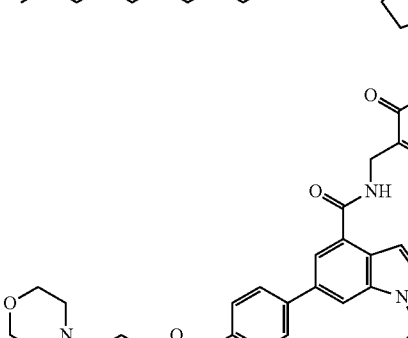 |

TABLE 3-continued

| Compound Number | Structure |
|---|---|
| C-19. | 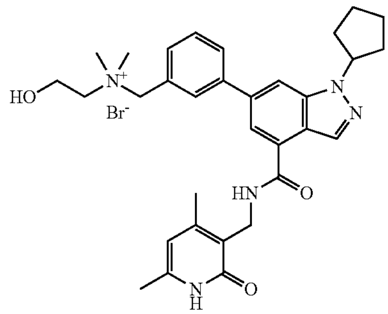 [SMILES: Cc1cc(C)c(CNC(=O)c2cc(-c3cccc(C[N+](C)(C)CCO)c3)cc3c2cnn3C2CCCC2)c(=O)[nH]1 ; [Br-]] |
| C-20. | 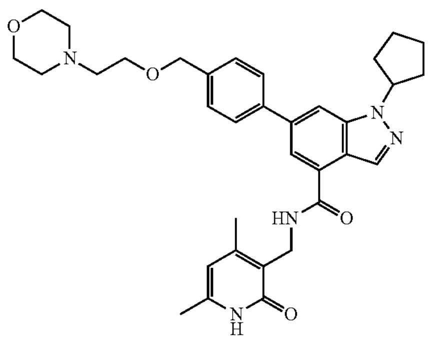 [SMILES: Cc1cc(C)c(CNC(=O)c2cc(-c3ccc(COCCN4CCOCC4)cc3)cc3c2cnn3C2CCCC2)c(=O)[nH]1] |
| C-21. | 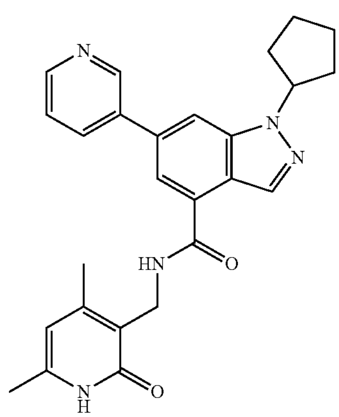 [SMILES: Cc1cc(C)c(CNC(=O)c2cc(-c3cccnc3)cc3c2cnn3C2CCCC2)c(=O)[nH]1] |
| C-22. | 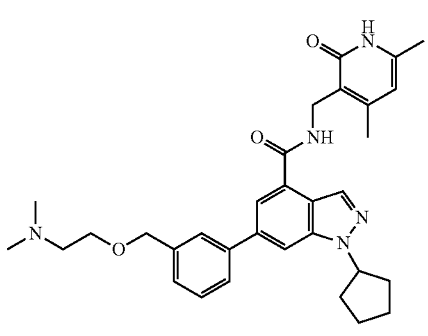 |
| C-23. | |
| C-24. | |
| C-25. | |
| C-26. | |

TABLE 3-continued

| Compound Number | Structure |
|---|---|
| C-27. | 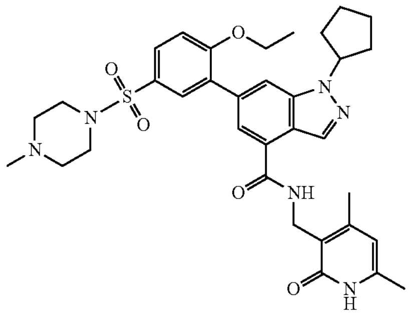 |
| C-28. | 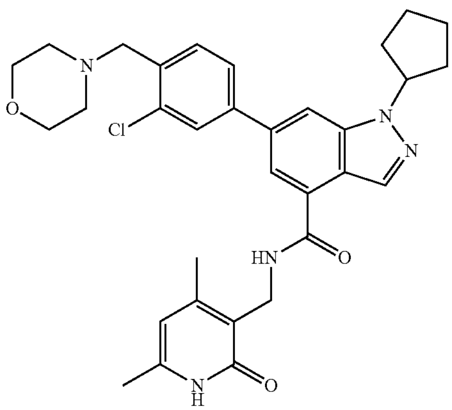 [SMILES: Cc1cc(C)c(CNC(=O)c2cc(-c3ccc(CN4CCOCC4)c(Cl)c3)cc3c2cnn3C2CCCC2)c(=O)[nH]1] |
| C-29. | 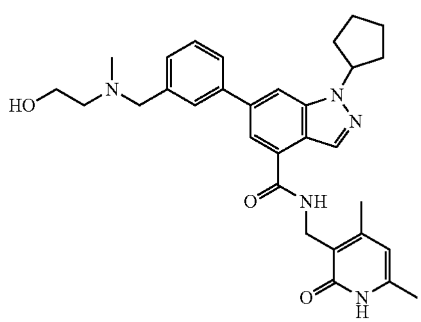 [SMILES: Cc1cc(C)c(CNC(=O)c2cc(-c3cccc(CN(C)CCO)c3)cc3c2cnn3C2CCCC2)c(=O)[nH]1] |
| C-30. | 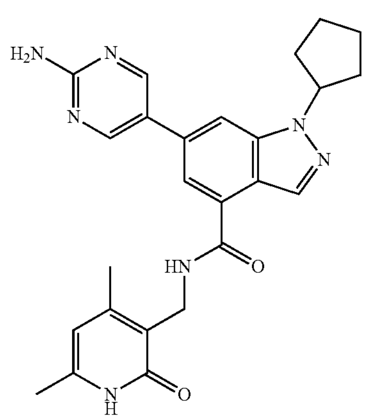 [SMILES: Cc1cc(C)c(CNC(=O)c2cc(-c3cnc(N)nc3)cc3c2cnn3C2CCCC2)c(=O)[nH]1] |
| C-31. | |
| C-32. | |
| C-33. | |

TABLE 3-continued
| Compound Number | Structure |
|---|---|
| C-34. | 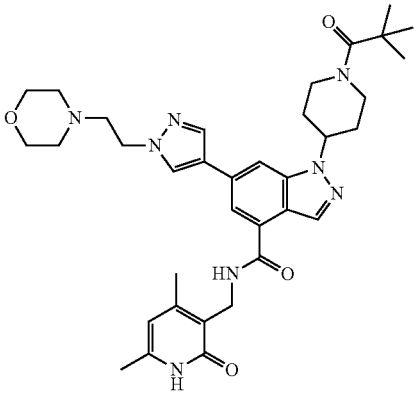 [SMILES: Cc1cc(C)c(CNC(=O)c2cc(-c3cnn(CCN4CCOCC4)c3)cc3c2cnn3C2CCN(C(=O)C(C)(C)C)CC2)c(=O)[nH]1] |
| C-35. | 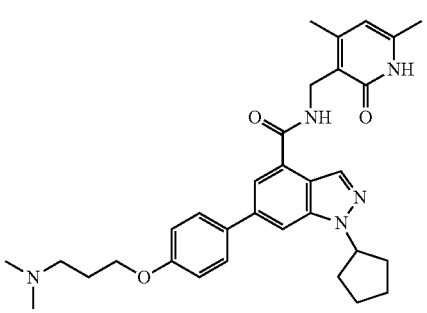 |
TABLE 4
| Compound Number | Structure |
|---|---|
| D-1. | 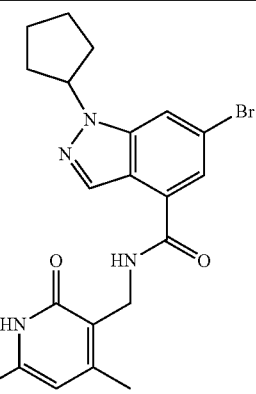 |
TABLE 4-continued
| Compound Number | Structure |
|---|---|
| D-2. | 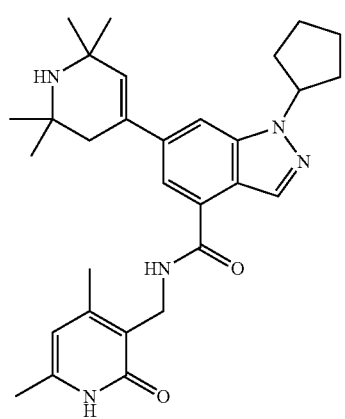 |
| D-3. | 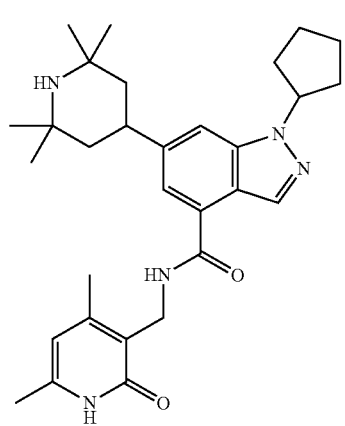 [SMILES: Cc1cc(C)c(CNC(=O)c2cc(C3CC(C)(C)NC(C)(C)C3)cc3c2cnn3C2CCCC2)c(=O)[nH]1] |
| D-4. | 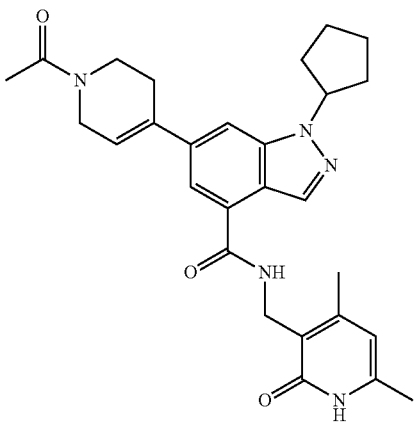 [SMILES: CC(=O)N1CC=C(c2cc(C(=O)NCc3c(C)cc(C)[nH]c3=O)c3cnn(C4CCCC4)c3c2)CC1] |

TABLE 4-continued
| Compound Number | Structure |
|---|---|
| D-5. | 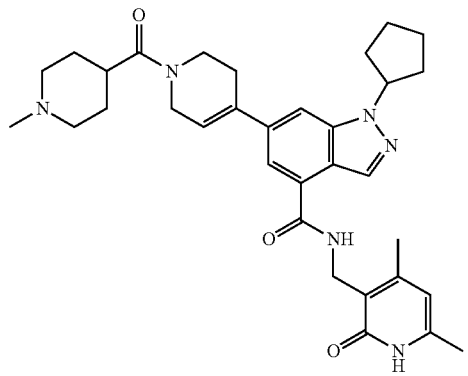 |
| D-6. | 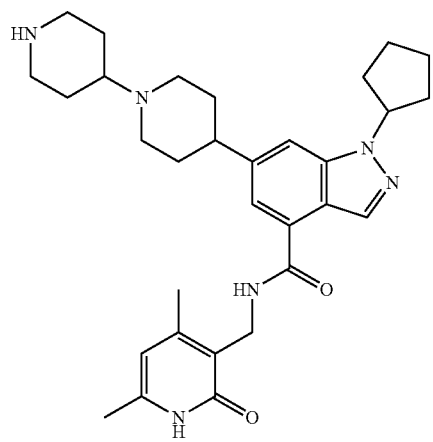 [SMILES: Cc1cc(C)c(CNC(=O)c2cc(C3CCN(C4CCNCC4)CC3)cc3c2cnn3C2CCCC2)c(=O)[nH]1] |
| D-7. | 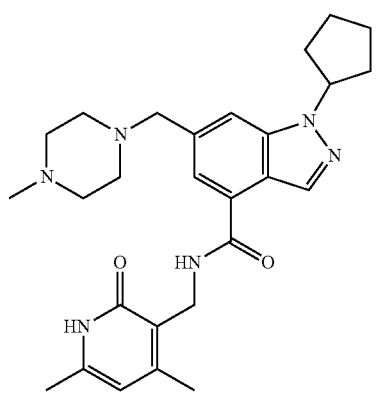 [SMILES: Cc1cc(C)c(CNC(=O)c2cc(CN3CCN(C)CC3)cc3c2cnn3C2CCCC2)c(=O)[nH]1] |
| D-8. | 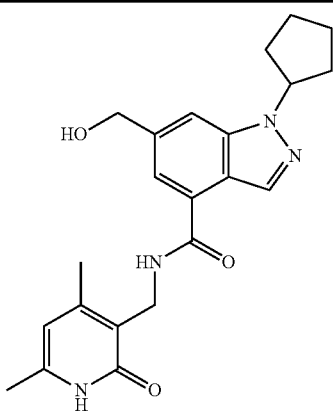 |
| D-9. | 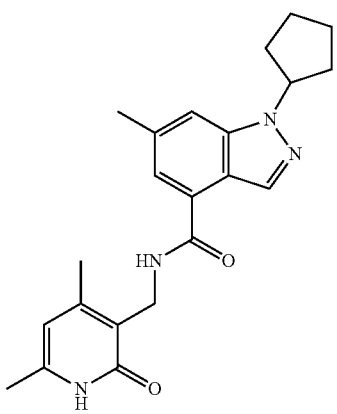 [SMILES: Cc1cc(C(=O)NCc2c(C)cc(C)[nH]c2=O)c2cnn(C3CCCC3)c2c1] |
| D-10. | 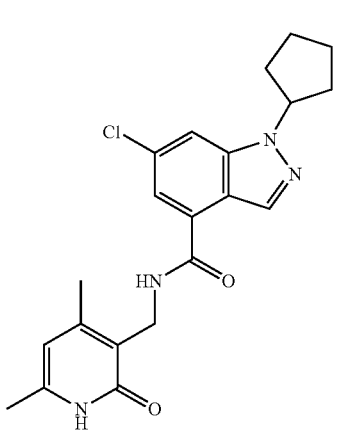 [SMILES: Cc1cc(C)c(CNC(=O)c2cc(Cl)cc3c2cnn3C2CCCC2)c(=O)[nH]1] |

TABLE 4-continued

| Compound Number | Structure |
|---|---|
| D-11. | (1-cyclopentyl-6-(trifluoromethyl)-1H-indazol-4-yl)-N-((4,6-dimethyl-2-oxo-1,2-dihydropyridin-3-yl)methyl)carboxamide |
| D-12. | tert-butyl 4-(6-bromo-4-(((4,6-dimethyl-2-oxo-1,2-dihydropyridin-3-yl)methyl)carbamoyl)-1H-indazol-1-yl)piperidine-1-carboxylate |
| D-13. | 6-bromo-N-((4,6-dimethyl-2-oxo-1,2-dihydropyridin-3-yl)methyl)-1-(1-pivaloylpiperidin-4-yl)-1H-indazole-4-carboxamide |
| D-14. | 1-(1-(azetidine-3-carbonyl)piperidin-4-yl)-6-bromo-N-((4,6-dimethyl-2-oxo-1,2-dihydropyridin-3-yl)methyl)-1H-indazole-4-carboxamide |
| D-15. | 1-(1-benzylpiperidin-4-yl)-6-bromo-N-((4,6-dimethyl-2-oxo-1,2-dihydropyridin-3-yl)methyl)-1H-indazole-4-carboxamide |

TABLE 4-continued

| Compound Number | Structure |
|---|---|
| D-16. | (structure: 6-bromo-1-[1-(1-methylpiperidin-4-yl)piperidin-4-yl]-1H-indazole-4-carboxamide linked via CH2 to 4,6-dimethyl-2-oxo-1,2-dihydropyridin-3-yl) |
| D-17. | (structure: 6-bromo-1-cyclopentyl-1H-indazole-4-carboxamide linked via CH2 to 3-((dimethylamino)methyl)-6-methyl-2-oxo-1,2-dihydropyridin-... with 4-((dimethylamino)methyl) substituent) |
| D-18. | (structure: 1-cyclopentyl-6-[4-(piperidine-4-carbonyl)piperazin-1-yl]-1H-indazole-4-carboxamide linked via CH2 to 4,6-dimethyl-2-oxo-1,2-dihydropyridin-3-yl) |
| D-19. | (structure: 1-cyclopentyl-6-(piperazin-1-yl)-1H-indazole-4-carboxamide linked via CH2 to 4,6-dimethyl-2-oxo-1,2-dihydropyridin-3-yl) |
| D-20. | (structure: 1-cyclopentyl-6-isopropyl-1H-indazole-4-carboxamide linked via CH2 to 4,6-dimethyl-2-oxo-1,2-dihydropyridin-3-yl) |
| D-21. | (structure: 1-cyclopentyl-6-[4-(2-hydroxyethyl)piperazin-1-yl]-1H-indazole-4-carboxamide linked via CH2 to 4,6-dimethyl-2-oxo-1,2-dihydropyridin-3-yl) |

TABLE 4-continued
| Compound Number | Structure |
|---|---|
| D-22. | 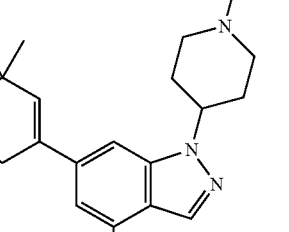 |
| D-23. | 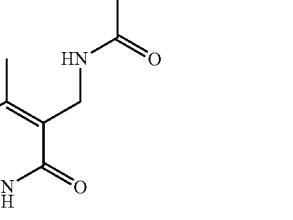 |
| D-24. | 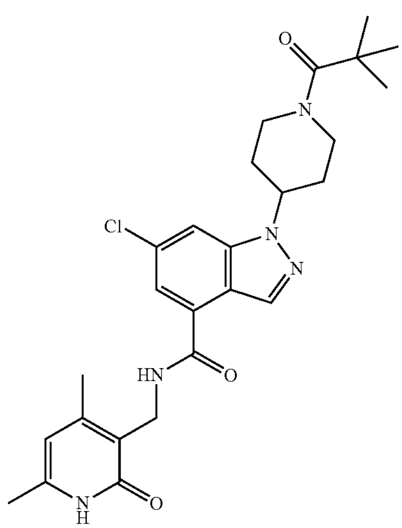 [SMILES: Cc1cc(C)c(CNC(=O)c2cc(Cl)cc3c2cnn3C2CCN(C(=O)C(C)(C)C)CC2)c(=O)[nH]1] |
| D-25. |  |
| D-26. | 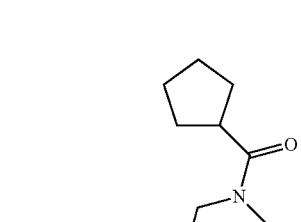 |

TABLE 4-continued
| Compound Number | Structure |
|---|---|
| D-27. | 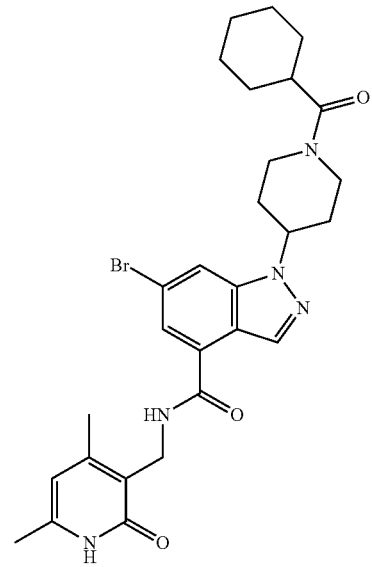 [SMILES: Cc1cc(C)c(CNC(=O)c2cc(Br)cc3c2cnn3C2CCN(C(=O)C3CCCCC3)CC2)c(=O)[nH]1] |
| D-28. | 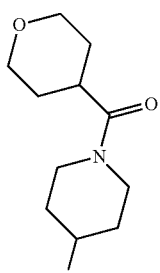 |
| D-29. | 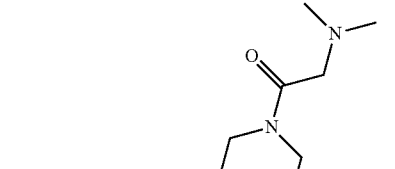 |
| D-30. | 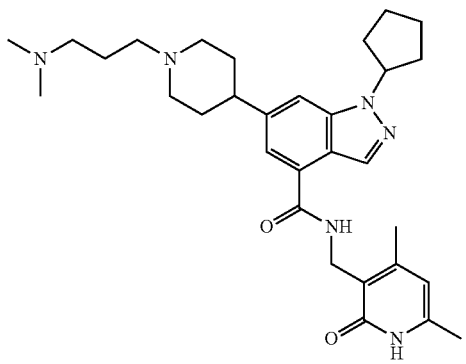 |
| D-31. | 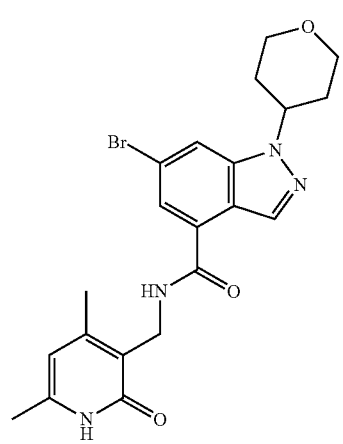 [SMILES: Cc1cc(C)c(CNC(=O)c2cc(Br)cc3c2cnn3C2CCOCC2)c(=O)[nH]1] |

TABLE 4-continued

| Compound Number | Structure |
|---|---|
| D-32. | 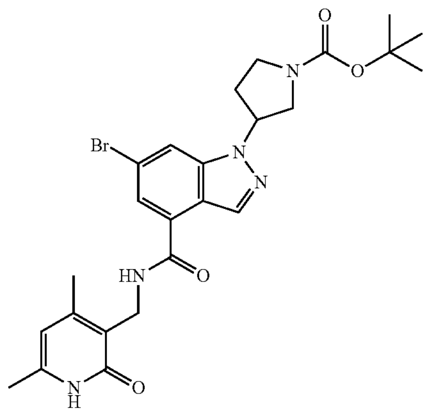 [SMILES: Cc1cc(C)c(CNC(=O)c2cc(Br)cc3c2cnn3C2CCN(C(=O)OC(C)(C)C)C2)c(=O)[nH]1] |
| D-33. | 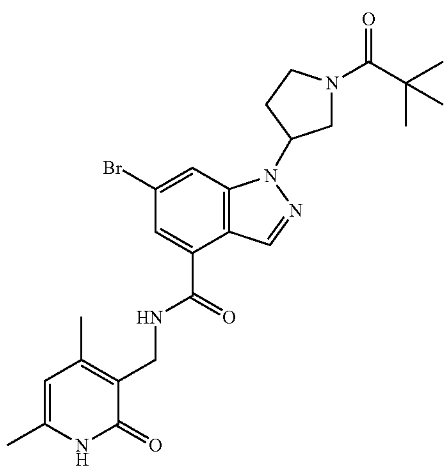 [SMILES: Cc1cc(C)c(CNC(=O)c2cc(Br)cc3c2cnn3C2CCN(C(=O)C(C)(C)C)C2)c(=O)[nH]1] |
| D-34. | 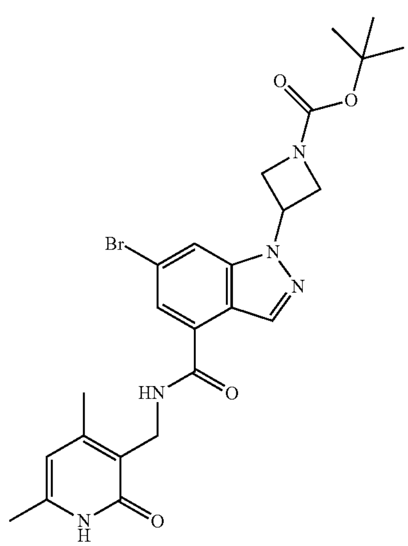 [SMILES: Cc1cc(C)c(CNC(=O)c2cc(Br)cc3c2cnn3C2CN(C(=O)OC(C)(C)C)C2)c(=O)[nH]1] |
| D-35. | |
| D-36. | |
| D-37. | |

TABLE 4-continued
| Compound Number | Structure |
|---|---|
| D-38. | 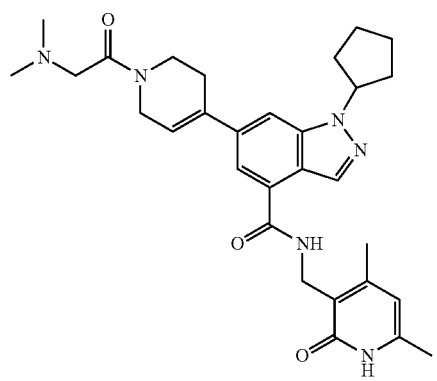 |
| D-39. | 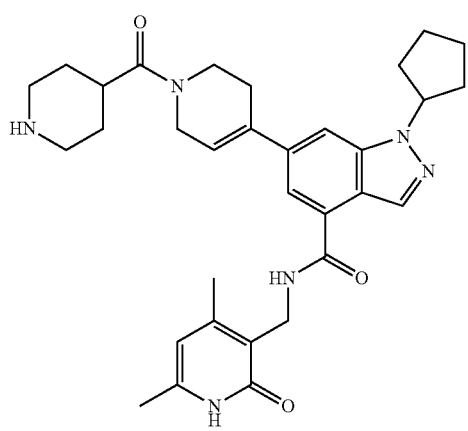 [SMILES: Cc1cc(C)c(CNC(=O)c2cc(C3=CCN(C(=O)C4CCNCC4)CC3)cc3c2cnn3C2CCCC2)c(=O)[nH]1] |
| D-40. | 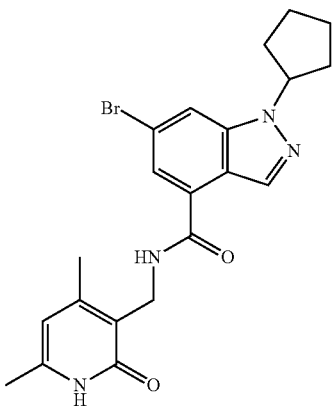 [SMILES: Cc1cc(C)c(CNC(=O)c2cc(Br)cc3c2cnn3C2CCCC2)c(=O)[nH]1] |
TABLE 4-continued
| Compound Number | Structure |
|---|---|
| D-41. | 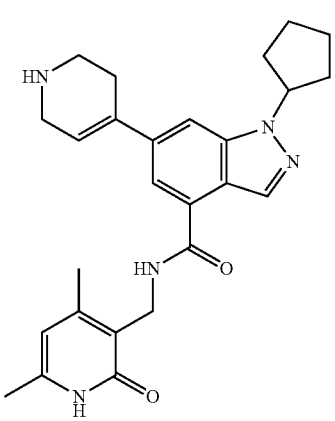 [SMILES: Cc1cc(C)c(CNC(=O)c2cc(C3=CCNCC3)cc3c2cnn3C2CCCC2)c(=O)[nH]1] |
| D-42. | 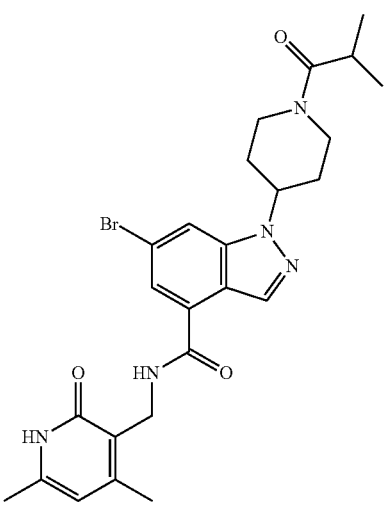 [SMILES: Cc1cc(C)c(CNC(=O)c2cc(Br)cc3c2cnn3C2CCN(C(=O)C(C)C)CC2)c(=O)[nH]1] |
| D-43. | 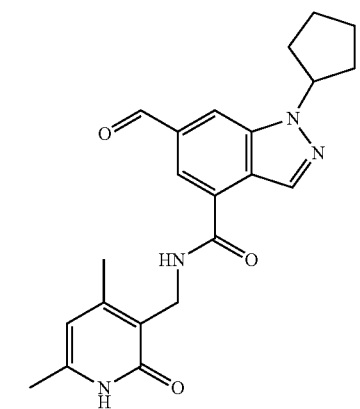 [SMILES: Cc1cc(C)c(CNC(=O)c2cc(C=O)cc3c2cnn3C2CCCC2)c(=O)[nH]1] |

TABLE 4-continued

| Compound Number | Structure |
|---|---|
| D-44. | 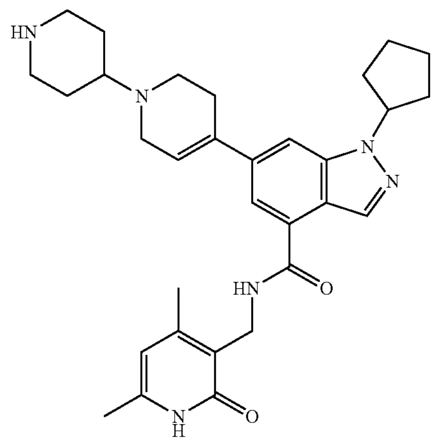 [SMILES: Cc1cc(C)c(CNC(=O)c2cc(C3=CCN(C4CCNCC4)CC3)cc3c2cnn3C2CCCC2)c(=O)[nH]1] |
| D-45. | 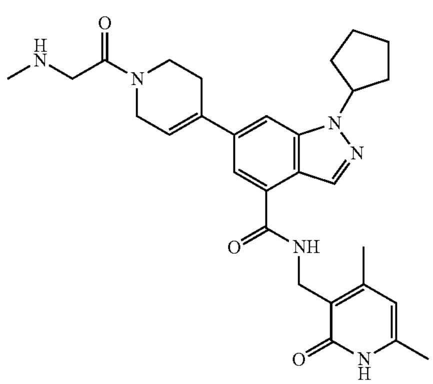 |
| D-46. | 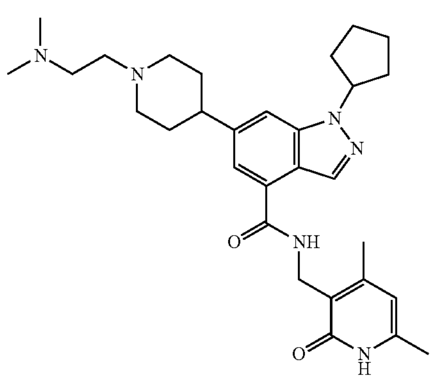 |
| D-47. | 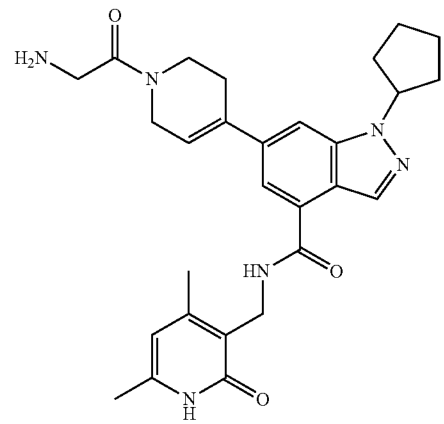 [SMILES: Cc1cc(C)c(CNC(=O)c2cc(C3=CCN(C(=O)CN)CC3)cc3c2cnn3C2CCCC2)c(=O)[nH]1] |
| D-48. | 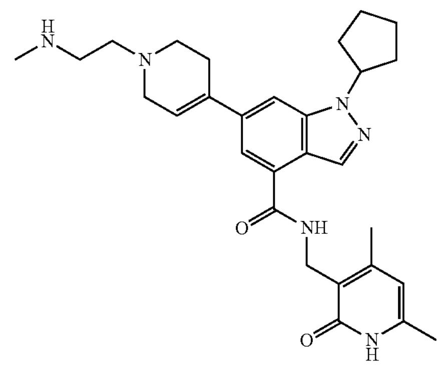 |
| D-49. | 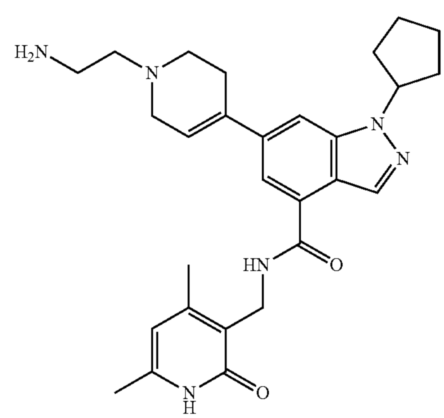 [SMILES: Cc1cc(C)c(CNC(=O)c2cc(C3=CCN(CCN)CC3)cc3c2cnn3C2CCCC2)c(=O)[nH]1] |
| D-50. | 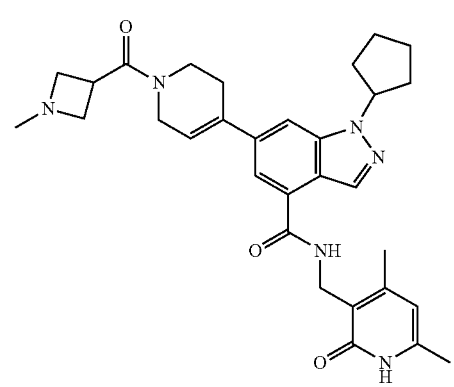 |

TABLE 4-continued
| Compound Number | Structure |
|---|---|
| D-51. | 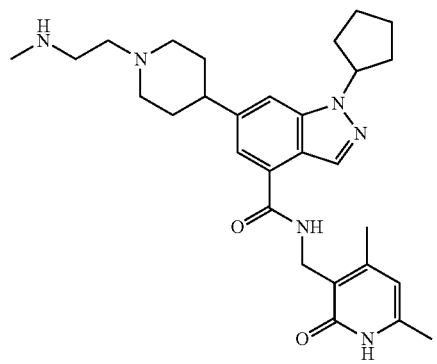 |
| D-52. | 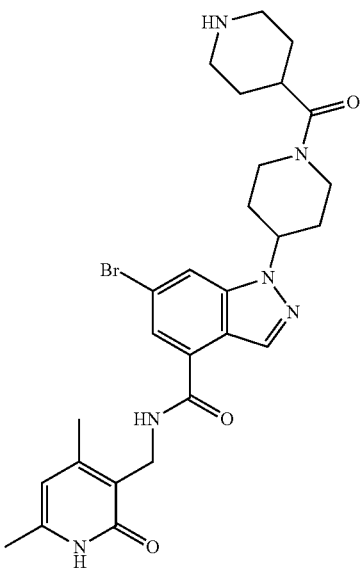 [SMILES: Cc1cc(C)c(CNC(=O)c2cc(Br)cc3c2cnn3C2CCN(C(=O)C3CCNCC3)CC2)c(=O)[nH]1] |
| D-53. | 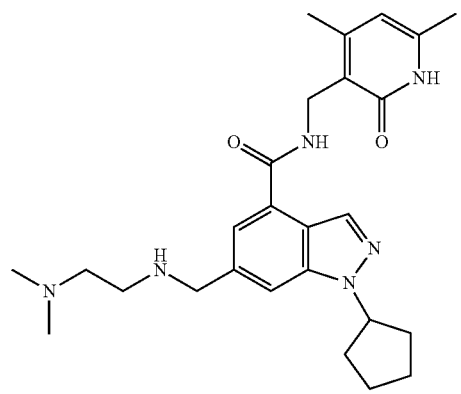 |
| D-54. | 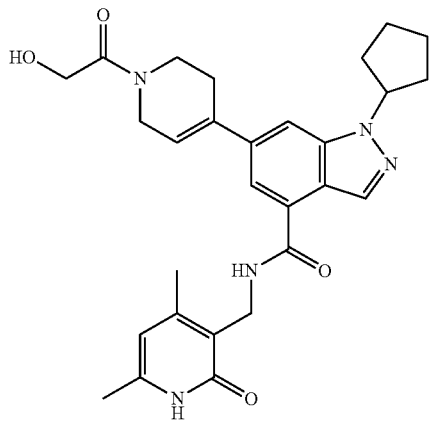 [SMILES: Cc1cc(C)c(CNC(=O)c2cc(C3=CCN(C(=O)CO)CC3)cc3c2cnn3C2CCCC2)c(=O)[nH]1] |
| D-55. | 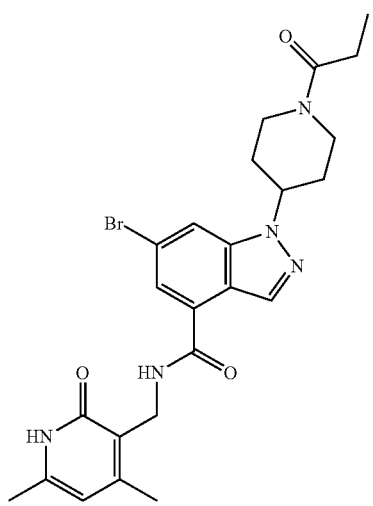 [SMILES: CCC(=O)N1CCC(n2ncc3c(C(=O)NCc4c(C)cc(C)[nH]c4=O)cc(Br)cc32)CC1] |
| D-56. | 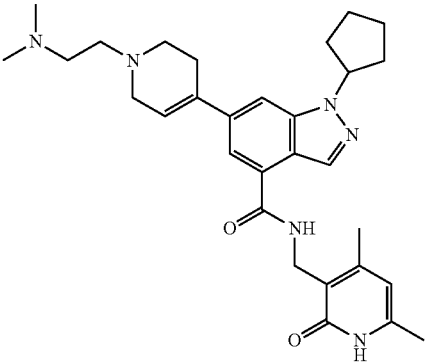 |

TABLE 4-continued

| Compound Number | Structure |
|---|---|
| D-57. | 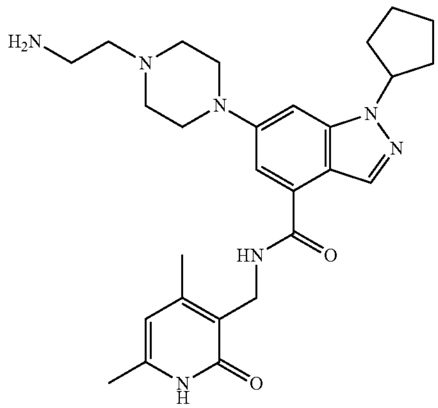 [SMILES: Cc1cc(C)c(CNC(=O)c2cc(N3CCN(CCN)CC3)cc3c2cnn3C2CCCC2)c(=O)[nH]1] |
| D-58. | 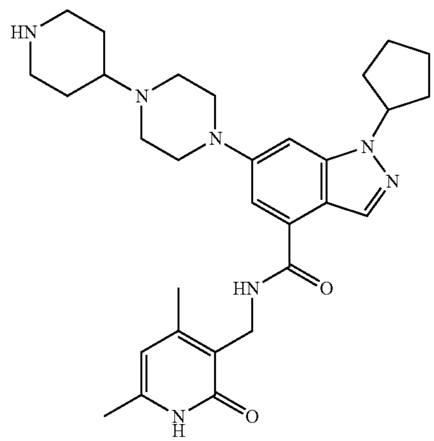 [SMILES: Cc1cc(C)c(CNC(=O)c2cc(N3CCN(C4CCNCC4)CC3)cc3c2cnn3C2CCCC2)c(=O)[nH]1] |
| D-59. | 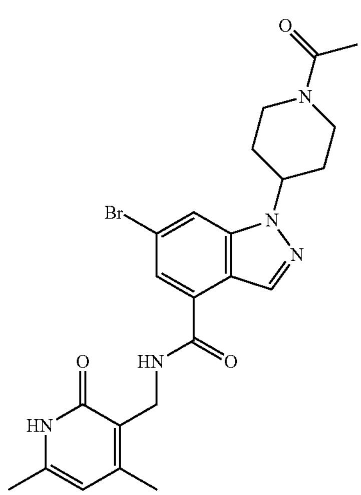 [SMILES: CC(=O)N1CCC(n2ncc3c(C(=O)NCc4c(C)cc(C)[nH]c4=O)cc(Br)cc32)CC1] |
| D-60. | |
| D-61. | |
| D-62. | |

TABLE 4-continued

| Compound Number | Structure |
|---|---|
| D-63. | |
| D-64. | |
| D-65. | |
| D-66. | 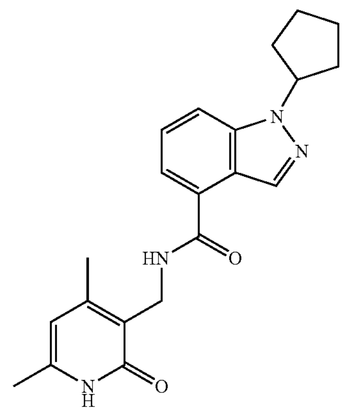 [SMILES: Cc1cc(C)c(CNC(=O)c2cccc3c2cnn3C2CCCC2)c(=O)[nH]1] |
| D-67. | 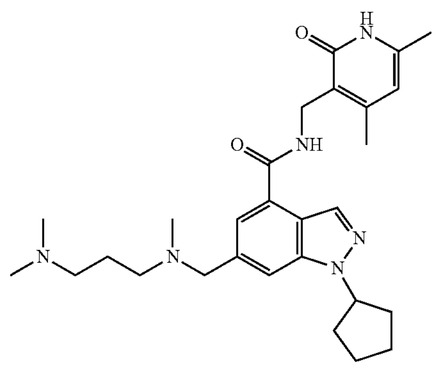 |
| D-68. | 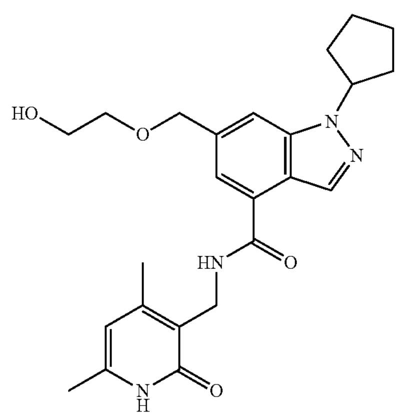 [SMILES: Cc1cc(C)c(CNC(=O)c2cc(COCCO)cc3c2cnn3C2CCCC2)c(=O)[nH]1] |
| D-69. | 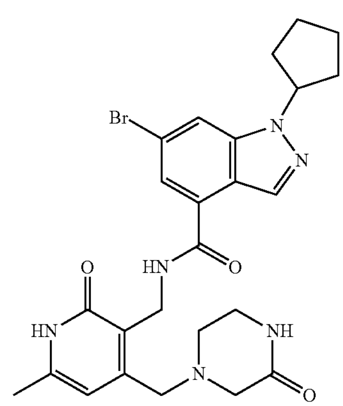 [SMILES: Cc1cc(CN2CCNC(=O)C2)c(CNC(=O)c2cc(Br)cc3c2cnn3C2CCCC2)c(=O)[nH]1] |

TABLE 4-continued
| Compound Number | Structure |
|---|---|
| D-70. | 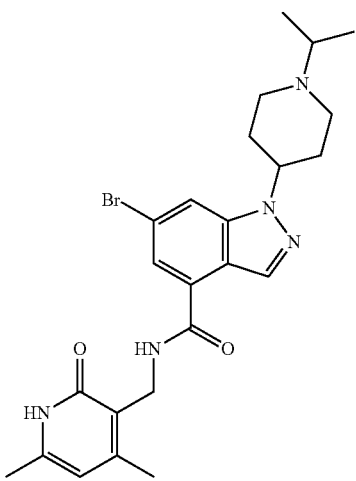 [SMILES: Cc1cc(C)c(CNC(=O)c2cc(Br)cc3c2cnn3C2CCN(C(C)C)CC2)c(=O)[nH]1] |
| D-71. | 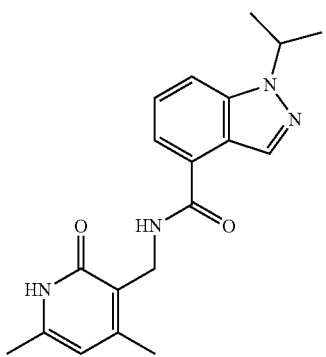 [SMILES: Cc1cc(C)c(CNC(=O)c2cccc3c2cnn3C(C)C)c(=O)[nH]1] |
| D-72. | 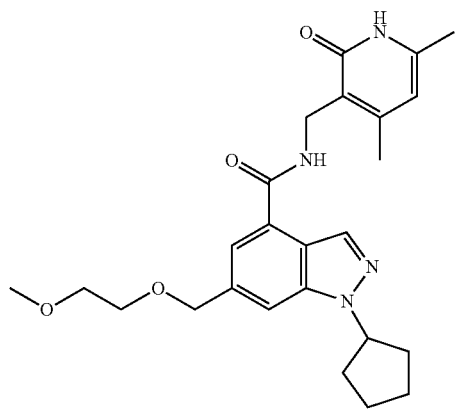 |
| D-73. | 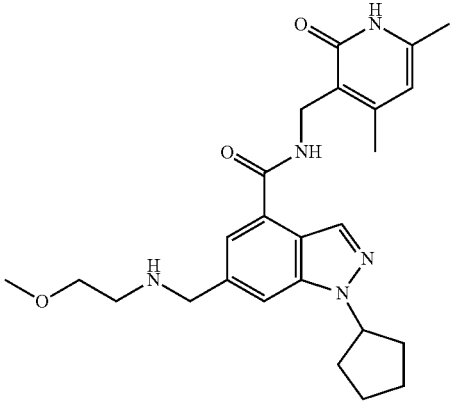 |
| D-74. | 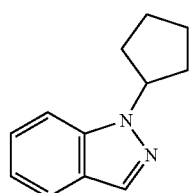 |
| D-75. | 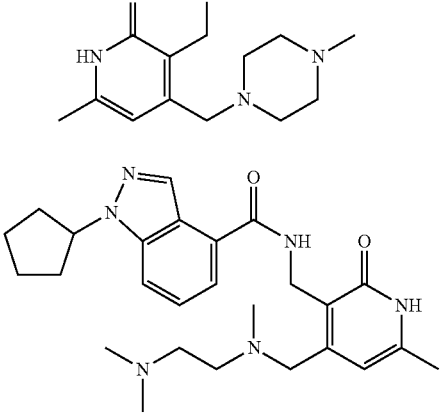 |
| D-76. | 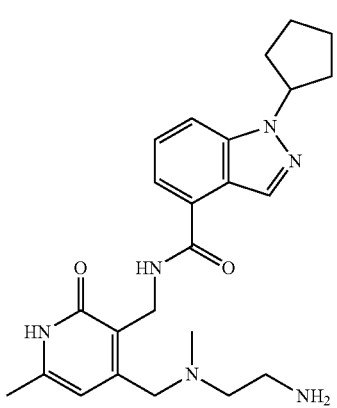 [SMILES: Cc1cc(CN(C)CCN)c(CNC(=O)c2cccc3c2cnn3C2CCCC2)c(=O)[nH]1]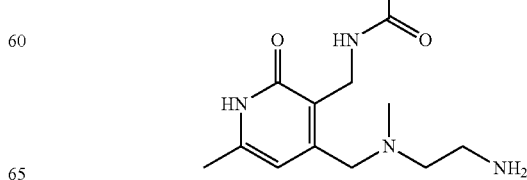 |

TABLE 4-continued
| Compound Number | Structure |
|---|---|
| D-77. | 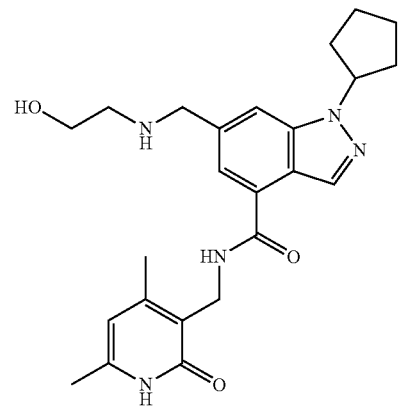 [SMILES: Cc1cc(C)c(CNC(=O)c2cc(CNCCO)cc3c2cnn3C2CCCC2)c(=O)[nH]1] |
| D-78. | 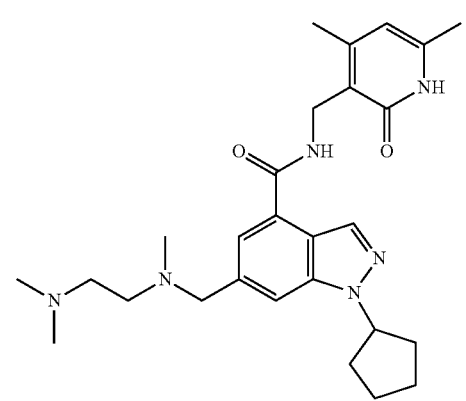 |
| D-79. | 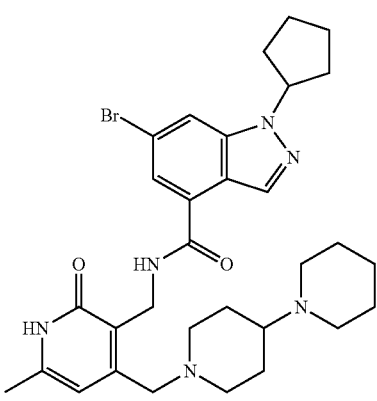 [SMILES: Cc1cc(CN2CCC(N3CCCCC3)CC2)c(CNC(=O)c2cc(Br)cc3c2cnn3C2CCCC2)c(=O)[nH]1] |
| D-80. | 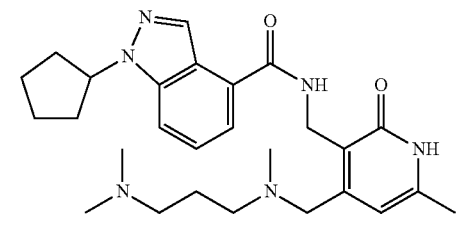 [SMILES: Cc1cc(CN(C)CCCN(C)C)c(CNC(=O)c2cccc3c2cnn3C2CCCC2)c(=O)[nH]1] |
| D-81. | 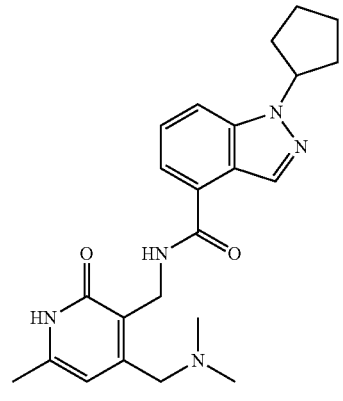 [SMILES: Cc1cc(CN(C)C)c(CNC(=O)c2cccc3c2cnn3C2CCCC2)c(=O)[nH]1] |
| D-82. | 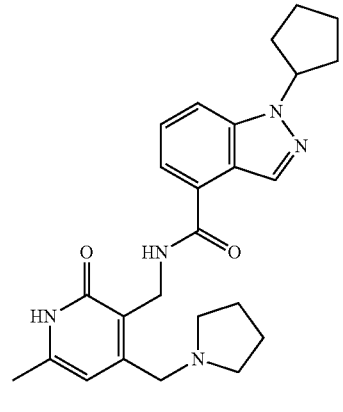 [SMILES: Cc1cc(CN2CCCC2)c(CNC(=O)c2cccc3c2cnn3C2CCCC2)c(=O)[nH]1] |
| D-83. | 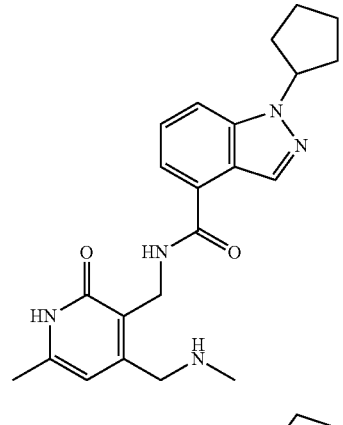 |
| D-84. | 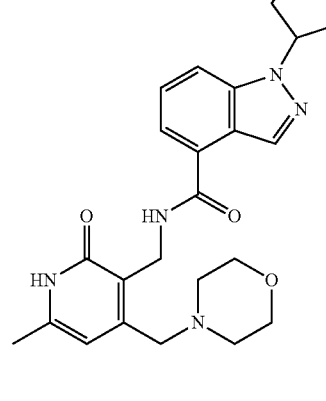 |

TABLE 4-continued

| Compound Number | Structure |
|---|---|
| D-85. | |
| D-86. | |
| D-87. | |
| D-88. | 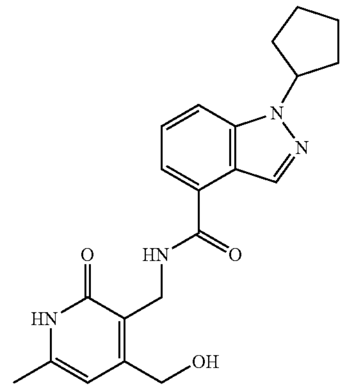 [SMILES: Cc1cc(CO)c(CNC(=O)c2cccc3c2cnn3C2CCCC2)c(=O)[nH]1] |
| D-89. | 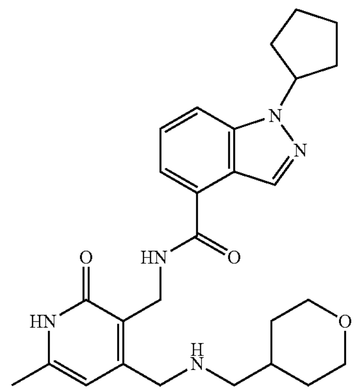 [SMILES: Cc1cc(CNCC2CCOCC2)c(CNC(=O)c2cccc3c2cnn3C2CCCC2)c(=O)[nH]1] |
| D-90. | 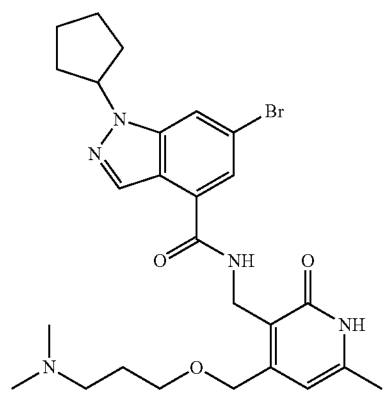 |
| D-91. | 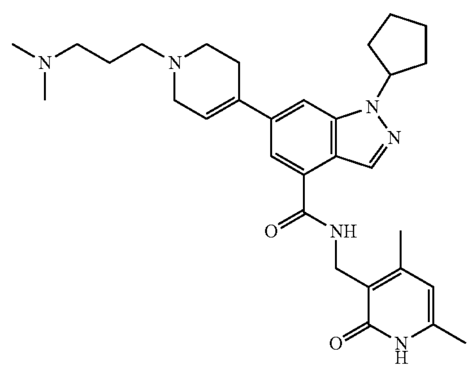 |

TABLE 4-continued
| Compound Number | Structure |
|---|---|
| D-93 | 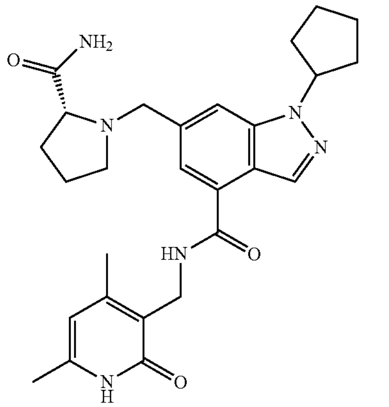 [SMILES: Cc1cc(C)c(CNC(=O)c2cc(CN3CCC[C@@H]3C(N)=O)cc3c2cnn3C2CCCC2)c(=O)[nH]1] |
| D-94 | 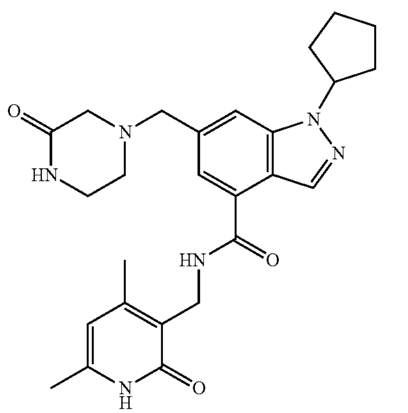 [SMILES: Cc1cc(C)c(CNC(=O)c2cc(CN3CCNC(=O)C3)cc3c2cnn3C2CCCC2)c(=O)[nH]1] |
| D-95 | 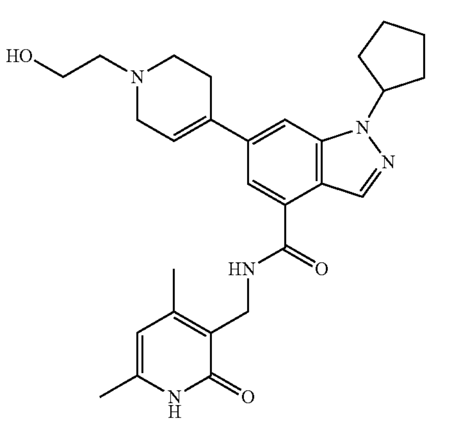 [SMILES: Cc1cc(C)c(CNC(=O)c2cc(C3=CCN(CCO)CC3)cc3c2cnn3C2CCCC2)c(=O)[nH]1] |
| D-96 |  |
| D-97 | |
| D-98 |  |

TABLE 5

| Compound Number | Structure |
|---|---|
| E-1. | 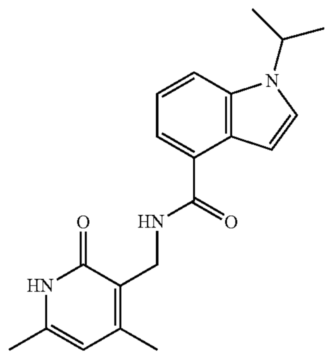 [SMILES: Cc1cc(C)c(CNC(=O)c2cccc3c2ccn3C(C)C)c(=O)[nH]1] |
| E-2. | 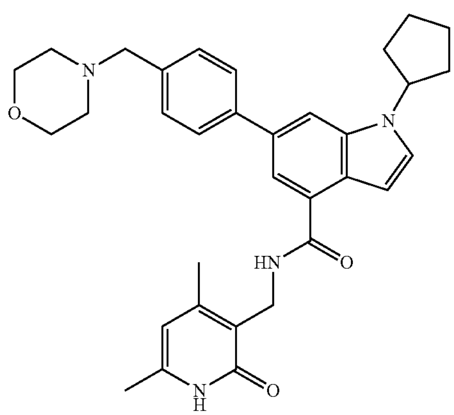 [SMILES: Cc1cc(C)c(CNC(=O)c2cc(-c3ccc(CN4CCOCC4)cc3)cc3c2ccn3C2CCCC2)c(=O)[nH]1] |

TABLE 6

| Compound Number | Structure |
|---|---|
| F-1. | 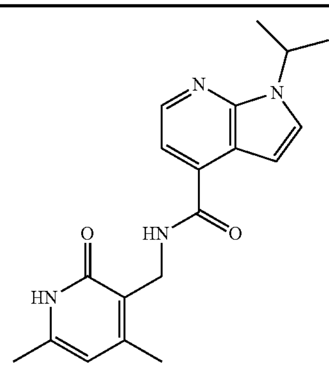 |
| F-2. | |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono-or multi-ring system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 8-12 membered bicyclic, or 11-14 membered tricyclic ring system having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted $—NH_2$. "Alkylamino" includes groups of compounds wherein nitrogen of $—NH_2$ is bound to at least one alkyl group. Examples of alkylamino groups include benzylamino, methylamino, ethylamino, phenethylamino, etc. "Dialkylamino" includes groups wherein the nitrogen of $—NH_2$ is bound to at least two additional alkyl groups. Examples of dialkylamino groups include, but are not limited to, dimethylamino and diethylamino "Arylamino" and "diarylamino" include groups wherein the nitrogen is bound to at least one or two aryl groups, respectively. "Aminoaryl" and "aminoaryloxy" refer to aryl and aryloxy substituted with amino "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—$OR_c$ wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. An example of keto-enol equilibria is between pyridin-2(1H)-one's and the corresponding pyridin-2-ol's, as shown below.

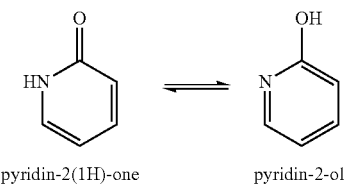 [SMILES: O=c1cccc[nH]1 ; Oc1ccccn1]

pyridin-2(1H)-one    pyridin-2-ol

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of Formula (I), (Ia), or (Ib) include the compounds themselves, as well as their salts, their solvates, and their prodrugs, if applicable. A salt, for example, can be formed between an anion and a positively charged group (e.g., amino) on a substituted 6,5-fused bicyclic heteroaryl compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a substituted 6,5-fused bicyclic heteroaryl compound. Suitable cations include sodium ion, potassium ion, magnesium ion, calcium ion, and an ammonium cation such as tetramethylammonium ion. The substituted 6,5-fused bicyclic heteroaryl compounds also include those salts containing quaternary nitrogen atoms. Examples of prodrugs include esters and other pharmaceutically acceptable derivatives, which, upon administration to a subject, are capable of providing active substituted 6,5-fused bicyclic heteroaryl compounds.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted 6,5-fused bicyclic heteroaryl compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

2. Synthesis of Substituted 6,5-fused Bicyclic Heteroaryl Compounds

The present invention provides methods for the synthesis of the compounds of Formulae (I), (Ia), and (Ib). The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with Formulae (I), (Ia), and (Ib) may be prepared according to the procedures illustrated in Schemes 1-4 below, from commercially available starting materials or starting materials which can be prepared using literature procedures. The R groups (such as $R_6$, $R_7$, and $R_{11}$) in Schemes 1-4 are as defined in Formula (I), (Ia), or (Ib), unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

Preferred protecting groups include, but are not limited to:
For the hydroxyl moiety: TBS, benzyl, THP, Ac
For carboxylic acids: benzyl ester, methyl ester, ethyl ester, allyl ester
For amines: Cbz, BOC, DMB
For diols: Ac (x2) TBS (x2), or when taken together acetonides For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:

AA ammonium acetate
Ac acetyl
ACN acetonitrile
AcOH acetic acid
atm atmosphere
Bn benzyl
BOC tert-butoxy carbonyl
BOP (benzotriazol-1-yloxy)tris(dimethylamino)phosphonium hexafluorophosphate
Cbz benzyloxy carbonyl
COMU (1-Cyano-2-ethoxy-2-oxoethylidenaminooxy)-dimethylamino-morpholino-carbenium hexafluorophosphate
d days
DBU 1,8-diazabicyclo[5.4.0]undec-7-ene
DCE 1,2 dichloroethane
DCM dichloromethane
DEAD Diethyl azodicarboxylate
DIAD Diisopropyl azodicarboxylate
DiBAL-H diisobutyl alumininium hydride
DIPEA N,N-diisopropylethylamine (Hunig's base)
DMAP N,N-dimethyl-4-aminopyridine
DMB 2,4 dimethoxy benzyl
DMF dimethylformamide
DMSO Dimethyl sulfoxide
DPPA Diphenylphosphonic azide
EA or EtOAc Ethyl acetate
EDC or EDCI N-(3-Dimethylaminopropyl)-N'-ethylcarbodiimide
ELS Evaporative Light Scattering
ESI− Electrospray negative mode
ESI+ Electrospray positive mode
Et$_2$O diethyl ether
Et$_3$N or TEA triethylamine
EtOH ethanol
FA formic acid
FC Flash chromatogrpahy
h hours
H$_2$O water
HATU O-(7-Azabenzotriazol-1-yl)-N,N,N',N'-tetramethyluronium hexafluorophosphate
HCl hydrochloric acid
HOAT 1-Hydroxy-7-azabenzotriazole
HOBt 1-Hydroxybenzotriazole
HO-Su N-Hydroxysuccinimide
HPLC High performance liquid chromatography
KHMDs Potassium hexamethyldisilazide
LC/MS or LC-MS liquid chromatography mass spectrum
LDA Lithium diisopropylamide
LG leaving group
LiHMDs Lithium hexamethyldisilazide
M Molar
m/z mass/charge ratio
m-CPBA meta-chloroperbenzoic acid
MeCN Acetonitrile
MeOD d$_4$-methanol
MeOH methanol
MgSO$_4$ magnesium sulfate
min minutes
MS Mass Spectrometry
Ms Mesyl
MS mass spectrum
MsCl Mesyl chloride
MsO Mesylate
MWI microwave irradiation
Na$_2$CO$_3$ sodium carbonate
NaHCO$_3$ sodium bicarbonate
NaHMDs Sodium hexamethyldisilazide
NaOH sodium hydroxide
NIS N-iodosuccinimide
NMR Nuclear Magnetic Resonance
o/n or O/N overnight
PE Petroleum Ether
PG protecting group
PMB para methoxybenzyl
PPAA 1-Propanephosphonic acid cyclic anhydride
ppm parts per million
prep HPLC preparative High performance liquid chromatography
prep TLC preparative thin layer chromatography
p-TsOH para-toluenesulfonic acid
PYBOP (Benzotriazol-1-yloxy)tripyrrolidinophosphonium hexafluorophosphate
rt or RT room temperature
SEM 2-(Trimethylsilyl)ethoxymethyl
SEMCl (Trimethylsilyl)ethoxymethyl chloride
SFC Super critical chromatography
SGC silica gel chromatogrpahy
STAB Sodium triacetoxy borohydride
TBAF tetra-n-butylammonium fluoride
TFA trifluoroacetic acid
TfO triflate
THF tetrahydrofuran
THP tetrahydropyran
TLC thin layer chromatography
Ts tosyl
TsOH tosic acid
UV ultraviolet

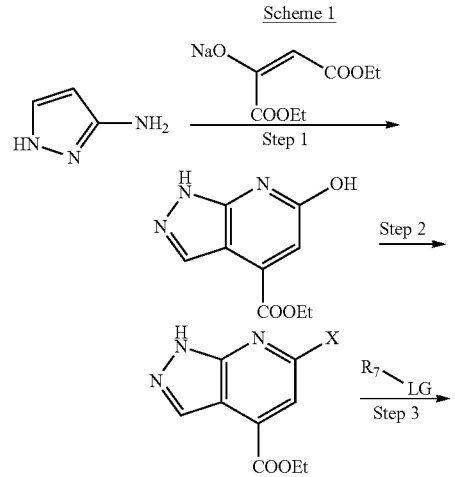

Scheme 1

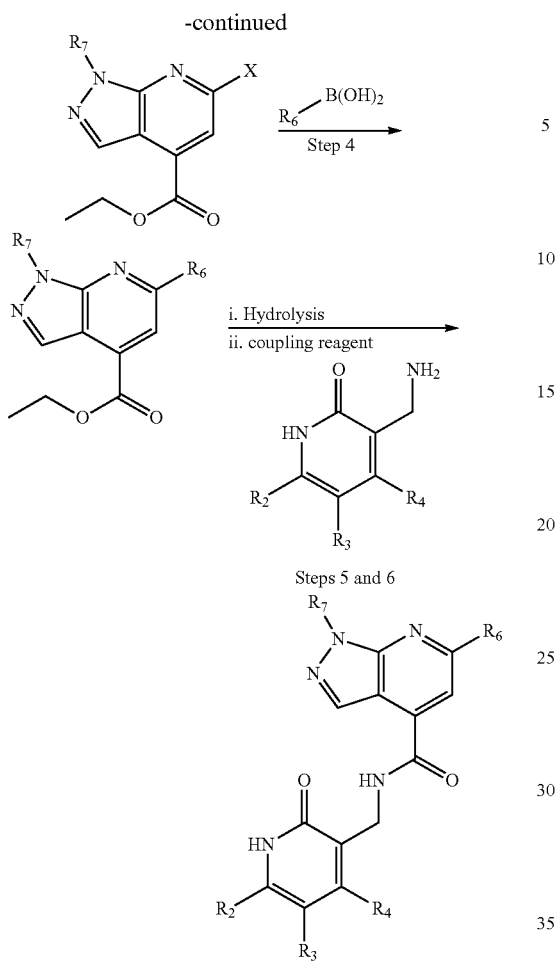

Steps 5 and 6

Scheme 1 shows the synthesis of modified pyrazolopyridine analogs following a general route that utilizes well-established chemistry. Condensation of 1H-pyrazol-3-amine with sodium (E)-1,4-diethoxy-1,4-dioxobut-2-en-2-olate in a polar solvent such as water using a mild acid catalyst such as acetic acid can provide the hydroxyl-pyrazolopyridine (Step 1). The hydroxyl group can then be converted to a leaving group "X" such as bromide using phosphoryl tribromide at elevated temperatures in an appropriate polar solvent such as acetonitrile to give the bromide (Step 2). Introduction of the $R_7$ can be done using an appropriate $R_7$-LG where LG is a leaving group such as OTs or Br. Subjecting the intermediate to $R_7$-LG in the presence of a mild base such as potassium carbonate in an appropriate polar solvent such as acetonitrile gives the desired substituted pyrazolopyridine (Step 3). A variety of $R_6$ substituents can then be introduced using standard transition metal-based protocols that rely upon a leaving group such as a bromide as a connection point or through direct $SN_{Ar}$ displacement of the bromide with a nucleophile. The bromide can be combined with an appropriate boronic ester derivative, in the presence of a mild base and a palladium catalyst in a polar solvent such as dioxane/water, at elevated temperature to give the desired pyrazolopyridine ester (Step 4). Alternatively, the bromide can be combined with a nucleophile such as an amine in the presence of a mild base such as potassium carbonate in a polar solvent such as acetone to give the desired pyrazolopyridine ester. The ester moiety can be converted to an amide using a standard two step protocol.

The ester can be hydrolyzed to the corresponding acid using a suitable base such as sodium hydroxide in a polar solvent such as ethanol (Step 5). The acid is then subjected to a standard amide coupling reaction whereupon the appropriate amine is added along with a suitable amide coupling reagent such as PYBOP in a suitable solvent such as DMSO to give the desired amide (Step 6).

Scheme 2

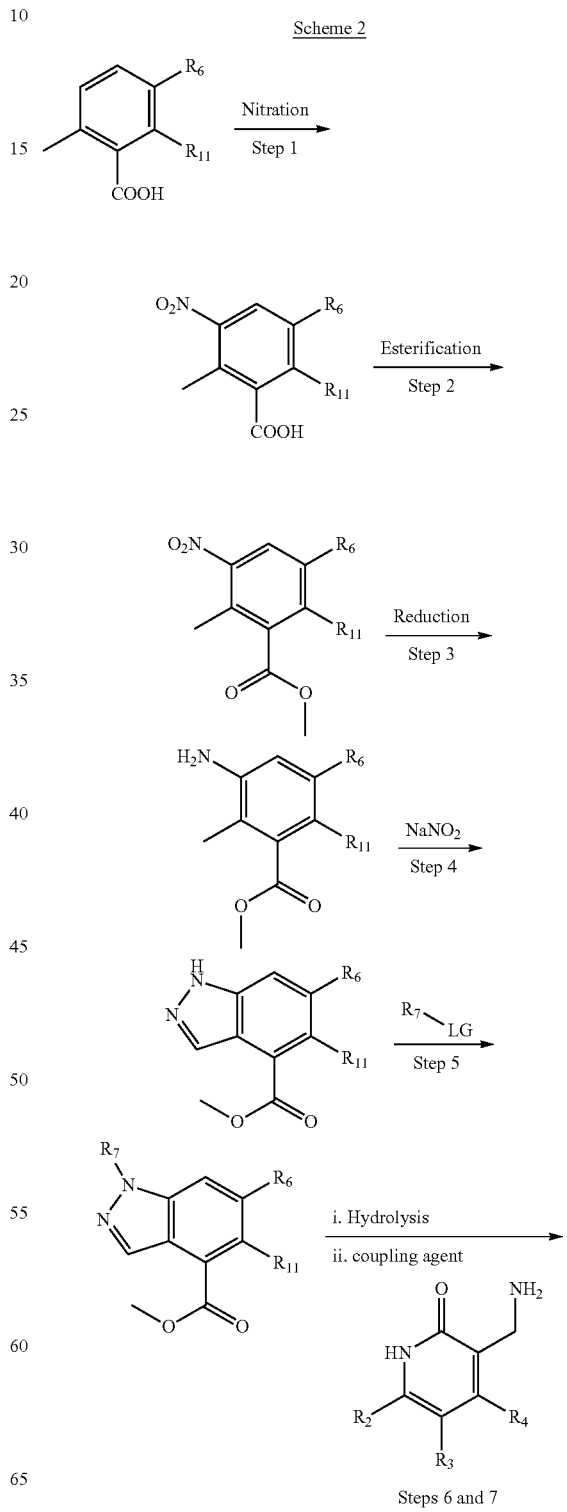

Steps 6 and 7

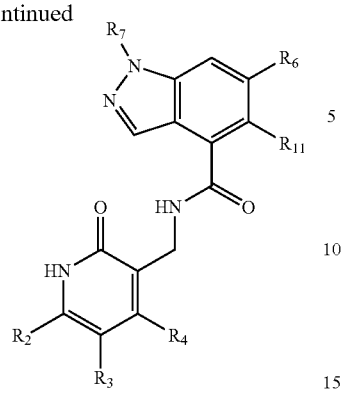

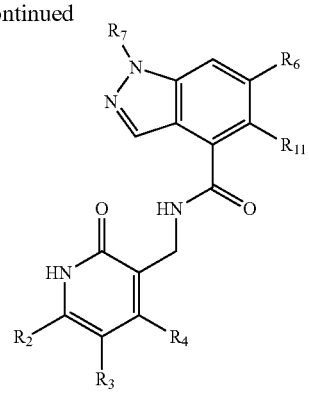

Scheme 2 shows the synthesis of modified indazole analogs following a general route that utilizes well-established chemistry. Introduction of a nitro group to a tolyl compound can be achieved using standard nitration conditions such as nitric acid in sulfuric acid (Step 1). The acid can be esterified by treatment with an alkylating agent such as methyliodide in the presence of a base such as sodium carbonate in an appropriate polar solvent such as DMF (Step 2). Reduction of the nitro group using an appropriate reducing agent such as iron with an acid such as ammonium chloride in a protic solvent such as ethanol can provide an aniline (Step 3). Diazotization with an appropriate reagent such as sodium nitrite in a polar solvent such as acetic acid can lead to cyclization to provide an indazole (Step 4). It will be apparent to one skilled in the art that there are multiple ways to synthesize indazoles (J. Org. Chem. 2006, 71, 8166-8172). Introduction of the $R_7$ to the indazole can be done using an appropriate $R_7$-LG where LG is a leaving group such as OTs or Br. Subjecting the intermediate to $R_7$-LG in the presence of a mild base such as cesium carbonate in an appropriate polar solvent such as DMF can give the desired $R_7$-substituted indazole ester (Step 5). The ester moiety can be converted to an amide using a standard two step protocol. The ester can be hydrolyzed to the corresponding acid using a suitable base such as sodium hydroxide in a polar solvent such as ethanol (Step 6). The acid can then be subjecting to a standard amide coupling reaction whereupon the appropriate amine can be added along with a suitable amide coupling reagent such as PYBOP in a suitable solvent such as DMSO to give the desired amide (Step 7).

Scheme 3

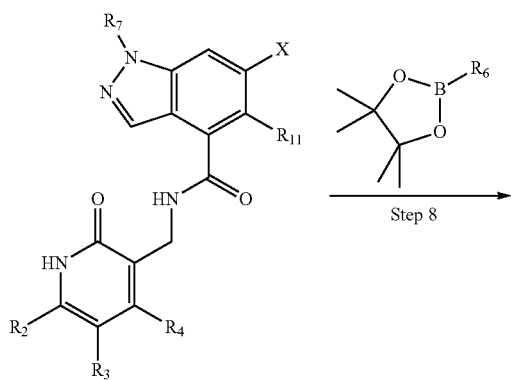

When $R_6$ is an appropriate group such as bromide or triflate, a variety of substituents could then be introduced using standard transition metal-based protocols. For example, the bromide can be combined with an appropriate boronic ester derivative, in the presence of a mild base and a palladium catalyst in a polar solvent such as dioxane/water, at elevated temperature to give the desired indazole (Step 8).

Scheme 4

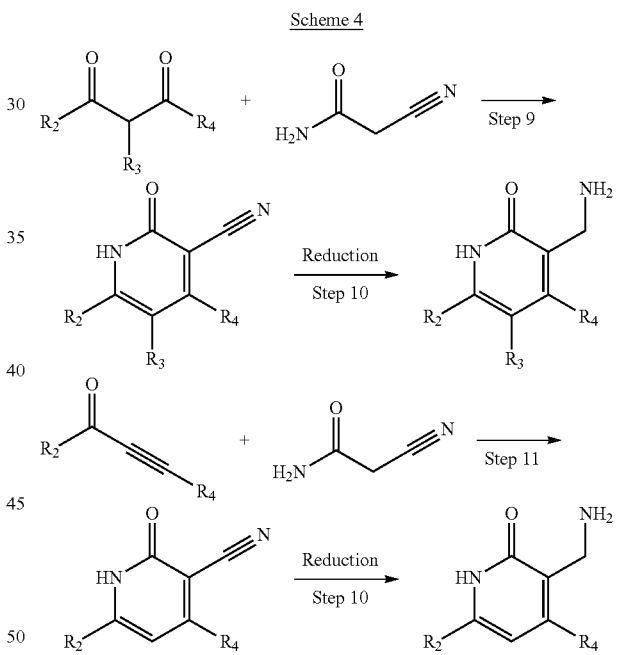

As shown in scheme 4, a diketone can be condensed with 2-cyanoacetamide in the presence of an appropriate reagent such as piperidine acetate in a polar solvent such as ethanol to provide a cyanopyridone (Step 9). Additionally, when $R_3$ is H, an appropriately substituted alkynyl ketone can be condensed with 2-cyanoacetamide in the presence of an appropriate reagent such as piperidine acetate in a polar solvent such as ethanol to provide a cyanopyridone (Step 11). The cyano group can be reduced under appropriate conditions such as hydrogenation in the presence of catalytic Raney nickel in a polar solvent such as ammonium in methanol to provide the amine (Step 10).

Additionally, depending upon the nature of the $R_2$, $R_3$, $R_4$, and $R_6$ group, further chemical modification can be employed to convert each of them independently into an alternative substituent. A representative sampling of such modifications can include hydrogenation, protecting group removal followed by additional amide coupling reactions, palladium catalyzed coupling reactions, reductive amination reactions, and alkylation reactions.

3. Methods of Treatment

The present invention provides methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, prodrug, metabolite, polymorph, solvate, or stereoisomeror thereof.

The disorder in which EZH2-mediated protein methylation plays a part can be cancer or a precancerous condition. The present invention further provides the use of a compound of the present invention, or a pharmaceutically acceptable salt, prodrug, metabolite, polymorph or solvate thereof, for the preparation of a medicament useful for the treatment of cancer.

The present invention also provides methods of protecting against a disorder in which EZH2-mediated protein methylation plays a part in a subject in need thereof by administering a therapeutically effective amount of compound of the present invention, or a pharmaceutically acceptable salt, prodrug, metabolite, polymorph or solvate thereof, to a subject in need of such treatment. The disorder can be cancer. The present invention also provides the use of compound of the present invention, or a pharmaceutically acceptable salt, prodrug, metabolite, polymorph, solvate, or stereoisomeror thereof, for the preparation of a medicament useful for the prevention of a cell proliferative disorder.

The compounds of this invention can be used to modulate protein (e.g., histone) methylation, e.g., to modulate histone methyltransferase or histone demethylase enzyme activity. Histone methylation has been reported to be involved in aberrant expression of certain genes in cancers, and in silencing of neuronal genes in non-neuronal cells. The compounds described herein can be used to treat these diseases, i.e., to decreases methylation or restores methylation to roughly its level in counterpart normal cells.

In general, compounds that are methylation modulators can be used for modulating cell proliferation, generally. For example, in some cases excessive proliferation may be reduced with agents that decrease methylation, whereas insufficient proliferation may be stimulated with agents that increase methylation. Accordingly, diseases that may be treated by the compounds of the invention include hyperproliferative diseases, such as benign cell growth and malignant cell growth.

As used herein, a "subject in need thereof" is a subject having a disorder in which EZH2-mediated protein methylation plays a part, or a subject having an increased risk of developing such disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or T is; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph, or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a protein methyltransferase of interest.

The present invention provides methods to assess biological activity of a compound of the present invention, or a pharmaceutically acceptable salt, prodrug, metabolite, polymorph or solvate thereof or methods of identifying a test compound as an inhibitor of a Y641 mutant of EZH2. In one embodiment the method includes combining an isolated Y641 mutant of EZH2 with a histone substrate, a methyl group donor (such as S-adenosylmethionine (SAM)), and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 in the histone substrate, thereby identifying the test compound as an inhibitor of the Y641 mutant of EZH2 when methylation of H3-K27 in the presence of the test compound is less than methylation of H3-K27 in the absence of the test compound. The assay to detect methylation of H3-K27 can be selected to measure the rate of methylation, the extent of methylation, or both the rate and extent of methylation.

The Y641 mutant of EZH2 is isolated as a PRC2 complex or functional equivalent thereof. As used herein, the term "isolated" means substantially separated from other components with which the complex may be found as it occurs in nature. A compound can be isolated without necessarily being purified. In one embodiment the mutant of EZH2 is isolated as a complex of a Y641 mutant of EZH2 together with EED and SUZ12. In another embodiment the mutant of EZH2 is isolated as a complex of a Y641 mutant of EZH2 together with EED, SUZ12, and RbAp48. Under appropriate conditions, a PRC2 complex or functional equivalent thereof exhibits histone methyltransferase activity for H3-K27. In one embodiment the complex is composed of recombinantly expressed component polypeptides, e.g., EZH2, EED, SUZ12, with or without RbAp48.

The isolated Y641 mutant of EZH2 is combined with a histone substrate. A histone substrate includes any suitable source of histone polypeptides or fragments thereof that can serve as substrate for EZH2. In one embodiment the histone substrate includes histones isolated from a subject. The histones can be isolated from cells of a subject using any suitable method; such methods are well known to persons skilled in the art and need not be further specified here. See, for example, Fang et al. (2004) *Methods Enzymol* 377:213-26. In accordance with the Examples below, in one embodiment the histone substrate is provided as nucleosomes. In accordance with the Examples below, in one embodiment the histone substrate is provided as avian (chicken) erythrocyte nucleosomes.

Histone substrate so provided may include an admixture of states of histone modification, including various states of H3-K27 methylation as judged by Western blotting with H3-K27 methylation state-specific antibodies. In one embodiment the histone substrate may be provided as purified full-length histone H3. Such purified full-length histone H3 may be provided as a homogeneous preparation in respect of states of H3-K27 methylation, or as an admixture of various states of H3-K27 methylation. Homogeneous preparations of isolated histone H3 in respect of states of H3-K27 methylation may be prepared in part by passage over an immunoaffinity column loaded with suitable H3-K27 methylation state-specific antibodies or by immunoprecipitation using magnetic beads coated with suitable H3-K27 methylation state-specific antibodies. Alternatively or in addition, the methylation state of H3-K27 can be characterized as part of performing the assay. For example, the starting material histone substrate might be characterized as containing 50 percent unmethylated H3-K27, 40 percent monomethylated H3-K27, 10 percent dimethylated H3-K27, and 0 percent trimethylated H3-K27.

In one embodiment the histone substrate includes a peptide library or a suitable peptide comprising one or more amino acid sequences related to histone H3, including, in particular, a sequence that encompasses H3-K27. For example, in one embodiment, the histone substrate is a peptide fragment that corresponds to amino acid residues 21-44 of histone H3. The peptide library or peptide can be prepared by peptide synthesis according to techniques well known in the art and optionally modified so as to incorporate any desired degree of methylation of lysine corresponding to H3-K27. As described in the Examples below, such peptides can also be modified to incorporate a label, such as biotin, useful in performing downstream assays. In one embodiment the label is appended to the amino (N)-terminus of the peptide(s). In one embodiment the label is appended to the carboxy (C)-terminus of the peptide(s).

Detection of methylation of H3-K27 can be accomplished using any suitable method. In one embodiment, the source of donor methyl groups includes methyl groups that are labeled with a detectable label. The detectable label in one embodiment is an isotopic label, e.g., tritium. Other types of labels may include, for example, fluorescent labels.

Detection of formation of trimethylated H3-K27 can be accomplished using any suitable method. For example, detection of formation of trimethylated H3-K27 can be accomplished using an assay to detect incorporation of labeled methyl groups, such as described above, optionally combined with a chromatographic or other method to separate labeled products by size, e.g., polyacrylamide gel electrophoresis (PAGE), capillary electrophoresis (CE), or high pressure liquid chromatography (HPLC). Alternatively or in addition, detection of formation of trimethylated H3-K27 can be accomplished using antibodies that are specific for trimethylated H3-K27.

Detection of conversion of monomethylated H3-K27 to dimethylated H3-K27 can be accomplished using any suitable method. In one embodiment the conversion is measured using antibodies specific for monomethylated H3-K27 and dimethylated H3-K27. For example, starting amounts or concentrations of monomethylated H3-K27 and dimethylated H3-K27 may be determined using appropriate antibodies specific for monomethylated H3-K27 and dimethylated H3-K27. Following the combination of enzyme, substrate, methyl group donor, and test compound, resulting amounts or concentrations of monomethylated H3-K27 and dimethylated H3-K27 may then be determined using appropriate antibodies specific for monomethylated H3-K27 and dimethylated H3-K27. The beginning and resulting amounts or concentrations of monomethylated H3-K27 and dimethylated H3-K27 can then be compared. Alternatively or in addition, beginning and resulting amounts or concentrations of monomethylated H3-K27 and dimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

Because the dimethylated form of H3-K27 may be further methylated in the same assay, a reduction in the amount or concentration of monomethylated H3-K27 may not appear to correspond directly to an increase in dimethylated H3-K27. In this instance, it may be presumed, however, that a reduction in the amount or concentration of monomethylated H3-K27 is, by itself, reflective of conversion of monomethylated H3-K27 to dimethylated H3-K27.

Detection of conversion of dimethylated H3-K27 to trimethylated H3-K27 can be accomplished using any suitable method. In one embodiment the conversion is measured using antibodies specific for dimethylated H3-K27 and trimethylated H3-K27. For example, starting amounts or concentrations of dimethylated H3-K27 and trimethylated H3-K27 may be determined using appropriate antibodies specific for dimethylated H3-K27 and trimethylated H3-K27. Following the combination of enzyme, substrate, and test compound, resulting amounts or concentrations of dimethylated H3-K27 and trimethylated H3-K27 may then be determined using appropriate antibodies specific for dimethylated H3-K27 and trimethylated H3-K27. The beginning and resulting amounts or concentrations of dimethylated H3-K27 and trimethylated H3-K27 can then be compared. Alternatively or in addition, beginning and resulting amounts or concentrations of dimethylated H3-K27 and trimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

A test agent is identified as an inhibitor of the Y641 mutant of EZH2 when methylation of H3-K27 with the test compound is less than methylation of H3-K27 without the test compound. In one embodiment, a test agent is identified as an inhibitor of the Y641 mutant of EZH2 when formation of trimethylated H3-K27 in the presence of the test compound is less than formation of trimethylated H3-K27 in the absence of the test compound.

The present invention also provides a method for identifying a selective inhibitor of a Y641 mutant of EZH2. In one embodiment the method includes combining an isolated Y641 mutant of EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the Y641 mutant of EZH2 and the test compound (M+) to (b) trimethylation with the Y641 mutant of EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the Y641 mutant of EZH2 when the ratio (a)/(b) is less than the ratio (c)/(d). In one embodiment the method further includes taking into account a negative control without test compound for either or both of the test mixture and the control mixture.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%.

Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine-131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

The disorder in which EZH2-mediated protein methylation plays a part can be a neurological disease. The compound of this invention can thus also be used for treating neurologic diseases such as epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluuysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which epigenetic methylation, which is mediated by EZH2, plays a role may be treatable or preventable using compounds and methods described herein 4. Pharmaceutical Compositions The present invention also provides pharmaceutical compositions comprising a compound of Formulae (I), (Ia), and (Ib) in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use.

A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage.

Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

5. EXAMPLES

General Procedure for Suzuki Coupling

To a stirred solution of bromo compound (1 equiv.) and boronate ester (1.2 equiv.) in dioxane/water mixture (5 mL+1 mL), $Na_2CO_3$ (3.6 equiv.) was added and solution purged with argon for 15 min. Then $Pd(PPh_3)_4$ (0.1 equiv.) was added and argon was purged again for 10 min. Reaction mass was heated at 100° C. for 2 h. On completion, reaction mixture was diluted with water and extracted with 10% MeOH/DCM. Combined organic layers were dried over $Na_2SO_4$ and solvent removed under reduced pressure to afford crude material which was purified by column chromatography over silica gel to afford desired compound (yield 75-90%).

General Procedure for Boc Deprotection:

A stirred solution of Boc protected amine (1 mmol) in DCM (5 mL) was cooled to 0° C. and TFA (2 mL) was added to it. Reaction mass was stirred at rt for 1 h. On completion, reaction was concentrated to dryness. Residue was basified with aqueous sodium bicarbonate till pH 8 and aqueous layer extracted with 20% MeOH/DCM. Combined organic layers were dried over sodium sulfate and concentrated to afford desired compound.

General Procedure for PYBOP Coupling:

To a solution of acid (1 equiv.) and amine (2 equiv.) in DMSO (3 mL for 1 mmol), PyBOP (1.5 equiv.) was added and reaction stirred at room temperature for overnight. On completion, water was added and solid that precipitates out was filtered and washed with water. Then this solid was stirred with acetonitrile for 10 min and filtered again to obtain pure desired compound.

General Procedure for Alkylation ((Reductive Amination with Aldehydes):

To a stirred solution of starting material (1 equiv.) and appropriate aldehyde (1.5 equiv.) in appropriate solvent (5 mL for 0.3 mmol; MeOH or DCE), acetic acid (1 equiv.) was added and reaction stirred at rt. Then reducing agent (1 equiv.; $NaBH_3CN$ or $Na(OAc)_3BH$) was added and reaction stirred overnight. On completion, solvent was removed under reduced pressure and residue purified by column chromatography over silica gel or as specified affording desired compound.

General Procedure for Methylation (Reductive Amination with Formalin Solution):

To a stirred solution of secondary amine (1 equiv.) in methanol (5 mL for 1 mmol), formalin solution (37-40% sol, 10 equiv.) was added at 5° C. and reaction stirred for 10 min. Then $NaBH_3CN$ (3 equiv.) was added and reaction stirred at rt for 1 h. On completion, methanol was removed under reduced pressure; water was added to the residue and aqueous phase extracted with 10% MeOH/DCM. Combined organic layers were dried over sodium sulfate and concentrated to obtain crude material which was purified by column chromatography or prep HPLC.

General Procedure Reaction of Benzyl Bromides

To a stirred solution of respective amino-alcohol (3 equiv.) in dry THF, NaH (3 equiv) was added at 0° C. Resulting reaction mass was stirred for 30 minutes. To this a solution of the benzyl bromide (1 equiv.) in THF was added at 0° C. and reaction mass stirred at room temperature for 1 h. On completion, reaction was quenched with water and extracted with 10% MeOH/DCM. Combined organic layer was dried over sodium sulfate and concentrated to give crude material which was purified by preparative HPLC to afford final target molecules as TFA salts.

Procedure for Pd—C Reduction:

To a stirred solution of starting material (0.1 g) in MeOH (5 mL) was added 10% Pd/C (0.1 g) and reaction stirred at room temperature under hydrogen (balloon pressure) for 4 h. On completion, the reaction mixture was filtered through a celite bed and the filtrate concentrated under reduce pressure to a obtain crude solid which was purified by solvent washing to afford final target molecules as TFA salts.

Example 1

The compounds listed in Tables 1-6 were synthesized by reaction schemes depicted in the general schemes above or by methods described below.

Synthesis of Compound A-1:1-cyclopentyl-N-((4,6-dimethyl-2-oxo-1,2-dihydropyridin-3-yl)methyl)-6-(4-(morpholinomethyl)phenyl)-1H-pyrazolo[3,4-b]pyridine-4-carboxamide Compound A-1

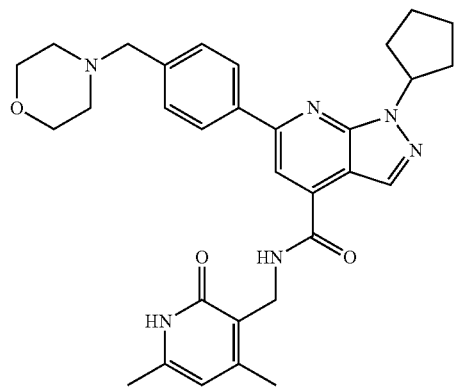

Step 1: Synthesis of 3-(aminomethyl)-4,6-dimethylpyridin-2(1H)-one

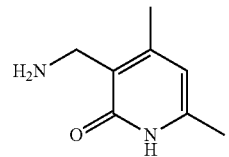

3-Cyano-2,4-dimethyl-2-hydroxypyridine (0.3 g, 2.0 mmol) was dissolved in MeOH (5 mL), to which catalytic amount of Raney Ni and of aqueous $NH_3$ (0.3 mL) were added and the reaction mixture was stirred under hydrogen pressure (bladder pressure) for 3-4 h. After completion of the reaction, catalyst was filtered off and the filtrate was concentrated under reduced pressure. The residue was thoroughly dried to provide the desired product (0.3 g, quantitative yield).

Step 2: Synthesis of ethyl 6-hydroxy-1H-pyrazolo[3,4-b]pyridine-4-carboxylate

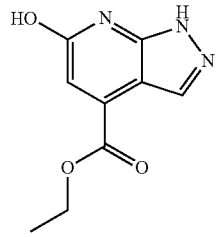

A stirred solution of 1H-pyrazol-3-amine (45 g, 542 mmol) in acetic acid (297 mL) and water (900 mL) was cooled to 0° C. and diethyl oxaloacetate sodium salt (113.85 g, 542.16 mmol) was added to it. Resulting solution was heated at 100° C. for overnight. After completion of reaction, solid was filtered and dried to obtain the desired intermediate (25 g, 22%).

Step 3: Synthesis of ethyl 6-bromo-1H-pyrazolo[3,4-b]pyridine-4-carboxylate

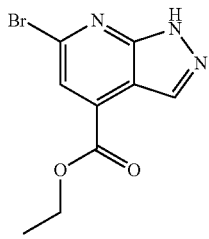

Ethyl 6-hydroxy-1H-pyrazolo[3,4-b]pyridine-4-carboxylate (25 g, 120 mmol) was suspended in acetonitrile (250 mL) and POBr$_3$ (69.56 g, 241.54 mmol) was added to it. The reaction mixture was refluxed for 6 h. On completion of reaction, acetonitrile was removed under reduced pressure and residue neutralized with saturated NaHCO$_3$ solution was added to it. Extraction was carried out using ethyl acetate; the combined organic layers were washed with water, brine and dried over anhydrous Na$_2$SO$_4$; filtered and concentrated under reduced pressure. The residue was purified by silica gel column chromatography to provide the desired intermediate (25 g, 77%).

Step 4: Synthesis of ethyl 6-bromo-1-cyclopentyl-1H-pyrazolo[3,4-b]pyridine-4-carboxylate

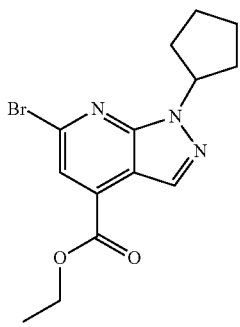 [SMILES: CCOC(=O)c1cc(Br)nc2c1cnn2C1CCCC1]

Ethyl 6-bromo-1H-pyrazolo[3,4-b]pyridine-4-carboxylate (3 g, 11.15 mmol) was dissolved in acetonitrile (30 mL) and K$_2$CO$_3$ (1.85 g, 13.38 mmol) and cyclopentyl bromide (3.35 g, 22.30 mmol) was added to it. The reaction mixture was refluxed for 3 h. On completion, acetonitrile was removed under reduced pressure and water was added to it. Extraction was carried out using ethyl acetate; the combined organic layers were washed with water, brine and dried over anhydrous Na$_2$SO$_4$. Solvent was removed under reduced pressure and residue was purified by silica gel column chromatography to obtain the desired intermediate (1.3 g, 50%).

Step 5: Synthesis of 6-bromo-1-cyclopentyl-N-((4,6-dimethyl-2-oxo-1,2-dihydropyridin-3-yl)methyl)-1H-pyrazolo[3,4-b]pyridine-4-carboxamide

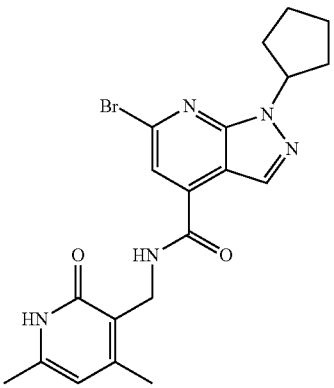 [SMILES: Cc1cc(C)c(CNC(=O)c2cc(Br)nc3c2cnn3C2CCCC2)c(=O)[nH]1]

Aqueous NaOH (0.308 g, 7.72 mmol) was added to a solution of ethyl 6-bromo-1-cyclopentyl-1H-pyrazolo[3,4-b]pyridine-4-carboxylate (1.3 g, 3.8 mmol) in EtOH (10 mL) and stirred at 60° C. for 1 h. After completion of the reaction, ethanol was removed under reduced pressure and it was acidified using 10% citric acid solution. Extraction was carried out using ethyl acetate; the combined organic layers were washed with water, brine and dried over anhydrous Na$_2$SO$_4$; filtered and concentrated under reduced pressure. The crude acid (1 g, 3.23 mmol) was then dissolved in DMSO (10 mL) and 3-(aminomethyl)-4,6-dimethylpyridin-2(1H)-one (0.98 g, 6.47 mmol) was added to it. The reaction mixture was stirred at room temperature for 15 min before PYBOP (2.52 g, 4.85 mmol) was added to it and stirring was continued overnight. After completion of the reaction, reaction mass was poured into ice to obtain solid, which was filtered and washed with acetonitrile followed by ether to provide the desired intermediate (1 g, 70%).

Step 6: Synthesis of 1-cyclopentyl-N-((4,6-dimethyl-2-oxo-1,2-dihydropyridin-3-yl)methyl)-6-(4-(morpholinomethyl)phenyl)-1H-pyrazolo[3,4-b]pyridine-4-carboxamide

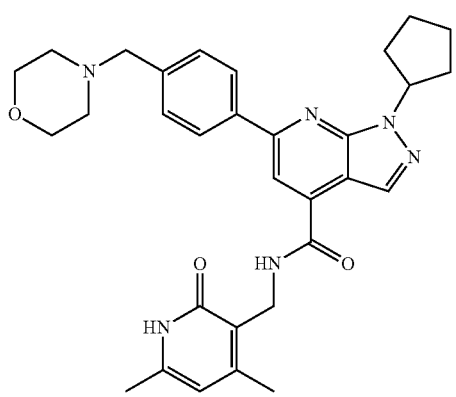 [SMILES: Cc1cc(C)c(CNC(=O)c2cc(-c3ccc(CN4CCOCC4)cc3)nc3c2cnn3C2CCCC2)c(=O)[nH]1]

A solution of 6-bromo-1-cyclopentyl-N-((4,6-dimethyl-2-oxo-1,2-dihydropyridin-3-yl)methyl)-1H-pyrazolo[3,4-b]pyridine-4-carboxamide (0.25 g, 0.56 mmol), boronic ester (0.163 g, 0.620 mmol) and Pd(PPh₃)₄ (0.065 g, 0.056 mmol) in 1,4-dioxane (3 mL) was purged with argon for 10 min. Then, 2 M Na₂CO₃ solution (0.216 g, 2.03 mmol) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na₂SO₄, filtered and concentrated under reduced pressure to afford crude material which was purified by column chromatography to give the desired compound (72% yield). LCMS: 541.30 (M+1)⁺; HPLC: 99.81% (@ 254 nm) (R$_t$,5.464); ¹H NMR (DMSO-d₆, 400 MHz) δ 11.55 (s, 1H), 8.95 (t, 1H, J=5.2 Hz), 8.36 (s, 1H), 8.20 (d, 2H, J=8.4 Hz), 8.14 (s, 1H), 7.48 (d, 2H, J=7.6 Hz), 5.89 (s, 1H), 5.51-5.48 (m, 1H), 4.40 (d, 2H, J=4.8 Hz), 3.60-3.58 (m, 4H), 3.54 (s, 2H), 2.38 (bs, 4H), 2.21 (s, 3H), 2.18-2.15 (s, 2H), 2.12 (s, 3H), 2.08-2.05 (m, 2H), 1.94-1.92 (m, 2H), 1.76-1.73 (m, 2H).

Synthesis of Compound A-2: N-((4,6-dimethyl-2-oxo-1,2-dihydropyridin-3-yl)methyl)-1-isopropyl-6-(4-(morpholinomethyl)phenyl)-1H-pyrazolo[3,4-b]pyridine-4-carboxamide Compound A-2

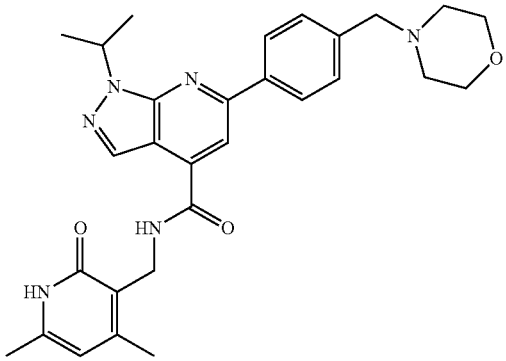

Step 1: Synthesis of ethyl 1-isopropyl-6-(trifluoromethylsulfonyloxy)-1H-pyrazolo[3,4-b]pyridine-4-carboxylate

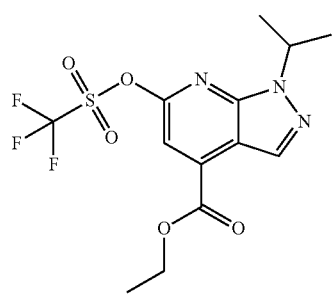 [SMILES: CCOC(=O)c1cc(OS(=O)(=O)C(F)(F)F)nc2c1cnn2C(C)C]

Trifluoromethanesulfonic anhydride (5.23 g, 18.5 mmol) was added to a cooled solution of ethyl 6-hydroxy-1-isopropyl-1H-pyrazolo[3,4-b]pyridine-4-carboxylate (4.2 g, 16.9 mmol) and pyridine (1.46 g, 18.5 mmol) in DCM (60 mL); and it was allowed to stirred at room temperature for 2 h. After completion of the reaction, saturated NaHCO₃ solution (60 mL) was added to it and extraction was carried out using DCM (30 mL×3). The combined organic layers were washed with water (100 mL); brine (100 mL); dried over anhydrous Na₂SO₄; filtered and concentrated under reduced pressure. The residue was finally purified by silica gel column chromatography to provide pure the desired intermediate (5 g, 77.8% yield).

Step 2: Synthesis of ethyl 6-(4-(hydroxymethyl)phenyl-1-isopropyl-1H-pyrazolo[3,4-b]pyridine-4-carboxylate

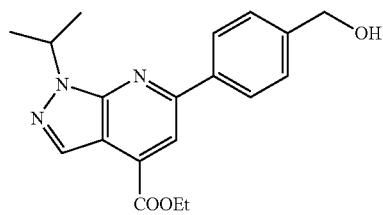 [SMILES: CCOC(=O)c1cc(-c2ccc(CO)cc2)nc2c1cnn2C(C)C]

A solution of ethyl 1-isopropyl-6-(trifluoromethylsulfonyloxy)-1H-pyrazolo[3,4-b]pyridine-4-carboxylate (1 g, 2.6 mmol), 4-(hydroxymethyl)phenyl boronic acid (0.438 g, 2.88 mmol) and Pd(PPh₃)₄ (0.303 g, 0.262 mmol) in 1,4-dioxane (15 mL) was purged with argon for 10 min. Then, 2M Na₂CO₃ solution (4.5 mL, 9.44 mmol) was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na₂SO₄, filtered and concentrated under reduced pressure to afford crude material which was purified by column chromatography to give the desired compound.

Step 3: Synthesis of N-((4,6-dimethyl-2-oxo-1,2-dihydropyridin-3-yl)methyl)-6-(4-(hydroxymethyl)phenyl)-1-isopropyl-1H-pyrazolo[3,4-b]pyridine-4-carboxamide

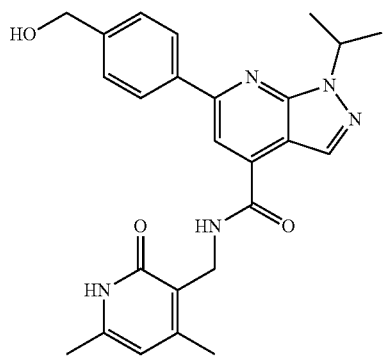 [SMILES: Cc1cc(C)c(CNC(=O)c2cc(-c3ccc(CO)cc3)nc3c2cnn3C(C)C)c(=O)[nH]1]

To a solution of ethyl 6-(4-(hydroxymethyl)phenyl-1-isopropyl-1H-pyrazolo[3,4-b]pyridine-4-carboxylate (0.81 g, 2.38 mmol) in EtOH (15 mL), aqueous NaOH (0.47 g, 11.94 mmol) was added and reaction mixture stirred at 60° C. for 1 h. After completion of the reaction, ethanol was removed under reduced pressure and it was acidified using 10% citric acid solution. Extraction was carried out using 5% MeOH/DCM. The combined organic layers were washed with water & dried over anhydrous Na₂SO₄, filtered and concentrated under reduced pressure to afford compound which was pure enough to use as such for next step. A solution of acid compound (0.61 g, 1.96 mmol) and 3-(aminomethyl)-4,6-dimethylpyridin-2(1H)-one (0.596 g, 3.92 mmol) in DMSO (5 mL) and was stirred at room temperature for 15 min. Then PYBOP (1.52 g, 2.94 mmol) was added to it and stirring was continued for 12 hr. After completion of the reaction, saturated NaHCO₃ solution was added to it and extraction was carried out using 20% MeOH/DCM. The combined organic layers were washed with water, dried over anhydrous Na₂SO₄, filtered and concentrated under reduced pressure to afford crude material which was purified by column chromatography to afford the desired compound as white solid (0.71 g, 81.4%).

Step 4: Synthesis of 6-(4-(bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide

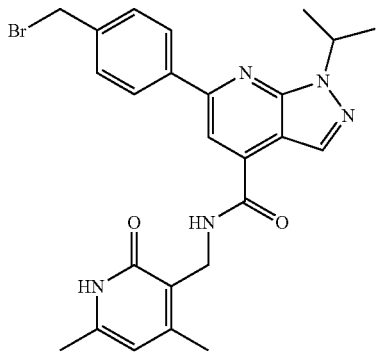 [SMILES: Cc1cc(C)c(CNC(=O)c2cc(-c3ccc(CBr)cc3)nc3c2cnn3C(C)C)c(=O)[nH]1]

To a stirred solution of N-((4,6-dimethyl-2-oxo-1,2-dihydropyridin-3-yl)methyl)-6-(4-(hydroxymethyl)phenyl)-1-isopropyl-1H-pyrazolo[3,4-b]pyridine-4-carboxamide (0.45 g, 1.01 mmol) in a DCM (10 mL) was added PPh₃ (0.477 g, 1.81 mmol) at 0° C. & then stirred for 5 min. After that CBr₄ (0.636 g, 1.92 mmol) was added & stirred at room temperature for 1 hr. After completion of reaction, turbid reaction mass was filtered & washed with small amount of DCM to afford the desired product as white solid (0.27 g, 52.9%).

Step 5: Synthesis of N-((4,6-dimethyl-2-oxo-1,2-dihydropyridin-3-yl)methyl)-1-isopropyl-6-(4-(morpholinomethyl)phenyl)-1H-pyrazolo[3,4-b]pyridine-4-carboxamide

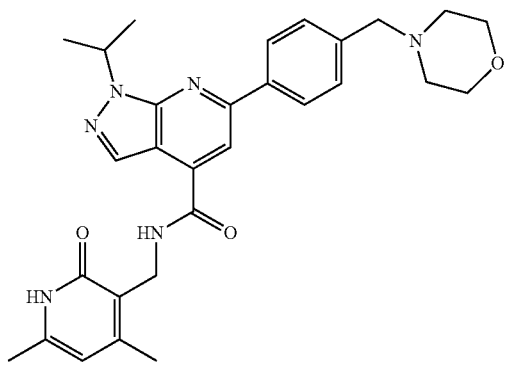 [SMILES: Cc1cc(C)c(CNC(=O)c2cc(-c3ccc(CN4CCOCC4)cc3)nc3c2cnn3C(C)C)c(=O)[nH]1]

To a stirred solution of 6-(4-(bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide (1 equiv.) in dry DMF, morpholine (5 equiv.) was added at 0° C. and reaction mixture was stirred for overnight. After completion of reaction, water was added to it and extraction was carried out using EtOAc. The combined organic layers were washed with water; dried over anhydrous Na₂SO₄; filtered and concentrated under reduced pressure. The residue was purified by column chromatography/preparative HPLC to give the desired compound (15% yield). LCMS: 515.25 (M+1)⁺; HPLC: 99.80% (@ 254 nm) (R$_t$: 5.168); ¹H NMR (DMSO-d₆, 400 MHz) δ 11.55 (s, 1H), 10.01 (bs, 1H), 8.94 (bs, 1H), 8.39 (s, 1H), 8.35 (d, J=7.6 Hz, 2H), 8.18 (s, 1H), 7.68 (d, J=7.2 Hz, 2H), 5.90 (s, 1H), 5.30 (m, 1H), 4.44-4.41 (m, 4H), 3.98 (m, 2H), 3.63-3.60 (m, 2H), 3.37-3.30 (m, 2H), 3.16 (m, 2H), 2.23 (s, 3H), 2.13 (s, 3H), 1.55 (d, J=6.4 Hz, 6H).

Synthesis of Compound A-3: N-((4,6-dimethyl-2-oxo-1,2-dihydropyridin-3-yl)methyl)-6-(3-((dimethylamino)methyl)phenyl)-1-isopropyl-1H-pyrazolo[3,4-b]pyridine-4-carboxamide Compound A-3

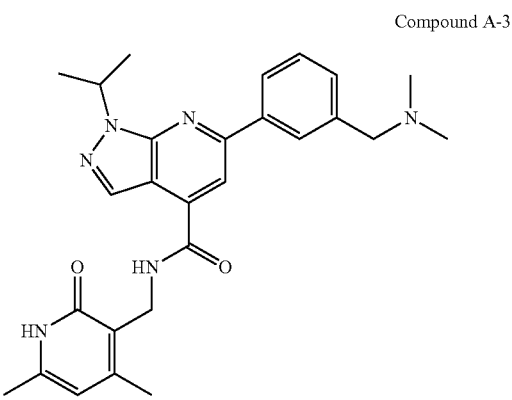

Step 1: Synthesis of ethyl 6-(3-(hydroxymethyl)phenyl)-1-isopropyl-1H-pyrazolo[3,4-b]pyridine-4-carboxylate

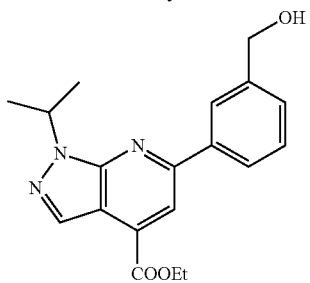

A solution of ethyl 1-isopropyl-6-(((trifluoromethyl)sulfonyl)oxy)-1H-pyrazolo[3,4-b]pyridine-4-carboxylate (1 g, 2.62 mmol), 3-(hydroxymethyl)phenyl boronic acid (0.438 g, 2.88 mmol) and Pd(PPh₃)₄ (0.303 g, 0.262 mmol) in 1,4-dioxane (15 mL) was purged with argon for 10 min. Then 2M Na₂CO₃ solution (4.5 mL, 9.4 mmol) was added to it and again argon was purged through it for 10 min. The reaction mixture was stirred at 100° C. for 1 h and after completion of the reaction water was added to it. Extraction was carried out using EtOAc the combined organic layers were washed with water dried over anhydrous Na₂SO₄; filtered and concentrated under reduced pressure. The residue was purified by column chromatography to give 0.81 g of target compound.

Step 2: Synthesis of 6-(3-(hydroxymethyl)phenyl)-1-isopropyl-1H-pyrazolo[3,4-b]pyridine-4-carboxylic acid

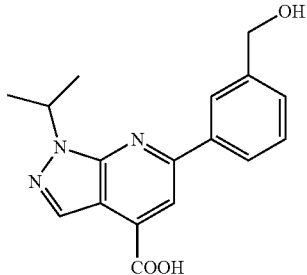 [SMILES: CC(C)n1ncc2c(C(=O)O)cc(-c3cccc(CO)c3)nc21]

To a solution of ethyl 6-(3-(hydroxymethyl)phenyl)-1-isopropyl-1H-pyrazolo[3,4-b]pyridine-4-carboxylate (0.81 g, 2.38 mmol) in EtOH (15 mL) aqueous NaOH (0.47 g, 11.94 mmol) was added and stirred at 60° C. for 1 h. After completion of the reaction, ethanol was removed under reduced pressure and it was acidified using 10% citric acid solution till pH 4. Extraction was carried out using 5% MeOH/DCM, the combined organic layers were washed with water & dried over anhydrous $Na_2SO_4$; filtered and concentrated under reduced pressure to afford the desired acid which was used without further purification.

Step 3: Synthesis of N-((4,6-dimethyl-2-oxo-1,2-dihydropyridin-3-yl)methyl)-6-(3-(hydroxymethyl)phenyl)-1-isopropyl-1H-pyrazolo[3,4-b]pyridine-4-carboxamide

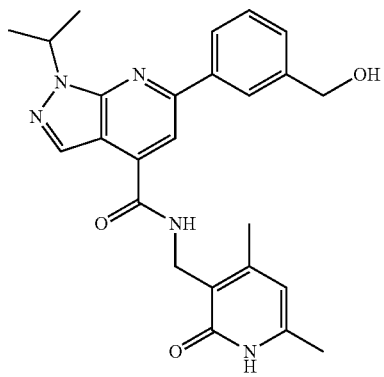 [SMILES: Cc1cc(C)c(CNC(=O)c2cc(-c3cccc(CO)c3)nc3c2cnn3C(C)C)c(=O)[nH]1]

A mixture of 6-(3-(hydroxymethyl)phenyl)-1-isopropyl-1H-pyrazolo[3,4-b]pyridine-4-carboxylic acid (0.65 g, 2.09 mmol), 3-(aminomethyl)-4,6-dimethylpyridin-2(1H)-one (0.64 g, 4.18 mmol) and PYBOP (1.63 g, 3.13 mmol) in DMSO (5 mL) was stirred at room temperature for 12 hr. After completion of the reaction, saturated $NaHCO_3$ solution was added to it and extraction was carried out using 20% MeOH/DCM. The combined organic layers were washed with water; dried over anhydrous $Na_2SO_4$; filtered and concentrated under reduced pressure. The residue was purified by column chromatography to give a white solid (0.71 g, 81.4%).

Step 4: Synthesis of 6-(3-(bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide

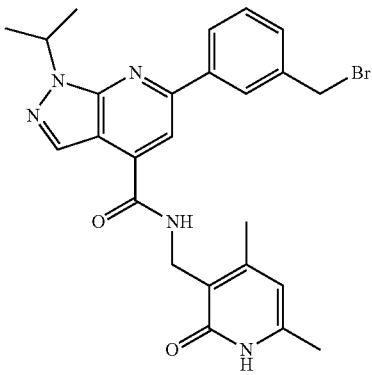 [SMILES: Cc1cc(C)c(CNC(=O)c2cc(-c3cccc(CBr)c3)nc3c2cnn3C(C)C)c(=O)[nH]1]

To a stirred solution of N-((4,6-dimethyl-2-oxo-1,2-dihydropyridin-3-yl)methyl)-6-(3-(hydroxymethyl)phenyl)-1-isopropyl-1H-pyrazolo[3,4-b]pyridine-4-carboxamide (0.45 g, 0.1.011 mmol) in a DCM (10 mL), $PPh_3$ (0.477 g, 1.81 mmol) was added at 0° C. & then stirred for 5 min. After that $CBr_4$ (0.636 g, 1.92 mmol) was added and stirred at room temperature for 1 hr. After completion of reaction, solid was filtered & washed with small amount of DCM to afford 0.30 g of pure desired product.

Step 5: Synthesis of N-((4,6-dimethyl-2-oxo-1,2-dihydropyridin-3-yl)methyl)-6-(3-((dimethylamino)methyl)phenyl)-1-isopropyl-1H-pyrazolo[3,4-b]pyridine-4-carboxamide

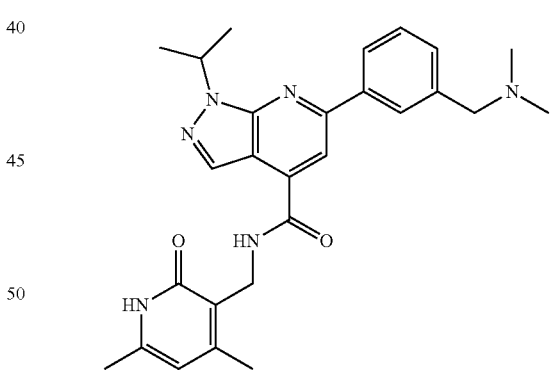

To a stirred solution of 6-(3-(bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide (1 equiv.) in a DMF, dimethylamine (5 equiv.) was added at 0° C. & resulting reaction mixture stirred for overnight. After completion of reaction, water was added to it and extraction was carried out using EtOAc. The combined organic layers were washed with water, dried over anhydrous $Na_2SO_4$, filtered and concentrated under reduced pressure to obtain the crude material which was purified by column chromatography to give pure final compounds (40% yield). LCMS: 473.20(M+1)$^+$; HPLC: 99.89% (@ 254 nm) ($R_t$:5.325); $^1$H NMR (DMSO-$d_6$, 400 MHz) δ 11.52 (s, 1H), 8.96 (bs, 1H), 8.35 (s, 1H), 8.13-8.10 (m, 3H), 7.50 (t, J=8.4 Hz, 1H), 7.43-7.41 (m, 1H), 5.89 (s, 1H), 5.34-5.31 (m, 1H), 4.41 (d, J=4 Hz, 2H), 3.50 (s, 2H), 2.23 (s, 3H), 2.19 (s, 6H), 2.12 (s, 3H), 1.54 (d, J=6.8 Hz, 6H).

Synthesis of Compound A-4:6-(2-aminopyrimidin-5-yl)-N-((4,6-dimethyl-2-oxo-1,2-dihydropyridin-3-yl)methyl)-1-isopropyl-1H-pyrazolo[3,4-b]pyridine-4-carboxamide Compound A-4

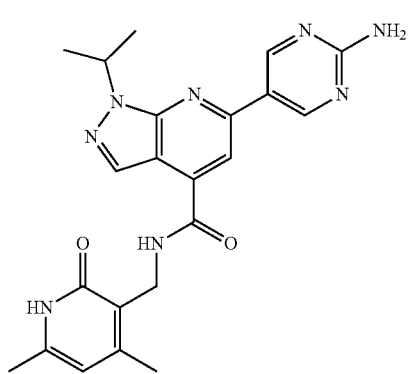

Step 1: Synthesis of ethyl 6-bromo-1-isopropyl-1H-pyrazolo[3,4-b]pyridine-4-carboxylate

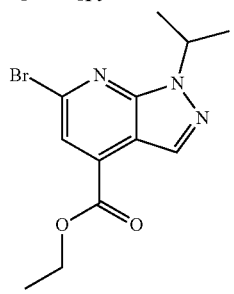

To a stirred solution of ethyl 6-bromo-1H-pyrazolo[3,4-b]pyridine-4-carboxylate (20 g, 74.3 mmol) in acetonitrile (200 mL), K₂CO₃ (15.39 g, 111.52 mmol) and 2-bromopropane (18.13 g, 148.64 mmol) was added to it. The reaction mixture was refluxed for 8 h. On completion, acetonitrile was removed under reduced pressure and water was added to it. Extraction was carried out using ethyl acetate; the combined organic layers were washed with water, brine and dried over anhydrous Na₂SO₄. Solvent was removed under reduced pressure and residue was purified by silica gel column chromatography to obtain the desired intermediate (13.5 g, 58.3%).

Step 2: Synthesis of 6-bromo-N-((4,6-dimethyl-2-oxo-1,2-dihydropyridin-3-yl)methyl)-1-isopropyl-1H-pyrazolo[3,4-b]pyridine-4-carboxamide

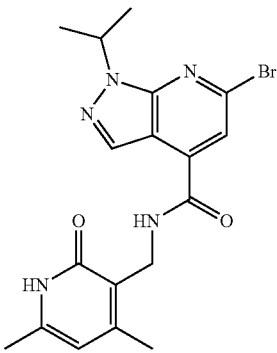 [SMILES: Cc1cc(C)c(CNC(=O)c2cc(Br)nc3c2cnn3C(C)C)c(=O)[nH]1]

Aqueous NaOH (0.964 g, 24.11 mmol) was added to a solution of ethyl 6-bromo-1-isopropyl-1H-pyrazolo[3,4-b]pyridine-4-carboxylate (5 g, 16.07 mmol) in EtOH (50 mL) and stirred at 60° C. for 1 h. After completion of the reaction, ethanol was removed under reduced pressure and it was acidified using 10% citric acid solution. Extraction was carried out using ethyl acetate; the combined organic layers were washed with water, brine and dried over anhydrous Na₂SO₄; filtered and concentrated under reduced pressure. The crude acid (3 g, 10.55 mmol) was then dissolved in DMSO (35 mL) and 3-(aminomethyl)-4,6-dimethylpyridin-2(1H)-one (3.2 g, 21.0 mmol) was added to it. The reaction mixture was stirred at room temperature for 15 min before PYBOP (8.23 g, 15.82 mmol) was added to it and stirring was continued overnight. After completion of the reaction, reaction mass was poured into ice to obtain solid, which was filtered and washed with acetonitrile followed by ether to provide the desired intermediate (3 g, 68%).

Step 3: Synthesis of 6-(2-aminopyrimidin-5-yl)-N-((4,6-dimethyl-2-oxo-1,2-dihydropyridin-3-yl)methyl)-1-isopropyl-1H-pyrazolo[3,4-b]pyridine-4-carboxamide

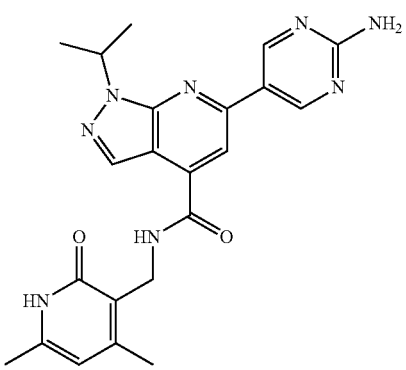 [SMILES: Cc1cc(C)c(CNC(=O)c2cc(-c3cnc(N)nc3)nc3c2cnn3C(C)C)c(=O)[nH]1]

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv.), (2-aminopyrimidin-5-yl) boronic acid (1.2 equiv.) and Pd(PPh₃)₄ (0.1 equiv.) in 1,4-dioxane was purged with argon for 10 min. Then, 2 M Na₂CO₃ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na₂SO₄, filtered and concentrated under reduced pressure to afford crude material which was purified by column chromatography to give the desired compound (45% yield). LCMS: 433.20(M+1)⁺; HPLC: 98.75% (@ 254 nm) (R$_t$:5.252); ¹H NMR (DMSO-d₆, 400 MHz) δ 11.55 (s, 1H), 9.09 (s, 2H), 8.84 (t, 1H), 8.33 (s, 1H), 8.07 (s, 1H), 7.15 (s, 2H), 5.89 (s, 1H), 5.32-5.28 (m, 1H), 4.40 (d, 2H, J=4.0 Hz), 2.22 (s, 3H), 2.12 (s, 3H), 1.51 (d, 6H, J=6.8 Hz).

Synthesis of Compound A-5: N-((4,6-dimethyl-2-oxo-1,2-dihydropyridin-3-yl)methyl)-1-isopropyl-6-(1-(2-morpholinoethyl)-1H-pyrazol-4-yl)-1H-pyrazolo[3,4-b]pyridine-4-carboxamide Compound A-5

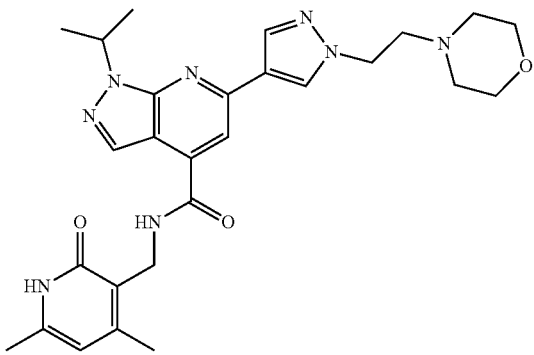

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv.), (1-(2-morpholinoethyl)-1H-pyrazol-4-yl)boronic acid (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the desired compound. LCMS: 519.00 (M+1)$^+$; HPLC: 97.07% (@ 254 nm) (R$_t$: 4.925; Method: Column. YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.55 (s, 1H), 8.76 (t, 1H), 8.46 (s, 1H), 8.26 (s, 1H), 8.14 (s, 1H), 7.85 (s, 1H), 5.89 (s, 1H), 5.34-5.31 (m, 1H), 4.39 (d, 2H, J=4.8 Hz), 4.30 (t, 2H, J=6.8 Hz), 3.54 (m, 4H), 2.76 (t, 2H, J=6.4 Hz), 2.42 (m, 4H), 2.22 (s, 3H), 2.12 (s, 3H), 1.51 (d, 6H, J=6.4 Hz).

Synthesis of Compound A-6: tert-butyl 4-(5-(4-(((4,6-dimethyl-2-oxo-1,2-dihydropyridin-3-yl)methyl)carbamoyl)-1-isopropyl-1H-pyrazolo[3,4-b]pyridin-6-yl)pyridin-2-yl)piperazine-1-carboxylate Compound A-6

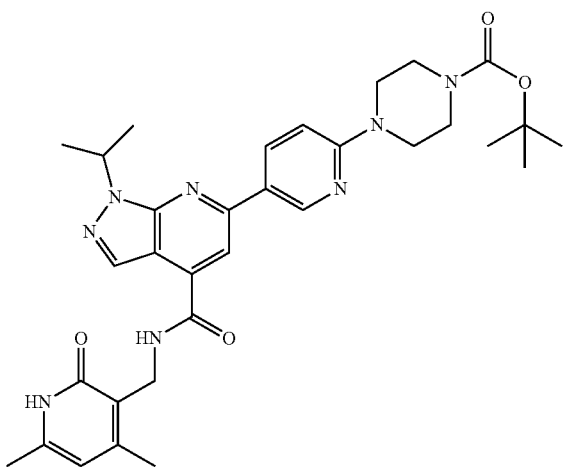

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv.) tert-butyl 4-(5-(4,4,5,5-tetramethyl-1,3,2-dioxaborolan-2-yl)pyridin-2-yl)piperazine-1-carboxylate (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the desired product (70% yield). LCMS: 601.30 (M+1)$^+$; HPLC: 99.80% (@ 254 nm), (R$_t$: 6.124); $^1$H NMR (DMSO-d$_6$, 400 MHz) δ 11.54 (s, 1H), 9.03 (d, 1H, J=2 Hz), 8.85 (t, 1H), 8.39 (dd, 1H, J=8.8, 2 Hz), 8.31 (s, 1H), 8.08 (s, 1H), 6.99 (d, 1H, J=9.2 Hz), 5.89 (s, 1H), 5.32-5.25 (m, 1H), 4.40 (d, 2H, J=4.4 Hz), 3.63 (t, 4H), 3.45 (bs, 4H), 2.22 (s, 3H), 2.12 (s, 3H), 1.53 (d, 6H, J=6.4 Hz), 1.43 (s, 9H).

Synthesis of Compound A-7: N-((4,6-dimethyl-2-oxo-1,2-dihydropyridin-3-yl)methyl)-1-isopropyl-6-(4-(piperazin-1-yl)phenyl)-1H-pyrazolo[3,4-b]pyridine-4-carboxamide Compound A-7

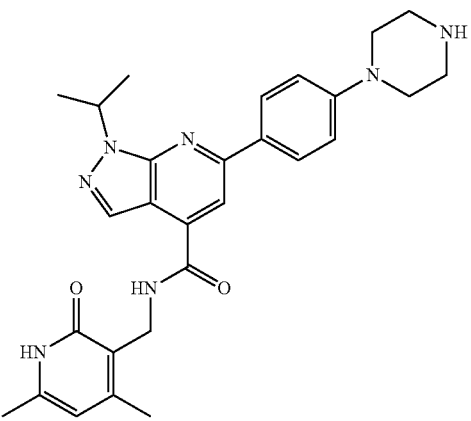

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv), tert-butyl 4-(4-(4,4,5,5-tetramethyl-1,3,2-dioxaborolan-2-yl)phenyl)piperazine-1-carboxylate (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the Boc protected intermediate. Boc-deprotection was achieved by using TFA-DCM (10 times by volume in 1:1 ratio, work up using NaHCO3) to give the desired compound (65% yield). LCMS: 500.15 (M+1)$^+$; HPLC: 99.23% (@ 254 nm), (R$_t$: 5.242); $^1$H NMR (DMSO-d$_6$, 400 MHz) δ 11.60 (bs, 1H), 9.23 (bs, 2H), 8.94 (bs, 1H), 8.31 (s, 1H), 8.19 (d, 2H, J=8.8 Hz), 8.08 (s, 1H), 7.14 (d, 2H, J=8.8 Hz), 5.91 (s, 1H), 5.33-5.26 (m, 1H), 4.40 (d, 2H, J=4.8 Hz), 3.51 (bs, 4H), 3.24 (bs, 4H), 2.22 (s, 3H), 2.13 (s, 3H), 1.53 (d, 6H, J=6.4 Hz).

Synthesis of Compound A-8: N-((4,6-dimethyl-2-oxo-1,2-dihydropyridin-3-yl)methyl)-1-isopropyl-6-(4-((4-methylpiperazin-1-yl)methyl)phenyl)-1H-pyrazolo[3,4-b]pyridine-4-carboxamide

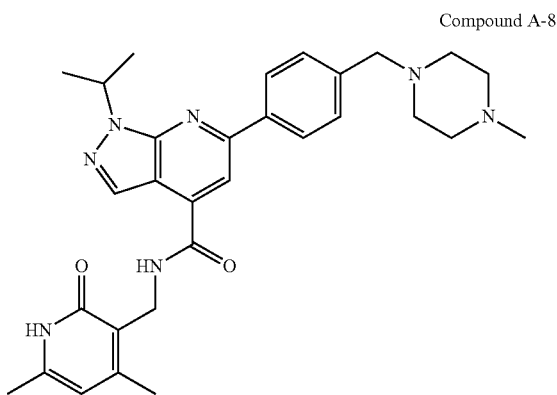

Compound A-8

To a stirred solution of 6-(4-(bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide (1 equiv.) in dry DMF, 1-methylpiperazine (5 equiv.) was added at 0° C. and reaction mixture was stirred for overnight. After completion of reaction, water was added to it and extraction was carried out using EtOAc. The combined organic layers were washed with water; dried over anhydrous $Na_2SO_4$; filtered and concentrated under reduced pressure. The residue was purified by column chromatography/preparative HPLC to give the desired compound (5% yield). LCMS: 528.25 $(M+1)^+$; HPLC: 98.21% (@ 254 nm) (Rt; 4.802); 1H NMR (DMSO-d6, 400 MHz) δ 11.55 (s, 1H), 8.94 (bs, 1H), 8.36 (s, 1H), 8.19 (d, J=8.4 Hz, 2H), 8.13 (s, 1H), 7.46 (d, J=7.6 Hz, 2H), 5.89 (s, 1H), 5.33-5.30 (m, 1H), 4.41 (d, J=4 Hz, 2H), 3.52 (s, 3H), 2.30-2.45 (m, 7H), 2.21 (s, 3H), 2.15 (s, 3H), 2.12 (s, 3H), 1.54 (d, J=6.8 Hz, 6H).

Synthesis of Compound A-9: N-((4,6-dimethyl-2-oxo-1,2-dihydropyridin-3-yl)methyl)-1-isopropyl-6-(4-(4-methylpiperazin-1-yl)phenyl)-1H-pyrazolo[3,4-b]pyridine-4-carboxamide

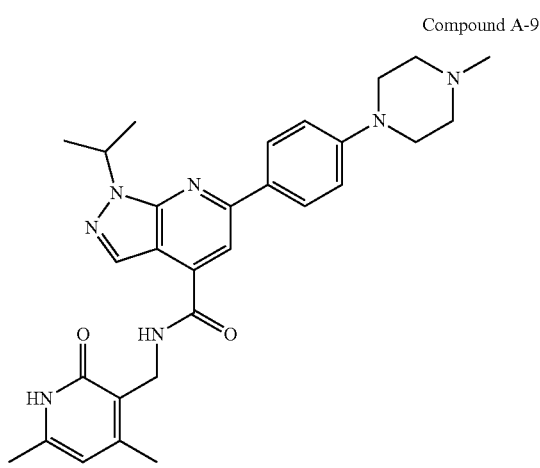

Compound A-9

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv), 1-methyl-4-(4-(4,4,5,5-tetramethyl-1,3,2-dioxaborolan-2-yl)phenyl)piperazine (1.2 equiv.) and $Pd(PPh_3)_4$ (0.1 equiv.) in 1,4-dioxane was purged with argon for 10 min. Then, 2 M $Na_2CO_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous $Na_2SO_4$, filtered and concentrated under reduced pressure to afford crude material which was purified by column chromatography to give the desired compound (57%). LCMS: 514.20 $(M+1)^+$; HPLC: 99.74% (@ 254 nm), (Rt; 5.183); 1H NMR (CDCl3, 400 MHz) δ 11.88 (bs, 1H), 8.30 (s, 1H), 8.16 (t, 1H), 8.08 (d, 2H, J=8.8 Hz), 7.91 (s, 1H), 6.97 (d, 2H, J=8.8 Hz), 5.94 (s, 1H), 5.43-5.36 (m, 1H), 4.66 (d, 2H, J=5.6 Hz), 3.30 (bs, 4H), 2.58 (bs, 4H), 2.41 (s, 3H), 2.36 (s, 3H), 2.19 (s, 3H), 1.60 (d, 6H, J=6.4 Hz).

Synthesis of Compound A-10: N-((4,6-dimethyl-2-oxo-1,2-dihydropyridin-3-yl)methyl)-1-isopropyl-6-(6-(piperazin-1-yl)pyridin-3-yl)-1H-pyrazolo[3,4-b]pyridine-4-carboxamide

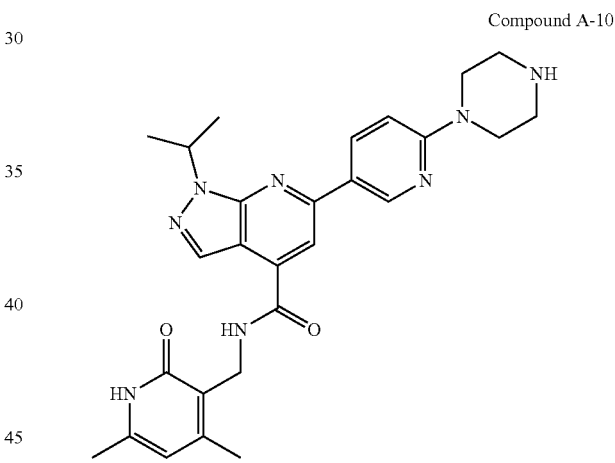

Compound A-10

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv), tert-butyl 4-(5-(4,4,5,5-tetramethyl-1,3,2-dioxaborolan-2-yl)pyridin-2-yl)piperazine-1-carboxylate (1.2 equiv.) and $Pd(PPh_3)_4$ (0.1 equiv.) in 1,4-dioxane was purged with argon for 10 min. Then, 2 M $Na_2CO_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous $Na_2SO_4$, filtered and concentrated under reduced pressure to afford crude material which was purified by column chromatography to give the Boc protected intermediate. Boc-deprotection was achieved by using TFA-DCM (10 times by volume in 1:1 ratio, work up using $NaHCO_3$) to give the desired compound (50% yield). LCMS: 501.20 $(M+1)^+$; HPLC: 98.58% (@ 254 nm), (Rt; 4.728); 1H NMR (DMSO-d6, 400 MHz) δ 11.56 (s, 1H), 9.07 (d, 1H, J=2 Hz), 8.87 (t, 1H), 8.82 (bs, 2H), 8.46

(dd, 1H, J=8.8, 2.4 Hz), 8.33 (s, 1H), 8.11 (s, 1H), 7.09 (d, 1H, J=8.8 Hz), 5.91 (s, 1H), 5.33-5.26 (m, 1H), 4.40 (d, 2H, J=4.8 Hz), 3.84 (t, 4H), 3.24 (bs, 4H), 2.23 (s, 3H), 2.13 (s, 3H), 1.54 (d, 6H, J=6.8 Hz).

Synthesis of Compound A-11: N-((4,6-dimethyl-2-oxo-1,2-dihydropyridin-3-yl)methyl)-1-isopropyl-6-(6-(4-methylpiperazin-1-yl)pyridin-3-yl)-1H-pyrazolo[3,4-b]pyridine-4-carboxamide Compound A-11

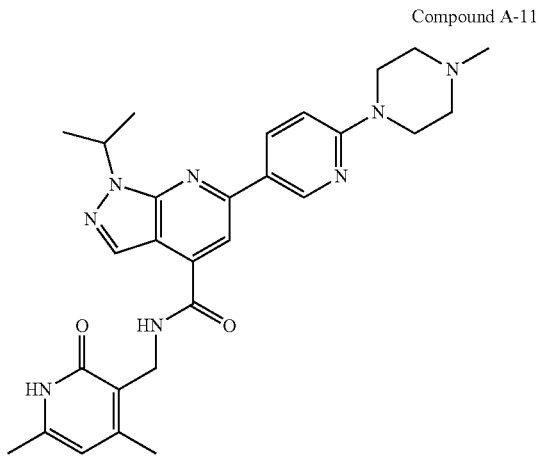

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv), 1-methyl-4-(5-(4,4,5,5-tetramethyl-1,3,2-dioxaborolan-2-yl)pyridin-2-yl)piperazine (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to give the desired compound (30% yield). LCMS: 515.20 (M+1)+; HPLC: 98.36% (@ 254 nm), (Rt; 4.876); 1H NMR (DMSO-d6, 400 MHz) δ 11.53 (s, 1H), 9.01 (s, 1H), 8.85 (t, 1H), 8.36 (d, 1H, J=8.8 Hz), 8.31 (s, 1H), 8.07 (s, 1H), 6.97 (d, 1H, J=8.4 Hz), 5.89 (s, 1H), 5.32-5.25 (m, 1H), 4.40 (d, 2H, J=4.4 Hz), 3.61 (t, 4H), 2.41 (t, 4H), 2.22 (s, 6H), 2.12 (s, 3H), 1.53 (d, 6H, J=6.8 Hz).

Synthesis of Compound A-12: N-((4,6-dimethyl-2-oxo-1,2-dihydropyridin-3-yl)methyl)-1-isopropyl-6-(4-(4-methylpiperazine-1-carbonyl)phenyl)-1H-pyrazolo[3,4-b]pyridine-4-carboxamide Compound A-12

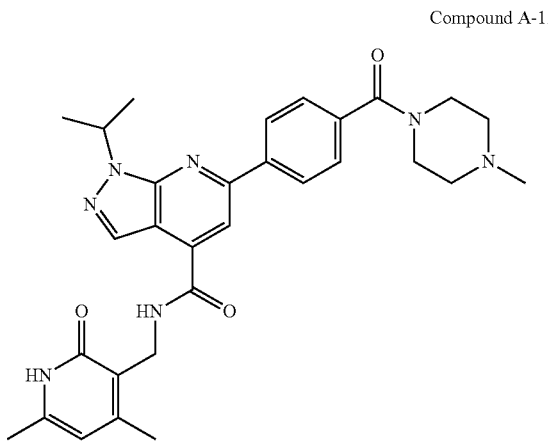

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv), (4-methylpiperazin-1-yl)(4-(4,4,5,5-tetramethyl-1,3,2-dioxaborolan-2-yl)phenyl)methanone (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to give the desired compound (33% yield). LCMS: 542.20 (M+1)+; HPLC: 98.72% (@ 254 nm), (Rt; 5.034); 1H NMR (DMSO-d6, 400 MHz) δ 11.55 (s, 1H), 8.96 (bs, 1H), 8.39 (s, 1H), 8.32 (d, 2H, J=8 Hz), 8.20 (s, 1H), 7.56 (d, 2H, J=7.6 Hz), 5.90 (s, 1H), 5.35-5.32 (m, 1H), 4.42 (d, 2H, J=4 Hz), 3.64 (bs, 2H), 3.38 (m, 2H), 2.37 (bs, 2H), 2.28 (bs, 2H), 2.22 (s, 3H), 2.20 (s, 3H), 2.12 (s, 3H), 1.55 (d, 6H, J=6.4 Hz).

Synthesis of Compound A-13: N-((4,6-dimethyl-2-oxo-1,2-dihydropyridin-3-yl)methyl)-6-(3-((3-(dimethylamino)propyl)carbamoyl)phenyl)-1-isopropyl-1H-pyrazolo[3,4-b]pyridine-4-carboxamide Compound A-13

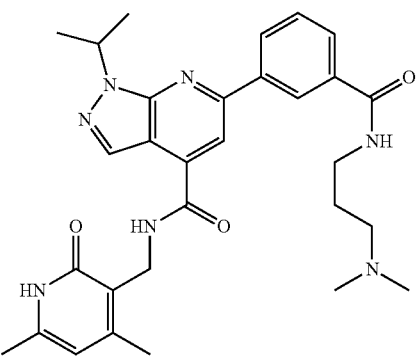

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv), N-(3-(dimethylamino)propyl)-3-(4,4,5,5-tetramethyl-1,3,2-dioxaborolan-2-yl)benzamide (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to give the desired compound (9% yield). LCMS: 544.20 (M+1)+; HPLC: 98.83% (@ 254 nm), (Rt; 5.258); 1H NMR (DMSO-d6, 400 MHz) δ 11.55 (s, 1H), 9.00 (t, 1H), 8.70 (t, 1H), 8.64 (s, 1H), 8.39 (s, 1H), 8.38 (s, 1H), 8.19 (s, 1H), 7.92 (d, 1H, J=8 Hz), 7.64 (t, 1H, J=7.6 Hz), 5.90 (s, 1H), 5.37-5.34 (m, 1H), 4.41 (d, 2H, J=4.4 Hz), 2.28 (t, 2H, J=6.8 Hz), 2.23 (s, 3H), 2.14 (s, 6H), 2.12 (s, 3H), 1.69 (t, 2H, J=6.8 Hz), 1.55 (d, 6H, J=6.4 Hz).

Synthesis of Compound A-14: 6-(4-(aminomethyl)phenyl)-N-((4,6-dimethyl-2-oxo-1,2-dihydropyridin-3-yl)methyl)-1-isopropyl-1H-pyrazolo[3,4-b]pyridine-4-carboxamide Compound A-14

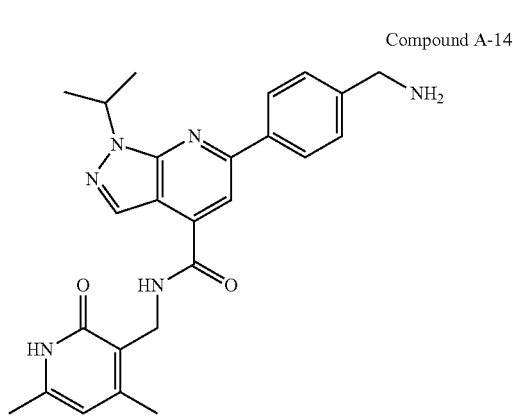 [SMILES: Cc1cc(C)c(CNC(=O)c2cc(-c3ccc(CN)cc3)nc3c2cnn3C(C)C)c(=O)[nH]1]

Step 1: Synthesis of N-((4,6-dimethyl-2-oxo-1,2-dihydropyridin-3-yl)methyl)-6-(4-(hydroxyl-methyl)phenyl)-1-isopropyl-1H-pyrazolo[3,4-b]pyridine-4-carboxamide

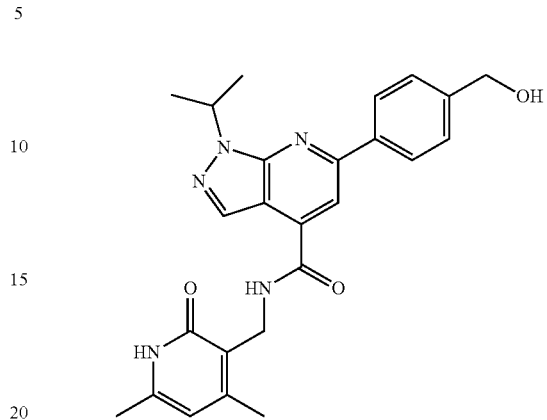

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv), tert-butyl 4-(4,4,5,5-tetramethyl-1,3,2-dioxaborolan-2-yl)benzylcarbamate (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the Boc protected intermediate. Boc-deprotection was achieved by using TFA-DCM (10 times by volume in 1:1 ratio, work up using NaHCO3) to give the desired compound (65% yield). LCMS: 445.15 (M+1)+; HPLC: 99.78% (@ 254 nm), (Rt; 4.950); 1H NMR (DMSO-d6, 400 MHz) δ 11.52 (s, 1H), 8.91 (t, 1H), 8.36 (s, 1H), 8.31 (d, 2H, J=8 Hz), 8.21 (bs, 2H), 8.16 (s, 1H), 7.61 (d, 2H, J=8.8 Hz), 5.88 (s, 1H), 5.34-5.30 (m, 1H), 4.40 (d, 2H, J=4.4 Hz), 4.12 (d, 2H, J=5.2 Hz), 2.21 (s, 3H), 2.11 (s, 3H), 1.53 (d, 6H, J=6.8 Hz).

Synthesis of Compound A-15: N-((4,6-dimethyl-2-oxo-1,2-dihydropyridin-3-yl)methyl)-6-(4-(((3-(dimethylamino)propyl)(methyl)amino)methyl)phenyl)-1-isopropyl-1H-pyrazolo[3,4-b]pyridine-4-carboxamide Compound A-15

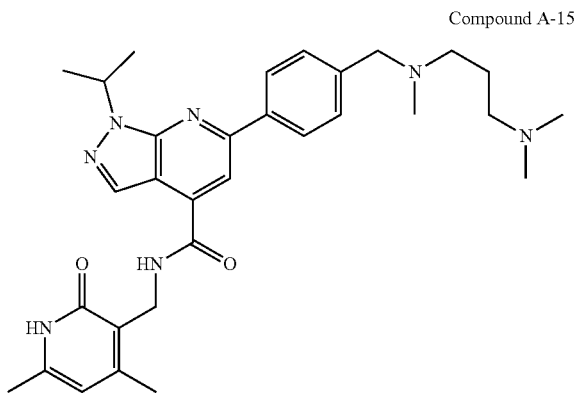

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (2.5 g, 5.98 mmol), (4-(hydroxymethyl)phenyl)boronic acid (1 g, 6.57 mmol) and Pd(PPh$_3$)$_4$ (0.69 g, 0.597 mmol) in 1,4-dioxane (30 mL) was purged with argon for 10 min. Then, 2 M Na$_2$CO$_3$ (2.3 g, 21.69 mmol) in water was added to it and again argon was purged through it for 10 min. The reaction mixture was stirred at 100° C. for 2 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the desired compound (2.6 g, 96.3%).

Step 2: Synthesis of 6-(4-(bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide

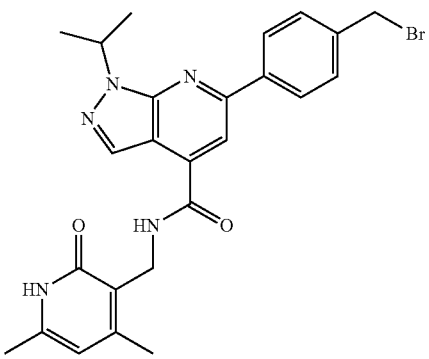 [SMILES: Cc1cc(C)c(CNC(=O)c2cc(-c3ccc(CBr)cc3)nc3c2cnn3C(C)C)c(=O)[nH]1]

To a stirred solution of N-((4,6-dimethyl-2-oxo-1,2-dihydropyridin-3-yl)methyl)-6-(4-(hydroxyl-methyl)phenyl)-1-isopropyl-1H-pyrazolo[3,4-b]pyridine-4-carboxamide (2.6 g, 5.84 mmol) in DCM (50 mL), triphenyl phosphine (6.1 g, 23.23 mmol) was added and stirred it at room temperature for 10 min. Finally CBr$_4$ (7.7 g, 23.23 mmol) was added portion-wise to it and resulting solution was stirred at room temperature for overnight. After completion of reaction, solid was filtered and dried to obtain the desired compound (1 g, 34.5%).

301

Step 3: Synthesis of N-((4,6-dimethyl-2-oxo-1,2-dihydropyridin-3-yl)methyl)-6-(4-(((3-(dimethylamino)propyl)(methyl)amino)methyl)phenyl)-1-isopropyl-1H-pyrazolo[3,4-b]pyridine-4-carboxamide

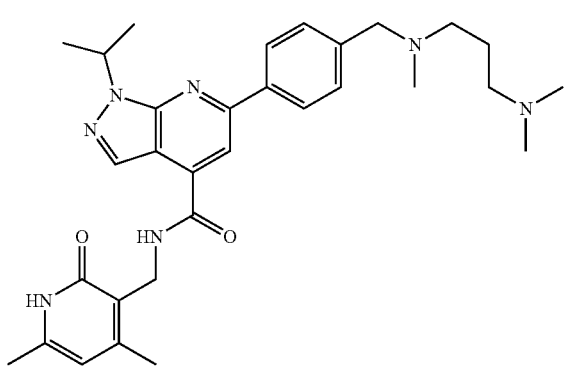

6-(4-(Bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide (1 equiv.) was suspended in DMF and N1,N1,N3-trimethylpropane-1,3-diamine (5 equiv.) was added to it. The reaction mixture was stirred at room temperature for overnight. On completion of reaction, solvent was removed under reduced pressure and residue was purified by prep. HPLC chromatography to provide the desired compound (30% yield). LCMS: 544.25 (M+1)$^+$; HPLC: 99.96% (@ 254 nm) (R$_t$;4.732); $^1$H NMR (DMSO-d$_6$, 400 MHz) δ 11.55 (bs, 1H), 10.14-9.80 (m, 1H), 8.95 (bs, 1H), 8.40-8.35 (m, 3H), 8.22-8.19 (m, 1H), 7.75-7.69 (m, 2H), 5.91 (s, 1H), 5.35-5.32 (m, 1H), 4.42 (d, 2H, J=3.6 Hz), 3.08-2.98 (m, 6H), 2.80-2.62 (m, 8H), 2.23 (s, 3H), 2.13 (s, 3H), 2.07 (m, 2H). 1.55 (d, 6H, J=6.4 Hz).

Synthesis of Compound A-16: N-((4,6-dimethyl-2-oxo-1,2-dihydropyridin-3-yl)methyl)-6-(3-(((3-(dimethylamino)propyl)(methyl)amino)methyl)phenyl)-1-isopropyl-1H-pyrazolo[3,4-b]pyridine-4-carboxamide Compound A-16

302

Step 1: Synthesis of N-((4,6-dimethyl-2-oxo-1,2-dihydropyridin-3-yl)methyl)-6-(3-(hydroxymethyl)phenyl)-1-isopropyl-1H-pyrazolo[3,4-b]pyridine-4-carboxamide

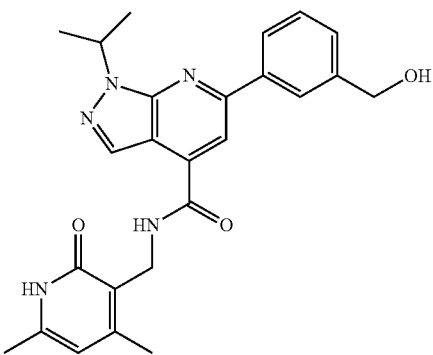 [SMILES: Cc1cc(C)c(CNC(=O)c2cc(-c3cccc(CO)c3)nc3c2cnn3C(C)C)c(=O)[nH]1]

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (2.5 g, 5.98 mmol), (3-(hydroxymethyl)phenyl)boronic acid (1 g, 6.57 mmol) and Pd(PPh$_3$)$_4$ (0.69 g, 0.598 mmol) in 1,4-dioxane (30 mL) was purged with argon for 10 min. Then, 2 M Na$_2$CO$_3$ (2.3 g, 21.69 mmol) in water was added to it and again argon was purged through it for 10 min. The reaction mixture was stirred at 100° C. for 2 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the desired compound (2.1 g, 80.7%).

Step 2: Synthesis of 6-(3-(bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide To a stirred solution of N-((4,6-dimethyl-2-oxo-1,2-dihydropyridin-3-yl)methyl)-6-(3-(hydroxymethyl)phenyl)-1-isopropyl-1H-pyrazolo[3,4-b]pyridine-4-carboxamide (2.1 g, 4.7 mmol) in DCM (35 mL), triphenyl phosphine (5 g, 19.06 mmol) was added and stirred it at room temperature for 10 min. Finally CBr$_4$ (6.2 g, 18.69 mmol) was added portion wise to it and resulting solution was stirred at room Step 3: Synthesis of N-((4,6-dimethyl-2-oxo-1,2-dihydropyridin-3-yl)methyl)-6-(3-(((3-(dimethylamino)propyl)(methyl)amino)methyl)phenyl)-1-isopropyl-1H-pyrazolo[3,4-b]pyridine-4-carboxamide

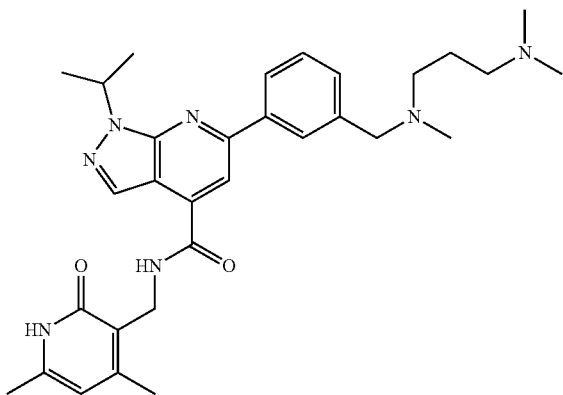

6-(3-(Bromomethyl)phenyl)-N-((4,6-dimethyl-2-oxo-1,2-dihydropyridin-3-yl)methyl)-1-isopropyl-1H-pyrazolo[3,4-b]pyridine-4-carboxamide (1 equiv.) was suspended in DMF and N1,N1,N3-trimethylpropane-1,3-diamine (5 equiv.) was added to it. The reaction mixture was stirred at room temperature for overnight. On completion of reaction, solvent was removed under reduced pressure and the residue was purified by prep. HPLC chromatography to provide the desired compound (25% yield). LCMS: 544.30 (M+1)$^+$; HPLC: 99.90% (@ 254 nm) (R$_t$;4.765); $^1$H NMR (DMSO-d$_6$, 400 MHz) δ 11.55 (bs, 1H), 10.2-9.6 (m, 1H), 8.92 (bs, 1H), 8.38 (s, 2H), 8.14 (s, 1H), 7.70-7.66 (m, 2H), 5.91 (s, 1H), 5.36-5.35 (m, 1H), 4.41 (d, 2H), 3.39 (4H merged in DMSO peak), 3.08-2.98 (m, 2H+3H), 2.79 (s, 6H), 2.24 (s, 3H), 2.13 (s, 3H). 2.13 (m, 2H), 1.55 (d, 6H, J=4.8 Hz).

Synthesis of Compound A-17:3-bromo-N-((4,6-dimethyl-2-oxo-1,2-dihydropyridin-3-yl)methyl)-1-isopropyl-6-(4-(morpholinomethyl)phenyl)-1H-pyrazolo[3,4-b]pyridine-4-carboxamide

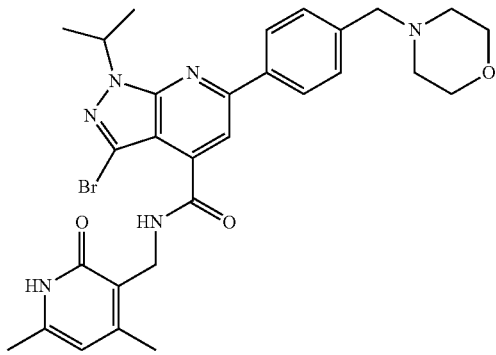

Compound A-17

Step 1: Synthesis of ethyl 3,6-dibromo-1-isopropyl-1H-pyrazolo[3,4-b]pyridine-4-carboxylate

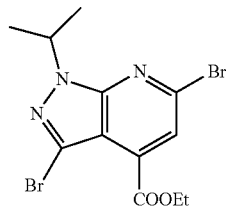 [SMILES: CCOC(=O)c1cc(Br)nc2c1c(Br)nn2C(C)C]

To a stirred solution of ethyl 6-bromo-1-isopropyl-1H-pyrazolo[3,4-b]pyridine-4-carboxylate (2 g, 6.43 mmol) in acetic acid (6 mL) was added bromine (5.14 g, 32.15 mmol) at 0° C. Resulting reaction mass was stirred at room temperature for 3 h. Reaction was monitored by TLC. On completion, reaction was quenched with ice, NaHCO$_3$ solution was added to it. Extraction was carried out using ethyl acetate; the combined organic layers were washed with water, brine and dried over anhydrous Na$_2$SO$_4$. Solvent was removed under reduced pressure and residue was purified by silica gel column chromatography to obtain the desired intermediate (1.2 g, 48%).

Step 2: Synthesis of ethyl 3-bromo-1-isopropyl-6-(4-(morpholinomethyl)phenyl)-1H-pyrazolo[3,4-b]pyridine-4-carboxylate

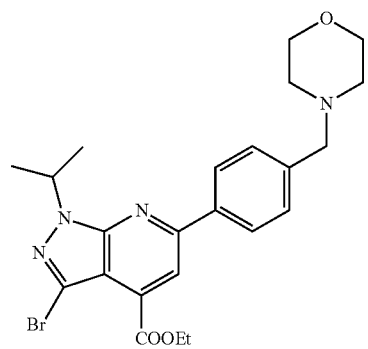 [SMILES: CCOC(=O)c1cc(-c2ccc(CN3CCOCC3)cc2)nc2c1c(Br)nn2C(C)C]

A solution of ethyl 3,6-dibromo-1-isopropyl-1H-pyrazolo[3,4-b]pyridine-4-carboxylate (1.2 g, 3.08 mmol), 4-(4-(4,4,5,5-tetramethyl-1,3,2-dioxaborolan-2-yl)benzyl)morpholine (0.935 g, 3.08 mmol) and Pd(PPh$_3$)$_4$ (0.178 g, 0.154 mmol) in 1,4-dioxane (33 mL) was purged with argon for 10 min. Then, 2M Na$_2$CO$_3$ solution (1.17 g, 11.10 mmol) was added to it and again argon was purged through it for 10 min. The reaction mixture was stirred at 100° C. for 1 h. After completion of the reaction, water was added to it and extraction was carried out using 10% MeOH/DCM. The combined organic layers were washed with water, dried over anhydrous Na$_2$SO$_4$, filtered and concentrated under reduced pressure to afford crude material which was purified by column chromatography to give the desired compound (0.8 g, 67.1%).

Step 3: Synthesis of 3-bromo-1-isopropyl-6-(4-(morpholinomethyl)phenyl)-1H-pyrazolo[3,4-b]pyridine-4-carboxylic acid

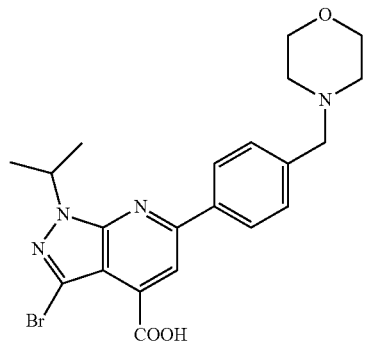 [SMILES: CC(C)n1nc(Br)c2c(C(=O)O)cc(-c3ccc(CN4CCOCC4)cc3)nc21]

To a solution of ethyl 3-bromo-1-isopropyl-6-(4-(morpholinomethyl)phenyl)-1H-pyrazolo[3,4-b]pyridine-4-carboxylate (1 g, 2.05 mmol) in EtOH (15 mL), aqueous NaOH (0.123 g, 3.08 mmol) was added and reaction mixture stirred at 60° C. for 1 h. After completion of the reaction, ethanol was removed under reduced pressure and it was acidified using 10% citric acid solution. Solid obtained was filtered and azeotrope it with toluene to give the desired compound (0.8 g, 84.9%).

Step 4: Synthesis of 3-bromo-N-((4,6-dimethyl-2-oxo-1,2-dihydropyridin-3-yl)methyl)-1-isopropyl-6-(4-(morpholinomethyl)phenyl)-1H-pyrazolo[3,4-b]pyridine-4-carboxamide

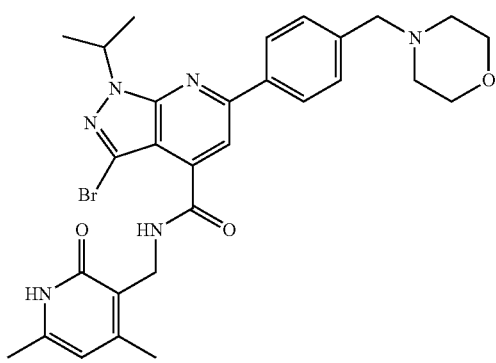 [SMILES: Cc1cc(C)c(CNC(=O)c2cc(-c3ccc(CN4CCOCC4)cc3)nc3c2c(Br)nn3C(C)C)c(=O)[nH]1]

A solution of 3-bromo-1-isopropyl-6-(4-(morpholinomethyl)phenyl)-1H-pyrazolo[3,4-b]pyridine-4-carboxylic acid (0.8 g, 1.74 mmol) and 3-(aminomethyl)-4,6-dimethylpyridin-2(1H)-one (0.531 g, 3.49 mmol) in DMSO (8 mL) and was stirred at room temperature for 15 min. Then PYBOP (1.36 g, 2.62 mmol) was added to it and stirring was continued for 12 hr. After completion of the reaction, reaction mass was poured into ice to obtain solid, which was filtered and solid was purified by silica gel column chromatography to obtain the desired compound (39% yield). LCMS: 593.20 (M+1)$^+$; HPLC: 97.49% (@ 254 nm) (R$_t$: 5.338); $^1$H NMR (DMSO-d$_6$, 400 MHz) δ 11.48 (bs, 1H), 8.67 (t, 1H, J=4.8 Hz), 8.18 (d, 2H, J=8.4 Hz), 7.73 (s, 1H), 7.47 (d, 2H, J=8.4 Hz), 5.87 (s, 1H), 5.33-5.30 (m, 1H), 4.40 (d, 2H, J=4.4 Hz), 3.58 (bs, 4H), 3.53 (s, 2H), 2.38 (bs, 4H), 2.26 (s, 3H), 2.11 (s, 3H), 1.52 (d, 6H, J=6.4 Hz).

Synthesis of Compounds A-18 through A-78, A-91 through A-110, A-125, and A-126

Compounds A-18 through A-78, A-91 through A-110, A-125, and A-126 were synthesized by methods similar to those described for Compounds A-1 through A-17 or by reaction schemes depicted in the general schemes.

Synthesis of Compound B-1: 1-(1-benzylpiperidin-4-yl)-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide Compound B-1

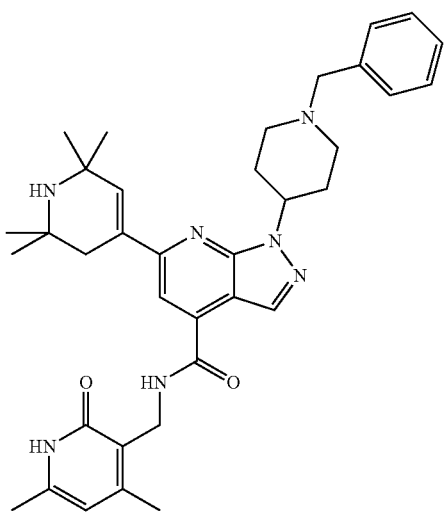

Step 1: Synthesis of 3-(aminomethyl)-4,6-dimethylpyridin-2(1H)-one

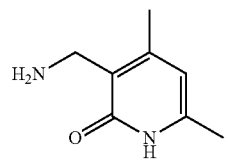

3-Cyano-2,4-dimethyl-2-hydroxypyridine (0.3 g, 2.0 mmol) was dissolved in MeOH (5 mL), to which catalytic amount of Raney Ni and of aqueous NH$_3$ (0.3 mL) were added and the reaction mixture was stirred under hydrogen pressure (bladder pressure) for 3-4 h. After completion of the reaction, catalyst was filtered off and the filtrate was concentrated under reduced pressure. The residue was thoroughly dried to provide the desired product (0.3 g, quantitative yield).

Step 2: Synthesis of ethyl 6-hydroxy-1H-pyrazolo[3,4-b]pyridine-4-carboxylate

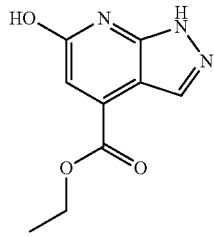

A stirred solution of 1H-pyrazol-3-amine (45 g, 542 mmol) in acetic acid (297 mL) and water (900 mL) was cooled to 0° C. and diethyl oxaloacetate sodium salt (113.85 g, 542.16 mmol) was added to it. Resulting solution was heated at 100° C. for overnight. After completion of reaction, solid was filtered and dried to obtain the desired intermediate (25 g, 22%).

Step 3: Synthesis of ethyl 6-bromo-1H-pyrazolo[3,4-b]pyridine-4-carboxylate

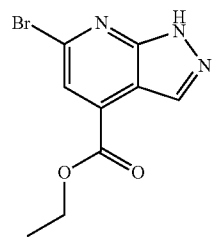

Ethyl 6-hydroxy-1H-pyrazolo[3,4-b]pyridine-4-carboxylate (25 g, 120 mmol) was suspended in acetonitrile (250 mL) and POBr$_3$ (69.56 g, 241.54 mmol) was added to it. The reaction mixture was refluxed for 6 h. On completion of reaction, acetonitrile was removed under reduced pressure and residue neutralized with saturated NaHCO$_3$ solution was added to it. Extraction was carried out using ethyl acetate; the combined organic layers were washed with water, brine and dried over anhydrous Na$_2$SO$_4$; filtered and concentrated under reduced pressure. The residue was purified by silica gel column chromatography to provide the desired intermediate (25 g, 77%).

Step 4: Synthesis of 6-bromo-N-((4,6-dimethyl-2-oxo-1,2-dihydropyridin-3-yl)methyl)-1H-pyrazolo[3,4-b]pyridine-4-carboxamide

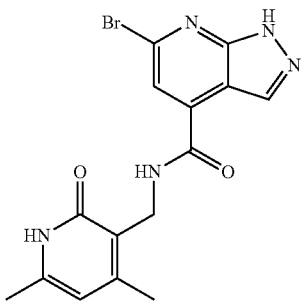 [SMILES: Cc1cc(C)c(CNC(=O)c2cc(Br)nc3[nH]ncc23)c(=O)[nH]1]

Aqueous NaOH (1.11 g, 27.88 mmol) was added to a solution of ethyl 6-bromo-1H-pyrazolo[3,4-b]pyridine-4-carboxylate (5 g, 18.58 mmol) in EtOH (50 mL) and stirred at 60° C. for 1 h. After completion of the reaction, ethanol was removed under reduced pressure and it was acidified using 10% citric acid solution. Solid obtained was filtered and dried under reduced pressure to obtain corresponding acid. The crude acid (4.4 g, 18.2 mmol) was then dissolved in DMSO (20 mL) and 3-(aminomethyl)-4,6-dimethylpyridin-2(1H)-one (5.55 g, 36.51 mmol) was added to it. The reaction mixture was stirred at room temperature for 15 min before PYBOP (14.24 g, 27.38 mmol) was added to it and stirring was continued overnight. After completion of the reaction, reaction mass was poured into ice to obtain a solid, which was filtered and washed with acetonitrile followed by ether to provide the desired intermediate (4 g, 58.5%).

Step 5: Synthesis of tert-butyl 4-(6-bromo-4-(((4,6-dimethyl-2-oxo-1,2-dihydropyridin-3-yl)methyl)carbamoyl)-1H-pyrazolo[3,4-b]pyridin-1-yl)piperidine-1-carboxylate

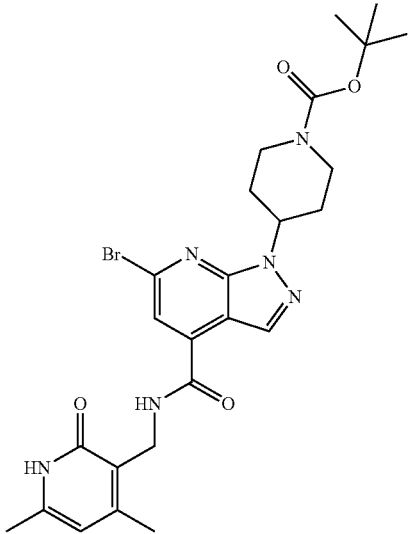 [SMILES: Cc1cc(C)c(CNC(=O)c2cc(Br)nc3c2cnn3C2CCN(C(=O)OC(C)(C)C)CC2)c(=O)[nH]1]

To a stirred solution of 6-bromo-N-((4,6-dimethyl-2-oxo-1,2-dihydropyridin-3-yl)methyl)-1H-pyrazolo[3,4-b]pyridine-4-carboxamide (0.5 g, 1.33 mmol) in DMF (5 mL), K$_2$CO$_3$ (0.275 g, 1.99 mmol) and tert-butyl 4-bromopiperidine-1-carboxylate (0.529 g, 2.01 mmol) was added. Resulting reaction mixture was stirred at 80° C. for 12 h. On completion of reaction, water was added to it and extraction was carried out using DCM; the combined organic layers were washed with water, brine and dried over anhydrous Na$_2$SO$_4$. Solvent was removed under reduced pressure and residue was purified by silica gel column chromatography to obtain the desired intermediate (0.5 g, 67.2%).

Step 6: Synthesis of tert-butyl 4-(4-(((4,6-dimethyl-2-oxo-1,2-dihydropyridin-3-yl)methyl)carbamoyl)-6-(2,2,6,6-tetramethyl-1,2,3,6-tetrahydropyridin-4-yl)-1H-pyrazolo[3,4-b]pyridin-1-yl)piperidine-1-carboxylate

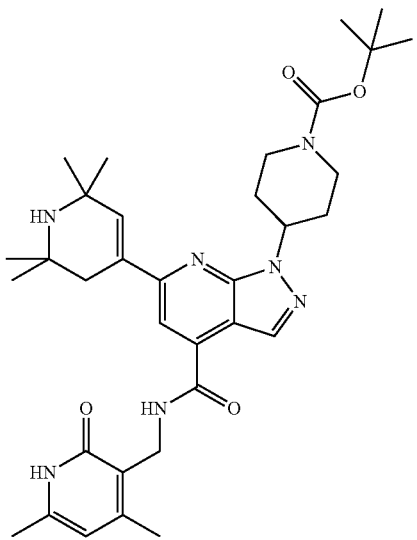 [SMILES: Cc1cc(C)c(CNC(=O)c2cc(C3=CC(C)(C)NC(C)(C)C3)nc3c2cnn3C2CCN(C(=O)OC(C)(C)C)CC2)c(=O)[nH]1]

A solution of tert-butyl 4-(6-bromo-4-(((4,6-dimethyl-2-oxo-1,2-dihydropyridin-3-yl)methyl)carbamoyl)-1H-pyrazolo[3,4-b]pyridin-1-yl)piperidine-1-carboxylate (0.5 g, 0.896 mmol), boronic ester (0.285 g, 1.075 mmol) and Pd(PPh₃)₄ (0.103 g, 0.089 mmol) in 1,4-dioxane (8 mL) was purged with argon for 10 min. Then, 2M Na₂CO₃ (0.341 g, 3.216 mmol) was added to it and argon was purged again for 10 min. The reaction mixture was stirred at 100° C. for 1 h. After completion of the reaction, water was added to it and extraction was carried out using 10% MeOH/DCM. The combined organic layers were washed with water, dried over anhydrous Na₂SO₄, filtered and concentrated under reduced pressure to afford crude material which was purified by prep HPLC to give the desired compound (0.5 g, 90.5%).

Step 7: Synthesis of N-((4,6-dimethyl-2-oxo-1,2-dihydropyridin-3-yl)methyl)-1-(piperidin-4-yl)-6-(2,2,6,6-tetramethyl-1,2,3,6-tetrahydropyridin-4-yl)-1H-pyrazolo[3,4-b]pyridine-4-carboxamide

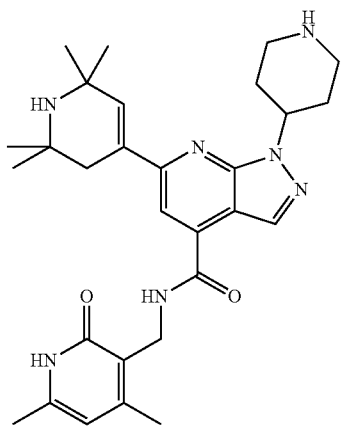 [SMILES: Cc1cc(C)c(CNC(=O)c2cc(C3=CC(C)(C)NC(C)(C)C3)nc3c2cnn3C2CCNCC2)c(=O)[nH]1]

To a stirred solution of tert-butyl 4-(4-(((4,6-dimethyl-2-oxo-1,2-dihydropyridin-3-yl)methyl)carbamoyl)-6-(2,2,6,6-tetramethyl-1,2,3,6-tetrahydropyridin-4-yl)-1H-pyrazolo[3,4-b]pyridin-1-yl)piperidine-1-carboxylate (0.5 g, 0.8 mmol) in DCM (10 mL), TFA (0.3 mL) was added at 0° C. and reaction stirred at room temperature for 1 h. After completion of reaction, solvent was removed under reduced pressure and residue neutralized with saturated NaHCO₃ solution Extraction was carried out using DCM; the combined organic layers were washed with water, brine and dried over anhydrous Na₂SO₄; filtered and concentrated under reduced pressure. Finally the residue was washed with diethyl ether to provide the desired compound (0.4 g, 95.7%).

Step 8: Synthesis of 1-(1-benzylpiperidin-4-yl)-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide

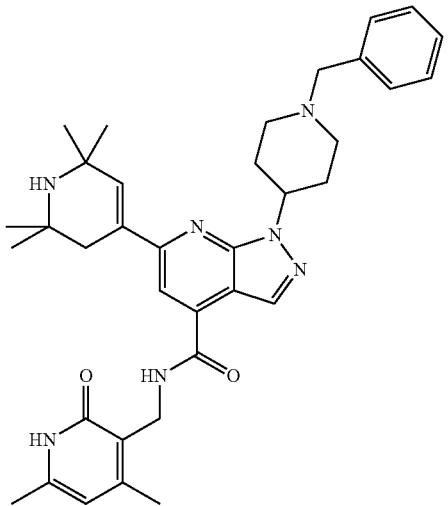 [SMILES: Cc1cc(C)c(CNC(=O)c2cc(C3=CC(C)(C)NC(C)(C)C3)nc3c2cnn3C2CCN(Cc3ccccc3)CC2)c(=O)[nH]1]

To a stirred solution of N-((4,6-dimethyl-2-oxo-1,2-dihydropyridin-3-yl)methyl)-1-(piperidin-4-yl)-6-(2,2,6,6-tetramethyl-1,2,3,6-tetrahydropyridin-4-yl)-1H-pyrazolo[3,4-b]pyridine-4-carboxamide (0.1 g, 0.193 mmol) in DMF (1 mL), K₂CO₃ (0.032 g, 0.232 mmol) and benzyl bromide (0.04 g, 0.232 mmol) were added. Resulting reaction mixture was stirred at 80° C. for 12 h. On completion of reaction, water was added to it and extraction was carried out using DCM; the combined organic layers were washed with water, brine and dried over anhydrous Na₂SO₄. Solvent was removed under reduced pressure and residue was purified by prep HPLC to provide the desired compound (21.3% yield). LCMS: 608.45 (M+1)⁺; HPLC: 94.92% (@ 254 nm) (R$_t$:4.640); ¹H NMR (DMSO-d₆, 400 MHz) δ 11.54 (s, 1H), 9.70 (bs, 1H), 8.86 (s, 1H), 8.37 (s, 1H), 7.90 (s, 1H), 7.54-7.52 (m, 5H), 6.85 (s, 1H), 5.90 (s, 1H), 5.17 (m, 1H), 4.40 (m, 4H), 3.55 (d, 2H, J=12 Hz), 3.41-3.35 (m, 2H), 2.83 (m, 2H), 2.32-2.41 (m, 2H), 2.23 (s, 3H), 2.22-2.13 (m, 2H), 2.12 (s, 3H), 1.57 (s, 6H), 1.47 (s, 6H).

Synthesis of Compound B-2:1-(1-acetylpiperidin-4-yl)-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide

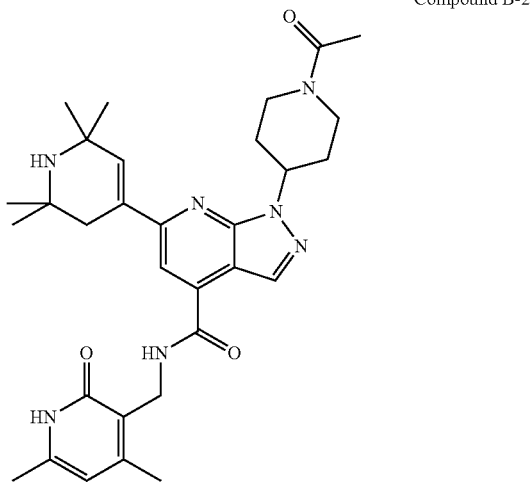

Compound B-2

N-((4,6-dimethyl-2-oxo-1,2-dihydropyridin-3-yl)methyl)-1-(piperidin-4-yl)-6-(2,2,6,6-tetramethyl-1,2,3,6-tetrahydropyridin-4-yl)-1H-pyrazolo[3,4-b]pyridine-4-carboxamide (0.1 g, 0.2 mmol) was suspended in pyridine (1 mL) and acetyl chloride (0.016 g, 0.205 mmol) was added to it. The reaction mixture was stirred at room temperature for 5 h. On completion of reaction, water was added to it and extraction was carried out using 10% MeOH/DCM; the combined organic layers were washed with water, brine and dried over anhydrous $Na_2SO_4$; filtered and concentrated under reduced pressure. The residue was purified by prep HPLC to provide the desired compound (30% yield). LCMS: 560.00 (M+1)$^+$; HPLC: 99.09% (@ 254 nm) (R$_t$: 4.685); $^1$H NMR (DMSO-d$_6$, 400 MHz) δ 11.56 (s, 1H), 8.85 (t, 1H, J=5.2 Hz), 8.74 (s, 2H), 8.32 (s, 1H), 7.87 (s, 1H), 6.84 (s, 1H), 5.90 (s, 1H), 5.12-5.06 (m, 1H), 4.48 (d, 2H, J=12 Hz), 4.38 (d, 2H, J=5.2 Hz), 3.97 (m, 2H), 3.33-3.30 (m, 1H), 2.83 (s, 2H), 2.23 (s, 3H), 2.12 (s, 3H), 2.08 (s, 3H), 2.03-1.91 (m, 4H), 1.57 (s, 6H) 1.47 (s, 6H).

Synthesis of Compound B-3: N-((4,6-dimethyl-2-oxo-1,2-dihydropyridin-3-yl)methyl)-1-(2-methylallyl)-6-(2,2,6,6-tetramethyl-1,2,3,6-tetrahydropyridin-4-yl)-1H-pyrazolo[3,4-b]pyridine-4-carboxamide Compound B-3

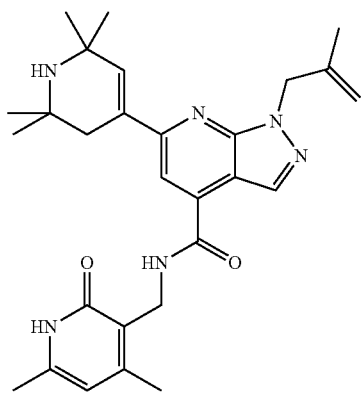

Step 1: Synthesis of 6-bromo-N-((4,6-dimethyl-2-oxo-1,2-dihydropyridin-3-yl)methyl)-1-(2-methylallyl)-1H-pyrazolo[3,4-b]pyridine-4-carboxamide

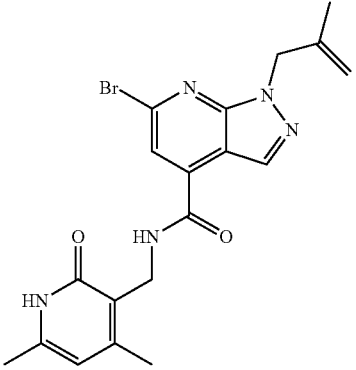 [SMILES: C=C(C)Cn1ncc2c(C(=O)NCc3c(C)cc(C)[nH]c3=O)cc(Br)nc21]

To a stirred solution of 6-bromo-N-((4,6-dimethyl-2-oxo-1,2-dihydropyridin-3-yl)methyl)-1H-pyrazolo[3,4-b]pyridine-4-carboxamide (0.4 g, 1.0 mmol) in DMF (4 mL), $K_2CO_3$ (0.152 g, 1.10 mmol) and 3 chloro-2-methylpropene (0.115 g, 1.27 mmol) were added. Resulting reaction mixture was stirred at 80° C. for 2 h. On completion of reaction, water was added to it and extraction was carried out using 20% MeOH/DCM; the combined organic layers were washed with water, brine and dried over anhydrous $Na_2SO_4$. Solvent was removed under reduced pressure and residue was purified by silica gel column chromatography to obtain the desired intermediate (0.2 g, 43.8%).

Step 2: Synthesis of N-((4,6-dimethyl-2-oxo-1,2-dihydropyridin-3-yl)methyl)-1-(2-methylallyl)-6-(2,2,6,6-tetramethyl-1,2,3,6-tetrahydropyridin-4-yl)-1H-pyrazolo[3,4-b]pyridine-4-carboxamide

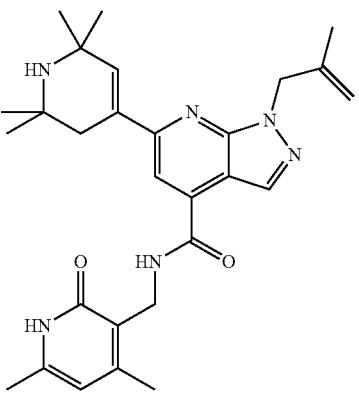 [SMILES: C=C(C)Cn1ncc2c(C(=O)NCc3c(C)cc(C)[nH]c3=O)cc(C3=CC(C)(C)NC(C)(C)C3)nc21]

A solution of 6-bromo-N-((4,6-dimethyl-2-oxo-1,2-dihydropyridin-3-yl)methyl)-1-(2-methylallyl)-1H-pyrazolo[3,4-b]pyridine-4-carboxamide (0.2 g, 0.45 mmol), boronic ester (0.147 g, 0.554 mmol) and Pd(PPh$_3$)$_4$ (0.053 g, 0.045 mmol) in 1,4-dioxane (3 mL) was purged with argon for 10 min. Then, 2M $Na_2CO_3$ solution (0.175 g, 1.65 mmol) was added to it and argon was purged again for 10 min. The reaction mixture was stirred at 100° C. for 1 h. After completion of the reaction, water was added to it and extraction was carried out using 10% MeOH/DCM. The combined organic layers were washed with water, dried over anhydrous $Na_2SO_4$, filtered and concentrated under reduced pressure to afford crude material which was purified by column chromatography to give the desired compound (44.2% yield). LCMS: 489.30 (M+1)$^+$; HPLC: 97.19% (@ 254 nm) (R$_t$:5.112); $^1$H NMR (DMSO-d$_6$, 400 MHz) δ 11.55 (s, 1H), 8.90 (t, 1H), 8.29 (s, 1H), 7.81 (s, 1H), 6.81 (s, 1H), 5.89 (s, 1H), 5.02 (s, 2H), 4.87 (s, 1H), 4.66 (s, 1H), 4.38 (d, 2H, J=5.2 Hz), 2.42 (m, 2H), 2.23 (s, 3H), 2.12 (s, 3H), 1.61 (s, 3H), 1.24 (s, 6H), 1.14 (s, 6H).

Synthesis of Compounds B-4 and B-5:1-cyclopentyl-N-((4,6-dimethyl-2-oxo-1,2-dihydropyridin-3-yl)methyl)-6-(2,2,6,6-tetramethylpiperidin-4-yl)-1H-pyrazolo[3,4-b]pyridine-4-carboxamide and 1-cyclopentyl-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide Compound B-4

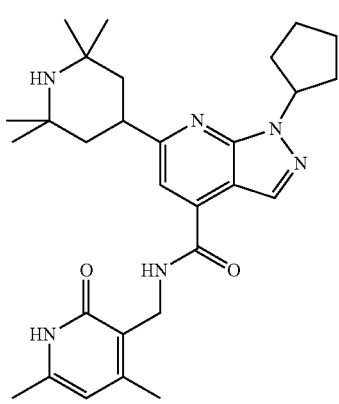

Compound B-5

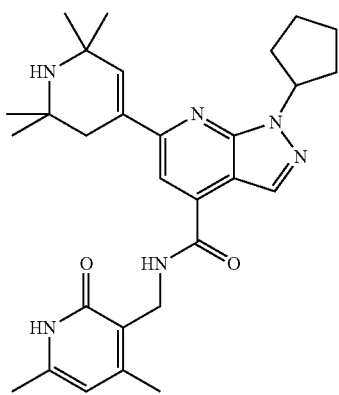

Step 1: Synthesis of ethyl 6-bromo-1-cyclopentyl-1H-pyrazolo[3,4-b]pyridine-4-carboxylate

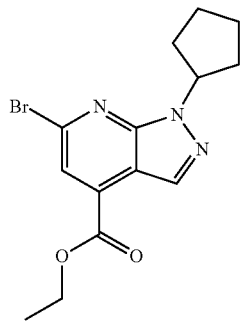 [SMILES: CCOC(=O)c1cc(Br)nc2c1cnn2C1CCCC1]

Ethyl 6-bromo-1H-pyrazolo[3,4-b]pyridine-4-carboxylate (3 g, 11.15 mmol) was dissolved in acetonitrile (30 mL) and K₂CO₃ (1.85 g, 13.38 mmol) and cyclopentyl bromide (3.35 g, 22.30 mmol) was added to it. The reaction mixture was refluxed for 3 h. On completion, acetonitrile was removed under reduced pressure and water was added to it. Extraction was carried out using ethyl acetate; the combined organic layers were washed with water, brine and dried over anhydrous Na₂SO₄. Solvent was removed under reduced pressure and residue was purified by silica gel column chromatography to obtain the desired intermediate (1.3 g, 50%).

Step 2: Synthesis of 6-bromo-1-cyclopentyl-N-((4,6-dimethyl-2-oxo-1,2-dihydropyridin-3-yl)methyl)-1H-pyrazolo[3,4-b]pyridine-4-carboxamide

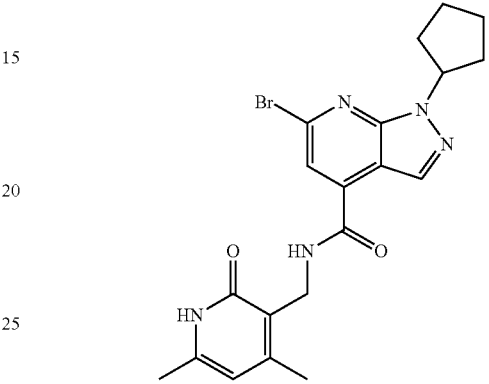

Aqueous NaOH (0.308 g, 7.72 mmol) was added to a solution of ethyl 6-bromo-1-cyclopentyl-1H-pyrazolo[3,4-b]pyridine-4-carboxylate (1.3 g, 3.8 mmol) in EtOH (10 mL) and stirred at 60° C. for 1 h. After completion of the reaction, ethanol was removed under reduced pressure and it was acidified using 10% citric acid solution. Extraction was carried out using ethyl acetate; the combined organic layers were washed with water, brine and dried over anhydrous Na₂SO₄; filtered and concentrated under reduced pressure. The crude acid (1 g, 3.23 mmol) was then dissolved in DMSO (10 mL) and 3-(aminomethyl)-4,6-dimethylpyridin-2(1H)-one (0.98 g, 6.47 mmol) was added to it. The reaction mixture was stirred at room temperature for 15 min before PYBOP (2.52 g, 4.85 mmol) was added to it and stirring was continued overnight. After completion of the reaction, reaction mass was poured into ice to obtain solid, which was filtered and washed with acetonitrile followed by ether to provide the desired intermediate (1 g, 70%).

Step 3: Synthesis of 1-cyclopentyl-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide (Compound B-5)

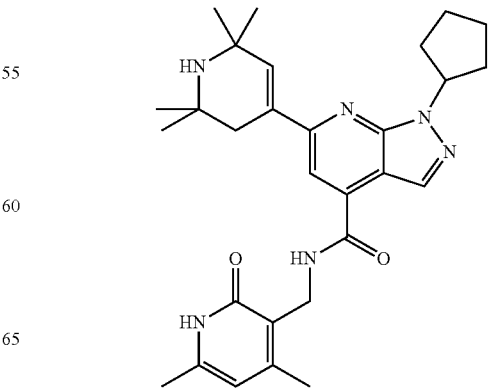

A solution of 6-bromo-1-cyclopentyl-N-((4,6-dimethyl-2-oxo-1,2-dihydropyridin-3-yl)methyl)-1H-pyrazolo[3,4-b]pyridine-4-carboxamide (0.5 g, 1.128 mmol), boronic ester (0.28 g, 1.24 mmol) and Pd(PPh$_3$)$_4$ (0.13 g, 0.11 mmol) in 1,4-dioxane (5 mL) was purged with argon for 10 min. Then, 2 M Na$_2$CO$_3$ (0.43 g, 4.063 mmol) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the desired compound (0.25 g, 44.1%). LCMS: 503.30 (M+1)$^+$; HPLC: 97.176% (@ 254 nm) (R$_t$: 5.599); $^1$H NMR (DMSO-d$_6$, 400 MHz) δ 11.55 (bs, 1H); 8.86 (s, 1H); 8.28 (s, 1H); 7.81 (s, 1H); 6.82 (s, 1H); 5.89 (s, 1H); 5.42-5.38 (m, 1H); 4.38 (d, J=4.8 Hz, 2H); 2.23 (s, 3H); 2.12 (s, 3H); 2.02-1.91 (m, 6H); 1.72 (m, 2H); 1.38-1.23 (m, 14H).

Step 4: Synthesis of 1-cyclopentyl-N-((4,6-dimethyl-2-oxo-1,2-dihydropyridin-3-yl)methyl)-6-(2,2,6,6-tetramethylpiperidin-4-yl)-1H-pyrazolo[3,4-b]pyridine-4-carboxamide

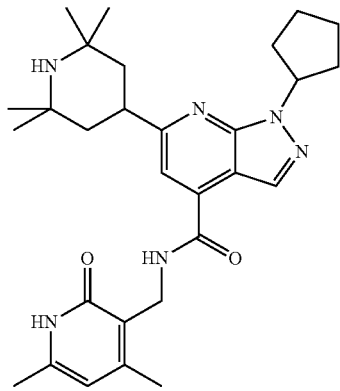 [SMILES: Cc1cc(C)c(CNC(=O)c2cc(C3CC(C)(C)NC(C)(C)C3)nc3c2cnn3C2CCCC2)c(=O)[nH]1]

To a stirred solution of 1-cyclopentyl-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide (0.06 g, 0.119 mmol) in EtOH (10 mL), 10% Pd/C in catalytic amount was added and stirred it at room temperature under hydrogen pressure (bladder pressure) for 3-5 hr. On completion of reaction, reaction mass filter it through celite bed, then filtrate was concentrated under reduce pressure. The residue was washed with acetonitrile followed by ether to provide the desired product (75% yield). LCMS:505.30 (M+1)$^+$; HPLC: 99.69% (@ 254 nm) (R$_t$:5.517); $^1$H NMR (CD3OD-d$_6$, 400 MHz) δ 11.54 (bs, 1H), 8.76 (t, 1H, J=4.8 Hz), 8.26 (s, 1H), 7.51 (s, 1H), 5.89 (s, 1H), 5.38-5.36 (m, 1H), 4.36 (d, 2H, J=4.8 Hz), 2.21 (s, 3H), 2.12 (s, 3H), 2.12 (m, 3H), 2.01-1.98 (m, 2H), 1.96-1.89 (m, 2H), 1.75-1.71 (m, 4H), 1.52 (m, 2H), 1.27 (s, 6H), 1.12 (s, 6H).

Synthesis of Compound B-6: N-((4,6-dimethyl-2-oxo-1,2-dihydropyridin-3-yl)methyl)-1-isopropyl-6-((1-methylpiperidin-4-yl)oxy)-1H-pyrazolo[3,4-b]pyridine-4-carboxamide Compound B-6

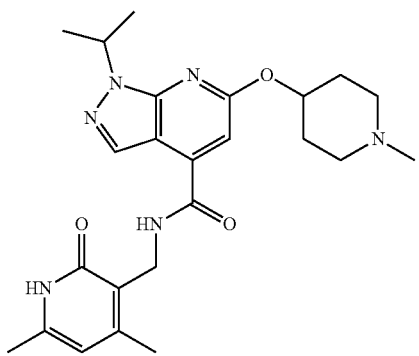

Step 1: Synthesis of ethyl 6-bromo-1-isopropyl-1H-pyrazolo[3,4-b]pyridine-4-carboxylate

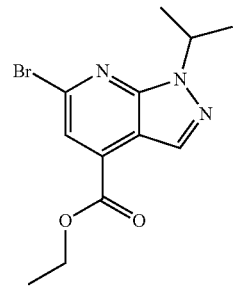 [SMILES: CCOC(=O)c1cc(Br)nc2c1cnn2C(C)C]

To a stirred solution of ethyl 6-bromo-1H-pyrazolo[3,4-b]pyridine-4-carboxylate (20 g, 74.3 mmol) in acetonitrile (200 mL), K$_2$CO$_3$ (15.39 g, 111.52 mmol) and 2-bromopropane (18.13 g, 148.64 mmol) was added to it. The reaction mixture was refluxed for 8 h. On completion, acetonitrile was removed under reduced pressure and water was added to it. Extraction was carried out using ethyl acetate; the combined organic layers were washed with water, brine and dried over anhydrous Na$_2$SO$_4$. Solvent was removed under reduced pressure and residue was purified by silica gel column chromatography to obtain the desired intermediate (13.5 g, 58.3%).

Step 2: Synthesis of ethyl 1-isopropyl-6-((1-methylpiperidin-4-yl)oxy)-1H-pyrazolo[3,4-b]pyridine-4-carboxylate

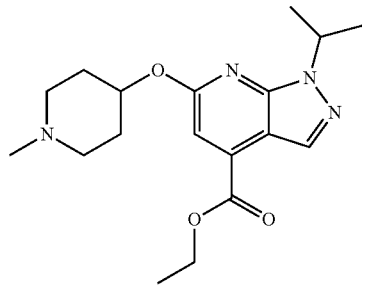 [SMILES: CCOC(=O)c1cc(OC2CCN(C)CC2)nc2c1cnn2C(C)C]

Ethyl 6-hydroxy-1-isopropyl-1H-pyrazolo[3,4-b]pyridine-4-carboxylate (1 equiv.) was suspended in DMF and K$_2$CO$_3$ (1.5 equiv.) and 4-bromo-1-methylpiperidine (1.5 equiv.) was added to it. The reaction mixture was stirred at room temperature for overnight. On completion of reaction, water was added to it and extraction was carried out using ethyl acetate; the combined organic layers were washed with water, brine and dried over anhydrous Na$_2$SO$_4$. Solvent was removed under reduced pressure and residue was purified by silica gel column chromatography to obtain the desired intermediate.

Step 3: synthesis of N-((4,6-dimethyl-2-oxo-1,2-dihydropyridin-3-yl)methyl)-1-isopropyl-6-((1-methylpiperidin-4-yl)oxy)-1H-pyrazolo[3,4-b]pyridine-4-carboxamide

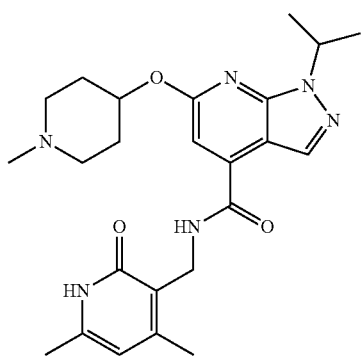 [SMILES: Cc1cc(C)c(CNC(=O)c2cc(OC3CCN(C)CC3)nc3c2cnn3C(C)C)c(=O)[nH]1]

Aqueous NaOH (2 equivalent) was added to a solution of ethyl 1-isopropyl-6-((1-methylpiperidin-4-yl)oxy)-1H-pyrazolo[3,4-b]pyridine-4-carboxylate (1 equivalent) in EtOH (10 times by volume) and stirred at 60° C. for 1 h. After completion of the reaction, ethanol was removed under reduced pressure and it was acidified using citric acid solution. Extraction was carried out using DCM; the combined organic layers were washed with water, brine and dried over anhydrous Na$_2$SO$_4$; filtered and concentrated under reduced pressure. The residue was then dissolved in DMSO (10 times by volume) and 3-(aminomethyl)-4,6-dimethylpyridin-2(1H)-one (2 equivalents) was added to it. The reaction mixture was stirred at room temperature for 15 min before PYBOP (1.5 equivalents) was added to it and stirring was continued for 5 to 16 h. After completion of the reaction, reaction mass was poured into ice water to obtain a solid which was filtered and washed with acetonitrile to provide the desired product (2.5% yield). LCMS: 453.20 (M+1)$^+$; HPLC: 96.37% (@ 254 nm) (R$_t$:4.742); $^1$H NMR (CD3OD, 400 MHz) δ 8.16 (s, 1H), 7.21-7.11 (m, 2H), 7.00 (s, 1H), 6.13 (s, 1H), 5.16-5.11 (m, 1H), 4.53 (d, 2H, J=5.2 Hz), 3.65 (d, 1H, J=13.2 Hz), 3.48-3.45 (m, 2H), 3.38-3.31 (m, 2H), 2.94 (s, 3H), 2.53 (d, 1H, J=12 Hz), 2.41 (s, 3H), 2.40 (m, 1H), 2.25 (s, 3H), 2.20-2.13 (m, 1H), 2.02-1.95 (1H), 1.54 (d, 6H, J=6.8 Hz).

Synthesis of Compound B-7: N-((4,6-dimethyl-2-oxo-1,2-dihydropyridin-3-yl)methyl)-6-(1-(4-(dimethylamino)butanoyl)piperidin-4-yl)-1-isopropyl-1H-pyrazolo[3,4-b]pyridine-4-carboxamide

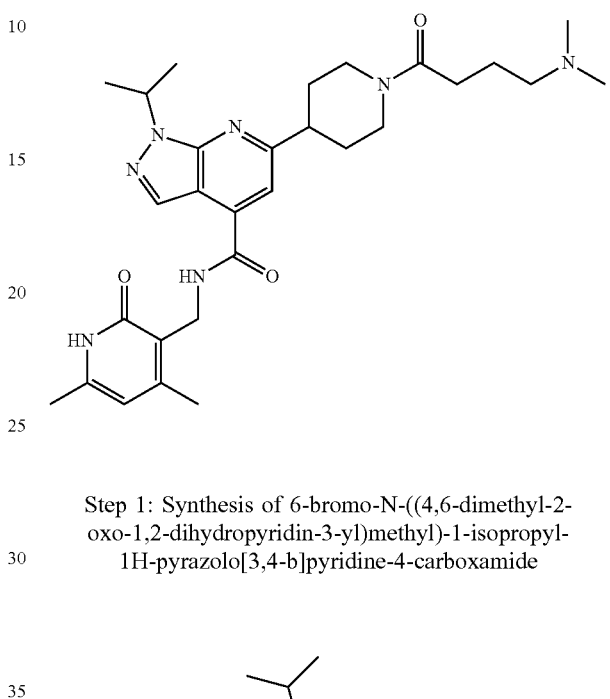

Compound B-7

Step 1: Synthesis of 6-bromo-N-((4,6-dimethyl-2-oxo-1,2-dihydropyridin-3-yl)methyl)-1-isopropyl-1H-pyrazolo[3,4-b]pyridine-4-carboxamide

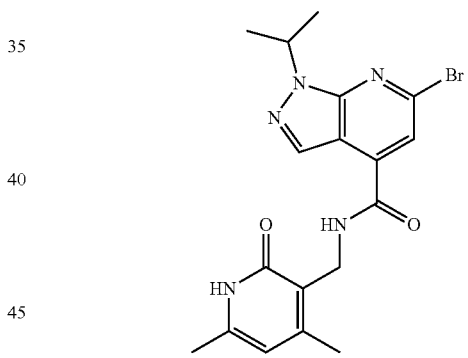

Aqueous NaOH (0.964 g, 24.11 mmol) was added to a solution of ethyl 6-bromo-1-isopropyl-1H-pyrazolo[3,4-b]pyridine-4-carboxylate (5 g, 16.07 mmol) in EtOH (50 mL) and stirred at 60° C. for 1 h. After completion of the reaction, ethanol was removed under reduced pressure and it was acidified using 10% citric acid solution. Extraction was carried out using ethyl acetate; the combined organic layers were washed with water, brine and dried over anhydrous Na$_2$SO$_4$; filtered and concentrated under reduced pressure. The crude acid (3 g, 10.55 mmol) was then dissolved in DMSO (35 mL) and 3-(aminomethyl)-4,6-dimethylpyridin-2(1H)-one (3.2 g, 21.0 mmol) was added to it. The reaction mixture was stirred at room temperature for 15 min before PYBOP (8.23 g, 15.82 mmol) was added to it and stirring was continued overnight. After completion of the reaction, reaction mass was poured into ice to obtain solid, which was filtered and washed with acetonitrile followed by ether to provide the desired intermediate (3 g, 68%).

Step 2: Synthesis of tert-butyl 4-(4-(((4,6-dimethyl-2-oxo-1,2-dihydropyridin-3-yl)methyl) carbamoyl)-1-isopropyl-1H-pyrazolo[3,4-b]pyridin-6-yl)-5,6-dihydropyridine-1(2H)-carboxylate

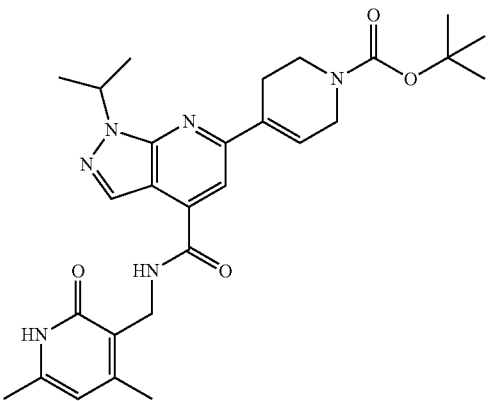 [SMILES: Cc1cc(C)c(CNC(=O)c2cc(C3=CCN(C(=O)OC(C)(C)C)CC3)nc3c2cnn3C(C)C)c(=O)[nH]1]

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (3.1 g, 7.4 mmol), tert-butyl 4-(4,4,5,5-tetramethyl-1,3,2-dioxaborolan-2-yl)-5,6-dihydropyridine-1(2H)-carboxylate (2.7 g, 8.7 mmol) and Pd(PPh$_3$)$_4$ (0.428 g, 0.370 mmol) in 1,4-dioxane (20 mL) was purged with argon for 10 min. Then, 2M Na$_2$CO$_3$ (2.8 g, 26.41) was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the desired intermediate (2.8 g, 73.7%).

Step 3: Synthesis of N-((4,6-dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide

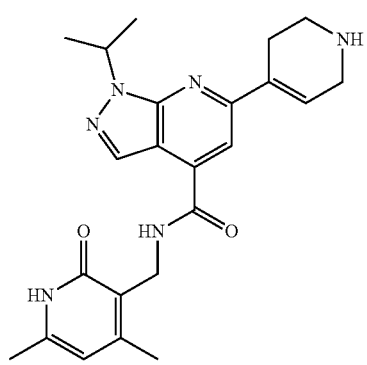 [SMILES: Cc1cc(C)c(CNC(=O)c2cc(C3=CCNCC3)nc3c2cnn3C(C)C)c(=O)[nH]1]

To a stirred solution of tert-butyl 4-(4-(((4,6-dimethyl-2-oxo-1,2-dihydropyridin-3-yl)methyl)carbamoyl)-1-isopropyl-1H-pyrazolo[3,4-b]pyridin-6-yl)-5,6-dihydropyridine-1(2H)-carboxylate (2.8 g, 5.4 mmol) in DCM (15 mL), TFA (13 mL) was added at 0° C. and stirred it at room temperature for 1 h. After completion of reaction, solvent was removed under reduced pressure and residue neutralized with saturated NaHCO$_3$ solution Extraction was carried out using DCM; the combined organic layers were washed with water, brine and dried over anhydrous Na$_2$SO$_4$; filtered and concentrated under reduced pressure, finally the residue was washed with diethyl ether to provide the desired intermediate (1.5 g, 66.4%).

Step 4: Synthesis of N-((4,6-dimethyl-2-oxo-1,2-dihydropyridin-3-yl)methyl)-6-(1-(4-(dimethylamino)butanoyl)-1,2,3,6-tetrahydropyridin-4-yl)-1-isopropyl-1H-pyrazolo[3,4-b]pyridine-4-carboxamide

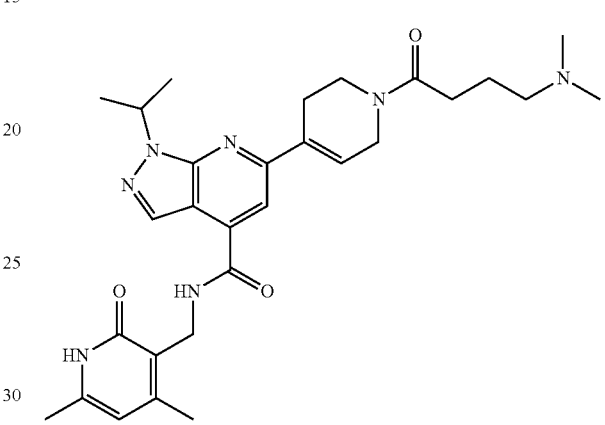

N-((4,6-dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (1 equiv.) was dissolved in DMSO, to which Et$_3$N (3 equiv.) and 4-(dimethylamino)butanoic acid (2 equiv.) was added. The reaction mixture was stirred at room temperature for 15 min before PYBOP (1.5 equiv.) was added to it and stirring was continued overnight. After completion of the reaction, water was added to it. Extraction was carried out using DCM; the combined organic layers were washed with water, brine and dried over anhydrous Na$_2$SO$_4$; filtered and concentrated under reduced pressure to afford crude material which was purified by column chromatography to give the desired product.

Step 5: Synthesis of N-((4,6-dimethyl-2-oxo-1,2-dihydropyridin-3-yl)methyl)-6-(1-(4-(dimethylamino)butanoyl)piperidin-4-yl)-1-isopropyl-1H-pyrazolo[3,4-b]pyridine-4-carboxamide

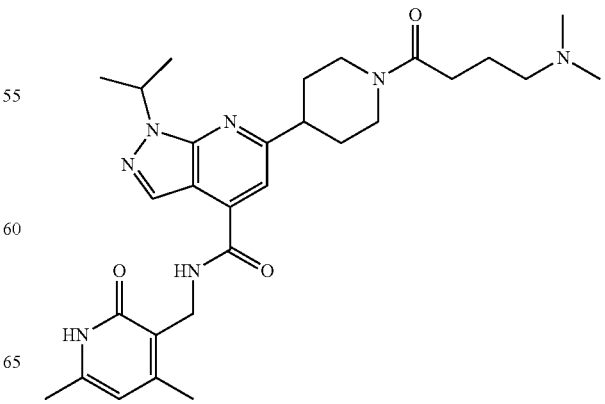

To a stirred solution of N-((4,6-dimethyl-2-oxo-1,2-dihydropyridin-3-yl)methyl)-6-(1-(4-(dimethylamino)butanoyl)-1,2,3,6-tetrahydropyridin-4-yl)-1-isopropyl-1H-pyrazolo[3,4-b]pyridine-4-carboxamide (1 equiv.) in EtOH, 10% Pd/C in catalytic amount was added and stirred it at room temperature under hydrogen pressure (bladder pressure) for 3-16 h hr. On completion of reaction, reaction mass was filtered through celite bed, then filtrate was concentrated under reduced pressure to give the desired product. LCMS: 536.40 (M+1)+; HPLC: 83.00% (@ 254 nm) (Rt:4.917); 1H NMR (DMSO-d6, 400 MHz) δ 11.54 (s, 1H), 8.75 (t, 1H), 8.27 (s, 1H), 7.52 (s, 1H), 5.89 (s, 1H), 5.20-5.17 (m, 1H), 4.57-4.54 (m, 1H), 4.36 (d, 2H, J=4.8 Hz), 4.01-3.98 (m, 1H), 3.32 (1H merged with DMSO peak), 3.19-305 (m, 2H), 2.72-2.67 (m, 2H), 2.40 (m, 2H), 2.40 (s, 6H) 2.20 (s, 3H), 2.12 (s, 3H), 2.04-1.91 (m, 2H), 1.79-1.63 (m, 4H), 1.48 (d, 6H, J=6.4 Hz).

Synthesis of Compound B-8: N-((4,6-dimethyl-2-oxo-1,2-dihydropyridin-3-yl)methyl)-1-isopropyl-6-(1-(1-methylazetidine-3-carbonyl)piperidin-4-yl)-1H-pyrazolo[3,4-b]pyridine-4-carboxamide Compound B-8

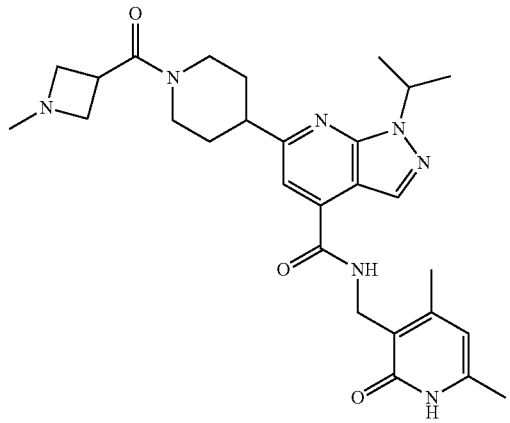

Step 1: Synthesis of N-((4,6-dimethyl-2-oxo-1,2-dihydropyridin-3-yl)methyl)-1-isopropyl-6-(1-(1-methylazetidine-3-carbonyl)-1,2,3,6-tetrahydropyridin-4-yl)-1H-pyrazolo[3,4-b]pyridine-4-carboxamide

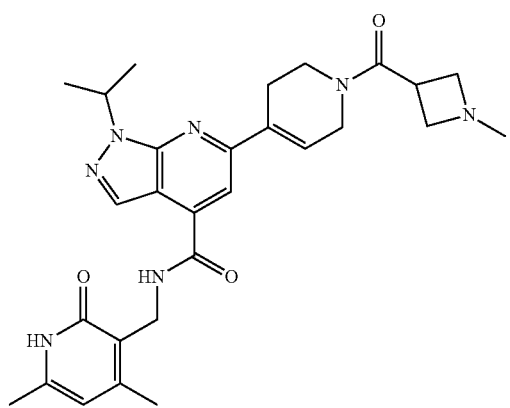

N-((4,6-dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (1 equiv.) was dissolved in DMSO, to which Et₃N (3 equiv.) and 1-methylazetidine-3-carboxylic acid (2 equiv.) was added. The reaction mixture was stirred at room temperature for 15 min before PYBOP (1.5 equiv.) was added to it and stirring was continued overnight. After completion of the reaction, water was added to it. Extraction was carried out using DCM; the combined organic layers were washed with water, brine and dried over anhydrous Na₂SO₄; filtered and concentrated under reduced pressure to afford crude material which was purified by column chromatography to give the desired product.

Step 2: Synthesis of N-((4,6-dimethyl-2-oxo-1,2-dihydropyridin-3-yl)methyl)-1-isopropyl-6-(1-(1-methylazetidine-3-carbonyl)piperidin-4-yl)-1H-pyrazolo[3,4-b]pyridine-4-carboxamide

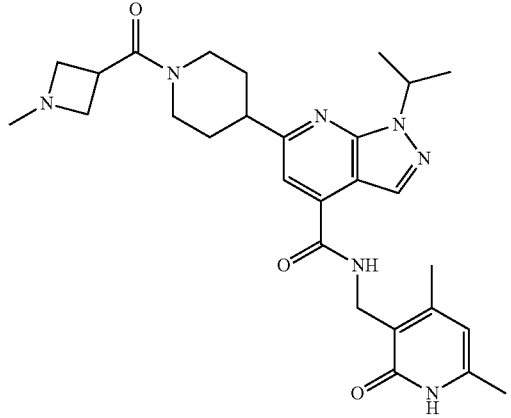

To a stirred solution of N-((4,6-dimethyl-2-oxo-1,2-dihydropyridin-3-yl)methyl)-1-isopropyl-6-(1-(1-methylazetidine-3-carbonyl)-1,2,3,6-tetrahydropyridin-4-yl)-1H-pyrazolo[3,4-b]pyridine-4-carboxamide (1 equiv.) in EtOH, 10% Pd/C in catalytic amount was added and stirred it at room temperature under hydrogen pressure (bladder pressure) for 3-16 h hr. On completion of reaction, reaction mass was filtered through celite bed, then filtrate was concentrated under reduced pressure to give the desired product 62% yield). LCMS: 520.35 (M+1)⁺; HPLC: 93.45% (@ 254 nm) (R$_t$;6.931); ¹H NMR (DMSO-d₆, 400 MHz) δ 11.54 (s, 1H), 8.75 (t, 1H, J=4.8 Hz), 8.27 (s, 1H), 7.51 (s, 1H), 5.88 (s, 1H), 5.20-5.17 (m, 1H), 4.50 (d, 1H, J=12.4 Hz), 4.36 (d, 2H, J=4.8 Hz), 3.69 (d, 1H, J=13.2 Hz), 3.43 (s, 3H), 3.13-3.06 (m, 4H), 2.69 (t, 1H, J=12 & 11.6 Hz), 2.20 (s, 3H), 2.17 (s, 3H), 2.12 (s, 3H), 1.93 (d, 2H, J=12 Hz), 1.65 (m, 2H), 1.48 (d, 6H, J=7.2 Hz).

Synthesis of Compound B-9: N-((4,6-dimethyl-2-oxo-1,2-dihydropyridin-3-yl)methyl)-1-isopropyl-6-(4-methylpiperazin-1-yl)-1H-pyrazolo[3,4-b]pyridine-4-carboxamide

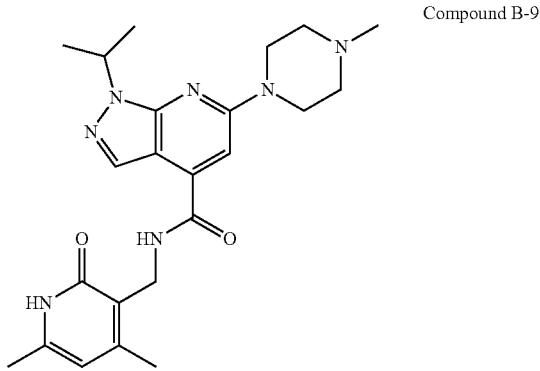
Compound B-9

Step 1 Synthesis of ethyl 1-isopropyl-6-(4-methylpiperazin-1-yl)-1H-pyrazolo[3,4-b]pyridine-4-carboxylate

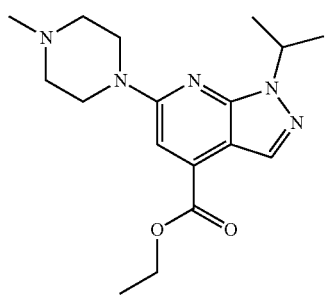 [SMILES: CCOC(=O)c1cc(N2CCN(C)CC2)nc2c1cnn2C(C)C]

To a stirred solution of ethyl 6-bromo-1-isopropyl-1H-pyrazolo[3,4-b]pyridine-4-carboxylate (0.3 g, 0.964 mmol) in acetonitrile (10 mL), $K_2CO_3$ (0.26 g, 1.93 mmol) and 1-methylpiperazine (0.289 g, 2.892 mmol) was added. The reaction mixture was refluxed for 3 h. On completion of reaction, acetonitrile was removed under reduced pressure and water was added to it. Extraction was carried out using DCM; the combined organic layers were washed with water, brine and dried over anhydrous $Na_2SO_4$. Solvent was removed under reduced pressure to obtain the desired intermediate (0.32 g, 94.9%).

Step 2: Synthesis of 1-isopropyl-6-(4-methylpiperazin-1-yl)-1H-pyrazolo[3,4-b]pyridine-4-carboxylic acid

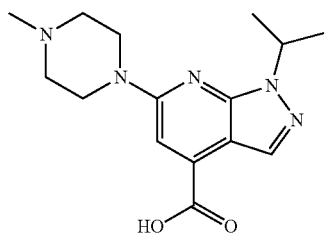 [SMILES: CC(C)n1ncc2c(C(=O)O)cc(N3CCN(C)CC3)nc21]

Aqueous NaOH (0.193 g, 4.833 mmol) was added to a solution of ethyl 1-isopropyl-6-(4-methylpiperazin-1-yl)-1H-pyrazolo[3,4-b]pyridine-4-carboxylate (0.32 g, 0.966 mmol) in EtOH (6 mL) and stirred at 60° C. for 1 h. After completion of the reaction, ethanol was removed under reduced pressure and it was acidified using 10% citric acid solution. Extraction was carried out using DCM; the combined organic layers were washed with water, brine; dried over anhydrous $Na_2SO_4$; filtered and concentrated under reduced pressure to give the desired compound (0.2 g, 64.9%).

Step 3: Synthesis of N-((4,6-dimethyl-2-oxo-1,2-dihydropyridin-3-yl)methyl)-1-isopropyl-6-(4-methylpiperazin-1-yl)-1H-pyrazolo[3,4-b]pyridine-4-carboxamide

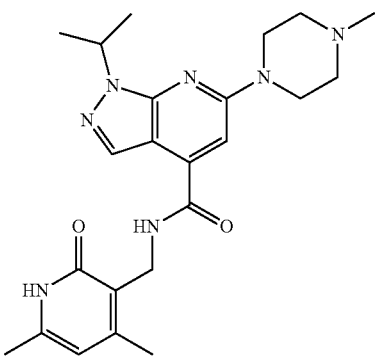

A solution of 1-isopropyl-6-(4-methylpiperazin-1-yl)-1H-pyrazolo[3,4-b]pyridine-4-carboxylic acid (0.2 g, 0.600 mmol) and 3-(aminomethyl)-4,6-dimethylpyridin-2(1H)-one (0.182 g, 1.197 mmol) in DMSO (2 mL) and was stirred at room temperature for 15 min. Then PyBOP (0.468 g, 0.900 mmol) was added to it and stirring was continued for 12 hr. After completion of the reaction, saturated $NaHCO_3$ solution was added to it and extraction was carried out using DCM. The combined organic layers were washed with water, dried over anhydrous $Na_2SO_4$, filtered and concentrated under reduced pressure to afford crude material which was purified by prep. HPLC to give the desired compound (53% yield). LCMS: 438.15 $(M+1)^+$; HPLC: 96.67% (@ 254 nm), $(R_t; 4.516)$; $^1H$ NMR (DMSO-$d_6$, 400 MHz) δ 11.54 (s, 1H), 9.75 (s, 1H), 8.62 (s, 1H), 8.06 (s, 1H), 7.20 (s, 1H), 5.89 (s, 1H), 5.04-4.99 (m, 1H), 4.58 (d, 2H, J=14 Hz), 4.36 (d, 2H, J=4.4 Hz), 3.55 (d, 2H, J=11.20 Hz), 3.24 (t, 2H, J=12.40 Hz), 3.12 (m, 2H), 2.84 (s, 3H), 2.20 (s, 3H), 2.12 (s, 3H), 1.45 (d, 6H, J=6.8 Hz).

Synthesis of Compound B-10: N-((4,6-dimethyl-2-oxo-1,2-dihydropyridin-3-yl)methyl)-1-(tetrahydro-2H-pyran-4-yl)-6-(2,2,6,6-tetramethyl-1,2,3,6-tetrahydropyridin-4-yl)-1H-pyrazolo[3,4-b]pyridine-4-carboxamide

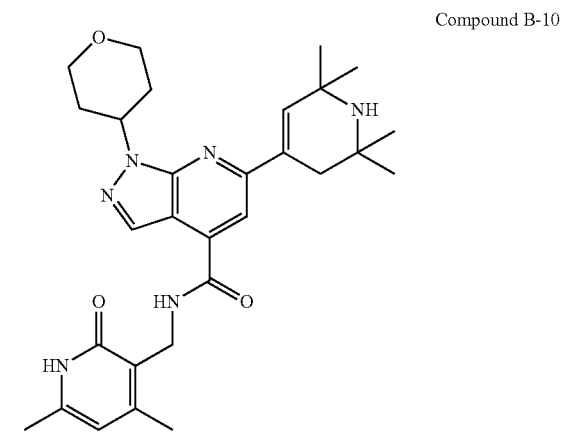
Compound B-10

Step 1: Synthesis of ethyl 6-bromo-1-(tetrahydro-2H-pyran-4-yl)-1H-pyrazolo[3,4-b]pyridine-4-carboxylate

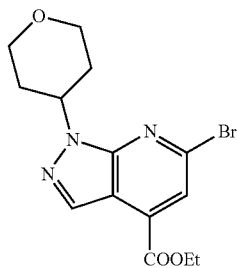 [SMILES: CCOC(=O)c1cc(Br)nc2c1cnn2C1CCOCC1]

Ethyl 6-bromo-1H-pyrazolo[3,4-b]pyridine-4-carboxylate (1 equiv.) was suspended in acetonitrile and $K_2CO_3$ (1.5 equiv.) and 4-bromotetrahydro-2H-pyran (2 equiv.) was added to it. The reaction mixture was refluxed for 8 h. On completion, acetonitrile was removed under reduced pressure and water was added to it. Extraction was carried out using ethyl acetate; the combined organic layers were washed with water, brine and dried over anhydrous $Na_2SO_4$. Solvent was removed under reduced pressure and residue was purified by silica gel column chromatography to obtain the desired intermediate.

Step 2: Synthesis of 6-bromo-N-((4,6-dimethyl-2-oxo-1,2-dihydropyridin-3-yl)methyl)-1-(tetrahydro-2H-pyran-4-yl)-1H-pyrazolo[3,4-b]pyridine-4-carboxamide

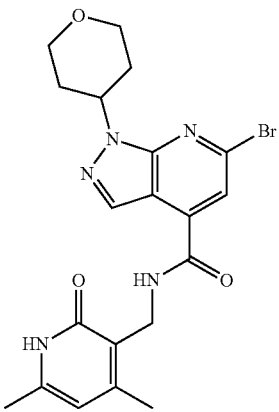 [SMILES: Cc1cc(C)c(CNC(=O)c2cc(Br)nc3c2cnn3C2CCOCC2)c(=O)[nH]1]

Aqueous NaOH (5 equivalent) was added to a solution of ethyl 6-bromo-1-cyclopentyl-1H-pyrazolo[3,4-b]pyridine-4-carboxylate (1 equivalent) in EtOH (10 times by volume) and stirred at 60° C. for 1 h. After completion of the reaction, ethanol was removed under reduced pressure and it was acidified using 10% citric acid solution. Extraction was carried out using EtOAc; the combined organic layers were washed with water, brine and dried over anhydrous $Na_2SO_4$; filtered and concentrated under reduced pressure. The residue was then dissolved in DMSO (10 times by volume) and 3-(aminomethyl)-4,6-dimethylpyridin-2(1H)-one (2 equivalents) was added to it. The reaction mixture was stirred at room temperature for 15 min before PYBOP (1.5 equivalents) was added to it and stirring was continued for 5 to 16 h. After completion of the reaction, water was added to it and extraction was carried out using EtOAc. The combined organic layers were washed with water; brine; dried over anhydrous $Na_2SO_4$; filtered and concentrated under reduced pressure. The residue was purified by silica gel column chromatography followed by ether wash to provide the desired intermediate.

Step 3: Synthesis of N-((4,6-dimethyl-2-oxo-1,2-dihydropyridin-3-yl)methyl)-1-(tetrahydro-2H-pyran-4-yl)-6-(2,2,6,6-tetramethyl-1,2,3,6-tetrahydropyridin-4-yl)-1H-pyrazolo[3,4-b]pyridine-4-carboxamide

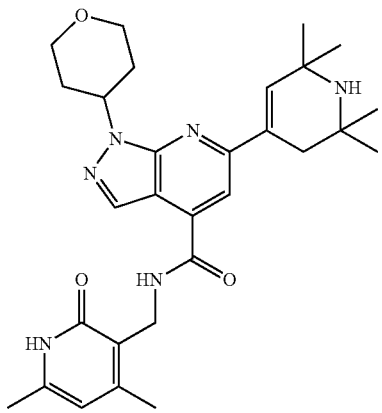

A solution of 6-bromo-N-((4,6-dimethyl-2-oxo-1,2-dihydropyridin-3-yl)methyl)-1-(tetrahydro-2H-pyran-4-yl)-1H-pyrazolo[3,4-b]pyridine-4-carboxamide (1 equiv.), 2,2,6,6-tetramethyl-4-(4,4,5,5-tetramethyl-1,3,2-dioxaborolan-2-yl)-1,2,3,6-tetrahydropyridine (1.2 equiv.) and $Pd(PPh_3)_4$ (0.1 equiv.) in 1,4-dioxane was purged with argon for 10 min. Then, 2 M $Na_2CO_3$ (3.6 equiv.) solution was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous $Na_2SO_4$, filtered and concentrated under reduced pressure to afford crude material which was purified by column chromatography to give the desired compound (14%). LCMS: 519.30 $(M+1)^+$; HPLC: 98.464% (@ 254 nm) ($R_t$: 4.823); $^1$H NMR (DMSO-$d_6$, 400 MHz) δ 11.55 (bs, 1H); 8.87 (s, 1H); 8.30 (s, 1H); 7.82 (s, 1H); 6.81 (s, 1H); 5.90 (s, 1H); 5.06 (m, 1H); 4.38 (s, 2H); 3.01 (d, J=11.2, 2H); 3.59 (t, J=12.0 Hz, 2H); 2.23 (s, 3H); 2.23-2.19 (m, 2H); 2.12 (s, 3H); 1.90 (d, J=12.0 Hz, 2H); 1.27-1.23 (m, 14H).

Synthesis of Compound B-11: N-((4,6-dimethyl-2-oxo-1,2-dihydropyridin-3-yl)methyl)-6-(4-hydroxypiperidin-1-yl)-1-isopropyl-1H-pyrazolo[3,4-b]pyridine-4-carboxamide

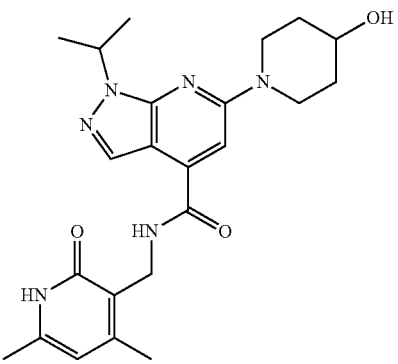

Compound B-11

Step 1: Synthesis of N-((4,6-dimethyl-2-dihydropyridin-3-yl)methyl)-1-isopropyl-6-(4-oxopiperidin-1-yl)-1H-pyrazolo[3,4-b]pyridine-4-carboxamide

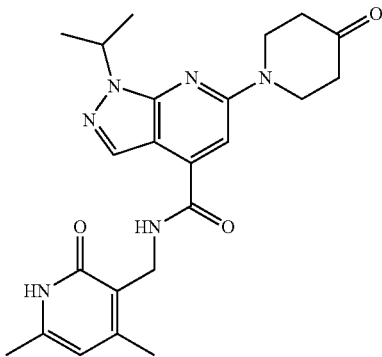 [SMILES: Cc1cc(C)c(CNC(=O)c2cc(N3CCC(=O)CC3)nc3c2cnn3C(C)C)c(=O)[nH]1]

To a solution of 6-bromo-N-((4,6-dimethyl-2-dihydropyridin-3-yl)methyl)-1-isopropyl-1H-pyrazolo[3,4-b]pyridine-4-carboxamide (0.1 g, 0.239 mmol) in DMF (2 mL), $K_2CO_3$ (0.198 g, 1.434 mmol) and piperidin-4-one HCl salt (0.186 g, 0.94 mmol) were added. The reaction mixture was heated at 80° C. for 16 h. Reaction was monitored by LCMS & TLC. On completion, reaction mass was poured into water and extraction was carried out using 5% MeOH/DCM. The combined organic layers were dried over anhydrous $Na_2SO_4$; filtered and concentrated under reduced pressure. The residue was purified by prep HPLC to provide the desired compound (0.03 g 28.8%).

Step 2: Synthesis of N-((4,6-dimethyl-2-oxo-1,2-dihydropyridin-3-yl)methyl)-6-(4-hydroxypiperidin-1-yl)-1-isopropyl-1H-pyrazolo[3,4-b]pyridine-4-carboxamide

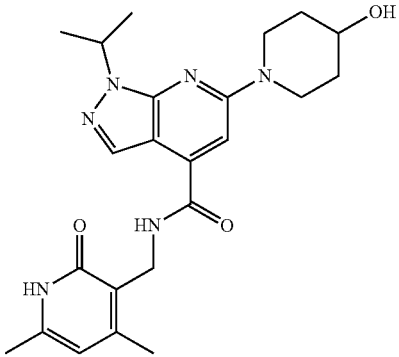 [SMILES: Cc1cc(C)c(CNC(=O)c2cc(N3CCC(O)CC3)nc3c2cnn3C(C)C)c(=O)[nH]1]

N-((4,6-Dimethyl-2-oxo-1,2-dihydropyridin-3-yl)methyl)-1-isopropyl-6-(4-oxopiperidin-1-yl)-1H-pyrazolo[3,4-b]pyridine-4-carboxamide (0.1 g, 0.229 mmol) was taken in MeOH (3 mL) and $NaBH_4$ (0.020 g, 0.458 mmol) was added at 0° C. The reaction mixture was stirred at room temperature for 4 h. On completion of reaction, MeOH was concentrated. And residue was purified by prep HPLC to provide the desired compound (0.034 g, 34%). LCMS: 439.20 (M+1)$^+$; HPLC: 98.22% (@ 254 nm), (R$_t$; 5.393); $^1$H NMR (DMSO-d$_6$, 400 MHz) δ 11.53 (s, 1H), 8.63 (bs, 1H), 7.97 (s, 1H), 7.11 (s, 1H), 5.88 (s, 1H), 4.98-4.95 (m, 1H), 4.34 (d, 2H, J=4.4 Hz), 4.15 (m, 2H), 3.74-3.72 (m, 1H), 3.23 (m, 3H), 2.19 (s, 3H), 2.12 (s, 3H), 1.82 (m, 2H), 1.43 (d, 6H, J=6.4 Hz), 1.38 (m, 2H).

Synthesis of Compound B-12:5-chloro-N-((4,6-dimethyl-2-oxo-1,2-dihydropyridin-3-yl)methyl)-1-isopropyl-6-(2,2,6,6-tetramethyl-1,2,3,6-tetrahydropyridin-4-yl)-1H-pyrazolo[3,4-b]pyridine-4-carboxamide

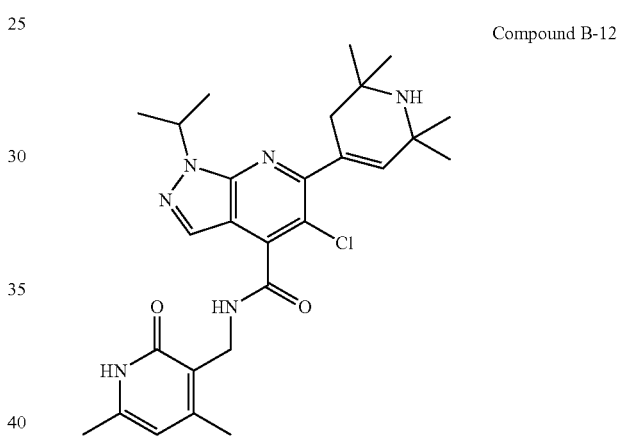

Compound B-12

Step 1 Synthesis of ethyl 5-chloro-6-hydroxy-1-isopropyl-1H-pyrazolo[3,4-b]pyridine-4-carboxylate

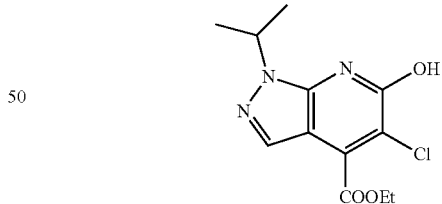

To a stirred solution of ethyl 6-hydroxy-1-isopropyl-1H-pyrazolo[3,4-b]pyridine-4-carboxylate (1.3 g, 5.2 mmol) in DMF (7 mL), N-chlorosuccinamide (1.11 g, 8.35 mmol) was added. The resulting reaction mixture was stirred at 60° C. for 1 h. On completion of reaction, water was added to it and extraction was carried out using ethyl acetate; the combined organic layers were washed with water, brine and dried over anhydrous $Na_2SO_4$. Solvent was removed under reduced pressure and residue was purified by silica gel column chromatography to obtain the desired intermediate (1 g, 69.9%).

329

Step 2 Synthesis of ethyl 5-chloro-1-isopropyl-6-(((trifluoromethyl)sulfonyl)oxy)-1H-pyrazolo[3,4-b]pyridine-4-carboxylate

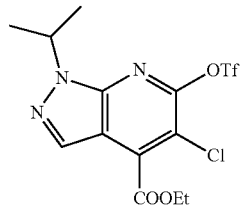 [SMILES: CCOC(=O)c1c(Cl)c(OS(=O)(=O)C(F)(F)F)nc2c1cnn2C(C)C]

To a stirred solution of ethyl 5-chloro-6-hydroxy-1-isopropyl-1H-pyrazolo[3,4-b]pyridine-4-carboxylate (1 g, 3.53 mmol) in DCM (10 mL), pyridine (0.336 mL, 4.24 mmol) was added followed by dropwise addition of triflic anhydride (0.716 mL, 4.24 mmol). The reaction mixture was stirred at room temperature for 1 h. On completion of reaction, water was added to it and extraction was carried out using DCM; the combined organic layers were washed with water, brine and dried over anhydrous $Na_2SO_4$. Solvent was removed under reduced pressure and residue was purified by silica gel column chromatography to obtain the desired intermediate (0.8 g, 54.8%).

Step 3: Synthesis of ethyl 5-chloro-1-isopropyl-6-(2,2,6,6-tetramethyl-1,2,3,6-tetrahydro pyridin-4-yl)-1H-pyrazolo[3,4-b]pyridine-4-carboxylate

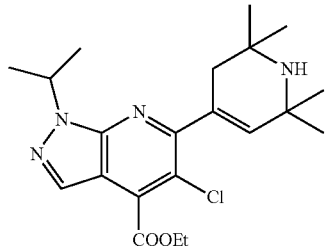 [SMILES: CCOC(=O)c1c(Cl)c(C2=CC(C)(C)NC(C)(C)C2)nc2c1cnn2C(C)C]

A solution of ethyl 5-chloro-1-isopropyl-6-(((trifluoromethyl)sulfonyl)oxy)-1H-pyrazolo[3,4-b]pyridine-4-carboxylate (0.2 g, 0.481 mmol), 2,2,6,6-tetramethyl-4-(4,4,5,5-tetramethyl-1,3,2-dioxaborolan-2-yl)-1,2,3,6-tetrahydropyridine (0.127 g, 0.481 mmol) and $Pd(PPh_3)_4$ (0.027 g, 0.024 mmol) in 1,4-dioxane (3 mL) was purged with argon for 10 min. Then, 2M $Na_2CO_3$ solution (0.183 g, 1.734 mmol) was added to it and again argon was purged through it for 10 min. The reaction mixture was stirred at 100° C. for 1 h. After completion of the reaction, water was added to it and extraction was carried out using 10% MeOH/DCM. The combined organic layers were washed with water, dried over anhydrous $Na_2SO_4$, filtered and concentrated under reduced pressure to afford crude material which was purified by column chromatography to give the desired compound (0.09 g, 45.6%).

330

Step 4: Synthesis of 5-chloro-1-isopropyl-6-(2,2,6,6-tetramethyl-1,2,3,6-tetrahydropyridin-4-yl)-1H-pyrazolo[3,4-b]pyridine-4-carboxylic acid

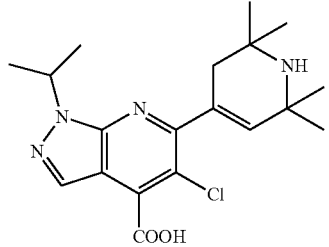

To a solution of intermediate 5 (0.09 g, 0.222 mmol) in EtOH (3 mL), aqueous NaOH (0.026 g, 0.668 mmol) was added and reaction mixture stirred at 60° C. for 1 h. After completion of the reaction, ethanol was removed under reduced pressure and it was acidified using 10% citric acid solution. Extraction was carried out using 5% MeOH/DCM. The combined organic layers were washed with water & dried over anhydrous $Na_2SO_4$, filtered and concentrated under reduced pressure to afford the desired compound (0.07 g, 87.5%), which was pure enough for further use.

Step 5: Synthesis of 5-chloro-N-((4,6-dimethyl-2-oxo-1,2-dihydropyridin-3-yl)methyl)-1-isopropyl-6-(2,2,6,6-tetramethyl-1,2,3,6-tetrahydropyridin-4-yl)-1H-pyrazolo[3,4-b]pyridine-4-carboxamide

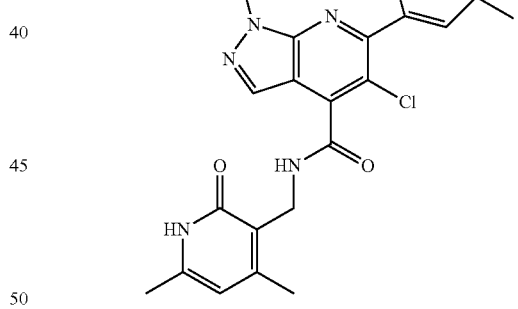

A solution of 5-chloro-1-isopropyl-6-(2,2,6,6-tetramethyl-1,2,3,6-tetrahydropyridin-4-yl)-1H-pyrazolo[3,4-b]pyridine-4-carboxylic acid (0.07 g, 0.18 mmol) and 3-(aminomethyl)-4,6-dimethylpyridin-2(1H)-one (0.056 g, 0.372 mmol) in DMSO (1 mL) and was stirred at room temperature for 15 min. Then PyBOP (0.145 g, 0.279 mmol) was added to it and stirring was continued for 12 h. After completion of the reaction, water was added to it and extraction was carried out using 10% MeOH/DCM. The combined organic layers were washed with water, dried over anhydrous $Na_2SO_4$, filtered and concentrated under reduced pressure to afford crude material which was purified by prep. HPLC to give the desired compound (26% yield). LCMS: 511.20(M+1)$^+$; HPLC: 91.79% (@ 254 nm) ($R_t$:4.914); $^1$H NMR (DMSO-$d_6$, 400 MHz) δ 11.55 (s, 1H), 8.74 (d, 3H, J=4 Hz), 8.05 (s, 1H), 6.06 (s, 1H), 5.89 (s, 1H), 5.15-5.08

(m, 1H), 4.36 (d, 2H, J=4.8 Hz), 2.59 (s, 2H), 2.23 (s, 3H), 2.11 (s, 3H), 1.54 (s, 6H), 1.49 (s, 6H), 1.48 (d, 6H, J=7.6 Hz).

Synthesis of Compound B-13: N-((4,6-dimethyl-2-oxo-1,2-dihydropyridin-3-yl)methyl)-1-isopropyl-3-methyl-6-(2,2,6,6-tetramethyl-1,2,3,6-tetrahydropyridin-4-yl)-1H-pyrazolo[3,4-b]pyridine-4-carboxamide Compound B-13

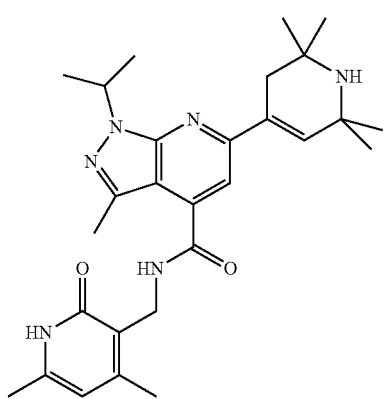

Step 1: ethyl 6-hydroxy-3-methyl-1H-pyrazolo[3,4-b]pyridine-4-carboxylate

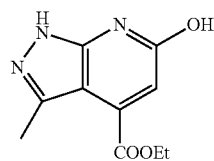

A stirred solution of 5-methyl-1H-pyrazol-3-amine (5 g, 51.48 mmol) in acetic acid (33 mL) and water (100 mL) was cooled to 0° C. and diethyl oxaloacetate sodium salt (10.81 g, 51.48 mmol) was added to it. Resulting solution was heated at 100° C. for overnight. After completion of reaction the solid was filtered and dried to obtain the desired intermediate (2.5 g, 21.9%).

Step 2: Synthesis of ethyl 6-bromo-3-methyl-1H-pyrazolo[3,4-b]pyridine-4-carboxylate

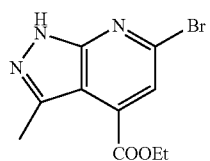

6-Hydroxy-3-methyl-1H-pyrazolo[3,4-b]pyridine-4-carboxylate (2.5 g, 11.3 mmol) was suspended in acetonitrile (25 mL) and POBr₃ (6.5 g, 22.6 mmol) was added to it. The reaction mixture was refluxed for 6 h. On completion of reaction, acetonitrile was removed under reduced pressure and residue neutralized with saturated NaHCO₃. Extraction was carried out using EtOAc and the combined organic layers were washed with water, brine and dried over anhydrous Na₂SO₄, filtered and concentrated under reduced pressure. The residue was purified by silica gel column chromatography to provide the target compound (2.5 g, 77.8%).

Step 3: Synthesis of ethyl 6-bromo-1-isopropyl-3-methyl-1H-pyrazolo[3,4-b]pyridine-4-carboxylate

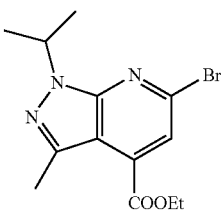 [SMILES: CCOC(=O)c1cc(Br)nc2c1c(C)nn2C(C)C]

Ethyl 6-bromo-3-methyl-1H-pyrazolo[3,4-b]pyridine-4-carboxylate (1 g, 3.52 mmol) was suspended in acetonitrile (10 mL) and K₂CO₃ (0.728 g, 5.28 mmol) and 2-bromopropane (0.866 g, 7.04 mmol) was added to it. The reaction mixture was refluxed for overnight. On completion of reaction, acetonitrile was removed under reduced pressure and water added to it. Extraction was carried out using ethyl acetate and the combined organic layers were washed with water, brine and dried over anhydrous Na₂SO₄. Solvent was removed under reduced pressure and residue was purified by silica gel column chromatography to obtain the desired intermediate (0.61 g, 53.5%). Structure was confirmed by NOE.

Step 4: Synthesis of 6-bromo-1-isopropyl-3-methyl-1H-pyrazolo[3,4-b]pyridine-4-carboxylic acid

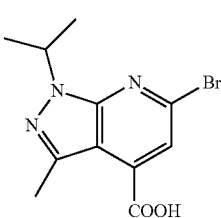 [SMILES: Cc1nn(C(C)C)c2nc(Br)cc(C(=O)O)c12]

To a solution of ethyl 6-bromo-1-isopropyl-3-methyl-1H-pyrazolo[3,4-b]pyridine-4-carboxylate (0.6 g, 1.84 mmol) in EtOH (10 mL), aqueous NaOH (0.11 g, 2.76 mmol, in 5 mL water) was added and reaction mixture stirred at 60° C. for 1 h. After completion of the reaction, ethanol was removed under reduced pressure and it was acidified using 10% citric acid solution. Extraction was carried out using 5% MeOH/DCM. The combined organic layers were washed with water & dried over anhydrous Na₂SO₄, filtered and concentrated under reduced pressure to afford target compound (0.35 g., 63.8%), which was not purified further.

Step 5: Synthesis of 6-bromo-N-((4,6-dimethyl-2-oxo-1,2-dihydropyridin-3-yl)methyl)-1-isopropyl-3-methyl-1H-pyrazolo[3,4-b]pyridine-4-carboxamide

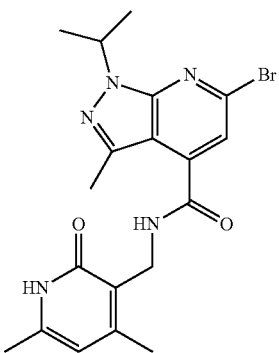 [SMILES: Cc1cc(C)c(CNC(=O)c2cc(Br)nc3c2c(C)nn3C(C)C)c(=O)[nH]1]

A solution of 6-bromo-1-isopropyl-3-methyl-1H-pyrazolo[3,4-b]pyridine-4-carboxylic acid (0.3 g, 1.01 mmol) and 3-(aminomethyl)-4,6-dimethylpyridin-2(1H)-one (0.306 g, 2.01 mmol) in DMSO (4 mL) and was stirred at room temperature for 15 min. Then PyBOP (0.78 g, 1.51 mmol) was added to it and stirring was continued for 12 h. After completion of the reaction, reaction mass was poured into ice to obtain solid, which was filtered and washed with acetonitrile followed by ether to provide 6-bromo-N-((4,6-dimethyl-2-oxo-1,2-dihydropyridin-3-yl)methyl)-1-isopropyl-3-methyl-1H-pyrazolo[3,4-b]pyridine-4-carboxamide (0.12 g, 27.5%).

Step 6: Synthesis of N-((4,6-dimethyl-2-oxo-1,2-dihydropyridin-3-yl)methyl)-1-isopropyl-3-methyl-6-(2,2,6,6-tetramethyl-1,2,3,6-tetrahydropyridin-4-yl)-1H-pyrazolo[3,4-b]pyridine-4-carboxamide

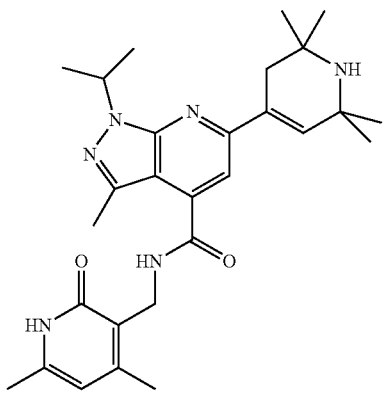

A solution of 6-bromo-N-((4,6-dimethyl-2-oxo-1,2-dihydropyridin-3-yl)methyl)-1-isopropyl-3-methyl-1H-pyrazolo[3,4-b]pyridine-4-carboxamide (0.1 g, 0.231 mmol), boronic ester (0.073 g, 0.277 mmol) and Pd(PPh$_3$)$_4$ (0.013 g, 0.011 mmol) in 1,4-dioxane (1 mL) was purged with argon for 10 min. Then, 2M Na$_2$CO$_3$ solution (0.08 g, 0.833 mmol) was added to it and again argon was purged through it for 10 min. The reaction mixture was stirred at 100° C. for 1 h. After completion of the reaction, water was added to it and extraction was carried out using 10% MeOH/DCM. The combined organic layers were washed with water, dried over anhydrous Na$_2$SO$_4$, filtered and concentrated under reduced pressure to afford crude material which was purified by column chromatography to give the desired final target (12% yield). LCMS: 491.35 (M+1)$^+$; HPLC: 99.28% (@ 254 nm), (R$_t$; 5.042; $^1$H NMR (DMSO-d$_6$, 400 MHz) δ 11.46 (bs, 1H), 8.61 (t, 1H, J=4.4 Hz), 7.34 (s, 1H), 6.73 (s, 1H), 5.87 (s, 1H), 5.16-5.10 (m, 1H), 4.36 (d, 2H, J=5.2 Hz), 2.38 (s, 3H), 2.22 (s, 3H), 2.11 (s, 3H), 1.45 (d, 6H, J=6.8 Hz), 1.26 (s, 6H), 1.23 (s, 2H), 1.17 (s, 6H).

Synthesis of Compound B-14:1-cyclobutyl-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide

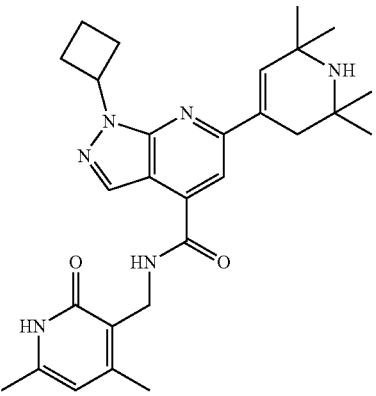

Compound B-14

Step 1: Synthesis of ethyl 6-bromo-1-cyclobutyl-1H-pyrazolo[3,4-b]pyridine-4-carboxylate

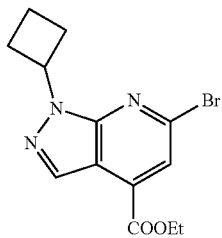 [SMILES: CCOC(=O)c1cc(Br)nc2c1cnn2C1CCC1]

Ethyl 6-bromo-1H-pyrazolo[3,4-b]pyridine-4-carboxylate (1 equiv.) was suspended in acetonitrile and K$_2$CO$_3$ (1.5 equiv.) and bromocyclobutane (2 equiv.) was added to it. The reaction mixture was refluxed for 8 h. On completion, acetonitrile was removed under reduced pressure and water was added to it. Extraction was carried out using ethyl acetate; the combined organic layers were washed with water, brine and dried over anhydrous Na$_2$SO$_4$. Solvent was removed under reduced pressure and residue was purified by silica gel column chromatography to obtain the desired intermediate.

Step 2: Synthesis of 6-bromo-1-cyclobutyl-N-((4,6-dimethyl-2-oxo-1,2-dihydropyridin-3-yl)methyl)-1H-pyrazolo[3,4-b]pyridine-4-carboxamide

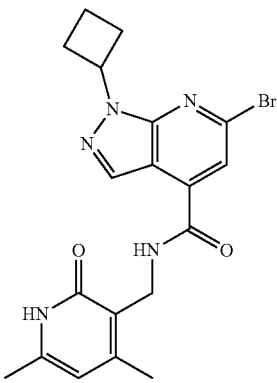 [SMILES: Cc1cc(C)c(CNC(=O)c2cc(Br)nc3c2cnn3C2CCC2)c(=O)[nH]1]

Aqueous NaOH (5 equivalent) was added to a solution of ethyl 6-bromo-1-cyclobutyl-1H-pyrazolo[3,4-b]pyridine-4-carboxylate (1 equivalent) in EtOH (10 times by volume) and stirred at 60° C. for 1 h. After completion of the reaction, ethanol was removed under reduced pressure and it was acidified using 10% citric acid solution. Extraction was carried out using EtOAc; the combined organic layers were washed with water, brine and dried over anhydrous $Na_2SO_4$; filtered and concentrated under reduced pressure. The residue was, then, dissolved in DMSO (10 times by volume) and 3-(aminomethyl)-4,6-dimethylpyridin-2(1H)-one (2 equivalents) was added to it. The reaction mixture was stirred at room temperature for 15 min before PYBOP (1.5 equivalents) was added to it and stirring was continued for 5 to 16 h. After completion of the reaction, water was added to it and extraction was carried out using EtOAc. The combined organic layers were washed with water; brine; dried over anhydrous $Na_2SO_4$; filtered and concentrated under reduced pressure. The residue was purified by silica gel column chromatography followed by ether wash to provide the desired intermediate.

Step 3: Synthesis of 1-cyclobutyl-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide

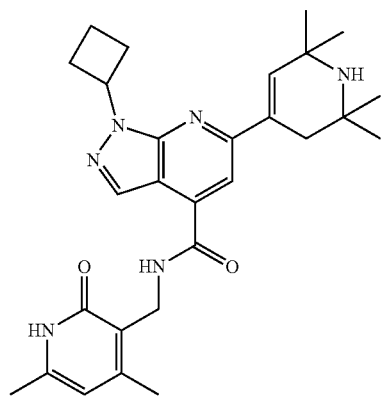

A solution of 6-bromo-1-cyclobutyl-N-((4,6-dimethyl-2-oxo-1,2-dihydropyridin-3-yl)methyl)-1H-pyrazolo[3,4-b]pyridine-4-carboxamide (1 equiv.),2,2,6,6-tetramethyl-4-(4,4,5,5-tetramethyl-1,3,2-dioxaborolan-2-yl)-1,2,3,6-tetrahydropyridine (1.2 equiv.) and $Pd(PPh_3)_4$ (0.1 equiv.) in 1,4-dioxane was purged with argon for 10 min. Then, 2 M $Na_2CO_3$ (3.6 equiv.) solution was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous $Na_2SO_4$, filtered and concentrated under reduced pressure to afford crude material which was purified by column chromatography to give the desired compound (80% yield). LCMS: 489.30(M+1)$^+$; HPLC: 95.97% (@ 254 nm) ($R_t$:5.425); $^1$H NMR (DMSO-$d_6$, 400 MHz) δ 11.55 (s, 1H), 8.89 (t, 1H), 8.31 (s, 1H), 7.79 (s, 1H), 6.81 (s, 1H), 5.89 (s, 1H), 5.52-5.44 (m, 1H), 4.37 (d, 2H, J=4.8 Hz), 2.73-2.63 (m, 2H), 2.43 (m, 4H), 2.22 (s, 3H), 2.12 (s, 3H), 1.94-1.88 (m, 2H), 1.24 (d, 6H, J=6 Hz), 1.15 (s, 6H).

Synthesis of Compound B-15: N-((4,6-dimethyl-2-oxo-1,2-dihydropyridin-3-yl)methyl)-1-(oxetan-3-yl)-6-(2,2,6,6-tetramethyl-1,2,3,6-tetrahydropyridin-4-yl)-1H-pyrazolo[3,4-b]pyridine-4-carboxamide Compound B-15

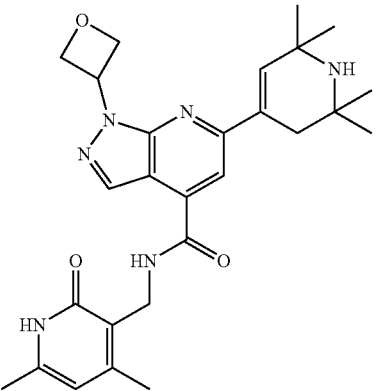

Step 1: Synthesis of ethyl 6-bromo-1-(oxetan-3-yl)-1H-pyrazolo[3,4-b]pyridine-4-carboxylate

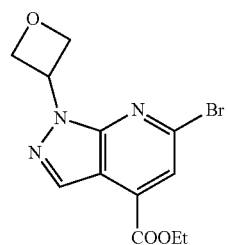 [SMILES: CCOC(=O)c1cc(Br)nc2c1cnn2C1COC1]

Ethyl 6-bromo-1H-pyrazolo[3,4-b]pyridine-4-carboxylate (1 equiv.) was suspended in acetonitrile and $K_2CO_3$ (1.5 equiv.) and 3-bromooxetane (2 equiv.) was added to it. The reaction mixture was refluxed for 8 h. On completion, acetonitrile was removed under reduced pressure and water was added to it. Extraction was carried out using ethyl acetate; the combined organic layers were washed with water, brine and dried over anhydrous $Na_2SO_4$. Solvent was removed under reduced pressure and residue was purified by silica gel column chromatography to obtain the desired intermediate.

Step 2: Synthesis of 6-bromo-N-((4,6-dimethyl-2-oxo-1,2-dihydropyridin-3-yl)methyl)-1-(oxetan-3-yl)-1H-pyrazolo[3,4-b]pyridine-4-carboxamide

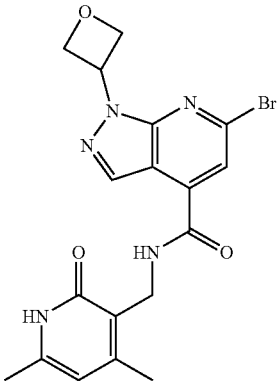 [SMILES: Cc1cc(C)c(CNC(=O)c2cc(Br)nc3c2cnn3C2COC2)c(=O)[nH]1]

Aqueous NaOH (5 equivalent) was added to a solution of ethyl 6-bromo-1-(oxetan-3-yl)-1H-pyrazolo[3,4-b]pyridine-4-carboxylate (1 equivalent) in EtOH (10 times by volume) and stirred at 60° C. for 1 h. After completion of the reaction, ethanol was removed under reduced pressure and it was acidified using 10% citric acid solution. Extraction was carried out using EtOAc; the combined organic layers were washed with water, brine and dried over anhydrous $Na_2SO_4$; filtered and concentrated under reduced pressure. The residue was, then, dissolved in DMSO (10 times by volume) and 3-(aminomethyl)-4,6-dimethylpyridin-2(1H)-one (2 equivalents) was added to it. The reaction mixture was stirred at room temperature for 15 min before PYBOP (1.5 equivalents) was added to it and stirring was continued for 5 to 16 h. After completion of the reaction, water was added to it and extraction was carried out using EtOAc. The combined organic layers were washed with water; brine; dried over anhydrous $Na_2SO_4$; filtered and concentrated under reduced pressure. The residue was purified by silica gel column chromatography followed by ether wash to provide the desired intermediate.

Step 3: Synthesis of N-((4,6-dimethyl-2-oxo-1,2-dihydropyridin-3-yl)methyl)-1-(oxetan-3-yl)-6-(2,2,6,6-tetramethyl-1,2,3,6-tetrahydropyridin-4-yl)-1H-pyrazolo[3,4-b]pyridine-4-carboxamide

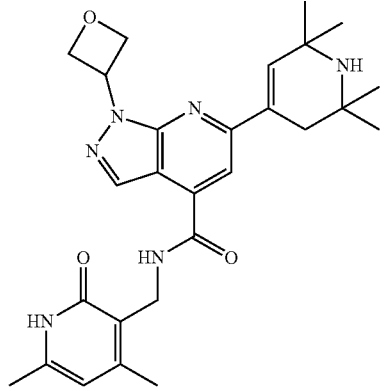

A solution of 6-bromo-N-((4,6-dimethyl-2-oxo-1,2-dihydropyridin-3-yl)methyl)-1-(oxetan-3-yl)-1H-pyrazolo[3,4-b]pyridine-4-carboxamide (1 equiv.), 2,2,6,6-tetramethyl-4-(4,4,5,5-tetramethyl-1,3,2-dioxaborolan-2-yl)-1,2,3,6-tetrahydropyridine (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) solution was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous $Na_2SO_4$, filtered and concentrated under reduced pressure to afford crude material which was purified by column chromatography to give the desired compound (44% yield). LCMS: 491.50 (M+1)$^+$; HPLC: 98.99% (@ 254 nm) (R$_t$:4.678); $^1$H NMR (DMSO-d$_6$, 400 MHz) δ 11.54 (bs, 1H), 8.93 (t, 1H), 8.43 (s, 1H), 7.83 (s, 1H), 6.84 (s, 1H), 6.21-6.14 (m, 1H), 5.89 (s, 1H), 5.08-5.02 (m, 4H), 4.38 (d, 2H, J=4.4 Hz), 2.42 (s, 2H), 2.23 (s, 3H), 2.12 (s, 3H), 1.24 (s, 6H), 1.14 (s, 6H).

Synthesis of Compound B-16:1-cyclohexyl-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide Compound B-16

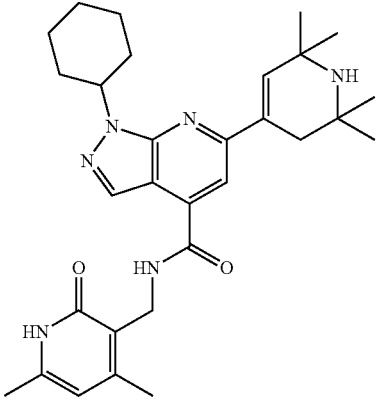

Step 1: Synthesis of ethyl 6-bromo-1-cyclohexyl-1H-pyrazolo[3,4-b]pyridine-4-carboxylate

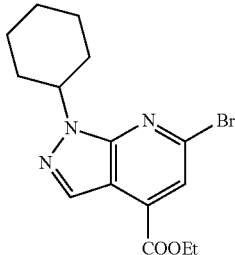 [SMILES: CCOC(=O)c1cc(Br)nc2c1cnn2C1CCCCC1]

Ethyl 6-bromo-1H-pyrazolo[3,4-b]pyridine-4-carboxylate (1 equiv.) was suspended in acetonitrile and K$_2$CO$_3$ (1.5 equiv.) and bromocyclohexane (2 equiv.) was added to it. The reaction mixture was refluxed for 8 h. On completion, acetonitrile was removed under reduced pressure and water was added to it. Extraction was carried out using ethyl acetate; the combined organic layers were washed with water, brine and dried over anhydrous $Na_2SO_4$. Solvent was removed under reduced pressure and residue was purified by silica gel column chromatography to obtain the desired intermediate.

Step 2: Synthesis of 6-bromo-1-cyclohexyl-N-((4,6-dimethyl-2-oxo-1,2-dihydropyridin-3-yl)methyl)-1H-pyrazolo[3,4-b]pyridine-4-carboxamide

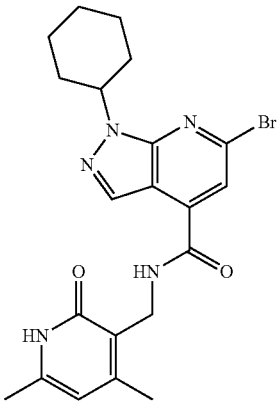 [SMILES: Cc1cc(C)c(CNC(=O)c2cc(Br)nc3c2cnn3C2CCCCC2)c(=O)[nH]1]

Aqueous NaOH (5 equivalent) was added to a solution of ethyl 6-bromo-1-cyclohexyl-1H-pyrazolo[3,4-b]pyridine-4-carboxylate (1 equivalent) in EtOH (10 times by volume) and stirred at 60° C. for 1 h. After completion of the reaction, ethanol was removed under reduced pressure and it was acidified using 10% citric acid solution. Extraction was carried out using EtOAc; the combined organic layers were washed with water, brine and dried over anhydrous Na$_2$SO$_4$; filtered and concentrated under reduced pressure. The residue was, then, dissolved in DMSO (10 times by volume) and 3-(aminomethyl)-4,6-dimethylpyridin-2(1H)-one (2 equivalents) was added to it. The reaction mixture was stirred at room temperature for 15 min before PYBOP (1.5 equivalents) was added to it and stirring was continued for 5 to 16 h. After completion of the reaction, water was added to it and extraction was carried out using EtOAc. The combined organic layers were washed with water; brine; dried over anhydrous Na$_2$SO$_4$; filtered and concentrated under reduced pressure. The residue was purified by silica gel column chromatography followed by ether wash to provide the desired intermediate.

Step 3: Synthesis of 1-cyclohexyl-N-((4,6-dimethyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide

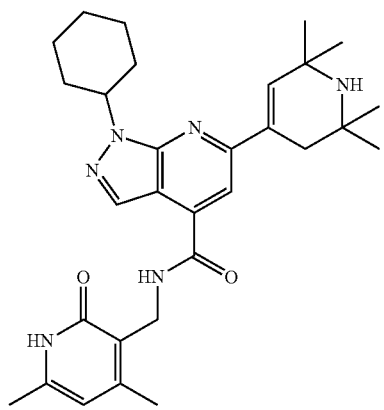

A solution of 6-bromo-1-cyclohexyl-N-((4,6-dimethyl-2-oxo-1,2-dihydropyridin-3-yl)methyl)-1H-pyrazolo[3,4-b]pyridine-4-carboxamide (1 equiv.), 2,2,6,6-tetramethyl-4-(4,4,5,5-tetramethyl-1,3,2-dioxaborolan-2-yl)-1,2,3,6-tetrahydropyridine (1.2 equiv.) and Pd(PPh$_3$)$_4$ (0.1 equiv.) in 1,4-dioxane was purged with argon for 10 min. Then, 2 M Na$_2$CO$_3$ (3.6 equiv.) solution was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the desired compound (7% yield). LCMS: 517.35 (M+1)$^+$; HPLC: 99.68% (@ 254 nm), (R$_t$: 5.761); $^1$H NMR (DMSO-d$_6$, 400 MHz) δ 11.54 (bs, 1H), 8.86 (t, 1H), 8.25 (s, 1H), 7.78 (s, 1H), 6.78 (s, 1H), 5.89 (s, 1H), 4.82-4.76 (m, 1H), 4.38 (d, 2H, J=4.8 Hz), 2.22 (s, 3H), 2.12 (s, 3H), 2.01-1.85 (m, 8H), 1.53-1.44 (m, 2H), 1.27 (bs, 6H), 1.23 (bs, 2H), 1.17 (bs, 6H).

Synthesis of Compound B-17: 6-acetyl-N-((4,6-dimethyl-2-oxo-1,2-dihydropyridin-3-yl)methyl)-1-isopropyl-1H-pyrazolo[3,4-b]pyridine-4-carboxamide Compound B-17

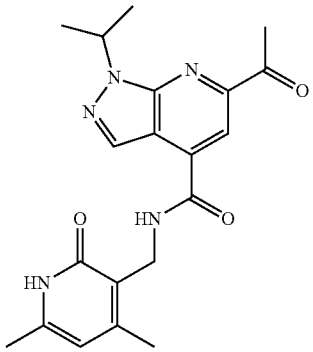

Step 1: Synthesis of N-((4,6-dimethyl-2-oxo-1,2-dihydropyridin-3-yl)methyl)-6-(1-ethoxyvinyl)-1-isopropyl-1H-pyrazolo[3,4-b]pyridine-4-carboxamide

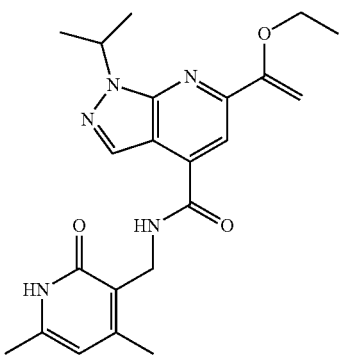 [SMILES: C=C(OCC)c1cc(C(=O)NCc2c(C)cc(C)[nH]c2=O)c2cnn(C(C)C)c2n1]

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (0.1 g, 0.24 mmol) and tributyl(1-ethoxyvinyl)stannane (0.09 mL, 0.26 mmol) in 1,4-dioxane (2 mL) was purged with argon for 10 min. Then, Pd(PPh$_3$)$_4$ (0.014 g, 0.012 mmol) was added to it and again argon was purged through it for 10 min. The reaction mixture was refluxed for 4 h. After completion of the reaction, solvent was removed under reduced pressure to afford crude material which was as such used for next step (0.12 g).

Step 2: Synthesis of 6-acetyl-N-((4,6-dimethyl-2-oxo-1,2-dihydropyridin-3-yl)methyl)-1-isopropyl-1H-pyrazolo[3,4-b]pyridine-4-carboxamide

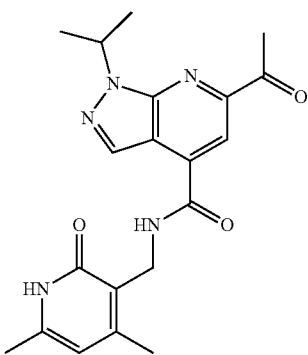 [SMILES: CC(=O)c1cc(C(=O)NCc2c(C)cc(C)[nH]c2=O)c2cnn(C(C)C)c2n1]

35% HCl (4 mL) was added to the N-((4,6-dimethyl-2-oxo-1,2-dihydropyridin-3-yl)methyl)-6-(1-ethoxyvinyl)-1-isopropyl-1H-pyrazolo[3,4-b]pyridine-4-carboxamide (0.12 g, 0.293 mmol) at 0° C. and stirred it at room temperature for 1 h. After completion of reaction, saturated NaHCO$_3$ solution was added to it and extraction was carried out by using 5% MeOH/DCM, the combined organic layers were washed with water, brine and dried over anhydrous Na$_2$SO$_4$; filtered and concentrated under reduced pressure. The residue was purified by silica gel column chromatography to provide the desired compound (90% yield). LCMS: 382.10 (M+1)$^+$; HPLC: 99.55% (@ 254 nm) (R$_t$:6.316); $^1$H NMR (DMSO-d$_6$, 400 MHz) δ 11.55 (s, 1H), 9.09 (bs, 1H), 8.48 (s, 1H), 8.14 (s, 1H), 5.89 (s, 1H), 5.35-5.29 (m, 1H), 4.36 (d, 2H, J=4.0 Hz), 2.75 (s, 3H), 2.21 (s, 3H), 2.12 (s, 3H), 1.56 (d, 6H, J=6.8 Hz).

Synthesis of Compound B-18: N4-((4,6-dimethyl-2-oxo-1,2-dihydropyridin-3-yl)methyl)-1-isopropyl-N6-methyl-1H-pyrazolo[3,4-b]pyridine-4,6-dicarboxamide Compound B-18

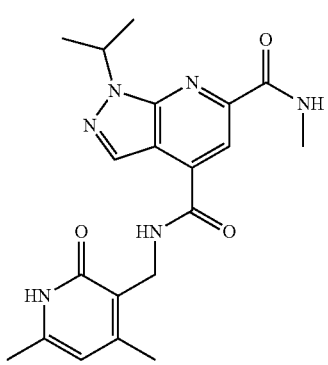

Step 1: Synthesis of N-((4,6-dimethyl-2-oxo-1,2-dihydropyridin-3-yl)methyl)-1-isopropyl-6-vinyl-1H-pyrazolo[3,4-b]pyridine-4-carboxamide

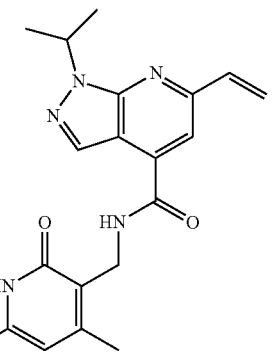

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 g, 2.39 mmol), 4,4,5,5-tetramethyl-2-vinyl-1,3,2-dioxaborolane (0.442 g, 2.87 mmol) and Pd(PPh$_3$)$_4$ (0.276 g, 0.238 mmol) in 1,4-dioxane (10 mL) was purged with argon for 10 min. Then, solution of Na$_2$CO$_3$ (0.91 g, 8.58 mmol) in water (4.3 mL) was added to it and again argon was purged through it for 10 min. The reaction mixture was stirred at 100° C. for 1 h. After completion of the reaction, water was added to it and extraction was carried out using 20% MeOH/DCM. The combined organic layers were washed with water, dried over anhydrous Na$_2$SO$_4$, filtered and concentrated under reduced pressure to afford crude material which was purified by column chromatography to give desired product (0.8 g, 91.6%).

Step 2: Synthesis of 6-(1,2-dihydroxyethyl)-N-((4,6-dimethyl-2-oxo-1,2-dihydropyridin-3-yl)methyl)-1-isopropyl-1H-pyrazolo[3,4-b]pyridine-4-carboxamide

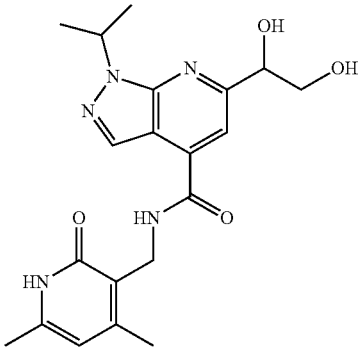 [SMILES: Cc1cc(C)c(CNC(=O)c2cc(C(O)CO)nc3c2cnn3C(C)C)c(=O)[nH]1]

To a stirred solution of N-((4,6-dimethyl-2-oxo-1,2-dihydropyridin-3-yl)methyl)-1-isopropyl-6-vinyl-1H-pyrazolo[3,4-b]pyridine-4-carboxamide (0.8 g, 2.19 mmol) in DCM (10 mL), N-Methylmorpholine-N-oxide (0.769 g, 6.57 mmol) was added at 0° C. Then OsO$_4$ (2.5% in t-BuOH) (0.139 g, 5.56 mL, 0.547 mmol) was added to it. Resulting solution was stirred at room temperature for 1 h. After completion of reaction, water was added to it and extraction was carried out using 20% MeOH/DCM. The combined organic layers were washed with water, dried over anhydrous Na$_2$SO$_4$, filtered and concentrated under reduced pressure to afford crude material which was purified by column chromatography to give the desired product (0.66 g, 75.4%).

Step 3: Synthesis of N-((4,6-dimethyl-2-oxo-1,2-dihydropyridin-3-yl)methyl)-6-formyl-1-isopropyl-1H-pyrazolo[3,4-b]pyridine-4-carboxamide

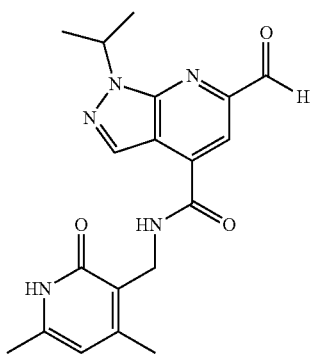 [SMILES: Cc1cc(C)c(CNC(=O)c2cc(C=O)nc3c2cnn3C(C)C)c(=O)[nH]1]

To a stirred solution of 6-(1,2-dihydroxyethyl)-N-((4,6-dimethyl-2-oxo-1,2-dihydropyridin-3-yl)methyl)-1-isopropyl-1H-pyrazolo[3,4-b]pyridine-4-carboxamide (0.66 g, 1.65 mmol) in 50% THF/Water (12 mL), NaIO$_4$ (1.06 g, 4.95 mmol) was added at 0° C. and stirred at room temperature for 1 h. After completion of reaction, solid was filtered and washed with water. Azeotrope it with toluene to obtain N-((4,6-dimethyl-2-oxo-1,2-dihydropyridin-3-yl)methyl)-6-formyl-1-isopropyl-1H-pyrazolo[3,4-b]pyridine-4-carboxamide (0.515 g, 84.8%).

Step 4: Synthesis of 4-(((4,6-dimethyl-2-oxo-1,2-dihydropyridin-3-yl)methyl)carbamoyl)-1-isopropyl-1H-pyrazolo[3,4-b]pyridine-6-carboxylic acid

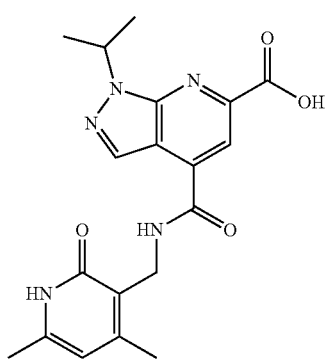 [SMILES: Cc1cc(C)c(CNC(=O)c2cc(C(=O)O)nc3c2cnn3C(C)C)c(=O)[nH]1]

To a stirred solution of N-((4,6-dimethyl-2-oxo-1,2-dihydropyridin-3-yl)methyl)-6-formyl-1-isopropyl-1H-pyrazolo[3,4-b]pyridine-4-carboxamide (0.515 g, 1.40 mmol) in DMF (3 mL), Oxone (0.861 g, 1.40 mmol) was added and stirred it at room temperature for 3 h. On completion of reaction, water was added to it and extraction was carried out using 20% MeOH/DCM. The combined organic layers were washed with water, dried over anhydrous Na$_2$SO$_4$, filtered and concentrated under reduced pressure to afford crude material which was as such used for next step.

Step 5: Synthesis of N4-((4,6-dimethyl-2-oxo-1,2-dihydropyridin-3-yl)methyl)-1-isopropyl-N6-methyl-1H-pyrazolo[3,4-b]pyridine-4,6-dicarboxamide

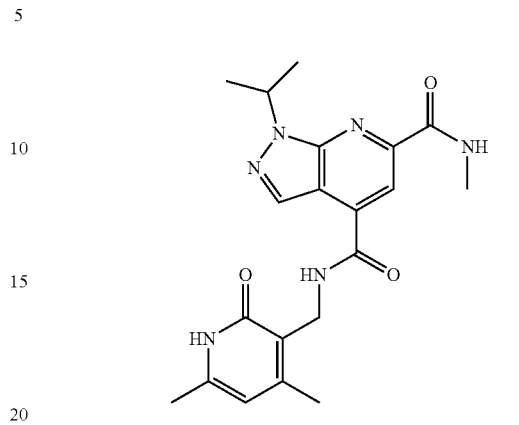

4-(((4,6-dimethyl-2-oxo-1,2-dihydropyridin-3-yl)methyl)carbamoyl)-1-isopropyl-1H-pyrazolo[3,4-b]pyridine-6-carboxylic acid (1 equiv.) was dissolved in DMSO and methylamine (2 equiv.) was added to it. The reaction mixture was stirred at room temperature for 15 min before PYBOP (1.5 equiv.) was added to it and stirring was continued overnight. After completion of the reaction, water was added to it and extraction was carried out using 20% MeOH/DCM. The combined organic layers were washed with water, dried over anhydrous Na$_2$SO$_4$, filtered and concentrated under reduced pressure to afford crude material which was purified by column chromatography/prep. HPLC to give the desired compound (8% yield). LCMS: 397.15 (M+1)$^+$; HPLC: 93.04% (@ 254 nm) (R$_t$:5.597); $^1$H NMR (DMSO-d$_6$, 400 MHz) δ 11.53 (s, 1H), 9.04 (t, 1H, J=4.4 Hz), 8.95 (d, 1H, J=4.8 Hz), 8.43 (s, 1H), 8.17 (s, 1H), 5.88 (s, 1H), 5.49-5.43 (m, 1H), 4.36 (d, 2H, J=4.8 Hz), 2.88 (d, 3H, J=4.4 Hz), 2.21 (s, 3H), 2.12 (s, 3H), 1.52 (d, 6H, J=6.8 Hz).

Synthesis of Compound B-19: N-((4,6-dimethyl-2-oxo-1,2-dihydropyridin-3-yl)methyl)-1-(1-phenylethyl)-6-(2,2,6,6-tetramethyl-1,2,3,6-tetrahydropyridin-4-yl)-1H-pyrazolo[3,4-b]pyridine-4-carboxamide

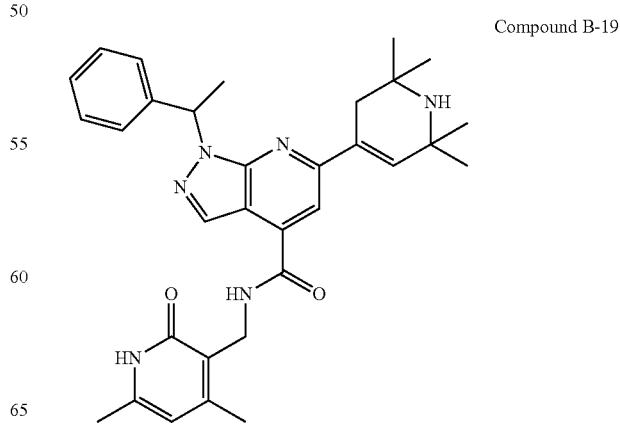

Compound B-19

Step 1: Synthesis of 6-bromo-N-((4,6-dimethyl-2-oxo-1,2-dihydropyridin-3-yl)methyl)-1H-pyrazolo[3,4-b]pyridine-4-carboxamide

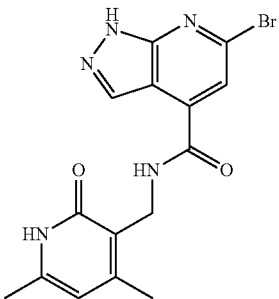 [SMILES: Cc1cc(C)c(CNC(=O)c2cc(Br)nc3[nH]ncc23)c(=O)[nH]1]

Aqueous NaOH (1.11 g, 27.88 mmol) was added to a solution of ethyl 6-bromo-1H-pyrazolo[3,4-b]pyridine-4-carboxylate (5 g, 18.6 mmol) in EtOH (50 mL) and stirred at 60° C. for 1 h. After completion of the reaction, ethanol was removed under reduced pressure and it was acidified using 10% citric acid solution. Solid obtained was filtered and dried under reduced pressure. The crude acid (4.4 g, 18.3 mmol) was then dissolved in DMSO (20 mL) and 3-(aminomethyl)-4,6-dimethylpyridin-2(1H)-one (5.55 g, 36.51 mmol) was added to it. The reaction mixture was stirred at room temperature for 15 min before PYBOP (14.24 g, 27.38 mmol) was added to it and stirring was continued overnight. After completion of the reaction, reaction mass was poured into ice to obtain solid, which was filtered and washed with acetonitrile followed by ether to provide the desired intermediate (4 g, 58.47%).

Step 2: Synthesis of 6-bromo-N-((4,6-dimethyl-2-oxo-1,2-dihydropyridin-3-yl)methyl)-1-(1-phenyl-ethyl)-1H-pyrazolo[3,4-b]pyridine-4-carboxamide

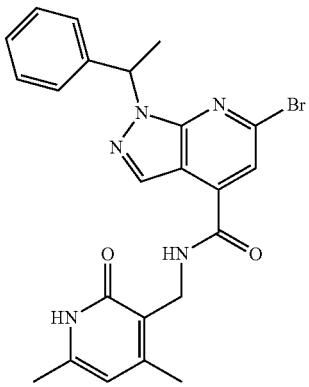 [SMILES: Cc1cc(C)c(CNC(=O)c2cc(Br)nc3c2cnn3C(C)c2ccccc2)c(=O)[nH]1]

6-Bromo-N-((4,6-dimethyl-2-oxo-1,2-dihydropyridin-3-yl)methyl)-1H-pyrazolo[3,4-b]pyridine-4-carboxamide (0.25 g, 0.66 mmol) was dissolved in DMF (3 mL) and $K_2CO_3$ (0.17 g, 0.79 mmol) and (1-bromoethyl)benzene (0.148 g, 0.799 mmol) was added to it. The reaction mixture was refluxed for overnight. On completion, water was added to it. Extraction was carried out using DCM; the combined organic layers were washed with water, brine and dried over anhydrous $Na_2SO_4$. Solvent was removed under reduced pressure and residue was purified by silica gel column chromatography to obtain the desired intermediate (0.26 g, 92.8%).

Step 3: Synthesis of N-((4,6-dimethyl-2-oxo-1,2-dihydropyridin-3-yl)methyl)-1-(1-phenyl ethyl)-6-(2,2,6,6-tetramethyl-1,2,3,6-tetrahydropyridin-4-yl)-1H-pyrazolo[3,4-b]pyridine-4-carboxamide

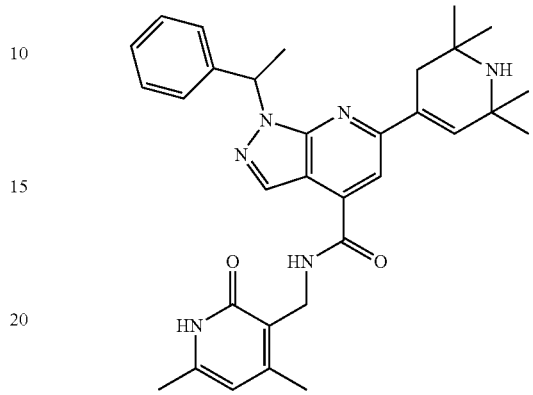

A solution of 6-bromo-N-((4,6-dimethyl-2-oxo-1,2-dihydropyridin-3-yl)methyl)-1-(1-phenylethyl)-1H-pyrazolo[3,4-b]pyridine-4-carboxamide (0.26 g, 0.54 mmol), 2,2,6,6-tetramethyl-4-(4,4,5,5-tetramethyl-1,3,2-dioxaborolan-2-yl)-1,2,3,6-tetrahydropyridine (0.172 g, 0.649 mmol) and $Pd(PPh_3)_4$ (0.062 g, 0.054 mmol) in 1,4-dioxane (3 mL) was purged with argon for 10 min. Then, 2 M $Na_2CO_3$ (0.206 g, 1.94 mmol) in water was added to it and again argon was purged through it for 10 min. The reaction mixture was stirred at 100° C. for 2 h. After completion of the reaction, water was added to it and extraction was carried out using 20% MeOH/DCM. The combined organic layers were washed with water, dried over anhydrous $Na_2SO_4$, filtered and concentrated under reduced pressure to afford crude material which was purified by prep. HPLC to give the desired compound (12% yield). LCMS 539.20 (M+1)$^+$; HPLC: 97.09% (@ 254 nm) ($R_t$:5.747); $^1H$ NMR (DMSO-$d_6$, 400 MHz) δ 11.54 (bs, 1H), 8.84 (t, 1H, J=5.2 Hz), 8.73-8.64 (m, 2H), 8.36 (s, 1H), 7.86 (s, 1H), 7.34-7.21 (m, 5H), 6.84 (s, 1H), 6.30 (q, 1H, J=6.8 Hz), 5.89 (s, 1H), 4.38 (d, 2H, J=5.2 Hz), 2.88-2.77 (m, 2H), 2.23 (s, 3H) 2.12 (s, 3H), 1.95 (d, 3H, J=7.2 Hz), 1.56 (s, 6H), 1.46 (s, 6H).

Synthesis of Compound B-20: N-((4,6-dimethyl-2-oxo-1,2-dihydropyridin-3-yl)methyl)-1-isopropyl-6-(1-(piperidine-4-carbonyl)-1,2,3,6-tetrahydropyridin-4-yl)-1H-pyrazolo[3,4-b]pyridine-4-carboxamide Compound B-20

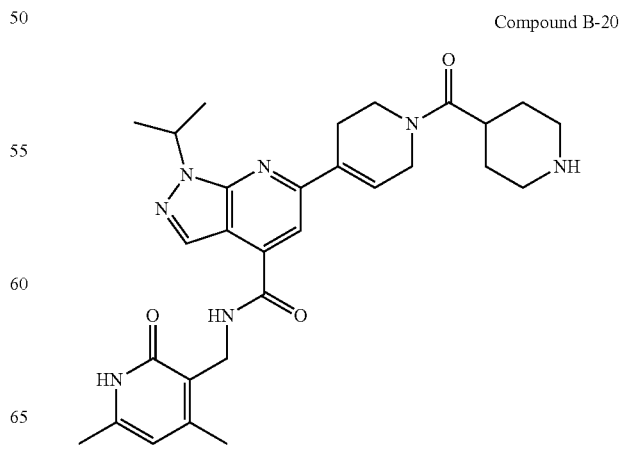

N-((4,6-Dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (1 equiv.) was dissolved in DMSO, to which Et$_3$N (3 equiv.) and 1-(tert-butoxycarbonyl)piperidine-4-carboxylic acid (2 equiv.) were added to it. The reaction mixture was stirred at room temperature for 15 min before PYBOP (1.5 equiv.) was added to it and stirring was continued overnight. After completion of the reaction, water was added to it. Extraction was carried out using DCM; the combined organic layers were washed with water, brine and dried over anhydrous Na$_2$SO$_4$; filtered and concentrated under reduced pressure to afford crude material which was taken up in purified by column chromatography. The Boc protecting group was removed using standard conditions to give the desired compound (83% yield). LCMS: 532.35 (M+1)$^+$; HPLC: 99.04% (@ 254 nm) (R$_t$;5.006); $^1$H NMR (DMSO-d$_6$, 400 MHz) δ 11.54 (bs, 1H), 8.83 (t, 1H), 8.47 (bs, 1H), 8.30 (s, 1H), 8.26 (bs, 1H), 7.86 (s, 1H), 6.92 (bs, 1H), 5.89 (s, 1H), 5.21-5.18 (m, 1H), 4.38 (d, 2H, J=4 Hz), 4.22 (bs, 2H), 3.75 (m, 2H), 3.32 (m, 3H), 2.96 (m, 2H), 2.80 (bs, 1H), 2.67 (bs, 1H), 2.20 (s, 3H), 2.12 (s, 3H), 1.84-1.73 (m, 4H), 1.51 (d, 6H, J=6.8 Hz).

Synthesis of Compound B-21:1-isopropyl-N-((4-(methoxymethyl)-6-methyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide Compound B-21

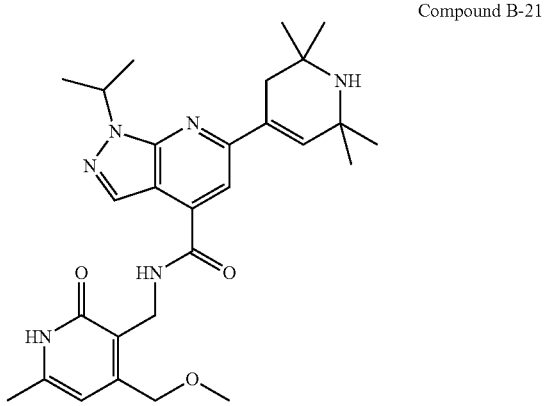

Step 1: Synthesis of 5-methoxypent-3-yn-2-one

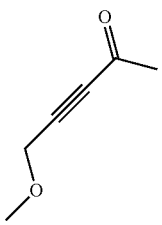

A stirred solution of 3-methoxyprop-1-yne (3 g, 42.8 mmol) in THF (60 mL) was cooled to 0° C. and n-BuLi (32 mL, 51.2 mmol, 1.6 M in hexanes) was added to it. After addition, reaction was gradually warmed to room temperature over a period of 2 h. The reaction was again cooled to −78° C. and BF$_3$OEt$_2$ (7.28 g, 51.3 mmol) was added to it. After 5 min acetic anhydride (5.72 g, 56.1 mmol) was added. The reaction was gradually warmed to room temperature over a period of 2 h. After this time, 1N NaOH was added to reaction mixture until solution become neutral. The biphasic solution was extracted with diethyl ether. Combined organic layers were dried over sodium sulfate and concentrated to obtain crude material which was purified by column over silica gel affording the desired compound (1.2 g, 24%).

Step 2: Synthesis of 4-(methoxymethyl)-6-methyl-2-oxo-1,2-dihydropyridine-3-carbonitrile

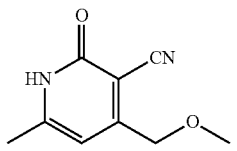

To a solution of 5-methoxypent-3-yn-2-one (1.2 g, 10.7 mmol) in 90% ethanol (22 mL), cyanoacetamide (1.08 g, 12.85 mmol) and piperidine acetate {prepared by the addition of piperidine to a solution of acetic acid (0.5 mL) in water (1 mL) till pH 8} were added and reaction heated at 90° C. for 16 h. On completion, ethanol was evaporated and water was added to residue. Solid obtained was filtered and washed with water. Then this solid was stirred with acetonitrile for 10 min and filtered again to obtain the desired intermediate (0.165 g, 8.68%).

Step 3: Synthesis of 3-(aminomethyl)-4-(methoxymethyl)-6-methylpyridin-2(1H)-one

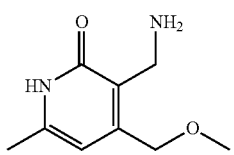

To a solution of 4-(methoxymethyl)-6-methyl-2-oxo-1,2-dihydropyridine-3-carbonitrile (0.165 g, 0.927 mmol) in methanol (10 mL), Raney Ni and ammonia (1 mL) were added and reaction stirred under hydrogen balloon pressure for 3 h. On completion, reaction mass was filtered through celite bed and filtrate concentrated to obtain the desired compound (0.13 g, 80%).

Step 4: Synthesis of 6-bromo-1-isopropyl-N-((4-(methoxymethyl)-6-methyl-2-oxo-1,2-dihydropyridin-3-yl)methyl)-1H-pyrazolo[3,4-b]pyridine-4-carboxamide

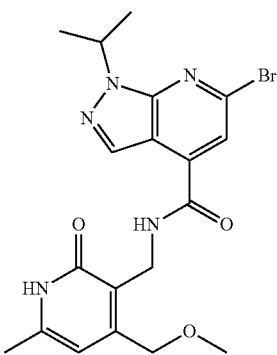 [SMILES: COCc1cc(C)[nH]c(=O)c1CNC(=O)c1cc(Br)nc2c1cnn2C(C)C]

To a solution of 6-bromo-1-isopropyl-1H-pyrazolo[3,4-b]pyridine-4-carboxylic acid (0.155 g, 0.549 mmol) in DMSO (2 mL), PyBOP (0.429 g, 0.823 mmol) was added and reaction stirred at room temperature for 15 min. Then 3-(aminomethyl)-4-(methoxymethyl)-6-methylpyridin-2(1H)-one (0.1 g, 0.549 mmol) was added and reaction stirred overnight. On completion, water was added and solid that precipitates out was filtered and washed with water to obtain the desired intermediate (0.06 g, 24.5%).

Step 5: Synthesis of 1-isopropyl-N-((4-(methoxymethyl)-6-methyl-2-oxo-1,2-dihydropyridin-3-yl)methyl)-6-(2,2,6,6-tetramethyl-1,2,3,6-tetrahydropyridin-4-yl)-1H-pyrazolo[3,4-b]pyridine-4-carboxamide

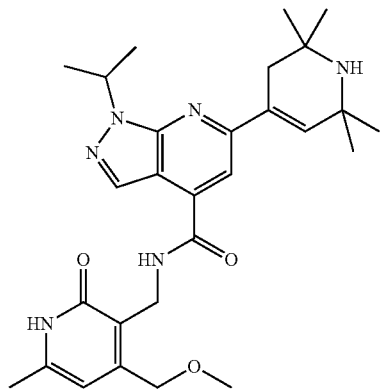

To a stirred solution of 6-bromo-1-isopropyl-N-((4-(methoxymethyl)-6-methyl-2-oxo-1,2-dihydropyridin-3-yl)methyl)-1H-pyrazolo[3,4-b]pyridine-4-carboxamide (0.06 g, 0.133 mmol) and (2,2,6,6-tetramethyl-1,2,3,6-tetrahydropyridin-4-yl)boronic acid (0.043 g, 0.160 mmol) in dioxane/water mixture (1.5 mL+0.5 mL), Na$_2$CO$_3$ (0.5 g, 0.5 mmol) was added and solution purged with argon for 15 min. Then Pd(PPh$_3$)$_4$ (0.008 g, 0.007 mmol) was added and argon was purged again for 10 min. Reaction mass was heated at 100° C. for 2 h. On completion, reaction mixture was diluted with water and extracted with 10% MeOH/DCM. Combined organic layers were dried over Na$_2$SO$_4$ and solvent removed under reduced pressure to obtain crude material which was purified by column chromatography over silica gel to afford the desired product (44% yield). LCMS: 507.25 (M+1)$^+$; HPLC: 99.64% (@ 254 nm) (R$_t$;5.159); $^1$H NMR (DMSO-d$_6$, 400 MHz) δ 11.68 (bs, 1H), 8.91 (t, 1H), 8.26 (s, 1H), 7.77 (s, 1H), 6.80 (s, 1H), 6.09 (s, 1H), 5.24-5.18 (m, 1H), 4.51 (s, 2H), 4.35 (d, 2H, J=4.4 Hz), 3.32 (3H merged in DMSO peak), 2.43 (s, 2H), 2.17 (s, 3H), 1.49 (d, 6H, J=6 Hz), 1.24 (s, 6H), 1.14 (s, 6H).

Synthesis of Compound B-22: N-((4,6-dimethyl-2-oxo-1,2-dihydropyridin-3-yl)methyl)-6-formyl-1-isopropyl-1H-pyrazolo[3,4-b]pyridine-4-carboxamide Compound B-22

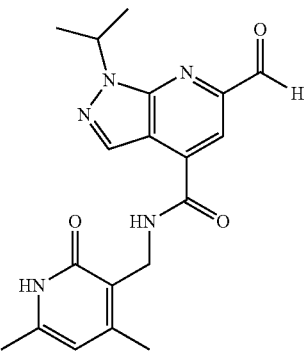

Step 1: Synthesis of N-((4,6-dimethyl-2-oxo-1,2-dihydropyridin-3-yl)methyl)-1-isopropyl-6-vinyl-1H-pyrazolo[3,4-b]pyridine-4-carboxamide A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 g, 2.39 mmol), boronic ester (0.442 g, 2.87 mmol) and Pd(PPh$_3$)$_4$ (0.276 g, 0.238 mmol) in 1,4-dioxane (10 mL) was purged with argon for 10 min. Then, solution of Na$_2$CO$_3$ (0.91 g, 8.58 mmol) in water (4.3 mL) was added to it and again argon was purged through it for 10 min. The reaction mixture was stirred at 100° C. for 1 h. After completion of the reaction, water was added to it and extraction was carried out using 20% MeOH/DCM. The combined organic layers were washed with water, dried over anhydrous Na₂SO₄, filtered and concentrated under reduced pressure to afford crude material which was purified by column chromatography to give the desired compound (0.8 g, 91.6%).

Step 2: Synthesis of 6-(1,2-dihydroxyethyl)-N-((4,6-dimethyl-2-oxo-1,2-dihydropyridin-3-yl)methyl)-1-isopropyl-1H-pyrazolo[3,4-b]pyridine-4-carboxamide

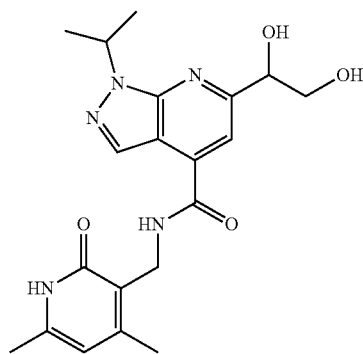 [SMILES: Cc1cc(C)c(CNC(=O)c2cc(C(O)CO)nc3c2cnn3C(C)C)c(=O)[nH]1]

To a stirred solution of N-((4,6-dimethyl-2-oxo-1,2-dihydropyridin-3-yl)methyl)-1-isopropyl-6-vinyl-1H-pyrazolo[3,4-b]pyridine-4-carboxamide (0.8 g, 2.19 mmol) in DCM (10 mL), N-Methylmorpholine-N-oxide (0.769 g, 6.57 mmol) was added at 0° C. Then 2.5% OsO₄ in t-BuOH (0.139 g, 5.56 mL, 0.547 mmol) was added to it. Resulting solution was stirred at room temperature for 1 h. After completion of reaction, water was added to it and extraction was carried out using 20% MeOH/DCM. The combined organic layers were washed with water, dried over anhydrous Na₂SO₄, filtered and concentrated under reduced pressure to afford crude material which was purified by column chromatography to give the desired compound (0.66 g, 75.4%).

Step 3: Synthesis of N-((4,6-dimethyl-2-oxo-1,2-dihydropyridin-3-yl)methyl)-6-formyl-1-isopropyl-1H-pyrazolo[3,4-b]pyridine-4-carboxamide

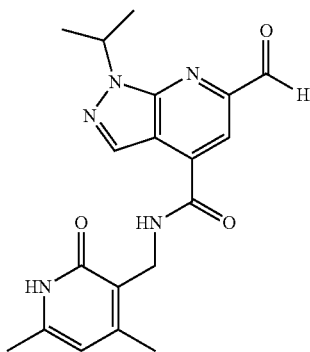 [SMILES: Cc1cc(C)c(CNC(=O)c2cc(C=O)nc3c2cnn3C(C)C)c(=O)[nH]1]

To a stirred solution of 6-(1,2-dihydroxyethyl)-N-((4,6-dimethyl-2-oxo-1,2-dihydropyridin-3-yl)methyl)-1-isopropyl-1H-pyrazolo[3,4-b]pyridine-4-carboxamide 0.66 g, 1.65 mmol) in 50% THF/Water (12 mL), NaIO₄ (1.06 g, 4.95 mmol) was added at 0° C. and stirred at room temperature for 1 h. After completion of reaction, solid was filtered and washed with water. Azeotrope with toluene to obtain the desired compound (0.515 g, 84.8%). LCMS: 368.05 (M+1)⁺; HPLC: 99.53% (@ 254 nm), (R$_t$; 5.901); ¹H NMR (DMSO-d₆, 400 MHz) δ 11.54 (s, 1H), 10.09 (s, 1H), 9.10 (bs, 1H), 8.53 (s, 1H), 8.11 (s, 1H), 5.89 (s, 1H), 5.37-5.31 (m, 1H), 4.37 (d, 2H, J=4.4 Hz), 2.21 (s, 3H), 2.12 (s, 3H), 1.55 (d, 6H, J=6.4 Hz).

Synthesis of Compound B-23: N-((4,6-dimethyl-2-oxo-1,2-dihydropyridin-3-yl)methyl)-1-isopropyl-6-(2,2,6,6-tetramethylpiperidin-4-yl)-1H-pyrazolo[3,4-b]pyridine-4-carboxamide Compound B-23

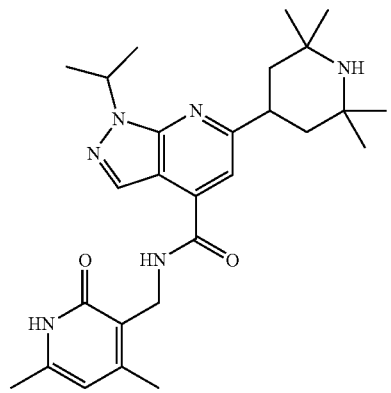

Step 1: Synthesis of N-((4,6-dimethyl-2-oxo-1,2-dihydropyridin-3-yl)methyl)-1-isopropyl-6-(2,2,6,6-tetramethyl-1,2,3,6-tetrahydropyridin-4-yl)-1H-pyrazolo[3,4-b]pyridine-4-carboxamide

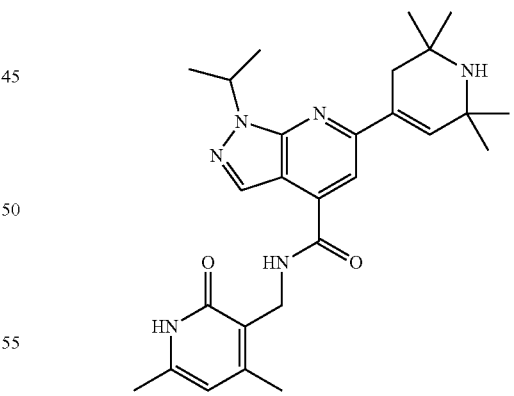

A solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv), 2,2,6,6-tetramethyl-4-(4,4,5,5-tetramethyl-1,3,2-dioxaborolan-2-yl)-1,2,3,6-tetramethylpyridine (1.2 equiv.) and Pd(PPh₃)₄ (0.1 equiv.) in 1,4-dioxane was purged with argon for 10 min. Then, 2 M Na₂CO₃ (3.6 equiv.) in water was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to give the desired intermediate.

Step 2: N-((4,6-dimethyl-2-oxo-1,2-dihydropyridin-3-yl)methyl)-1-isopropyl-6-(2,2,6,6-tetramethylpiperidin-4-yl)-1H-pyrazolo[3,4-b]pyridine-4-carboxamide

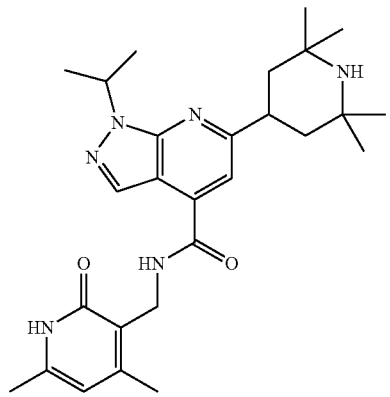

To a stirred solution of N-((4,6-dimethyl-2-oxo-1,2-dihydropyridin-3-yl)methyl)-1-isopropyl-6-(2,2,6,6-tetramethyl-1,2,3,6-tetrahydropyridin-4-yl)-1H-pyrazolo[3,4-b]pyridine-4-carboxamide (0.07 g, 0.147 mmol) in MeOH (2 mL) was added 10% Pd/C in catalytic amount and stirred it at room temperature under hydrogen pressure (bladder pressure) for 3 hr. On completion of reaction, filter it through celite bed, then filtrate was concentrated under reduce pressure. The crude material was purified by column chromatography to give the desired compound (71% yield). LCMS: 479.20 (M+1)$^+$; HPLC: 99.04% (@ 254 nm), (R$_t$; 5.075); $^1$H NMR (DMSO-d$_6$, 400 MHz) δ 11.53 (s, 1H), 8.70 (t, 1H), 8.27 (s, 1H), 7.70 (bs, 1H), 7.53 (s, 1H), 5.89 (s, 1H), 5.22-5.15 (m, 1H), 4.38 (d, 2H, J=5.2 Hz), 3.57 (m, 1H), 2.22 (s, 3H), 2.12 (s, 3H), 2.00-1.90 (m, 2H), 1.90-1.80 (m, 2H), 1.50 (s, 6H), 1.49 (s, 9H), 1.40 (s, 3H).

Synthesis of Compound B-24: N-((4,6-dimethyl-2-oxo-1,2-dihydropyridin-3-yl)methyl)-1-isopropyl-6-(piperidin-4-yl)-1H-pyrazolo[3,4-b]pyridine-4-carboxamide Compound B-24

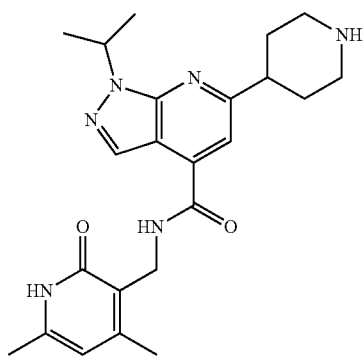

Step 1: Synthesis of ethyl 6-(1-(tert-butoxycarbonyl)-1,2,3,6-tetrahydropyridin-4-yl)-1-isopropyl-1H-pyrazolo[3,4-b]pyridine-4-carboxylate

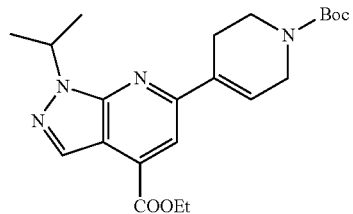 [SMILES: CCOC(=O)c1cc(C2=CCN(C(=O)OC(C)(C)C)CC2)nc2c1cnn2C(C)C]

A solution of ethyl 1-isopropyl-6-((((trifluoromethyl)sulfonyl)oxy)-1H-pyrazolo[3,4-b]pyridine-4-carboxylate (0.45 g, 1.181 mmol), boronic acid (0.4 g, 1.299 mmol) and Pd(PPh$_3$)$_4$ (0.137 g, 0.118 mmol) in 1,4-dioxane (6 mL) was purged with argon for 10 min. Then, 2 M Na$_2$CO$_3$ (0.45 g, 4.252 mmol) was added to it and again argon was purged through it for 10 min. The reaction mixture was stirred at 100° C. for 1 h. After completion of the reaction, water was added to it and extraction was carried out using EtOAc. The combined organic layers were washed with water, dried over anhydrous Na$_2$SO$_4$, filtered and concentrated under reduced pressure to afford crude material which was purified by column chromatography to give the desired compound (0.45 g, 92.0%).

Step 2: Synthesis of ethyl 6-(1-(tert-butoxycarbonyl)piperidin-4-yl)-1-isopropyl-1H-pyrazolo[3,4-b]pyridine-4-carboxylate

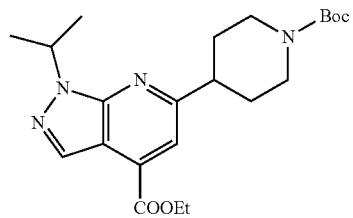 [SMILES: CCOC(=O)c1cc(C2CCN(C(=O)OC(C)(C)C)CC2)nc2c1cnn2C(C)C]

To a stirred solution of ethyl 6-(1-(tert-butoxycarbonyl)-1,2,3,6-tetrahydropyridin-4-yl)-1-isopropyl-1H-pyrazolo[3,4-b]pyridine-4-carboxylate (0.45 g, 1.086 mmol) in EtOH (10 mL), 10% Pd/C in catalytic amount was added and stirred it at room temperature under hydrogen pressure (bladder pressure) for 3 hr. On completion of reaction, reaction mass was filtered through celite bed, then filtrate was concentrated under reduce pressure to give the desired compound (0.34 g, 75%).

Step 3: Synthesis of tert-butyl 4-(4-(((4,6-dimethyl-2-oxo-1,2-dihydropyridin-3-yl)methyl)carbamoyl)-1-isopropyl-1H-pyrazolo[3,4-b]pyridin-6-yl)piperidine-1-carboxylate

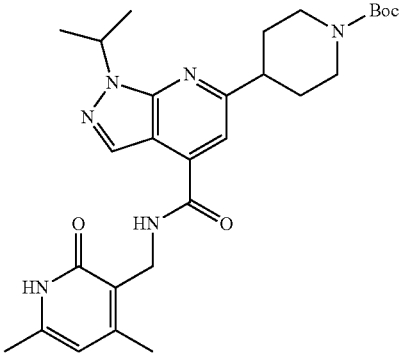 [SMILES: Cc1cc(C)c(CNC(=O)c2cc(C3CCN(C(=O)OC(C)(C)C)CC3)nc3c2cnn3C(C)C)c(=O)[nH]1]

Aqueous NaOH (0.065 g, 1.634 mmol) was added to a solution of ethyl 6-(1-(tert-butoxycarbonyl)piperidin-4-yl)-1-isopropyl-1H-pyrazolo[3,4-b]pyridine-4-carboxylate (0.34 g, 0.817 mmol) in EtOH (4 mL) and stirred at 60° C. for 1 h. After completion of the reaction, ethanol was removed under reduced pressure and it was acidified using 10% citric acid solution. Extraction was carried out using ethyl acetate; the combined organic layers were washed with water, brine and dried over anhydrous $Na_2SO_4$; filtered and concentrated under reduced pressure. The crude acid (0.3 g, 0.773 mmol) was then dissolved in DMSO (3 mL) and 3-(aminomethyl)-4,6-dimethylpyridin-2(1H)-one (0.235 g, 1.546 mmol) was added to it. The reaction mixture was stirred at room temperature for 15 min before PYBOP (0.603 g, 1.159 mmol) was added to it and stirring was continued overnight. After completion of the reaction, reaction mass was poured into ice to obtain solid, which was filtered and washed with acetonitrile followed by ether to provide the desired intermediate (0.2 g, 50.0%).

Step 4: Synthesis of N-((4,6-dimethyl-2-oxo-1,2-dihydropyridin-3-yl)methyl)-1-isopropyl-6-(piperidin-4-yl)-1H-pyrazolo[3,4-b]pyridine-4-carboxamide

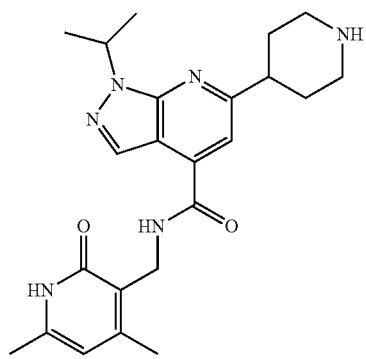 [SMILES: Cc1cc(C)c(CNC(=O)c2cc(C3CCNCC3)nc3c2cnn3C(C)C)c(=O)[nH]1]

Tert-butyl 4-(4-(((4,6-dimethyl-2-oxo-1,2-dihydropyridin-3-yl)methyl)carbamoyl)-1-isopropyl-1H-pyrazolo[3,4-b]pyridin-6-yl)piperidine-1-carboxylate (0.2 g, 0.383 mmol) was taken in DCM (3 mL), to it TFA (0.6 mL) was added at 0° C. and stirred at room temperature for 3 h. On completion of reaction, DCM was removed under reduced pressure, saturated $NaHCO_3$ solution was added to it and extraction was carried out using DCM. The combined organic layers were washed with water, dried over anhydrous $Na_2SO_4$, filtered and concentrated under reduced pressure to afford crude material which was purified by column chromatography to give the desired compound (60% yield). LCMS: 423.25 (M+1)$^+$; HPLC: 99.121% (@ 254 nm) ($R_t$; 4.628); $^1$H NMR (DMSO-d$_6$, 400 MHz) δ 8.75 (t, J=4.8 Hz, 1H); 8.26 (s, 1H); 7.49 (s, 1H); 5.89 (s, 1H); 5.22-5.16 (m, 1H); 4.36 (d, J=4.8 Hz, 2H); 3.04 (d, J=12.0 Hz, 2H); 2.84-2.92 (m, 1H); 2.60 (t, J=, 8.4 Hz, 2H); 2.20 (s, 3H); 2.10 (s, 3H); 1.65-1.81 (m, 4H); 1.49 (d, J=6.8 Hz, 6H).

Synthesis of Compound B-25: N-((4-ethyl-6-methyl-2-oxo-1,2-dihydropyridin-3-yl)methyl)-1-isopropyl-6-(2,2,6,6-tetramethyl-1,2,3,6-tetrahydropyridin-4-yl)-1H-pyrazolo[3,4-b]pyridine-4-carboxamide Compound B-25

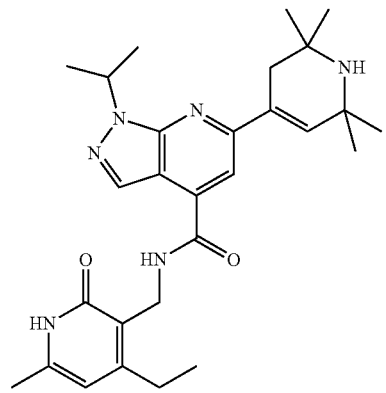

Step 1: Synthesis of 4-ethyl-2-hydroxy-6-methylnicotinonitrile

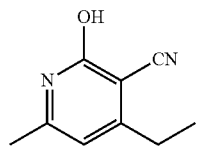

To a solution of hex-3-yn-2-one (1.5 g, 15.6 mmol) in 90% ethanol (30 mL), cyanoacetamide (1.58 g, 18.72 mmol) and piperidine acetate {prepared by the addition of piperidine to a solution of acetic acid (0.258 mL) in water (0.65 mL) till pH 8} were added and reaction heated at 90° C. for 12 h. On completion, ethanol was evaporated and water was added to residue. Solid obtained was filtered and washed with water. Then this solid was stirred with acetonitrile for 10 min and filtered again to obtain the desired intermediate (1.5 g, 60%).

Step 2: Synthesis of 3-(aminomethyl)-4-ethyl-6-methylpyridin-2-ol

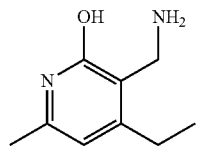

To a solution of 4-ethyl-2-hydroxy-6-methylnicotinonitrile (0.5 g, 3.08 mmol) in methanol (10 mL), Raney Ni and ammonia (1 mL) were added and reaction stirred under hydrogen balloon pressure for 3 h. On completion, reaction mass was filtered through celite bed and filtrate concentrated to obtain the desired product (0.45 g, 87.9%).

Step 3: Synthesis of 6-bromo-N-((4-ethyl-6-methyl-2-oxo-1,2-dihydropyridin-3-yl)methyl)-1-isopropyl-1H-pyrazolo[3,4-b]pyridine-4-carboxamide

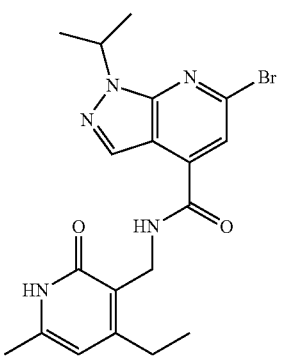 [SMILES: CCc1cc(C)[nH]c(=O)c1CNC(=O)c1cc(Br)nc2c1cnn2C(C)C]

To a solution of 6-bromo-N-((4,6-dimethyl-2-oxo-1,2-dihydropyridin-3-yl)methyl)-1-isopropyl-1H-pyrazolo[3,4-b]pyridine-4-carboxamide (1 equiv.) in DMSO (3 mL for 1 mmol), PyBOP (1.5 equiv.) was added and reaction stirred at room temperature for 15 min. Then 3-(aminomethyl)-4-ethyl-6-methylpyridin-2(1H)-one (2 equiv.) was added and reaction stirred overnight. On completion, water was added and solid that precipitates out was filtered and washed with water. Then this solid was stirred with acetonitrile for 10 min and filtered again to obtain the desired intermediate.

Step 4: Synthesis of N-((4-ethyl-6-methyl-2-oxo-1,2-dihydropyridin-3-yl)methyl)-1-isopropyl-6-(2,2,6,6-tetramethyl-1,2,3,6-tetrahydropyridin-4-yl)-1H-pyrazolo[3,4-b]pyridine-4-carboxamide

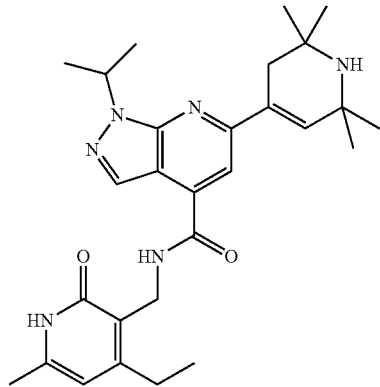

To a stirred solution of 6-bromo-N-((4-ethyl-6-methyl-2-oxo-1,2-dihydropyridin-3-yl)methyl)-1-isopropyl-1H-pyrazolo[3,4-b]pyridine-4-carboxamide (0.37 g, 0.85 mmol) and 2,2,6,6-tetramethyl-4-(4,4,5,5-tetramethyl-1,3,2-dioxaborolan-2-yl)-1,2,3,6-tetrahydropyridine (1.2 equiv.) in dioxane/water mixture (3 mL+1 mL for 1 mmol), Na$_2$CO$_3$ (3.6 equiv.) was added and solution purged with argon for 15 min. Then Pd(PPh$_3$)$_4$ (0.05 equiv.) was added and argon was purged again for 10 min. Reaction mass was heated at 100° C. for 2 h. On completion, reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford the desired compound. (38% yield). LCMS: 491.25 (M+1)$^+$; HPLC: 95.01% (@ 254 nm) (R$_t$:5.463); $^1$H NMR (DMSO-d$_6$, 400 MHz) δ 11.55 (s, 1H), 8.87 (s, 1H), 8.26 (s, 1H), 7.79 (s, 1H), 6.80 (s, 1H), 5.91 (s, 1H), 5.22-5.19 (m, 1H), 4.39 (d, 2H, J=4.0 Hz), 2.42-2.40 (m, 4H), 2.24 (s, 3H), 1.49 (d, 6H, J=6 Hz). 1.24 (s, 6H), 1.14 (s, 6H), 1.11 (m, 3H).

Synthesis of Compound B-26: N-((4,6-dimethyl-2-oxo-1,2-dihydropyridin-3-yl)methyl)-3-ethyl-1-isopropyl-6-(2,2,6,6-tetramethyl-1,2,3,6-tetrahydropyridin-4-yl)-1H-pyrazolo[3,4-b]pyridine-4-carboxamide

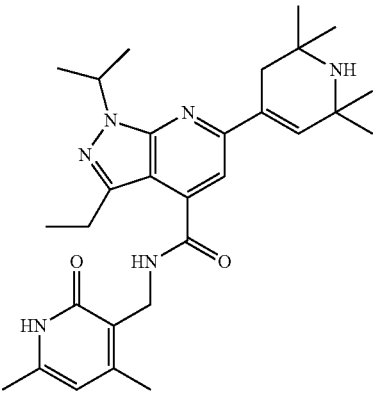

Compound B-26

Step 1: Synthesis of ethyl 3-ethyl-6-hydroxy-1H-pyrazolo[3,4-b]pyridine-4-carboxylate

A stirred solution of 5-ethyl-1H-pyrazol-3-amine (1 g, 9.00 mmol) in acetic acid (6.6 mL) and water (20 mL) was cooled to 0° C. and diethyl oxaloacetate sodium salt (1.88 g, 9.00 mmol) was added to it. Resulting solution was heated at 100° C. for overnight. After completion of the reaction, the solid was filtered and dried to obtain the desired intermediate (0.52 g, 24.6%).

Step 2: Synthesis of ethyl 6-bromo-3-ethyl-1H-pyrazolo[3,4-b]pyridine-4-carboxylate

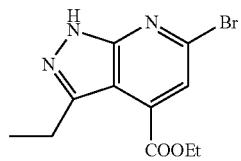 [SMILES: CCOC(=O)c1cc(Br)nc2[nH]nc(CC)c12]

Ethyl 3-ethyl-6-hydroxy-1H-pyrazolo[3,4-b]pyridine-4-carboxylate (0.52 g, 2.21 mmol) was suspended in acetonitrile (6 mL) and POBr₃ (1.27 g, 4.42 mmol) was added to it. The reaction mixture was refluxed for 6 h. On completion of reaction, acetonitrile was removed under reduced pressure and residue neutralized with saturated NaHCO₃. Extraction was carried out using EtOAc; the combined organic layers were washed with water, brine and dried over anhydrous Na₂SO₄; filtered and concentrated under reduced pressure. The residue was purified by silica gel column chromatography to provide the desired intermediate (0.45 g, 68.5%).

Step 3: Synthesis of ethyl 6-bromo-3-ethyl-1-isopropyl-1H-pyrazolo[3,4-b]pyridine-4-carboxylate

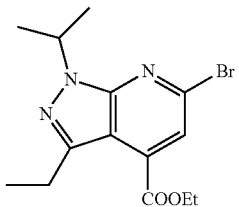 [SMILES: CCOC(=O)c1cc(Br)nc2c1c(CC)nn2C(C)C]

Ethyl 6-bromo-3-ethyl-1H-pyrazolo[3,4-b]pyridine-4-carboxylate (0.45 g, 1.51 mmol) was suspended in acetonitrile (5 mL) and K₂CO₃ (0.312 g, 2.26 mmol) and 2-bromopropane (0.372 g, 3.02 mmol) was added to it. The reaction mixture was refluxed for overnight. On completion of reaction, acetonitrile was removed under reduced pressure and water was added to it. Extraction was carried out using ethyl acetate; the combined organic layers were washed with water, brine and dried over anhydrous Na₂SO₄. Solvent was removed under reduced pressure and residue was purified by silica gel column chromatography to give the desired intermediate (0.4 g, 87.7%).

Step 4: Synthesis of 6-bromo-3-ethyl-1-isopropyl-1H-pyrazolo[3,4-b]pyridine-4-carboxylic acid

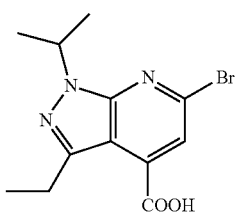 [SMILES: CCc1nn(C(C)C)c2nc(Br)cc(C(=O)O)c12]

To a solution of ethyl 6-bromo-3-ethyl-1-isopropyl-1H-pyrazolo[3,4-b]pyridine-4-carboxylate (0.4 g, 1.176 mmol) in EtOH (7 mL), aqueous NaOH (0.062 g, 1.529 mmol in 1 mL water) was added and reaction mixture stirred at 60° C. for 1 h. After completion of the reaction, ethanol was removed under reduced pressure and it was acidified using 2N HCl and 10% citric acid solution. Solid obtained was filtered and azeotrope it with toluene to give the desired compound (0.3 g, 81.7%).

Step 5: Synthesis of 6-bromo-N-((4,6-dimethyl-2-oxo-1,2-dihydropyridin-3-yl)methyl)-3-ethyl-1-isopropyl-1H-pyrazolo[3,4-b]pyridine-4-carboxamide

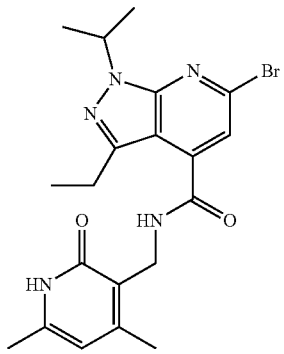 [SMILES: CCc1nn(C(C)C)c2nc(Br)cc(C(=O)NCc3c(C)cc(C)[nH]c3=O)c12]

A solution of 6-bromo-3-ethyl-1-isopropyl-1H-pyrazolo[3,4-b]pyridine-4-carboxylic acid (0.3 g, 0.901 mmol) and 3-(aminomethyl)-4,6-dimethylpyridin-2(1H)-one (0.292 g, 1.92 mmol) in DMSO (4 mL) and was stirred at room temperature for 15 min. Then PyBOP (0.75 g, 1.44 mmol) was added to it and stirring was continued for 12 hr. After completion of the reaction, reaction mass was poured into ice to obtain solid, which was filtered and washed with acetonitrile followed by ether to provide the desired intermediate (0.35 g, 81.6%).

Step 6: Synthesis of N-((4,6-dimethyl-2-oxo-1,2-dihydropyridin-3-yl)methyl)-3-ethyl-1-isopropyl-6-(2,2,6,6-tetramethyl-1,2,3,6-tetrahydropyridin-4-yl)-1H-pyrazolo[3,4-b]pyridine-4-carboxamide

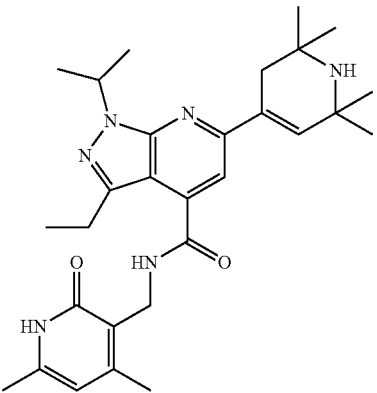

A solution of 6-bromo-N-((4,6-dimethyl-2-oxo-1,2-dihydropyridin-3-yl)methyl)-3-ethyl-1-isopropyl-1H-pyrazolo[3,4-b]pyridine-4-carboxamide (0.15 g, 0.336 mmol), 2,2,6,6-tetramethyl-4-(4,4,5,5-tetramethyl-1,3,2-dioxaborolan-2-yl)-1,2,3,6-tetrahydropyridine (0.106 g, 0.403 mmol) and Pd(PPh₃)₄ (0.020 g, 0.017 mmol) in 1,4-dioxane (3 mL) was purged with argon for 10 min. Then, 2M Na₂CO₃ solution (0.128 g, 1.21 mmol) was added to it and again argon was purged through it for 10 min. The reaction mixture was stirred at 100° C. for 1 h. After completion of the reaction, water was added to it and extraction was carried out using 10% MeOH/DCM. The combined organic layers were washed with water, dried over anhydrous Na$_2$SO$_4$, filtered and concentrated under reduced pressure to afford crude material which was purified by column chromatography to give the desired compound (59% yield). LCMS: 505.30 (M+1)$^+$; HPLC: 99.84% (@ 254 nm) (R$_t$:5.386); $^1$H NMR (DMSO-d$_6$, 400 MHz) δ 11.49 (s, 1H), 8.68 (t, 1H), 7.32 (s, 1H), 6.72 (s, 1H), 5.88 (s, 1H), 5.17-5.10 (m, 1H), 4.33 (d, 2H, J=4.4 Hz), 2.84-2.79 (q, 2H, J=7.6 Hz), 2.39 (s, 2H), 2.25 (s, 3H), 2.11 (s, 3H), 1.46 (d, 6H, J=6.8 Hz), 1.22 (s, 6H), 1.13 (s, 6H), 1.06 (t, 3H, J=7.6 Hz).

Synthesis of Compound B-27: N-((4,6-dimethyl-2-oxo-1,2-dihydropyridin-3-yl)methyl)-1-isopropyl-6-(1-(methylsulfonyl)piperidin-4-yl)-1H-pyrazolo[3,4-b]pyridine-4-carboxamide

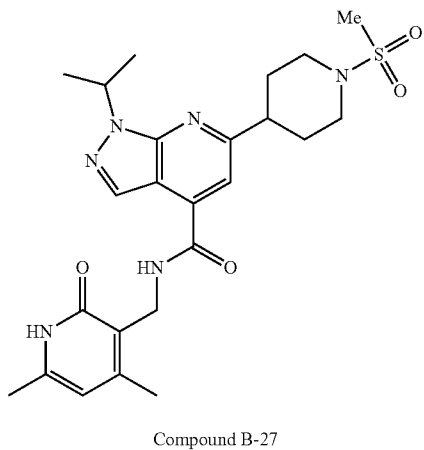 [SMILES: Cc1cc(C)c(CNC(=O)c2cc(C3CCN(S(C)(=O)=O)CC3)nc3c2cnn3C(C)C)c(=O)[nH]1]

Compound B-27

Step 1: Synthesis of N-((4,6-dimethyl-2-oxo-1,2-dihydropyridin-3-yl)methyl)-1-isopropyl-6-(1-(methylsulfonyl)-1,2,3,6-tetrahydropyridin-4-yl)-1H-pyrazolo[3,4-b]pyridine-4-carboxamide

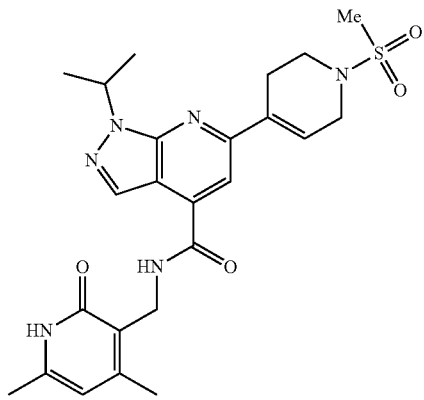 [SMILES: Cc1cc(C)c(CNC(=O)c2cc(C3=CCN(S(C)(=O)=O)CC3)nc3c2cnn3C(C)C)c(=O)[nH]1]

To a stirred solution of N-((4,6-dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (0.2 g, 0.476 mmol) in pyridine (1.5 mL), mesyl chloride (0.081 g, 0.714 mmol) was added at 0° C. and stirred it at room temperature for 1 h. After completion of reaction, solvent was removed under reduced pressure and water was added to it. Extraction was carried out using DCM; the combined organic layers were washed with water, brine and dried over anhydrous Na$_2$SO$_4$; filtered and concentrated under reduced pressure to afford crude material which was purified by column chromatography to give the desired compound. LCMS: 499.20 (M+1)$^+$; HPLC: 98.22% (@ 254 nm) (R$_t$:6.278); $^1$H NMR (DMSO-d$_6$, 400 MHz) δ 11.55 (s, 1H), 8.85 (t, 1H), 8.31 (s, 1H), 7.86 (s, 1H), 6.94 (s, 1H), 5.89 (s, 1H), 5.22 (m, 1H), 4.38 (d, 2H, J=4.8 Hz), 3.98 (m, 2H), 3.42 (t, 2H, J=5.6 Hz), 2.96 (s, 3H), 2.84 (m, 2H), 2.21 (s, 3H), 2.13 (s, 3H), 1.50 (d, 6H, J=6.8 Hz).

Step 2: Synthesis of N-((4,6-dimethyl-2-oxo-1,2-dihydropyridin-3-yl)methyl)-1-isopropyl-6-(1-(methylsulfonyl)piperidin-4-yl)-1H-pyrazolo[3,4-b]pyridine-4-carboxamide

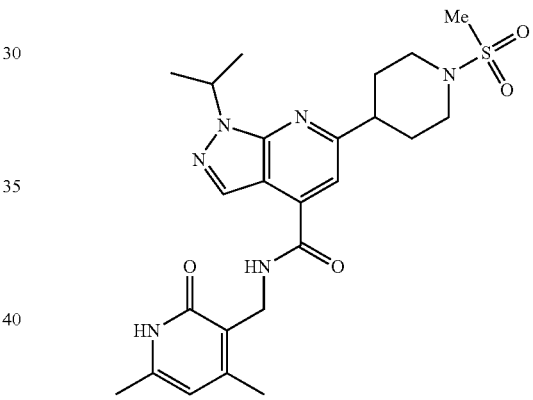

To a stirred solution of N-((4,6-dimethyl-2-oxo-1,2-dihydropyridin-3-yl)methyl)-1-isopropyl-6-(1-(methylsulfonyl)-1,2,3,6-tetrahydropyridin-4-yl)-1H-pyrazolo[3,4-b]pyridine-4-carboxamide (0.08 g, 0.16 mmol) in EtOH (2 mL), 10% Pd/C in catalytic amount was added and stirred it at room temperature under hydrogen pressure (balloon pressure) for 3-4 hr. On completion of reaction, reaction mass was filtered through celite bed, then filtrate was concentrated under reduce pressure, finally the residue was washed with diethyl ether to provide the desired compound (12% yield). LCMS: 501.15 (M+1)$^+$; HPLC: 94.05% (@ 254 nm) (R$_t$; 6.087); $^1$H NMR (DMSO-d$_6$, 400 MHz) δ 11.55 (s, 1H), 8.77 (t, 1H, J=4.8 Hz), 8.29 (s, 1H), 7.56 (s, 1H), 5.89 (s, 1H), 5.21-5.17 (m, 1H), 4.37 (d, 2H, J=4.4 Hz), 3.69 (m, 2H), 3.01-2.96 (m, 1H), 2.91 (s, 3H), 2.87-2.84 (m, 2H), 2.20 (s, 3H), 2.12 (s, 3H), 2.08-1.99 (m, 2H), 1.93-1.83 (m, 2H), 1.49 (d, 6H, J=6.8 Hz).

363

Synthesis of Compound B-28: N-((4,6-dimethyl-2-oxo-1,2-dihydropyridin-3-yl)methyl)-1-isopropyl-6-(1-(piperidine-3-carbonyl)-1,2,3,6-tetrahydropyridin-4-yl)-1H-pyrazolo[3,4-b]pyridine-4-carboxamide

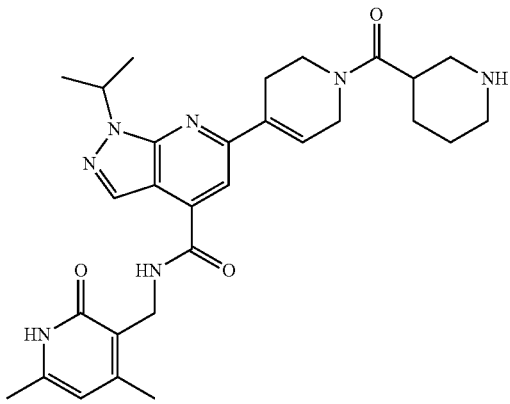

Compound B-28

N-((4,6-Dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (1 equiv.) was dissolved in DMSO, to it Et$_3$N (3 equiv.) and piperidine-3-carboxylic acid (2 equiv.) was added to it. The reaction mixture was stirred at room temperature for 15 min before PYBOP (1.5 equiv.) was added to it and stirring was continued overnight. After completion of the reaction, water was added to it. Extraction was carried out using DCM; the combined organic layers were washed with water, brine and dried over anhydrous Na$_2$SO$_4$; filtered and concentrated under reduced pressure to afford crude material which was purified by column chromatography to give the desired compound (85% yield). LCMS: 532.35 (M+1)$^+$; HPLC: 99.84% (@ 254 nm) (R$_t$;5.059); $^1$H NMR (DMSO-d$_6$, 400 MHz) δ 11.55 (bs, 1H), 8.83 (t, 1H), 8.44 (bs, 2H), 8.30 (s, 1H), 7.86 (s, 1H), 6.92 (bs, 1H), 5.89 (s, 1H), 5.21-5.18 (m, 1H), 4.38 (d, 2H, J=4.4 Hz), 4.31 (bs, 1H), 4.23 (bs, 1H), 3.74 (m, 2H), 3.14 (m, 4H), 2.97 (m, 1H), 2.82 (m, 1H), 2.70 (m, 1H), 2.20 (s, 3H), 2.12 (s, 3H), 1.89 (m, 1H), 1.74 (m, 2H), 1.60 (m, 1H), 1.51 (d, 6H, J=6.4 Hz).

Synthesis of Compound B-29: of 6-([1,4'-bipiperidin]-4-yl)-N-((4,6-dimethyl-2-oxo-1,2-dihydropyridin-3-yl)methyl)-1-isopropyl-1H-pyrazolo[3,4-b]pyridine-4-carboxamide

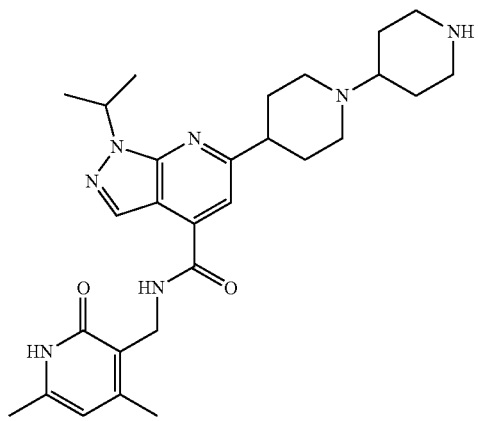

Compound B-29

364

Step 1: Synthesis of tert-butyl 4-(4-(4-(((4,6-dimethyl-2-oxo-1,2-dihydropyridin-3-yl)methyl)carbamoyl)-1-isopropyl-1H-pyrazolo[3,4-b]pyridin-6-yl)-5,6-dihydropyridin-1(2H)-yl)piperidine-1-carboxylate

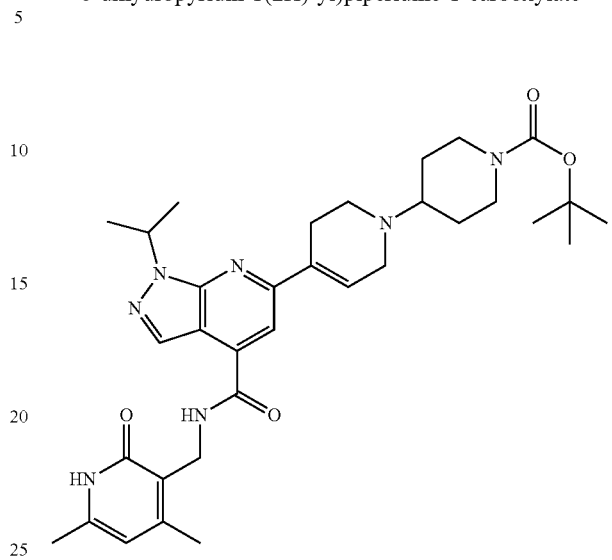

To a stirred solution of N-((4,6-dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (1 g, 2.38 mmol) in methanol (15 mL) was added tert-butyl 4-oxopiperidine-1-carboxylate (1.18 g, 5.95 mmol) and acetic acid (0.17 g, 2.85 mmol) stirred it at room temperature for 2 days. Then NaBH$_3$CN (0.224 g, 3.57 mmol) was added to it resulting reaction mixture was stirred at room temperature for 8 h. After completion of reaction, solvent was removed under reduced pressure and water was added to it. Extraction was carried out using ethyl acetate. The combined organic layers were washed with water, dried over anhydrous Na$_2$SO$_4$, filtered and concentrated under reduced pressure to afford crude material which was purified by column chromatography to give the desired compound (0.5 g, 34.5%).

Step 2: Synthesis of N-((4,6-dimethyl-2-oxo-1,2-dihydropyridin-3-yl)methyl)-1-isopropyl-6-(1-(piperidin-4-yl)-1,2,3,6-tetrahydropyridin-4-yl)-1H-pyrazolo[3,4-b]pyridine-4-carboxamide

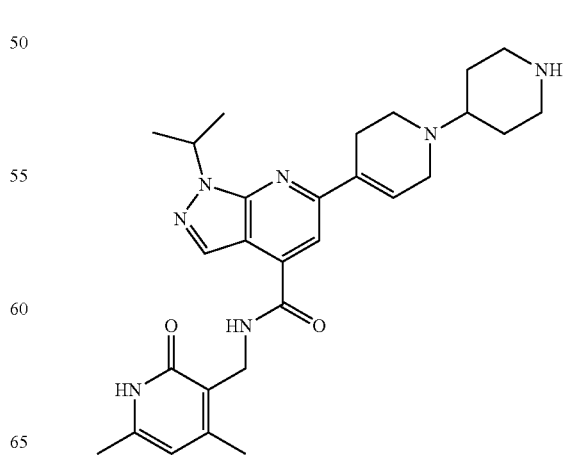

Tert-butyl 4-(4-(4-(((4,6-dimethyl-2-oxo-1,2-dihydropyridin-3-yl)methyl)carbamoyl)-1-isopropyl-1H-pyrazolo[3,4-b]pyridin-6-yl)-5,6-dihydropyridin-1(2H)-yl)piperidine-1-carboxylate (0.5 g, 0.829 mmol) was taken in DCM (6 mL), TFA (2 mL) was added and stirred at room temperature for 1 h. After completion of reaction, solvent was removed under reduced pressure, neutralized with saturated NaHCO$_3$ solution. Extraction was carried out using DCM; the combined organic layers were washed with water, brine and dried over anhydrous Na$_2$SO$_4$; filtered and concentrated under reduced pressure, finally the residue was washed with acetonitrile followed by diethyl ether to provide the desired compound. LCMS: 504.35 (M+1)$^+$; HPLC: 99.26% (@ 254 nm) (R$_t$:4.223); $^1$H NMR (DMSO-d$_6$, 400 MHz) δ 11.56 (bs, 1H), 10.25 (bs, 1H), 8.87 (t, 1H, J=4.8 Hz), 8.80 (bs, 1H), 8.55 (bs, 1H), 8.34 (s, 1H), 7.89 (s, 1H), 6.93 (bs, 1H), 5.90 (s, 1H), 5.21 (m, 1H), 4.39 (d, 2H, J=4.8 Hz), 4.08 (bs, 2H), 3.75 (bs, 2H), 3.30 (m, 3H), 3.16-3.12 (m, 1H), 2.96 (m, 3H), 2.32 (m, 2H), 2.21 (s, 3H), 2.12 (s, 3H), 1.86 (m, 2H), 1.52 (d, 6H, J=6.8 Hz).

Step 3: Synthesis of 6-([1,4'-bipiperidin]-4-yl)-N-((4,6-dimethyl-2-oxo-1,2-dihydropyridin-3-yl)methyl)-1-isopropyl-1H-pyrazolo[3,4-b]pyridine-4-carboxamide

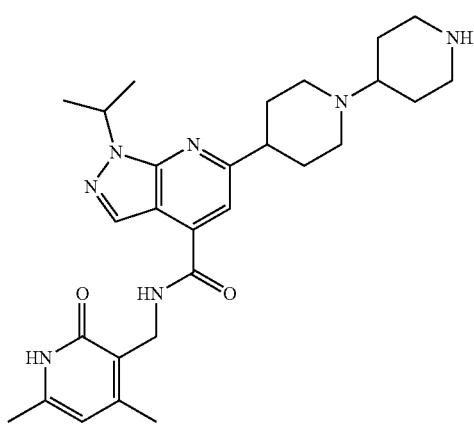 [SMILES: Cc1cc(C)c(CNC(=O)c2cc(C3CCN(C4CCNCC4)CC3)nc3c2cnn3C(C)C)c(=O)[nH]1]

To a stirred solution of N-((4,6-dimethyl-2-oxo-1,2-dihydropyridin-3-yl)methyl)-1-isopropyl-6-(1-(piperidin-4-yl)-1,2,3,6-tetrahydropyridin-4-yl)-1H-pyrazolo[3,4-b]pyridine-4-carboxamide (0.08 g, 0.159 mmol) in EtOH (2 mL), 10% Pd/C in catalytic amount was added and stirred it at room temperature under hydrogen pressure (balloon pressure) for 3-4 hr. On completion of reaction, reaction mass was filtered through celite bed, then filtrate was concentrated under reduce pressure, finally the residue was washed with diethyl ether to provide the desired compound (62% yield). LCMS: 506.40 (M+1)$^+$; HPLC: 90.48% (@ 254 nm) (R$_t$; 4.196); $^1$H NMR (DMSO-d$_6$, 400 MHz) δ 11.55 (bs, 1H), 9.79 (bs, 1H), 8.76 (t, 1H), 8.58 (bs, 1H), 8.27 (s, 1H), 7.47 (s, 1H), 5.90 (s, 1H), 5.17 (m, 1H), 4.37 (d, 2H, J=4.4 Hz), 3.60 (bs, 2H), 3.45 (bs, 2H), 3.16 (m, 4H), 2.95 (m, 4H), 2.21 (s, 3H), 2.12 (s, 3H), 2.25-2.05 (m, 4H), 1.85 (m, 2H), 1.50 (d, 6H, J=6.4 Hz).

Synthesis of Compound B-30: 6-(1-(azetidine-3-carbonyl)-1,2,3,6-tetrahydropyridin-4-yl)-N-((4,6-dimethyl-2-oxo-1,2-dihydropyridin-3-yl)methyl)-1-isopropyl-1H-pyrazolo[3,4-b]pyridine-4-carboxamide Compound B-30

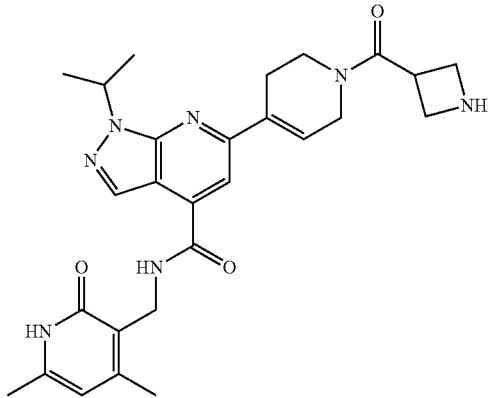

N-((4,6-Dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (1 equiv.) was dissolved in DMSO, to it Et$_3$N (3 equiv.) and azetidine-3-carboxylic acid (2 equiv.) was added to it. The reaction mixture was stirred at room temperature for 15 min before PYBOP (1.5 equiv.) was added to it and stirring was continued overnight. After completion of the reaction, water was added to it. Extraction was carried out using DCM; the combined organic layers were washed with water, brine and dried over anhydrous Na$_2$SO$_4$; filtered and concentrated under reduced pressure to afford crude material which was purified by column chromatography to give the desired compound (81.9% yield). LCMS: 504.25 (M+1)$^+$; HPLC: 99.74% (@ 254 nm) (R$_t$:4.829); $^1$H NMR (DMSO-d$_6$, 400 MHz) δ 11.55 (bs, 1H), 8.84 (m, 2H), 8.64 (bs, 1H), 8.30 (s, 1H), 7.86 (s, 1H), 6.93 (s, 1H), 5.89 (s, 1H), 5.22-5.17 (m, 1H), 4.38 (d, 2H, J=4.8 Hz), 4.26 (bs, 1H), 4.20-4.10 (m, 4H), 4.05-3.97 (m, 1H), 3.75 (t, 1H, J=5.2 Hz), 3.49 (m, 2H), 2.74 (m, 2H), 2.20 (s, 3H), 2.12 (s, 3H), 1.51 (d, 6H, J=6.4 Hz).

Synthesis of Compound B-31: N-((4,6-dimethyl-2-oxo-1,2-dihydropyridin-3-yl)methyl)-1-isopropyl-6-(1-(1-methylpyrrolidine-3-carbonyl)-1,2,3,6-tetrahydropyridin-4-yl)-1H-pyrazolo[3,4-b]pyridine-4-carboxamide Compound B-31

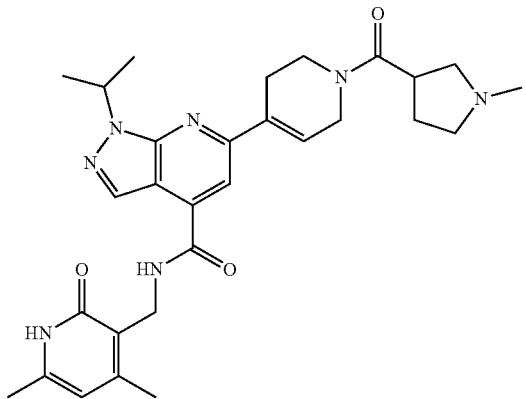

Step 1: Synthesis of N-((4,6-dimethyl-2-oxo-1,2-dihydropyridin-3-yl)methyl)-1-isopropyl-6-(1-(pyrrolidine-3-carbonyl)-1,2,3,6-tetrahydropyridin-4-yl)-1H-pyrazolo[3,4-b]pyridine-4-carboxamide

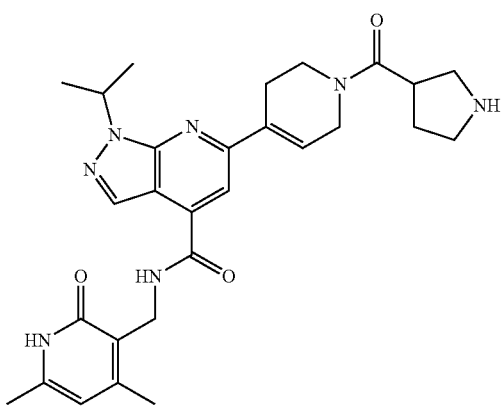 [SMILES: Cc1cc(C)c(CNC(=O)c2cc(C3=CCN(C(=O)C4CCNC4)CC3)nc3c2cnn3C(C)C)c(=O)[nH]1]

N-((4,6-Dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (1 equiv.) was dissolved in DMSO, to it $Et_3N$ (3 equiv.) and pyrrolidine-3-carboxylic acid (2 equiv.) was added to it. The reaction mixture was stirred at room temperature for 15 min before PYBOP (1.5 equiv.) was added to it and stirring was continued overnight. After completion of the reaction, water was added to it. Extraction was carried out using DCM; the combined organic layers were washed with water, brine and dried over anhydrous $Na_2SO_4$; filtered and concentrated under reduced pressure to afford crude material which was purified by column chromatography to give the desired compound.

Step 2: Synthesis of N-((4,6-dimethyl-2-oxo-1,2-dihydropyridin-3-yl)methyl)-1-isopropyl-6-(1-(1-methylpyrrolidine-3-carbonyl)-1,2,3,6-tetrahydropyridin-4-yl)-1H-pyrazolo[3,4-b]pyridine-4-carboxamide

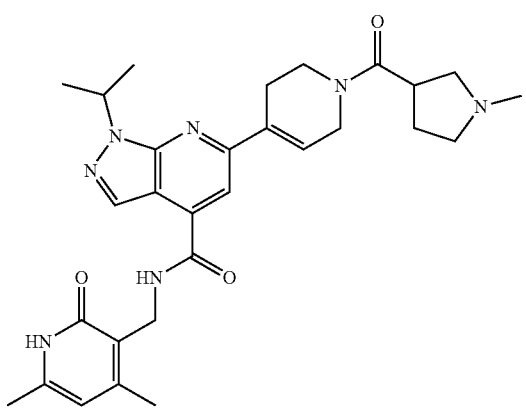

To a stirred solution of N-((4,6-dimethyl-2-oxo-1,2-dihydropyridin-3-yl)methyl)-1-isopropyl-6-(1-(pyrrolidine-3-carbonyl)-1,2,3,6-tetrahydropyridin-4-yl)-1H-pyrazolo[3,4-b]pyridine-4-carboxamide (1 equiv.) in methanol was added formalin (5 equiv.) stirred it at room temperature for 10 min. Then $NaBH_3CN$ (1 equiv.) was added to it Resulting reaction mixture was stirred at room temperature for 1 h. After completion of reaction, solvent was removed under reduced pressure and water was added to it. Extraction was carried out using 10% MeOH/DCM. The combined organic layers were washed with water, dried over anhydrous $Na_2SO_4$, filtered and concentrated under reduced pressure to afford crude material which was purified by column chromatography to give the desired compound (30% yield). LCMS: 532.35 $(M+1)^+$; HPLC: 89.75% (@ 254 nm) $(R_t;7.188)$; $^1H$ NMR (DMSO-$d_6$, 400 MHz) δ 11.55 (s, 1H), 8.84 (bs, 1H), 8.30 (s, 1H), 7.84 (d, 1H, J=10 Hz), 6.91 (bs, 1H), 5.89 (s, 1H), 5.21 (m, 1H), 4.38 (d, 2H, J=4.4 Hz), 4.29 (bs, 1H), 4.21 (bs, 1H), 3.70 (bs, 2H), 2.76 (m, 2H), 2.66 (bs, 1H), 2.43 (m, 1H), 2.32 (m, 1H), 2.22 (s, 3H), 2.20 (s, 3H), 2.12 (s, 3H), 2.00-1.94 (m, 4H), 1.50 (d, 6H, J=6.8 Hz).

Synthesis of Compound B-32: N-((4,6-dimethyl-2-oxo-1,2-dihydropyridin-3-yl)methyl)-1-isopropyl-6-(1-(1-methylpiperidine-3-carbonyl)-1,2,3,6-tetrahydropyridin-4-yl)-1H-pyrazolo[3,4-b]pyridine-4-carboxamide Compound B-32

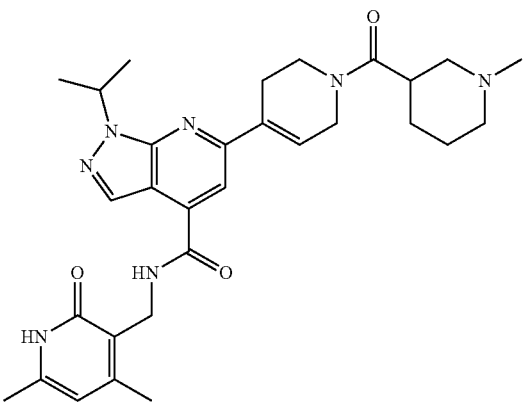

Step 1: Synthesis of N-((4,6-dimethyl-2-oxo-1,2-dihydropyridin-3-yl)methyl)-1-isopropyl-6-(1-(piperidine-3-carbonyl)-1,2,3,6-tetrahydropyridin-4-yl)-1H-pyrazolo[3,4-b]pyridine-4-carboxamide

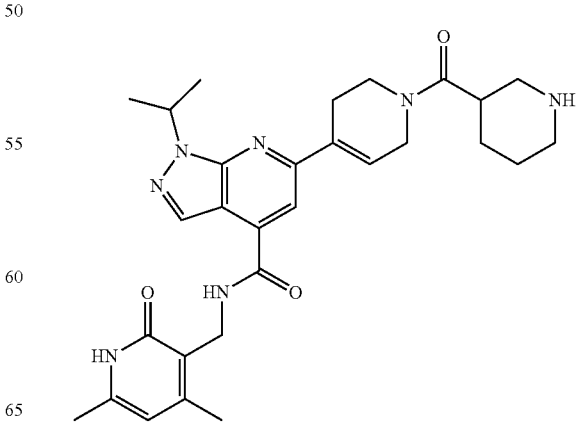

N-((4,6-Dimethyl-2-oxo-1,2-dihydropyridin-3-yl)methyl)-1-isopropyl-6-(1,2,3,6-tetrahydropyridin-4-yl)-1H-pyrazolo[3,4-b]pyridine-4-carboxamide (1 equiv.) was dissolved in DMSO, to it Et$_3$N (3 equiv.) and piperidine-3-carboxylic acid (2 equiv.) was added to it. The reaction mixture was stirred at room temperature for 15 min before PYBOP (1.5 equiv.) was added to it and stirring was continued overnight. After completion of the reaction, water was added to it. Extraction was carried out using DCM; the combined organic layers were washed with water, brine and dried over anhydrous Na$_2$SO$_4$; filtered and concentrated under reduced pressure to afford crude material which was purified by column chromatography to give the desired compound.

Step 2: Synthesis of N-((4,6-dimethyl-2-oxo-1,2-dihydropyridin-3-yl)methyl)-1-isopropyl-6-(1-(1-methylpiperidine-3-carbonyl)-1,2,3,6-tetrahydropyridin-4-yl)-1H-pyrazolo[3,4-b]pyridine-4-carboxamide

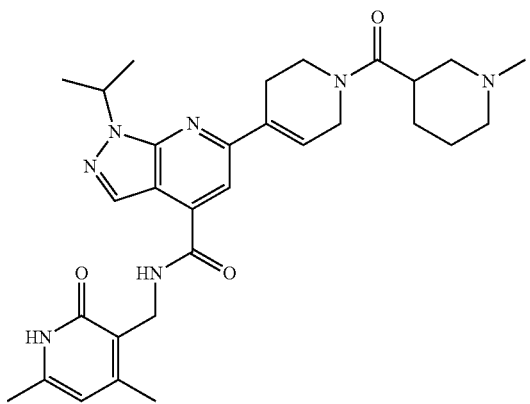

To a stirred solution of N-((4,6-dimethyl-2-oxo-1,2-dihydropyridin-3-yl)methyl)-1-isopropyl-6-(1-(piperidine-3-carbonyl)-1,2,3,6-tetrahydropyridin-4-yl)-1H-pyrazolo[3,4-b]pyridine-4-carboxamide (1 equiv.) in methanol was added formalin (5 equiv.) stirred it at room temperature for 10 min. Then NaBH$_3$CN (1 equiv.) was added to it Resulting reaction mixture was stirred at room temperature for 1 h. After completion of reaction, solvent was removed under reduced pressure and water was added to it. Extraction was carried out using 10% MeOH/DCM. The combined organic layers were washed with water, dried over anhydrous Na$_2$SO$_4$, filtered and concentrated under reduced pressure to afford crude material which was purified by column chromatography to give the desired compound (195 yield). LCMS: 546.40 (M+1)$^+$; HPLC: 94.91% (@ 254 nm) (R$_t$:7.295); $^1$H NMR (DMSO-d$_6$, 400 MHz) δ 11.55 (s, 1H), 8.84 (bs, 1H), 8.30 (d, 1H, J=2 Hz), 7.84 (d, 1H, J=9.2 Hz), 6.90 (s, 1H), 5.89 (s, 1H), 5.20 (m, 1H), 4.38 (d, 2H, J=4 Hz), 4.33 (bs, 1H), 4.19 (bs, 1H), 3.72 (bs, 2H), 2.90-2.65 (m, 5H), 2.20 (s, 3H), 2.15 (s, 3H), 2.12 (s, 3H), 1.91 (m, 1H), 1.80-1.70 (m, 3H), 1.61 (m, 1H), 1.50 (d, 6H, J=6 Hz), 1.28 (m, 1H).

Synthesis of Compound B-33: N-((4,6-dimethyl-2-oxo-1,2-dihydropyridin-3-yl)methyl)-1-isopropyl-6-(1-(1-(2-(methylsulfonyl)ethyl)piperidin-4-yl)-1,2,3,6-tetrahydropyridin-4-yl)-1H-pyrazolo[3,4-b]pyridine-4-carboxamide Compound B-33

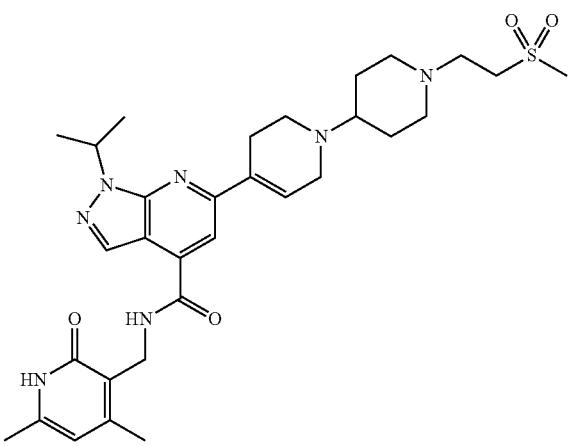

To a stirred solution of N-((4,6-dimethyl-2-oxo-1,2-dihydropyridin-3-yl)methyl)-1-isopropyl-6-(1-(piperidin-4-yl)-1,2,3,6-tetrahydropyridin-4-yl)-1H-pyrazolo[3,4-b]pyridine-4-carboxamide (0.2 g, 0.397 mmol) in MeOH (2 mL), methyl vinyl sulfone (0.063 g, 0.596 mmol) was added and stirred it at room temperature for 12 h. After completion of reaction, solvent was removed under reduced pressure and water was added to it. Extraction was carried out using 10% MeOH/DCM; the combined organic layers were washed with water, brine and dried over anhydrous Na$_2$SO$_4$; filtered and concentrated under reduced pressure, finally the residue was washed with diethyl ether to provide the desired compound (41% yield). LCMS: 610.45 (M+1)$^+$; HPLC: 97.26% (@ 254 nm) (R$_t$:6.037); $^1$H NMR (DMSO-d$_6$, 400 MHz) δ 11.54 (s, 1H), 8.82 (t, 1H), 8.27 (s, 1H), 7.80 (s, 1H), 6.88 (s, 1H), 5.89 (s, 1H), 5.21-5.17 (m, 1H), 4.37 (d, 2H, J=4.4 Hz), 3.32-3.25 (m, 4H), 3.02 (s, 3H), 2.95 (d, 2H, J=10.40 Hz), 2.73 (d, 2H, J=4 Hz), 2.67 (bs, 4H), 2.32 (m, 2H), 2.20 (s, 3H), 2.12 (s, 3H), 1.99-1.94 (m, 2H), 1.81-1.79 (m, 2H), 1.49 (d, 6H, J=6.4 Hz), 1.45 (m, 1H).

Synthesis of Compound B-34: N-((4,6-dimethyl-2-oxo-1,2-dihydropyridin-3-yl)methyl)-1-isopropyl-6-(1-(1-methylpiperidine-4-carbonyl)-1,2,3,6-tetrahydropyridin-4-yl)-1H-pyrazolo[3,4-b]pyridine-4-carboxamide Compound B-34

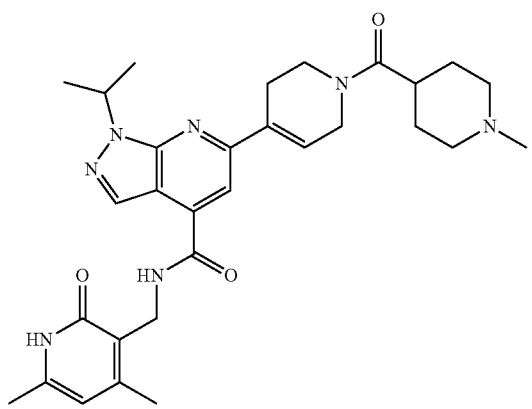

To a stirred solution N-((4,6-dimethyl-2-oxo-1,2-dihydropyridin-3-yl)methyl)-1-isopropyl-6-(1-(piperidine-4-carbonyl)-1,2,3,6-tetrahydropyridin-4-yl)-1H-pyrazolo[3,4-b]pyridine-4-carboxamide (1 equiv.) in methanol was added formalin (5 equiv.) stirred it at room temperature for 10 min. Then NaBH₃CN (1 equiv.) was added to it Resulting reaction mixture was stirred at room temperature for 1 h. After completion of reaction, solvent was removed under reduced pressure and water was added to it. Extraction was carried out using 10% MeOH/DCM. The combined organic layers were washed with water, dried over anhydrous Na$_2$SO$_4$, filtered and concentrated under reduced pressure to afford crude material which was purified by column chromatography to give the desired compound (29% yield). LCMS: 546.30 (M+1)⁺; HPLC: 99.94% (@ 254 nm) (R$_t$:5.067); ¹H NMR (DMSO-d$_6$, 400 MHz) δ 11.53 (bs, 1H), 8.83 (bs, 1H), 8.30 (s, 1H), 7.83 (d, 1H, J=13.20 Hz), 6.90 (bs, 1H), 5.89 (s, 1H), 5.25-5.15 (m, 1H), 4.38 (d, 2H, J=3.6 Hz), 4.31 (bs, 1H), 4.20 (bs, 1H), 3.71 (bs, 2H), 2.77 (bs, 3H), 2.65 (bs, 2H), 2.20 (s, 3H), 2.14 (s, 3H), 2.12 (s, 3H), 1.91 (bs, 2H), 1.60 (bs, 4H), 1.50 (d, 6H, J=6.4 Hz).

Synthesis of Compound B-35: N-((4,6-dimethyl-2-oxo-1,2-dihydropyridin-3-yl)methyl)-1-isopropyl-6-(1'-(methylsulfonyl)-[1,4'-bipiperidin]-4-yl)-1H-pyrazolo[3,4-b]pyridine-4-carboxamide Compound B-35

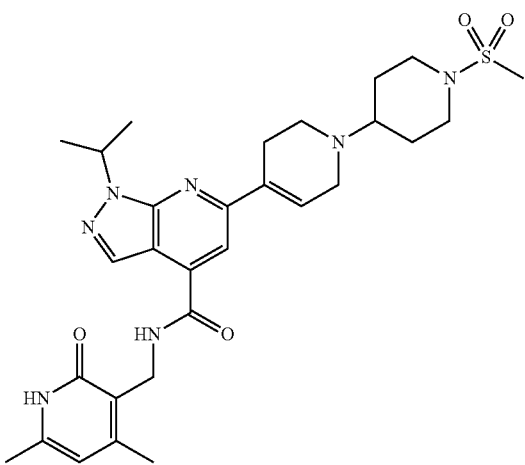

Step 1: Synthesis of N-((4,6-dimethyl-2-oxo-1,2-dihydropyridin-3-yl)methyl)-1-isopropyl-6-(1-(1-(methylsulfonyl)piperidin-4-yl)-1,2,3,6-tetrahydropyridin-4-yl)-1H-pyrazolo[3,4-b]pyridine-4-carboxamide To a stirred solution of N-((4,6-dimethyl-2-oxo-1,2-dihydropyridin-3-yl)methyl)-1-isopropyl-6-(1-(piperidin-4-yl)-1,2,3,6-tetrahydropyridin-4-yl)-1H-pyrazolo[3,4-b]pyridine-4-carboxamide (0.2 g, 0.397 mmol) in DCM (5 mL), Et₃N (0.06 g, 0.596 mmol) and mesyl chloride (0.046 g, 0.403 mmol) were added at 0° C. and stirred it at room temperature for 2 h. After completion, reaction was quenched with ice-water. Extraction was carried out using DCM; the combined organic layers were washed with water, brine and dried over anhydrous Na$_2$SO$_4$; filtered and concentrated under reduced pressure to afford crude material which was purified by prep. HPLC to give the desired compound. LCMS: 582.30 (M+1)⁺; HPLC: 92.74% (@ 254 nm) (R$_t$:5.006); ¹H NMR (DMSO-d$_6$, 400 MHz) δ 11.55 (s, 1H), 9.86 (bs, 1H), 8.87 (t, 1H, J=4.8 Hz), 8.34 (s, 1H), 7.90 (s, 1H), 6.93 (s, 1H), 5.90 (s, 1H), 5.23-5.20 (m, 1H), 4.39 (d, 2H, J=4.4 Hz), 4.08 (bs, 2H), 3.80 (bs, 2H), 3.72 (d, 2H, J=11.60 Hz), 3.30 (bs, 2H), 3.15 (d, 2H, J=15.60 Hz), 2.93 (s, 3H), 2.84-2.76 (m, 2H), 2.27 (m, 1H), 2.21 (s, 3H), 2.12 (s, 3H), 1.81-1.73 (m, 2H), 1.51 (d, 6H, J=6.8 Hz).

Step 2: Synthesis of N-((4,6-dimethyl-2-oxo-1,2-dihydropyridin-3-yl)methyl)-1-isopropyl-6-(1'-(methylsulfonyl)-[1,4'-bipiperidin]-4-yl)-1H-pyrazolo[3,4-b]pyridine-4-carboxamide

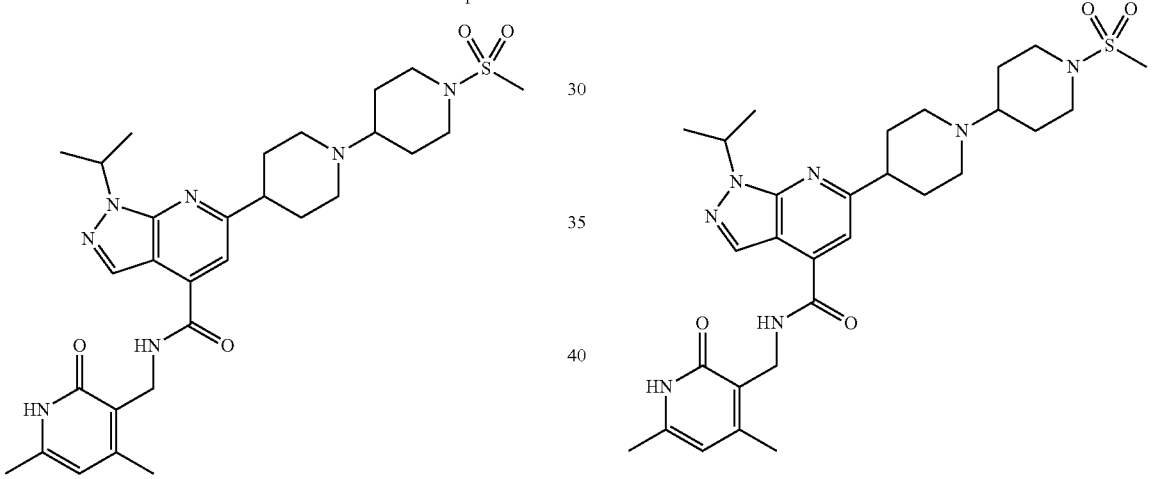

To a stirred solution of N-((4,6-dimethyl-2-oxo-1,2-dihydropyridin-3-yl)methyl)-1-isopropyl-6-(1-(1-(methylsulfonyl)piperidin-4-yl)-1,2,3,6-tetrahydropyridin-4-yl)-1H-pyrazolo[3,4-b]pyridine-4-carboxamide (0.06 g, 0.18 mmol) in EtOH (2 mL), 10% Pd/C in catalytic amount was added and stirred it at room temperature under hydrogen pressure (balloon pressure) for 3-4 hr. On completion of reaction, reaction mass was filtered through celite bed, then filtrate was concentrated under reduced pressure, finally the residue was washed with diethyl ether to provide the desired compound (27% yield). LCMS: 584.35 (M+1)⁺; HPLC: 96.59% (@ 254 nm) (R$_t$:4.927); ¹H NMR (CD3OD, 400 MHz) δ 8.28 (s, 1H), 7.43 (s, 1H), 6.13 (s, 1H), 5.27 (bs, 1H), 4.55 (s, 2H), 3.94 (d, 2H, J=10.4 Hz), 5.74 (d, 2H, J=10.8 Hz), 3.40 (m, 2H), 3.30 (m, 2H), 2.89 (s, 3H), 2.85 (m, 2H), 2.41-2.25 (m, 12H), 1.90 (m, 2H), 1.56 (d, 6H, J=4.4 Hz).

Syntheses of Compounds B-36 through B-148, B-151 through B-156, and B-164

Compounds B-36 through B-148, B-151 through B-156, and B-164 were synthesized by methods similar to those described for Compounds B-1 through B-35 or by reaction schemes depicted in the general schemes.

373

Synthesis of Compound C-1: 1-cyclopentyl-N-((4,6-dimethyl-2-oxo-1,2-dihydropyridin-3-yl)methyl)-6-(4-(morpholinomethyl)phenyl)-1H-indazole-4-carboxamide Compound C-1

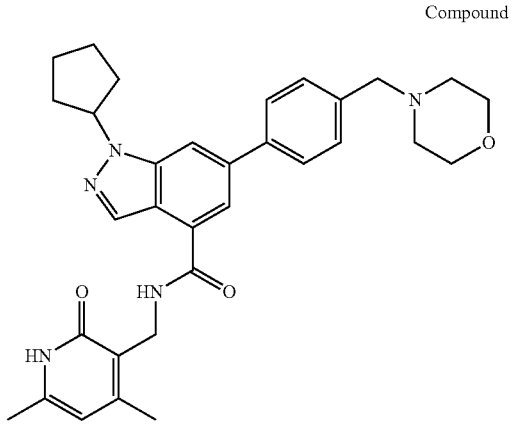

Step 1: Synthesis of 3-(aminomethyl)-4,6-dimethylpyridin-2(1H)-one

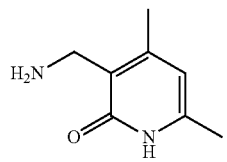

3-Cyano-2,4-dimethyl-2-hydroxypyridine (0.3 g, 2.0 mmol) was dissolved in MeOH (5 mL), to which catalytic amount of Raney Ni and of aqueous NH₃ (0.3 mL) were added and the reaction mixture was stirred under hydrogen pressure (bladder pressure) for 3-4 h. After completion of the reaction, catalyst was filtered off and the filtrate was concentrated under reduced pressure. The residue was thoroughly dried to provide the desired product (0.3 g, quantitative yield).

Step 2: 5-bromo-2-methyl-3-nitrobenzoic acid

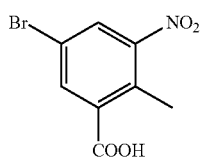

1,3-dibromo-5,5-dimethyl-2,4-imidazolidinedione (13.0 g, 45.7 mmol) was added to a mixture of 2-methyl-3-nitrobenzoic acid (15 g, 82.8 mmol) in conc. H₂SO₄ (60 mL), and the reaction mixture stirred at room temperature for 5 h. After completion of reaction, the mixture was slowly poured onto ice cold water (400 mL). The precipitated was filtered and dried under vacuum to obtain desired 5-bromo-2-methyl-3-nitrobenzoic acid (21 g, 98.2%).

374

Step 3: methyl 5-bromo-2-methyl-3-nitrobenzoate

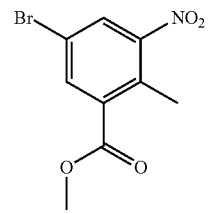

To a stirred solution of 5-bromo-2-methyl-3-nitrobenzoic acid (16 g, 61.5 mmol) in DMF (160 mL), was added iodomethane (35.7 g, 248 mmol) and sodium carbonate (26.3 g, 248 mmol). The resulting reaction mixture was stirred at 60° C. for 8 h. On completion, the reaction mixture was filtered and the inorganic solid residue washed with ethyl acetate. The combined filtrates were concentrated under vacuum till dry and re-dissolved in ethyl acetate before washing with 5% sodium bicarbonate solution (700 mL) followed by 5M HCl solution (300 mL). The organic layer was finally washed with brine, dried over sodium sulfate and concentrated to afford pure methyl 5-bromo-2-methyl-3-nitrobenzoate (16 g, 94.5%).

Step 4: methyl 3-amino-5-bromo-2-methylbenzoate

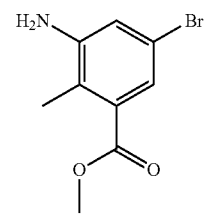

A mixture of methyl 5-bromo-2-methyl-3-nitrobenzoate (17 g, 62.0 mmol) in ethanol (85 mL) had NH₄Cl solution (17 g in 85 mL water, 317.8 mmol) followed by Fe powder (27.8 g, 498.1 mmol) added. The resulting reaction mixture was stirred at 90° C. for 1 h. On completion, reaction mixture was filtered and the filtrate was concentrated till dry. The resulting solid was dissolved in sat. sodium bicarbonate solution and extracted with ethyl acetate. The combined organic layers were dried over sodium sulfate and concentrated to afford solid methyl 3-amino-5-bromo-2-methylbenzoate (15 g, 99.1%).

Step 5: methyl 1-acetyl-6-bromo-1H-indazole-4-carboxylate

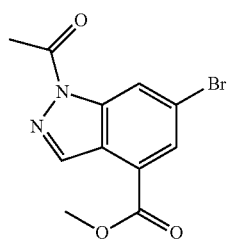 [SMILES: COC(=O)c1cc(Br)cc2c1cnn2C(C)=O]

To a stirred solution of methyl 3-amino-5-bromo-2-methylbenzoate (15 g, 61.5 mmol) in chloroform (150 mL), was added potassium acetate (6.32 g, 64.4 mmol) and acetic anhydride (12.6 g, 122.9 mmol) and reaction mixture was stirred at room temperature for 12 h. After this time, tert-butyl nitrite (25.3 g, 246.1 mmol) and 18-crown-6 (5.7 g, 21.5 mmol) were added and reaction stirred again at 65° C. for 3 h. On completion, the reaction mass was cooled to room temperature, diluted with chloroform (500 mL) and washed with sat. sodium bicarbonate solution. The organic layer was dried over sodium sulfate and concentrated to afford the title compound (18 g, 98.3%).

Step 6: methyl 6-bromo-1H-indazole-4-carboxylate

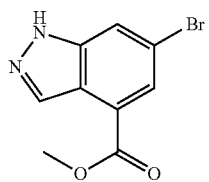

To a stirred solution of methyl 1-acetyl-6-bromo-1H-indazole-4-carboxylate (18 g, 61.0 mmol) in methanol (350 mL), 6N HCl (350 mL) was added and stirred it at 60° C. for 8 h. On completion of reaction, solvent was removed under reduced pressure then basified with saturated NaHCO$_3$ solution till pH 8. The solid precipitate was filtered and dried under vacuum before being stirred in diethyl ether for 15 min, filtered and dried to afford methyl 6-bromo-1H-indazole-4-carboxylate (11 g, 71.7%).

Step 7: methyl 6-bromo-1-cyclopentyl-1H-indazole-4-carboxylate

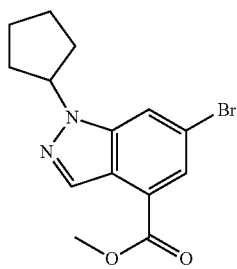 [SMILES: COC(=O)c1cc(Br)cc2c1cnn2C1CCCC1]

To a stirred solution of methyl 6-bromo-1H-indazole-4-carboxylate (10 g, 39.3 mmol) in acetonitrile (100 mL), was added cesium carbonate (19.2 g, 59.05 mmol) followed by bromocyclopentane (11.93 g, 78.3 mmol). The reaction mass was stirred at 90° C. for 3-4 h. On completion of reaction, acetonitrile was removed under reduced pressure and water added. Extraction was carried out using ethyl acetate and the combined organic layers were washed with water, brine and dried over anhydrous Na$_2$SO$_4$. The solvent was removed under reduced pressure and the residue purified by silica gel column chromatography to obtain methyl 6-bromo-1-cyclopentyl-1H-indazole-4-carboxylate (3.7 g, 29.2%). The regiochemistry of the cyclopentyl group was confirmed by a NOE experiment.

Step 8: 6-bromo-1-cyclopentyl-N-((4,6-dimethyl-2-oxo-1,2-dihydropyridin-3-yl)methyl)-1H-indazole-4-carboxamide

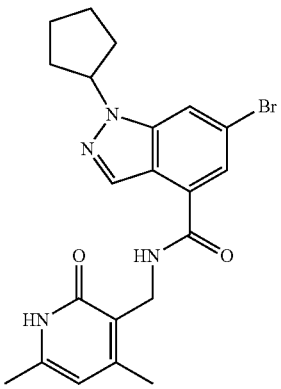 [SMILES: Cc1cc(C)c(CNC(=O)c2cc(Br)cc3c2cnn3C2CCCC2)c(=O)[nH]1]

Aqueous NaOH (0.68 g, 17.18 mmol) was added to a solution of methyl 6-bromo-1-cyclopentyl-1H-indazole-4-carboxylate (3.7 g, 11.45 mmol) in EtOH (40 mL) and stirred at 60° C. for 1 h. After completion of the reaction, ethanol was removed under reduced pressure and the residue acidified using 1N HCl solution. The resulting precipitate was filtered and dried under vacuum. This crude acid (3.2 g, 10.3 mmol) was then dissolved in DMSO (20 mL) and 3-(aminomethyl)-4,6-dimethylpyridin-2(1H)-one (3.15 g, 20.77 mmol) added to it. The reaction mixture was stirred at room temperature for 15 min before PYBOP (8.1 g, 15.5 mmol) was added and left to stir overnight. After completion of the reaction, reaction mass was poured into ice to obtain solid which was filtered and washed with acetonitrile then ether to provide the desired 6-bromo-1-cyclopentyl-N-((4,6-dimethyl-2-oxo-1,2-dihydropyridin-3-yl)methyl)-1H-indazole-4-carboxamide (2.6 g, 56.5%). LCMS: 443.05 (M+1)$^+$; HPLC: 95.00% (@ 254 nm) (R$_t$;7.195); $^1$H NMR (DMSO-d$_6$, 400 MHz) δ 11.52 (s, 1H), 8.61 (t, 1H, J=4.8 Hz), 8.36 (s, 1H), 8.19 (s, 1H), 7.70 (s, 1H), 5.88 (s, 1H), 5.23-5.20 (m, 1H), 4.33 (d, 2H, J=4.8 Hz), 2.20 (s, 3H), 2.12 (s, 3H), 1.98 (m, 2H), 1.97-1.90 (m, 2H), 1.87-1.86 (m, 2H), 1.73-1.67 (m, 2H).

Step 9: 1-cyclopentyl-N-((4,6-dimethyl-2-oxo-1,2-dihydropyridin-3-yl)methyl)-6-(4-(morpholinomethyl)phenyl)-1H-indazole-4-carboxamide

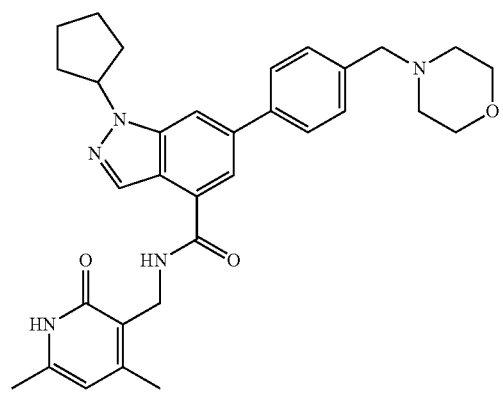 [SMILES: Cc1cc(C)c(CNC(=O)c2cc(-c3ccc(CN4CCOCC4)cc3)cc3c2cnn3C2CCCC2)c(=O)[nH]1]

To a stirred solution of 6-bromo-1-cyclopentyl-N-((4,6-dimethyl-2-oxo-1,2-dihydropyridin-3-yl)methyl)-1H-indazole-4-carboxamide (0.25 g, 0.56 mmol), 4-(4-(4,4,5,5-tetramethyl-1,3,2-dioxaborolan-2-yl)benzyl)morpholine (0.20 g, 0.67 mmol) and Pd(PPh$_3$)$_4$ (0.032 g, 0.027 mmol) in 1,4-dioxane (4 mL) and purged with argon for 10 min. 2M Na$_2$CO$_3$ solution (0.22 g, 2.03 mmol) was then added to it before a further argon purge for 10 min. The reaction mixture was stirred at 100° C. for 3 h. After completion of the reaction, water was added and extraction carried out using 10% MeOH/DCM. The combined organic layers were washed with water, dried over anhydrous Na$_2$SO$_4$, filtered and concentrated under reduced pressure to afford crude material which was purified by column chromatography to give -cyclopentyl-N-((4,6-dimethyl-2-oxo-1,2-dihydropyridin-3-yl)methyl)-6-(4-(morpholinomethyl)phenyl)-1H-indazole-4-carboxamide (68.4% yield). LCMS: 540.25 (M+1)$^+$; HPLC: 99.15% (@ 254 nm) (R$_t$:5.583); $^1$H NMR (DMSO-d$_6$, 400 MHz) δ 11.51 (bs, 1H), 8.62 (t, 1H, J=4.8 Hz), 8.36 (s, 1H), 8.10 (s, 1H), 7.85 (s, 1H), 7.80 (d, 2H, J=8 Hz), 7.43 (d, 2H, J=8 Hz), 5.88 (s, 1H), 5.34-5.31 (m, 1H), 4.38 (d, 2H, J=4.8 Hz), 3.59-3.58 (m, 4H), 3.52 (s, 2H), 2.38 (m, 4H), 2.21 (s, 3H), 2.11 (s, 3H), 2.04-1.99 (m, 2H), 1.88 (m, 4H), 1.72-1.69 (m, 2H).

Synthesis of Compound C-2: 1-cyclopentyl-N-((4,6-dimethyl-2-oxo-1,2-dihydropyridin-3-yl)methyl)-6-(6-formylpyridin-3-yl)-1H-indazole-4-carboxamide Compound C-2

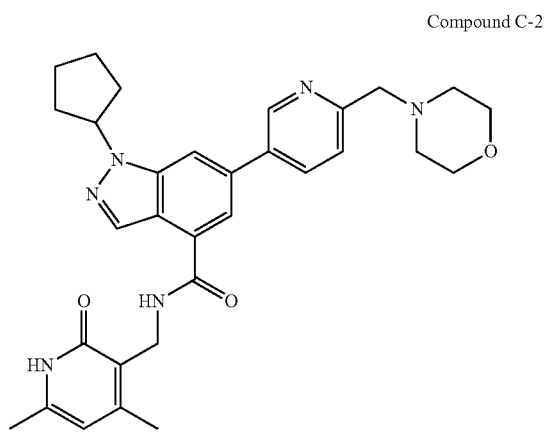 [SMILES: Cc1cc(C)c(CNC(=O)c2cc(-c3ccc(CN4CCOCC4)nc3)cc3c2cnn3C2CCCC2)c(=O)[nH]1]

Step 1: 1-cyclopentyl-N-((4,6-dimethyl-2-oxo-1,2-dihydropyridin-3-yl)methyl)-6-(6-formylpyridin-3-yl)-1H-indazole-4-carboxamide

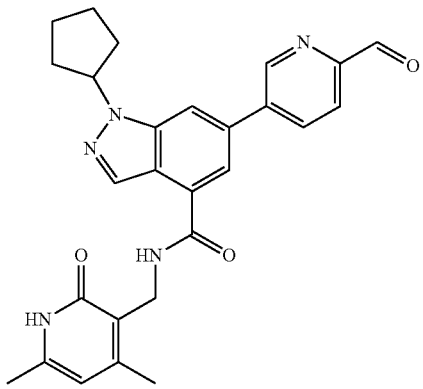 [SMILES: Cc1cc(C)c(CNC(=O)c2cc(-c3ccc(C=O)nc3)cc3c2cnn3C2CCCC2)c(=O)[nH]1]

A solution of 6-bromo-1-cyclopentyl-N-((4,6-dimethyl-2-oxo-1,2-dihydropyridin-3-yl)methyl)-1H-indazole-4-carboxamide (0.1 g, 0.2 mmol), 5-(4,4,5,5-tetramethyl-1,3,2-dioxaborolan-2-yl)picolinaldehyde (0.064 g, 0.274 mmol) and Pd(PPh$_3$)$_4$ (0.013 g, 0.011 mmol) in 1,4-dioxane (2 mL) was purged with argon for 10 min. A solution of 2M Na$_2$CO$_3$ (0.087 g, 0.820 mmol) was then added to it and argon again purged for 10 min. The reaction mixture was stirred at 100° C. for 1 h. After completion of the reaction, water was added and extraction was carried out using ethyl acetate. The combined organic layers were washed with water, dried over anhydrous Na$_2$SO$_4$, filtered and concentrated under reduced pressure to afford crude material which was purified by column chromatography to give 1-cyclopentyl-N-((4,6-dimethyl-2-oxo-1,2-dihydropyridin-3-yl)methyl)-6-(6-formylpyridin-3-yl)-1H-indazole-4-carboxamide (0.1 g, 94.3%).

Step 2: 1-cyclopentyl-N-((4,6-dimethyl-2-oxo-1,2-dihydropyridin-3-yl)methyl)-6-(6-formylpyridin-3-yl)-1H-indazole-4-carboxamide

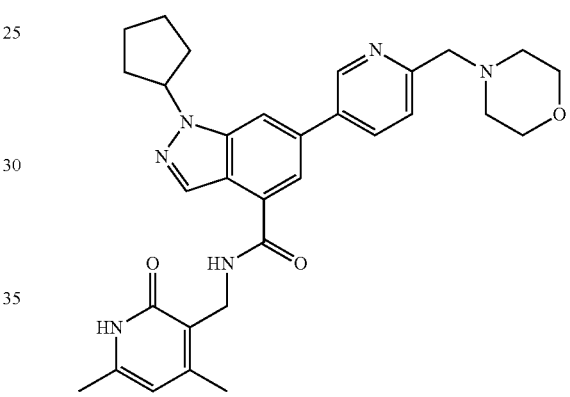

To a stirred solution of 1-cyclopentyl-N-((4,6-dimethyl-2-oxo-1,2-dihydropyridin-3-yl)methyl)-6-(6-formylpyridin-3-yl)-1H-indazole-4-carboxamide (0.1 g, 0.212 mmol) in methanol (2 mL) was added acetic acid (0.013 g, 0.212 mmol) and morpholine (0.056 g, 0.636 mmol) and stirred it at room temperature for 3 h. Then NaBH$_3$CN (0.014 g, 0.212 mmol) was added to it and the reaction mixture stirred at room temperature overnight. After completion of reaction, solvent was removed under reduced pressure and water was added to it. Extraction was carried out using 10% MeOH/DCM. The combined organic layers were washed with water, dried over anhydrous Na$_2$SO$_4$, filtered and concentrated under reduced pressure to afford crude material which was purified by column chromatography to give corresponding 1-cyclopentyl-N-((4,6-dimethyl-2-oxo-1,2-dihydropyridin-3-yl)methyl)-6-(6-(morpholinomethyl)pyridin-3-yl)-1H-indazole-4-carboxamide (0.049 g, 43.4%). LCMS: 541.30 (M+1)$^+$; HPLC: 94.30% (@ 254 nm) (R$_t$:5.379); $^1$H NMR (DMSO-d$_6$, 400 MHz) δ 11.52 (s, 1H), 8.98 (s, 1H), 8.62 (t, 1H, J=4.4&4.8 Hz), 8.39 (s, 1H), 8.21 (s, 2H), 7.90 (s, 1H), 7.56 (d, 1H, J=8.4 Hz), 5.88 (s, 1H), 5.35-5.31 (m, 1H), 4.39 (d, 2H, J=4.8 Hz), 3.65 (s, 2H), 3.60 (t, 4H, J=4&4.4 Hz), 2.44 (bs, 4H), 2.21 (s, 3H), 2.15 (bs, 2H), 2.11 (s, 3H), 2.05-1.98 (m, 2H), 1.89 (bs, 2H), 1.75-1.65 (m, 2H).

Synthesis of Compound C-3: 1-cyclopentyl-N-((4,6-dimethyl-2-oxo-1,2-dihydropyridin-3-yl)methyl)-6-(4-((dimethylamino)methyl)phenyl)-1H-indazole-4-carboxamide

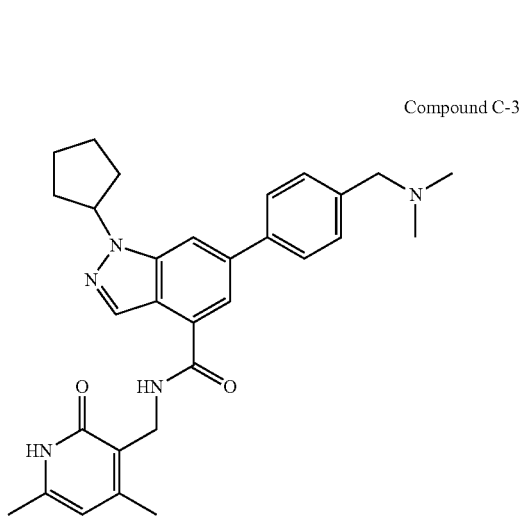

Compound C-3

Step 1: 1-cyclopentyl-N-((4,6-dimethyl-2-oxo-1,2-dihydropyridin-3-yl)methyl)-6-(4-(hydroxymethyl)phenyl)-1H-indazole-4-carboxamide

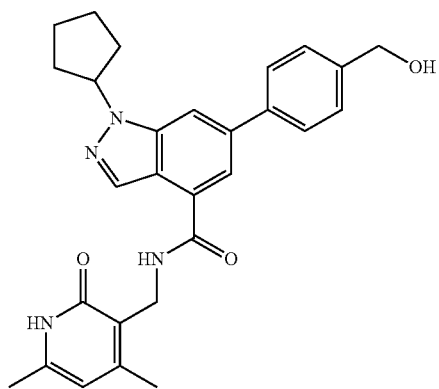 [SMILES: Cc1cc(C)c(CNC(=O)c2cc(-c3ccc(CO)cc3)cc3c2cnn3C2CCCC2)c(=O)[nH]1]

A solution of 6-bromo-1-cyclopentyl-N-((4,6-dimethyl-2-oxo-1,2-dihydropyridin-3-yl)methyl)-1H-indazole-4-carboxamide (1.5 g, 3.5 mmol), (4-(hydroxymethyl)phenyl) boronic acid (0.65 g, 4.30 mmol) and Pd(PPh$_3$)$_4$ (0.41 g, 0.35 mmol) in 1,4-dioxane (20 mL) was purged with argon for 10 min. 2 M Na$_2$CO$_3$ solution (1.37 g, 12.91 mmol) was then added to it and argon purged again for 10 min. The reaction mixture was stirred at 100° C. for 2 h. After completion of the reaction, water was added to it and extraction was carried out using DCM. The combined organic layers were washed with water, dried over anhydrous Na$_2$SO$_4$, filtered and concentrated under reduced pressure to afford crude material which was purified by column chromatography to give 1-cyclopentyl-N-((4,6-dimethyl-2-oxo-1,2-dihydropyridin-3-yl)methyl)-6-(4-(hydroxymethyl)phenyl)-1H-indazole-4-carboxamide (1.5 g, 89.3%).

Step 2: 6-(4-(bromomethyl)phenyl)-1-cyclopentyl-N-((4,6-dimethyl-2-oxo-1,2-dihydropyridin-3-yl)methyl)-1H-indazole-4-carboxamide

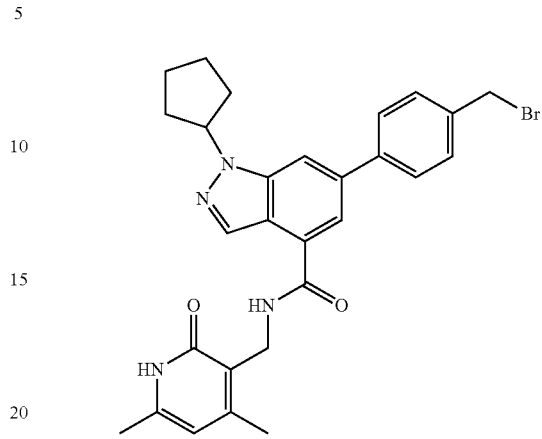

To a stirred solution of 1-cyclopentyl-N-((4,6-dimethyl-2-oxo-1,2-dihydropyridin-3-yl)methyl)-6-(4-(hydroxymethyl)phenyl)-1H-indazole-4-carboxamide (1.5 g, 3.2 mmol) in DCM (20 mL), triphenyl phosphine (1.33 g, 5.10 mmol) was added and stirred at room temperature for 10 min. CBr$_4$ (1.69 g, 5.10 mmol) was then added portion-wise to it and the resulting solution stirred at room temperature overnight. After completion, water was added and extraction was carried out using DCM. The combined organic layers were washed with water, dried over anhydrous Na$_2$SO$_4$, filtered and concentrated under reduced pressure to afford crude material which was purified by column chromatography to give 6-(4-(bromomethyl)phenyl)-1-cyclopentyl-N-((4,6-dimethyl-2-oxo-1,2-dihydropyridin-3-yl)methyl)-1H-indazole-4-carboxamide (1.0 g, 58.8%).

Step 3: 1-cyclopentyl-N-((4,6-dimethyl-2-oxo-1,2-dihydropyridin-3-yl)methyl)-6-(4-((dimethylamino)methyl)phenyl)-1H-indazole-4-carboxamide

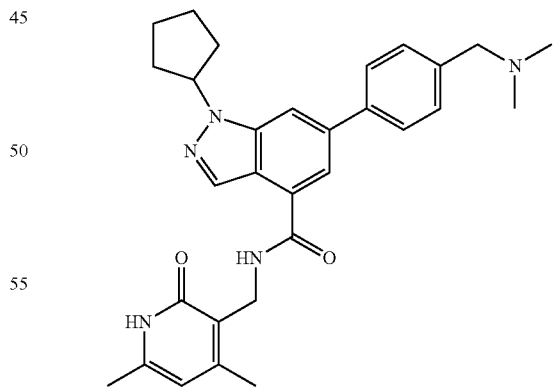

To a stirred solution of 6-(4-(bromomethyl)phenyl)-1-cyclopentyl-N-((4,6-dimethyl-2-oxo-1,2-dihydropyridin-3-yl)methyl)-1H-indazole-4-carboxamide (0.15 g, 0.28 mmol) in DMF (1 mL), dimethyl amine (0.163 g, 1.407 mmol) was added and stirred it at room temperature for overnight. On completion, reaction was quenched with ice cold water and extracted using 10% MeOH/DCM. The combined organic layers were washed with water, dried over anhydrous Na$_2$SO$_4$, filtered and concentrated under reduced pressure to afford crude material which was purified by prep. HPLC to provide the TFA salt of the target compound (0.77 g, 55.7%). LCMS: 498.35 (M+1)$^+$; HPLC: 99.95% (@ 254 nm) (R$_t$; 5.488; $^1$H NMR (DMSO-d$_6$, 400 MHz) δ 11.53 (bs, 1H), 9.80 (bs, 1H), 8.64 (t, 1H, J=4.8 Hz), 8.38 (s, 1H), 8.19 (s, 1H), 8.00 (d, 2H, J=7.6 Hz), 7.90 (s, 1H), 7.62 (d, 2H, J=8.4 Hz), 5.89 (s, 1H), 5.36-5.31 (m, 1H), 4.39 (d, 2H, J=4.8 Hz), 4.35 (d, 2H, J=4.4 Hz), 2.77 (s, 6H), 2.22 (s, 3H), 2.16-2.14 (m, 2H), 2.12 (s, 3H), 2.04-1.99 (m, 2H), 1.93-1.89 (m, 2H), 1.73-1.70 (m, 2H).

Synthesis of Compound C-4: 1-cyclopentyl-N-((4,6-dimethyl-2-oxo-1,2-dihydropyridin-3-yl)methyl)-6-(4-((3-(dimethylamino)propoxy)methyl)phenyl)-1H-indazole-4-carboxamide Compound C-4

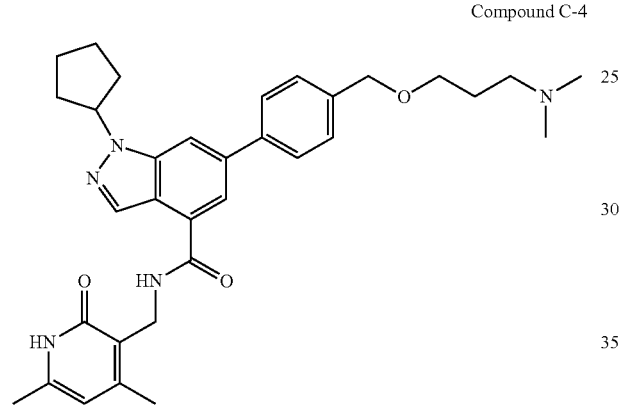

To a suspension of 60% NaH (0.0112 g, 0.281 mmol) in THF (5 mL), 3-(dimethylamino)propan-1-ol (0.039 g, 0.375 mmol) was added at 0° C. followed by the addition of 6-(4-(bromomethyl)phenyl)-1-cyclopentyl-N-((4,6-dimethyl-2-oxo-1,2-dihydropyridin-3-yl)methyl)-1H-indazole-4-carboxamide (0.1 g, 0.187 mmol) and stirred at room temperature for 30 min. On completion of reaction, reaction was quenched with ice cold water and extraction carried out using 10% MeOH/DCM. The combined organic layers were washed with water, dried over anhydrous Na$_2$SO$_4$, filtered and concentrated under reduced pressure to afford crude material which was purified by prep. HPLC to provide the TFA salt of 1-cyclopentyl-N-((4,6-dimethyl-2-oxo-1,2-dihydropyridin-3-yl)methyl)-6-(4-((3-(dimethylamino)propoxy)methyl)phenyl)-1H-indazole-4-carboxamide. LCMS: 556.35 (M+1)$^+$; HPLC: 99.88% (@ 254 nm) (R$_t$;5.470); $^1$H NMR (DMSO-d$_6$, 400 MHz) δ 11.53 (s, 1H), 8.65 (t, 1H), 8.39 (s, 1H), 8.22 (s, 1H), 8.02 (d, 2H, J=8 Hz), 7.92 (s, 1H), 7.68 (d, 2H, J=8 Hz), 5.89 (s, 1H), 5.37-5.33 (m, 1H), 4.59 (s, 2H), 4.39 (d, 2H, J=4.8 Hz), 3.39-3.38 (m, 4H), 3.00 (s, 6H), 2.35 (m, 2H), 2.22 (s, 3H), 2.14-2.12 (m, 2H), 2.12 (s, 3H), 2.04-2.00 (m, 2H), 1.90 (m, 2H), 1.71-1.70 (m, 2H).

Synthesis of Compound C-5: N-((4,6-dimethyl-2-oxo-1,2-dihydropyridin-3-yl)methyl)-1-isopropyl-6-(4-(morpholinomethyl)phenyl)-1H-indazole-4-carboxamide Compound C-5

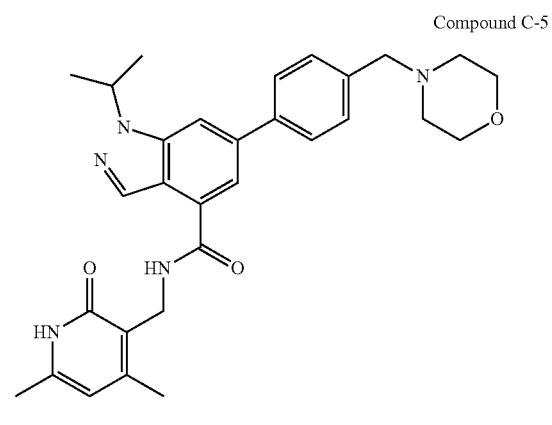 [SMILES: Cc1cc(C)c(CNC(=O)c2cc(-c3ccc(CN4CCOCC4)cc3)cc(NC(C)C)c2C=N)c(=O)[nH]1]

Step 1: methyl 6-bromo-1-isopropyl-1H-indazole-4-carboxylate

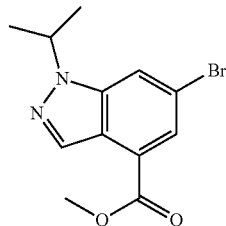 [SMILES: COC(=O)c1cc(Br)cc2c1cnn2C(C)C]

To a stirred solution of methyl 6-bromo-1H-indazole-4-carboxylate (4 g, 14.92 mmol) in acetonitrile (30 mL), cesium carbonate (9.7 g, 29.8 mmol) was added followed by 2-iodopropane (3.8 g, 22.3 mmol) and the reaction mixture stirred at 90° C. for 2 h. On completion, the reaction mixture was concentrated under reduced pressure and the residue diluted with water and extracted with ethyl acetate. The combined organic layers were washed with water, brine and dried over sodium sulfate. Solvent was removed under reduced pressure to afford crude material which was purified by column chromatography to afford methyl 6-bromo-1-isopropyl-1H-indazole-4-carboxylate (1.5 g, 32.6%).

Step 2: 6-bromo-N-((4,6-dimethyl-2-oxo-1,2-dihydropyridin-3-yl)methyl)-1-isopropyl-1H-indazole-4-carboxamide

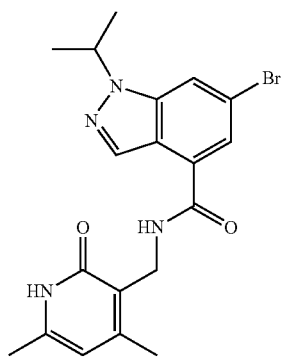 [SMILES: Cc1cc(C)c(CNC(=O)c2cc(Br)cc3c2cnn3C(C)C)c(=O)[nH]1]

Aqueous NaOH (1.5 equiv in 1 mL water) was added to a solution of methyl 6-bromo-1-isopropyl-1H-indazole-4-carboxylate (1.5 g, 4.8 mmol) in EtOH (20 mL) and stirred at 60° C. for 1 h. After completion of the reaction, ethanol was removed under reduced pressure and acidified using 1N HCl solution. Extraction was carried out using ethyl acetate and the combined organic layers washed with water, brine and dried over anhydrous $Na_2SO_4$ before filtration and concentrated under reduced pressure. The crude acid (1.26 g, 4.45 mmol) was then dissolved in DMSO (5 mL) and 3-(aminomethyl)-4,6-dimethylpyridin-2(1H)-one (1.35 g, 8.90 mmol) was added. The reaction mixture was stirred at room temperature for 15 min before PYBOP (3.47 g, 6.67 mmol) was added to it and stirring continued overnight. After completion of the reaction, the mixture was poured into ice and the resulting precipitate filtered and washed with acetonitrile followed by ether to provide 6-bromo-N-((4,6-dimethyl-2-oxo-1,2-dihydropyridin-3-yl)methyl)-1-isopropyl-1H-indazole-4-carboxamide (0.8 g, 43.2%).

Step 3: N-((4,6-dimethyl-2-oxo-1,2-dihydropyridin-3-yl)methyl)-1-isopropyl-6-(4-(morpholinomethyl)phenyl)-1H-indazole-4-carboxamide

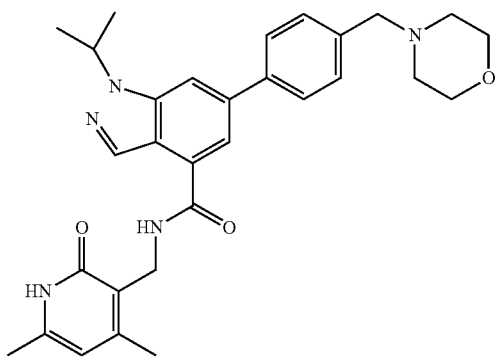 [SMILES: Cc1cc(C)c(CNC(=O)c2cc(-c3ccc(CN4CCOCC4)cc3)cc(NC(C)C)c2C=N)c(=O)[nH]1]

A solution of 6-bromo-N-((4,6-dimethyl-2-oxo-1,2-dihydropyridin-3-yl)methyl)-1-isopropyl-1H-indazole-4-carboxamide (0.30 g, 0.72 mmol), 4-(4-(4,4,5,5-tetramethyl-1,3,2-dioxaborolan-2-yl)benzyl)morpholine (0.26 g, 0.865 mmol) and $Pd(PPh_3)_4$ (0.042 g, 0.036 mmol) in 1,4-dioxane (6 mL) was purged with argon for 10 min. 2M $Na_2CO_3$ solution (0.27 g, 2.54 mmol) was then added before an additional argon purged for 10 min. The reaction mixture was stirred at 80° C. for 2 h. After completion of the reaction, water was added to it and extraction was carried out using EtOAc. The combined organic layers were washed with water, dried over anhydrous $Na_2SO_4$, filtered and concentrated under reduced pressure to afford crude material which was purified by column chromatography to give corresponding N-((4,6-dimethyl-2-oxo-1,2-dihydropyridin-3-yl)methyl)-1-isopropyl-6-(4-(morpholinomethyl)phenyl)-1H-indazole-4-carboxamide (0.20 g, 55.7%). LCMS: 514.25 $(M+1)^+$; HPLC: 99.71% (@ 254 nm) ($R_t$;5.075); $^1H$ NMR (DMSO-$d_6$, 400 MHz) δ 11.53 (s, 1H), 8.63 (t, 1H), 8.37 (s, 1H), 8.09 (s, 1H), 7.85 (s, 1H), 7.81 (d, 2H, J=6.8 Hz), 7.43 (d, 2H, J=7.6 Hz), 5.88 (s, 1H), 5.17-5.14 (m, 1H), 4.38 (d, 2H, J=3.2 Hz), 3.59 (m, 4H), 3.52 (s, 2H), 2.38 (m, 4H), 2.21 (s, 3H), 2.12 (s, 3H), 1.49 (d, 6H, J=6.8 Hz).

Synthesis of Compound C-6: 1-cyclopentyl-N-((4,6-dimethyl-2-oxo-1,2-dihydropyridin-3-yl)methyl)-6-(2-methyl-4-(morpholinomethyl)phenyl)-1H-indazole-4-carboxamide Compound C-6

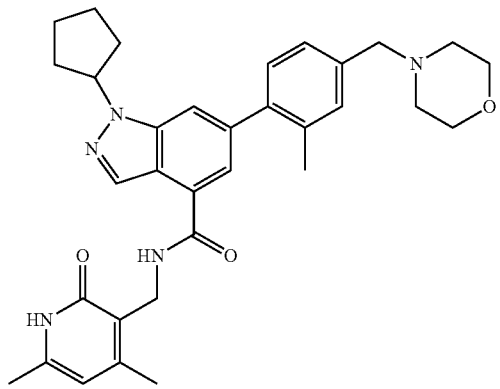

Step 1: 1-cyclopentyl-N-((4,6-dimethyl-2-oxo-1,2-dihydropyridin-3-yl)methyl)-6-(4-formyl-2-methylphenyl)-1H-indazole-4-carboxamide

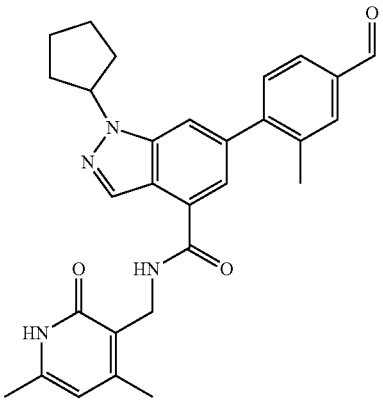 [SMILES: Cc1cc(C)c(CNC(=O)c2cc(-c3ccc(C=O)cc3C)cc3c2cnn3C2CCCC2)c(=O)[nH]1]

A solution of 6-bromo-1-cyclopentyl-N-((4,6-dimethyl-2-oxo-1,2-dihydropyridin-3-yl)methyl)-1H-indazole-4-carboxamide (0.2 g, 0.45 mmol), 3-methyl-4-(4,4,5,5-tetramethyl-1,3,2-dioxaborolan-2-yl)benzaldehyde (0.138 g, 0.56 mmol) and $Pd(PPh_3)_4$ (0.052 g, 0.045 mmol) in 1,4-dioxane (6 mL) was purged with argon for 10 min. 2 M $Na_2CO_3$ solution (0.14 g, 1.35 mmol) was then added to it and mixture purged with argon again for 10 min. The reaction mixture was stirred at 100° C. for 2 h. After completion of the reaction, water was added to it and the extraction was carried out using 5% MeOH in DCM. The combined organic layers were washed with water, dried over anhydrous $Na_2SO_4$, filtered and concentrated under reduced pressure to afford crude material which was purified by column chromatography to 1-cyclopentyl-N-((4,6-dimethyl-2-oxo-1,2-dihydropyridin-3-yl)methyl)-6-(4-formyl-2-methylphenyl)-1H-indazole-4-carboxamide (0.15 g, 69%).

Step 2: 1-cyclopentyl-N-((4,6-dimethyl-2-oxo-1,2-dihydropyridin-3-yl)methyl)-6-(2-methyl-4-(morpholinomethyl)phenyl)-1H-indazole-4-carboxamide Step 1: 1-cyclopentyl-N-((4,6-dimethyl-2-oxo-1,2-dihydropyridin-3-yl)methyl)-6-(5-formylfuran-2-yl)-1H-indazole-4-carboxamide

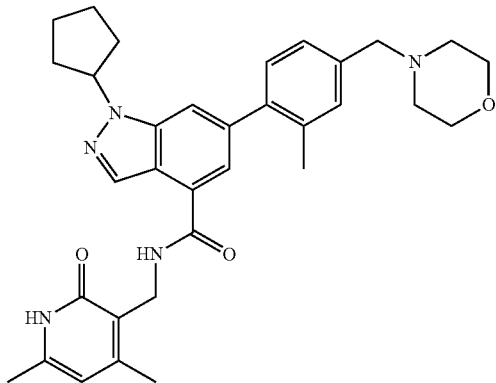 [SMILES: Cc1cc(C)c(CNC(=O)c2cc(-c3ccc(CN4CCOCC4)cc3C)cc3c2cnn3C2CCCC2)c(=O)[nH]1]

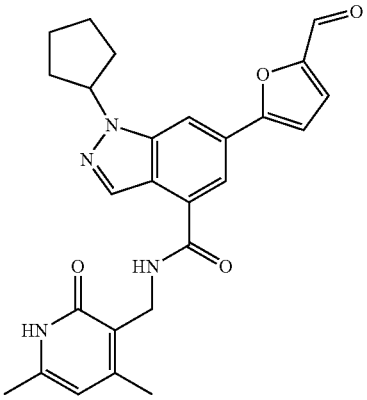 [SMILES: Cc1cc(C)c(CNC(=O)c2cc(-c3ccc(C=O)o3)cc3c2cnn3C2CCCC2)c(=O)[nH]1]

To a stirred solution of 1-cyclopentyl-N-((4,6-dimethyl-2-oxo-1,2-dihydropyridin-3-yl)methyl)-6-(4-formyl-2-methylphenyl)-1H-indazole-4-carboxamide (0.15 g, 0.31 mmol) in methanol (5 mL), morpholine (0.081 g, 0.93 mmol) and acetic acid (0.01 g, 0.311 mmol) were added at room temperature and reaction stirred at room temperature for 18 h. Then NaBH$_3$CN (0.023 g, 0.37 mmol) was added and reaction stirred again at room temperature for 18 h. On completion, methanol was removed under reduced pressure and water added to the residue. The aqueous phase was extracted with 10% MeOH/DCM and the combined organic layers dried over sodium sulfate and concentrated to obtain crude material which was purified by column chromatography to afford 1-cyclopentyl-N-((4,6-dimethyl-2-oxo-1,2-dihydropyridin-3-yl)methyl)-6-(2-methyl-4-(morpholinomethyl)phenyl)-1H-indazole-4-carboxamide (34% yield). LCMS: 554.30 (M+1)$^+$; HPLC: 95.54% (@ 254 nm) (R$_t$: 5.595); $^1$H NMR (DMSO-d$_6$, 400 MHz) δ 11.49 (s, 1H), 8.52 (t, 1H), 8.38 (s, 1H), 7.78 (s, 1H), 7.54 (s, 1H), 7.02-7.28 (m, 3H), 5.86 (s, 1H), 5.22-5.26 (m, 1H), 4.34 (d, 2H, J=4.4 Hz), 3.58 (t, 4H), 3.47 (s, 2H), 2.37 (s, 4H), 2.25 (s, 3H), 2.18 (s, 3H), 2.09-2.06 (m, 2H), 2.09 (s, 3H), 1.98-2.03 (m, 2H), 1.86 (m, 2H), 1.66-1.69 (m, 2H).

Synthesis of Compound C-7: 1-cyclopentyl-N-((4,6-dimethyl-2-oxo-1,2-dihydropyridin-3-yl)methyl)-6-(5-(((2-(methylsulfonyl)ethyl)amino)methyl)furan-2-yl)-1H-indazole-4-carboxamide Compound C-7

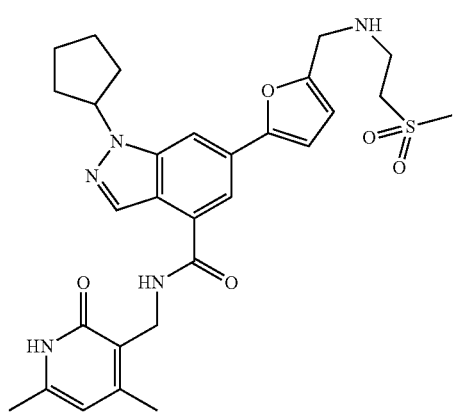

To a stirred solution of 6-bromo-1-cyclopentyl-N-((4,6-dimethyl-2-oxo-1,2-dihydropyridin-3-yl)methyl)-1H-indazole-4-carboxamide (0.2 g, 0.45 mmol) and (5-formylfuran-2-yl)boronic acid (0.075 g, 0.542 mmol), in dioxane/water mixture (4 mL+1 mL), Cs$_2$CO$_3$ (0.368 g, 1.13 mmol) was added and solution purged with argon for 15 min. Pd(PPh$_3$)$_4$ (0.052 g, 0.045 mmol) was then added and argon was purged again for 10 min. The reaction mixture was heated at 100° C. for 2 h. On completion, the reaction mixture was diluted with water and extracted with 10% MeOH/DCM. The combined organic layers were dried over Na$_2$SO$_4$ and solvent removed under reduced pressure to afford crude material which was purified by column chromatography to afford 1-cyclopentyl-N-((4,6-dimethyl-2-oxo-1,2-dihydropyridin-3-yl)methyl)-6-(5-formylfuran-2-yl)-1H-indazole-4-carboxamide (0.09 g, 43.4%).

Step 2: 2-(methylsulfonyl)ethanamine

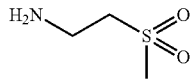

To a stirred solution of 2-(methylsulfonyl)acetonitrile (1 g, 8.40 mmol) in dry THF (20 mL), borane DMS (1.2 g, 16.8 mmol) was added under cooling condition very slowly. Resulting reaction mixture was heated at 40° C. for 2 h and then at room temperature for 12 h. After 12 h MeOH (20 mL) was added at 0° C. very slowly and reaction mixture was refluxed at 80° C. for 1 h. MeOH was removed using reduced pressure and again MeOH (5 mL) was added and heated for 1 h. After 1 h MeOH was removed under reduced pressure and dioxane in HCl was added and heated for 1 h at 100° C. On completion, the reaction mixture was cooled and DCM added with the resulting precipitate filtered and washed with 10% MeOH/DCM, giving a white solid which was dried under vacuum to yield 2-(methylsulfonyl)ethanamine (0.95 g, 90%).

Step 3: 1-cyclopentyl-N-((4,6-dimethyl-2-oxo-1,2-dihydropyridin-3-yl)methyl)-6-(5-(((2-(methylsulfonyl)ethyl)amino)methyl)furan-2-yl)-1H-indazole-4-carboxamide

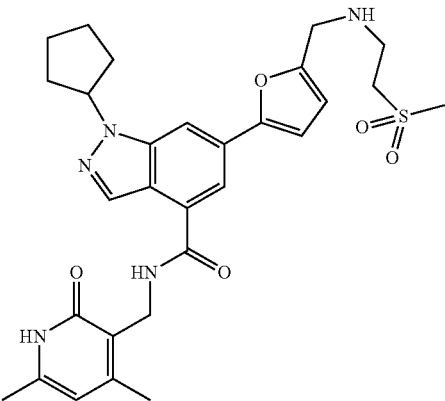

To a stirred solution 1-cyclopentyl-N-((4,6-dimethyl-2-oxo-1,2-dihydropyridin-3-yl)-methyl)-6-(5-formylfuran-2-yl)-1H-indazole-4-carboxamide (0.09 g, 0.19 mmol) in methanol (2 mL), 2-(methylsulfonyl)ethanamine (0.072 g, 0.581 mmol) and DIPEA (0.05 g, 0.39 mmol) was added at room temperature and reaction stirred for 3 h. Then NaBH$_3$CN (0.012 g, 0.196 mmol) was added and reaction stirred at room temperature for 18 h. On completion, methanol was removed under reduced pressure and then water was added to the residue. The aqueous phase was extracted with 10% MeOH/DCM and the combined organic layers were dried over sodium sulfate and concentrated to obtain crude material which was purified by column chromatography to afford 1-cyclopentyl-N-((4,6-dimethyl-2-oxo-1,2-dihydropyridin-3-yl)methyl)-6-(5-(((2-(methylsulfonyl)ethyl)amino)methyl)furan-2-yl)-1H-indazole-4-carboxamide. LCMS: 566.90 (M+1)$^+$; HPLC: 90.05% (@ 254 nm) (R$_t$; 5.253); $^1$H NMR (MeOD, 400 MHz) δ 8.31 (s, 1H), 8.07 (s, 1H), 7.87 (s, 1H), 6.92 (s, 1H), 6.44 (s, 1H), 6.13 (s, 1H), 5.18-5.42 (m, 1H), 4.59 (s, 2H), 4.57 (s, 2H), 3.91 (s, 2H), 3.16 (t, 2H, J=6.4 Hz), 3.02 (s, 3H), 2.42 (s, 3H), 2.25 (s, 3H), 2.19-2.23 (m, 2H), 2.11-2.14 (m, 2H), 1.98 (m, 2H), 1.80 (m, 2H).

Synthesis of Compounds C-8 and C-9: 1-cyclopentyl-N-((4,6-dimethyl-2-oxo-1,2-dihydropyridine-3-yl)methyl)-6-(3-(hydroxymethyl)phenyl)-1H-indazole-4-carboxamide and 1-cyclopentyl-N-((4,6-dimethyl-2-oxo-1,2-dihydropyridin-3-yl)methyl)-6-(3-(((2-hydroxyethyl)amino)methyl)phenyl)-1H-indazole-4-carboxamide Compound C-8

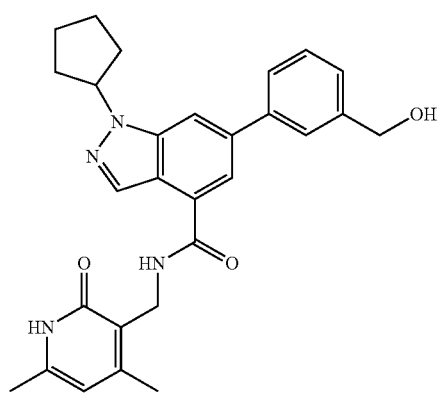

C-Compound 9

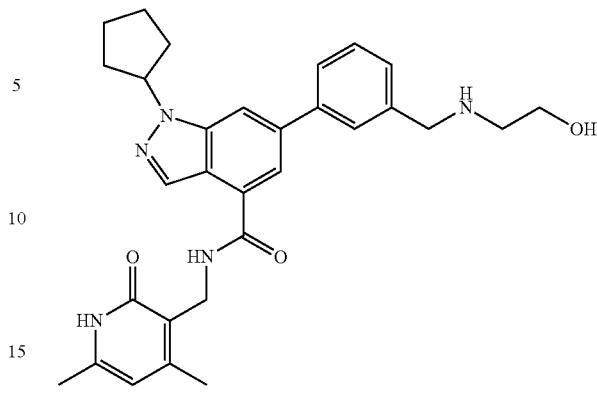

Step 1: 1-cyclopentyl-N-((4,6-dimethyl-2-oxo-1,2-dihydropyridine-3-yl)methyl)-6-(3-(hydroxymethyl)phenyl)-1H-indazole-4-carboxamide Compound C-8

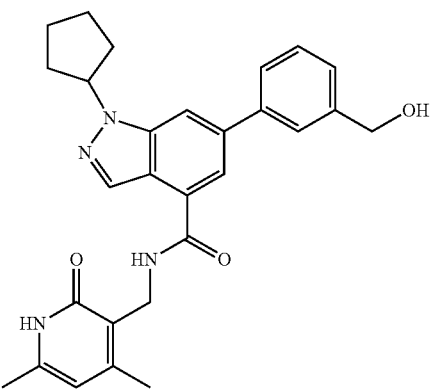

A solution of 6-bromo-1-cyclopentyl-N-((4,6-dimethyl-2-oxo-1,2-dihydropyridin-3-yl)methyl)-1H-indazole-4-carboxamide (1.5 g, 3.4 mmol), 3-hydroxyphenyl boronic acid (0.614 g, 4.07 mmol) and Pd(PPh$_3$)$_4$ (0.391 g, 0.33 mmol) in 1,4-dioxane (20 mL) was purged with argon for 10 min. Then, 2 M Na$_2$CO$_3$ solution (1.29 g, 12.21 mmol) was added to it and argon was purged again for 10 min. The reaction mixture was stirred at 80° C. for 2 h. After completion of the reaction, water was added to it and extraction carried out using DCM. The combined organic layers were washed with water, dried over anhydrous Na$_2$SO$_4$, filtered and concentrated under reduced pressure to afford crude material which was purified by column chromatography over silica gel (60-120 mesh size) to afford 1-cyclopentyl-N-((4,6-dimethyl-2-oxo-1,2-dihydropyridine-3-yl)methyl)-6-(3-(hydroxymethyl)phenyl)-1H-indazole-4-carboxamide (1.2 g, 75.4%). LCMS: 471.20 (M+1)$^+$; HPLC: 97.18% (@ 254 nm) (R$_t$;6.614); $^1$H NMR (DMSO-d$_6$, 400 MHz) δ 11.51 (s, 1H), 8.63 (t, 1H, J=4.8 Hz), 8.35 (s, 1H), 8.08 (s, 1H), 7.84 (s, 1H), 7.77 (s, 1H), 7.71 (d, 1H, J=7.6 Hz), 7.45 (t, 1H, J=7.6 Hz), 7.36 (d, 1H, J=7.2 Hz), 5.88 (s, 1H), 5.35-5.26 (m, 1H), 5.25 (t, 1H, J=4.4 Hz), 4.60 (d, 2H, J=6 Hz), 4.39 (d, 2H, J=4.4 Hz), 2.21 (s, 3H), 2.18-2.12 (m, 2H), 2.11 (s, 3H), 2.05-1.97 (m, 2H), 1.92-1.86 (m, 2H), 1.74-1.68 (m, 2H).

Step 2: 6-(3-(bromomethyl)phenyl)-1-cyclopentyl-N-((dimethyl-2-oxo-1,2-dihydropyridin-3-yl)methyl)-1H-indazole-4-carboxamide

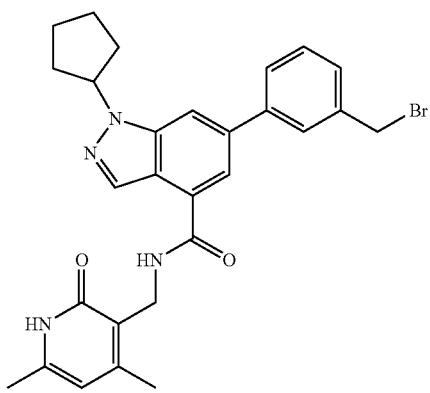 [SMILES: Cc1cc(C)c(CNC(=O)c2cc(-c3cccc(CBr)c3)cc3c2cnn3C2CCCC2)c(=O)[nH]1]

To a stirred solution of 1-cyclopentyl-N-((4,6-dimethyl-2-oxo-1,2-dihydropyridine-3-yl)methyl)-6-(3-(hydroxymethyl)phenyl)-1H-indazole-4-carboxamide (1.2 g, 2.6 mmol) in DCM (15 mL), triphenyl phosphine (2 g, 7.7 mmol) was added and reaction mixture stirred at room temperature for 10 min. Finally CBr$_4$ (2.53 g, 7.65 mmol) was added portion-wise and resulting solution was stirred at room temperature for 18 h. On completion, water was added to the reaction mixture and aqueous layer extracted with 10% MeOH/DCM. Combined organic layer was dried over sodium sulfate and concentrated to give crude material which was purified by column chromatography over silica gel (60-120 mesh size) to afford 6-(3-(bromomethyl)phenyl)-1-cyclopentyl-N-((dimethyl-2-oxo-1,2-dihydropyridin-3-yl)methyl)-1H-indazole-4-carboxamide (1.0 g, 74.1%).

Step 3: 1-cyclopentyl-N-((4,6-dimethyl-2-oxo-1,2-dihydropyridin-3-yl)methyl)-6-(3-(((2-hydroxyethyl)amino)methyl)phenyl)-1H-indazole-4-carboxamide Compound C-9

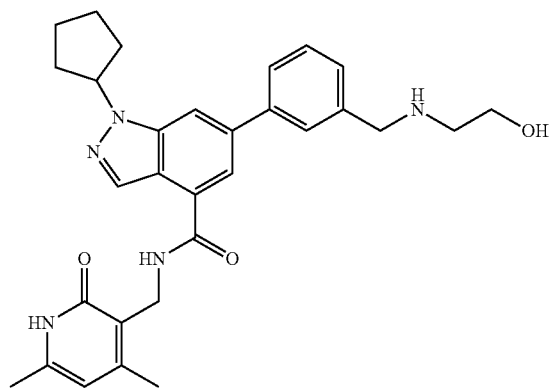

6-(3-(bromomethyl)phenyl)-1-cyclopentyl-N-((dimethyl-2-oxo-1,2-dihydropyridin-3-yl)methyl)-1H-indazole-4-carboxamide was reacted with 2-aminoethanol using a general procedure for amination of benzyl bromides to afford the target compound as a TFA salt (19.3% yield). LCMS: 514.20 (M+1)$^+$; HPLC: 98.23% (@ 254 nm) (R$_t$;5.465); $^1$H NMR (DMSO-d$_6$, 400 MHz) δ 11.53 (s, 1H), 8.91 (bs, 2H), 8.58 (t, 1H, J=4.8 Hz), 8.35 (s, 1H), 8.11 (s, 1H), 7.98 (s, 1H), 7.78 (d, 1H, J=7.2 Hz), 7.87 (s, 1H), 7.52-7.58 (m, 2H), 5.89 (s, 1H), 5.26-5.32 (m, 2H), 4.38 (d, 2H, J=4.4 Hz), 4.27 (t, 2H), 3.67 (t, 2H, J=4.8 Hz), 3.02 (m, 2H), 2.23 (s, 3H), 2.15-2.18 (m, 2H), 2.12 (s, 3H), 1.90-2.08 (m, 4H), 1.70-1.73 (m, 2H).

Synthesis of Compound C-10: 1-cyclopentyl-N-((4,6-dimethyl-2-oxo-1,2-dihydropyridin-3-yl)methyl)-6-(3-(3-(methylamino)propoxy)phenyl)-1H-indazole-4-carboxamide Compound C-10

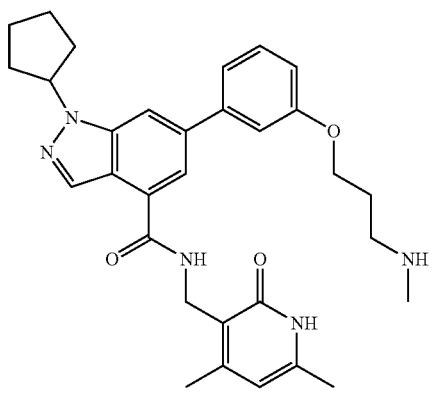

Step 1: Synthesis of methyl 1-cyclopentyl-6-(3-hydroxyphenyl)-1H-indazole-4-carboxylate

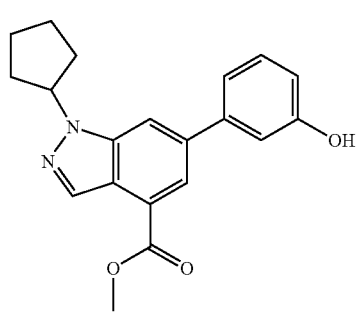 [SMILES: COC(=O)c1cc(-c2cccc(O)c2)cc2c1cnn2C1CCCC1]

A solution of methyl 6-bromo-1-cyclopentyl-1H-indazole-4-carboxylate (1 g, 3.93 mmol), (3-hydroxyphenyl)boronic acid (1.43 g, 4.72 mmol) and Pd(PPh$_3$)$_4$ (0.227 g, 0.196 mmol) in 1,4-dioxane (10.5 mL) was purged with argon for 10 min. Then, 2 M Na$_2$CO$_3$ solution (1.5 g, 14.2 mmol) was added to it and again argon was purged through it for 10 min. The reaction mixture was stirred at 100° C. for 1 h. After completion of the reaction, water was added to it and extraction was carried out using 5% MeOH/DCM. The combined organic layers were washed with water, dried over anhydrous Na$_2$SO$_4$, filtered and concentrated under reduced pressure to afford crude material which was purified by column chromatography over silica gel (60-120 mesh size) to afford the title compound (0.8 g, 61%).

Step 2: methyl 1-cyclopentyl-6-(3-(3-hydroxy-propoxy)phenyl)-1H-indazole-4-carboxylate

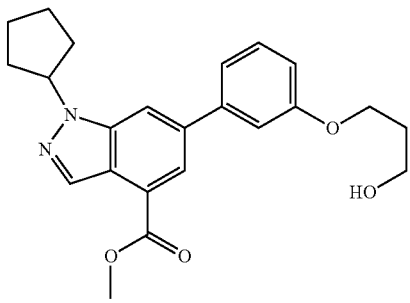 [SMILES: COC(=O)c1cc(-c2cccc(OCCCO)c2)cc2c1cnn2C1CCCC1]

To a stirred solution of methyl 1-cyclopentyl-6-(3-(3-hydroxypropoxy)phenyl)-1H-indazole-4-carboxylate (0.30 g, 0.89 mmol) in DMF (5 mL), 3-bromopropane-1-ol (0.37 g, 2.67 mmol) and $K_2CO_3$ (0.184 g, 1.33 mmol) were added and the resulting reaction mixture heated at 100° C. for 18 h. On completion, water was added to reaction mixture and extracted with 10% MeOH/DCM. Combined organic layers were dried and concentrated under reduced pressure giving crude material which was purified by column chromatography over silica gel to afford methyl 1-cyclopentyl-6-(3-(3-hydroxypropoxy)phenyl)-1H-indazole-4-carboxylate (0.2 g, 57%).

Step 3: 1-cyclopentyl-N-((4,6-dimethyl-2-oxo-1,2-dihydropyridin-3-yl)methyl)-6-(3-(3-hydroxypropoxy)phenyl)-1H-indazole-4-carboxamide

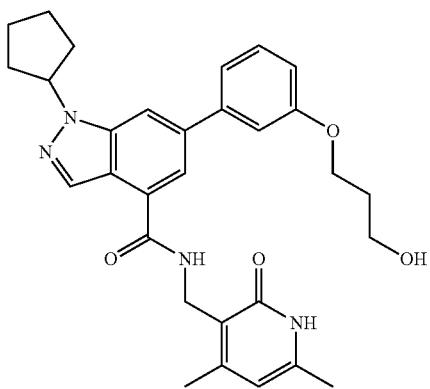

Aqueous NaOH (0.06 g, 1.52 mmol) was added to a solution methyl 1-cyclopentyl-6-(3-(3-hydroxypropoxy) phenyl)-1H-indazole-4-carboxylate (0.4 g, 1.0 mmol) in EtOH (4 mL) and stirred at 60° C. for 1 h. After completion of the reaction, ethanol was removed under reduced pressure and acidified using dilute HCl up to pH 6 and then with citric acid to pH 4. The solid precipitate was filtered and dried under vacuum to afford desired acid (0.35 g, 90%). The acid (0.35 g, 0.923 mmol) was then dissolved in DMSO (5 mL) and 3-(aminomethyl)-4,6-dimethylpyridin-2(1H)-one (0.28 g, 1.84 mmol) was added to it. The reaction mixture was stirred at room temperature for 15 min before PyBOP (0.72 g, 1.38 mmol) was added to it and stirring was continued for overnight. On completion, reaction mixture was poured into ice and extracted with 10% MeOH/DCM. Combined organic layers were dried and concentrated under reduced pressure giving crude material which was purified by column chromatography over silica gel (60-120 mesh size) to afford 1-cyclopentyl-N-((4,6-dimethyl-2-oxo-1,2-dihydropyridin-3-yl)methyl)-6-(3-(3-hydroxypropoxy)phenyl)-1H-indazole-4-carboxamide (0.35 g, 73%).

Step 4: 6-(3-(3-bromopropoxy)phenyl)-1-cyclopentyl-N-((4,6-dimethyl-2-oxo-1,2-dihydropyridin-3-yl)methyl)-1H-indazole-4-carboxamide

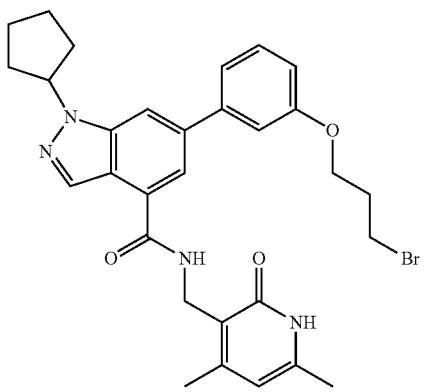 [SMILES: Cc1cc(C)c(CNC(=O)c2cc(-c3cccc(OCCCBr)c3)cc3c2cnn3C2CCCC2)c(=O)[nH]1]

To a stirred solution of 1-cyclopentyl-N-((4,6-dimethyl-2-oxo-1,2-dihydropyridin-3-yl)methyl)-6-(3-(3-hydroxypropoxy)phenyl)-1H-indazole-4-carboxamide (0.35 g, 0.68 mmol) in DCM (5 mL), triphenyl phosphine (0.285 g, 1.08 mmol) was added and the reaction mixture stirred at room temperature for 10 min. Finally $CBr_4$ (0.36 g, 1.08 mmol) was added portion wise and resulting solution was stirred at room temperature for 4 h. On completion, water was added to the reaction mixture and extracted with 5% MeOH/DCM. The combined organic layer was dried over sodium sulfate and concentrated to give crude material which was purified by column chromatography over silica gel to afford 6-(3-(3-bromopropoxy)phenyl)-1-cyclopentyl-N-((4,6-dimethyl-2-oxo-1,2-dihydropyridin-3-yl)methyl)-1H-indazole-4-carboxamide (0.28 g, 71%).

Step 5: 1-cyclopentyl-N-((4,6-dimethyl-2-oxo-1,2-dihydropyridin-3-yl)methyl)-6-(3-(3-(methylamino)propoxy)phenyl)-1H-indazole-4-carboxamide

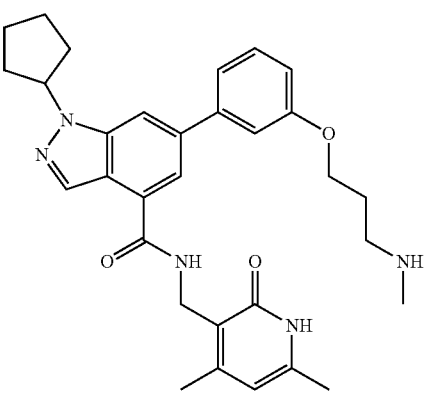 [SMILES: CNCCCOc1cccc(-c2cc(C(=O)NCc3c(C)cc(C)[nH]c3=O)c3cnn(C4CCCC4)c3c2)c1]

To a stirred solution of 6-(3-(3-bromopropoxy)phenyl)-1-cyclopentyl-N-((4,6-dimethyl-2-oxo-1,2-dihydropyridin-3-yl)methyl)-1H-indazole-4-carboxamide (1 equiv.) in THF, methylamine (3 equiv. in THF) was added and resulting reaction mass was heated at 60° C. in a sealed flask. On completion, solvent was removed under reduced pressure and crude material obtained was purified by preparative HPLC affording 1-cyclopentyl-N-((4,6-dimethyl-2-oxo-1,2-dihydropyridin-3-yl)methyl)-6-(3-(3-(methylamino)propoxy)phenyl)-1H-indazole-4-carboxamide as the TFA salt (22% yield). LCMS: 528.29 (M+1)$^+$; HPLC: 97.33% (@ 254 nm) (R$_t$;5.863); $^1$H NMR (DMSO-d$_6$, 400 MHz) δ 11.51 (s, 1H), 8.63 (t, 1H), 8.35-8.37 (m, 3H), 8.10 (s, 1H), 7.82 (s, 1H), 7.38-7.46 (m, 3H), 6.99 (d, 1H, J=7.2 Hz), 5.88 (s, 1H), 5.30-5.37 (m, 1H), 4.37 (d, 2H, J=4.8 Hz), 4.16 (t, 2H, J=6 Hz), 3.06-3.19 (m, 3H), 2.61 (t, 3H, J=5.2 Hz), 2.22 (s, 3H), 2.13-2.17 (m, 2H), 2.11 (s, 3H), 1.97-2.09 (m, 3H), 1.84-1.89 (m, 2H), 1.69-1.72 (m, 2H).

Synthesis of Compound C-11: 1-cyclopentyl-N-((4,6-dimethyl-2-oxo-1,2-dihydropyridin-3-yl)methyl)-6-(3-(3-(dimethylamino)propoxy)phenyl)-1H-indazole-4-carboxamide Compound C-11

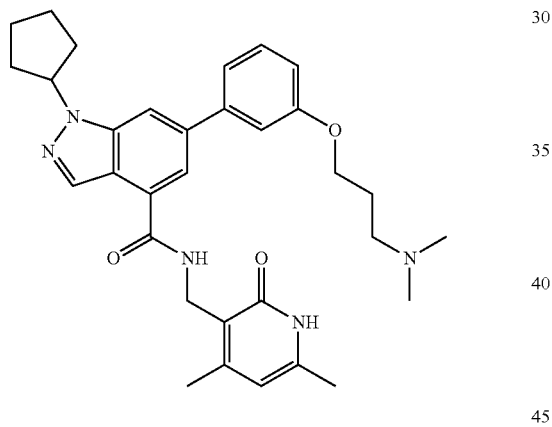

To a stirred solution of 6-(3-(3-bromopropoxy)phenyl)-1-cyclopentyl-N-((4,6-dimethyl-2-oxo-1,2-dihydropyridin-3-yl)methyl)-1H-indazole-4-carboxamide (1 equiv.) in THF, dimethylamine (3 equiv. in THF) was added and resulting reaction mass was heated at 60° C. in a sealed flask. On completion, solvent was removed under reduced pressure and crude material obtained was purified by preparative HPLC affording 1-cyclopentyl-N-((4,6-dimethyl-2-oxo-1,2-dihydropyridin-3-yl)methyl)-6-(3-(3-(methylamino)propoxy)phenyl)-1H-indazole-4-carboxamide as the TFA salt (23% yield). LCMS: 542.25 (M+1)$^+$; HPLC: 98.61% (@ 254 nm) (R$_t$;5.936); $^1$H NMR (DMSO-d$_6$, 400 MHz) δ 11.51 (s, 1H), 9.38 (bs, 1H), 8.62 (t, 1H, J=4.4 Hz), 8.35 (s, 1H), 8.10 (s, 1H), 7.82 (s, 1H), 7.38-7.46 (m, 3H), 6.99 (d, 1H, J=7.6 Hz), 5.88 (s, 1H), 5.30-5.37 (m, 1H), 4.37 (d, 2H, J=4.4 Hz), 4.15 (t, 2H, J=6 Hz), 3.23-3.28 (m, 2H), 2.83 (d, 6H, J=4.8 Hz), 2.22 (s, 3H), 2.13-2.16 (m, 4H), 2.11 (s, 3H), 1.89-2.05 (m, 4H), 1.69-1.72 (m, 2H).

Synthesis of Compound C-12: 1-cyclopentyl-N-((4,6-dimethyl-2-oxo-1,2-dihydropyridin-3-yl)methyl)-6-(4-(3-(methylamino)propoxy)phenyl)-1H-indazole-4-carboxamide Compound C-12

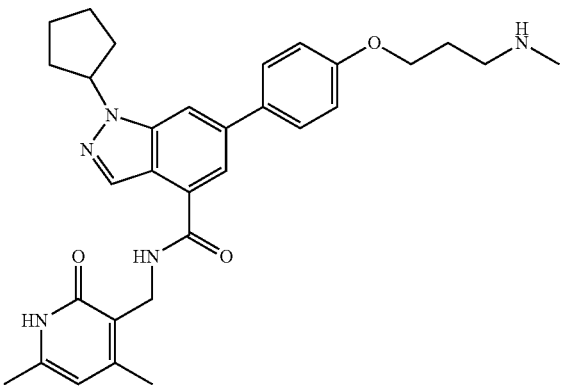

Step 1: methyl 1-cyclopentyl-6-(4-hydroxyphenyl)-1H-indazole-4-carboxylate

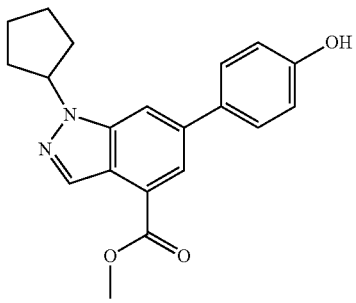 [SMILES: COC(=O)c1cc(-c2ccc(O)cc2)cc2c1cnn2C1CCCC1]

A solution of methyl 6-bromo-1-cyclopentyl-1H-indazole-4-carboxylate (1.5 g, 4.6 mmol), (4-hydroxyphenyl)boronic acid (0.768 g, 5.56 mmol) and Pd(PPh$_3$)$_4$ (0.536 g, 0.464 mmol) in 1,4-dioxane (15 mL) was purged with argon for 10 min. Then, 2 M Na$_2$CO$_3$ solution (1.77 g, 16.7 mmol) was added to it and again argon was purged through it for 10 min. The reaction mixture was stirred at 100° C. for 2 h. After completion of the reaction, water was added to it and extraction was carried out using 5% MeOH in DCM. The combined organic layers were washed with water, dried over anhydrous Na$_2$SO$_4$, filtered and concentrated under reduced pressure to afford crude material which was purified by column chromatography over silica gel to afford methyl 1-cyclopentyl-6-(4-hydroxyphenyl)-1H-indazole-4-carboxylate (1.1 g, 71%).

Step 2: methyl 1-cyclopentyl-6-(4-(3-hydroxy-propoxy)phenyl)-1H-indazole-4-carboxylate

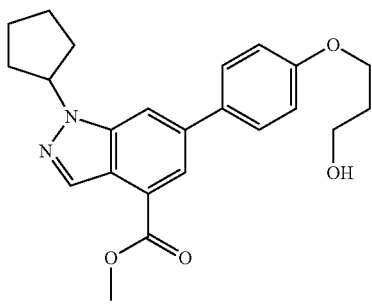 [SMILES: COC(=O)c1cc(-c2ccc(OCCCO)cc2)cc2c1cnn2C1CCCC1]

To a stirred solution of methyl 1-cyclopentyl-6-(4-hydroxyphenyl)-1H-indazole-4-carboxylate (0.5 g, 1.48 mmol) in DMF (15 mL), 3-bromopropane-1-ol (0.616 g, 4.46 mmol) and K2CO3 (0.306 g, 2.23 mmol) were added, resulting reaction mass was heated at 100° C. for 4 h. On completion, water was added to reaction mass and extracted with ethyl acetate. Combined organic layers were dried and concentrated under reduced pressure giving crude material which was purified by column chromatography over silica gel (60-120 mesh size) to afford methyl 1-cyclopentyl-6-(4-(3-hydroxypropoxy)phenyl)-1H-indazole-4-carboxylate (0.4 g, 68.2%).

Step 3: 1-cyclopentyl-N-((4,6-dimethyl-2-oxo-1,2-dihydropyridin-3-yl)methyl)-6-(4-(3-hydroxypropoxy)phenyl)-1H-indazole-4-carboxamide

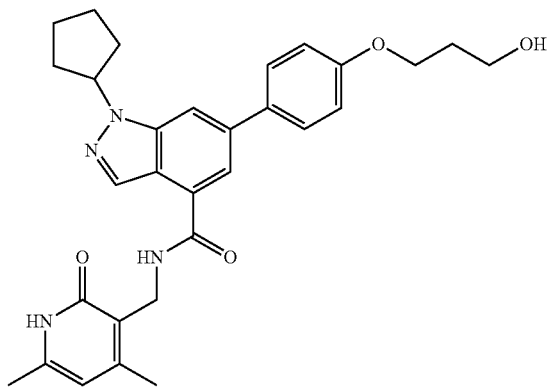 [SMILES: Cc1cc(C)c(CNC(=O)c2cc(-c3ccc(OCCCO)cc3)cc3c2cnn3C2CCCC2)c(=O)[nH]1]

Aqueous NaOH (0.06 g, 1.52 mmol) was added to a solution of methyl 1-cyclopentyl-6-(4-(3-hydroxypropoxy)phenyl)-1H-indazole-4-carboxylate (0.4 g, 1.01 mmol) in EtOH (4 mL) and stirred at 60° C. for 1 h. After completion of the reaction, ethanol was removed under reduced pressure and acidified using dilute HCl up to pH 6 and then with citric acid to pH 4. The solid precipitate was filtered and dried under vacuum to afford desired acid (0.23 g, 59.57%). The acid (0.23 g, 0.61 mmol) was then dissolved in DMSO (5 mL) and 3-(aminomethyl)-4,6-dimethylpyridin-2(1H)-one (0.183 g, 1.21 mmol) was added to it. The reaction mixture was stirred at room temperature for 15 min before PyBOP (0.472 g, 0.907 mmol) was added to it and stirring was continued for overnight. After completion, reaction mass was poured into ice to and extracted with 10% MeOH/DCM. Combined organic layers were dried and concentrated under reduced pressure giving crude material which was purified by column chromatography over silica gel (60-120 mesh size) to afford 1-cyclopentyl-N-((4,6-dimethyl-2-oxo-1,2-dihydropyridin-3-yl)methyl)-6-(4-(3-hydroxypropoxy)phenyl)-1H-indazole-4-carboxamide (0.23 g, 87.8%).

Step 4: 1-cyclopentyl-N-((4,6-dimethyl-2-oxo-1,2-dihydropyridin-3-yl)methyl)-6-(4-(3-(methylamino)propoxy)phenyl)-1H-indazole-4-carboxamide

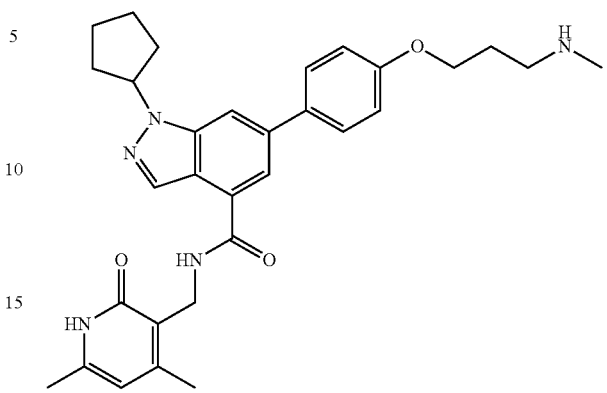

To a stirred solution of 1-cyclopentyl-N-((4,6-dimethyl-2-oxo-1,2-dihydropyridin-3-yl)methyl)-6-(4-(3-hydroxypropoxy)phenyl)-1H-indazole-4-carboxamide (0.115 g, 0.265 mmol) in DCM (5 mL), triphenyl phosphine (0.137 g, 0.525 mmol) was added and reaction stirred at room temperature for 10 min. Finally CBr4 (0.173 g, 0.525 mmol) was added portion wise to it and resulting solution was stirred at room temperature for 4 h. On completion, methyl amine (2M solution in THF, 1.32 mmol) was added and reaction stirred at room temperature for 18 h and then heated at 60° C. for 12 h. On completion, solvents were removed under reduced pressure giving crude material which was purified by preparative HPLC to afford 1-cyclopentyl-N-((4,6-dimethyl-2-oxo-1,2-dihydropyridin-3-yl)methyl)-6-(4-(3-(methylamino)propoxy)phenyl)-1H-indazole-4-carboxamide as the TFA salt (16.9% yield). LCMS: 528.95 (M+1)$^+$; HPLC: 95.55% (@ 254 nm) (R$_t$:5.670); $^1$H NMR (DMSO-d$_6$, 400 MHz) δ 11.52 (s, 1H), 8.60 (t, 1H, J=5.2 Hz), 8.32-8.35 (m, 3H), 8.05 (s, 1H), 7.81-7.84 (m, 3H), 7.06 (d, 2H, J=8.4 Hz), 5.89 (s, 1H), 5.29-5.33 (m, 1H), 4.37 (d, 2H, J=4.8 Hz), 4.12 (t, 2H, J=6 Hz), 3.07-3.12 (m, 2H), 2.60-2.67 m, 3H), 2.21 (s, 3H), 2.14-2.20 (m, 2H), 2.12 (s, 3H), 1.97-2.08 (m, 4H), 1.88 (m, 2H), 1.69-1.72 (m, 2H).

Synthesis of Compound C-13: (R)-6-(4-((2-carbamoylpyrrolidin-1-yl)methyl)phenyl)-1-cyclopentyl-N-((4,6-dimethyl-2-oxo-1,2-dihydropyridin-3-yl)methyl)-1H-indazole-4-carboxamide Compound C-13

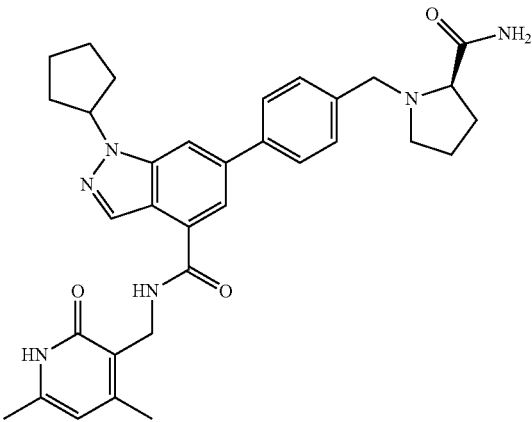

Step 1: Synthesis of 1-cyclopentyl-N-((4,6-dimethyl-2-oxo-1,2-dihydropyridin-3-yl)methyl)-6-(4-formylphenyl)-1H-indazole-4-carboxamide

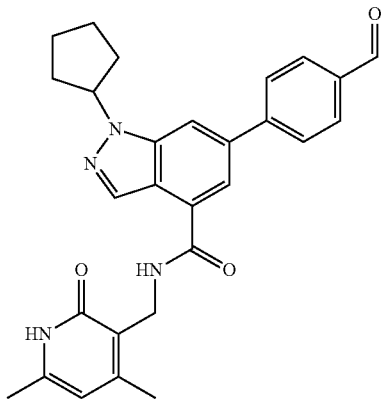 [SMILES: Cc1cc(C)c(CNC(=O)c2cc(-c3ccc(C=O)cc3)cc3c2cnn3C2CCCC2)c(=O)[nH]1]

A solution of 6-bromo-1-cyclopentyl-N-((4,6-dimethyl-2-oxo-1,2-dihydropyridin-3-yl)methyl)-1H-indazole-4-carboxamide (0.7 g, 1.6 mmol), 4-formyl boronic acid (0.26 g, 1.73 mmol) and Pd(PPh$_3$)$_4$ (0.182 g, 0.158 mmol) in 1,4-dioxane (10.5 mL) was purged with argon for 10 min. Then, 2 M Na$_2$CO$_3$ solution (0.60 g, 5.61 mmol) was added to it and again argon was purged through it for 10 min. The reaction mixture was stirred at 100° C. for 2 h. After completion of the reaction, water was added to it and extraction was carried out using 5% MeOH in DCM. The combined organic layers were washed with water, dried over anhydrous Na$_2$SO$_4$, filtered and concentrated under reduced pressure to afford crude material which was purified by column chromatography over silica gel (60-120 mesh size) to afford Synthesis of 1-cyclopentyl-N-((4,6-dimethyl-2-oxo-1,2-dihydropyridin-3-yl)methyl)-6-(4-formylphenyl)-1H-indazole-4-carboxamide (0.68 g, 92.6%).

Step 2: (R)-6-(4-((2-carbamoylpyrrolidin-1-yl)methyl)phenyl)-1-cyclopentyl-N-((4,6-dimethyl-2-oxo-1,2-dihydropyridin-3-yl)methyl)-1H-indazole-4-carboxamide

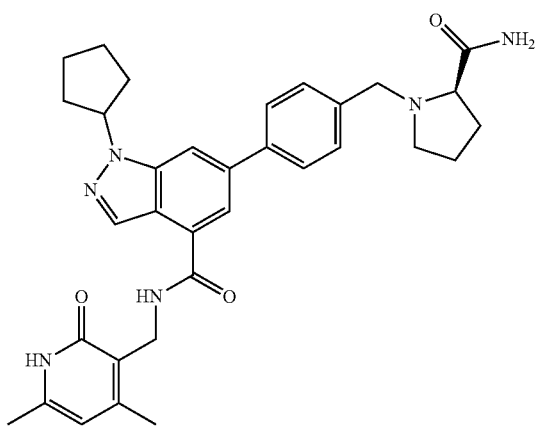 [SMILES: Cc1cc(C)c(CNC(=O)c2cc(-c3ccc(CN4CCC[C@@H]4C(N)=O)cc3)cc3c2cnn3C2CCCC2)c(=O)[nH]1]

To a stirred solution of 1-cyclopentyl-N-((4,6-dimethyl-2-oxo-1,2-dihydropyridin-3-yl)methyl)-6-(4-formylphenyl)-1H-indazole-4-carboxamide (0.175 g, 0.373 mmol) in methanol (3 mL) acetic acid (0.022 g, 0.373 mmol) and respective amine [[[amine quantity?]]] was added, resulting reaction mass was stirred at room temperature for 4 h. To this reaction mixture sodium cyanoborohydride (0.028 g, 0.448 mmol) was added at cooling condition and reaction mixture was stirred at room temperature for 48 h. On completion solvent was removed under reduced pressure and water was added to it, and then extracted with 10% MeOH/DCM. Combined organic layers were washed with water, dried over anhydrous Na$_2$SO$_4$, filtered and concentrated under reduced pressure to afford crude. The crude was purified by prep HPLC affording desired compound as TFA salt (12.3% yield). LCMS: 567.30 (M+1)$^+$; HPLC: 97.31% (@ 254 nm) (R$_t$:5.366); $^1$H NMR (DMSO-d$_6$, 400 MHz) δ 11.52 (s, 1H), 9.71 (s, 1H), 8.64 (t, 1H, J=4.4 Hz), 8.37 (s, 1H), 8.17 (s, 1H), 7.94-7.97 (m, 3H), 7.87 (s, 1H), 7.61-7.67 (m, 3H), 5.89 (s, 1H), 5.31-5.38 (m, 1H), 4.38-4.45 (m, 4H), 4.41-4.13 (m, 1H), 3.32 (2H merged in solvent peak), 2.22 (s, 3H), 2.14-2.21 (m, 3H), 2.12 (s, 3H), 1.82-2.08 (m, 7H), 1.70-1.72 (m, 2H).

Synthesis of Compound C-14: 1-cyclopentyl-N-((4,6-dimethyl-2-oxo-1,2-dihydropyridin-3-yl)methyl)-6-(2-ethoxy-4-((4-ethylpiperazin-1-yl)sulfonyl)phenyl)-1H-indazole-4-carboxamide Compound C-14

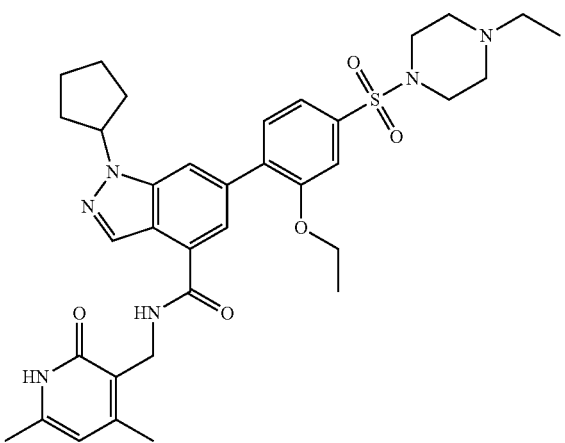 [SMILES: CCOc1cc(S(=O)(=O)N2CCN(CC)CC2)ccc1-c1cc(C(=O)NCc2c(C)cc(C)[nH]c2=O)c2cnn(C3CCCC3)c2c1]

Step 1: 1-cyclopentyl-N-((4,6-dimethyl-2-oxo-1,2-dihydropyridin-3-yl)methyl)-6-(4,4,5,5-tetramethyl-1,3,2-dioxaborolan-2-yl)-1H-indazole-4-carboxamide

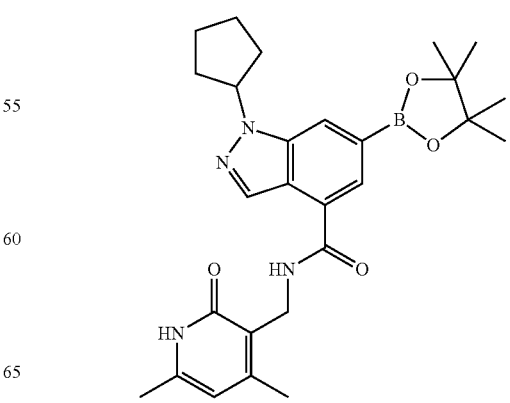

A solution of methyl 6-bromo-1-cyclopentyl-1H-indazole-4-carboxylate (1 g, 2.2 mmol), bis(pinacolato)diboron (2.78 g, 10.9 mmol) and potassium acetate (0.64 g, 6.5 mmol) in DMSO (15 mL) was purged with argon for 15 min. Then $Pd_2Cl_2$(dppf).DCM (0.089 g, 0.11 mmol) was added. Resulting reaction mixture was stirred at 80° for 4 h. On completion, reaction was diluted with ethyl acetate and washed thoroughly with water, brine and dried over sodium sulfate. Solvent was removed to obtain crude material which was purified by column chromatography over silica gel affording 1-cyclopentyl-N-((4,6-dimethyl-2-oxo-1,2-dihydropyridin-3-yl)methyl)-6-(4,4,5,5-tetramethyl-1,3,2-dioxaborolan-2-yl)-1H-indazole-4-carboxamide (0.8 g, 72.7%).

Step 2: 1-cyclopentyl-N-((4,6-dimethyl-2-oxo-1,2-dihydropyridin-3-yl)methyl)-6-(2-ethoxy-4-((4-ethylpiperazin-1-yl)sulfonyl)phenyl)-1H-indazole-4-carboxamide

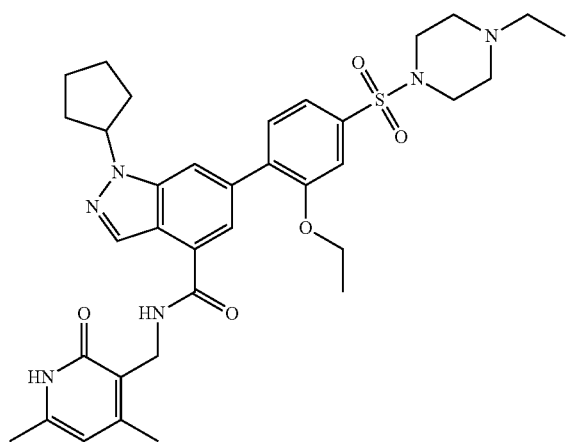

To a stirred solution of 1-cyclopentyl-N-((4,6-dimethyl-2-oxo-1,2-dihydropyridin-3-yl)methyl)-6-(4,4,5,5-tetramethyl-1,3,2-dioxaborolan-2-yl)-1H-indazole-4-carboxamide (1.2 equiv.) and 1-((4-bromo-3-ethoxyphenyl)sulfonyl)-4-ethylpiperazine (1 equiv.) in dioxane/water mixture (5 mL+1 mL), $Na_2CO_3$ (3.6 equiv.) was added and solution purged with argon for 15 min. Then $Pd(PPh_3)_4$ (0.1 equiv.) was added and argon was purged again for 10 min. Reaction mixture was heated at 100° C. for 2 h. On completion, reaction mixture was diluted with water and extracted with 10% MeOH/DCM. Combined organic layers were dried over $Na_2SO_4$ and solvent removed under reduced pressure to afford crude material. The crude was purified by prep HPLC affording desired compound as TFA salt. LCMS: 661.35 (M+1)$^+$; HPLC: 99.73% (@ 254 nm) ($R_t$;6.134); $^1$H NMR (DMSO-d$_6$, 400 MHz) δ 11.51 (s, 1H), 9.10 (bs, 1H), 8.52 (t, 1H, J=4.8 Hz), 8.35 (s, 1H), 7.99 (s, 1H), 7.80 (d, 1H, J=9.2 Hz), 7.79 (s, 1H), 7.63 (s, 1H), 7.43 (d, 1H, J=8.8 Hz), 5.89 (s, 1H), 5.21-5.28 (m, 1H), 4.36 (d, 2H, J=4.4 Hz), 4.20 (q, 2H, J=7.2 Hz), 3.81 (d, 2H, J=12.4 Hz), 3.45 (2H merged in solvent peak), 3.12 (d, 6H, J=5.6 Hz), 2.22 (s, 3H), 2.13-2.21 (m, 2H), 2.12 (s, 3H), 2.0-2.07 (m, 2H), 1.88-1.95 (m, 2H), 1.69-1.75 (m, 2H), 1.29 (t, 3H, J=6.8 Hz), 1.55 (t, 3H, J=7.2 Hz).

Synthesis of Compound C-15: 1-cyclopentyl-N-((4,6-dimethyl-2-oxo-1,2-dihydropyridin-3-yl)methyl)-6-(5-(morpholinomethyl)pyridin-2-yl)-1H-indazole-4-carboxamide Compound C-15

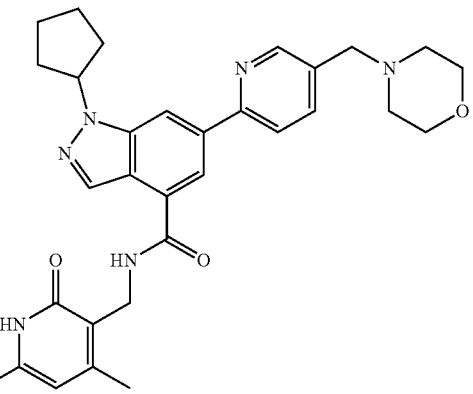

Step 1: 1-cyclopentyl-N-((4,6-dimethyl-2-oxo-1,2-dihydropyridin-3-yl)methyl)-6-(5-formylpyridin-2-yl)-1H-indazole-4-carboxamide

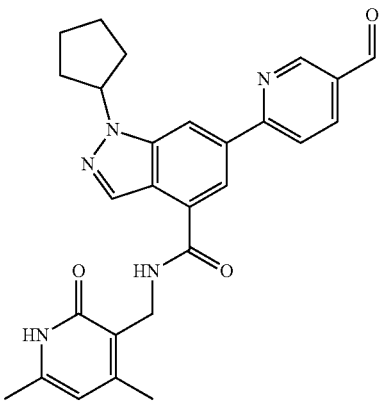 [SMILES: Cc1cc(C)c(CNC(=O)c2cc(-c3ccc(C=O)cn3)cc3c2cnn3C2CCCC2)c(=O)[nH]1]

To a stirred solution of 1-cyclopentyl-N-((4,6-dimethyl-2-oxo-1,2-dihydropyridin-3-yl)methyl)-6-(4,4,5,5-tetramethyl-1,3,2-dioxaborolan-2-yl)-1H-indazole-4-carboxamide (0.15 g, 0.31 mmol) and 6-bromonicotinaldehyde (0.047 g, 0.25 mmol) in dioxane/water mixture (2 mL+0.5 mL), $Cs_2CO_3$ (0.219 g, 0.239 mmol) was added and solution purged with argon for 15 min. Then $Pd(PPh_3)_4$ (0.031 g, 0.025 mmol) was added and argon was purged again for 10 min. Reaction mixture was heated at 100° C. for 2 h. On completion, reaction mixture was diluted with water and extracted with 10% MeOH/DCM. Combined organic layers were dried over $Na_2SO_4$ and solvent removed under reduced pressure to afford crude material which was purified by column chromatography over silica gel to afford 1-cyclopentyl-N-((4,6-dimethyl-2-oxo-1,2-dihydropyridin-3-yl)methyl)-6-(5-formylpyridin-2-yl)-1H-indazole-4-carboxamide (0.053 g, 37%).

Step 2: 1-cyclopentyl-N-((4,6-dimethyl-2-oxo-1,2-dihydropyridin-3-yl)methyl)-6-(5-(morpholinomethyl)pyridin-2-yl)-1H-indazole-4-carboxamide

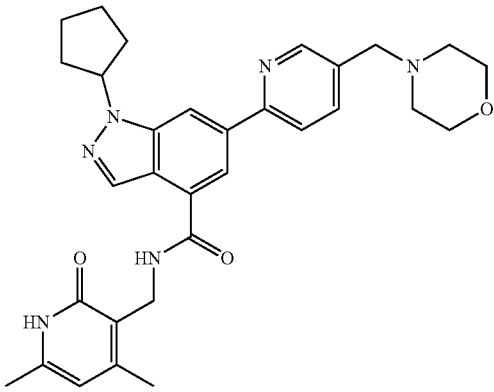 [SMILES: Cc1cc(C)c(CNC(=O)c2cc(-c3ccc(CN4CCOCC4)cn3)cc3c2cnn3C2CCCC2)c(=O)[nH]1]

To a stirred solution of 1-cyclopentyl-N-((4,6-dimethyl-2-oxo-1,2-dihydropyridin-3-yl)methyl)-6-(5-formylpyridin-2-yl)-1H-indazole-4-carboxamide (0.053 g, 0.113 mmol) in methanol (2 mL), morpholine (0.028 g, 0.33 mmol) and acetic acid (0.007 g, 0.113 mmol) were added and reaction mixture stirred at room temperature for 2 h. After this time, reaction mixture was cooled to 0° C. and NaBH₃CN (0.007 g, 0.113 mmol) was added to it. Resulting reaction mixture was stirred again at room temperature for 6 h. On completion, methanol was removed under reduced pressure and residue diluted with water. Aqueous layer was extracted with 20% MeOH/DCM. Combined organic solvent was removed under reduced pressure and residue purified by column chromatography over silica gel affording target 1-cyclopentyl-N-((4,6-dimethyl-2-oxo-1,2-dihydropyridin-3-yl)methyl)-6-(5-(morpholinomethyl)pyridin-2-yl)-1H-indazole-4-carboxamide as off white solid (50.8% yield). LCMS: 541.30 (M+1)⁺; HPLC: 99.93% (@ 254 nm) (R$_t$;5.205); ¹H NMR (MeOD, 400 MHz) δ 7.81 (s, 1H), 7.59 (s, 2H), 7.33 (s, 1H), 7.23 (d, 1H, J=8 Hz), 7.12 (d, 1H, J=7.2 Hz), 5.32 (s, 1H), 4.44-4.47 (m, 1H), 3.78 (s, 2H), 2.90 (m, 4H), 2.82 (s, 2H), 1.71 (m, 4H), 1.61 (s, 3H), 1.44 (s, 3H), 1.35-1.43 (m, 2H), 1.34-1.36 (m, 2H), 1.84 (m, 2H), 0.99 (m, 2H).

Synthesis of Compounds C-16 through C-35

Compounds C-16 through C-35 were synthesized by methods similar to those described for Compounds C-1 through C-15 or by reaction schemes depicted in the general schemes.

Synthesis of Compound D-1: 5-bromo-1-cyclopentyl-N-((4,6-dimethyl-2-oxo-1,2-dihydropyridin-3-yl)methyl)-1H-indazole-4-carboxamide Compound D-1

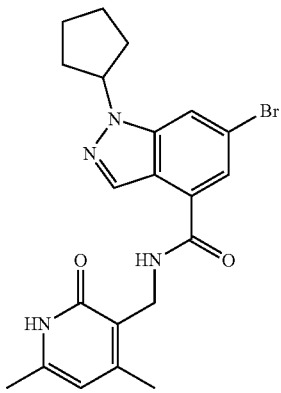

Step 1: Synthesis of 3-(aminomethyl)-4,6-dimethylpyridin-2(1H)-one

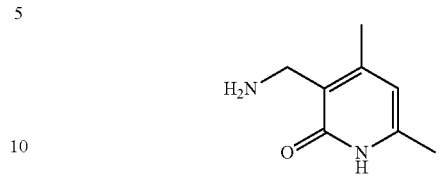

3-Cyano-2,4-dimethyl-2-hydroxypyridine (0.3 g, 2.0 mmol) was dissolved in MeOH (5 mL), to which catalytic amount of Raney Ni and of aqueous NH₃ (0.3 mL) were added and the reaction mixture was stirred under hydrogen pressure (bladder pressure) for 3-4 h. After completion of the reaction, catalyst was filtered off and the filtrate was concentrated under reduced pressure. The residue was thoroughly dried to provide the desired product (0.3 g, quantitative yield).

Step 2: 5-bromo-2-methyl-3-nitrobenzoic acid

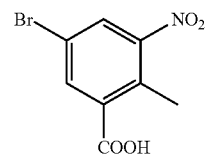

1,3-Dibromo-5,5-dimethyl-2,4-imidazolidinedione (13.0 g, 45.7 mmol) was added to a mixture of 2-methyl-3-nitrobenzoic acid (15 g, 82.8 mmol) in conc. H₂SO₄ (60 mL), and the reaction mixture stirred at room temperature for 5 h. After completion of reaction, the mixture was slowly poured onto ice cold water (400 mL). The precipitated was filtered and dried under vacuum to obtain desired 5-bromo-2-methyl-3-nitrobenzoic acid (21 g, 98.2%).

Step 3: methyl 5-bromo-2-methyl-3-nitrobenzoate

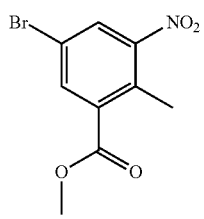

To a stirred solution of 5-bromo-2-methyl-3-nitrobenzoic acid (16 g, 61.5 mmol) in DMF (160 mL), was added iodomethane (35.7 g, 248 mmol) and sodium carbonate (26.3 g, 248 mmol). The resulting reaction mixture was stirred at 60° C. for 8 h. On completion, the reaction mixture was filtered and the inorganic solid residue washed with ethyl acetate. The combined filtrates were concentrated under vacuum till dry and re-dissolved in ethyl acetate before washing with 5% sodium bicarbonate solution (700 mL) followed by 5M HCl solution (300 mL). The organic layer was finally washed with brine, dried over sodium sulfate and concentrated to afford pure methyl 5-bromo-2-methyl-3-nitrobenzoate (16 g, 94.5%).

Step 4: methyl 3-amino-5-bromo-2-methylbenzoate

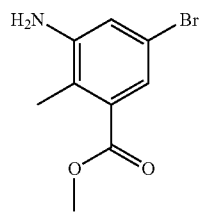

A mixture of methyl 5-bromo-2-methyl-3-nitrobenzoate (17 g, 62.0 mmol) in ethanol (85 mL) had NH₄Cl solution (17 g in 85 mL water, 317.8 mmol) followed by Fe powder (27.8 g, 498.1 mmol) added. The resulting reaction mixture was stirred at 90° C. for 1 h. On completion, the reaction mixture was filtered and the filtrate was concentrated till dry. The resulting solid was dissolved in sat. sodium bicarbonate solution and extracted with ethyl acetate. The combined organic layers were dried over sodium sulfate and concentrated to afford solid methyl 3-amino-5-bromo-2-methylbenzoate (15 g, 99.1%).

Step 5: methyl 1-acetyl-6-bromo-1H-indazole-4-carboxylate

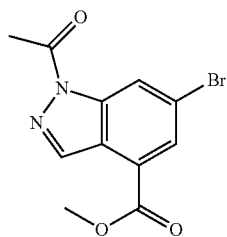 [SMILES: COC(=O)c1cc(Br)cc2c1cnn2C(C)=O]

To a stirred solution of methyl 3-amino-5-bromo-2-methylbenzoate (15 g, 61.5 mmol) in chloroform (150 mL), was added potassium acetate (6.32 g, 64.4 mmol) and acetic anhydride (12.6 g, 122.9 mmol) and reaction mixture was stirred at room temperature for 12 h. After this time, tert-butyl nitrite (25.3 g, 246.1 mmol) and 18-crown-6 (5.7 g, 21.5 mmol) were added and reaction stirred again at 65° C. for 3 h. On completion, the reaction mass was cooled to room temperature, diluted with chloroform (500 mL) and washed with sat. sodium bicarbonate solution. The organic layer was dried over sodium sulfate and concentrated to afford the title compound (18 g, 98.3%).

Step 6: methyl 6-bromo-1H-indazole-4-carboxylate

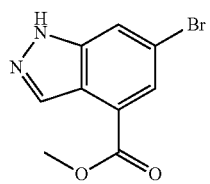

To a stirred solution of methyl 1-acetyl-6-bromo-1H-indazole-4-carboxylate (18 g, 61.0 mmol) in methanol (350 mL), 6N HCl (350 mL) was added and stirred it at 60° C. for 8 h. On completion of reaction, solvent was removed under reduced pressure then basified with saturated NaHCO₃ solution till pH 8. The solid precipitate was filtered and dried under vacuum before being stirred in diethyl ether for 15 min, filtered and dried to afford methyl 6-bromo-1H-indazole-4-carboxylate (11 g, 71.7%).

Step 7: methyl 6-bromo-1-cyclopentyl-1H-indazole-4-carboxylate

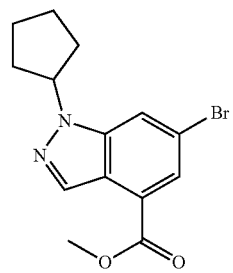 [SMILES: COC(=O)c1cc(Br)cc2c1cnn2C1CCCC1]

To a stirred solution of methyl 6-bromo-1H-indazole-4-carboxylate (10 g, 39.3 mmol) in acetonitrile (100 mL), was added cesium carbonate (19.2 g, 59.05 mmol) followed by bromocyclopentane (11.93 g, 78.3 mmol). The reaction mass was stirred at 90° C. for 3-4 h. On completion of reaction, acetonitrile was removed under reduced pressure and water added. Extraction was carried out using ethyl acetate and the combined organic layers were washed with water, brine and dried over anhydrous Na₂SO₄. The solvent was removed under reduced pressure and the residue purified by silica gel column chromatography to obtain methyl 6-bromo-1-cyclopentyl-1H-indazole-4-carboxylate (3.7 g, 29.2%). The regiochemistry of the cyclopentyl group was confirmed by a NOE experiment.

Step 8: 6-bromo-1-cyclopentyl-N-((4,6-dimethyl-2-oxo-1,2-dihydropyridin-3-yl)methyl)-1H-indazole-4-carboxamide

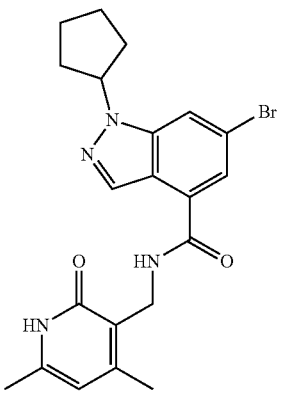 [SMILES: Cc1cc(C)c(CNC(=O)c2cc(Br)cc3c2cnn3C2CCCC2)c(=O)[nH]1]

Aqueous NaOH (0.68 g, 17.18 mmol) was added to a solution of methyl 6-bromo-1-cyclopentyl-1H-indazole-4-carboxylate (3.7 g, 11.45 mmol) in EtOH (40 mL) and stirred at 60° C. for 1 h. After completion of the reaction, ethanol was removed under reduced pressure and the residue acidified using 1N HCl solution. The resulting precipitate was filtered and dried under vacuum. This crude acid (3.2 g, 10.3 mmol) was then dissolved in DMSO (20 mL) and 3-(aminomethyl)-4,6-dimethylpyridin-2(1H)-one (3.15 g, 20.77 mmol) added to it. The reaction mixture was stirred at room temperature for 15 min before PYBOP (8.1 g, 15.5 mmol) was added and left to stir overnight. After completion of the reaction, reaction mass was poured into ice to obtain solid which was filtered and washed with acetonitrile then ether to provide the desired 6-bromo-1-cyclopentyl-N-((4,6-dimethyl-2-oxo-1,2-dihydropyridin-3-yl)methyl)-1H-indazole-4-carboxamide (2.6 g, 56.5%). LCMS: 443.05 (M+1)$^+$; HPLC: 95.00% (@ 254 nm) (R$_t$:7.195); $^1$H NMR (DMSO-d$_6$, 400 MHz) δ 11.52 (s, 1H), 8.61 (t, 1H, J=4.8 Hz), 8.36 (s, 1H), 8.19 (s, 1H), 7.70 (s, 1H), 5.88 (s, 1H), 5.23-5.20 (m, 1H), 4.33 (d, 2H, J=4.8 Hz), 2.20 (s, 3H), 2.12 (s, 3H), 1.98 (m, 2H), 1.97-1.90 (m, 2H), 1.87-1.86 (m, 2H), 1.73-1.67 (m, 2H).

Synthesis of Compound D-2: 1-cyclopentyl-N-((4,6-dimethyl-2-oxo-1,2-dihydropyridin-3-yl)methyl)-6-(2,2,6,6-tetramethyl-1,2,3,6-tetrahydropyridin-4-yl)-1H-indazole-4-carboxamide Compound D-2

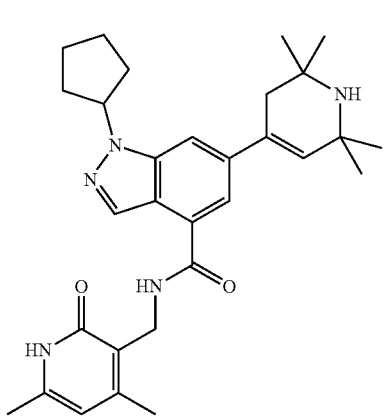

To a stirred solution of 6-bromo-1-cyclopentyl-N-((4,6-dimethyl-2-oxo-1,2-dihydropyridin-3-yl)methyl)-1H-indazole-4-carboxamide (0.5 g, 1.12 mmol), was added 2,2,6,6-tetramethyl-4-(4,4,5,5-tetramethyl-1,3,2-dioxaborolan-2-yl)-1,2,3,6-tetrahydropyridine (0.36 g, 1.35 mmol) and Pd(PPh$_3$)$_4$ (0.066 g, 0.057 mmol) in 1,4-dioxane (10 mL) and the flask purged with argon for 10 min. 2M Na$_2$CO$_3$ solution (0.43 g, 4.06 mmol) was then added and the flask again purged with argon for 10 min. The reaction mixture was stirred at 100° C. for 1 h. After completion, water was added and extraction carried out using 10% MeOH/DCM. The combined organic layers were washed with water, dried over anhydrous Na$_2$SO$_4$, filtered and concentrated under reduced pressure to afford crude material which was purified by column chromatography to give 1-cyclopentyl-N-((4,6-dimethyl-2-oxo-1,2-dihydropyridin-3-yl)methyl)-6-(2,2,6,6-tetramethyl-1,2,3,6-tetrahydropyridin-4-yl)-1H-indazole-4-carboxamide (0.53 g, 77.6%). LCMS: 502.55 (M+1)$^+$; HPLC: 99.25% (@ 254 nm) (R$_t$:5.528); $^1$H NMR (DMSO-d$_6$, 400 MHz) δ 11.52 (bs, 1H), 8.54 (t, 1H), 8.26 (s, 1H), 7.75 (s, 1H), 7.62 (s, 1H), 6.26 (s, 1H), 5.88 (s, 1H), 5.29-5.24 (m, 1H), 4.37 (d, 2H, J=5.2 Hz), 2.32 (m, 2H), 2.23 (s, 3H), 2.12 (s, 3H), 1.99-1.93 (m, 4H), 1.92-1.88 (m, 2H), 1.72-1.69 (m, 2H), 1.23 (s, 6H), 1.17 (s, 6H).

Synthesis of Compound D-3: 1-cyclopentyl-N-((4,6-dimethyl-2-oxo-1,2-dihydropyridin-3-yl)methyl)-6-(2,2,6,6-tetramethylpiperidin-4-yl)-1H-indazole-4-carboxamide Compound D-3

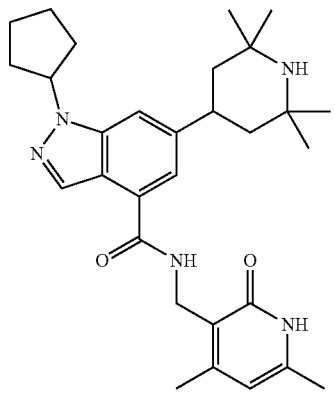

To a stirred solution of 1-cyclopentyl-N-((4,6-dimethyl-2-oxo-1,2-dihydropyridin-3-yl)methyl)-6-(2,2,6,6-tetramethyl-1,2,3,6-tetrahydropyridin-4-yl)-1H-indazole-4-carboxamide (0.15 g, 0.29 mmol) in MeOH (2 mL), 10% Pd/C in catalytic amount was added and stirred it at room temperature under a hydrogen balloon for 3 hr. On completion of reaction, reaction mixture was filtered through a celite bed and the filtrate concentrated under reduced pressure to give 1-cyclopentyl-N-((4,6-dimethyl-2-oxo-1,2-dihydropyridin-3-yl)methyl)-6-(2,2,6,6-tetramethylpiperidin-4-yl)-1H-indazole-4-carboxamide (0.09, 66.4%). LCMS: 504.25 (M+1)$^+$; HPLC: 99.77% (@ 254 nm) (R$_t$:5.460); $^1$H NMR (DMSO-d$_6$, 400 MHz) δ 11.55 (bs, 1H), 8.43 (t, 1H, J=5.2 Hz), 8.26 (s, 1H), 7.70 (s, 1H), 7.50 (s, 1H), 5.89 (s, 1H), 5.22-5.18 (m, 1H), 4.36 (d, 2H, J=5.2 Hz), 3.33 (1H merged with DMSO peak), 2.22 (s, 3H), 2.12 (s, 3H), 2.09 (m, 2H), 1.99-1.87 (m, 4H), 1.73-1.66 (m, 4H), 1.52 (m, 2H), 1.32 (s, 6H), 1.18 (s, 6H).

Synthesis of Compound D-4: 6-(1-acetyl-1,2,3,6-tetrahydropyridin-4-yl)-1-cyclopentyl-N-((4,6-dimethyl-2-oxo-1,2-dihydropyridin-3-yl)methyl)-1H-indazole-4-carboxamide Compound D-4

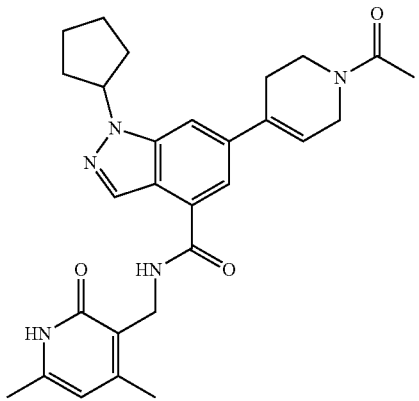

407

Step 1: tert-butyl 4-(1-cyclopentyl-4-(((4,6-dimethyl-2-oxo-1,2-dihydropyridin-3-yl)methyl)carbamoyl)-1H-indazol-6-yl)-5,6-dihydropyridine-1(2H)-carboxylate

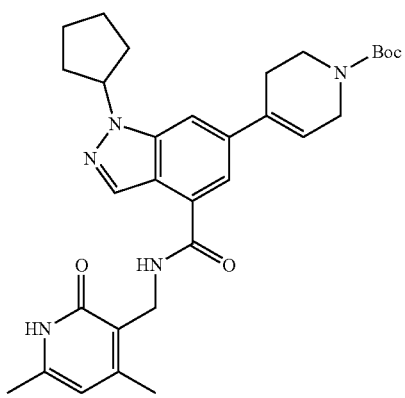 [SMILES: Cc1cc(C)c(CNC(=O)c2cc(C3=CCN(C(=O)OC(C)(C)C)CC3)cc3c2cnn3C2CCCC2)c(=O)[nH]1]

6-bromo-1-cyclopentyl-N-((4,6-dimethyl-2-oxo-1,2-dihydropyridin-3-yl)methyl)-1H-indazole-4-carboxamide (5 g) was converted to tert-butyl 4-(1-cyclopentyl-4-(((4,6-dimethyl-2-oxo-1,2-dihydropyridin-3-yl)methyl)carbamoyl)-1H-indazol-6-yl)-5,6-dihydropyridine-1(2H)-carboxylate (3.8 g, 61.9%) using the general procedure for Suzuki coupling.

Step 2: 1-cyclopentyl-N-((4,6-dimethyl-2-oxo-1,2-dihydropyridin-3-yl)methyl)-6-(1,2,3,6-tetrahydropyridin-4-yl)-1H-indazole-4-carboxamide

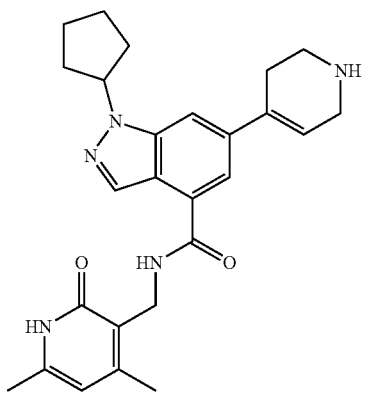 [SMILES: Cc1cc(C)c(CNC(=O)c2cc(C3=CCNCC3)cc3c2cnn3C2CCCC2)c(=O)[nH]1]

tert-butyl 4-(1-cyclopentyl-4-(((4,6-dimethyl-2-oxo-1,2-dihydropyridin-3-yl)methyl)carbamoyl)-1H-indazol-6-yl)-5,6-dihydropyridine-1(2H)-carboxylate (4 g) was converted to 1-cyclopentyl-N-((4,6-dimethyl-2-oxo-1,2-dihydropyridin-3-yl)methyl)-6-(1,2,3,6-tetrahydropyridin-4-yl)-1H-indazole-4-carboxamide (2.5 g, 76.68%) using general procedure for Boc deprotection. LCMS: 446.25 (M+1)+; HPLC: 99.35% (@ 254 nm) (R$_t$;5.024); $^1$H NMR (DMSO-d$_6$, 400 MHz) δ 11.50 (bs, 1H), 8.54 (t, 1H), 8.28 (s, 1H), 7.75 (s, 1H), 7.67 (s, 1H), 6.40 (s, 1H), 5.88 (s, 1H), 5.24 (m, 1H), 4.35 (d, 2H, J=5.2 Hz), 3.25 (m, 2H), 2.93 (t, 2H, J=4.8 & 5.2 Hz), 2.45 (bs, 2H), 2.20 (s, 3H), 2.12 (s, 3H), 2.10 (m, 2H), 2.02-1.94 (m, 2H), 1.86 (m, 2H), 1.68 (m, 2H).

408

Step 3: 6-(1-acetyl-1,2,3,6-tetrahydropyridin-4-yl)-1-cyclopentyl-N-((4,6-dimethyl-2-oxo-1,2-dihydropyridin-3-yl)methyl)-1H-indazole-4-carboxamide

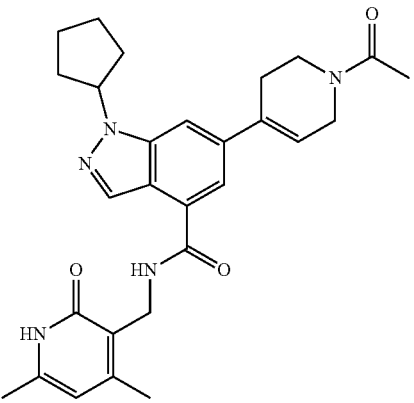 [SMILES: CC(=O)N1CC=C(c2cc(C(=O)NCc3c(C)cc(C)[nH]c3=O)c3cnn(C4CCCC4)c3c2)CC1]

A stirred solution of 1-cyclopentyl-N-((4,6-dimethyl-2-oxo-1,2-dihydropyridin-3-yl)methyl)-6-(1,2,3,6-tetrahydropyridin-4-yl)-1H-indazole-4-carboxamide (0.1 g, 0.2 mmol) in DCM (3 mL) was cooled to 0° C. Triethyl amine (0.05 g, 0.49 mmol) and acetyl chloride (0.02 g, 0.27 mmol) were then added. The reaction mixture was stirred at room temperature for 12 h. On completion, the reaction mixture was concentrated until dryness and water added to the residue to obtain solid which was filtered washed with acetonitrile affording a solid which was purified by prep. HPLC to provide the TFA salt of the target molecule. LCMS: 488.30 (M+1)+; HPLC: 96.21% (@ 254 nm) (R$_t$;6.266); $^1$H NMR (DMSO-d$_6$, 400 MHz) δ 11.40 (bs, 1H), 8.54 (bs, 1H), 8.30 (s, 1H), 7.82 (d, 1H, J=7.2 Hz), 7.69 (s, 1H), 6.37 (bs, 1H), 5.88 (s, 1H), 5.24 (m, 1H), 4.36 (d, 2H, J=3.2 Hz), 4.15 (d, 2H, J=18.8 Hz), 3.67 (m, 2H), 2.67 (bs, 1H), 2.57 (bs, 1H), 2.20 (s, 3H), 2.11 (s, 6H), 2.05 (s, 2H), 1.99 (m, 2H), 1.87 (m, 2H), 1.69 (m, 2H).

Synthesis of Compound D-5: 1-cyclopentyl-N-((4,6-dimethyl-2-oxo-1,2-dihydropyridin-3-yl)methyl)-6-(1-(1-methylpiperidine-4-carbonyl)-1,2,3,6-tetrahydropyridin-4-yl)-1H-indazole-4-carboxamide Compound D-5

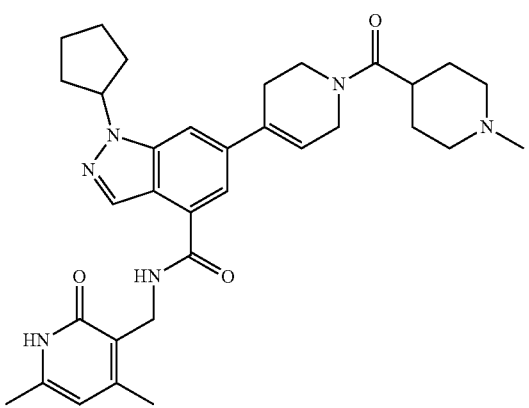

Step 1: 1-cyclopentyl-N-((4,6-dimethyl-2-oxo-1,2-dihydropyridin-3-yl)methyl)-6-(1-(piperidine-4-carbonyl)-1,2,3,6-tetrahydropyridin-4-yl)-1H-indazole-4-carboxamide

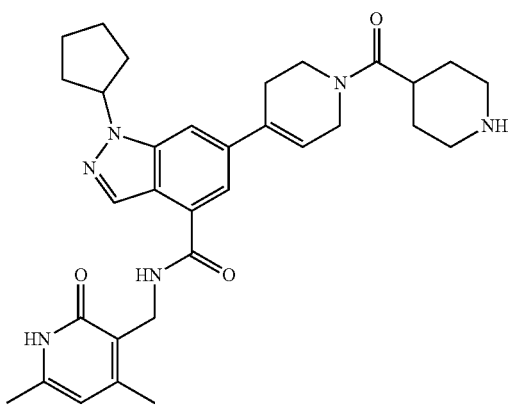 [SMILES: Cc1cc(C)c(CNC(=O)c2cc(C3=CCN(C(=O)C4CCNCC4)CC3)cc3c2cnn3C2CCCC2)c(=O)[nH]1]

1-cyclopentyl-N-((4,6-dimethyl-2-oxo-1,2-dihydropyridin-3-yl)methyl)-6-(1,2,3,6-tetrahydropyridin-4-yl)-1H-indazole-4-carboxamide was converted to 1-cyclopentyl-N-((4,6-dimethyl-2-oxo-1,2-dihydropyridin-3-yl)methyl)-6-(1-(piperidine-4-carbonyl)-1,2,3,6-tetrahydropyridin-4-yl)-1H-indazole-4-carboxamide the general PyBOP coupling with 1-(tert-butoxycarbonyl)piperidine-4-carboxylic acid and deprotected with general boc deprotection procedure. The compound was purified by prep. To yield HPLC the TFA salt. LCMS: 557.35 (M+1)$^+$; HPLC: 98.46% (@ 254 nm) (R$_t$:5.266); $^1$H NMR (DMSO-d$_6$, 400 MHz) δ 11.52 (s, 1H), 8.52-8.50 (m, 2H), 8.30 (s, 1H), 8.25 (bs, 1H), 7.82 (d, 1H, J=10 Hz), 7.69 (s, 1H), 6.39 (d, 1H, J=12 Hz), 5.88 (s, 1H), 5.25 (m, 1H), 4.36 (d, 2H, J=4.4 Hz), 4.28 (bs, 1H), 4.15 (bs, 1H), 3.78-3.70 (m, 2H), 3.31 (d, 2H, J=10.8 Hz), 3.09-2.93 (m, 5H), 2.69 (bs, 1H), 2.59 (bs, 1H), 2.20 (s, 3H), 2.12 (s, 3H), 2.09 (m, 2H), 1.99 (m, 2H), 1.90-1.68 (m, 6H).

Step 2: 1-cyclopentyl-N-((4,6-dimethyl-2-oxo-1,2-dihydropyridin-3-yl)methyl)-6-(1-(1-methylpiperidine-4-carbonyl)-1,2,3,6-tetrahydropyridin-4-yl)-1H-indazole-4-carboxamide

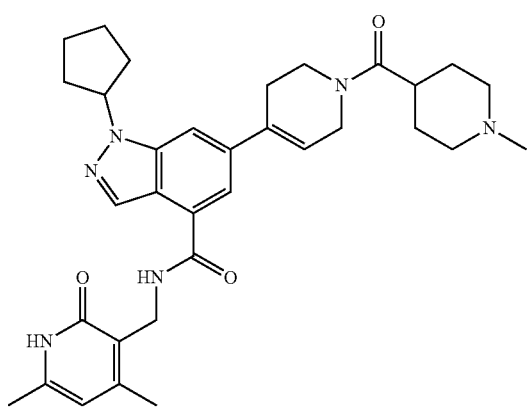

1-Cyclopentyl-N-((4,6-dimethyl-2-oxo-1,2-dihydropyridin-3-yl)methyl)-6-(1,2,3,6-tetrahydropyridin-4-yl)-1H-indazole-4-carboxamide was converted to desired 1-cyclopentyl-N-((4,6-dimethyl-2-oxo-1,2-dihydropyridin-3-yl)methyl)-6-(1-(1-methylpiperidine-4-carbonyl)-1,2,3,6-tetrahydropyridin-4-yl)-1H-indazole-4-carboxamide using a general reductive amination methylation procedure. Crude material obtained was purified by column chromatography over silica gel (73.5%). LCMS: 571.45 (M+1)$^+$; HPLC: 94.84% (@ 254 nm) (R$_t$:5.354); $^1$H NMR (DMSO-d$_6$, 400 MHz) δ 11.52 (s, 1H), 8.53 (t, 1H), 8.30 (s, 1H), 7.82 (s, 1H), 7.69 (s, 1H), 6.38 (d, 1H, J=11.6 Hz), 5.88 (s, 1H), 5.24 (m, 1H), 4.36 (d, 2H, J=4.4 Hz), 4.24 (bs, 1H), 4.41 (s, 1H), 7.71 (d, 2H, J=4.4 Hz), 2.76 (m, 2H), 2.67 (m, 1H), 2.61 (m, 1H), 2.56 (m, 1H), 2.19 (s, 3H), 2.15 (s, 3H), 2.11 (s, 3H), 1.99-1.80 (m, 8H), 1.72-1.59 (m, 6H).

Synthesis of Compound D-6: 6-([1,4'-bipiperidin]-4-yl)-1-cyclopentyl-N-((4,6-dimethyl-2-oxo-1,2-dihydropyridin-3-yl)methyl)-1H-indazole-4-carboxamide Compound D-6

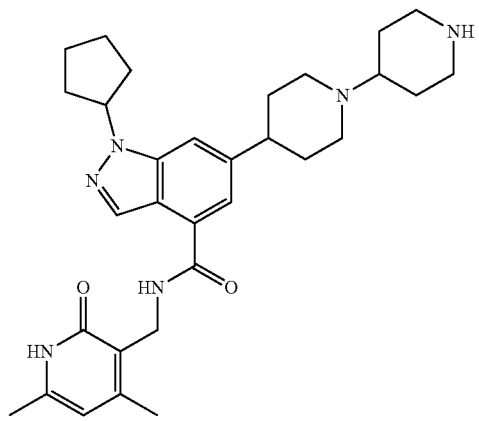

Step 1: 1-cyclopentyl-N-((4,6-dimethyl-2-oxo-1,2-dihydropyridin-3-yl)methyl)-6-(1-(piperidin-4-yl)-1,2,3,6-tetrahydropyridin-4-yl)-1H-indazole-4-carboxamide

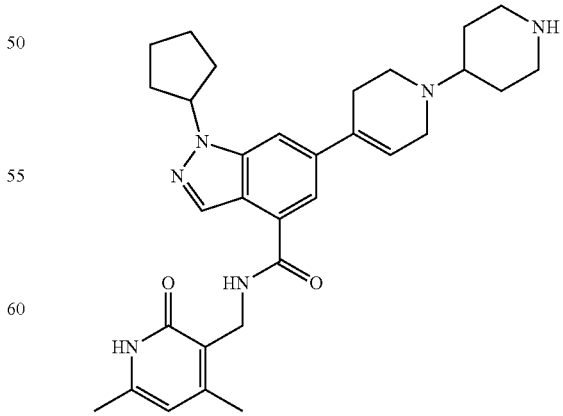

1-cyclopentyl-N-((4,6-dimethyl-2-oxo-1,2-dihydropyridin-3-yl)methyl)-6-(1,2,3,6-tetrahydropyridin-4-yl)-1H-indazole-4-carboxamide was combined with tert-butyl 4-oxopiperidine-1-carboxylate using a general reductive amination procedure and product treated to the general Boc deprotection procedure and purified by prep. HPLC to afford 1-cyclopentyl-N-((4,6-dimethyl-2-oxo-1,2-dihydropyridin-3-yl)methyl)-6-(1-(piperidin-4-yl)-1,2,3,6-tetrahydropyridin-4-yl)-1H-indazole-4-carboxamide as the TFA salt. LCMS: 529.40 (M+1)$^+$; HPLC: 98.80% (@ 254 nm) (R$_t$; 4.495); $^1$H NMR (DMSO-d$_6$, 400 MHz) δ 11.53 (s, 1H), 10.17 (bs, 1H), 8.78 (bs, 1H), 8.54 (m, 2H), 8.32 (s, 1H), 7.92 (s, 1H), 7.73 (s, 1H), 6.46 (s, 1H), 5.89 (s, 1H), 5.28 (m, 1H), 4.37 (d, 2H, J=4.8 Hz), 4.00 (m, 2H), 3.75 (m, 1H), 2.97 (m, 4H), 2.40-2.25 (m, 2H), 2.21 (s, 3H), 2.12 (s, 3H), 2.10 (m, 2H), 2.05-1.65 (m, 12H).

Step 2: 6-([1,4'-bipiperidin]-4-yl)-1-cyclopentyl-N-((4,6-dimethyl-2-oxo-1,2-dihydropyridin-3-yl)methyl)-1H-indazole-4-carboxamide

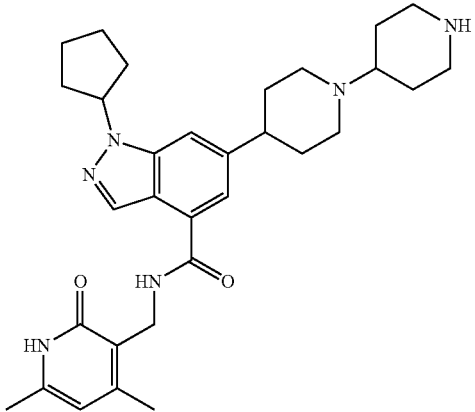 [SMILES: Cc1cc(C)c(CNC(=O)c2cc(C3CCN(C4CCNCC4)CC3)cc3c2cnn3C2CCCC2)c(=O)[nH]1]

6-([1,4'-bipiperidin]-4-yl)-1-cyclopentyl-N-((4,6-dimethyl-2-oxo-1,2-dihydropyridin-3-yl)methyl)-1H-indazole-4-carboxamide was prepared using a general Pd—C reduction procedure from 1-cyclopentyl-N-((4,6-dimethyl-2-oxo-1,2-dihydropyridin-3-yl)methyl)-6-(1-(piperidin-4-yl)-1,2,3,6-tetrahydropyridin-4-yl)-1H-indazole-4-carboxamide as the TFA salt (50% yield). LCMS: 531.30 (M+1)$^+$; HPLC: 79.88% (@ 254 nm) (R$_t$;4.560); $^1$H NMR (CD3OD, 400 MHz) δ 8.27 (s, 1H), 7.63 (s, 1H), 7.45 (s, 1H), 6.13 (s, 1H), 5.15 (m, 1H), 4.55 (s, 2H), 3.80-3.60 (m, 5H), 3.25 (m, 2H), 3.20-3.05 (m, 3H), 2.46 (bs, 2H), 2.42 (s, 3H), 2.25 (s, 3H), 2.22 (m, 2H), 2.20-2.05 (m, 8H), 1.97 (m, 2H), 1.78 (m, 2H).

Synthesis of Compound D-7: 1-cyclopentyl-N-((4,6-dimethyl-2-oxo-1,2-dihydropyridin-3-yl)methyl)-6-(4-1-cyclopentyl-N-((4,6-dimethyl-2-oxo-1,2-dihydropyridin-3-yl)methyl)-6-((4-methylpiperazin-1-yl)methyl)-1H-indazole-4-carboxamide Compound D-7

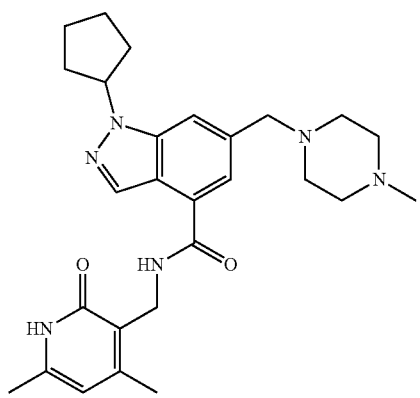

Step 1: 1-cyclopentyl-N-((4,6-dimethyl-2-oxo-1,2-dihydropyridin-3-yl)methyl)-6-vinyl-1H-indazole-4-carboxamide

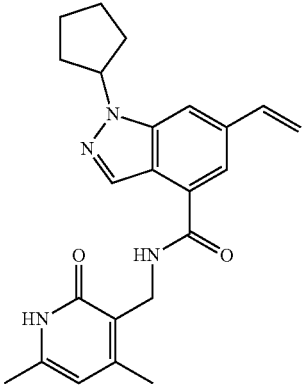 [SMILES: C=Cc1cc(C(=O)NCc2c(C)cc(C)[nH]c2=O)c2cnn(C3CCCC3)c2c1]

A solution of 6-bromo-1-cyclopentyl-N-((4,6-dimethyl-2-oxo-1,2-dihydropyridin-3-yl)methyl)-1H-indazole-4-carboxamide (1.5 g, 3.386 mmol), 4,4,5,5-tetramethyl-2-vinyl-1,3,2-dioxaborolane (0.625 g, 4.063 mmol) and Pd(PPh$_3$)$_4$ (0.392 g, 0.034 mmol) in 1,4-dioxane (15 mL) and purged with argon for 10 min. A solution of 2M Na$_2$CO$_3$ (1.29 g, 12.18 mmol) was then added to it before a further argon purge for 10 min. The reaction mixture was stirred at 100° C. for 1 h. After completion of the reaction, water was added to it and extraction was carried out using 10% MeOH/DCM. The combined organic layers were washed with water, dried over anhydrous Na$_2$SO$_4$, filtered and concentrated under reduced pressure to afford crude material which was purified by column chromatography to give 1-cyclopentyl-N-((4,6-dimethyl-2-oxo-1,2-dihydropyridin-3-yl)methyl)-6-vinyl-1H-indazole-4-carboxamide (0.9 g, 68.2%).

Step 2: 1-cyclopentyl-6-(1,2-dihydroxyethyl)-N-((4,6-dimethyl-2-oxo-1,2-dihydropyridin-3-yl)methyl)-1H-indazole-4-carboxamide

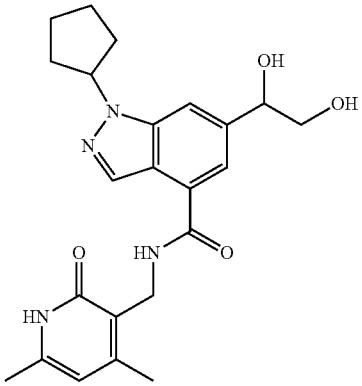 [SMILES: Cc1cc(C)c(CNC(=O)c2cc(C(O)CO)cc3c2cnn3C2CCCC2)c(=O)[nH]1]

To a stirred solution of 1-cyclopentyl-N-((4,6-dimethyl-2-oxo-1,2-dihydropyridin-3-yl)methyl)-6-vinyl-1H-indazole-4-carboxamide (0.9 g, 2.3 mmol) in DCM (10 mL), was added N-methylmorpholine-N-oxide (0.81 g, 6.92 mmol) at 0° C., OsO$_4$ (0.147 g, 0.576 mmol, 2.5% solution in t-BuOH) was then added. The resulting solution was stirred at room temperature for 1 h. After completion of reaction, water was added and extraction carried out using 10% MeOH/DCM. The combined organic layers were washed with water, dried over anhydrous Na$_2$SO$_4$, filtered and concentrated under reduced pressure to afford crude material which was purified by column chromatography to give title compound 1-cyclopentyl-6-(1,2-dihydroxyethyl)-N-((4,6-dimethyl-2-oxo-1,2-dihydropyridin-3-yl)methyl)-1H-indazole-4-carboxamide (0.6 g, 61.3%).

Step 3: 1-cyclopentyl-N-((4,6-dimethyl-2-oxo-1,2-dihydropyridin-3-yl)methyl)-6-formyl-1H-indazole-4-carboxamide

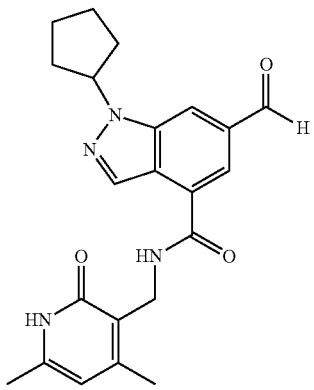 [SMILES: Cc1cc(C)c(CNC(=O)c2cc(C=O)cc3c2cnn3C2CCCC2)c(=O)[nH]1]

To a stirred solution of 1-cyclopentyl-6-(1,2-dihydroxyethyl)-N-((4,6-dimethyl-2-oxo-1,2-dihydropyridin-3-yl)methyl)-1H-indazole-4-carboxamide (0.6 g, 1.4 mmol) in 50% THF/Water (16 mL), was added NaIO$_4$ (0.9 g, 4.2 mmol) at 0° C. and stirred at room temperature for 1 h. After completion of reaction, solvent was removed under reduced pressure and water was added to it. Extraction was carried out using 10% MeOH/DCM. The combined organic layers were washed with water, dried over anhydrous Na$_2$SO$_4$, filtered and concentrated under reduced pressure to afford crude material which was purified by column chromatography to give 1-cyclopentyl-N-((4,6-dimethyl-2-oxo-1,2-dihydropyridin-3-yl)methyl)-6-formyl-1H-indazole-4-carboxamide (0.4 g, 72.1%).

Step 4: 1-cyclopentyl-N-((4,6-dimethyl-2-oxo-1,2-dihydropyridin-3-yl)methyl)-6-((4-methylpiperazin-1-yl)methyl)-1H-indazole-4-carboxamide

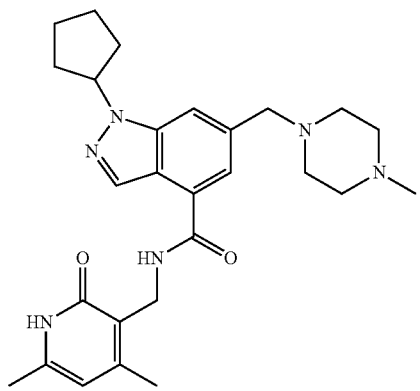

To a stirred solution of 1-cyclopentyl-N-((4,6-dimethyl-2-oxo-1,2-dihydropyridin-3-yl)methyl)-6-formyl-1H-indazole-4-carboxamide (0.1 g, 0.255 mmol) in methanol (2 mL) was added acetic acid (0.015 g, 0.255 mmol) and 1-methylpiperazine (0.077 g, 0.765 mmol) and stirred it at room temperature for 3 h. NaBH$_3$CN (0.016 g, 0.255 mmol) was then added. The resulting reaction mixture was stirred at room temperature overnight. After completion of reaction, the solvent was removed under reduced pressure and water was added. Extraction was carried out using 10% MeOH/DCM. The combined organic layers were washed with water, dried over anhydrous Na$_2$SO$_4$, filtered and concentrated under reduced pressure to afford crude material which was purified by column chromatography to give 1-cyclopentyl-N-((4,6-dimethyl-2-oxo-1,2-dihydropyridin-3-yl)methyl)-6-((4-methylpiperazin-1-yl)methyl)-1H-indazole-4-carboxamide (0.027 g, 28.8%). LCMS: 477.25 (M+1)$^+$; HPLC: 99.71% (@ 254 nm) (R$_t$:4.649); $^1$H NMR (DMSO-d$_6$, 400 MHz) δ 11.53 (s, 1H), 8.39 (t, 1H, J=4.8 Hz), 8.27 (s, 1H), 7.71 (s, 1H), 7.50 (s, 1H), 5.89 (s, 1H), 5.19-5.14 (m, 1H), 4.35 (d, 2H, J=5.2 Hz), 3.58 (s, 2H), 2.39-2.33 (m, 8H), 2.21 (s, 3H), 2.12 (s, 3H), 2.07 (s, 3H), 2.00 (m, 2H), 1.99-1.96 (m, 2H), 1.91-1.86 (m, 2H), 1.69-1.68 (m, 2H).

Synthesis of Compound D-8: 1-cyclopentyl-N-((4,6-dimethyl-2-oxo-1,2-dihydropyridin-3-yl)methyl)-6-(hydroxymethyl)-1H-indazole-4-carboxamide

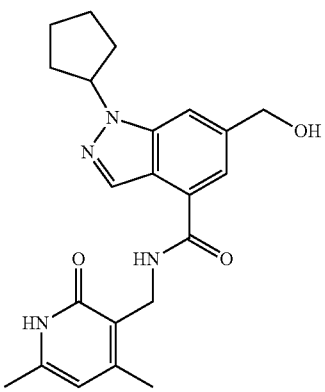

Synthesis of Compound D-8

A stirred solution of 1-cyclopentyl-N-4,6-dimethyloxo,2-dihydropyridine-3-yl)methyl)-6-formyl-1H-indazole-4-carboxamide (0.1 g, 0.255 mmol) in methanol (2 mL) was cooled to 0° C. and NaBH$_4$ (0.096 g, 0.257 mmol) was added to it. The resulting reaction mixture was stirred at room temperature for 3 h. On completion, the reaction mixture was evaporated under reduced pressure and water was added to the residue. The aqueous phase was extracted with 10% MeOH/DCM and the combined organic layers dried over Na$_2$SO$_4$ and the solvent removed under reduced pressure to obtain crude material which was purified by column chromatography over silica gel affording desired compound (0.05 g, 50%). LCMS: 395.20 (M+1)$^+$; HPLC: 95.70% (@ 254 nm) (R$_t$:5.532); $^1$H NMR (DMSO-d$_6$, 400 MHz) δ 11.52 (s, 1H), 8.36 (t, 1H), 8.27 (s, 1H), 7.74 (s, 1H), 7.50 (s, 1H), 5.88 (s, 1H), 5.35 (t, 1H, J=6&5.2 Hz), 5.16 (m, 1H), 4.64 (d, 2H, J=5.6 Hz), 4.35 (d, 2H, J=5.2 Hz), 2.21 (s, 3H), 2.12 (s, 3H), 2.10 (m, 2H), 2.01-1.96 (m, 2H), 1.86 (m, 2H), 1.69 (m, 2H).

415

Synthesis of Compound D-9: 1-cyclopentyl-N-((4,6-dimethyl-2-oxo-1,2-dihydropyridin-3-yl)methyl)-6-methyl-1H-indazole-4-carboxamide

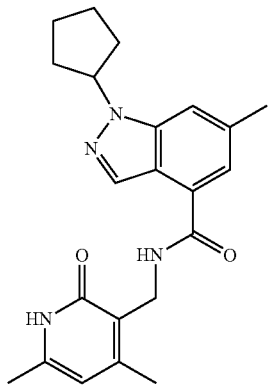

Compound D-9

Step 1: 6-(bromomethyl)-1-cyclopentyl-N-((4,6-dimethyl-2-oxo-1,2-dihydro pyridine-3-yl)methyl)-1H-indazole-4-carboxamide

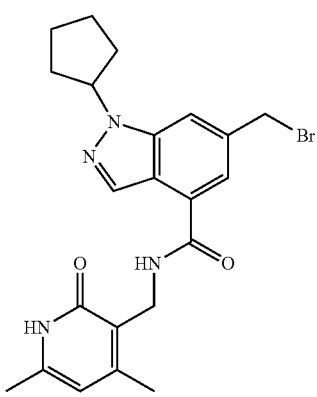 [SMILES: Cc1cc(C)c(CNC(=O)c2cc(CBr)cc3c2cnn3C2CCCC2)c(=O)[nH]1]

To a stirred solution of 1-cyclopentyl-N-((4,6-dimethyl-2-oxo-1,2-dihydropyridin-3-yl)methyl)-6-(hydroxymethyl)-1H-indazole-4-carboxamide (0.75 g, 1.90 mmol) in DCM (10 mL), triphenyl phosphine (0.998 g, 3.807 mmol) was added at room temperature. The mixture was cooled to 0° C. after 5 minutes then carbon tetrabromide (1.26 g, 3.80 mmol) was added. On completion, reaction mixture was evaporated under reduced pressure and the crude residue purified by column chromatography over silica gel to afford desired 6-(bromomethyl)-1-cyclopentyl-N-((4,6-dimethyl-2-oxo-1,2-dihydro pyridine-3-yl)methyl)-1H-indazole-4-carboxamide (0.45 g, 51.84%).

416

Step 2: 1-cyclopentyl-N-((4,6-dimethyl-2-oxo-1,2-dihydropyridin-3-yl)methyl)-6-methyl-1H-indazole-4-carboxamide

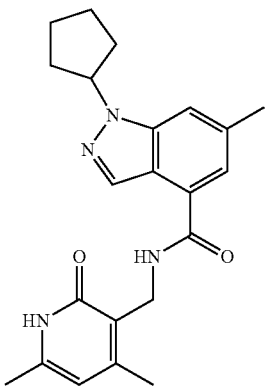

6-(bromomethyl)-1-cyclopentyl-N-((4,6-dimethyl-2-oxo-1,2-dihydro pyridine-3-yl)methyl)-1H-indazole-4-carboxamide (0.05 g, 0.13 mmol) was dissolved in methanol (2 mL) and Pd—C (10%, 0.01 g) was added to it. The resulting reaction mixture was stirred at room temperature for 1 h. On completion, the reaction mixture was filtered and concentrated to obtain solid compound which was washed with ether and pentane affording pure target compound (0.045 g, 91.89%). LCMS: 379.30 (M+1)$^+$; HPLC: 98.15% (@ 254 nm) (R$_t$;6.603); $^1$H NMR (CD3OD, 400 MHz) δ 8.28 (s, 1H), 7.63 (s, 1H), 7.48 (s, 1H), 6.70 (s, 1H), 5.12 (m, 1H), 4.61 (s, 2H), 2.56 (s, 3H), 2.55 (s, 3H), 2.42 (s, 3H), 2.19-2.14 (m, 2H), 2.12-2.04 (m, 2H), 2.00-1.92 (m, 2H), 1.82-1.75 (m, 2H).

Synthesis of Compound D-10: 6-chloro-1-cyclopentyl-N-((4,6-dimethyl-2-oxo-1,2-dihydropyridin-3-yl)methyl)-1H-indazole-4-carboxamide

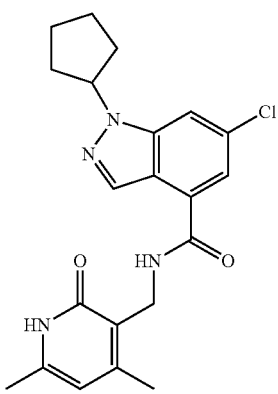

Compound D-10

Step 1: 5-chloro-2-methyl-3-nitrobenzoic acid

A stirred solution of 5-chloro-2-methylbenzoic acid (1 mmol) in conc. H$_2$SO$_4$ (2 mL) was cooled to −10° C. and nitrating mixture (0.4 mL of conc. H$_2$SO$_4$+0.1 mL of conc. HNO$_3$) was added to it in dropwise manner. The reaction mixture was stirred at the same temperature for 20 min then warmed to room temperature. The solid precipitate was filtered and dried to obtain 5-chloro-2-methyl-3-nitrobenzoic acid which was used in next step without further purification (yield 60-70%).

Step 2: methyl 5-chloro-2-methyl-3-nitrobenzoate

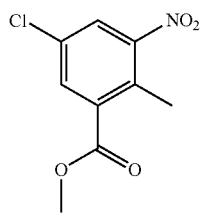

To a stirred solution of 5-chloro-2-methyl-3-nitrobenzoic acid (1 equiv.) in DMF (3 ml per 1 mmol), iodomethane (4 equiv.) and sodium carbonate (4 equiv.) were added. The resulting reaction mixture was stirred at 60° C. for 8 h. On completion, the reaction mixture was filtered and the inorganic solid residue washed with ethyl acetate. The combined filtrate was concentrated under vacuum till dryness. The residue was re-dissolved in ethyl acetate and washed with 5% sodium bicarbonate solution followed by 5M HCl solution. Organic layer was finally washed with brine, dried over sodium sulfate and concentrated to afford pure methyl 5-chloro-2-methyl-3-nitrobenzoate (90-95%).

Step 3: methyl 3-amino-5-chloro-2-methylbenzoate

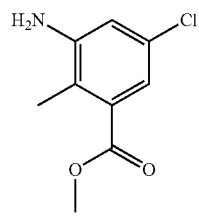

To a stirred solution of methyl 5-chloro-2-methyl-3-nitrobenzoate (1 equiv.) in ethanol (2 mL per 1 mmol), was added NH$_4$Cl solution (5.1 equiv., dissolved in water. Volume of water equivalent to volume of ethanol) followed by Fe powder (8 equiv.). The resulting reaction mixture was stirred at 90° C. for 1 h. On completion, reaction mixture was filtered and the filtrate concentrated until dryness. The resulting solid which was dissolved in saturated sodium bicarbonate solution and the aqueous layer extracted with ethyl acetate. Combined organic layers were dried over sodium sulfate and concentrated to afford solid methyl 3-amino-5-chloro-2-methylbenzoate in quantitative yield.

Step 4: methyl 6-chloro-1H-indazole-4-carboxylate

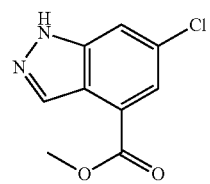

To a stirred solution of methyl 3-amino-5-chloro-2-methylbenzoate (1 equiv.) in chloroform (13 mL per 1 mmol), potassium acetate (1.05 equiv.) and acetic anhydride (2 equiv.) were added and reaction mixture stirred at room temperature for 12 h. After this time, tert-butyl nitrite (4 equiv.) and 18-crown-6 (0.35 equiv.) were added and the reaction stirred again at 65° C. for 3 h. On completion, the reaction mixture was cooled to room temperature, diluted with chloroform (500 mL) and washed with sat. sodium bicarbonate solution. The organic layer was dried over sodium sulfate and concentrated to afford the title compound (yield 90-95%).

Step 5: methyl 1-acetyl-6-chloro-1H-indazole-4-carboxylate

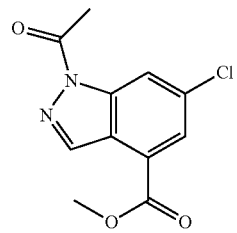 [SMILES: COC(=O)c1cc(Cl)cc2c1cnn2C(C)=O]

To a stirred solution of methyl 6-chloro-1H-indazole-4-carboxylate (1 equiv.) in methanol (7 mL per 1 mmol), 6N HCl (7 mL per 1 mmol) was added and the mixture stirred at 60° C. for 3 h. On completion of reaction, the solvent was removed under reduced pressure and basified with saturated NaHCO$_3$ solution till pH 8. The resulting solid precipitate was filtered and dried under vacuum. Finally, the solid was stirred in diethyl ether for 15 min, filtered and dried to afford methyl 1-acetyl-6-chloro-1H-indazole-4-carboxylate (yield 70-75%).

Step 6: methyl 6-chloro-1-cyclopentyl-1H-indazole-4-carboxylate

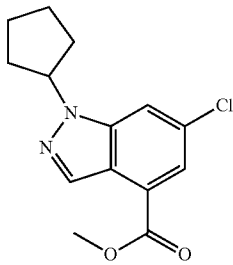 [SMILES: COC(=O)c1cc(Cl)cc2c1cnn2C1CCCC1]

To a stirred solution of methyl 1-acetyl-6-chloro-1H-indazole-4-carboxylate (1 equiv.) in acetonitrile (3 mL per 1 mmol), cesium carbonate (1.5 equiv.) was added followed by bromocyclopentane (2 equiv.). The reaction mixture was stirred at 90° C. for 3-4 h. On completion of reaction, acetonitrile was removed under reduced pressure and water was added. Extraction was carried out using ethyl acetate and the combined organic layers were washed with water, brine and dried over anhydrous $Na_2SO_4$. The solvent was then removed under reduced pressure and residue was purified by silica gel column chromatography to obtain methyl 6-chloro-1-cyclopentyl-1H-indazole-4-carboxylate (yield 30-35%). The structure was confirmed as the desired regioisomer by NOE.

Step 7: 6-chloro-1-cyclopentyl-N-((4,6-dimethyl-2-oxo-1,2-dihydropyridin-3-yl)methyl)-1H-indazole-4-carboxamide

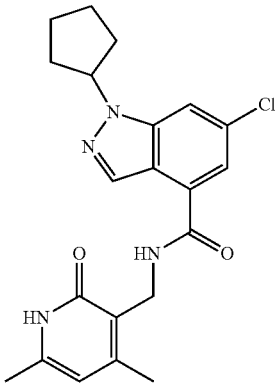 [SMILES: Cc1cc(C)c(CNC(=O)c2cc(Cl)cc3c2cnn3C2CCCC2)c(=O)[nH]1]

To a stirred solution of methyl 6-chloro-1-cyclopentyl-1H-indazole-4-carboxylate (1 equiv.) in ethanol (3 mL per 1 mmol), aqueous NaOH solution (1.5 equiv in 1 mL water) was added and the reaction mixture stirred at 60° C. for 4 h. On completion, ethanol was removed under reduced pressure and the residue acidified with 1N HCl to pH 6. The resulting solid precipitate was filtered, washed with water and dried to obtain pure corresponding acid (yield 80-90%). To a solution of this acid (1 equiv.) in DMSO (2 mL for 1 mmol), PyBOP (1.5 equiv.) was added and reaction stirred at room temperature for 15 min. At this point, 3-(aminomethyl)-4,6-dimethylpyridin-2(1H)-one (2 equiv.) was added and reaction stirred overnight. On completion, water was added and the precipitate was filtered and washed with water. This solid was then stirred with acetonitrile for 10 min and filtered again to obtain pure target molecule 6-chloro-1-cyclopentyl-N-((4,6-dimethyl-2-oxo-1,2-dihydropyridin-3-yl)methyl)-1H-indazole-4-carboxamide (yield 50-60%). LCMS: 399.10 (M+1)$^+$; HPLC: 99.52% (@ 254 nm) ($R_t$; 7.047); $^1$H NMR (DMSO-$d_6$, 400 MHz) δ 11.59 (s, 1H), 8.59 (t, 1H, J=4.8 Hz), 8.35 (s, 1H), 8.04 (s, 1H), 7.59 (d, 1H, J=1.2 Hz), 5.88 (s, 1H), 5.17-5.24 (m, 1H), 4.33 (d, 2H, J=4.8 Hz), 2.19 (s, 3H), 2.12 (s, 3H), 2.07-2.11 (m, 2H), 1.92-1.98 (m, 2H), 1.84-1.87 (m, 2H), 1.66-1.69 (m, 2H).

Synthesis of Compound D-11: 1-cyclopentyl-N-((4,6-dimethyl-2-oxo-1,2-dihydropyridin-3-yl)methyl)-6-(trifluoromethyl)-1H-indazole-4-carboxamide

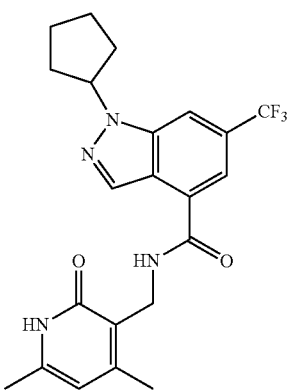

Compound D-11

Step 1: 2-methyl-3-nitro-5-(trifluoromethyl)benzoic acid

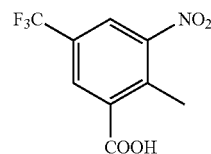 [SMILES: Cc1c(C(=O)O)cc(C(F)(F)F)cc1[N+](=O)[O-]]

A stirred solution of 2-methyl-5-(trifluoromethyl)benzoic acid (1 mmol) in conc. $H_2SO_4$ (2 mL) was cooled to −10° C. and a nitrating mixture (0.4 mL of conc. $H_2SO_4$+0.1 mL of conc. $HNO_3$) was added to it in dropwise manner. The reaction mixture was stirred at same temperature for 20 min before warming to room temperature. The resulting precipitate was filtered off and dried to obtain 2-methyl-3-nitro-5-(trifluoromethyl)benzoic acid which was used in next step without further purification (yield 60-70%).

Step 2: methyl 2-methyl-3-nitro-5-(trifluoromethyl)benzoate

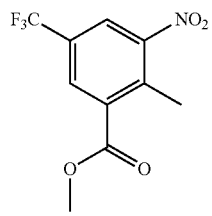 [SMILES: COC(=O)c1cc(C(F)(F)F)cc([N+](=O)[O-])c1C]

To a stirred solution of 2-methyl-3-nitro-5-(trifluoromethyl)benzoic acid (1 equiv.) in DMF (3 ml per 1 mmol), iodomethane (4 equiv.) and sodium carbonate (4 equiv.) were added. The resulting reaction mixture was stirred at 60° C. for 8 h. On completion, reaction mixture was filtered and the inorganic solid residue washed with ethyl acetate. The combined filtrate was concentrated under vacuum till dryness and the residue re-dissolved in ethyl acetate before washing with 5% sodium bicarbonate solution followed by 5M HCl solution. the organic layer was finally washed with brine, dried over sodium sulfate and concentrated to afford pure methyl 2-methyl-3-nitro-5-(trifluoromethyl)benzoate (yield 90-95%).

Step 3: methyl 3-amino-2-methyl-5-(trifluoromethyl)benzoate

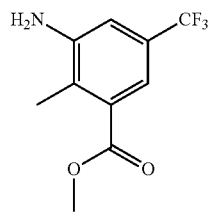

To a stirred solution of methyl 2-methyl-3-nitro-5-(trifluoromethyl)benzoate (1 equiv.) in ethanol (2 mL per 1 mmol), was added $NH_4Cl$ solution (5.1 equiv., dissolved in water. Volume of water equivalent to volume of ethanol) followed by Fe powder (8 equiv.). the resulting reaction mixture was stirred at 90° C. for 1 h. On completion, the reaction mixture was filtered and the filtrate concentrated till dryness. The resulting solid was dissolved in saturated sodium bicarbonate solution and the aqueous layer extracted with ethyl acetate. The combined organic layers were dried over sodium sulfate and concentrated to afford solid methyl 3-amino-2-methyl-5-(trifluoromethyl)benzoate in quantitative yield.

Step 4: methyl 6-(trifluoromethyl)-1H-indazole-4-carboxylate

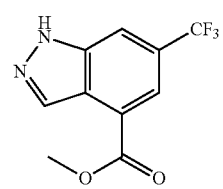 [SMILES: COC(=O)c1cc(C(F)(F)F)cc2[nH]ncc12]

To a stirred solution of methyl 3-amino-2-methyl-5-(trifluoromethyl)benzoate (1 equiv.) in chloroform (13 mL per 1 mmol), potassium acetate (1.05 equiv.) and acetic anhydride (2 equiv.) were added and reaction mixture stirred at room temperature for 12 h. After this time, tert-butyl nitrite (4 equiv.) and 18-crown-6 (0.35 equiv.) were added and reaction stirred again at 65° C. for 3 h. On completion, the reaction mixture was cooled to room temperature, diluted with chloroform (500 mL) and washed with sat. sodium bicarbonate solution. the organic layer was dried over sodium sulfate and concentrated to afford title the compound (yield 90-95%).

Step 5: methyl 1-acetyl-6-(trifluoromethyl)-1H-indazole-4-carboxylate

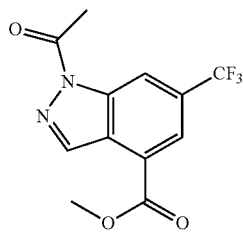 [SMILES: COC(=O)c1cc(C(F)(F)F)cc2c1cnn2C(C)=O]

To a stirred solution of methyl 6-(trifluoromethyl)-1H-indazole-4-carboxylate (1 equiv.) in methanol (7 mL per 1 mmol), 6N HCl (7 mL per 1 mmol) was added and stirred it at 60° C. for 3 h. On completion of reaction, the solvent was removed under reduced pressure and the residue basified with saturated $NaHCO_3$ solution till pH 8. The resulting precipitate was filtered and dried under vacuum. Finally, the solid was stirred in diethyl ether for 15 min, filtered and dried to afford methyl 1-acetyl-6-(trifluoromethyl)-1H-indazole-4-carboxylate (yield 70-75%).

Step 6: methyl 1-cyclopentyl-6-(trifluoromethyl)-1H-indazole-4-carboxylate

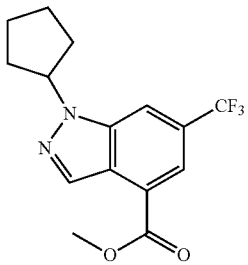 [SMILES: COC(=O)c1cc(C(F)(F)F)cc2c1cnn2C1CCCC1]

To a stirred solution of methyl 1-acetyl-6-(trifluoromethyl)-1H-indazole-4-carboxylate (1 equiv.) in acetonitrile (3 mL per 1 mmol), cesium carbonate (1.5 equiv.) was added followed by bromocyclopentane (2 equiv.). The reaction mixture was stirred at 90° C. for 3-4 h. On completion of reaction, acetonitrile was removed under reduced pressure and water was added. Extraction was carried out using ethyl acetate and the combined organic layers washed with water, brine and dried over anhydrous $Na_2SO_4$. Solvent was removed under reduced pressure and residue was purified by silica gel column chromatography to obtain methyl 1-cyclopentyl-6-(trifluoromethyl)-1H-indazole-4-carboxylate (yield 30-35%). The structure was confirmed as the desired regioisomer by NOE.

Step 7: 1-cyclopentyl-N-((4,6-dimethyl-2-oxo-1,2-dihydropyridin-3-yl)methyl)-6-(trifluoromethyl)-1H-indazole-4-carboxamide

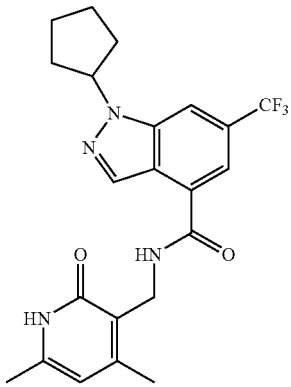 [SMILES: Cc1cc(C)c(CNC(=O)c2cc(C(F)(F)F)cc3c2cnn3C2CCCC2)c(=O)[nH]1]

To a stirred solution of methyl 1-cyclopentyl-6-(trifluoromethyl)-1H-indazole-4-carboxylate (1 equiv.) in ethanol (3 mL for 1 mmol), aqueous NaOH solution (1.5 equiv in 1 mL water) was added and reaction stirred at 60° C. for 4 h. On completion, ethanol was removed under reduced pressure and residue acidified with 1N HCl to pH 6. Solid that precipitates out was filtered, washed with water and dried to obtain pure corresponding acid (yield 80-90%). To a solution of this acid (1 equiv.) in DMSO (2 mL for 1 mmol), PyBOP (1.5 equiv.) was added and reaction stirred at rt for 15 min. Then 3-(aminomethyl)-4,6-dimethylpyridin-2(1H)-one (2 equiv.) was added and reaction stirred overnight. On completion, water was added and solid that precipitates out was filtered and washed with water. Then this solid was stirred with acetonitrile for 10 min and filtered again to obtain 1-cyclopentyl-N-((4,6-dimethyl-2-oxo-1,2-dihydropyridin-3-yl)methyl)-6-(trifluoromethyl)-1H-indazole-4-carboxamide (yield 50-60%). LCMS: 433.15 (M+1)+; HPLC: 99.51% (@ 254 nm) (R$_t$;7.326); $^1$H NMR (DMSO-d$_6$, 400 MHz) δ 11.53 (s, 1H), 8.76 (t, 1H), 8.50 (s, 1H), 8.38 (s, 1H), 7.85 (s, 1H), 5.88 (s, 1H), 5.38-5.41 (m, 1H), 4.35 (d, 2H, J=4.4 Hz), 2.21 (s, 3H), 2.12-2.20 (m, 2H), 2.12 (s, 3H), 1.88-2.00 (m, 4H), 1.69-1.71 (m, 2H).

Synthesis of Compound D-12: tert-butyl 4-(6-bromo-4-(((4,6-dimethyl-2-oxo-1,2-dihydropyridin-3-yl)methyl)carbamoyl)-1H-indazol-1-yl)piperidine-1-carboxylate Compound D-12

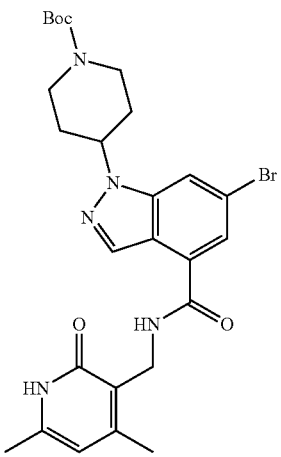

Step 1: tert-butyl 4-hydroxypiperidine-1-carboxylate

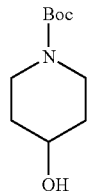

To a solution of piperidin-4-ol (25 g, 247 mmol) in DCM (250 mL), triethyl amine (52 mL, 371 mmol) was added and the resulting solution was cooled to 0° C. Boc anhydride (64.75 g, 297 mmol) was added to it slowly and the reaction mixture was stirred at room temp overnight. Water was added to reaction and the organic layer separated. The organic layer was further washed with water, brine and dried over sodium sulfate. Solvent was removed under reduced pressure to afford desired tert-butyl 4-hydroxypiperidine-1-carboxylate (50 g, crude).

Step 2: tert-butyl 4-(tosyloxy)piperidine-1-carboxylate

To a solution of tert-butyl 4-hydroxypiperidine-1-carboxylate (50 g, 248.7 mmol) in DCM (500 mL), triethyl amine (104 mL, 746 mmol) was added and resulting solution cooled to 0° C. p-Toluenesolfonyl chloride was then added to it portion-wise and the reaction continued at room temperature overnight. On completion, water was added to reaction and organic layer separated. The organic layer was further washed with water, brine and dried over sodium sulfate. Solvent was removed under reduced pressure to afford crude material which was purified by silica gel chromatography affording desired tert-butyl 4-(tosyloxy)piperidine-1-carboxylate (40 g).

Step 3: methyl 6 bromo-1-(tert-butoxycarbonyl) piperidine-4-yl)-1H-indazole-4-carboxylate To a solution of methyl 6-bromo-1H-indazole-4-carboxylate (5 g, 19.6 mmol) in DMF (22 mL), cesium carbonate (9.5 gm, 29.4 mmol) and tert-butyl 4-(tosyloxy)piperidine-1-carboxylate (6.95 g, 19.6 mmol) were added and resulting solution was heated at 80° C. for 18 h. On completion, water was added to reaction mixture and the aqueous phase extracted with ethyl acetate. The combined organic layers were further washed with water, brine and dried over sodium sulfate. The solvent was removed under reduced pressure to afford crude material which was purified by silica gel chromatography affording desired methyl 6 bromo-1-(tert-butoxycarbonyl)piperidine-4-yl)-1H-indazole-4-carboxylate (2.4 g, 28%).

Step 4: tert-butyl 4-(6-bromo-4-(((4,6-dimethyl-2-oxo-1,2-dihydropyridin-3-yl)methyl)carbamoyl)-1H-indazol-1-yl)piperidine-1-carboxylate

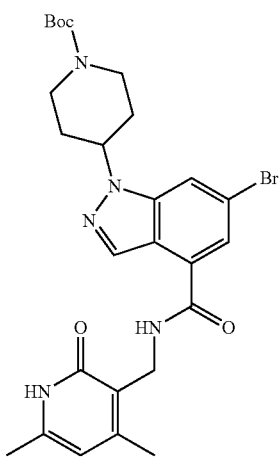 [SMILES: Cc1cc(C)c(CNC(=O)c2cc(Br)cc3c2cnn3C2CCN(C(=O)OC(C)(C)C)CC2)c(=O)[nH]1]

To a stirred solution of methyl 6 bromo-1-(tert-butoxycarbonyl)piperidine-4-yl)-1H-indazole-4-carboxylate (1 equiv.) in ethanol (3 mL per 1 mmol), aqueous NaOH solution (1.5 equiv.) was added and reaction stirred at 60° C. for 4 h. On completion, the ethanol was removed under reduced pressure and residue acidified with 1N HCl to pH 4-5. The resulting precipitate was filtered, washed with water and dried to obtain pure acid (yield 75-80%). To a stirred solution of this acid (1 equiv.) in DMSO (1.5 ml for 1 mmol) was added PyBop (1.5 equiv) and 3-(aminomethyl)-4,6-dimethylpyridin-2(1H)-one (2 equiv). The resulting reaction mixture was stirred at room temperature for 12 h. Upon completion, water was added to reaction mixture and the resulting precipitate filtered and washed with acetonitrile to obtain tert-butyl 4-(6-bromo-4-(((4,6-dimethyl-2-oxo-1,2-dihydropyridin-3-yl)methyl)carbamoyl)-1H-indazol-1-yl)piperidine-1-carboxylate (yield 55-60%). LCMS: 558.15 (M+1)$^+$; HPLC: 98.66% (@ 254 nm) (R$_t$: 7.314); $^1$H NMR (DMSO-d$_6$, 400 MHz) δ 11.52 (s, 1H), 8.61 (t, 1H), 8.37 (s, 1H), 8.26 (s, 1H), 7.71 (s, 1H), 5.88 (s, 1H), 4.92 (m, 1H), 4.33 (d, 2H, J=4.4 Hz), 4.10-4.07 (m, 2H), 2.96 (bs, 2H), 2.19 (s, 3H), 2.12 (s, 3H), 1.90 (bs, 4H), 1.42 (s, 9H).

Synthesis of Compound D-13: 6-bromo-N-((4,6-dimethyl-2-oxo-1,2-dihydropyridin-3-yl)methyl)-1-(piperidin-4-yl)-1H-indazole-4-carboxamide Compound D-13

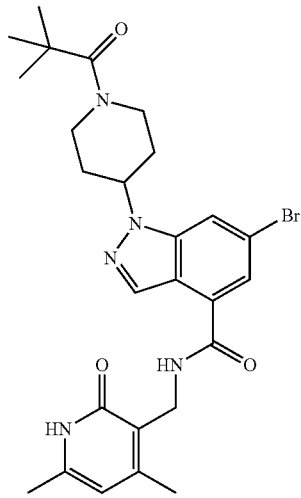

Step 1: 6-bromo-N-((4,6-dimethyl-2-oxo-1,2-dihydropyridin-3-yl)methyl)-1-(piperidin-4-yl)-1H-indazole-4-carboxamide

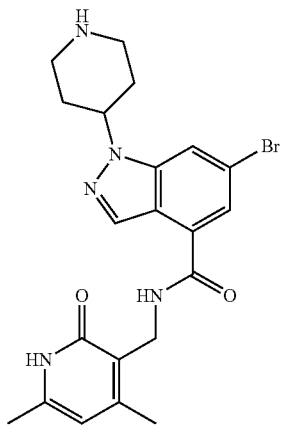 [SMILES: Cc1cc(C)c(CNC(=O)c2cc(Br)cc3c2cnn3C2CCNCC2)c(=O)[nH]1]

A stirred solution of tert-butyl 4-(6-bromo-4-(((4,6-dimethyl-2-oxo-1,2-dihydropyridin-3-yl)methyl)carbamoyl)-1H-indazol-1-yl)piperidine-1-carboxylate (1 mmol) in DCM (5 mL) was cooled to 0° C. and TFA (2 mL) was added to it. The reaction mixture was stirred at room temperature for 1 h. On completion, the reaction was concentrated to dryness and the residue basified with aqueous sodium bicarbonate till pH 8 and aqueous layer extracted with 20% MeOH/DCM. The combined organic layers were dried over sodium sulfate and concentrated to afford 6-bromo-N-((4,6-dimethyl-2-oxo-1,2-dihydropyridin-3-yl)methyl)-1-(piperidin-4-yl)-1H-indazole-4-carboxamide.

Step 2: 6-bromo-N-((4,6-dimethyl-2-oxo-1,2-dihydropyridin-3-yl)methyl)-1-(piperidin-4-yl)-1H-indazole-4-carboxamide

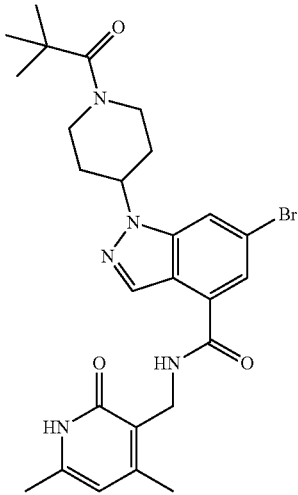 [SMILES: Cc1cc(C)c(CNC(=O)c2cc(Br)cc3c2cnn3C2CCN(C(=O)C(C)(C)C)CC2)c(=O)[nH]1]

To a stirred solution of 6-bromo-N-((4,6-dimethyl-2-oxo-1,2-dihydropyridin-3-yl)methyl)-1-(piperidin-4-yl)-1H-indazole-4-carboxamide (1 equiv.) in DMSO (1.5 ml per 1 mmol), triethylamine (3 equiv.), PyBOP (1.5 equiv.) and pivalic acid (2 equiv.) were added and resulting reaction mixture stirred at room temperature for 12 h. On completion, water was added to reaction mixture, the resulting precipitate was filtered and washed with acetonitrile to obtain 6-bromo-N-((4,6-dimethyl-2-oxo-1,2-dihydropyridin-3-yl)methyl)-1-(piperidin-4-yl)-1H-indazole-4-carboxamide (75% yield). LCMS: 542.15 (M+1)$^+$; HPLC: 99.26% (@ 254 nm) (R$_t$;6.583); $^1$H NMR (DMSO-d$_6$, 400 MHz) δ 11.50 (s, 1H), 8.60 (t, 1H), 8.37 (s, 1H), 8.27 (s, 1H), 7.71 (s, 1H), 5.87 (s, 1H), 5.01 (m, 1H), 4.43 (d, 2H, J=12.4 Hz), 4.33 (d, 2H, J=4.4 Hz), 3.01 (t, 2H, J=11.6&11.2 Hz), 2.19 (s, 3H), 2.12 (s, 3H), 2.00-1.85 (m, 4H), 1.23 (s, 9H).

Synthesis of Compound D-14: 1-(1-(azetidine-3-carbonyl)piperidin-4-yl)-6-bromo-N-((4,6-dimethyl-2-oxo-1,2-dihydropyridin-3-yl)methyl)-1H-indazole-4-carboxamide Compound D-14

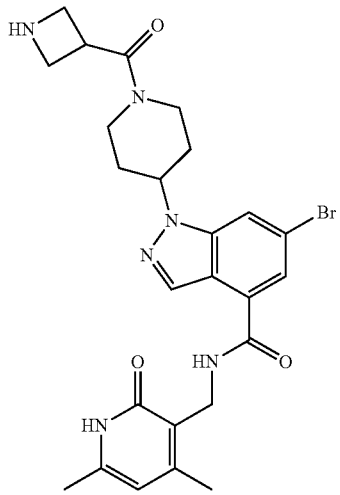

6-bromo-N-((4,6-dimethyl-2-oxo-1,2-dihydropyridin-3-yl)methyl)-1-(piperidin-4-yl)-1H-indazole-4-carboxamide was coupled with 1-(tert-butoxycarbonyl)azetidine-3-carboxylic acid using the general PyBOP coupling procedure followed by the general Boc deprotection method. The crude material was purified by prep HPLC to yield 1-(1-(azetidine-3-carbonyl)piperidin-4-yl)-6-bromo-N-((4,6-dimethyl-2-oxo-1,2-dihydropyridin-3-yl)methyl)-1H-indazole-4-carboxamide as the TFA salt (13% yield).

LCMS: 541.15 (M+1)$^+$; HPLC: 99.01% (@ 254 nm) (R$_t$;4.738); $^1$H NMR (DMSO-d$_6$, 400 MHz) δ 11.50 (s, 1H), 8.61 (t, 1H, J=4.4 Hz), 8.38 (s, 1H), 8.27 (s, 1H), 7.73 (s, 1H), 5.88 (s, 1H), 5.00 (m, 1H), 4.55 (d, 1H), 4.33 (d, 2H, J=4.4 Hz), 4.15-4.05 (m, 4H), 4.00-3.95 (m, 1H), 3.65 (d, 1H) 3.22 (m, 1H), 2.87 (t, 1H), 2.19 (s, 3H), 2.12 (s, 3H), 2.00-1.85 (m, 4H).

Synthesis of Compound D-15: 1-(1-benzylpiperidin-4-yl)-6-bromo-N-((4,6-dimethyl-2-oxo-1,2-dihydropyridin-3-yl)methyl)-1H-indazole-4-carboxamide Compound D-15

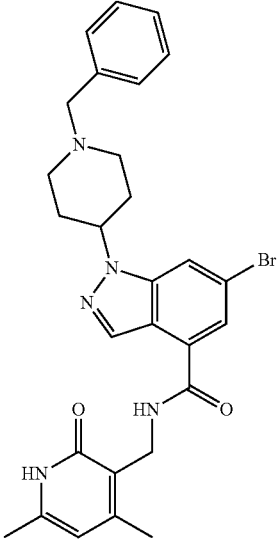

To a stirred solution of 6-bromo-N-((4,6-dimethyl-2-oxo-1,2-dihydropyridin-3-yl)methyl)-1-(piperidin-4-yl)-1H-indazole-4-carboxamide (1 equiv.) and benzaldehyde (1.5 equiv.) in methanol (5 mL per 0.3 mmol), acetic acid (1 equiv.) was added and reaction stirred at room temperature for 5 h. Then NaBH$_3$CN (1 equiv.) was added and the reaction stirred overnight. On completion, the solvent was removed under reduced pressure and the residue purified by column chromatography (27%). LCMS: 548.10 (M+1)$^+$; HPLC: 99.16% (@ 254 nm) (R$_t$;5.349); $^1$H NMR (DMSO-d$_6$, 400 MHz) δ 11.51 (s, 1H), 8.59 (t, 1H, J=4.8 Hz), 8.36 (s, 1H), 8.25 (s, 1H), 7.69 (d, 1H, J=1.2 Hz), 7.34 (d, 4H, J=4.4 Hz), 7.27-7.24 (m, 1H), 5.87 (s, 1H), 4.70 (m, 1H), 4.33 (d, 2H, J=4.8 Hz), 3.55 (s, 2H), 2.93 (d, 2H, J=10 Hz), 2.30-2.20 (m, 2H), 2.19 (s, 3H), 2.12 (s, 3H), 2.09 (m, 2H), 1.87 (m, 2H).

Synthesis of Compound D-16: 6-bromo-N-((4,6-dimethyl-2-oxo-1,2-dihydropyridin-3-yl)methyl)-1-(1'-methyl-[1,4'-bipiperidin]-4-yl)-1H-indazole-4-carboxamide

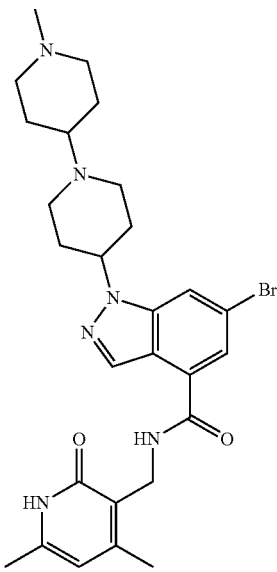

Compound D-16

To a stirred solution of 6-bromo-N-((4,6-dimethyl-2-oxo-1,2-dihydropyridin-3-yl)methyl)-1-(piperidin-4-yl)-1H-indazole-4-carboxamide (1 equiv.) and 1-methylpiperidin-4-one (1.5 equiv.) in methanol (5 mL per 0.3 mmol), acetic acid (1 equiv.) was added and reaction stirred at room temperature for 5 h. Then NaBH$_3$CN (1 equiv.) was added and the reaction stirred overnight. On completion, the solvent was removed under reduced pressure and the residue purified by column chromatography (24% yield). LCMS: 555.15 (M+1)$^+$; HPLC: 92.59% (@ 254 nm) (R$_t$:4.143); $^1$H NMR (DMSO-d$_6$, 400 MHz) δ 11.52 (s, 1H), 8.60 (t, 1H, J=5.2 Hz), 8.35 (s, 1H), 8.24 (s, 1H), 7.68 (s, 1H), 5.88 (s, 1H), 4.63-4.68 (m, 1H), 4.32 (d, 2H, J=4.8 Hz), 2.97 (d, 2H, J=11.6 Hz), 2.79 (d, 2H, J=10.8 Hz), 2.22-2.40 (m, 3H), 2.19 (s, 3H), 2.13 (s, 3H), 2.11 (s, 3H), 1.99-2.08 (m, 2H), 1.81-1.88 (m, 4H), 1.69 (d, 2H, J=11.2 Hz), 1.43-1.48 (m, 2H).

Synthesis of Compound D-17: 6-bromo-1-cyclopentyl-N-((4-((dimethylamino)methyl)-6-methyl-2-oxo-1,2-dihydropyridin-3-yl)methyl)-1H-indazole-4-carboxamide

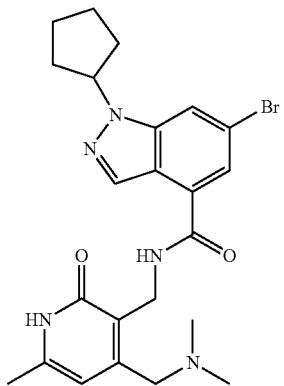 [SMILES: Cc1cc(CN(C)C)c(CNC(=O)c2cc(Br)cc3c2cnn3C2CCCC2)c(=O)[nH]1]

Step 1: tert-butyldimethyl(prop-2-yn-1-yloxy)silane

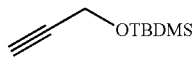

To a solution of propargyl alcohol (15 g, 267 mmol) in DMF (60 mL), imidazole (21.85 g, 321 mmol) was added at 0° C. followed by the slow addition of a solution of TBDMS-Cl (47.2 mL, 272 mmol) in DMF (70 mL). Resulting reaction mixture was stirred at 0° C. for 30 min and then at room temperature for overnight. On completion, water was added to the reaction mixture and the aqueous layer extracted with 20% ethyl acetate/hexane. The combined organic layers were dried over sodium sulfate and concentrated to obtain crude material which was purified by column chromatography over silica gel affording tert-butyldimethyl (prop-2-yn-1-yloxy)silane (45.5 g, 32.9%).

Step 2: 5-((tert-butyldimethylsilyl)oxy)pent-3-yn-2-one

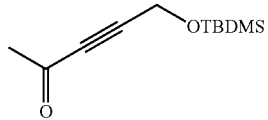

To a solution of tert-butyldimethyl(prop-2-yn-1-yloxy) silane (15.1 g, 88.3%) in THF (300 mL), n-BuLi (67 mL, 105.9 mmol, 1.6 N in hexane) was added slowly at −78° C. After the addition was complete, the temperature was increased slowly to 10° C. over a period of 2 h. The reaction mixture was cooled again to −78° C. and BF$_3$.OEt$_2$ (14 mL, 105.9 mmol) added slowly and reaction mixture stirred at this temperature for 5 min. Acetic anhydride (11 mL, 115.6 mmol) was slowly added and the reaction was continued while temperature was allowed to rise to room temperature over a period of 2 h. After this time, reaction mass was quenched with 1N NaOH till pH 7-8 and biphasic solution was extracted with ethyl acetate. The organic layer was concentrated to obtain crude material which was further purified by column chromatography over silica gel to yield 5-((tert-butyldimethylsilyl)oxy)pent-3-yn-2-one (9.2 g, 52.6%).

Step 3: 4-(((tert-butyldimethylsilyl)oxy)methyl)-2-hydroxy-6-methyl nicotinonitrile

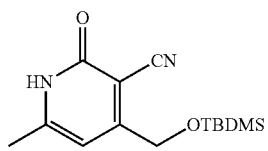 [SMILES: Cc1cc(CO[Si](C)(C)C(C)(C)C)c(C#N)c(=O)[nH]1]

To a solution of 5-((tert-butyldimethylsilyl)oxy)pent-3-yn-2-one (9.2 g, 43 mmol) in 90% ethanol (185 mL), cyanoacetamide (4.35 g, 51.8 mmol) and piperidine acetate. were added and reaction heated at 85° C. for 4 h. The piperidine acetate was prepared by the addition of piperidine to a solution of acetic acid (2.2 mL) in water (4.4 mL) till pH 8. On completion, ethanol was evaporated and water was added to residue. The resulting solid was filtered and washed with 200 mL water before being was stirred again with acetonitrile for 10 min and filtered again to obtain 4-(((tert-butyldimethylsilyl)oxy)methyl)-6-methyl-2-oxo-1,2-dihydropyridine-3-carbonitrile (3.82 g, 29.6%).

Step 4: 3-(aminomethyl)-4-(((tert-butyldimethylsilyl)oxy)methyl)-6-methylpyridin-2(1H)-one

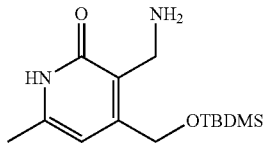 [SMILES: Cc1cc(CO[Si](C)(C)C(C)(C)C)c(CN)c(=O)[nH]1]

To a solution of 4-(((tert-butyldimethylsilyl)oxy)methyl)-6-methyl-2-oxo-1,2-dihydropyridine-3-carbonitrile (3.8 g, 13.7 mmol) in methanol (200 mL), Raney Ni and ammonia (20 mL) were added and reaction stirred under hydrogen balloon pressure for 15 h. On completion, reaction mixture was filtered through a celite bed and the filtrate concentrated to obtain 3-(aminomethyl)-4-(((tert-butyldimethylsilyl)oxy)methyl)-6-methylpyridin-2(1H)-one as an off white solid (3.2 g, 83.1%).

Step 5: 6-bromo-1-cyclopentyl-1H-indazole-4-carboxylic acid

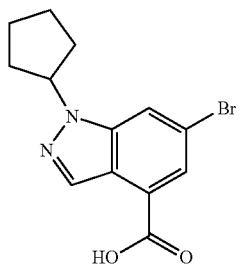 [SMILES: O=C(O)c1cc(Br)cc2c1cnn2C1CCCC1]

To a stirred solution of methyl 6-bromo-1-cyclopentyl-1H-indazole-4-carboxylate (3 g, 9.28 mmol) in ethanol (30 mL), aqueous NaOH solution (0.56 g in 3 mL water, 13.93 mmol) was added and reaction stirred at 60° C. for 4 h. On completion, ethanol was removed under reduced pressure and residue acidified with 1N HCl to pH 6. The resulting precipitate was filtered, washed with water and dried to 6-bromo-1-cyclopentyl-1H-indazole-4-carboxylic acid (2.3 g, 80.4%).

Step 6: 6-bromo-1-cyclopentyl-N-((4-(hydroxymethyl)-6-methyl-2-oxo-1,2-dihydropyridin-3-yl)methyl)-1H-indazole-4-carboxamide

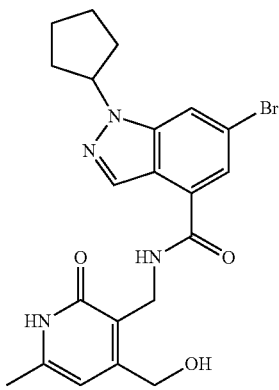 [SMILES: Cc1cc(CO)c(CNC(=O)c2cc(Br)cc3c2cnn3C2CCCC2)c(=O)[nH]1]

To a solution of 6-bromo-1-cyclopentyl-1H-indazole-4-carboxylic acid (2.3 g, 7.5 mmol) in DMSO (30 mL), PyBOP (5.82 g, 11.20 mmol) was added and reaction stirred at room temperature for 15 min. 3-(Aminomethyl)-4-(((tert-butyldimethylsilyl)oxy)methyl)-6-methylpyridin-2(1H)-one (2.52 g, 8.96 mmol) was then added and reaction mixture stirred overnight. On completion, water was added and the resulting precipitate filtered and washed with water. This solid was then stirred with acetonitrile for 10 min and filtered again to obtain 6-bromo-1-cyclopentyl-N-((4-(hydroxymethyl)-6-methyl-2-oxo-1,2-dihydropyridin-3-yl)methyl)-1H-indazole-4-carboxamide (1.4 g, 40.9%).

Step 7: 6-bromo-1-cyclopentyl-N-((4-((dimethylamino)methyl)-6-methyl-2-oxo-1,2-dihydropyridin-3-yl)methyl)-1H-indazole-4-carboxamide

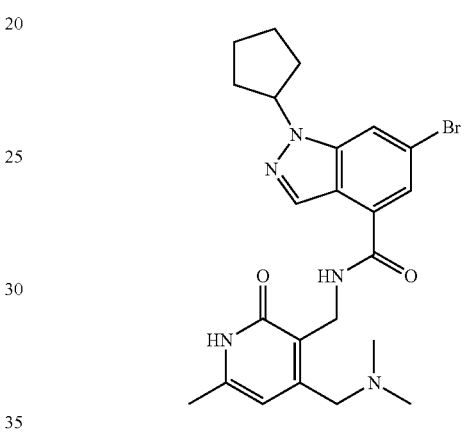

To a stirred solution of 6-bromo-1-cyclopentyl-N-((4-(hydroxymethyl)-6-methyl-2-oxo-1,2-dihydropyridin-3-yl)methyl)-1H-indazole-4-carboxamide (0.6 g, 1.3 mmol) in DCM (5 mL), triphenylphosphine (0.54 g, 2.06 mmol) was added at 0° C. followed by carbon tetrabromide (0.684 g, 2.262 mmol) at the same temperature. Reaction mixture was stirred at room temperature for 2 h. On completion, the reaction mixture was purified by column over silica gel to afford intermediate 6-bromo-N-((4-(bromomethyl)-6-methyl-2-oxo-1,2-dihydropyridin-3-yl)methyl)-1-cyclopentyl-1H-indazole-4-carboxamide (0.4 g, 58.8%). To a solution of this intermediate in DMF, respective amine (5 equiv.) was added and reaction stirred for overnight at room temperature. On completion, reaction mixture was poured into water and extracted with 15% MeOH/DCM. The combined organic layers were dried over sodium sulfate and concentrated to obtain crude material which was purified by prep HPLC affording 6-bromo-1-cyclopentyl-N-((4-((dimethylamino)methyl)-6-methyl-2-oxo-1,2-dihydropyridin-3-yl)methyl)-1H-indazole-4-carboxamide (19.2% yield). LCMS: 486.05 (M+1)$^+$; HPLC: 99.59% (@ 254 nm) (R$_t$:5.723); $^1$H NMR (DMSO-d$_6$, 400 MHz) δ 11.65 (s, 1H), 8.83 (s, 1H), 8.36 (s, 1H), 8.20 (s, 1H), 7.62 (s, 1H), 6.07 (s, 1H), 5.23-5.18 (m, 1H), 4.41 (d, 2H, J=4 Hz), 3.37 (m, 2H), 2.16 (s, 6H), 2.15-2.05 (m, 5H), 1.99-1.91 (m, 2H), 1.86 (m, 2H), 1.69 (m, 2H).

Synthesis of Compounds D-18 and D-19: 1-cyclopentyl-N-((4,6-dimethyl-2-oxo-1,2-dihydropyridin-3-yl)methyl)-6-(4-(piperidine-4-carbonyl)piperazin-1-yl)-1H-indazole-4-carboxamide and 1-cyclopentyl-N-((4,6-dimethyl-2-oxo-1,2-dihydropyridin-3-yl)methyl)-6-(piperazin-1-yl)-1H-indazole-4-carboxamide

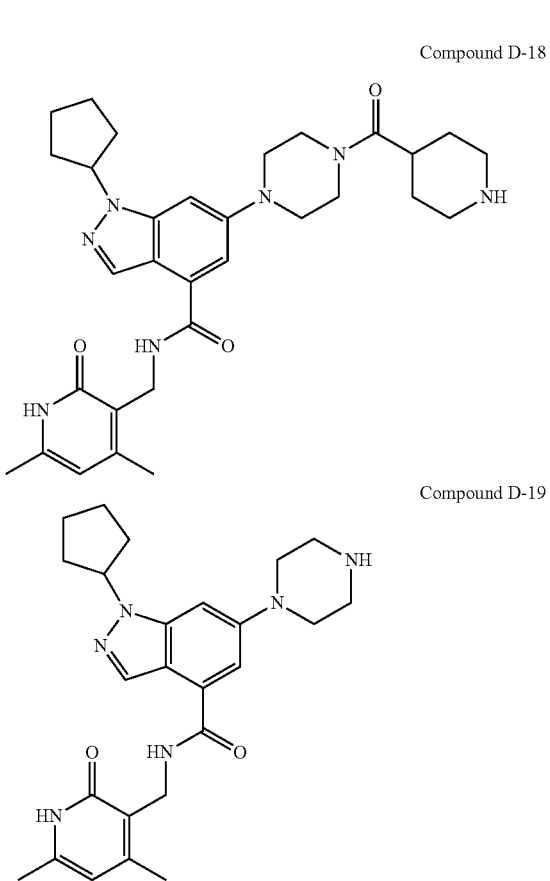

Compound D-18

Compound D-19

Step 1: methyl 6-(4-(tert-butoxycarbonyl)piperazin-1-yl)-1-cyclopentyl-1H-indazole-4-carboxylate

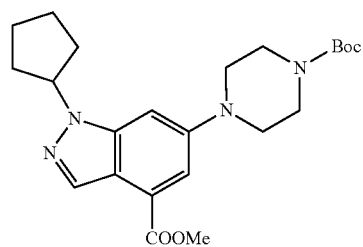 [SMILES: COC(=O)c1cc(N2CCN(C(=O)OC(C)(C)C)CC2)cc2c1cnn2C1CCCC1]

To a stirred solution of methyl 6-bromo-1-cyclopentyl-1H-indazole-4-carboxylate (5 g, 15.527 mmol) in DMSO (25 mL), 1-Boc piperazine (4.3 g, 23.3 mmol), $K_2CO_3$ (4.28 g, 31.05 mmol), CuI (0.295 g, 1.55 mmol) and L-proline (0.357 g, 3.1 mmol) were added in given order and resulting reaction mixture heated to 100° C. for 48 h. On completion, the reaction mixture was poured into water and extracted with DCM. The combined organic layers were washed with water and dried over sodium sulfate. The solvent was removed under reduced pressure to obtain crude residue which was purified by column chromatography over silica gel affording methyl 6-(4-(tert-butoxycarbonyl)piperazin-1-yl)-1-cyclopentyl-1H-indazole-4-carboxylate (2 g, 30%).

Step 2: 6-(4-(tert-butoxycarbonyl)piperazin-1-yl)-1-cyclopentyl-1H-indazole-4-carboxylic acid

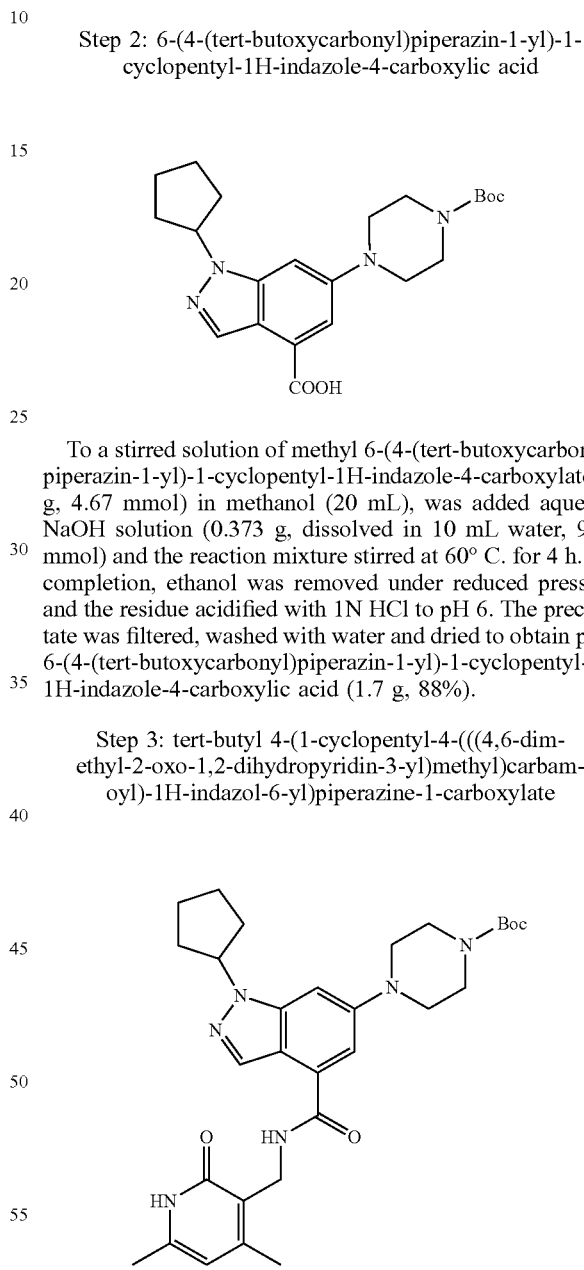

To a stirred solution of methyl 6-(4-(tert-butoxycarbonyl)piperazin-1-yl)-1-cyclopentyl-1H-indazole-4-carboxylate (2 g, 4.67 mmol) in methanol (20 mL), was added aqueous NaOH solution (0.373 g, dissolved in 10 mL water, 9.34 mmol) and the reaction mixture stirred at 60° C. for 4 h. On completion, ethanol was removed under reduced pressure and the residue acidified with 1N HCl to pH 6. The precipitate was filtered, washed with water and dried to obtain pure 6-(4-(tert-butoxycarbonyl)piperazin-1-yl)-1-cyclopentyl-1H-indazole-4-carboxylic acid (1.7 g, 88%).

Step 3: tert-butyl 4-(1-cyclopentyl-4-(((4,6-dimethyl-2-oxo-1,2-dihydropyridin-3-yl)methyl)carbamoyl)-1H-indazol-6-yl)piperazine-1-carboxylate To a solution of 6-(4-(tert-butoxycarbonyl)piperazin-1-yl)-1-cyclopentyl-1H-indazole-4-carboxylic acid (1.7 g, 4.1 mmol) in DMSO (10 mL), amine (1.248 g, 8.212 mmol) was added and the reaction mixture stirred at room temperature for 10 min. PYBOP (3.202 g, 6.159 mmol) was then added and the reaction mixture stirred at room temperature overnight. On completion, the reaction mixture was poured into water and extracted with DCM. The combined organic layers were washed with water and dried over sodium sulfate. Solvent was removed under reduced pressure to obtain crude residue which was purified by column chromatography over silica gel affording desired compound (2 g, 88%).

Step 4: Synthesis of 1-cyclopentyl-N-((4,6-dimethyl-2-oxo-1,2-dihydropyridin-3-yl)methyl)-6-(piperazin-1-yl)-1H-indazole-4-carboxamide

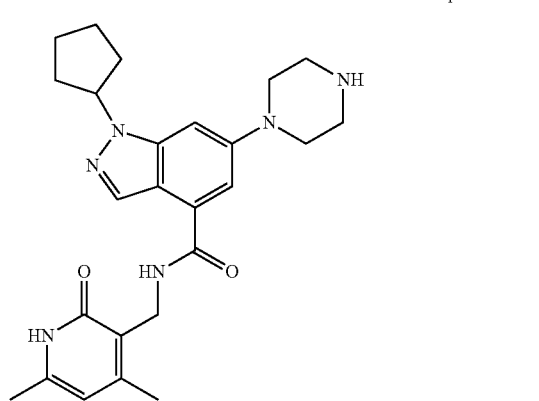

Compound D-19 tert-Butyl 4-(1-cyclopentyl-4-(((4,6-dimethyl-2-oxo-1,2-dihydropyridin-3-yl)methyl)carbamoyl)-1H-indazol-6-yl)piperazine-1-carboxylate (0.1 g) was converted to the target molecule using the general Boc deprotection procedure. The crude reaction mixture was purified by prep HPLC to afford the TFA salt. LCMS: 449.30 (M+1)$^+$; HPLC: 99.11% (@ 254 nm) (R$_t$;4.824); $^1$H NMR (DMSO-d$_6$, 400 MHz) δ 11.52 (bs, 1H), 8.80 (bs, 2H), 8.41 (t, 1H), 8.17 (s, 1H), 7.34 (s, 1H), 7.21 (s, 1H), 5.88 (s, 1H), 5.18-5.11 (m, 1H), 4.35 (d, 2H, J=4 Hz), 3.46 (bs, 4H), 3.28 (bs, 4H), 2.20 (s, 3H), 2.11 (s, 3H), 2.08-2.05 (m, 2H), 1.98-1.90 (m, 2H), 1.86 (m, 2H), 1.67 (m, 2H).

Step 5: 1-cyclopentyl-N-((4,6-dimethyl-2-oxo-1,2-dihydropyridin-3-yl)methyl)-6-(4-(piperidine-4-carbonyl)piperazin-1-yl)-1H-indazole-4-carboxamide Compound D-18

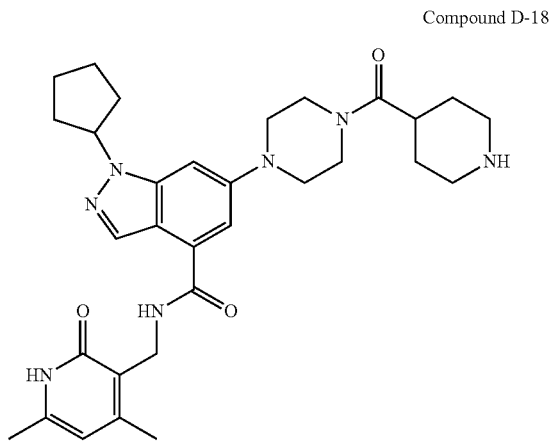 [SMILES: Cc1cc(C)c(CNC(=O)c2cc(N3CCN(C(=O)C4CCNCC4)CC3)cc3c2cnn3C2CCCC2)c(=O)[nH]1]

1-Cyclopentyl-N-((4,6-dimethyl-2-oxo-1,2-dihydropyridin-3-yl)methyl)-6-(piperazin-1-yl)-1H-indazole-4-carboxamide was converted to the target compound in a 58% yield using the by general PyBOP coupling procedure. Finally, Boc deprotection with the general procedure produced a crude residue which was triturated with diethyl ether to afford pure 1-cyclopentyl-N-((4,6-dimethyl-2-oxo-1,2-dihydropyridin-3-yl)methyl)-6-(4-(piperidine-4-carbonyl)piperazin-1-yl)-1H-indazole-4-carboxamide as the TFA salt (65.3% yield).

Synthesis of Compound D-20: 1-cyclopentyl-N-((4,6-dimethyl-2-oxo-1,2-dihydropyridin-3-yl)methyl)-6-isopropyl-1H-indazole-4-carboxamide

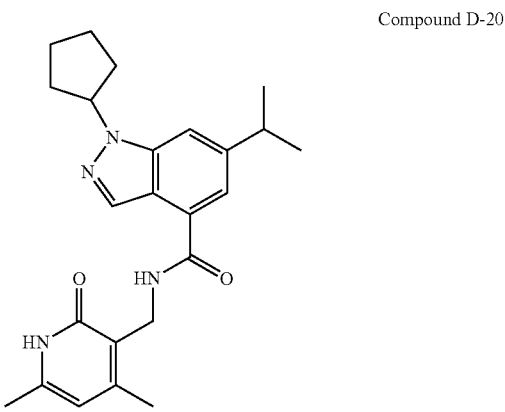 [SMILES: Cc1cc(C)c(CNC(=O)c2cc(C(C)C)cc3c2cnn3C2CCCC2)c(=O)[nH]1]

Compound D-20

Step 1: 1-cyclopentyl-N-((4,6-dimethyl-2-oxo-1,2-dihydropyridin-3-yl)methyl)-6-(prop-1-en-2-yl)-1H-indazole-4-carboxamide

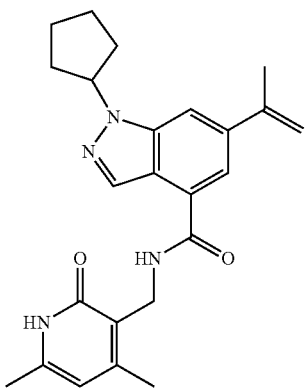 [SMILES: C=C(C)c1cc(C(=O)NCc2c(C)cc(C)[nH]c2=O)c2cnn(C3CCCC3)c2c1]

6-Bromo-1-cyclopentyl-N-((4,6-dimethyl-2-oxo-1,2-dihydropyridin-3-yl)methyl)-1H-indazole-4-carboxamide was converted to desired compound in 70-80% yield using the general Suzuki coupling procedure.

Step 2: 1-cyclopentyl-N-((4,6-dimethyl-2-oxo-1,2-dihydropyridin-3-yl)methyl)-6-isopropyl-1H-indazole-4-carboxamide

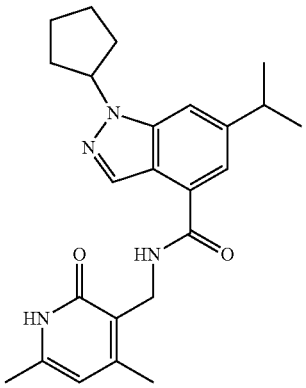 [SMILES: Cc1cc(C)c(CNC(=O)c2cc(C(C)C)cc3c2cnn3C2CCCC2)c(=O)[nH]1]

1-Cyclopentyl-N-((4,6-dimethyl-2-oxo-1,2-dihydropyridin-3-yl)methyl)-6-(prop-1-en-2-yl)-1H-indazole-4-carboxamide was reduced using the standard Pd—C hydrogenation conditions and purified by prep HPLC to afford the target compound as a TFA salt (35% yield). LCMS: 407.25 $(M+1)^+$; HPLC: 97.79% (@ 254 nm) ($R_t$;7.285); $^1$H NMR (DMSO-$d_6$, 400 MHz) δ 11.54 (s, 1H), 8.43 (t, 1H), 8.25 (s, 1H), 7.64 (s, 1H), 7.48 (s, 1H), 5.89 (s, 1H), 5.18 (m, 1H), 4.36 (d, 2H, J=4 Hz), 3.04 (m, 1H), 2.21 (s, 3H), 2.12 (s, 3H), 2.08 (m, 2H), 1.98 (m, 2H), 1.86 (m, 2H), 1.69 (m, 2H), 1.28 (d, 6H, J=6.8 Hz).

Syntheses of Compounds D-21 though D-91 and D-93 through D-98

Compounds D-21 though D-91 and D-93 through D-98 were synthesized by methods similar to those described for Compounds D-1 through D-20 or by reaction schemes depicted in the general schemes.

Syntheses of Compounds E-1, E-2, F-1, and F-2

Compounds E-1, E-2, F-1, and F-2 were synthesized by methods similar to those described herein.

Example 2

Bioassay Protocol and General Methods

Protocol for Wild-Type and Mutant PRC2 Enzyme Assays

General Materials. S-adenosylmethionine (SAM), S-adenosylhomocyteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol. 384-well streptavidin Flashplates were purchased from PerkinElmer.

Substrates. Peptides representative of human histone H3 residues 21-44 containing either an unmodified lysine 27 (H3K27me0) or dimethylated lysine 27 (H3K27me2) were synthesized with a C-terminal G(K-biotin) linker-affinity tag motif and a C-terminal amide cap by 21$^{st}$ Century Biochemicals. The peptides were high-performance liquid chromatography (HPLC) purified to greater than 95% purity and confirmed by liquid chromatography mass spectrometry (LC-MS). The sequences are listed below.

H3K27me0:
(SEQ ID NO: 1)
ATKAARKSAPATGGVKKPHRYRPGGK(biotin)-amide

H3K27me2:
(SEQ ID NO: 2)
ATKAARK(me2)SAPATGGVKKPHRYRPGGK(biotin)-amide

Chicken erythrocyte oligonucleosomes were purified from chicken blood according to established procedures.

Recombinant PRC2 Enzymes. Human PRC2 enzymes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates. The assays were all performed in a buffer consisting of 20 mM bicine (pH=7.6), 0.5 mM DTT, 0.005% BSG and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 μL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 7, below. The assays were stopped by the addition of non-radioactive SAM (10 μL) to a final concentration of 600 μM, which dilutes the $^3$H-SAM to a level where its incorporation into the peptide substrate is no longer detectable. 50 μL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 7

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate. The assays was performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 µL) were spotted into polypropylene 384-well V-bottom plates (Greiner) using a Platemate 2×3 outfitted with a 384-channel pipet head (Thermo). DMSO (1 µL) was added to columns 11, 12, 23, 24, rows A-H for the maximum signal control, and SAH, a known product and inhibitor of PRC2 (1 µL) was added to columns 11, 12, 23, 24, rows I-P for the minimum signal control. A cocktail (40 µL) containing the wild-type PRC2 enzyme and chicken erythrocyte oligonucleosome was added by Multidrop Combi (Thermo). The compounds were allowed to incubate with PRC2 for 30 min at 25° C., then a cocktail (10 µL) containing a mixture of non-radioactive and $^3$H-SAM was added to initiate the reaction (final volume=51 µL). The final concentrations were as follows: wild-type PRC2 enzyme was 4 nM, non-radioactive SAM was 430 nM, $^3$H-SAM was 120 nM, chicken erythrocyte olignonucleosome was 120 nM, SAH in the minimum signal control wells was 1 mM and the DMSO concentration was 1%. The assay was stopped by the addition of non-radioactive SAM (10 µL) to a final concentration of 600 µM, which dilutes the $^3$H-SAM to a level where its incorporation into the chicken erythrocyte oligonucleosome substrate is no longer detectable. 50 µL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^3$H-labeled chicken erythrocyte oligonucleosome bound to the Flashplate surface, measured as disintegrations per minute (dpm) or alternatively, referred to as counts per minute (cpm).

% Inhibition Calculation $$\% \, inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-parameter IC50 Fit $$Y = Bottom + \frac{(Top - Bottom)}{1 + \left( \frac{X}{IC_{50}} \right)^{Hill\ Coefficient}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

IC50 values for the PRC2 enzyme assays on peptide substrates are presented in Table 3 below. In this table, "A" indicates IC50 values of 10 µM and <50 µM; "B" indicates IC50 values of >3 µM and <10 µM; "C" indicates IC50 values of >1 µM and <3 µM; "D" indicates IC50 values of >0.3 µM and <1 µM; and "E" indicates IC50 values of <0.3 µM.

The compounds listed in Tables 1-6 were tested and the results were described in Tables 8-13 below.

TABLE 8

| Compound Number | EZH2 IC50 |
|---|---|
| A-1 | E |
| A-2 | D |
| A-3 | D |
| A-4 | D |
| A-5 | D |
| A-6 | D |
| A-7 | E |
| A-8 | D |
| A-9 | D |
| A-10 | E |
| A-11 | D |
| A-12 | D |
| A-13 | E |
| A-14 | E |
| A-15 | E |
| A-16 | D |
| A-17 | E |
| A-18 | E |
| A-19 | D |
| A-20 | D |
| A-21 | D |
| A-22 | D |
| A-23 | D |
| A-24 | D |
| A-25 | D |
| A-26 | D |
| A-27 | D |
| A-28 | D |
| A-29 | D |
| A-30 | D |
| A-31 | D |
| A-32 | D |
| A-33 | D |
| A-34 | D |
| A-35 | D |
| A-36 | D |
| A-37 | D |
| A-38 | D |
| A-39 | D |
| A-40 | D |
| A-41 | D |
| A-42 | D |
| A-43 | D |
| A-44 | D |
| A-45 | D |
| A-46 | D |
| A-47 | D |
| A-48 | C |
| A-49 | C |
| A-50 | C |
| A-51 | C |
| A-52 | C |
| A-53 | C |
| A-54 | C |
| A-55 | C |
| A-56 | C |
| A-57 | C |
| A-58 | C |

TABLE 8-continued

| Compound Number | EZH2 IC50 |
|---|---|
| A-59 | C |
| A-60 | C |
| A-61 | C |
| A-62 | C |
| A-63 | C |
| A-64 | C |
| A-65 | B |
| A-66 | C |
| A-67 | C |
| A-68 | B |
| A-69 | B |
| A-70 | B |
| A-71 | A |
| A-72 | A |
| A-73 | A |
| A-74 | A |
| A-75 | A |
| A-76 | A |
| A-77 | A |
| A-78 | A |
| A-91 | D |
| A-92 | C |
| A-93 | C |
| A-94 | B |
| A-95 | B |
| A-96 | B |
| A-97 | B |
| A-98 | A |
| A-99 | A |
| A-100 | A |
| A-101 | A |
| A-102 | A |
| A-103 | A |
| A-104 | A |
| A-105 | A |
| A-106 | A |
| A-107 | A |
| A-108 | A |
| A-109 | A |
| A-110 | A |
| A-125 | C |
| A-126 | D |

TABLE 9

| Compound Number | EZH2 IC50 |
|---|---|
| B-1 | E |
| B-2 | D |
| B-3 | C |
| B-4 | E |
| B-5 | E |
| B-6 | D |
| B-7 | D |
| B-8 | E |
| B-9 | C |
| B-10 | D |
| B-11 | C |
| B-12 | C |
| B-13 | D |
| B-14 | D |
| B-15 | D |
| B-16 | E |
| B-17 | C |
| B-18 | C |
| B-19 | D |
| B-20 | E |
| B-21 | D |
| B-22 | E |
| B-23 | D |
| B-24 | D |
| B-25 | E |
| B-26 | D |

TABLE 9-continued

| Compound Number | EZH2 IC50 |
|---|---|
| B-27 | D |
| B-28 | E |
| B-29 | E |
| B-30 | E |
| B-31 | E |
| B-32 | E |
| B-33 | E |
| B-34 | E |
| B-35 | E |
| B-36 | D |
| B-37 | D |
| B-38 | D |
| B-39 | D |
| B-40 | D |
| B-41 | D |
| B-42 | D |
| B-43 | D |
| B-44 | D |
| B-45 | D |
| B-46 | D |
| B-47 | D |
| B-48 | D |
| B-49 | D |
| B-50 | D |
| B-51 | D |
| B-52 | D |
| B-53 | D |
| B-54 | D |
| B-55 | D |
| B-56 | D |
| B-57 | D |
| B-58 | D |
| B-59 | D |
| B-60 | D |
| B-61 | D |
| B-62 | D |
| B-63 | D |
| B-64 | D |
| B-65 | D |
| B-66 | D |
| B-67 | D |
| B-68 | D |
| B-69 | D |
| B-70 | D |
| B-71 | D |
| B-72 | D |
| B-73 | D |
| B-74 | D |
| B-75 | D |
| B-76 | D |
| B-77 | D |
| B-78 | D |
| B-79 | D |
| B-80 | D |
| B-81 | D |
| B-82 | D |
| B-83 | D |
| B-84 | D |
| B-85 | D |
| B-86 | C |
| B-87 | C |
| B-88 | C |
| B-89 | C |
| B-90 | C |
| B-91 | C |
| B-92 | C |
| B-93 | C |
| B-94 | C |
| B-95 | C |
| B-96 | C |
| B-97 | C |
| B-98 | C |
| B-99 | C |
| B-100 | C |
| B-101 | C |
| B-102 | C |
| B-103 | C |

TABLE 9-continued

| Compound Number | EZH2 IC50 |
|---|---|
| B-104 | C |
| B-105 | C |
| B-106 | C |
| B-107 | C |
| B-108 | C |
| B-109 | C |
| B-110 | C |
| B-111 | C |
| B-112 | C |
| B-113 | C |
| B-114 | C |
| B-115 | C |
| B-116 | C |
| B-117 | C |
| B-118 | C |
| B-119 | C |
| B-120 | C |
| B-121 | C |
| B-122 | B |
| B-123 | B |
| B-124 | B |
| B-125 | B |
| B-126 | B |
| B-127 | B |
| B-128 | B |
| B-129 | B |
| B-130 | B |
| B-131 | B |
| B-132 | B |
| B-133 | B |
| B-134 | B |
| B-135 | B |
| B-136 | B |
| B-137 | B |
| B-138 | B |
| B-139 | B |
| B-140 | B |
| B-141 | B |
| B-142 | B |
| B-143 | B |
| B-144 | B |
| B-145 | A |
| B-146 | A |
| B-147 | A |
| B-148 | A |
| B-151 | A |
| B-152 | A |
| B-153 | A |
| B-154 | A |
| B-155 | A |
| B-156 | A |
| B-164 | B |

TABLE 10

| Compound Number | EZH2 IC50 |
|---|---|
| C-1 | E |
| C-2 | E |
| C-3 | E |
| C-4 | E |
| C-5 | E |
| C-6 | E |
| C-7 | D |
| C-8 | D |
| C-9 | E |
| C-10 | E |
| C-11 | E |
| C-12 | E |
| C-13 | E |
| C-14 | E |
| C-15 | E |
| C-16 | E |
| C-17 | E |
| C-18 | E |
| C-19 | E |
| C-20 | E |
| C-21 | E |
| C-22 | E |
| C-23 | E |
| C-24 | E |
| C-25 | E |
| C-26 | E |
| C-27 | E |
| C-28 | E |
| C-29 | E |
| C-30 | E |
| C-31 | E |
| C-32 | E |
| C-33 | E |
| C-34 | E |
| C-35 | E |

TABLE 11

| Compound Number | EZH2 IC50 |
|---|---|
| D-1 | D |
| D-2 | E |
| D-3 | E |
| D-4 | E |
| D-5 | E |
| D-6 | E |
| D-7 | E |
| D-8 | D |
| D-9 | D |
| D-10 | E |
| D-11 | D |
| D-12 | E |
| D-13 | E |
| D-14 | E |
| D-15 | D |
| D-16 | E |
| D-17 | E |
| D-18 | E |
| D-19 | D |
| D-20 | D |
| D-21 | D |

TABLE 11-continued

| Compound Number | EZH2 IC50 |
|---|---|
| D-22 | C |
| D-23 | E |
| D-24 | E |
| D-25 | E |
| D-26 | D |
| D-27 | D |
| D-28 | D |
| D-29 | D |
| D-30 | E |
| D-31 | D |
| D-32 | D |
| D-33 | E |
| D-34 | C |
| D-35 | C |
| D-36 | C |
| D-37 | E |
| D-38 | E |
| D-39 | E |
| D-40 | E |
| D-41 | E |
| D-42 | E |
| D-43 | E |
| D-44 | E |
| D-45 | E |
| D-46 | E |
| D-47 | E |
| D-48 | E |
| D-49 | E |
| D-50 | E |
| D-51 | E |
| D-52 | E |
| D-53 | D |
| D-54 | D |
| D-55 | D |
| D-56 | D |
| D-57 | D |
| D-58 | D |
| D-59 | D |
| D-60 | D |
| D-61 | D |
| D-62 | D |
| D-63 | D |
| D-64 | D |
| D-65 | D |
| D-66 | D |
| D-67 | D |
| D-68 | D |
| D-69 | C |
| D-70 | C |
| D-71 | C |
| D-72 | C |
| D-73 | C |
| D-74 | C |
| D-75 | C |
| D-76 | C |
| D-77 | C |
| D-78 | C |
| D-79 | C |
| D-80 | C |
| D-81 | B |
| D-82 | B |
| D-83 | B |
| D-84 | B |
| D-85 | B |
| D-86 | B |
| D-87 | B |
| D-88 | A |
| D-89 | A |
| D-90 | A |
| D-91 | D |
| D-93 | D |
| D-94 | D |
| D-95 | E |
| D-96 | E |
| D-97 | E |
| D-98 | D |

TABLE 12

| Compound Number | EZH2 IC50 |
|---|---|
| E-1 | C |
| E-2 | E |

TABLE 13

| Compound Number | EZH2 IC50 |
|---|---|
| F-1 | B |
| F-2 | D |

Incorporation by Reference

The entire disclosure of each of the patent documents and scientific articles referred to herein is incorporated by reference for all purposes.

Equivalents

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (I) or a pharmaceutically acceptable salt thereof:

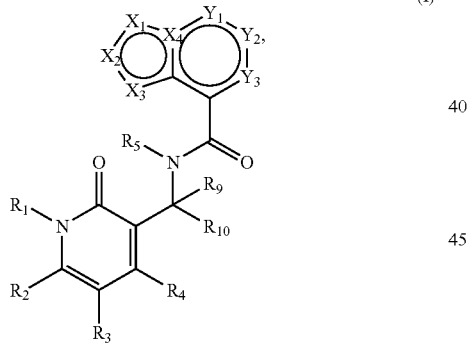

wherein:

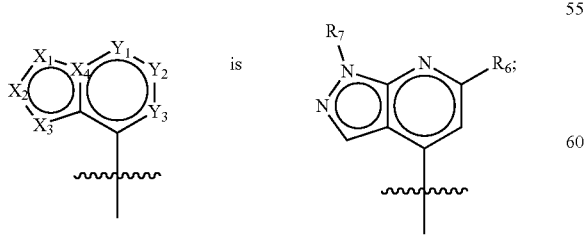

each of $R_1$, $R_5$, $R_9$, and $R_{10}$, independently, is H or $C_1$-$C_6$ alkyl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 7-membered heterocycloalkyl, or 5 to 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl;

$R_6$ is H, halo, $C_1$-$C_3$ alkyl substituted with one or more -$Q_2$-$T_2$, $C_2$-$C_6$ alkenyl, $C_4$-$C_6$ cycloalkyl, C(O)H, O$R_a$, —C(O)$R_a$, phenyl, 5 to 6-membered heteroaryl containing 1-3 heteroatoms selected from N, O, and S, or 4 to 7-membered heterocycloalkyl, in which $R_a$ is $C_1$-$C_6$ alkyl or 4 to 7-membered heterocycloalkyl, and each of the phenyl, the 5 to 6-membered heteroaryl, and the 4 to 7-membered heterocycloalkyl is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —O$R_c$, —N$R_c R_d$, —(N$R_c R_d R_d$)$^+$A$^-$, —C(O)$R_c$, —C(O)O$R_c$,—C(O)N$R_c R_d$, —N$R_d$C(O)$R_c$, —N$R_d$C(O)O$R_c$, —S(O)$_2 R_c$, —S(O)$_2$N$R_c R_d$, or $R_{S4}$, in which each of $R_c$, $R_d$, and $R_{d'}$, independently is H or $R_{S5}$, $A^-$ is a pharmaceutically acceptable anion, each of $R_{S4}$ and $R_{S5}$, independently, is $C_1$-$C_6$ alkyl, $C_3$-$C_8$ cycloalkyl, $C_6$-$C_{10}$ aryl, 4 to 7-membered heterocycloalkyl, or 5 to 6-membered heteroaryl, or $R_c$ and $R_d$, together with the N atom to which they are attached, form a 4 to 7-membered heterocycloalkyl ring having 0 or 1 additional heteroatoms to the N atom, and each of $R_{S4}$, $R_{S5}$, and the 4 to 7-membered heterocycloalkyl ring containing $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of H, halo, cyano, $C_1$-$C_6$ alkyl, $C_3$-$C_8$ cycloalkyl, $C_6$-$C_{10}$ aryl, 4 to 7-membered heterocycloalkyl, 5 to 6-membered heteroaryl, $OR_e$, $COOR_e$, —$S(O)_2R_e$, —$NR_eR_f$, and —$C(O)NR_eR_f$, each of $R_e$ and $R_f$ independently being H or $C_1$-$C_6$ alkyl; or -$Q_3$-$T_3$ is oxo; or -$Q_2$-$T_2$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl; provided that -$Q_2$-$T_2$ is not H; and $R_7$ is $C_1$-$C_6$ alkyl, $C_3$-$C_8$ cycloalkyl or 4 to 7-membered heterocycloalkyl, each optionally substituted with one or more -$Q_5$-$T_5$, wherein $Q_5$ is a bond, C(O), or $C_1$-$C_3$ alkyl linker, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, or 5 to 6-membered heteroaryl and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5 to 6-membered heteroaryl except when $T_5$ is H, halo, hydroxyl, or cyano; or -$Q_5$-$T_5$ is oxo;

provided that the compound is not
N-((4,6-dimethyl-2-oxo-1,2-dihydropyridin-3-yl) methyl)-6-(2,5-dimethylthiophen-3-yl)-1-isopropyl-1H-pyrazolo[3,4-b]pyridine-4-carboxamide,
6-(2,3-dihydro-1,4-benzodioxin-6-yl)-N-[(1,2-dihydro-4,6-dimethyl-2-oxo-3-pyridinyl)methyl]-1-(1-methylethyl)-1H-pyrazolo[3,4-b]pyridine-4-carboxamide,
or
6-cyclopropyl-N-((4,6-dimethyl-2-oxo-1,2-dihydropyridin-3-yl)methyl)-1-isopropyl-1H-pyrazolo[3,4-b]pyridine-4-carboxamide.

2. The compound of claim 1, wherein $R_6$ is phenyl substituted with one or more -$Q_2$-$T_2$; or $R_6$ is 5 to 6-membered heteroaryl containing 1-3 heteroatoms selected from N, O, and S and optionally substituted with one or more -$Q_2$-$T_2$, provided that the heteroaryl is not thiophenyl; or $R_6$ is halo, $C_1$-$C_3$ alkyl substituted with one or more -$Q_2$-$T_2$, $C_2$-$C_6$ alkenyl, $C_4$-$C_6$ cycloalkyl, C(O)H, $OR_a$, or —C(O)$R_a$, in which $R_a$ is $C_1$-$C_6$ alkyl or 4 to 7-membered heterocycloalkyl; or $R_6$ is 4 to 7-membered heterocycloalkyl optionally substituted with one or more -$Q_2$-$T_2$, in which -$Q_2$-$T_2$ is oxo or $Q_2$ is a bond and $T_2$ is —$OR_c$, —$NR_cR_d$, —$C(O)R_c$, —$C(O)OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

3. The compound of claim 1, wherein $R_7$ is 5 to 6-membered heterocycloalkyl optionally substituted with one or more -$Q_5$-$T_5$.

4. The compound of claim 1, wherein $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl; or $Q_5$ is a bond and $T_5$ is $C_1$-$C_6$ alkyl, $C_3$-$C_8$ cycloalkyl, or 4 to 7-membered heterocycloalkyl; or $Q_5$ is CO and $T_5$ is $C_1$-$C_6$ alkyl, $C_1$-$C_6$ alkoxyl, $C_3$-$C_8$ cycloalkyl, or 4 to 7-membered heterocycloalkyl; or $Q_5$ is $C_1$-$C_3$ alkyl linker and $T_5$ is H or $C_6$-$C_{10}$ aryl.

5. The compound of claim 1, wherein each of $R_2$ and $R_4$, independently is H or $C_1$-$C_6$ alkyl optionally substituted with amino, mono-$C_1$-$C_6$ alkylamino, di-$C_1$-$C_6$ alkylamino, or $C_6$-$C_{10}$ aryl.

6. The compound of claim 1, wherein $R_1$ is H.

7. The compound of claim 1, wherein $R_3$ is H.

8. A pharmaceutical composition comprising a compound of claim 1 or a pharmaceutically acceptable salt thereof and a pharmaceutically acceptable carrier.

9. The compound of claim 2, wherein $R_6$ is phenyl or a 5 to 6-membered heteroaryl containing 1-3 heteroatoms selected from N, O, and S, which is substituted with one or more -$Q_2$-$T_2$.

10. The compound of claim 2, wherein $R_6$ is phenyl which is substituted with one or more -$Q_2$-$T_2$.

11. The compound of claim 9, wherein $Q_2$ is an unsubstituted $C_1$-$C_3$ alkyl linker.

12. The compound of claim 9, wherein $T_2$ is a 4- to 7-membered heterocycloalkyl optionally substituted with one or more -$Q_3$-$T_3$.

13. The compound of claim 1, wherein $Q_2$ is an unsubstituted $C_1$-$C_3$ alkyl linker.

14. The compound of claim 1, wherein $T_2$ is a 4- to 7-membered heterocycloalkyl optionally substituted with one or more -$Q_3$-$T_3$.

15. The compound of claim 1, wherein $T_2$ is —$OR_c$, —$NR_cR_d$, —$C(O)R_c$, —$C(O)OR_c$, or —$S(O)_2R_c$.

16. The compound of claim 1, wherein $R_2$ and $R_4$ are methyl.

17. The compound of claim 1, wherein $R_5$, $R_9$, and $R_{10}$ is H.

18. A compound of claim 1 selected from:

| Compound Number | Structure |
|---|---|
| A-1 | *[structure: 6-(4-(morpholinomethyl)phenyl)-1-cyclopentyl-1H-pyrazolo[3,4-b]pyridine-4-carboxamide N-linked to (4,6-dimethyl-2-oxo-1,2-dihydropyridin-3-yl)methyl]* |
| A-2 | *[structure: 6-(4-(morpholinomethyl)phenyl)-1-isopropyl-1H-pyrazolo[3,4-b]pyridine-4-carboxamide N-linked to (4,6-dimethyl-2-oxo-1,2-dihydropyridin-3-yl)methyl]* |
| A-3 | *[structure: 6-(3-((dimethylamino)methyl)phenyl)-1-isopropyl-1H-pyrazolo[3,4-b]pyridine-4-carboxamide N-linked to (4,6-dimethyl-2-oxo-1,2-dihydropyridin-3-yl)methyl]* |
| A-4 | *[structure: 6-(2-aminopyrimidin-5-yl)-1-isopropyl-1H-pyrazolo[3,4-b]pyridine-4-carboxamide N-linked to (4,6-dimethyl-2-oxo-1,2-dihydropyridin-3-yl)methyl]* |

| Compound Number | Structure |
|---|---|
| A-5 | 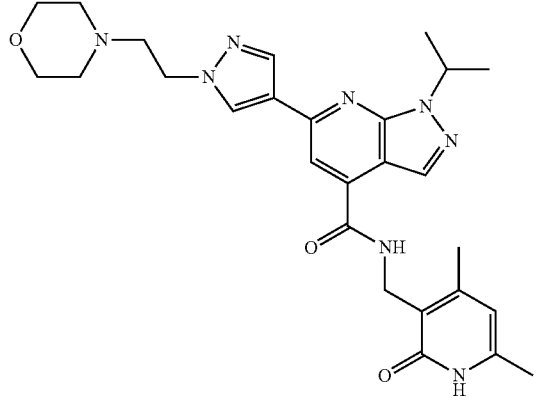 [SMILES: Cc1cc(C)c(CNC(=O)c2cc(-c3cnn(CCN4CCOCC4)c3)nc3c2cnn3C(C)C)c(=O)[nH]1] |
| A-6 | 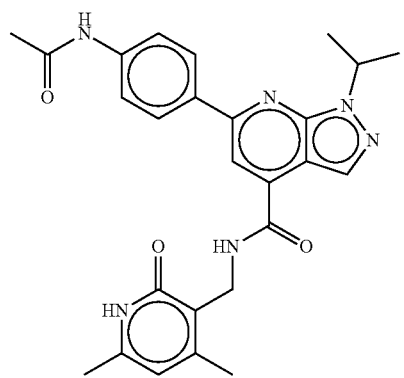 |
| A-7 | 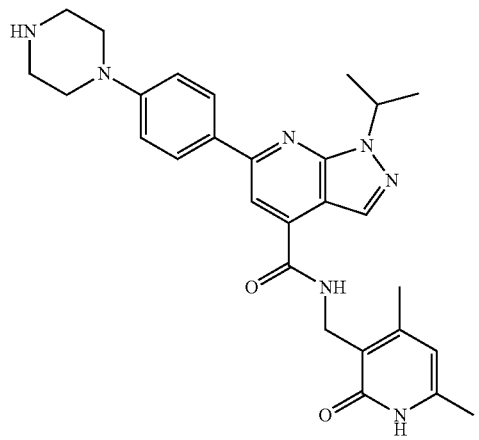 |
| A-8 | 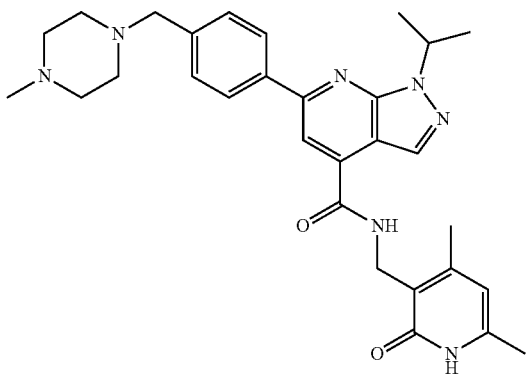 |

| Compound Number | Structure |
|---|---|
| A-9 | 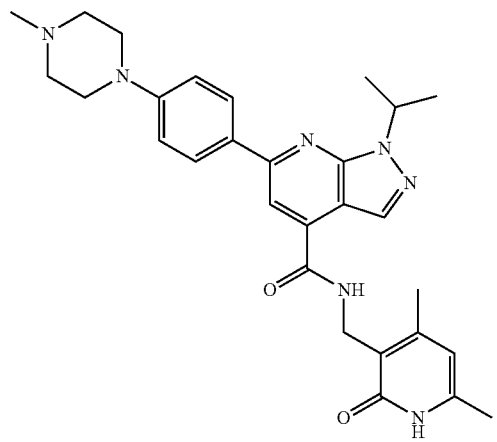 |
| A-10 | 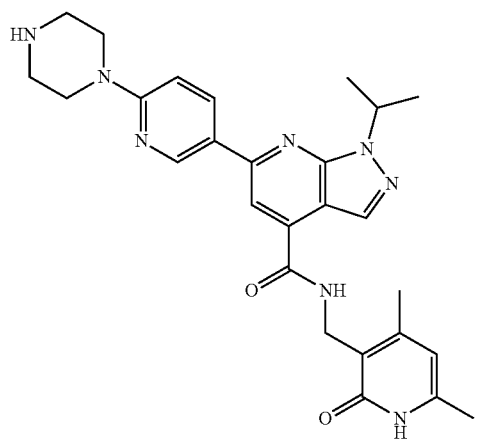 [SMILES: Cc1cc(C)c(CNC(=O)c2cc(-c3ccc(N4CCNCC4)nc3)nc3c2cnn3C(C)C)c(=O)[nH]1] |
| A-11 | 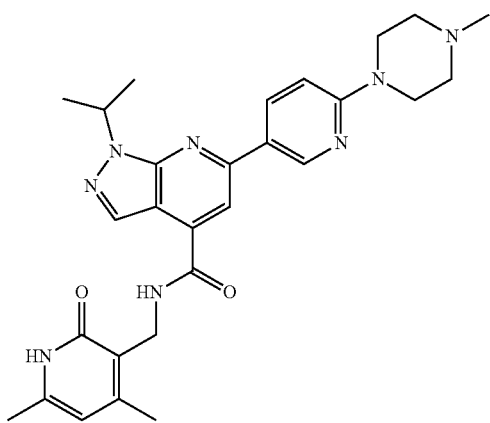 |

-continued
| Compound Number | Structure |
|---|---|
| A-12 | 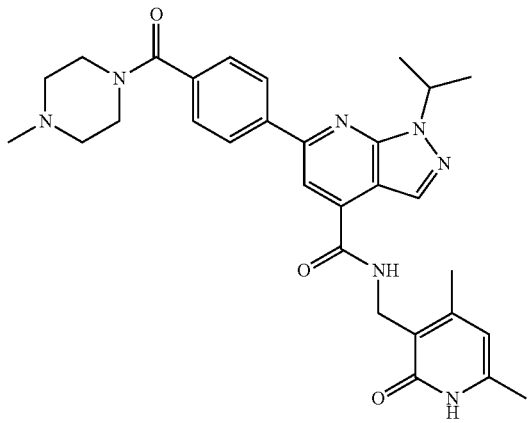 |
| A-13 | 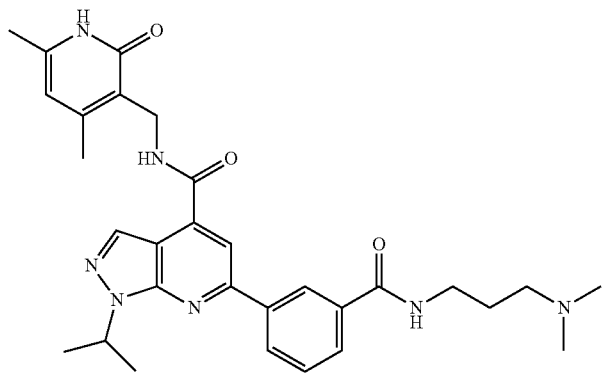 |
| A-14 | 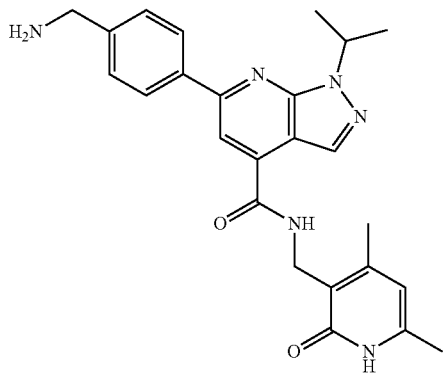 [SMILES: Cc1cc(C)c(CNC(=O)c2cc(-c3ccc(CN)cc3)nc3c2cnn3C(C)C)c(=O)[nH]1] |
| A-15 | 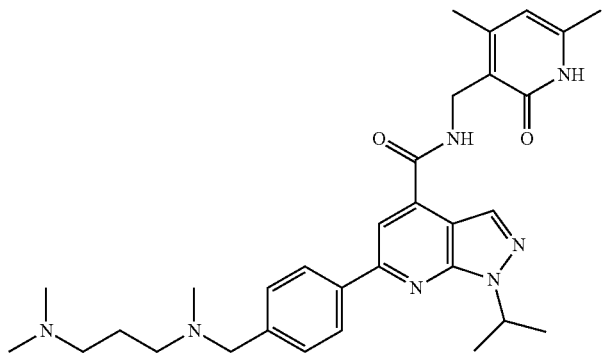 |

-continued
| Compound Number | Structure |
|---|---|
| A-16 | 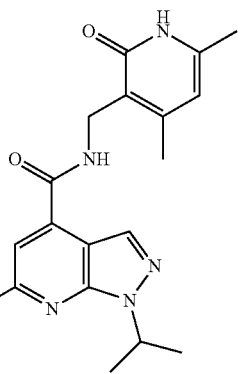 |
| A-17 | 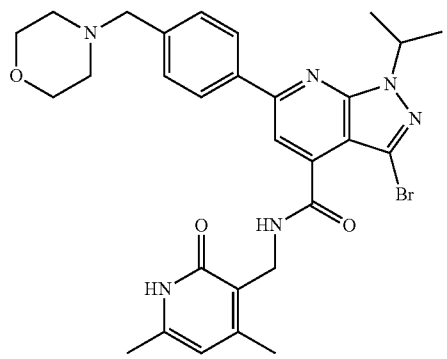 [SMILES: Cc1cc(C)c(CNC(=O)c2cc(-c3ccc(CN4CCOCC4)cc3)nc3c2c(Br)nn3C(C)C)c(=O)[nH]1] |
| A-18 | 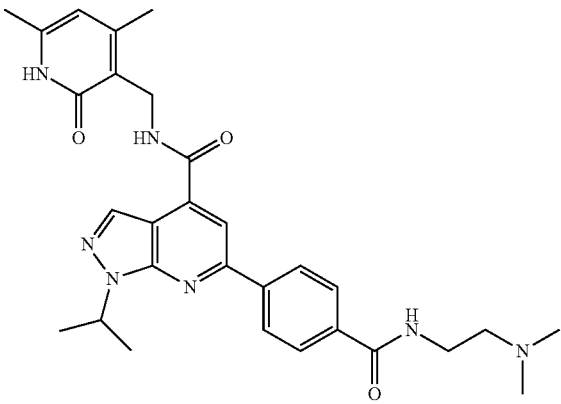 |
| A-19 | 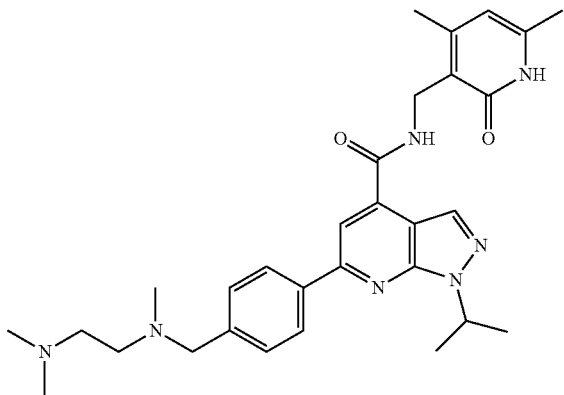 |

| Compound Number | Structure |
|---|---|
| A-20 | 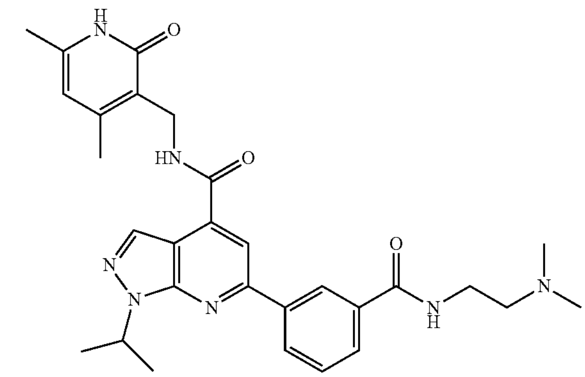 |
| A-21 | 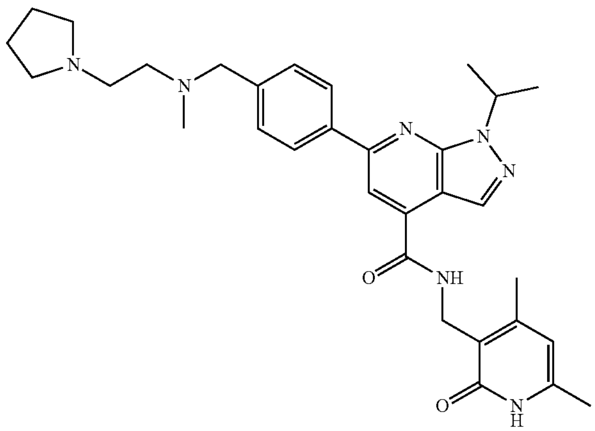 [SMILES: Cc1cc(C)c(CNC(=O)c2cc(-c3ccc(CN(C)CCN4CCCC4)cc3)nc3c2cnn3C(C)C)c(=O)[nH]1] |
| A-22 | 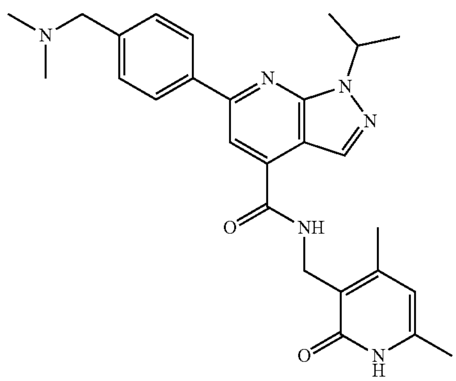 |
| A-23 | 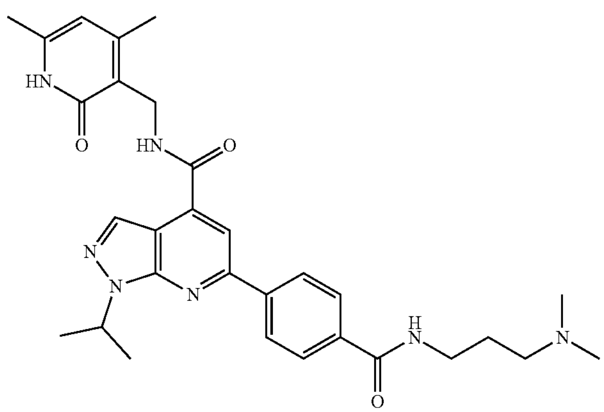 |

-continued
| Compound Number | Structure |
|---|---|
| A-24 | 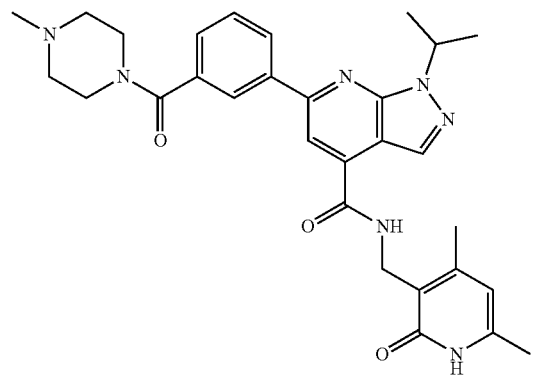 |
| A-25 | 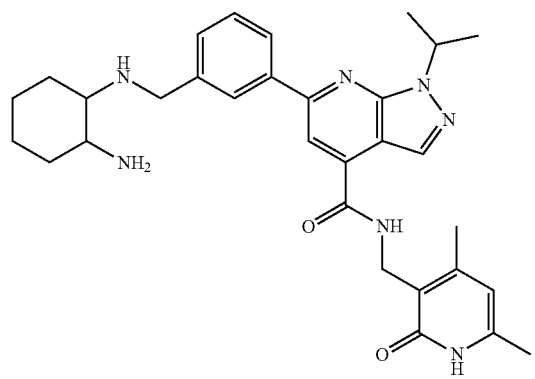 [SMILES: Cc1cc(C)c(CNC(=O)c2cc(-c3cccc(CNC4CCCCC4N)c3)nc3c2cnn3C(C)C)c(=O)[nH]1] |
| A-26 | 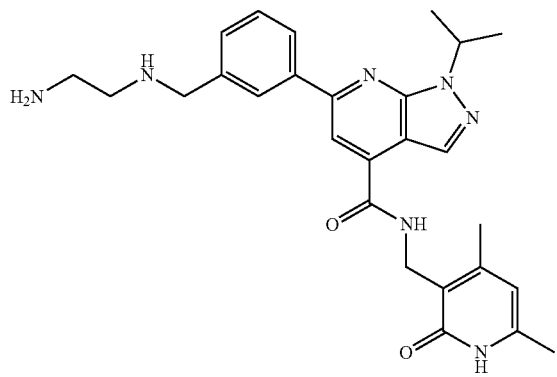 [SMILES: Cc1cc(C)c(CNC(=O)c2cc(-c3cccc(CNCCN)c3)nc3c2cnn3C(C)C)c(=O)[nH]1] |
| A-27 | 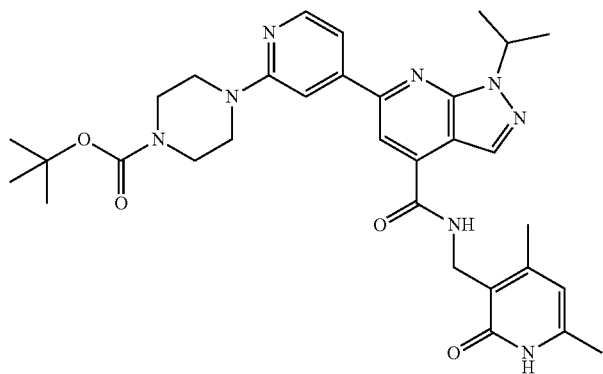 [SMILES: Cc1cc(C)c(CNC(=O)c2cc(-c3ccnc(N4CCN(C(=O)OC(C)(C)C)CC4)c3)nc3c2cnn3C(C)C)c(=O)[nH]1] |

-continued
| Compound Number | Structure |
|---|---|
| A-28 | 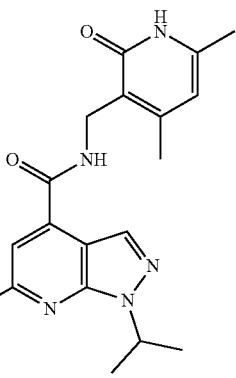 |
| A-29 | 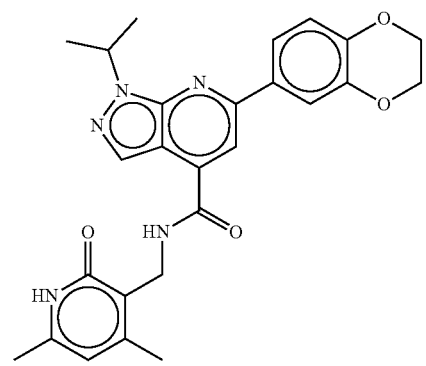 |
| A-30 | 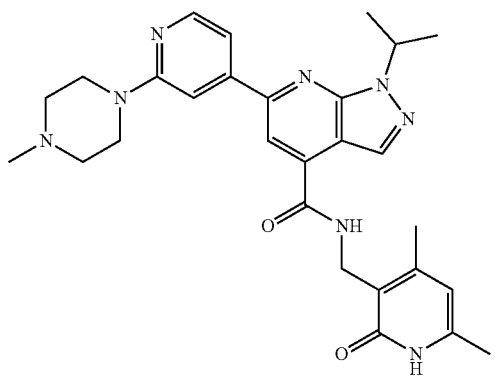 |
| A-31 | 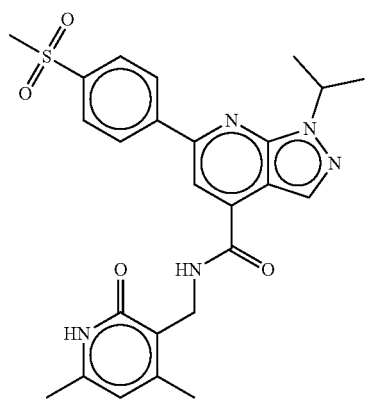 |

467
468
-continued
| Compound Number | Structure |
|---|---|
| A-32 | 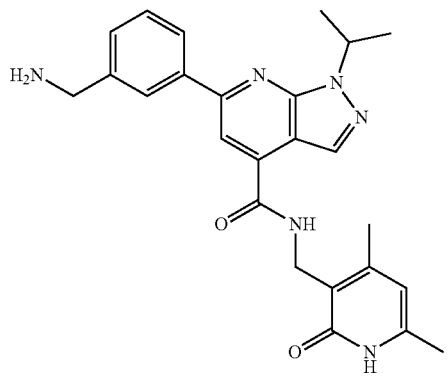 [SMILES: Cc1cc(C)c(CNC(=O)c2cc(-c3cccc(CN)c3)nc3c2cnn3C(C)C)c(=O)[nH]1] |
| A-33 | 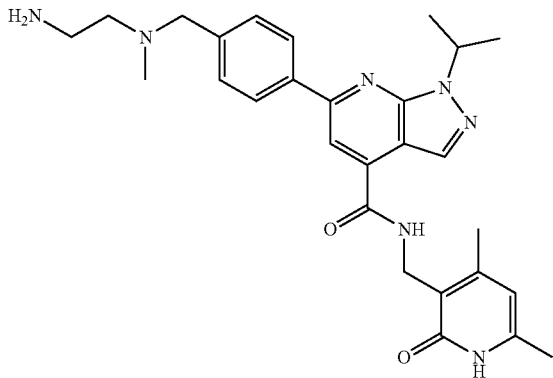 [SMILES: Cc1cc(C)c(CNC(=O)c2cc(-c3ccc(CN(C)CCN)cc3)nc3c2cnn3C(C)C)c(=O)[nH]1] |
| A-34 | 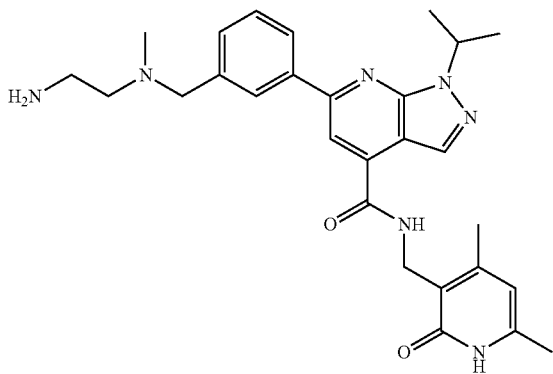 [SMILES: Cc1cc(C)c(CNC(=O)c2cc(-c3cccc(CN(C)CCN)c3)nc3c2cnn3C(C)C)c(=O)[nH]1] |
| A-35 | 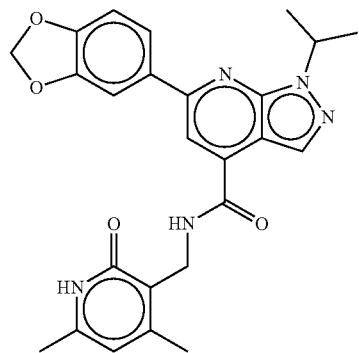 |

-continued
| Compound Number | Structure |
|---|---|
| A-36 | 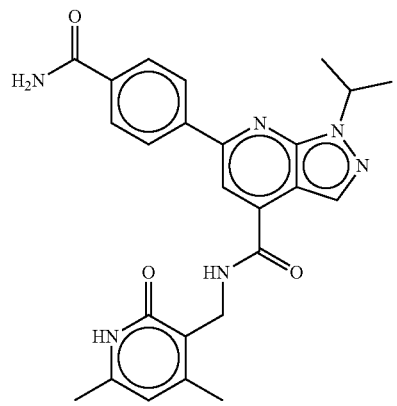 |
| A-37 | 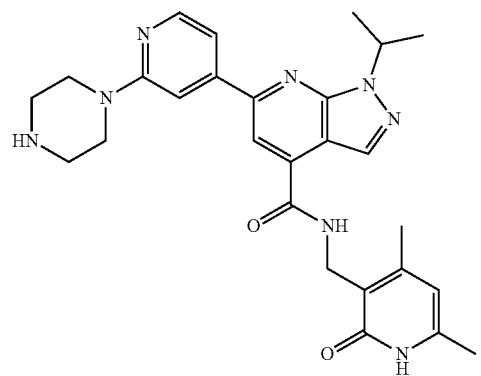 [SMILES: Cc1cc(C)c(CNC(=O)c2cc(-c3ccnc(N4CCNCC4)c3)nc3c2cnn3C(C)C)c(=O)[nH]1] |
| A-38 | 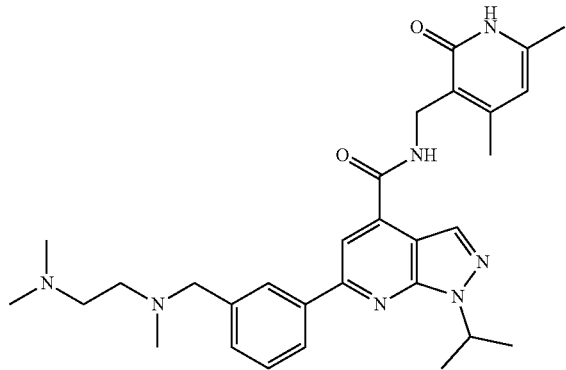 |
| A-39 | 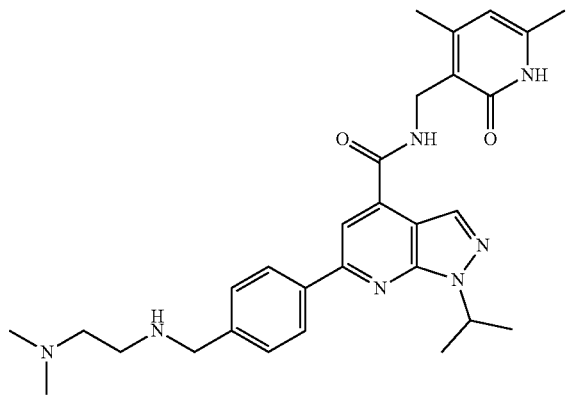 |

| Compound Number | Structure |
|---|---|
| A-40 | 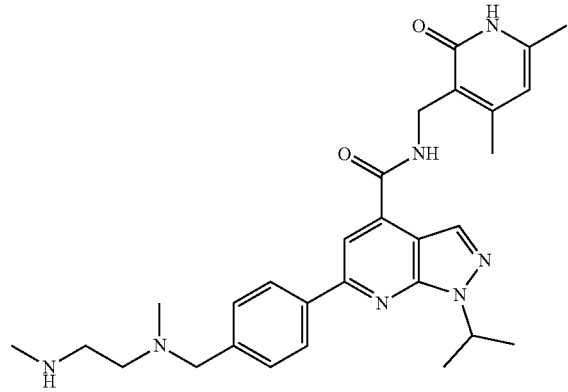 |
| A-41 | 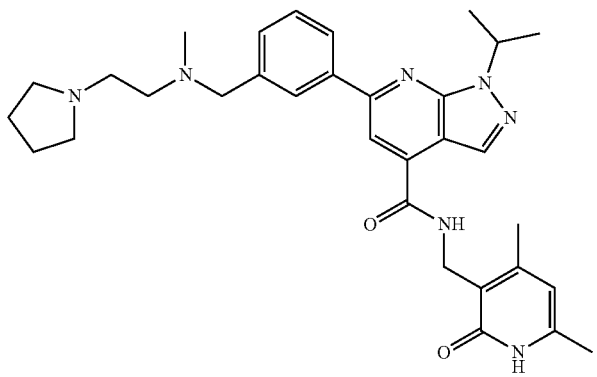 [SMILES: Cc1cc(C)c(CNC(=O)c2cc(-c3cccc(CN(C)CCN4CCCC4)c3)nc3c2cnn3C(C)C)c(=O)[nH]1] |
| A-42 | 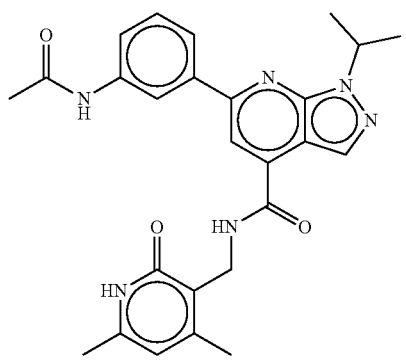 |
| A-43 | 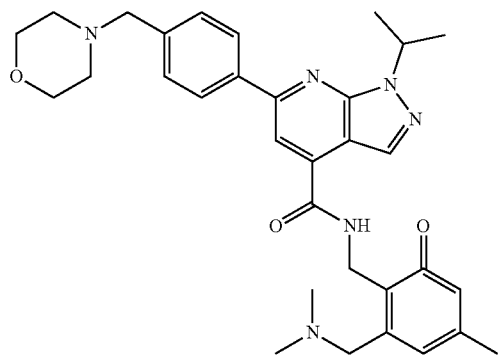 |

-continued
| Compound Number | Structure |
|---|---|
| A-44 | 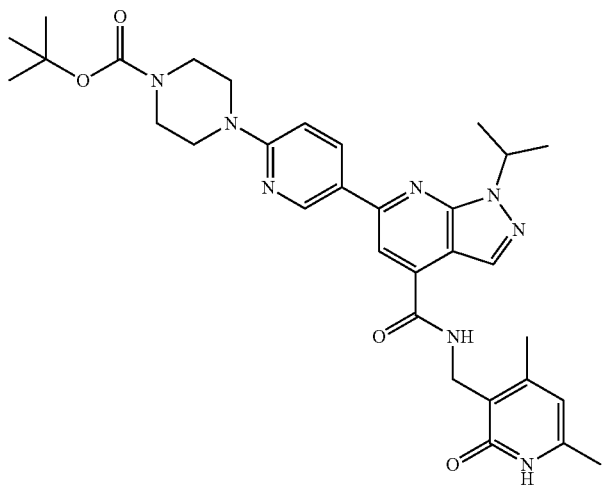 |
| A-45 | 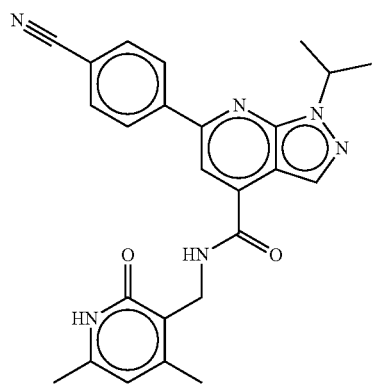 |
| A-46 | 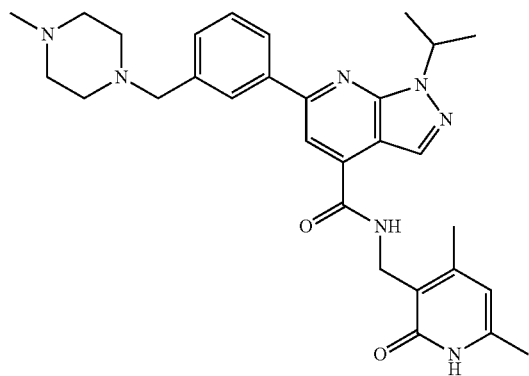 |

| Compound Number | Structure |
|---|---|
| A-48 | 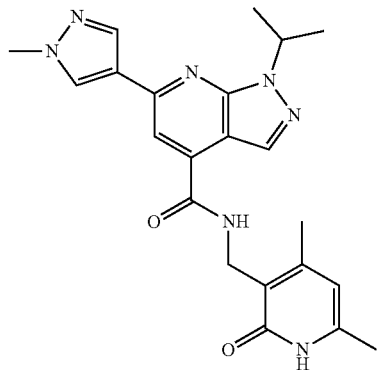 |
| A-49 | 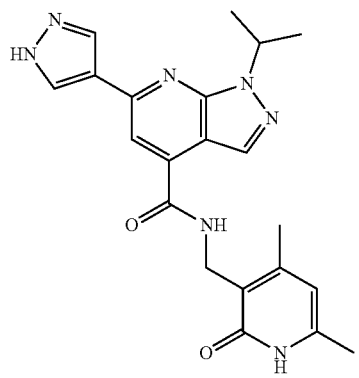 [SMILES: Cc1cc(C)c(CNC(=O)c2cc(-c3cn[nH]c3)nc3c2cnn3C(C)C)c(=O)[nH]1] |
| A-50 | 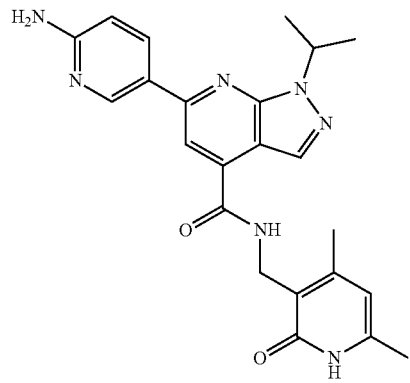 [SMILES: Cc1cc(C)c(CNC(=O)c2cc(-c3ccc(N)nc3)nc3c2cnn3C(C)C)c(=O)[nH]1] |

-continued
| Compound Number | Structure |
|---|---|
| A-51 | 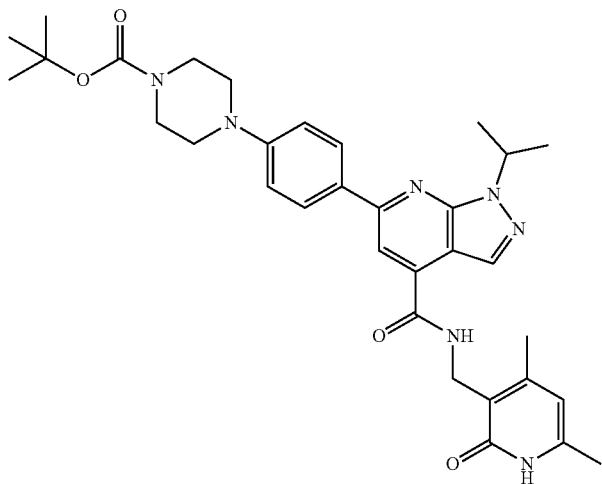 [SMILES: Cc1cc(C)c(CNC(=O)c2cc(-c3ccc(N4CCN(C(=O)OC(C)(C)C)CC4)cc3)nc3c2cnn3C(C)C)c(=O)[nH]1] |
| A-52 | 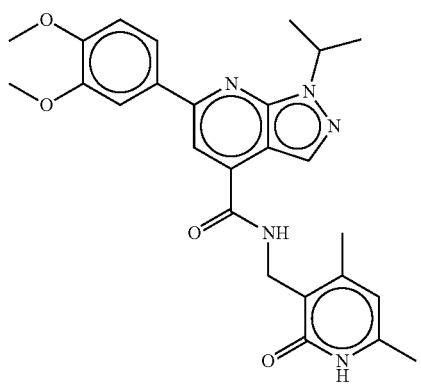 |
| A-53 | 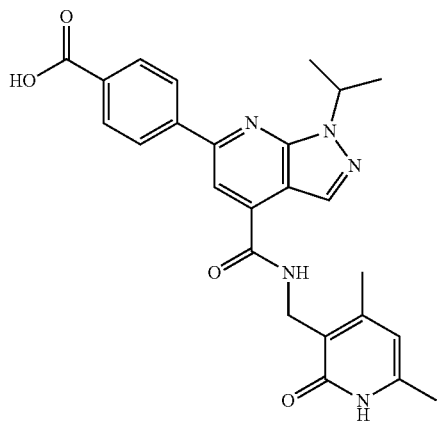 [SMILES: Cc1cc(C)c(CNC(=O)c2cc(-c3ccc(C(=O)O)cc3)nc3c2cnn3C(C)C)c(=O)[nH]1] |

-continued

| Compound Number | Structure |
|---|---|
| A-54 | 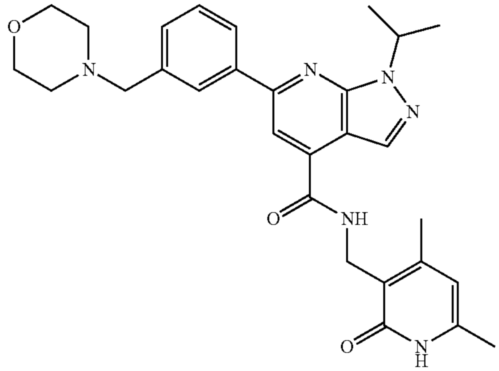 [SMILES: Cc1cc(C)c(CNC(=O)c2cc(-c3cccc(CN4CCOCC4)c3)nc3c2cnn3C(C)C)c(=O)[nH]1] |
| A-55 | 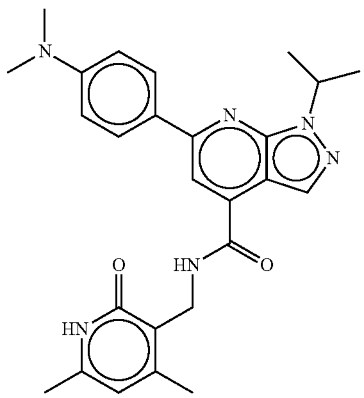 |
| A-56 | 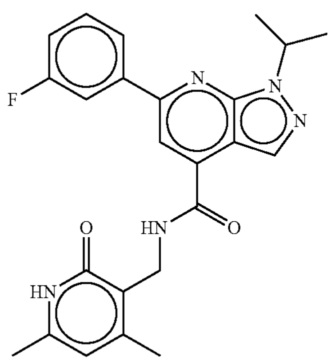 |
| A-57 | 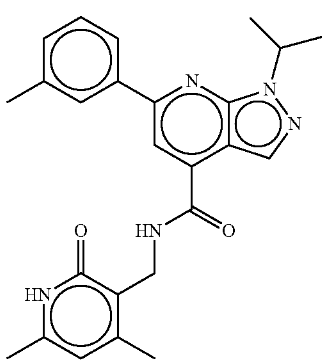 |

-continued
| Compound Number | Structure |
|---|---|
| A-58 | 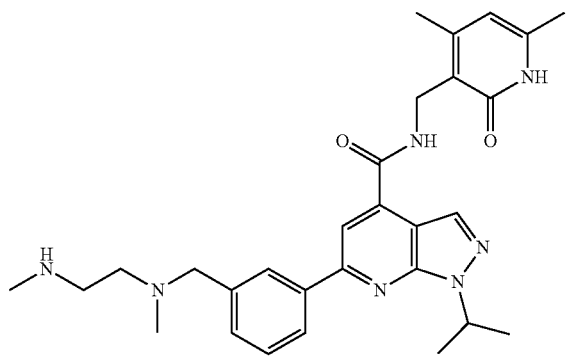 |
| A-59 | 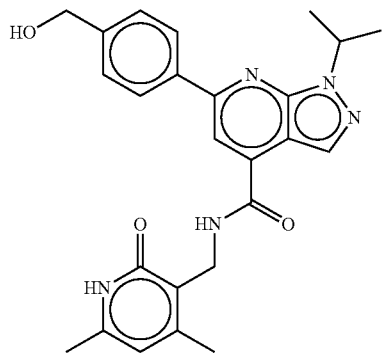 |
| A-60 | 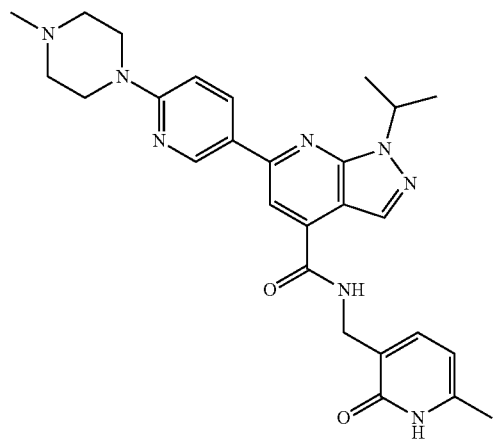 |
| A-61 | 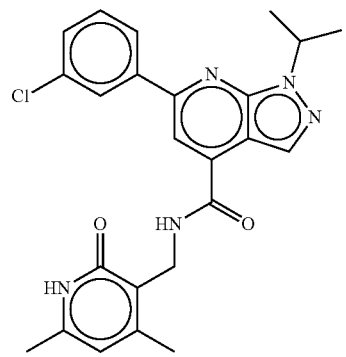 |

-continued
| Compound Number | Structure |
|---|---|
| A-62 | 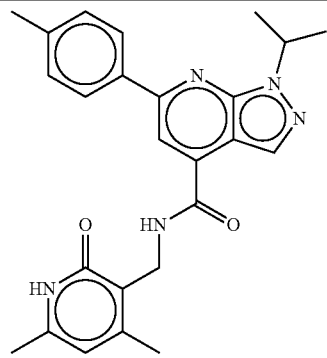 |
| A-63 | 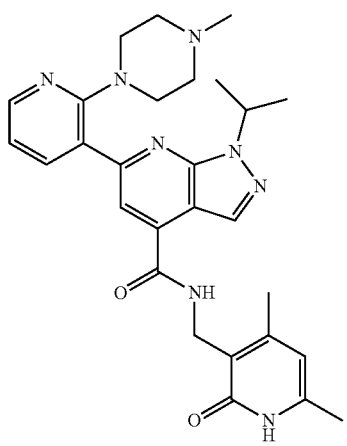 [SMILES: Cc1cc(C)c(CNC(=O)c2cc(-c3cccnc3N3CCN(C)CC3)nc3c2cnn3C(C)C)c(=O)[nH]1] |
| A-64 | 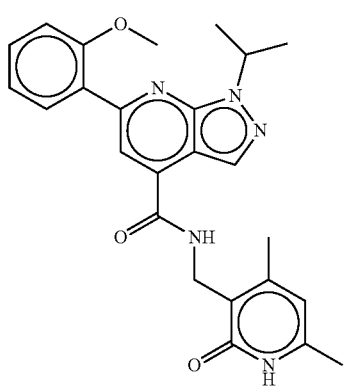 |

-continued
| Compound Number | Structure |
|---|---|
| A-66 | 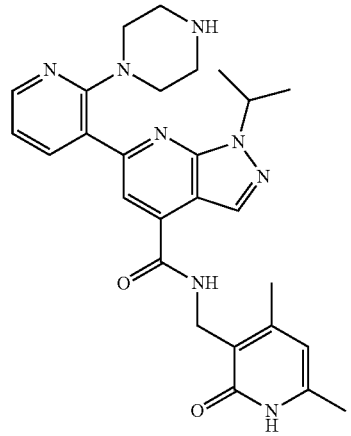 [SMILES: Cc1cc(C)c(CNC(=O)c2cc(-c3cccnc3N3CCNCC3)nc3c2cnn3C(C)C)c(=O)[nH]1] |
| A-67 | 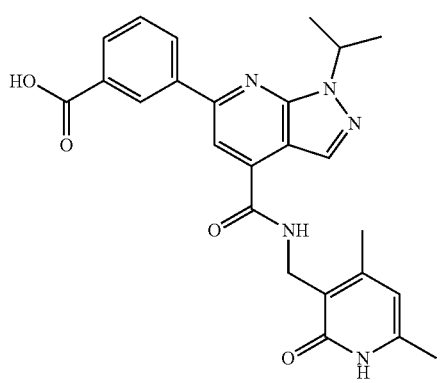 [SMILES: Cc1cc(C)c(CNC(=O)c2cc(-c3cccc(C(=O)O)c3)nc3c2cnn3C(C)C)c(=O)[nH]1] |
| A-68 | 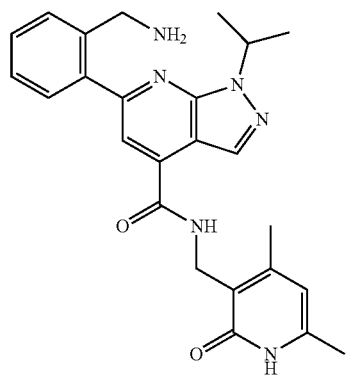 [SMILES: Cc1cc(C)c(CNC(=O)c2cc(-c3ccccc3CN)nc3c2cnn3C(C)C)c(=O)[nH]1] |
| A-69 | 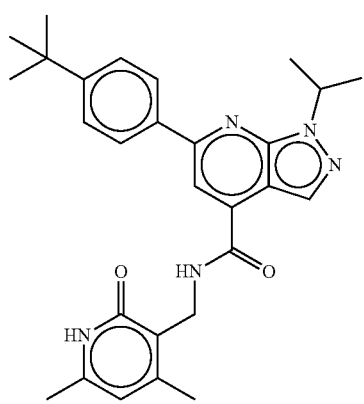 |

| Compound Number | Structure |
|---|---|
| A-70 | 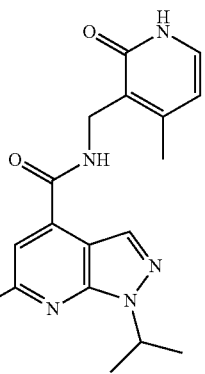 |
| A-72 | 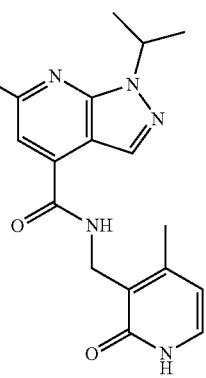 |
| A-73 | 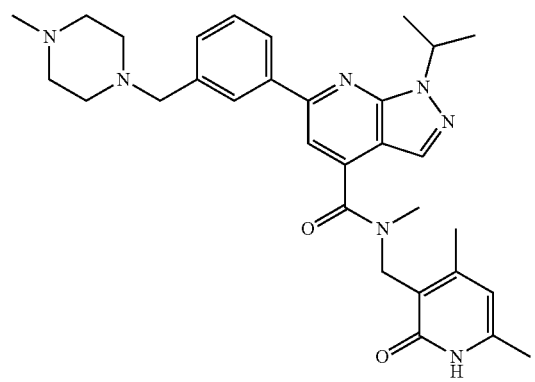 |
| A-74 | 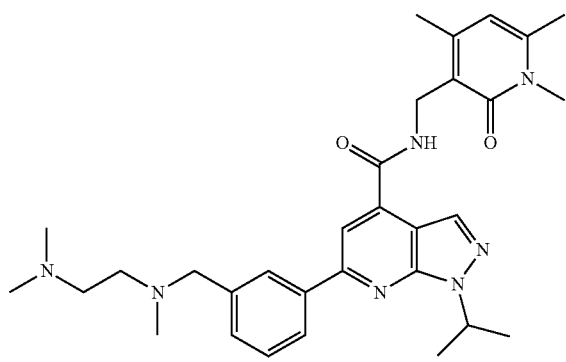 |

-continued
| Compound Number | Structure |
|---|---|
| A-75 | 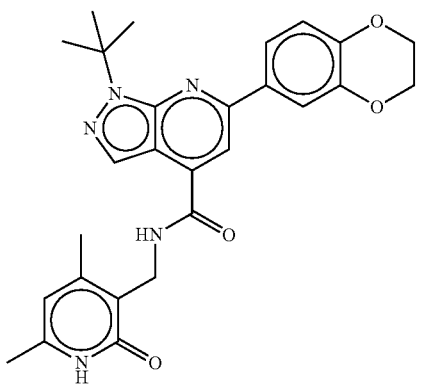 |
| A-76 | 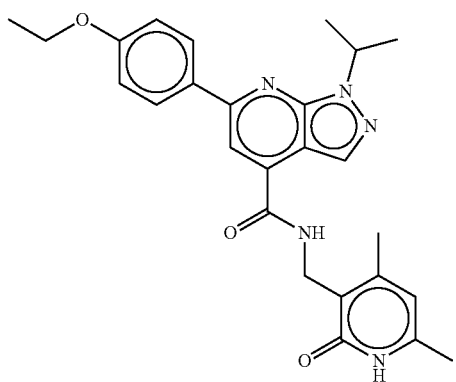 |
| A-77 | 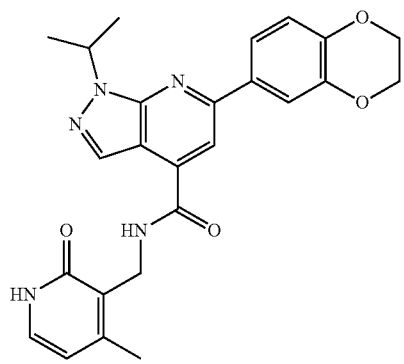 [SMILES: Cc1cc[nH]c(=O)c1CNC(=O)c1cc(-c2ccc3c(c2)OCCO3)nc2c1cnn2C(C)C] |
| A-78 | 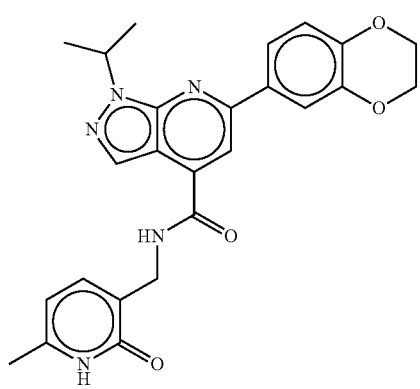 |

| Compound Number | Structure |
|---|---|
| A-91 | 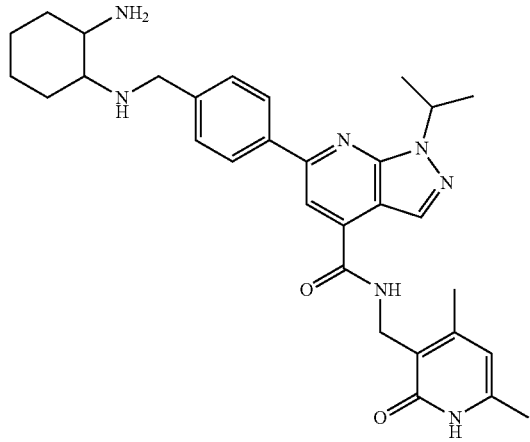 [SMILES: Cc1cc(C)c(CNC(=O)c2cc(-c3ccc(CNC4CCCCC4N)cc3)nc3c2cnn3C(C)C)c(=O)[nH]1] |
| A-92 | 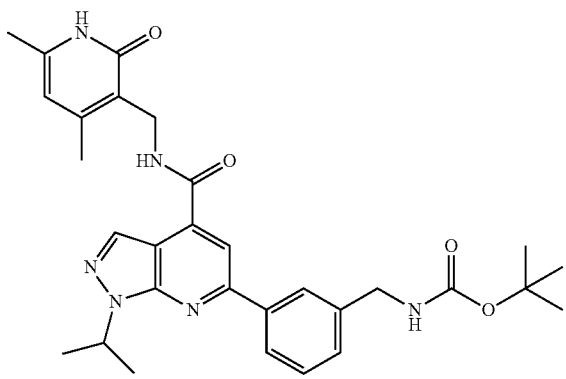 [SMILES: Cc1cc(C)c(CNC(=O)c2cc(-c3cccc(CNC(=O)OC(C)(C)C)c3)nc3c2cnn3C(C)C)c(=O)[nH]1] |
| A-93 | 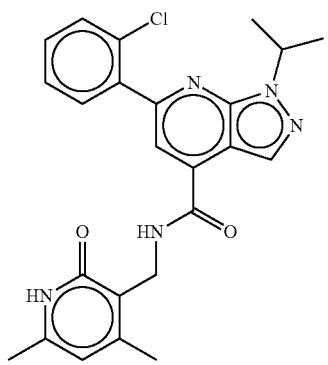 |

-continued
| Compound Number | Structure |
|---|---|
| A-95 | 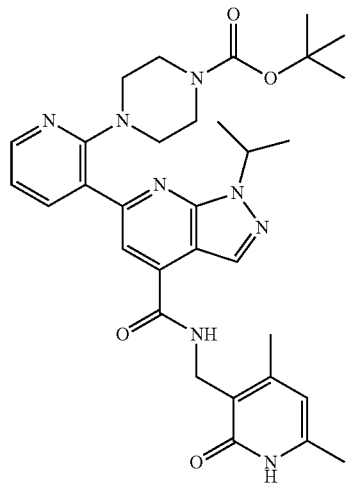 [SMILES: Cc1cc(C)c(CNC(=O)c2cc(-c3cccnc3N3CCN(C(=O)OC(C)(C)C)CC3)nc3c2cnn3C(C)C)c(=O)[nH]1] |
| A-96 | 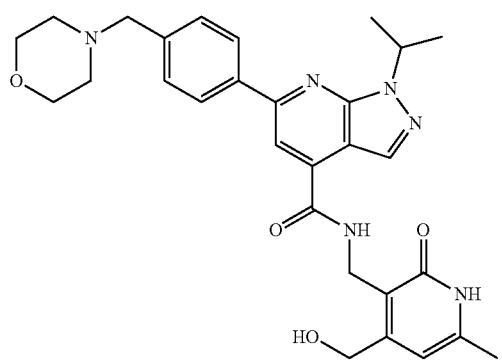 [SMILES: Cc1cc(CO)c(CNC(=O)c2cc(-c3ccc(CN4CCOCC4)cc3)nc3c2cnn3C(C)C)c(=O)[nH]1] |
| A-97 | 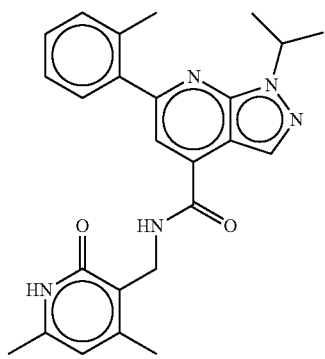 |

-continued
| Compound Number | Structure |
|---|---|
| A-98 | 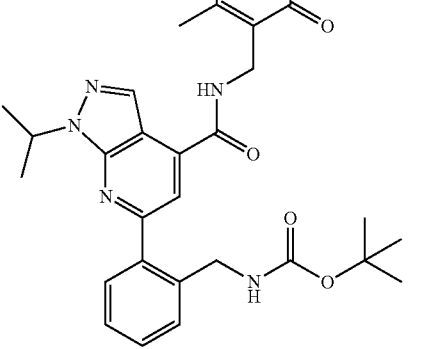 |
| A-99 | 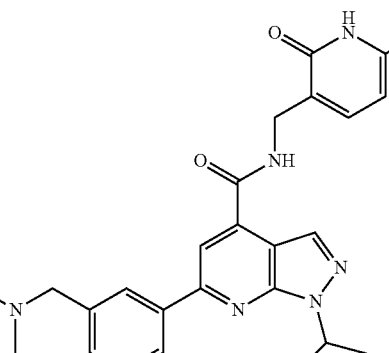 |
| A-100 | 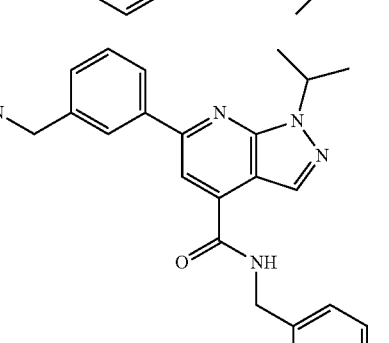 |
| A-101 | 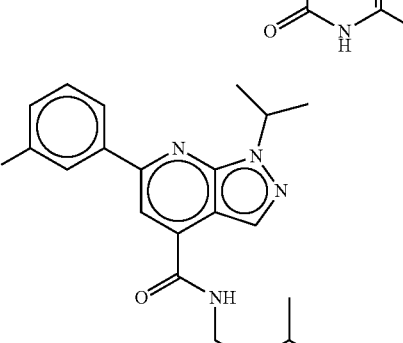 |

-continued
| Compound Number | Structure |
|---|---|
| A-102 | 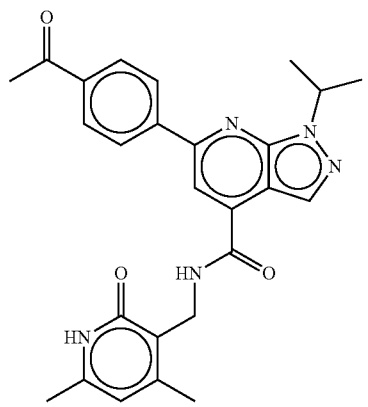 |
| A-103 | 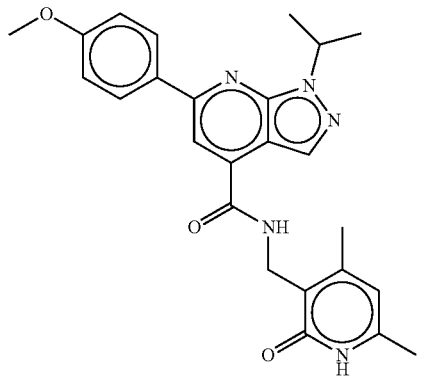 |
| A-104 | 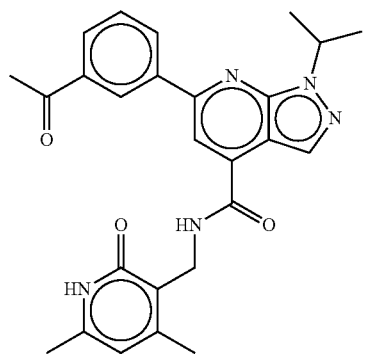 |
| A-105 | 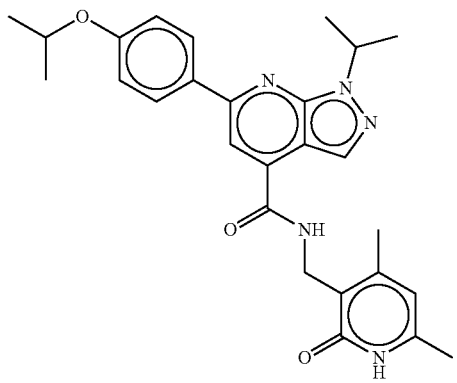 |

-continued
| Compound Number | Structure |
|---|---|
| A-106 | 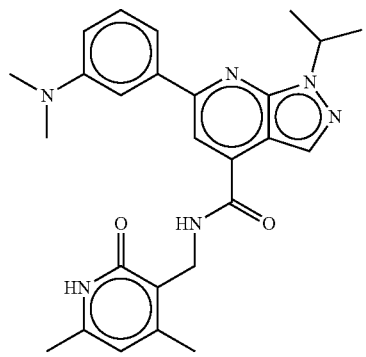 |
| A-107 | 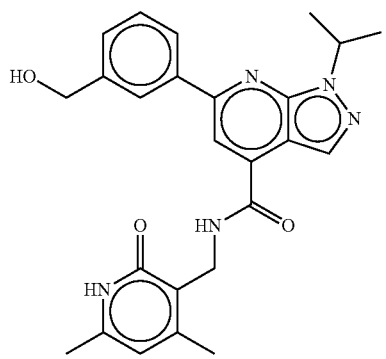 |
| A-108 | 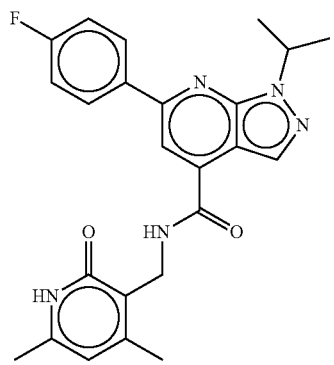 |
| A-110 | 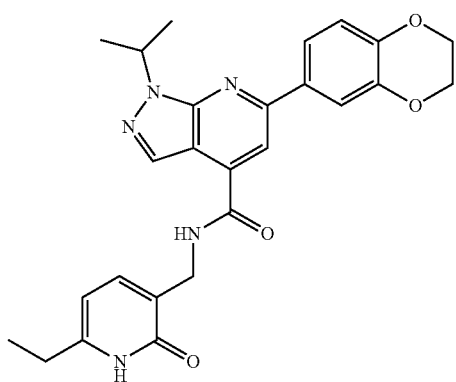 [SMILES: CCc1ccc(CNC(=O)c2cc(-c3ccc4c(c3)OCCO4)nc3c2cnn3C(C)C)c(=O)[nH]1] |

| Compound Number | Structure |
|---|---|
| A-125 | 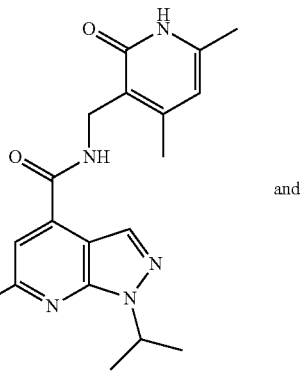 and |
| A-126 | 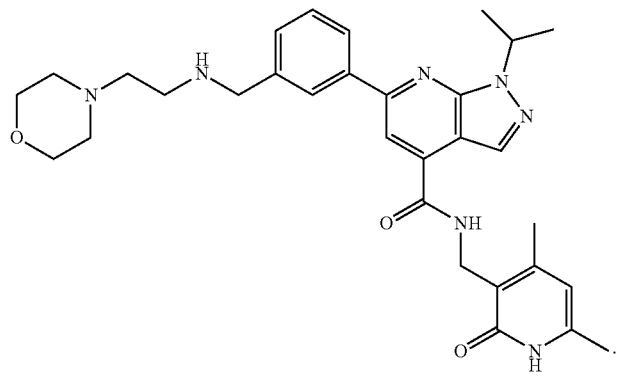 [SMILES: Cc1cc(C)c(CNC(=O)c2cc(-c3cccc(CNCCN4CCOCC4)c3)nc3c2cnn3C(C)C)c(=O)[nH]1] |
19. A compound of claim 1 selected from:
| Compound Number | Structure |
|---|---|
| B-1 | 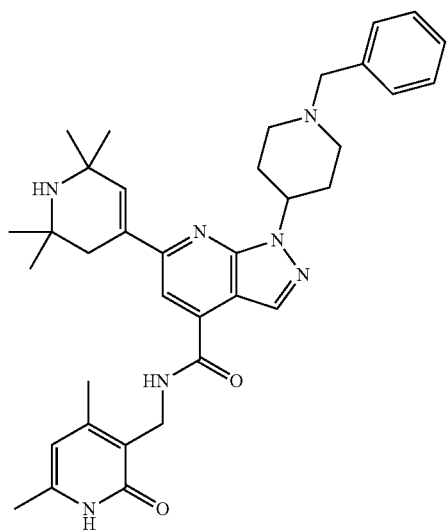 [SMILES: Cc1cc(C)c(CNC(=O)c2cc(C3=CC(C)(C)NC(C)(C)C3)nc3c2cnn3C2CCN(Cc3ccccc3)CC2)c(=O)[nH]1] |

-continued
| Compound Number | Structure |
|---|---|
| B-2 | 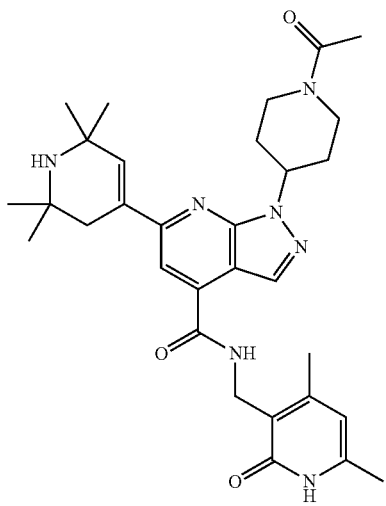 |
| B-4 | 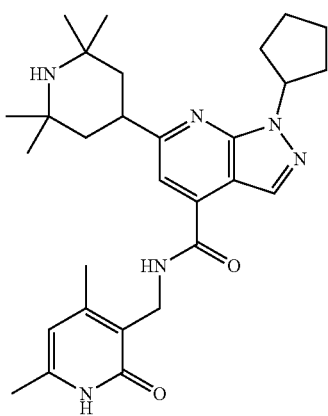 [SMILES: Cc1cc(C)c(CNC(=O)c2cc(C3CC(C)(C)NC(C)(C)C3)nc3c2cnn3C2CCCC2)c(=O)[nH]1] |
| B-5 | 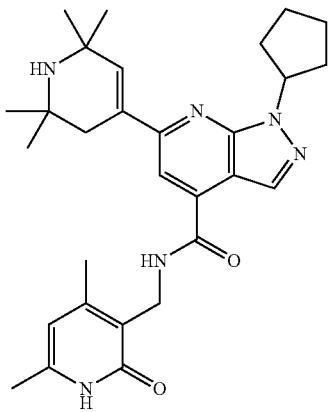 [SMILES: Cc1cc(C)c(CNC(=O)c2cc(C3=CC(C)(C)NC(C)(C)C3)nc3c2cnn3C2CCCC2)c(=O)[nH]1] |

-continued
| Compound Number | Structure |
|---|---|
| B-6 | 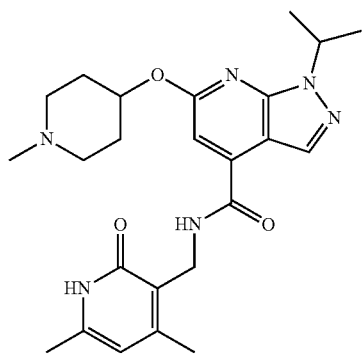 [SMILES: Cc1cc(C)c(CNC(=O)c2cc(OC3CCN(C)CC3)nc3c2cnn3C(C)C)c(=O)[nH]1] |
| B-7 | 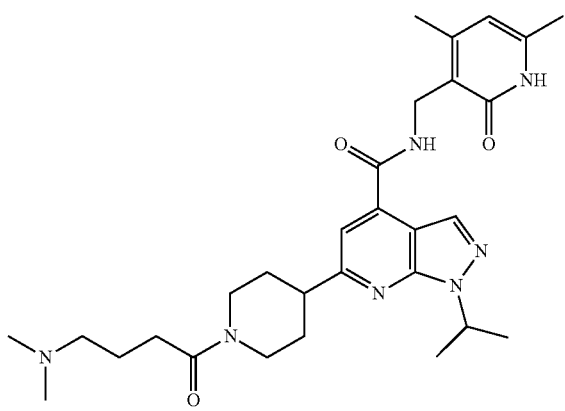 |
| B-8 | 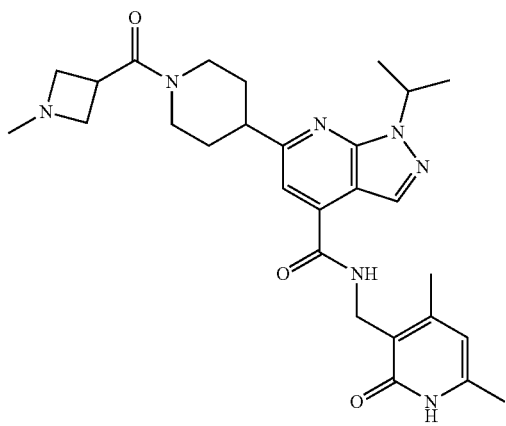 |
| B-9 | 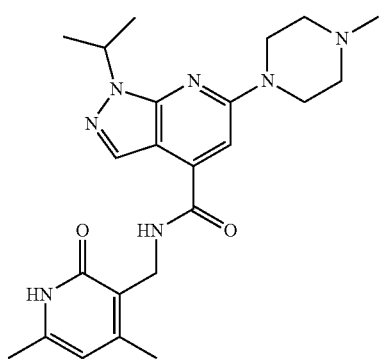 |

-continued
| Compound Number | Structure |
|---|---|
| B-10 | 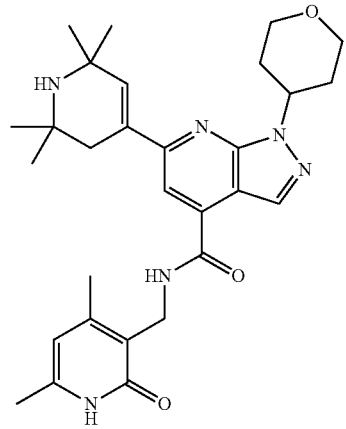 [SMILES: Cc1cc(C)c(CNC(=O)c2cc(C3=CC(C)(C)NC(C)(C)C3)nc3c2cnn3C2CCOCC2)c(=O)[nH]1] |
| B-11 | 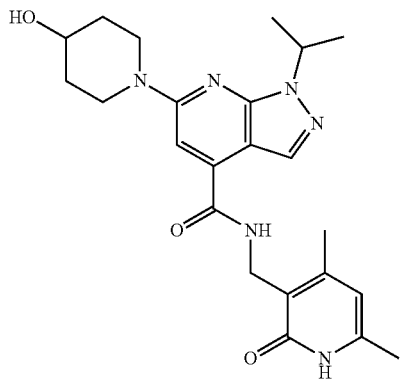 [SMILES: Cc1cc(C)c(CNC(=O)c2cc(N3CCC(O)CC3)nc3c2cnn3C(C)C)c(=O)[nH]1] |
| B-14 | 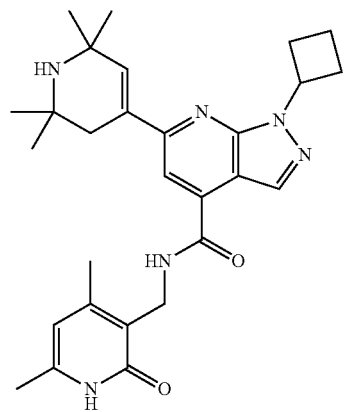 [SMILES: Cc1cc(C)c(CNC(=O)c2cc(C3=CC(C)(C)NC(C)(C)C3)nc3c2cnn3C2CCC2)c(=O)[nH]1] |

-continued
| Compound Number | Structure |
|---|---|
| B-15 | 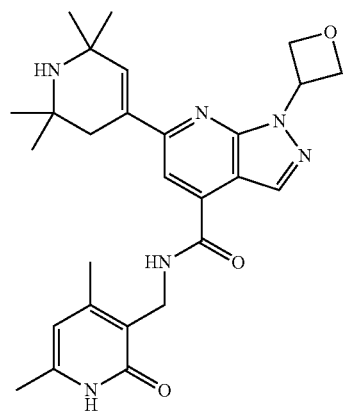 [SMILES: Cc1cc(C)c(CNC(=O)c2cc(C3=CC(C)(C)NC(C)(C)C3)nc3c2cnn3C2COC2)c(=O)[nH]1] |
| B-16 | 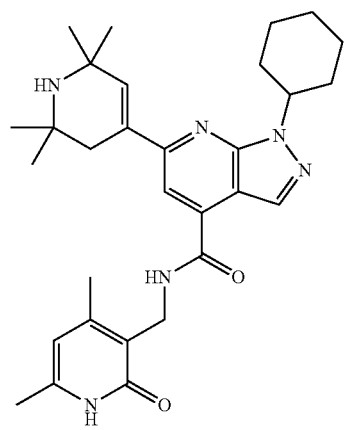 [SMILES: Cc1cc(C)c(CNC(=O)c2cc(C3=CC(C)(C)NC(C)(C)C3)nc3c2cnn3C2CCCCC2)c(=O)[nH]1] |
| B-17 | 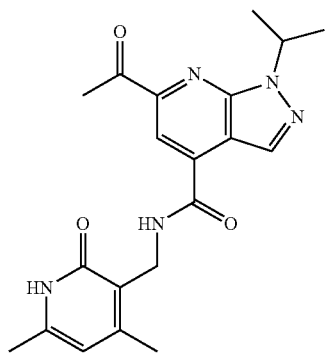 [SMILES: CC(=O)c1cc(C(=O)NCc2c(C)cc(C)[nH]c2=O)c2cnn(C(C)C)c2n1] |

-continued
| Compound Number | Structure |
|---|---|
| B-19 | 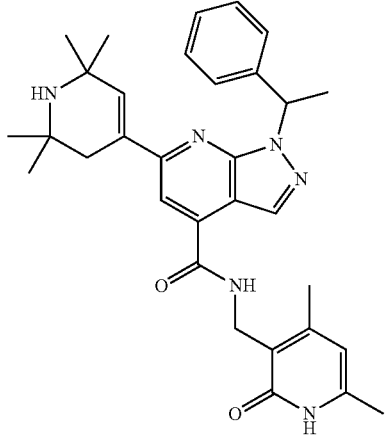 |
| B-20 | 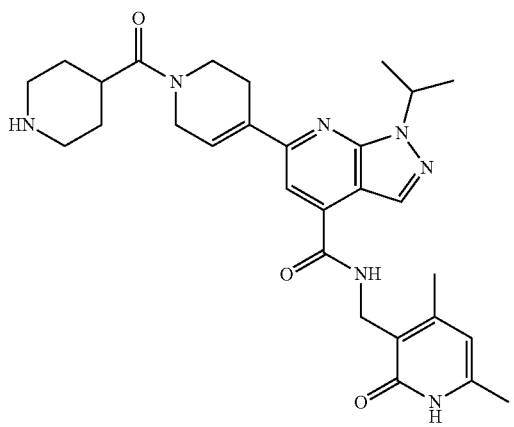 [SMILES: Cc1cc(C)c(CNC(=O)c2cc(C3=CCN(C(=O)C4CCNCC4)CC3)nc3c2cnn3C(C)C)c(=O)[nH]1] |
| B-21 | 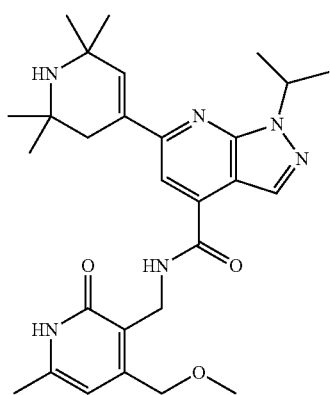 [SMILES: COCc1cc(C)[nH]c(=O)c1CNC(=O)c1cc(C2=CC(C)(C)NC(C)(C)C2)nc2c1cnn2C(C)C] |

-continued
| Compound Number | Structure |
|---|---|
| B-23 | 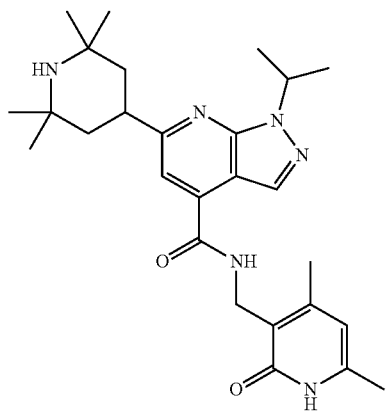 |
| B-24 | 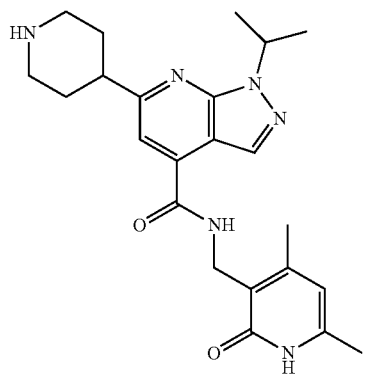 [SMILES: Cc1cc(C)c(CNC(=O)c2cc(C3CCNCC3)nc3c2cnn3C(C)C)c(=O)[nH]1] |
| B-25 | 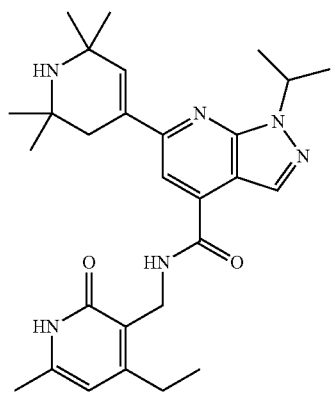 [SMILES: CCc1cc(C)[nH]c(=O)c1CNC(=O)c1cc(C2=CC(C)(C)NC(C)(C)C2)nc2c1cnn2C(C)C] |

| Compound Number | Structure |
|---|---|
| B-27 | 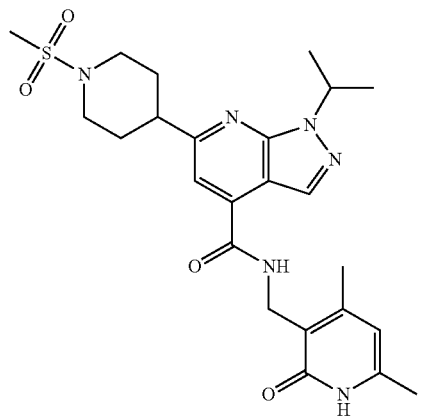 |
| B-28 | 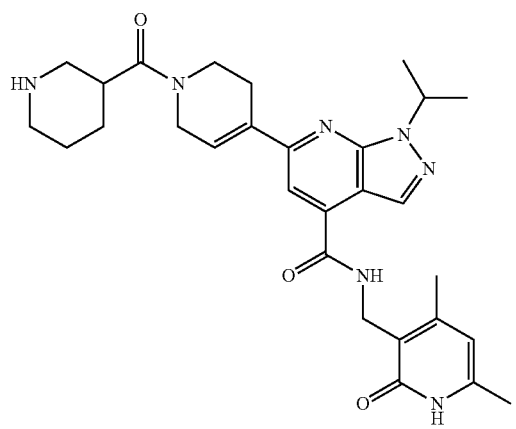 [SMILES: Cc1cc(C)c(CNC(=O)c2cc(C3=CCN(C(=O)C4CCCNC4)CC3)nc3c2cnn3C(C)C)c(=O)[nH]1] |
| B-29 | 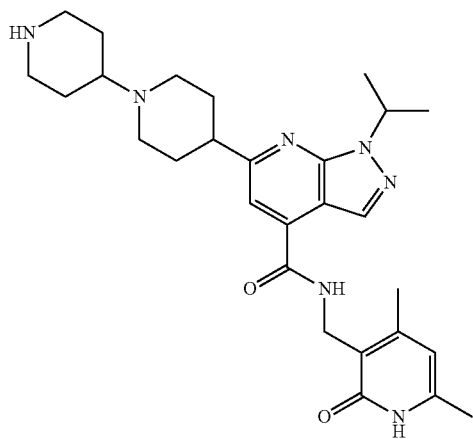 [SMILES: Cc1cc(C)c(CNC(=O)c2cc(C3CCN(C4CCNCC4)CC3)nc3c2cnn3C(C)C)c(=O)[nH]1] |

-continued
| Compound Number | Structure |
|---|---|
| B-30 | 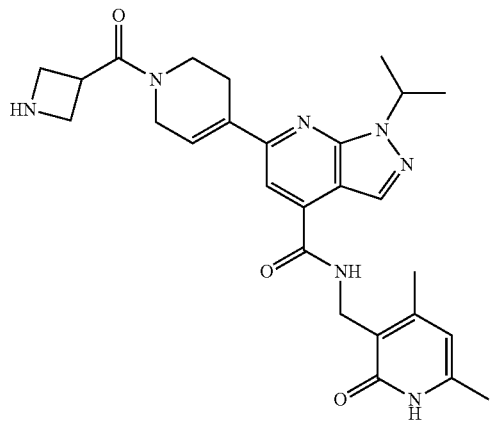 [SMILES: Cc1cc(C)c(CNC(=O)c2cc(C3=CCN(C(=O)C4CNC4)CC3)nc3c2cnn3C(C)C)c(=O)[nH]1] |
| B-31 | 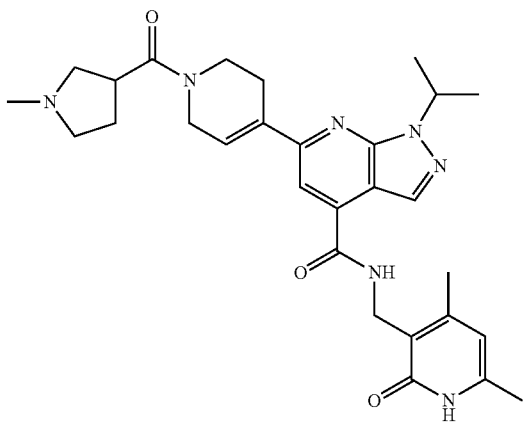 |
| B-32 | 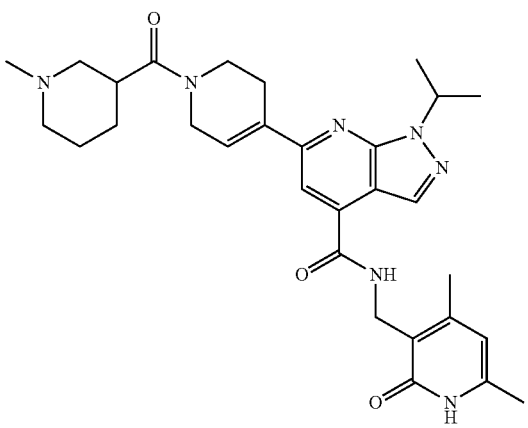 |

| Compound Number | Structure |
|---|---|
| B-33 | 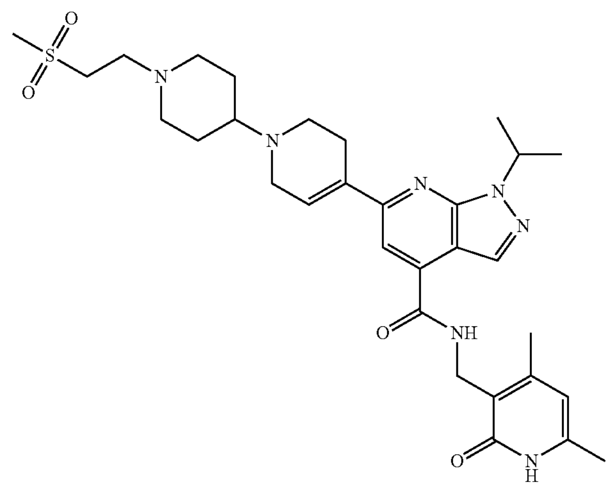 |
| B-34 | 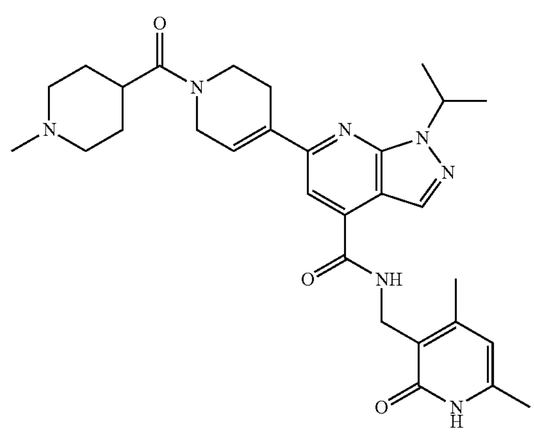 |
| B-35 | 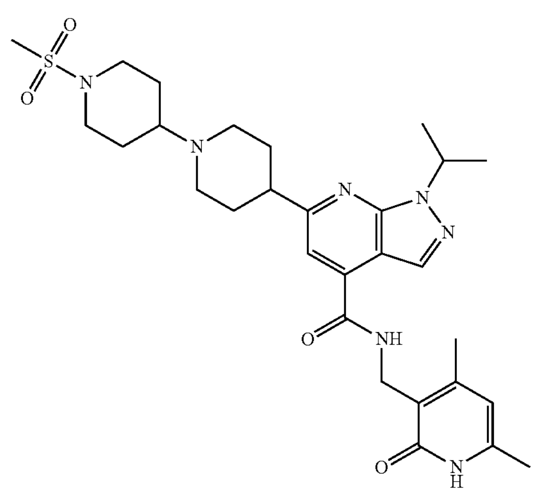 |

-continued
| Compound Number | Structure |
|---|---|
| B-36 | 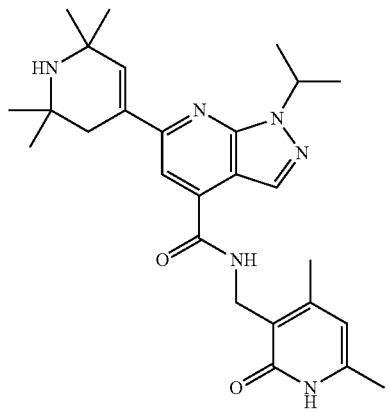 |
| B-37 | 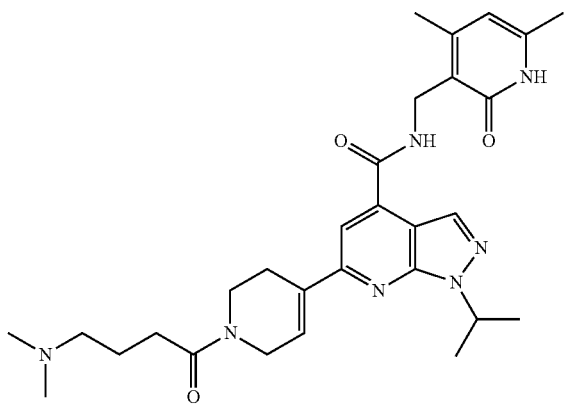 |
| B-38 | 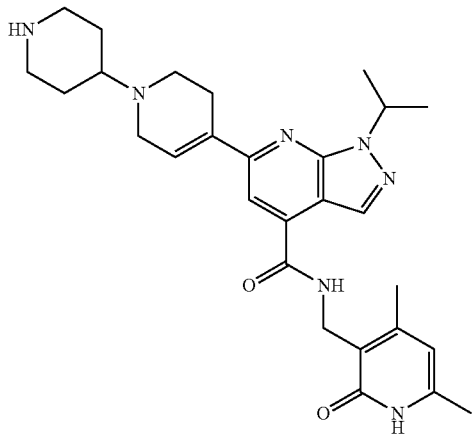 [SMILES: Cc1cc(C)c(CNC(=O)c2cc(C3=CCN(C4CCNCC4)CC3)nc3c2cnn3C(C)C)c(=O)[nH]1] |

| Compound Number | Structure |
|---|---|
| B-39 | 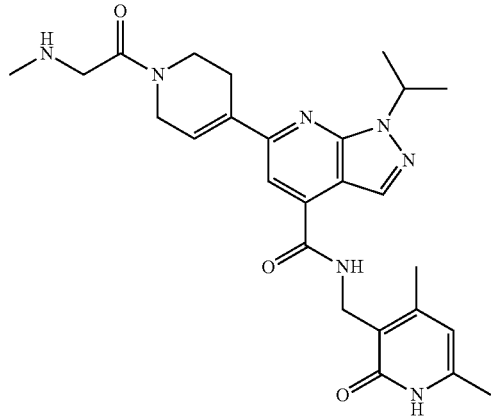 |
| B-40 | 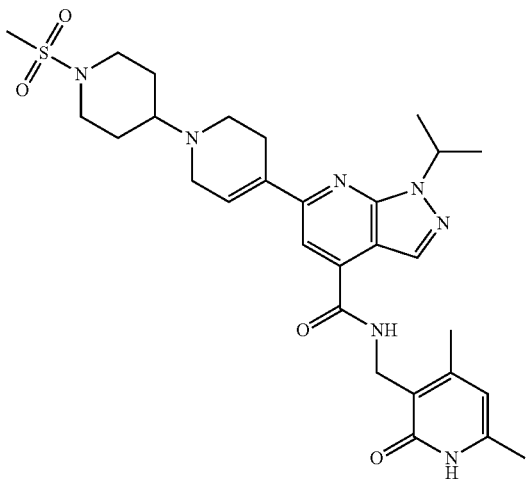 |
| B-41 | 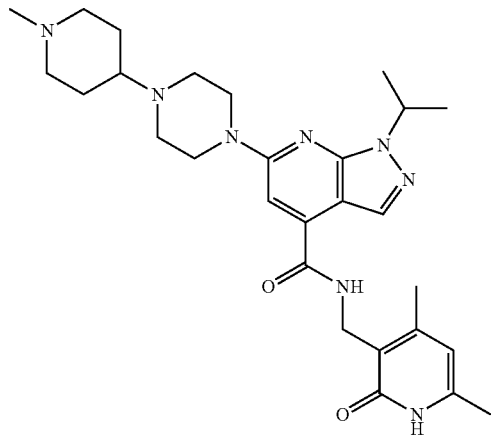 |

| Compound Number | Structure |
|---|---|
| B-42 | 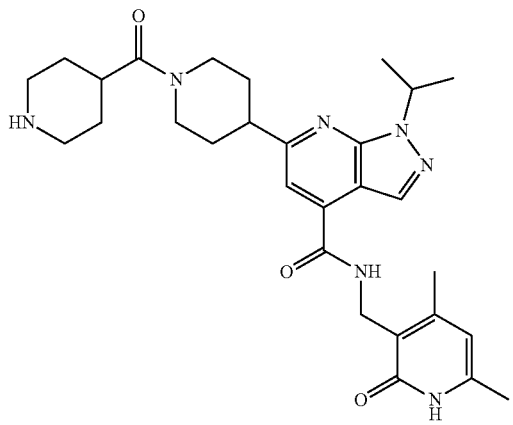 [SMILES: Cc1cc(C)c(CNC(=O)c2cc(C3CCN(C(=O)C4CCNCC4)CC3)nc3c2cnn3C(C)C)c(=O)[nH]1] |
| B-43 | 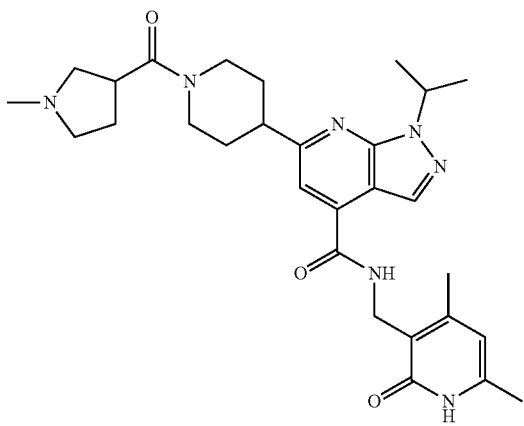 |
| B-44 | 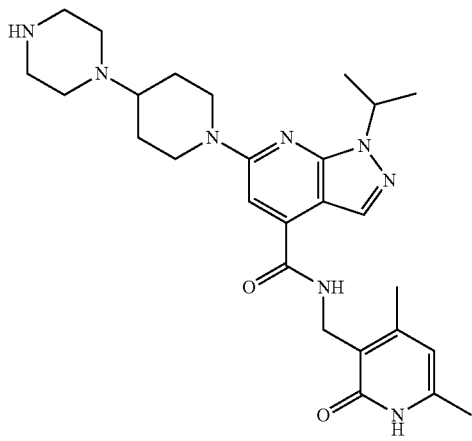 |

| Compound Number | Structure |
|---|---|
| B-45 | 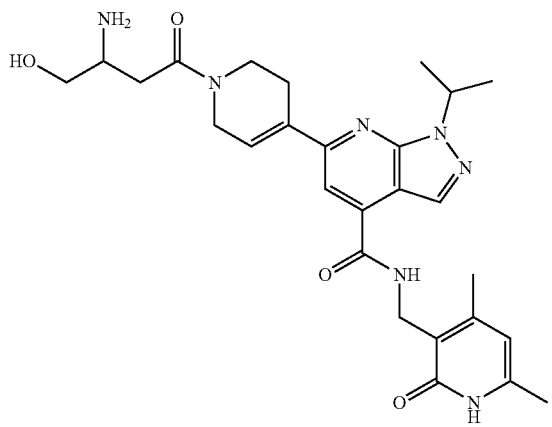 [SMILES: Cc1cc(C)c(CNC(=O)c2cc(C3=CCN(C(=O)CC(N)CO)CC3)nc3c2cnn3C(C)C)c(=O)[nH]1] |
| B-46 | 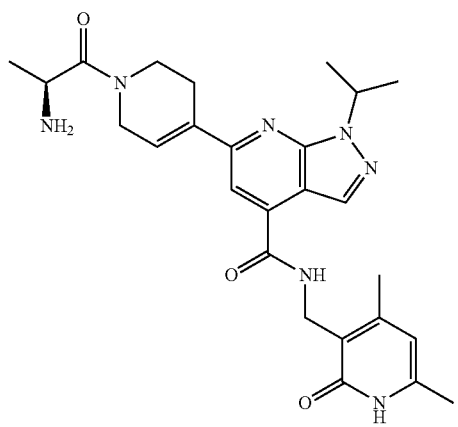 [SMILES: Cc1cc(C)c(CNC(=O)c2cc(C3=CCN(C(=O)[C@H](C)N)CC3)nc3c2cnn3C(C)C)c(=O)[nH]1] |
| B-47 | 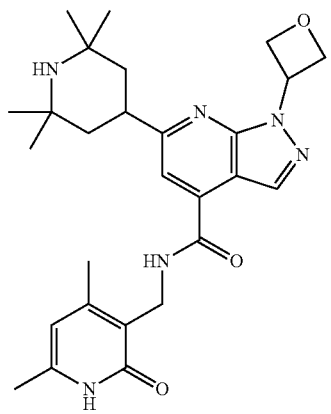 [SMILES: Cc1cc(C)c(CNC(=O)c2cc(C3CC(C)(C)NC(C)(C)C3)nc3c2cnn3C2COC2)c(=O)[nH]1] |

| Compound Number | Structure |
|---|---|
| B-48 | 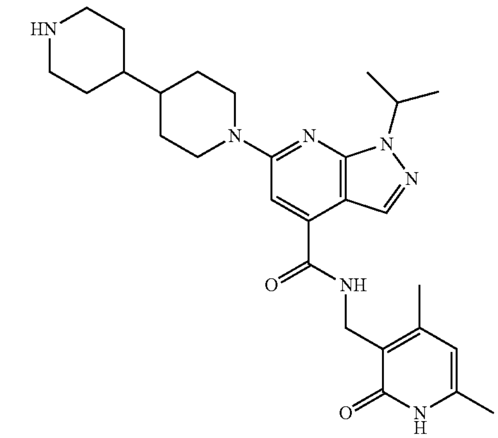 |
| B-49 | 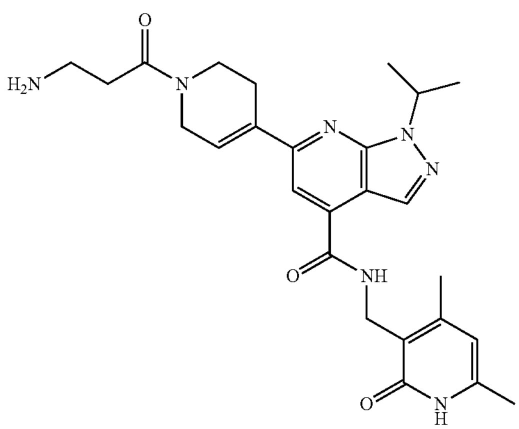 [SMILES: Cc1cc(C)c(CNC(=O)c2cc(C3=CCN(C(=O)CCN)CC3)nc3c2cnn3C(C)C)c(=O)[nH]1] |
| B-50 | 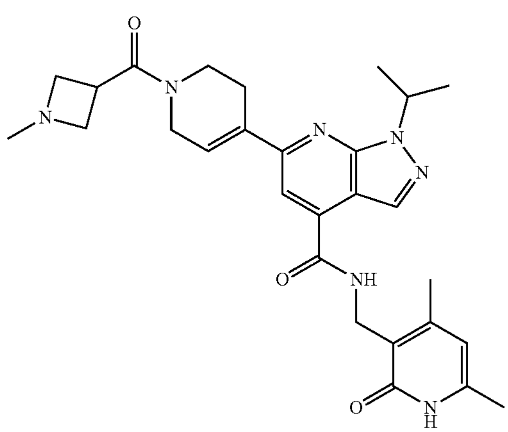 |

-continued
| Compound Number | Structure |
|---|---|
| B-51 | 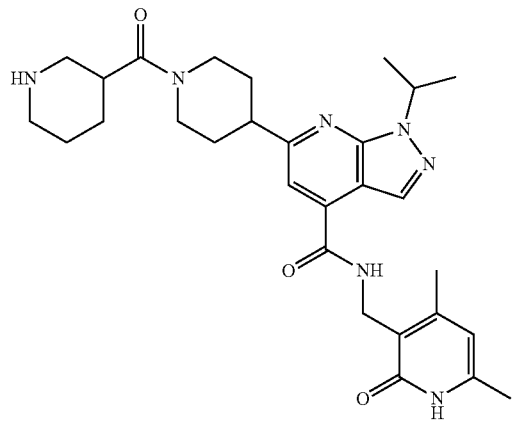 [SMILES: Cc1cc(C)c(CNC(=O)c2cc(C3CCN(C(=O)C4CCCNC4)CC3)nc3c2cnn3C(C)C)c(=O)[nH]1] |
| B-52 | 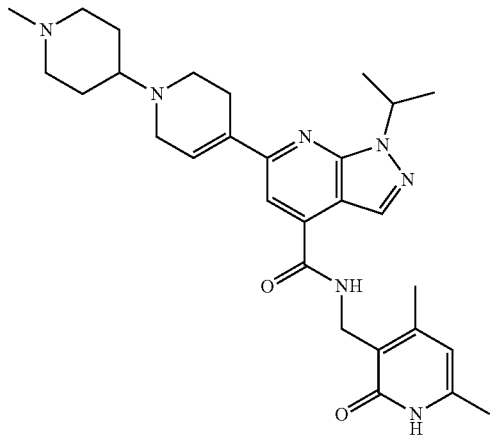 |
| B-53 | 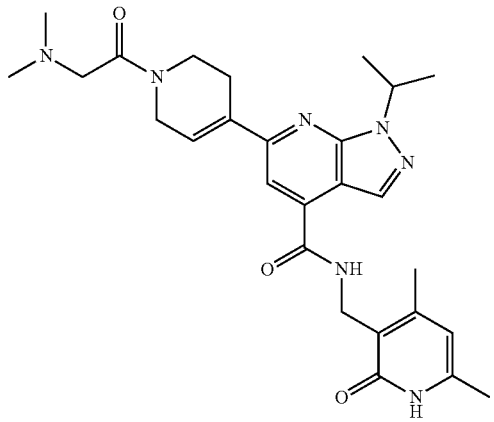 |

-continued
| Compound Number | Structure |
|---|---|
| B-54 | 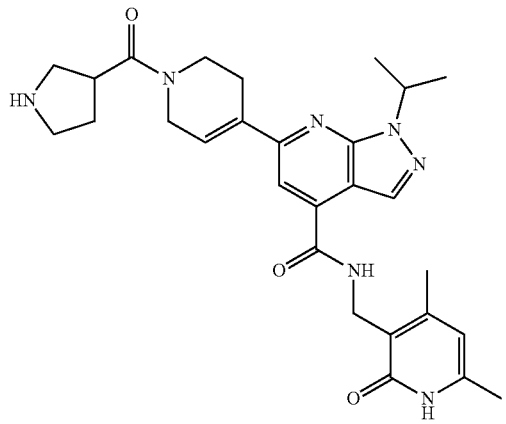 [SMILES: Cc1cc(C)c(CNC(=O)c2cc(C3=CCN(C(=O)C4CCNC4)CC3)nc3c2cnn3C(C)C)c(=O)[nH]1] |
| B-55 | 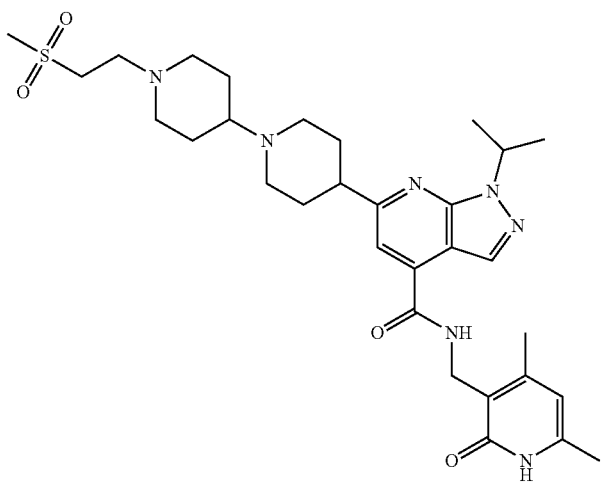 |
| B-56 | 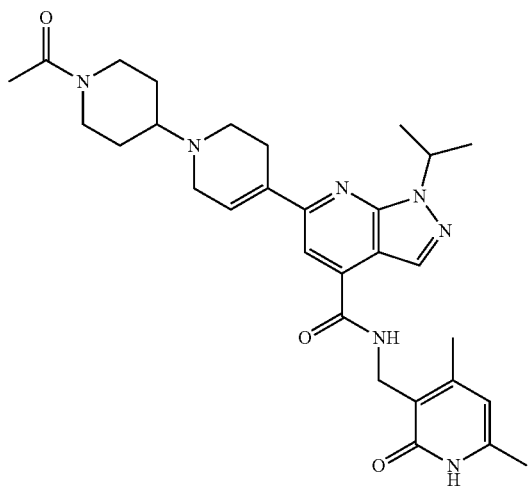 [SMILES: CC(=O)N1CCC(N2CC=C(c3cc(C(=O)NCc4c(C)cc(C)[nH]c4=O)c4cnn(C(C)C)c4n3)CC2)CC1] |

-continued
| Compound Number | Structure |
|---|---|
| B-57 | 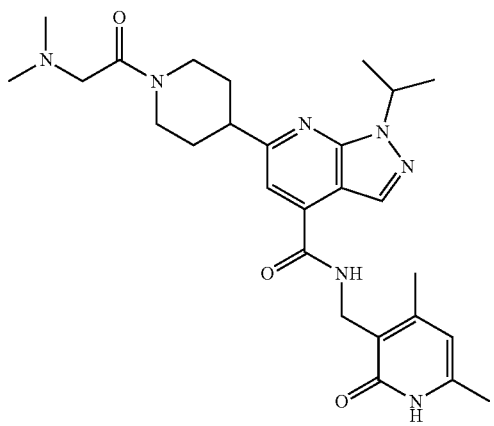 |
| B-58 | 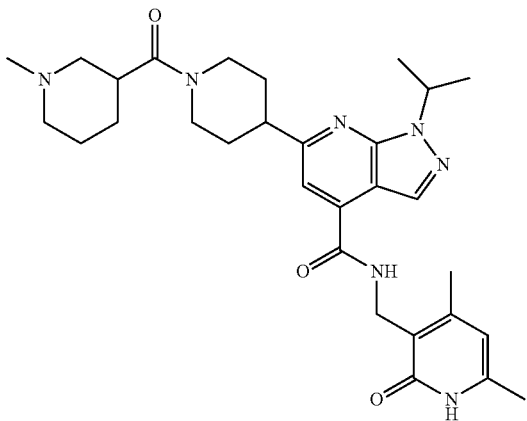 |
| B-59 | 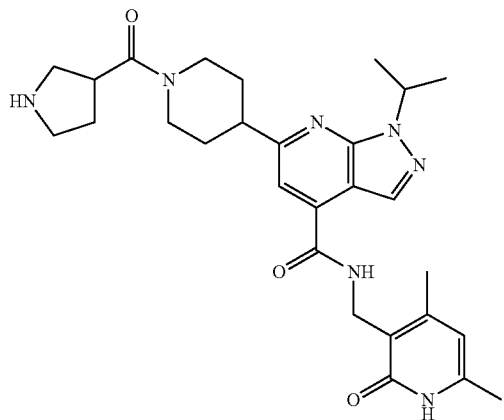 [SMILES: Cc1cc(C)c(CNC(=O)c2cc(C3CCN(C(=O)C4CCNC4)CC3)nc3c2cnn3C(C)C)c(=O)[nH]1] |

| Compound Number | Structure |
|---|---|
| B-60 | 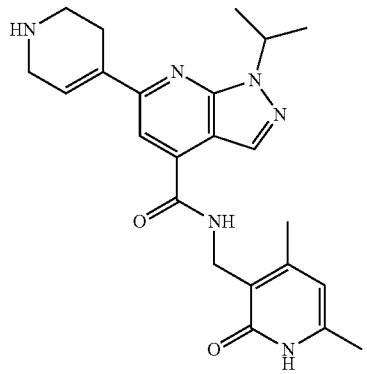 [SMILES: Cc1cc(C)c(CNC(=O)c2cc(C3=CCNCC3)nc3c2cnn3C(C)C)c(=O)[nH]1] |
| B-61 | 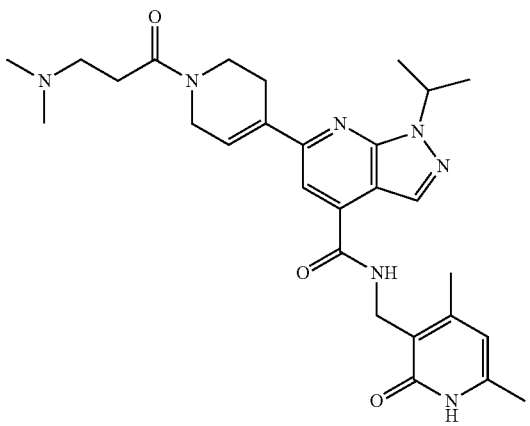 |
| B-62 | 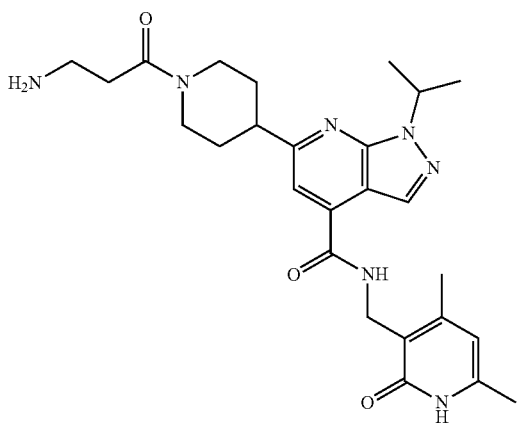 [SMILES: Cc1cc(C)c(CNC(=O)c2cc(C3CCN(C(=O)CCN)CC3)nc3c2cnn3C(C)C)c(=O)[nH]1] |

-continued
| Compound Number | Structure |
|---|---|
| B-63 | 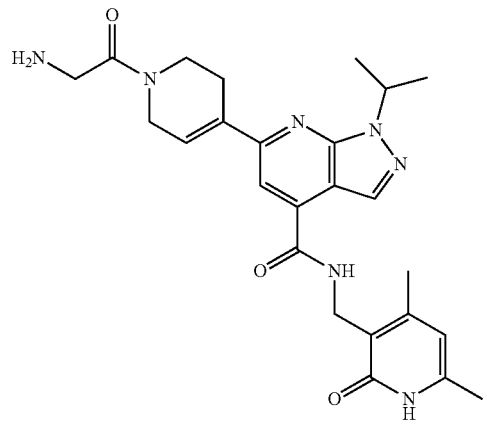 [SMILES: Cc1cc(C)c(CNC(=O)c2cc(C3=CCN(C(=O)CN)CC3)nc3c2cnn3C(C)C)c(=O)[nH]1] |
| B-64 | 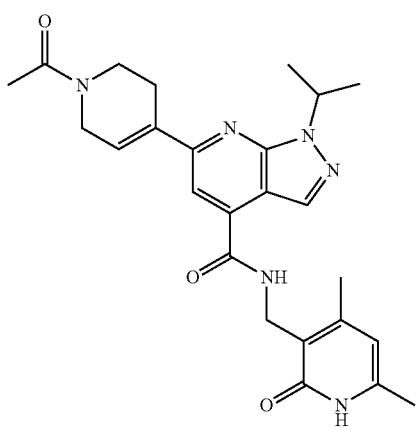 [SMILES: CC(=O)N1CC=C(c2cc(C(=O)NCc3c(C)cc(C)[nH]c3=O)c3cnn(C(C)C)c3n2)CC1] |
| B-65 | 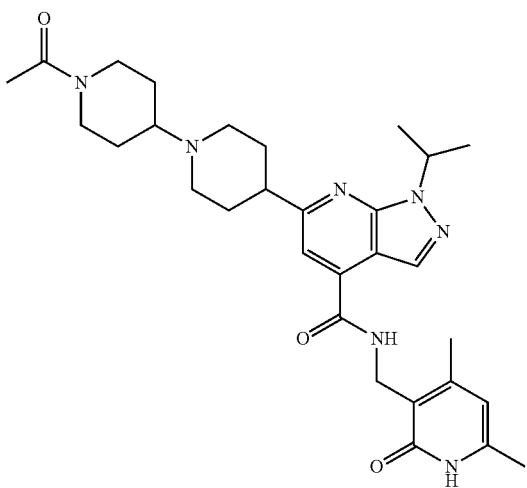 [SMILES: CC(=O)N1CCC(N2CCC(c3cc(C(=O)NCc4c(C)cc(C)[nH]c4=O)c4cnn(C(C)C)c4n3)CC2)CC1] |

| Compound Number | Structure |
|---|---|
| B-66 | 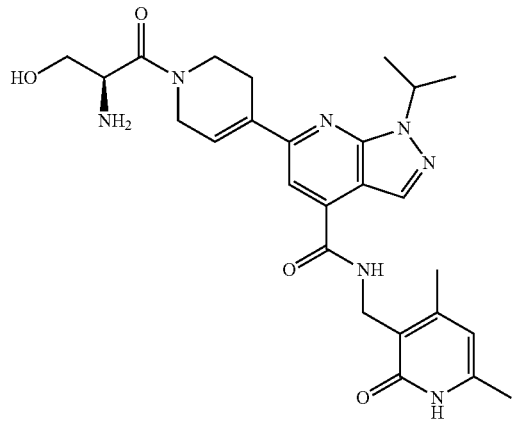 [SMILES: Cc1cc(C)c(CNC(=O)c2cc(C3=CCN(C(=O)[C@@H](N)CO)CC3)nc3c2cnn3C(C)C)c(=O)[nH]1] |
| B-67 | 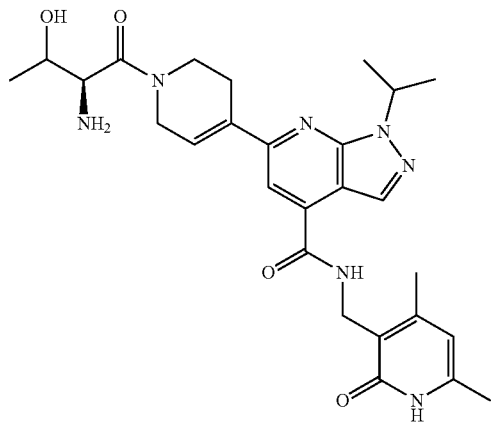 [SMILES: Cc1cc(C)c(CNC(=O)c2cc(C3=CCN(C(=O)[C@@H](N)C(C)O)CC3)nc3c2cnn3C(C)C)c(=O)[nH]1] |
| B-68 | 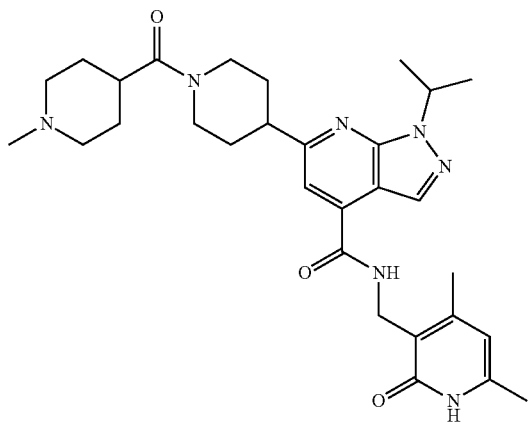 |

| Compound Number | Structure |
|---|---|
| B-69 | 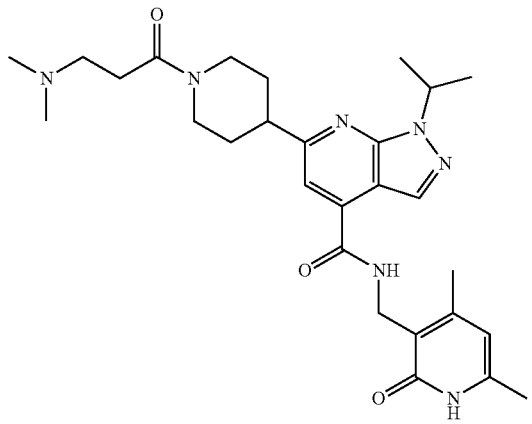 |
| B-70 | 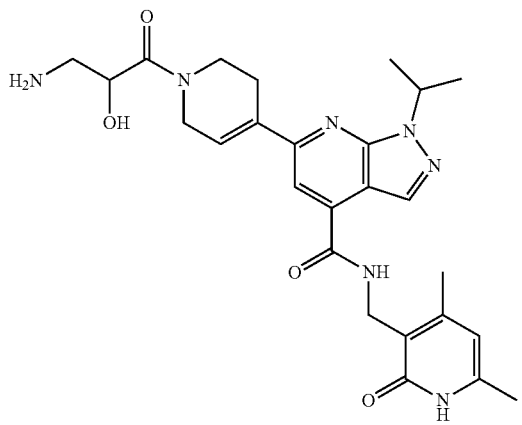 [SMILES: Cc1cc(C)c(CNC(=O)c2cc(C3=CCN(C(=O)C(O)CN)CC3)nc3c2cnn3C(C)C)c(=O)[nH]1] |
| B-71 | 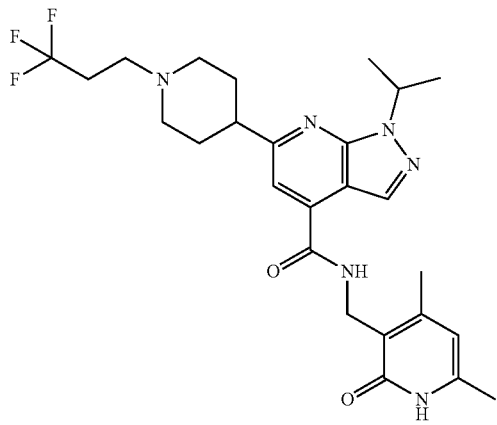 |

| Compound Number | Structure |
|---|---|
| B-72 | 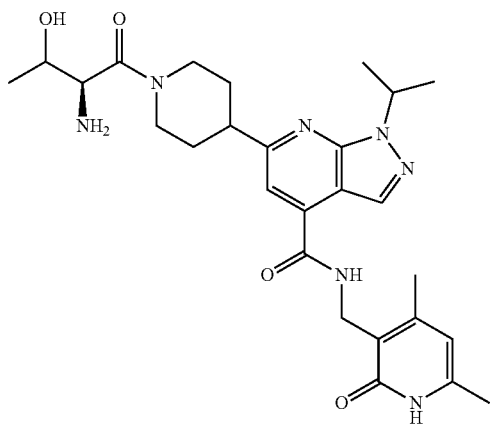 [SMILES: Cc1cc(C)c(CNC(=O)c2cc(C3CCN(C(=O)[C@@H](N)C(C)O)CC3)nc3c2cnn3C(C)C)c(=O)[nH]1] |
| B-73 | 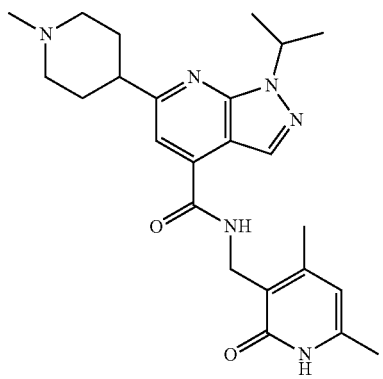 |
| B-74 | 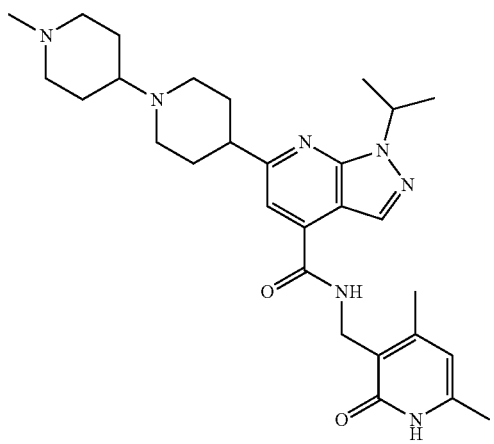 |

-continued
| Compound Number | Structure |
|---|---|
| B-75 | 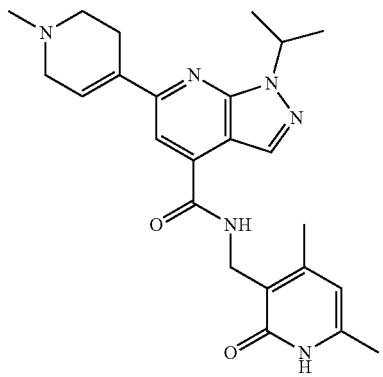 |
| B-76 | 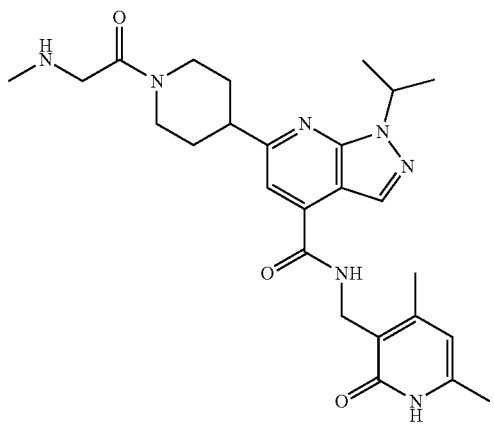 |
| B-77 | 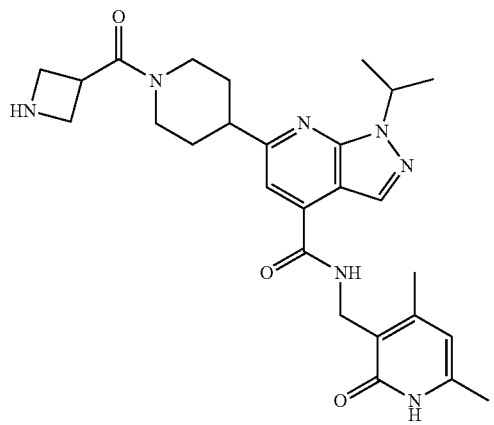 [SMILES: Cc1cc(C)c(CNC(=O)c2cc(C3CCN(C(=O)C4CNC4)CC3)nc3c2cnn3C(C)C)c(=O)[nH]1] |

-continued
| Compound Number | Structure |
|---|---|
| B-78 | 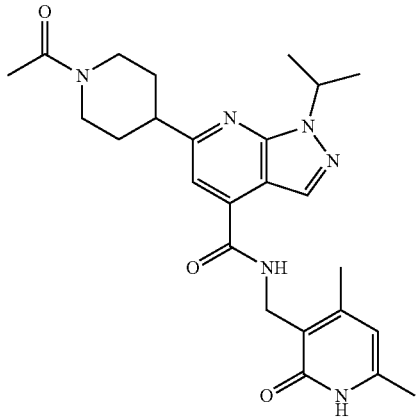 [SMILES: CC(=O)N1CCC(c2cc(C(=O)NCc3c(C)cc(C)[nH]c3=O)c3cnn(C(C)C)c3n2)CC1] |
| B-79 | 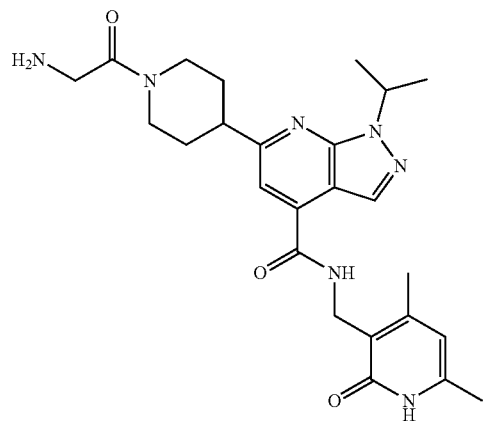 [SMILES: Cc1cc(C)c(CNC(=O)c2cc(C3CCN(C(=O)CN)CC3)nc3c2cnn3C(C)C)c(=O)[nH]1] |
| B-80 | 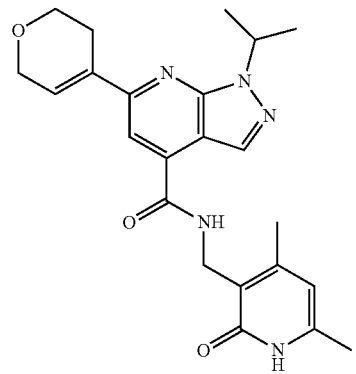 [SMILES: Cc1cc(C)c(CNC(=O)c2cc(C3=CCOCC3)nc3c2cnn3C(C)C)c(=O)[nH]1] |

-continued
| Compound Number | Structure |
|---|---|
| B-81 | 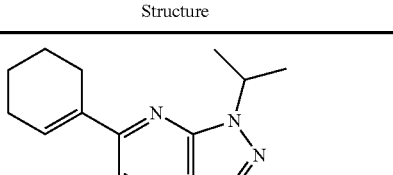 |
| B-82 | 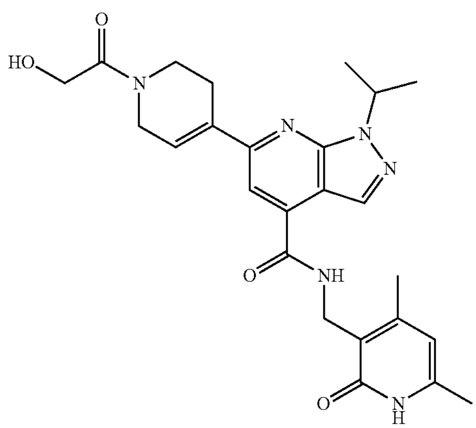 [SMILES: Cc1cc(C)c(CNC(=O)c2cc(C3=CCN(C(=O)CO)CC3)nc3c2cnn3C(C)C)c(=O)[nH]1] |
| B-83 | 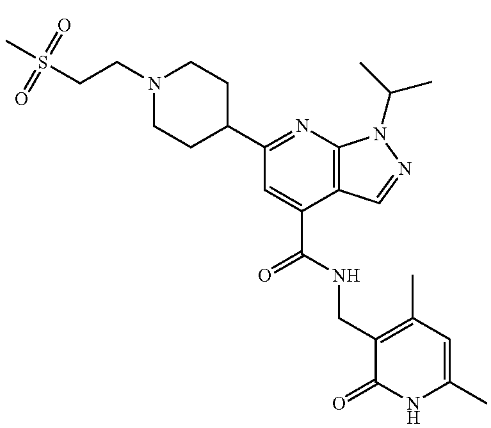 |

| Compound Number | Structure |
|---|---|
| B-84 | 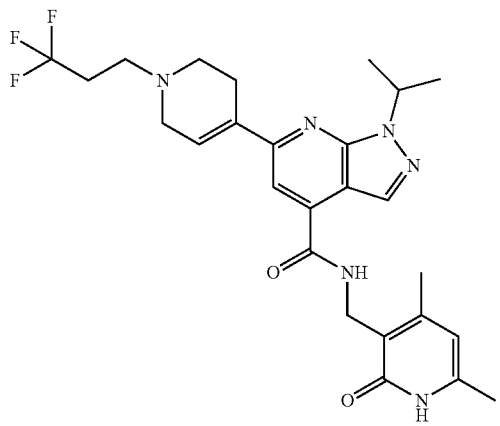 [SMILES: Cc1cc(C)c(CNC(=O)c2cc(C3=CCN(CCC(F)(F)F)CC3)nc3c2cnn3C(C)C)c(=O)[nH]1] |
| B-85 | 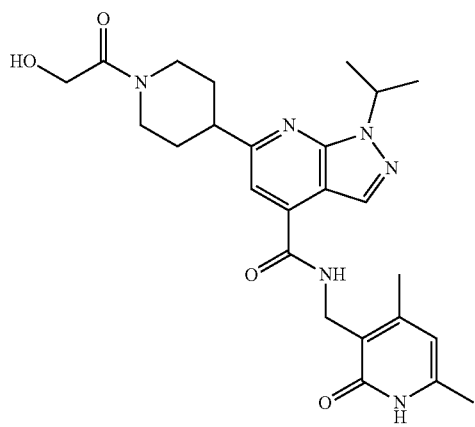 |
| B-86 | 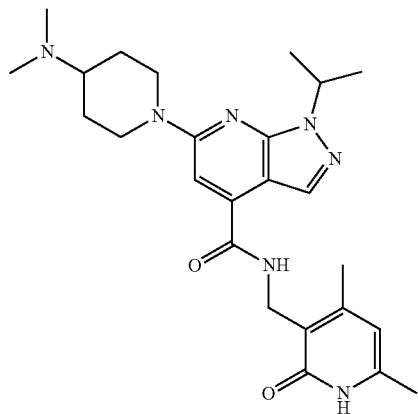 |

| Compound Number | Structure |
|---|---|
| B-87 | 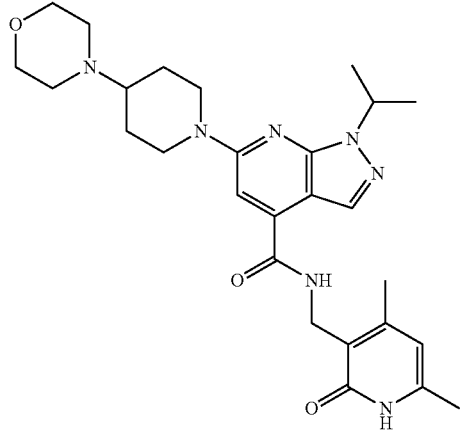 [SMILES: Cc1cc(C)c(CNC(=O)c2cc(N3CCC(N4CCOCC4)CC3)nc3c2cnn3C(C)C)c(=O)[nH]1] |
| B-88 | 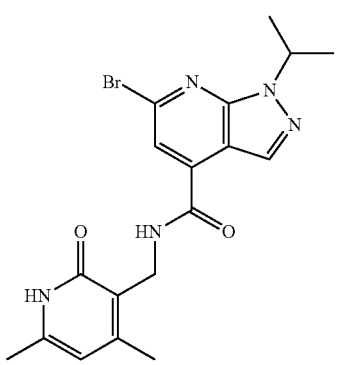 [SMILES: Cc1cc(C)c(CNC(=O)c2cc(Br)nc3c2cnn3C(C)C)c(=O)[nH]1] |
| B-89 | 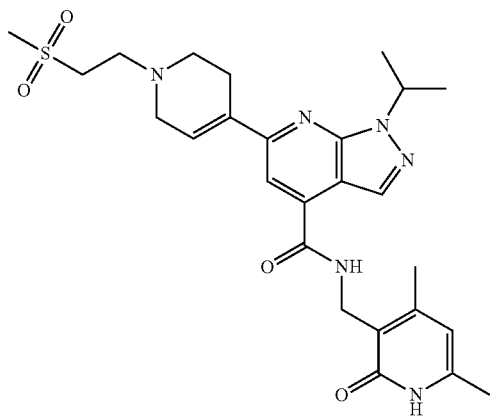 |
| B-92 | 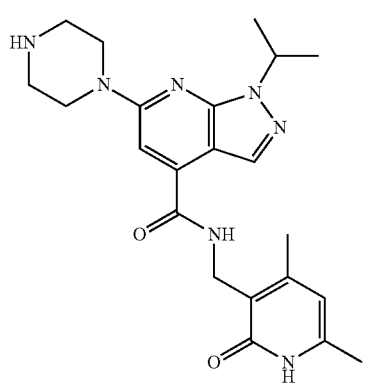 [SMILES: Cc1cc(C)c(CNC(=O)c2cc(N3CCNCC3)nc3c2cnn3C(C)C)c(=O)[nH]1] |

-continued
| Compound Number | Structure |
|---|---|
| B-94 | 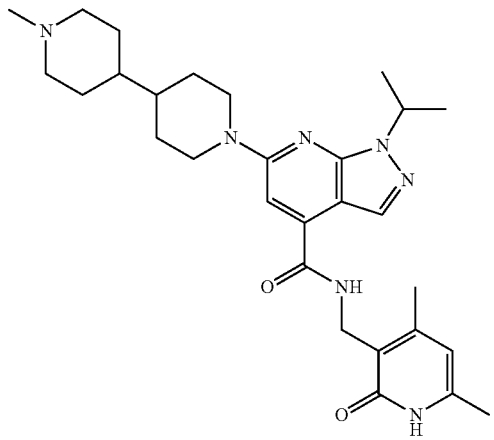 |
| B-95 | 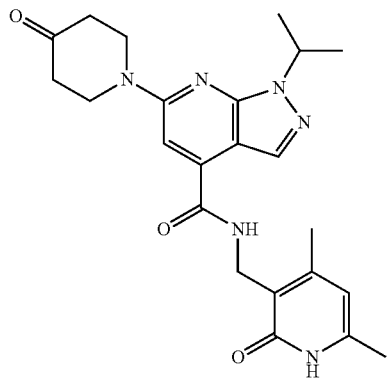 [SMILES: Cc1cc(C)c(CNC(=O)c2cc(N3CCC(=O)CC3)nc3c2cnn3C(C)C)c(=O)[nH]1] |
| B-96 | 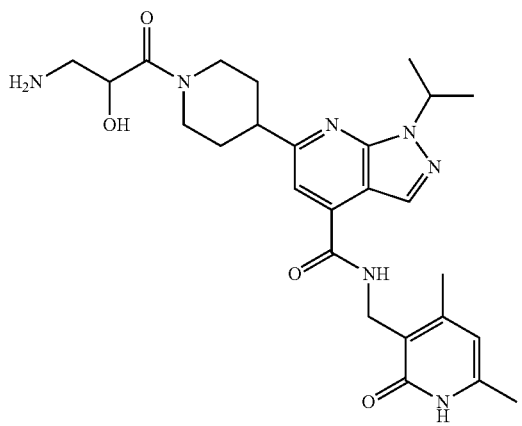 [SMILES: Cc1cc(C)c(CNC(=O)c2cc(C3CCN(C(=O)C(O)CN)CC3)nc3c2cnn3C(C)C)c(=O)[nH]1] |

-continued
| Compound Number | Structure |
|---|---|
| B-98 | 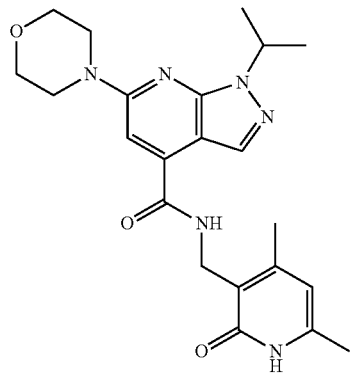 [SMILES: Cc1cc(C)c(CNC(=O)c2cc(N3CCOCC3)nc3c2cnn3C(C)C)c(=O)[nH]1] |
| B-99 | 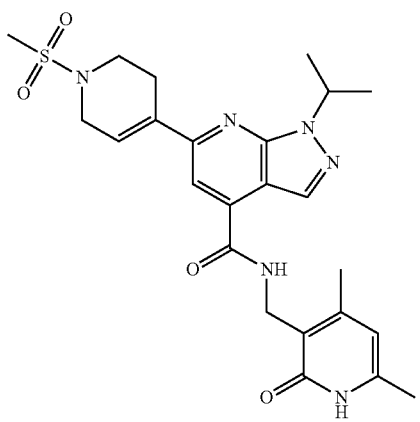 |
| B-100 | 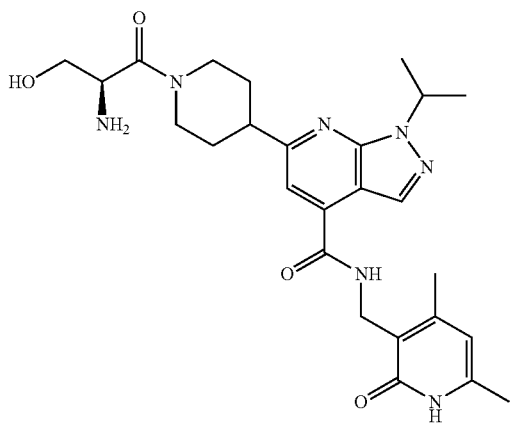 [SMILES: Cc1cc(C)c(CNC(=O)c2cc(C3CCN(C(=O)[C@@H](N)CO)CC3)nc3c2cnn3C(C)C)c(=O)[nH]1] |

| Compound Number | Structure |
|---|---|
| B-101 | 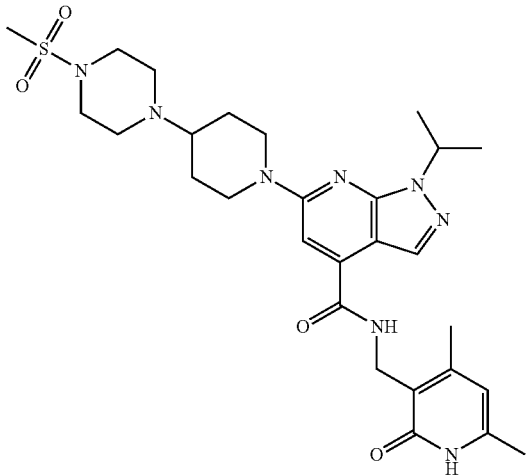 |
| B-102 | 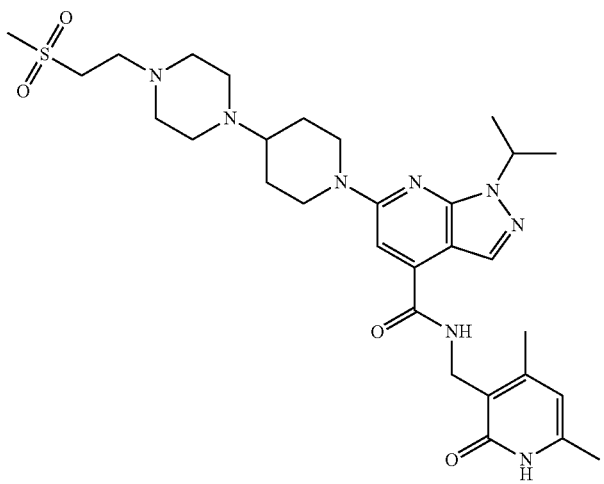 |
| B-103 | 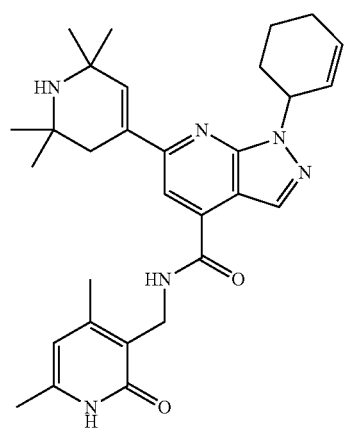 [SMILES: Cc1cc(C)c(CNC(=O)c2cc(C3=CC(C)(C)NC(C)(C)C3)nc3c2cnn3C2C=CCCC2)c(=O)[nH]1] |

-continued
| Compound Number | Structure |
|---|---|
| B-104 | 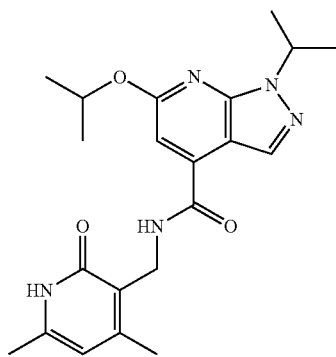 [SMILES: Cc1cc(C)c(CNC(=O)c2cc(OC(C)C)nc3c2cnn3C(C)C)c(=O)[nH]1] |
| B-105 | 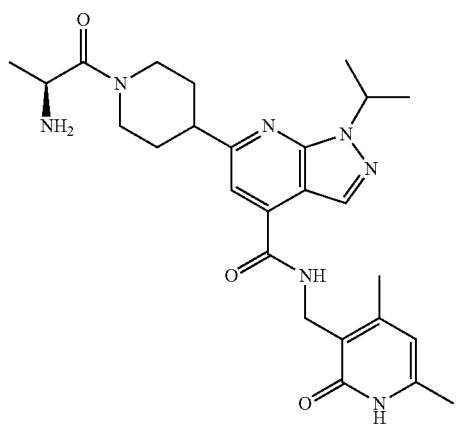 [SMILES: Cc1cc(C)c(CNC(=O)c2cc(C3CCN(C(=O)[C@H](C)N)CC3)nc3c2cnn3C(C)C)c(=O)[nH]1] |
| B-106 | 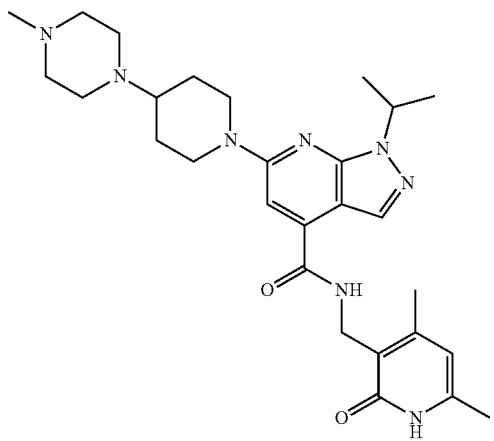 |

| Compound Number | Structure |
|---|---|
| B-107 | 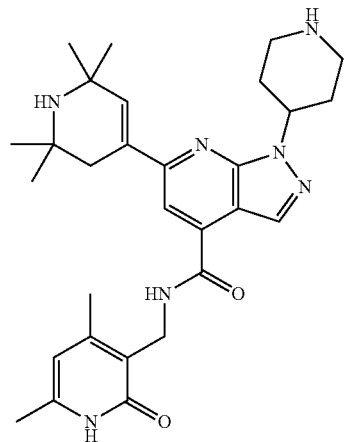 [SMILES: Cc1cc(C)c(CNC(=O)c2cc(C3=CC(C)(C)NC(C)(C)C3)nc3c2cnn3C2CCNCC2)c(=O)[nH]1] |
| B-108 | 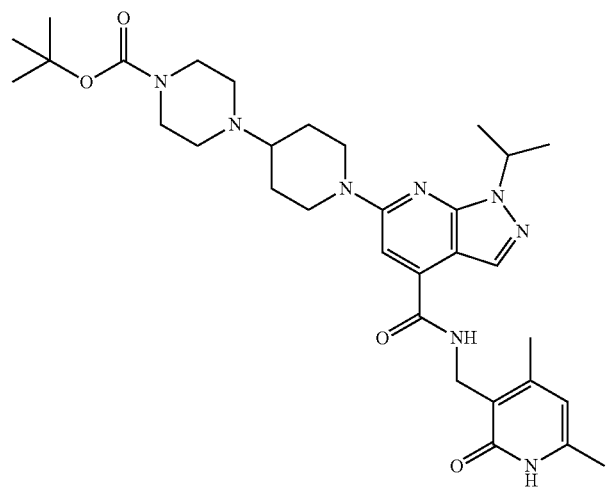 [SMILES: Cc1cc(C)c(CNC(=O)c2cc(N3CCC(N4CCN(C(=O)OC(C)(C)C)CC4)CC3)nc3c2cnn3C(C)C)c(=O)[nH]1] |
| B-110 | 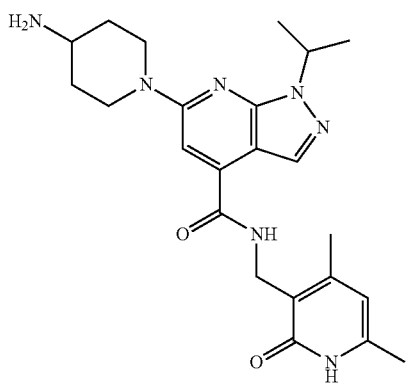 [SMILES: Cc1cc(C)c(CNC(=O)c2cc(N3CCC(N)CC3)nc3c2cnn3C(C)C)c(=O)[nH]1] |

| Compound Number | Structure |
|---|---|
| B-112 | 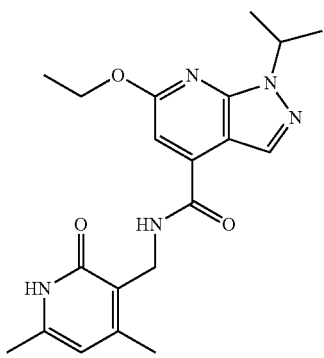 [SMILES: CCOc1cc(C(=O)NCc2c(C)cc(C)[nH]c2=O)c2cnn(C(C)C)c2n1] |
| B-113 | 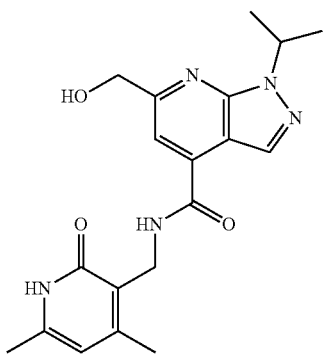 [SMILES: Cc1cc(C)c(CNC(=O)c2cc(CO)nc3c2cnn3C(C)C)c(=O)[nH]1] |
| B-115 | 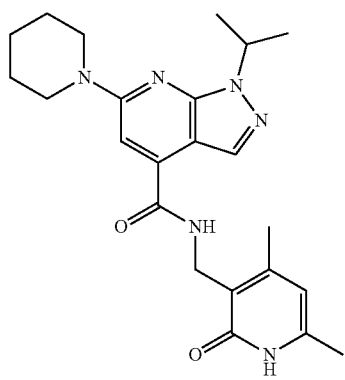 [SMILES: Cc1cc(C)c(CNC(=O)c2cc(N3CCCCC3)nc3c2cnn3C(C)C)c(=O)[nH]1] |
| B-116 | 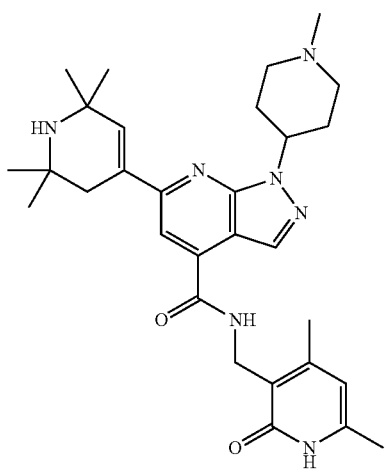 |

-continued
| Compound Number | Structure |
|---|---|
| B-118 | 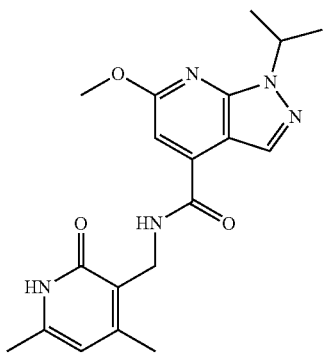 [SMILES: COc1cc(C(=O)NCc2c(C)cc(C)[nH]c2=O)c2cnn(C(C)C)c2n1] |
| B-119 | 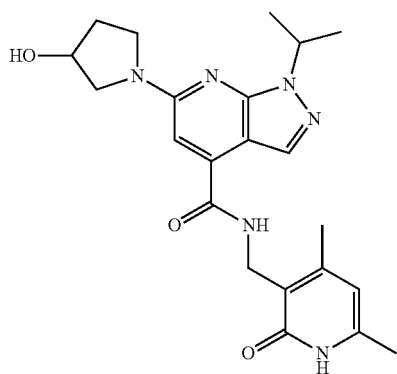 [SMILES: Cc1cc(C)c(CNC(=O)c2cc(N3CCC(O)C3)nc3c2cnn3C(C)C)c(=O)[nH]1] |
| B-122 | 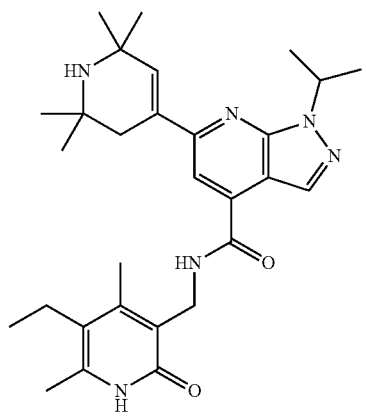 [SMILES: CCc1c(C)[nH]c(=O)c(CNC(=O)c2cc(C3=CC(C)(C)NC(C)(C)C3)nc3c2cnn3C(C)C)c1C] |
| B-123 | 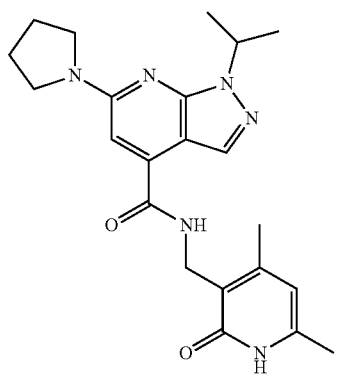 [SMILES: Cc1cc(C)c(CNC(=O)c2cc(N3CCCC3)nc3c2cnn3C(C)C)c(=O)[nH]1] |

-continued
| Compound Number | Structure |
|---|---|
| B-126 | 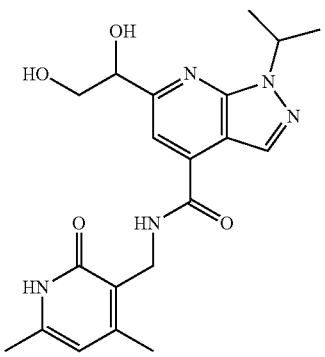 [SMILES: Cc1cc(C)c(CNC(=O)c2cc(C(O)CO)nc3c2cnn3C(C)C)c(=O)[nH]1] |
| B-129 | 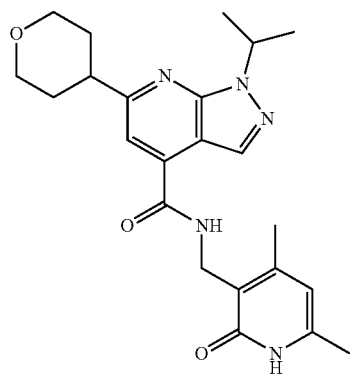 [SMILES: Cc1cc(C)c(CNC(=O)c2cc(C3CCOCC3)nc3c2cnn3C(C)C)c(=O)[nH]1] |
| B-130 | 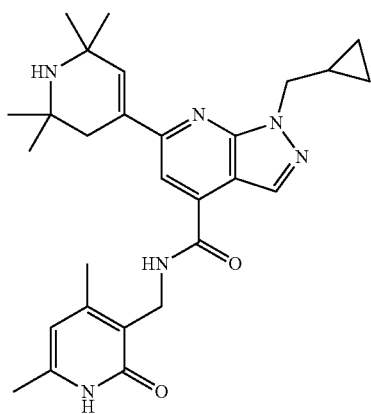 [SMILES: Cc1cc(C)c(CNC(=O)c2cc(C3=CC(C)(C)NC(C)(C)C3)nc3c2cnn3CC2CC2)c(=O)[nH]1] |
| B-131 | 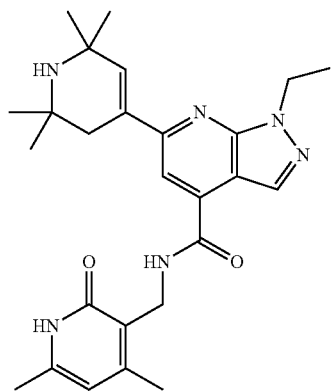 [SMILES: CCn1ncc2c(C(=O)NCc3c(C)cc(C)[nH]c3=O)cc(C3=CC(C)(C)NC(C)(C)C3)nc21] |

-continued
| Compound Number | Structure |
|---|---|
| B-137 | 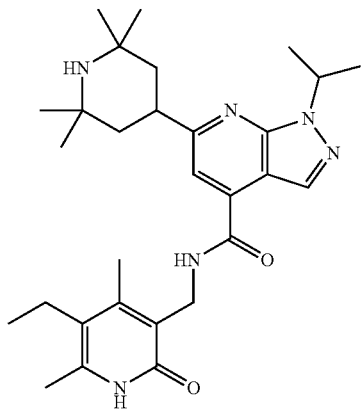 [SMILES: CCc1c(C)[nH]c(=O)c(CNC(=O)c2cc(C3CC(C)(C)NC(C)(C)C3)nc3c2cnn3C(C)C)c1C] |
| B-138 | 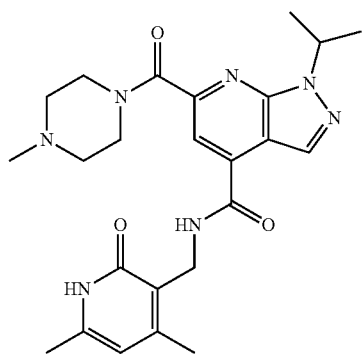 [SMILES: Cc1cc(C)c(CNC(=O)c2cc(C(=O)N3CCN(C)CC3)nc3c2cnn3C(C)C)c(=O)[nH]1] |
| B-139 | 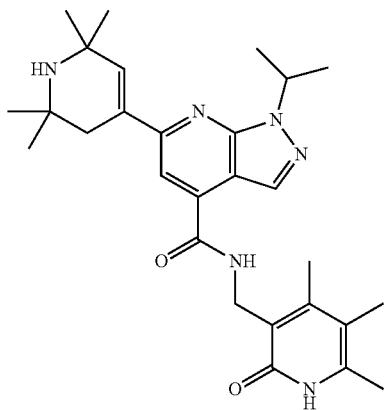 |

-continued
| Compound Number | Structure |
|---|---|
| B-142 | 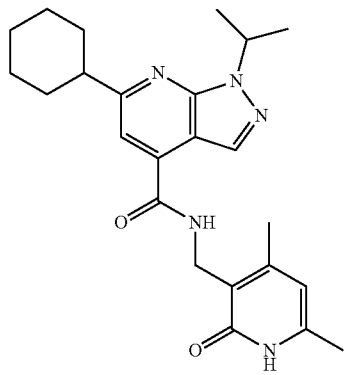 [SMILES: Cc1cc(C)c(CNC(=O)c2cc(C3CCCCC3)nc3c2cnn3C(C)C)c(=O)[nH]1] |
| B-143 | 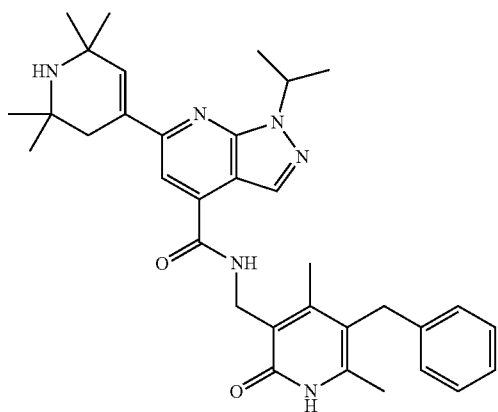 |
| B-144 | 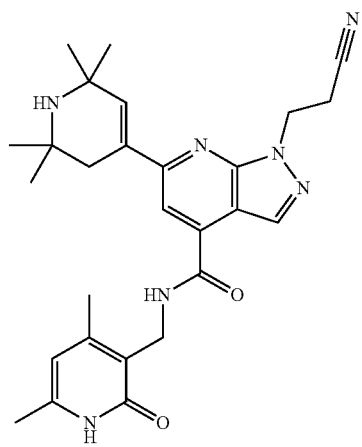 [SMILES: Cc1cc(C)c(CNC(=O)c2cc(C3=CC(C)(C)NC(C)(C)C3)nc3c2cnn3CCC#N)c(=O)[nH]1] |

| Compound Number | Structure |
|---|---|
| B-145 | 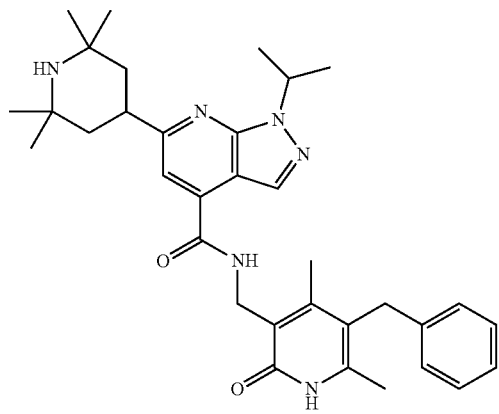 |
| B-146 | 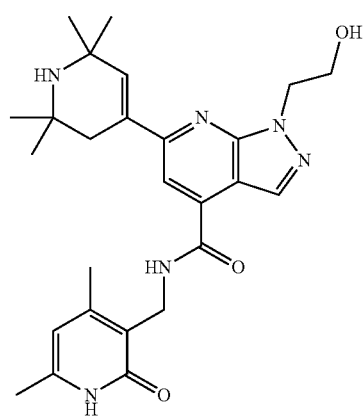 [SMILES: Cc1cc(C)c(CNC(=O)c2cc(C3=CC(C)(C)NC(C)(C)C3)nc3c2cnn3CCO)c(=O)[nH]1] |
| B-148 | 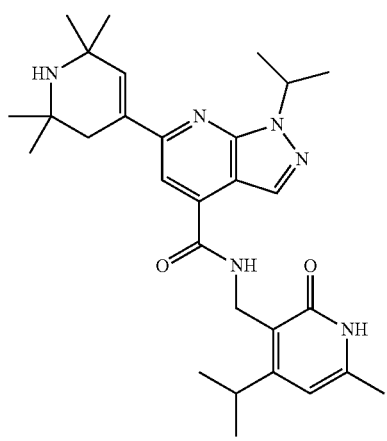 |

-continued
| Compound Number | Structure |
|---|---|
| B-151 | 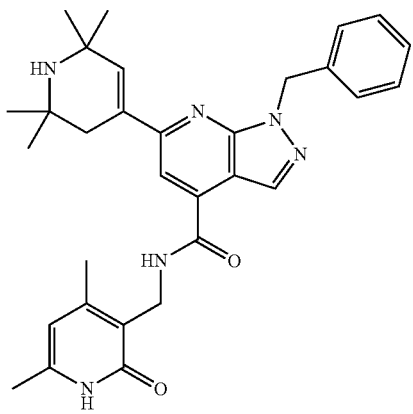 [SMILES: Cc1cc(C)c(CNC(=O)c2cc(C3=CC(C)(C)NC(C)(C)C3)nc3c2cnn3Cc2ccccc2)c(=O)[nH]1] |
| B-152 | 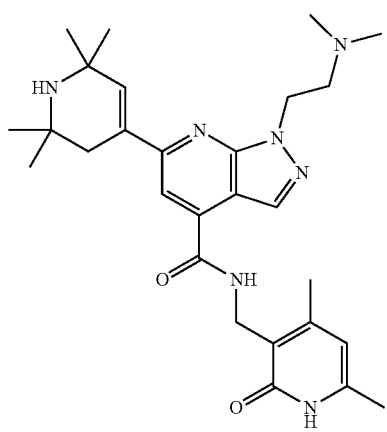 |
| B-153 | 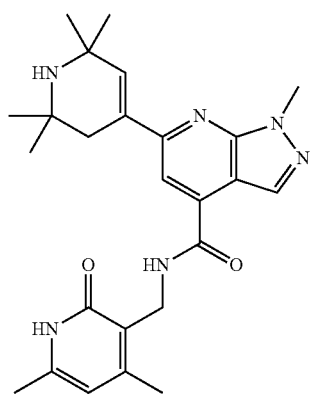 [SMILES: Cc1cc(C)c(CNC(=O)c2cc(C3=CC(C)(C)NC(C)(C)C3)nc3c2cnn3C)c(=O)[nH]1] |

-continued
| Compound Number | Structure |
|---|---|
| B-156 | 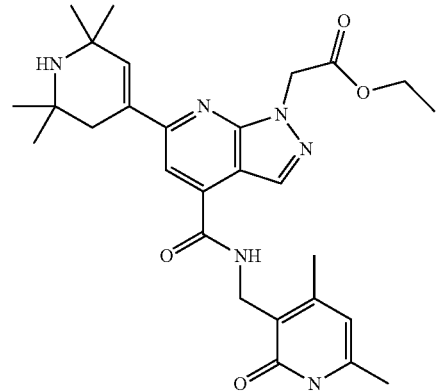 and |
| B-164 | 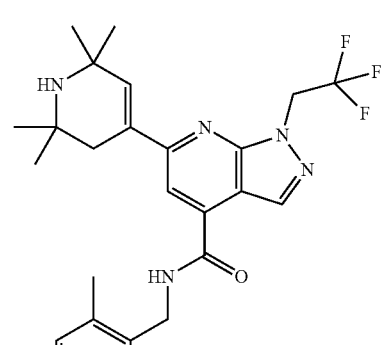 |
* * * * *

SEQUENCE LISTING

<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (26)..(26)
<223> OTHER INFORMATION: wherein a biotin and an amide are conjugated

```
<400> SEQUENCE: 1

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (7)..(7)
<223> OTHER INFORMATION: wherein the lysine is dimethylated
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 2

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```

UNITED STATES PATENT AND TRADEMARK OFFICE
CERTIFICATE OF CORRECTION

PATENT NO. : 9,637,472 B2  
APPLICATION NO. : 14/536162  
DATED : May 2, 2017  
INVENTOR(S) : Kevin Wayne Kuntz et al.

Page 1 of 2

It is certified that error appears in the above-identified patent and that said Letters Patent is hereby corrected as shown below:

In the Claims

At Column 471, in Claim 18, Compound A-43:

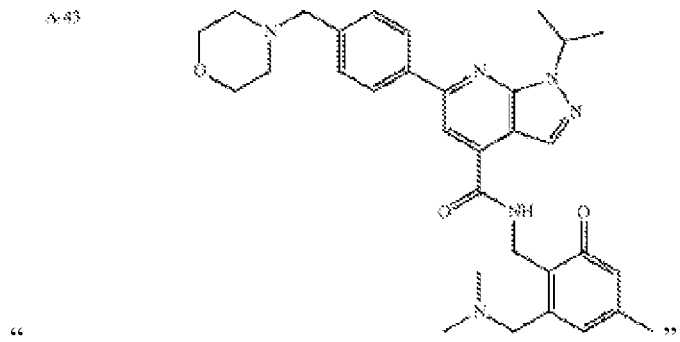

"

Should read:

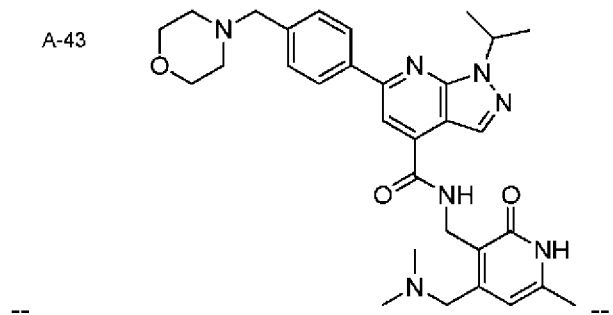

--

Signed and Sealed this  
Fourth Day of July, 2017

Joseph Matal  
*Performing the Functions and Duties of the  
Under Secretary of Commerce for Intellectual Property and  
Director of the United States Patent and Trademark Office*

CERTIFICATE OF CORRECTION (continued)
U.S. Pat. No. 9,637,472 B2

Page 2 of 2

At Column 473, in Claim 18, Compound A-44:

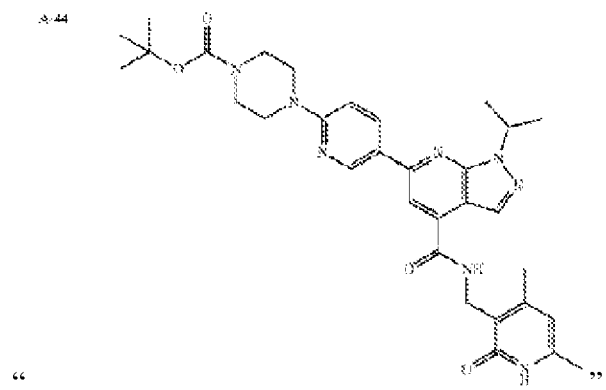

"

Should read:

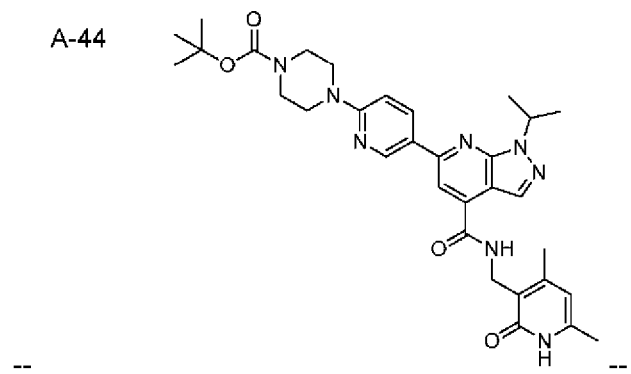

--    --